(12) United States Patent
Perlroth et al.

(10) Patent No.: US 11,584,790 B2
(45) Date of Patent: Feb. 21, 2023

(54) COMPLEMENT FACTOR D ANTAGONIST ANTIBODIES AND CONJUGATES THEREOF

(71) Applicant: KODIAK SCIENCES INC., Palo Alto, CA (US)

(72) Inventors: Daniel Victor Perlroth, Palo Alto, CA (US); Wah Yuen To, San Mateo, CA (US); Hong Liang, Hillsborough, CA (US); Rachel Marie DeVay Jacobson, Belmont, CA (US); Fernando Corrêa, Hayward, CA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 214 days.

(21) Appl. No.: 15/952,092

(22) Filed: Apr. 12, 2018

(65) Prior Publication Data
US 2018/0334496 A1    Nov. 22, 2018

Related U.S. Application Data

(60) Provisional application No. 62/485,718, filed on Apr. 14, 2017.

(51) Int. Cl.
| | | |
|---|---|---|
| *C07K 16/18* | (2006.01) | |
| *C07K 16/40* | (2006.01) | |
| *C07K 14/47* | (2006.01) | |
| *A61K 47/68* | (2017.01) | |

(52) U.S. Cl.
CPC .......... *C07K 16/18* (2013.01); *A61K 47/6843* (2017.08); *A61K 47/6885* (2017.08); *C07K 16/40* (2013.01); *C07K 14/472* (2013.01); *C07K 2317/24* (2013.01); *C07K 2317/33* (2013.01); *C07K 2317/34* (2013.01); *C07K 2317/41* (2013.01); *C07K 2317/51* (2013.01); *C07K 2317/515* (2013.01); *C07K 2317/55* (2013.01); *C07K 2317/565* (2013.01); *C07K 2317/734* (2013.01); *C07K 2317/76* (2013.01); *C07K 2317/92* (2013.01); *C07K 2317/94* (2013.01); *C12Y 304/21046* (2013.01)

(58) Field of Classification Search
CPC ...... C07K 16/18; C07K 16/40; C07K 14/472; C07K 2317/24; C07K 2317/33; C07K 2317/34; C07K 2317/41; C07K 2317/51; C07K 2317/515; C07K 2317/55; C07K 2317/565; C07K 2317/734; C07K 2317/76; C07K 2317/92; C07K 2317/94; A61K 47/6843; A61K 47/6885; C12Y 304/21046; A61P 27/02; A61P 37/06
See application file for complete search history.

(56) References Cited

U.S. PATENT DOCUMENTS

| | | |
|---|---|---|
| 4,485,045 A | 11/1984 | Regen |
| 4,544,545 A | 10/1985 | Ryan et al. |
| 4,634,664 A | 1/1987 | Oestberg |
| 4,634,666 A | 1/1987 | Engleman et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Jukka et al. |
| 4,800,159 A | 1/1989 | Mullis et al. |
| 4,816,567 A | 3/1989 | Cabilly et al. |
| 4,892,538 A | 1/1990 | Aebischer et al. |
| 5,013,556 A | 5/1991 | Woodle et al. |
| 5,047,335 A | 9/1991 | Paulson et al. |
| 5,219,740 A | 6/1993 | Dusty et al. |
| 5,225,539 A | 7/1993 | Winter |
| 5,278,299 A | 1/1994 | Wong et al. |
| 5,283,187 A | 2/1994 | Aebischer et al. |
| 5,422,120 A | 6/1995 | Kim |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,580,859 A | 12/1996 | Felgner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,663,425 A | 9/1997 | Detroit et al. |
| 5,681,746 A | 10/1997 | Bodner et al. |
| 5,733,743 A | 3/1998 | Johnson et al. |
| 5,770,429 A | 6/1998 | Lonberg et al. |
| 5,789,650 A | 8/1998 | Lonberg et al. |

(Continued)

FOREIGN PATENT DOCUMENTS

| | | |
|---|---|---|
| CN | 106905431 A | 6/2017 |
| EP | 0345242 | 12/1989 |

(Continued)

OTHER PUBLICATIONS

Katschke et al., J Biol Chemistry 287: 12886-12892 (Year: 2012).*

(Continued)

*Primary Examiner* — Phuong Huynh

(74) *Attorney, Agent, or Firm* — Knobbe, Martens, Olson & Bear, LLP

(57) ABSTRACT

The present invention provides antagonizing antibodies that bind to complement factor D (CFD), conjugates thereof, and methods of using same. The anti-CFD antibodies can be used therapeutically alone or in combination with other therapeutics to treat age related macular degeneration and other diseases.

45 Claims, 62 Drawing Sheets

Specification includes a Sequence Listing.

(56) References Cited

U.S. PATENT DOCUMENTS

| | | | |
|---|---|---|---|
| 5,814,318 A | 9/1998 | Lonberg et al. | |
| 5,814,482 A | 9/1998 | Dubensky, Jr. et al. | |
| 5,834,597 A | 11/1998 | Tso et al. | |
| 5,837,242 A | 11/1998 | Holliger et al. | |
| 5,858,657 A | 1/1999 | Winter et al. | |
| 5,859,205 A | 1/1999 | Adair et al. | |
| 5,871,907 A | 2/1999 | Winter et al. | |
| 5,872,218 A | 2/1999 | Wolf et al. | |
| 5,874,299 A | 2/1999 | Lonberg et al. | |
| 5,877,218 A | 3/1999 | Herzig et al. | |
| 5,877,397 A | 3/1999 | Lonberg et al. | |
| 6,376,471 B1 | 4/2002 | Lawrence, III et al. | |
| 6,407,213 B1 | 6/2002 | Carter et al. | |
| 6,413,942 B1 | 7/2002 | Felger et al. | |
| 6,436,908 B1 | 8/2002 | Koch et al. | |
| 6,624,821 B1 | 9/2003 | Shin et al. | |
| 6,881,557 B2 | 4/2005 | Foote | |
| 6,956,107 B2* | 10/2005 | Fung | C07K 16/40 435/326 |
| 7,521,541 B2 | 4/2009 | Eigenbrot et al. | |
| 7,667,004 B2* | 2/2010 | Zhong | C07K 16/22 530/388.1 |
| 7,893,173 B2 | 2/2011 | Matyjaszewski et al. | |
| 8,003,097 B2 | 8/2011 | Schroeter et al. | |
| 8,008,453 B2 | 8/2011 | Gegg et al. | |
| 8,067,002 B2 | 11/2011 | An et al. | |
| 8,273,352 B2 | 9/2012 | Huang et al. | |
| 8,455,622 B2 | 6/2013 | McDonagh et al. | |
| 8,753,625 B2 | 6/2014 | Fung et al. | |
| 8,765,432 B2 | 7/2014 | Charles et al. | |
| 8,846,021 B2 | 9/2014 | Charles | |
| 8,969,526 B2* | 3/2015 | Baehner | A61P 3/10 530/387.1 |
| 9,840,553 B2 | 12/2017 | Perlroth et al. | |
| 10,363,290 B2 | 7/2019 | Perlroth et al. | |
| 10,407,510 B2* | 9/2019 | Kelley | A61K 39/39591 |
| 10,702,608 B2 | 7/2020 | Charles et al. | |
| 11,066,465 B2 | 7/2021 | Perlroth et al. | |
| 11,071,771 B2 | 7/2021 | Perlroth et al. | |
| 11,155,610 B2 | 10/2021 | Perlroth et al. | |
| 2003/0235536 A1 | 12/2003 | Blumberg et al. | |
| 2005/0041080 A1 | 2/2005 | Hall et al. | |
| 2006/0167230 A1 | 7/2006 | Koga et al. | |
| 2008/0269318 A1* | 10/2008 | Romano | A61P 27/02 514/443 |
| 2009/0060906 A1 | 3/2009 | Barry et al. | |
| 2009/0249503 A1 | 10/2009 | Rosendahl | |
| 2010/0166700 A1 | 7/2010 | Charles | |
| 2010/0291065 A1 | 11/2010 | Kabanov et al. | |
| 2011/0165648 A1 | 7/2011 | Campagne et al. | |
| 2012/0100166 A1* | 4/2012 | Roschke | C07K 14/47 424/185.1 |
| 2012/0213705 A1 | 8/2012 | Dimasi et al. | |
| 2013/0034517 A1 | 2/2013 | Charles et al. | |
| 2013/0045522 A1 | 2/2013 | Charles et al. | |
| 2013/0337534 A1 | 12/2013 | Charles | |
| 2014/0024776 A1 | 1/2014 | Charles et al. | |
| 2014/0065137 A1* | 3/2014 | Huang | A61P 19/02 424/133.1 |
| 2015/0004128 A1 | 1/2015 | Charles et al. | |
| 2015/0050714 A1 | 2/2015 | Charles | |
| 2015/0093390 A1 | 4/2015 | Bansal | |
| 2015/0158952 A1 | 6/2015 | Mao et al. | |
| 2015/0376271 A1 | 9/2015 | Yan et al. | |
| 2015/0337053 A1 | 11/2015 | McCarthy et al. | |
| 2016/0184445 A1 | 6/2016 | Perlroth et al. | |
| 2016/0199501 A1 | 7/2016 | Charles et al. | |
| 2016/0287715 A1 | 10/2016 | Charles et al. | |
| 2016/0369005 A1 | 12/2016 | Lippincott et al. | |
| 2017/0007710 A1 | 1/2017 | Charles et al. | |
| 2017/0143841 A1 | 5/2017 | Charles et al. | |
| 2017/0190766 A1 | 7/2017 | Perlroth et al. | |
| 2018/0244762 A1 | 8/2018 | Perlroth et al. | |
| 2018/0319893 A1 | 11/2018 | Stephen et al. | |
| 2019/0255155 A1 | 8/2019 | Perlroth et al. | |
| 2019/0270806 A1 | 9/2019 | Jacobson et al. | |
| 2019/0330335 A1* | 10/2019 | Schwabe | A61P 1/04 |
| 2020/0000930 A1 | 1/2020 | Charles | |
| 2020/0171179 A1 | 6/2020 | Charles et al. | |
| 2020/0261590 A1 | 8/2020 | Charles et al. | |
| 2020/0262905 A1 | 8/2020 | Perlroth et al. | |
| 2021/0107999 A1 | 4/2021 | Ehrlich et al. | |
| 2021/0324063 A1 | 10/2021 | Perlroth et al. | |
| 2021/0402015 A1 | 12/2021 | Charles et al. | |
| 2022/0096643 A1 | 3/2022 | Charles | |

FOREIGN PATENT DOCUMENTS

| | | | |
|---|---|---|---|
| EP | 0282160 | 5/1995 | |
| EP | 0282610 B1 | 5/1995 | |
| EP | 0524968 | 6/1995 | |
| WO | WO 1990/07936 | 7/1990 | |
| WO | WO 90/11092 | 10/1990 | |
| WO | WO 1991/00904 | 1/1991 | |
| WO | WO 1991/02805 | 3/1991 | |
| WO | WO 1991/10741 | 7/1991 | |
| WO | WO 91/14445 | 10/1991 | |
| WO | WO 1991/17271 | 11/1991 | |
| WO | WO 1992/01047 | 1/1992 | |
| WO | WO 1993/03769 | 3/1993 | |
| WO | WO 93/10218 | 5/1993 | |
| WO | WO 1993/11230 | 6/1993 | |
| WO | WO 1993/12227 | 6/1993 | |
| WO | WO 1993/19191 | 9/1993 | |
| WO | WO 1993/25234 | 12/1993 | |
| WO | WO 1993/25673 | 12/1993 | |
| WO | WO 1993/25698 | 12/1993 | |
| WO | WO 1994/03622 | 2/1994 | |
| WO | WO 1994/12649 | 6/1994 | |
| WO | WO 1994/016748 | 8/1994 | |
| WO | WO 94/23697 | 10/1994 | |
| WO | WO 1994/28938 | 12/1994 | |
| WO | WO 1995/00655 | 1/1995 | |
| WO | WO 95/07994 | 3/1995 | |
| WO | WO 95/13796 | 5/1995 | |
| WO | WO 1995/11984 | 5/1995 | |
| WO | WO 95/30763 | 11/1995 | |
| WO | WO 96/17072 | 6/1996 | |
| WO | WO 1997/14702 | 4/1997 | |
| WO | WO 1997/14703 | 4/1997 | |
| WO | WO 97/42338 | 11/1997 | |
| WO | WO 99/42133 A1 | 8/1999 | |
| WO | WO 2000/09560 | 2/2000 | |
| WO | WO 2004/020405 | 3/2004 | |
| WO | WO 2007/100902 | 9/2007 | |
| WO | WO 2008/020827 | 2/2008 | |
| WO | WO 2008/055206 A2 | 5/2008 | |
| WO | WO 2008/155134 | 12/2008 | |
| WO | WO 2009/052249 | 4/2009 | |
| WO | WO 2009/052439 | 4/2009 | |
| WO | WO-2009052439 A2* | 4/2009 | G06Q 99/00 |
| WO | WO 2009/134711 A1 | 11/2009 | |
| WO | WO 2011/057014 A1 | 5/2011 | |
| WO | WO 2011/075185 | 6/2011 | |
| WO | WO 2011/075736 | 6/2011 | |
| WO | WO 2011/101284 | 8/2011 | |
| WO | WO 2011/130694 | 10/2011 | |
| WO | WO 2012/145746 A1 | 10/2012 | |
| WO | WO 2013/051937 | 4/2013 | |
| WO | WO 2013/059137 | 4/2013 | |
| WO | WO 2013/093809 | 6/2013 | |
| WO | WO 2015/035342 | 3/2015 | |
| WO | WO 2015/168468 A1 | 11/2015 | |
| WO | WO 2015/200905 | 12/2015 | |
| WO | WO 2016/061562 | 4/2016 | |
| WO | WO 2017/075173 A2 | 5/2017 | |
| WO | WO 2017/117464 | 7/2017 | |
| WO | WO 2017/129064 A1 | 8/2017 | |

(56) References Cited

FOREIGN PATENT DOCUMENTS

| WO | WO 2018/191548 | 10/2018 |
|----|----------------|---------|
| WO | WO 2019/169341 | 9/2019  |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Roitt et al., in Immunology second edition, Gower Medical Publishing New York, pp. 5.8 and 5.9. (Year: 1989).*
MacCallum et al., Mol. Biol 262: 732-745 (Year: 1996).*
Paul, Fundamental Immunology, 3rd Edition, pp. 292-295 (Year: 1993).*
Rudikoff et al., Proc Natl Acad Sci USA 79: 1979 (Year: 1982).*
Piatesi et al., ChemBio Chem 5: 460-466 (Year: 2004).*
Wu et al., J. Mol. Biol. 294: 151-162 (Year: 1999).*
International Search Report for International App. No. PCT/US2018/027378, dated Sep. 27, 2018, in 6 pages.
Anderson, W.F., "Human gene therapy," Science, vol. 256, No. 5058, pp. 808-813, May 8, 1992.
Binder S, Stanzel BV, Krebs I, Glittenberg C. 2007. Transplantation of the RPE in AMD. Prog Retn Eye Res. 26:516-554.
Boyd et al., "The effect of the removal of sialic acid, galactose and total carbohydrate on the functional activity of Campath-1H", Molecular Immunology, vol. 32: dated Dec. 1995, pp. 1311-1318.
Capel et al., "Heterogeneity of human IgG Fc receptors", Immunomethods, 4(1): dated Feb. 1994 pp. 25-34.
Capon, D. et al., "Designing CD4 immunoadhesins for AIDS therapy," Nature, vol. 337, pp. 525-531, 1989.
Chiou et al., Gene Therapeutics: Methods and Applications of Direct Gene Transfer, J.A. Wolff, ed., 1994.
Chothia, C. et al., "Canonical structures for the hypervariable regions of immunoglobulins," Journal of Molecular Biology, vol. 196, Issue 4, pp. 901-917, Aug. 20, 1987.
Chothia, C. et al., "Conformations of immunoglobulin hypervariable regions," Nature, vol. 342, pp. 877-883, Dec. 1989.
Connelly, "In Vivo Gene Delivery and Expression of Physiological Levels of Functional Human Factor VIII in Mice" Human Gene Therapy, 1995, 1:185.
Curiel, "High-Efficiency Gene Transfer Mediated by Adenovirus Coupled to DNA-Polylysine Complexes" Hum. Gene Ther., 1992, 3 (2):pp. 147-154.
Dayhoff, M.O. (ed.) Atlas of Protein Sequence and Structure, National Biomedical Research Foundation, Washington DC vol. 5, Suppl. 3, pp. 345-358. 1978.
De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
De Haas et al., "Fc gamma receptors of phagocytes", Journal of Laboratory and Clinical Medicine, 126(4): dated Oct. 1995, pp. 330-341.
Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Findeis et al., "Targeted delivery of DNA for gene therapy via receptors" Trends Biotechnol., 1993, 11: pp. 202-205.
Friedman, D.S. et al., "Prevalence of age-related macular degeneration in the United States," Arch. Ophthalmol., vol. 122, No. 4, pp. 564-572, Apr. 2004.
Greene T.W. et al., "Protective Groups in Organic Synthesis," 3rd Edition, John Wiley and Sons, Inc., New York, 1999.

Guyer et al., "Immunoglobulin Binding by Mouse Intestinal Epithelial Cell Receptors", The Journal of Immunology, 117(2): dated Aug. 1, 1976, pp. 587-893.
Klein R, Klein BE, Jensen SC, Meuer SM. 1997. The five-year incidence and progression of age-related maculopathy: The Beaver Dam Eye Study. Ophthal. 104:7-21.
Hein J., Unified Approach to Alignment and Phylogenies pp. 626-645 Methods in Enzymology vol. 183, Academic Press, Inc., San Diego, CA. 1990.
Higgins, D.G. and Sharp, P.M., "Fast and sensitive multiple sequence alignments on a microcomputer" CABIOS 5: dated 1989, pp. 151-153.
Hinton et al., "Engineered human IgG antibodies with longer serum half-lives in primates", Journal of Biological Chemistry, 279(8): dated Feb. 20, 2004 in 5 pages.
Hsu et al., "Differential N-Glycan Patterns of Secreted and Intracellular IgG Produced in Trichoplusia ni Cells" Journey of Biol. Chem. vol. 272: dated 1997, pp. 9062-9070.
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Hwang et al., "Hepatic uptake and degradation of unilamellar sphingomyelin/cholesterol liposomes: a kinetic study", Proceedings of the National Academy of Sciences of the United States of America, 77(7): dated Jul. 1980, pp. 4030-4034.
Iwahashi et al.,"CDR substitutions of a humanized monoclonal antibody (CC49): contributions of individual CDRs to antigen binding and immunogenicity," Mol. Immunol. 36: Issue 15-16, 1079-1091, 1999.
Jaffe, G. et al., "Intraocular drug delivery," CRC Press, Mar. 2006.
Jefferis et al., "Glycosylation of Antibody Molecules: Structural and Functional Significance", Antibody Engineering, vol. 65: dated 1997, pp. 111-128.
Johnson et al., "Kabat Database and its applications: 30 years after the first variability plot", Nucleic Acids Research, 28(1): Jan. 1, 2000, pp. 214-218.
Kabat, E.A. et al., "Sequences of proteins of immunological interest," in 10 pages, 1991 (includes title page and table of contents only).
Kaplitt, "Long-term gene expression and phenotypic correction using adeno-associated virus vectors in the mammalian brain" Nature Genetics, 1994, 8:148.
Kimura, "Retroviral Delivery of DNA into the Livers of Transgenic Mice Bearing Premalignant and Malignant Hepatocellular Carcinomas" Human Gene Therapy, 1994, 5(7): pp. 845-852.
Kim et al., "Identifying amino acid residues that influence plasma clearance of murine IgG1 fragments by site-directed mutagenesis", European Journal of Immunology, 24(3): dated Mar. 1994.
Kohler et al, "Continuous cultures of fused cells secreting antibody of predefined specificity", Nature, vol. 256: dated 1975, pp. 495-497.
Kunik et al., "Paratome: an online tool for systematic indentification of antigen-binding regions in antibodies based on sequence or structure", Nucleic Acids Research, vol. 40: Jun. 6, 2012, W521-524.
Lazar et al., "Engineered antibody Fc variants with enhanced effector function", Proc Natl Acad Sci U S A, 103(11): dated Mar. 14, 2006 in 6 pages.
Lefranc et al., "IMGT unique numbering for immunoglobulin and T cell receptor variable domains and Ig superfamily V-like domains", Developmental and Comparative Immunology, vol. 27: dated 2003, pp. 55-77.
MacCallum, R. et al., Antibody-Antigen Interactions: Contact Analysis and Binding Site Toopgraphy, J/. Mol Biol., vol. 262, pp. 732-745, (1996).
Makabe et al., "Thermodynamic Consequences of Mutations in Vernier Zone Residues of a Humanized Anti-human Epidermal Growth Factor Receptor Murine Antibody, 528", Journal of Biological Chemistry, vol. 283: dated Jan. 11, 2008, pp. 1156-1166.
Martin et al., "Modeling antibody hypervariable loops: A combined algorithm", Proc. Natl. Acad. Sci. USA, vol. 86: dated Dec. 1989, pp. 9268-9272.

(56) References Cited

OTHER PUBLICATIONS

McCafferty et al., "Phage antibodies: filamentous phage displaying antibody variable domains", Nature, vol. 348: dated 1990, pp. 552-554.
McPherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
Neuberger, M., "Generating high-avidity human Mabs in mice," Nature Biotechnology, vol. 14, pp. 826, 1996.
Östberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Philip, "Efficient and sustained gene expression in primary T lymphocytes and primary and cultured tumor cells mediated by adeno-associated virus plasmid DNA complexed to cationic liposomes." Mol. Cell Biol., 1994, 14(4): pp. 2411-2418.
Ravetch et al., "FC Receptors," 1991, Ann. Rev. Immunol., vol. 9:457-92.
Robinson, D.F, "Comparison of Labeled Trees with Valency Three," Journal of Combinational Theory 11: pp. 105-119 (1997).
Samudrala et al., "Ab initio protein structure prediction using a combined hierarchical approach", Proteins, Structure, and Genetics Suppl, 37(S3): dated 1999, pp. 194-198.
Saitou, N., Nei, M., "The neighbor-joining method: a new method for reconstructing phylogenetic trees." Mol. Biol. Evol. vol. 4: dated 1987, pp. 406-425.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tonkinson, J. et al., "New Drugs: Antisense Oligodeoxynucleotides as Clinical Therapeutic Agents," Cancer Investigation, vol. 14, No. 1, pp. 54-65, 1996.
Umana et al., "Engineered glycoforms of an antineuroblastoma IgG1 with optimized antibody-dependent cellular cytotoxic activity." 1999, Nature Biotech. 17:176-180.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wilbur, W.J. and Lipman, D.J., "Rapid similarity searches of nucleic acid and protein data banks" 1983, Proc. Natl. Acad. Sci. USA 80: pp. 726-730.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Woffendin, "Nonviral and viral delivery of a human immunodeficiency virus protective gene into primary human T cells" Proc. Natl. Acad. Sci., 1994, 91: pp. 11581-11585.
Wright et al., "Effect of glycosylation on antibody function: implications for genetic engineering", Trends Biotechnol, 15(1): dated Jan. 1997, pp. 26-32.
Wu et al., "Receptor-mediated Gene Delivery and Expression in Viuo" J. Biol. Chem., 1988, 263(29): pp. 14621-14624.

Wu et al., "Receptor-mediated Gene Delivery in Vivo" J. Biol. Chem., 1991, 266.
Wu, G.Y. et al., "Receptor-mediated in vitro gene transformation by a soluble DNA carrier system," Journal of Biological Chemistry, vol. 262, pp. 4429-4432, Apr. 5, 1987.
Wu et al., "Incorporation of Adenovirus into a Ligand-based DNA Carrier System Results in Retention of Original Receptor Specificity and Enhances Targeted Gene Expression" J. Biol. Chem., 1994, 269 (15): pp. 11542-11546.
Wu, "Targeting Genes: Delivery and Persistent Expression of a Foreign Gene Driven by Mammalian Regulatory Elements in Vivo" J. Biol. Chem., 1989, 264(29):16985-19687.
Wyss et al., "Current Opinion in Biotechnology," vol. 7 (4): pp. 409-146, 1996.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Zenke et al., "Receptor-mediated endocytosis of transferrin-polycation conjugates: an efficient way to introduce DNA into hematopoietic cells." Proc. Natl. Acad. Sci. USA, 1990, 87(10):3655-3659.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 16/424,265, filed Aug. 11, 2014.
File History of U.S. Appl. No. 12/281,071, filed Aug. 28, 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 15/368,376, filed Dec. 2, 2016.
File History of U.S. Appl. No. 13/641,342, filed Dec. 2, 2016.
File History of U.S. Appl. No. 16/781,869, filed Mar. 2, 2016.
File History of U.S. Appl. No. 16/779,102, filed Mar. 2, 2016.
File History of U.S. Appl. No. 16/795,450, filed Jun. 29, 2015.
File History of U.S. Appl. No. 15/820,325, filed Nov. 21, 2017.
File History of U.S. Appl. No. 14/932,913, filed Nov. 4, 2015.
File History of U.S. Appl. No. 16/402,602, filed Nov. 4, 2015.
File History of U.S. Appl. No. 16/290,128, filed Mar. 1, 2019.
Examination Report dated Feb. 22, 2021 in Australian Application No. 2018250695 in 4 pages.
Extended European Search Report dated Jan. 21, 2021 in EP Application No. 18784891.6 in 15 pages.
Joralemon et al., PEGylated Polymers for Medicine From Conjugation to Self-Assembled Systems, Chemical Communications, vol. 46, No. 9, pp. 1377, 2010.
RecName: Full=Complement factor D; EC=3.4.21.46; AltName: Full=Adipsin; AltName: Full=C3 convertase activator; AltName: Full=Properdin factor D; Flags: Precursor, UNIPROT, Jul. 21, 1986 (Jul. 21, 1986), XP002614847, [retrieved on Jul. 21, 1986].
U.S. Appl. No. 09/253,689, filed Feb. 20, 1999, Fung et al.
Invitation to Pay Additional Fees for PCT/US2018/027378 mailed Aug. 1, 2018.
International Preliminary Report on Patentability for PCT/US2018/027378 dated Oct. 24, 2019.
File History of U.S. Appl. No. 14/916,180, filed Mar. 2, 2016.
Office Action dated Jul. 29, 2019, U.S. Appl. No. 15/820,325.
Office Action dated Sep. 30, 2020 in Canadian Application No. 3,059,938.
Katschke, K. et al., "Inhibiting Alternative Pathway Complement Activation by Targeting the Factor D Exosite—Supplementary Material", The Journal of Biological Chemistry, Apr. 2012, vol. 287, No. 16, in 11 pages.
Kim, J.K. et al., "Localization of the site of the murine IgG1 molecule that is involved in binding to the murine intestinal Fc receptor", European Journal of Immunology, Oct. 1994, vol. 24(10), pp. 2429-2434.
Office Action for Australian Application No. AU 2018250695 in 5 pages, dated Nov. 19, 2021.

(56) References Cited

OTHER PUBLICATIONS

Office Action for Canadian Application No. CA 3,059,938 in 4 pages, dated Sep. 27, 2021.
Office Action for Australian Application No. AU 2018250695 in 5 pages, dated Feb. 9, 2022.
Office Action for Canadian Application No. CA 3,059,938 in 4 pages, dated Aug. 12, 2022.
Office Action for European Application No. EP 18784891.6 in 6 pages, dated Jan. 2, 2023.

\* cited by examiner

FIG. 1

ILGGREAEAHARPYMASVQLNGAHLCGGVLVAEQWVLSAAHCLEDAADGKVQVLLGAHS
LSQPEPSKRLYDVLRAVPHPDSQPDTIDHDLLLLQLSEKATLGPAVRPLPWQRVDRDVAP
GTLCDVAGWGIVNHAGRRPDSLQHVLLPVLDRATCNRRTHHDGAITERLMCAESNRRDS
CKGDSGGPLVCGGVLEGVVTSGSRVCGNRKKPGIYTRVASYAAWIDSVLA (SEQ ID NO: 1)

COMPOUND L

COMPOUND K

FIG. 2C
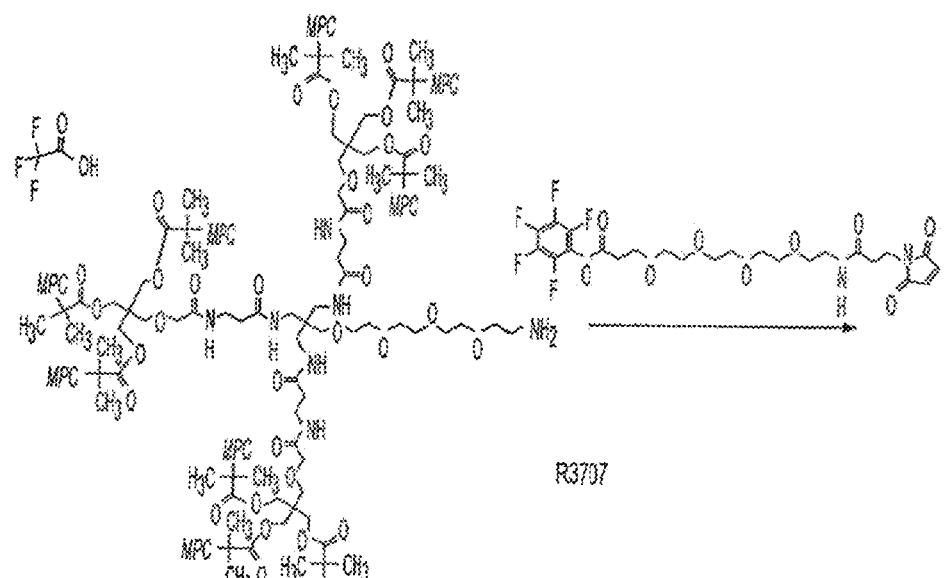
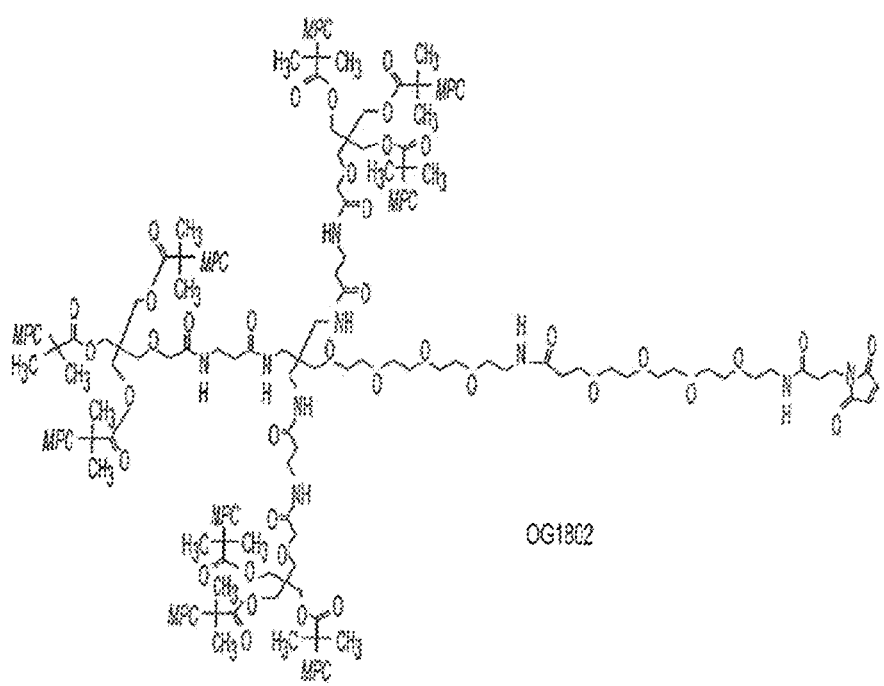

FIG. 2H
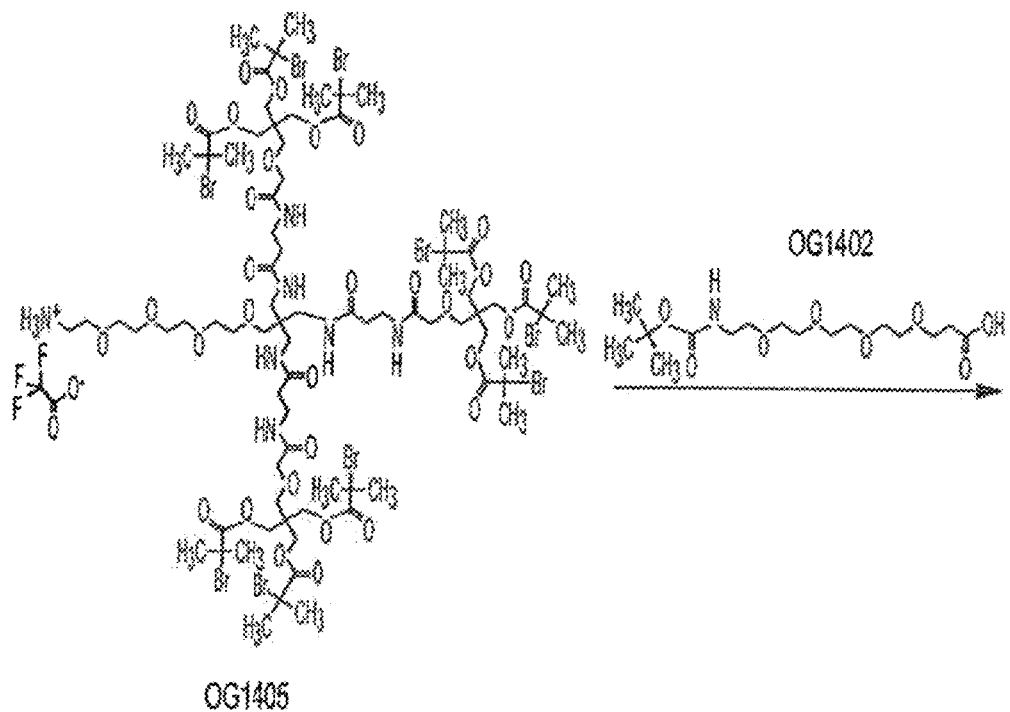
OG1402
OG1405
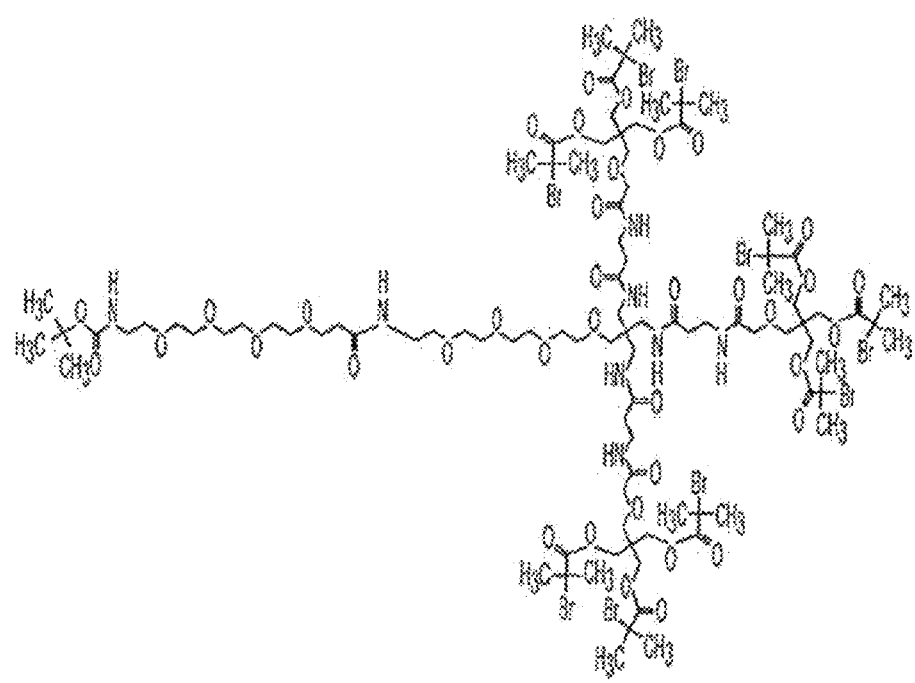

FIG. 2J
OG1801
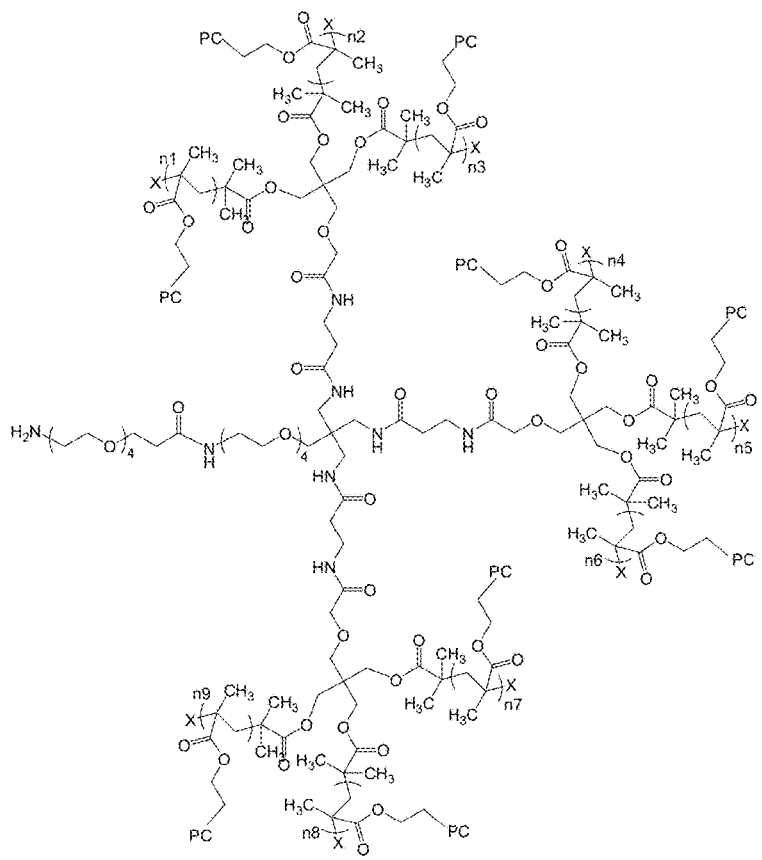
PC =
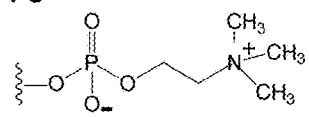
X=a) OR where R=H, methyl, ethyl, propyl, isopropyl, b) H, or c) any halide, including Br
n1, n2, n3, n4, n5, n6, n7, n8 and n9 are the same or different such that the sum of n1, n2, n3, n4, n5, n6, n6, n7, n8 and n9 is 2500 plus or minus 15%.

FIG. 2K
OG1802
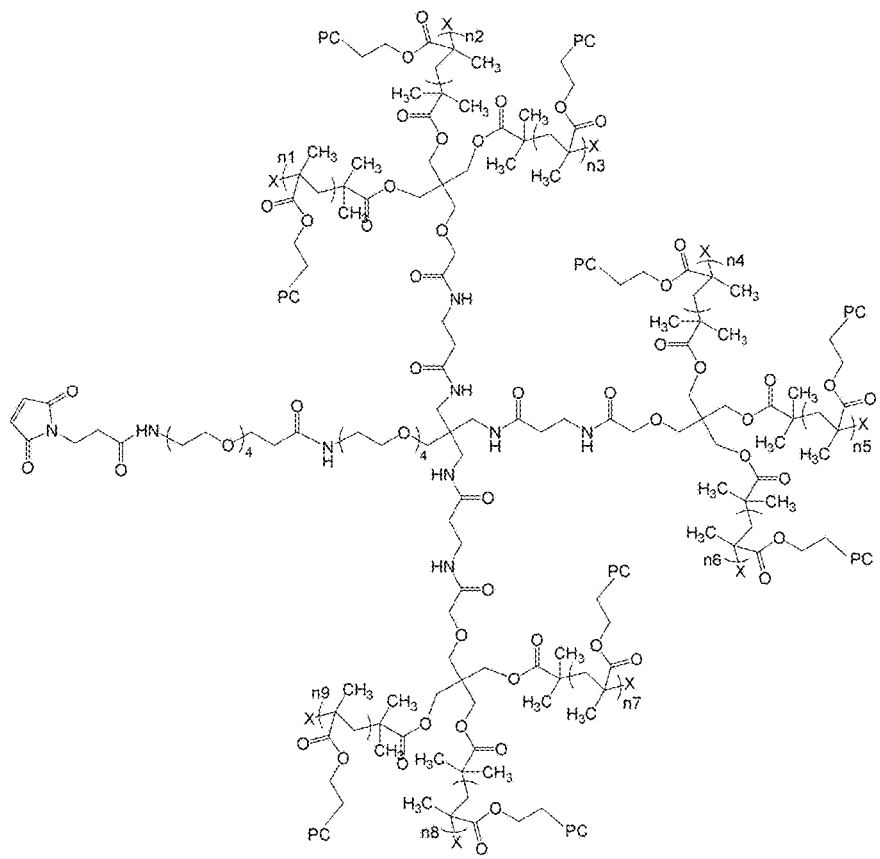
Definitions:
PC =
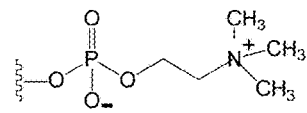
X=a) OR where R=H, methyl, ethyl, propyl, isopropyl, b) H, or c) any halide, including Br
n1, n2, n3, n4, n5, n6, n7, n8 and n9 are the same or different such that the sum of n1, n2, n3, n4, n5, n6, n6, n7, n8 and n9 is 2500 plus or minus 15%.

COMPOUND E

34I54I59D84S/54R101V

Single cycle kinetics of 34I54I59D84S/54R101V on cyno Factor D on a Protein A chip FIG. 20
25 Degrees Single Cycle Kinetics on a Protein A Chip
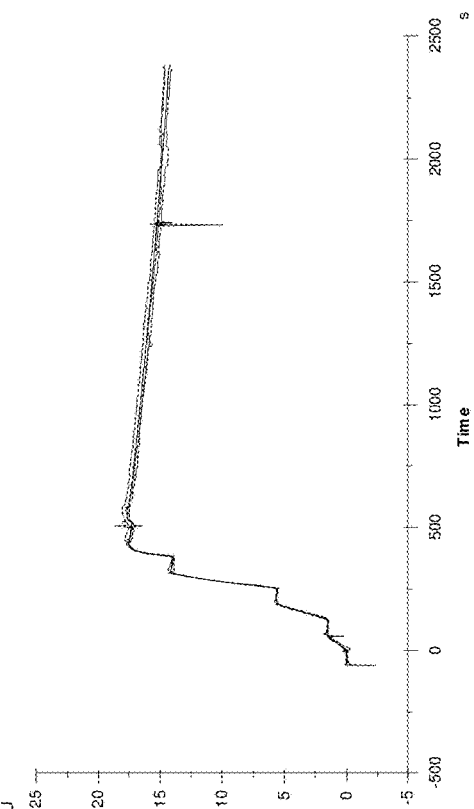
OG1965
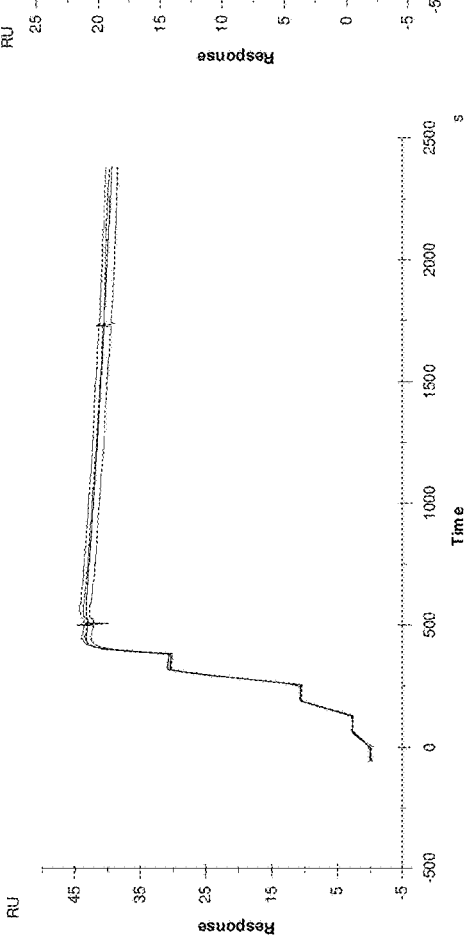
OG1970
Kinetic Exclusion Assay data at 37 degrees and Biacore data at 25 degrees
| Molecule | Platform (°C) | $K_{on}$ (M) | $K_{off}$ (M) | $K_D$ (pM) |
|---|---|---|---|---|
| OG1965 | Biacore (25°) | $2.52 \times 10^7$ | $6.30 \times 10^{-5}$ | 2.50 |
| | KinExA (37°) | $3.06 \times 10^7$ | $1.79 \times 10^{-4}$ | 5.86 |
| OG1970 | Biacore (25°) | $2.16 \times 10^7$ | $1.33 \times 10^{-4}$ | 6.14 |
| | KinExA (37°) | $3.67 \times 10^7$ | $2.96 \times 10^{-4}$ | 8.07 |

Factor B Cleavage Assay ELISA

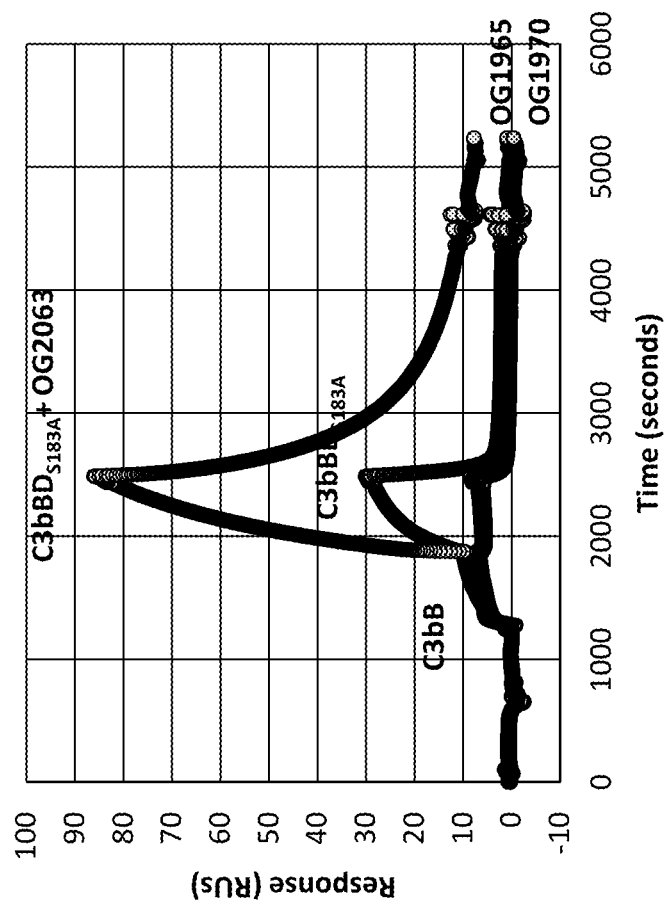

SEQUENCE LISTING

```
<160> NUMBER OF SEQ ID NOS: 590

<210> SEQ ID NO 1
<211> LENGTH: 228
<212> TYPE: PRT
<213> ORGANISM: Artificial Sequence
<220> FEATURE:
<223> OTHER INFORMATION: Mature form of human complement factor D

<400> SEQUENCE: 1

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
            20                  25                  30
```

```
Glu Gln Trp Val Leu Ser Ala Ala His Cys Leu Glu Asp Ala Ala Asp
            35                  40                  45

Gly Lys Val Gln Val Leu Leu Gly Ala His Ser Leu Ser Gln Pro Glu
 50                  55                  60

Pro Ser Lys Arg Leu Tyr Asp Val Leu Arg Ala Val Pro His Pro Asp
 65                  70                  75                  80

Ser Gln Pro Asp Thr Ile Asp His Asp Leu Leu Leu Gln Leu Ser
                 85                  90                  95

Glu Lys Ala Thr Leu Gly Pro Ala Val Arg Pro Leu Pro Trp Gln Arg
                100                 105                 110

Val Asp Arg Asp Val Ala Pro Gly Thr Leu Cys Asp Val Ala Gly Trp
            115                 120                 125

Gly Ile Val Asn His Ala Gly Arg Arg Pro Asp Ser Leu Gln His Val
130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
                195                 200                 205

Lys Pro Gly Ile Tyr Thr Arg Val Ala Ser Tyr Ala Ala Trp Ile Asp
            210                 215                 220

Ser Val Leu Ala
225

<210> SEQ ID NO 2
<211> LENGTH: 120
<212> TYPE: PRT
<213> ORGANISM: Artificial Sequence
<220> FEATURE:
<223> OTHER INFORMATION: mAb KCD002 heavy chain

<400> SEQUENCE: 2

Glu Val Lys Leu Val Glu Ser Gly Gly Leu Val Gln Pro Gly Ser
 1               5                  10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
         35                  40                  45

Gly Asn Ile Asn Tyr Asp Gly Ser Ser Thr Tyr Tyr Leu Asp Ser Leu
 50                  55                  60

Lys Ser Arg Phe Ile Ile Ser Arg Asp Ser Ala Lys Asn Ile Leu Tyr
 65                  70                  75                  80

Leu Gln Met Ser Ser Leu Lys Ser Glu Asp Thr Ala Thr Tyr Phe Cys
                85                  90                  95

Ala Arg Gly Glu Asp Phe Tyr Leu Tyr Ala Met Asp Tyr Trp Gly Gln
            100                 105                 110

Gly Thr Ser Val Thr Val Ser Ser
        115                 120

<210> SEQ ID NO 3

<400> SEQUENCE: 3
```

```
<210> SEQ ID NO 4
<211> LENGTH: 107
<212> TYPE: PRT
<213> ORGANISM: Artificial Sequence
<220> FEATURE:
<223> OTHER INFORMATION: mAb KCD002 light chain

<400> SEQUENCE: 4

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile His Ser Tyr
            20                  25                  30

Leu Ala Trp Tyr Gln Gln Lys Gln Gly Lys Ser Pro Gln Leu Ile Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Pro
                85                  90                  95

Thr Phe Gly Gly Gly Thr Lys Leu Glu Ile Lys
            100                 105

<210> SEQ ID NO 5
<211> LENGTH: 116
<212> TYPE: PRT
<213> ORGANISM: Artificial Sequence
<220> FEATURE:
<223> OTHER INFORMATION: mAb KCD003 heavy chain

<400> SEQUENCE: 5

Glu Val Gln Leu Gln Gln Ser Arg Pro Glu Leu Val Lys Pro Gly Ala
1               5                   10                  15

Ser Val Lys Ile Phe Cys Lys Ala Ser Gly Tyr Thr Phe Thr Asp Tyr
            20                  25                  30

Tyr Met Asn Trp Met Arg Gln Arg His Gly Thr Leu Glu Trp Ile
        35                  40                  45

Gly Asp Ile Asn Pro Asn Asn Gly Asp Pro Ser Tyr Asn Gln Lys Phe
    50                  55                  60

Lys Asp Lys Ala Thr Leu Thr Val Asp Lys Ser Ser Ser Thr Ala Ser
65                  70                  75                  80

Met Glu Leu Arg Ser Leu Thr Ser Asp Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 6
<211> LENGTH: 112
<212> TYPE: PRT
<213> ORGANISM: Artificial Sequence
<220> FEATURE:
<223> OTHER INFORMATION: mAb KCD003 light chain

<400> SEQUENCE: 6

Asp Val Leu Met Thr Gln Thr Pro Leu Ser Leu Pro Val Ser Leu Gly
1               5                   10                  15
```

Glu Gln Ala Ser Ile Ser Cys Arg Ser Gln Thr Ile Val His Ser
                20                  25                  30

Asn Gly Asp Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 7
<211> LENGTH: 116
<212> TYPE: PRT
<213> ORGANISM: Artificial Sequence
<220> FEATURE:
<223> OTHER INFORMATION: mAb KCD005 heavy chain

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Cys Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Gly Asp Ser Ala Val Tyr Tyr Cys
                85                  90                  95

Thr Arg Glu Gly Ala Ser Phe Ala Phe Trp Gly Gln Gly Thr Leu Val
            100                 105                 110

Thr Val Ser Ala
    115

<210> SEQ ID NO 8
<211> LENGTH: 112
<212> TYPE: PRT
<213> ORGANISM: Artificial Sequence
<220> FEATURE:
<223> OTHER INFORMATION: mAb KCD005 light chain

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
                20                  25                  30

Asn Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly

```
                    85                  90                  95

Ser His Val Pro Val Thr Phe Gly Ala Gly Thr Lys Leu Glu Leu Lys
            100                 105                 110
```

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 116
<212> TYPE: PRT
<213> ORGANISM: Artificial Sequence
<220> FEATURE:
<223> OTHER INFORMATION: mAb KCD009 heavy chain

<400> SEQUENCE: 15

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Arg Asn Tyr
            20                  25                  30

Gly Met Asn Trp Val Lys Gln Gly Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Val Arg Asp Gly Pro Gly Phe Ala Tyr Trp Gly Gln Gly Thr Leu Val
            100                 105                 110

Thr Val Ser Ala
```

```
                                115

<210> SEQ ID NO 16
<211> LENGTH: 112
<212> TYPE: PRT
<213> ORGANISM: Artificial Sequence
<220> FEATURE:
<223> OTHER INFORMATION: mAb KCD009 light chain

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Leu Ile Ile Glu His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Gly
                85                  90                  95

Ser His Val Pro Val Thr Phe Gly Ala Gly Thr Asn Leu Glu Leu Lys
            100                 105                 110

<210> SEQ ID NO 17
<211> LENGTH: 114
<212> TYPE: PRT
<213> ORGANISM: Artificial Sequence
<220> FEATURE:
<223> OTHER INFORMATION: mAb KCD010 heavy chain

<400> SEQUENCE: 17

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asp Met Asp Trp Val Lys Gln Ser His Gly Lys Ser Leu Glu Trp Ile
        35                  40                  45

Gly His Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Gly Thr Gly Asp Phe Ala Tyr Trp Gly His Gly Thr Leu Val Thr Val
            100                 105                 110

Ser Ala

<210> SEQ ID NO 18
<211> LENGTH: 108
<212> TYPE: PRT
<213> ORGANISM: Artificial Sequence
<220> FEATURE:
<223> OTHER INFORMATION: mAb KCD010 light chain

<400> SEQUENCE: 18

Gln Ile Val Leu Thr Gln Ser Pro Ala Ile Met Ser Val Ser Pro Gly
1               5                   10                  15
```

Glu Lys Val Thr Leu Thr Cys Ser Ala Ser Ser Ser Val Ser Ser
            20                  25                  30

Tyr Leu Tyr Trp Tyr Gln Lys Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Ala Gly Thr Lys Leu Glu Leu Lys
            100                 105

<210> SEQ ID NO 19
<211> LENGTH: 114
<212> TYPE: PRT
<213> ORGANISM: Artificial Sequence
<220> FEATURE:
<223> OTHER INFORMATION: mAb KCD023 heavy chain

<400> SEQUENCE: 19

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Ile Asp Trp Val Lys Gln Ser His Gly Lys Ser Leu Glu Trp Ile
        35                  40                  45

Gly Asp Ile Asn Pro Asn Asn Gly Gly Ile Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Gly Thr Gly Asp Tyr Ala Tyr Trp Gly Gln Gly Thr Leu Val Thr Val
            100                 105                 110

Ser Ala

<210> SEQ ID NO 20
<211> LENGTH: 108
<212> TYPE: PRT
<213> ORGANISM: Artificial Sequence
<220> FEATURE:
<223> OTHER INFORMATION: mAb KCD023 light chain

<400> SEQUENCE: 20

Gln Ile Val Leu Thr Gln Ser Pro Ala Phe Met Ser Ala Ser Pro Gly
1               5                   10                  15

Glu Lys Val Thr Leu Thr Cys Ser Ala Ser Ser Ser Val Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Ala Gly Thr Lys Leu Glu Leu Lys
            100                 105

<210> SEQ ID NO 21
<211> LENGTH: 118
<212> TYPE: PRT
<213> ORGANISM: Artificial Sequence
<220> FEATURE:
<223> OTHER INFORMATION: mAb KCD036 heavy chain

<400> SEQUENCE: 21

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Thr Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Lys Phe
    50                  55                  60

Lys Gly Lys Ala Thr Phe Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg His Tyr Gly Ser Ser Trp Asp Tyr Trp Gly Gln Gly Thr
            100                 105                 110

Thr Leu Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: mAb KCD036 light chain

<400> SEQUENCE: 22

Asp Ile Lys Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Glu Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 23
<211> LENGTH: 113
<212> TYPE: PRT
<213> ORGANISM: Artificial Sequence
<220> FEATURE:
<223> OTHER INFORMATION: mAb KCD040 heavy chain

<400> SEQUENCE: 23

Glu Val Gln Leu Gln Gln Ser Gly Ala Glu Leu Val Lys Pro Gly Ala

-continued

```
                1               5                  10                 15
Ser Val Lys Leu Ser Cys Thr Ala Ser Asp Phe Asn Ile Lys Asp Thr
                20                 25                 30

Tyr Met His Trp Val Met Gln Arg Pro Glu Gln Gly Leu Glu Trp Ile
        35                 40                 45

Gly Lys Ile Asp Pro Ala Asn Gly Asn Thr Glu Phe Asp Pro Lys Phe
    50                 55                 60

Gln Gly Lys Ala Thr Ile Thr Ala Asp Thr Ser Ser Asn Thr Ala Tyr
65                 70                 75                 80

Leu Gln Leu Thr Ser Leu Thr Ser Glu Asp Thr Ala Val Tyr Tyr Cys
                85                 90                 95

Thr Arg Ala Met Asp Tyr Trp Gly Gln Gly Thr Ser Val Thr Val Ser
            100                105                110

Ser

<210> SEQ ID NO 24
<211> LENGTH: 106
<212> TYPE: PRT
<213> ORGANISM: Artificial Sequence
<220> FEATURE:
<223> OTHER INFORMATION: mAb KCD040 light chain

<400> SEQUENCE: 24

Gln Ile Val Leu Thr Gln Ser Pro Ala Ile Met Ser Ala Ser Pro Gly
1               5                  10                 15

Glu Lys Val Thr Met Thr Cys Ser Ala Gly Ser Ser Val Ser Tyr Met
                20                 25                 30

Tyr Trp Tyr Gln Gln Lys Pro Gly Ser Ser Pro Arg Val Leu Ile Tyr
            35                 40                 45

Asp Thr Ser Asn Leu Ala Ser Gly Val Pro Val Arg Phe Ser Gly Ser
        50                 55                 60

Gly Ser Gly Thr Ser Tyr Ser Leu Thr Ile Ser Arg Met Glu Ala Glu
65                 70                 75                 80

Asp Ala Ala Thr Tyr Tyr Cys Gln Gln Trp Ser Asn Tyr Pro Tyr Thr
                85                 90                 95

Phe Gly Gly Gly Thr Lys Leu Glu Ile Lys
            100                105

<210> SEQ ID NO 25
<211> LENGTH: 113
<212> TYPE: PRT
<213> ORGANISM: Artificial Sequence
<220> FEATURE:
<223> OTHER INFORMATION: mAb KCD042 heavy chain

<400> SEQUENCE: 25

Glu Val Gln Leu Gln Gln Ser Gly Ala Glu Leu Val Lys Pro Gly Ala
1               5                  10                 15

Ser Val Arg Leu Ser Cys Thr Ala Ser Gly Phe Asn Ile Lys His Thr
                20                 25                 30

Tyr Ile His Trp Val Ser Gln Arg Pro Glu Gln Gly Leu Glu Trp Ile
            35                 40                 45

Gly Lys Ile Asp Pro Ala Asn Gly Asn Thr Lys Tyr Asp Pro Lys Phe
        50                 55                 60

Gln Gly Lys Ala Thr Ile Thr Ala Asp Thr Ser Ser Asn Thr Ala Tyr
65                 70                 75                 80

Leu Gln Leu Ser Ser Leu Thr Ser Glu Asp Thr Ala Val Tyr Tyr Cys
```

85                  90                  95

Val Asn Ala Met Glu Tyr Trp Gly Gln Gly Thr Ser Val Thr Val Ser
               100                 105                 110

Ser

<210> SEQ ID NO 26
<211> LENGTH: 106
<212> TYPE: PRT
<213> ORGANISM: Artificial Sequence
<220> FEATURE:
<223> OTHER INFORMATION: mAb KCD042 light chain

<400> SEQUENCE: 26

Gln Ser Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Asp Met
                20                  25                  30

Tyr Trp Phe Gln Gln Arg Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Trp Thr
                85                  90                  95

Phe Gly Gly Gly Thr Lys Leu Glu Ile Lys
               100                 105

<210> SEQ ID NO 27
<211> LENGTH: 113
<212> TYPE: PRT
<213> ORGANISM: Artificial Sequence
<220> FEATURE:
<223> OTHER INFORMATION: mAb KCD044 heavy chain

<400> SEQUENCE: 27

Glu Val Gln Leu Gln Gln Ser Gly Ala Glu Leu Val Lys Pro Gly Ala
1               5                   10                  15

Ser Val Arg Leu Ser Cys Thr Ala Ser Gly Phe Asn Ile Lys His Thr
                20                  25                  30

Tyr Met His Trp Val Ser Gln Arg Pro Glu Arg Gly Leu Glu Trp Ile
            35                  40                  45

Gly Lys Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Leu Asn Ala Met Glu Tyr Trp Gly Gln Gly Thr Ser Val Thr Val Ser
               100                 105                 110

Ser

<210> SEQ ID NO 28
<211> LENGTH: 106
<212> TYPE: PRT
<213> ORGANISM: Artificial Sequence
<220> FEATURE:
<223> OTHER INFORMATION: mAb KCD044 light chain

<400> SEQUENCE: 28

Gln Ser Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Asp Met
            20                  25                  30

Tyr Trp Tyr Gln Gln Arg Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Trp Thr
                85                  90                  95

Phe Gly Gly Gly Thr Lys Leu Glu Ile Lys
            100                 105

<210> SEQ ID NO 29
<211> LENGTH: 113
<212> TYPE: PRT
<213> ORGANISM: Artificial Sequence
<220> FEATURE:
<223> OTHER INFORMATION: mAb KCD047 heavy chain

<400> SEQUENCE: 29

Glu Val Gln Leu Gln Gln Ser Gly Ala Glu Phe Val Lys Pro Gly Ala
1               5                   10                  15

Ser Val Arg Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Lys Asp Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Ala Met Asp Tyr Trp Gly Gln Gly Thr Ser Val Thr Val Ser
            100                 105                 110

Ser

<210> SEQ ID NO 30
<211> LENGTH: 106
<212> TYPE: PRT
<213> ORGANISM: Artificial Sequence
<220> FEATURE:
<223> OTHER INFORMATION: mAb KCD047 light chain

<400> SEQUENCE: 30

Gln Ile Val Leu Thr Gln Ser Pro Ala Val Met Ser Ala Ser Pro Gly
1               5                   10                  15

Glu Lys Val Ala Met Thr Cys Ser Ala Ser Ser Ser Val Thr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu

```
                65                  70                  75                  80
Asp Ala Ala Thr Tyr Tyr Cys Gln Gln Trp Ser Thr Tyr Pro Phe Pro
                85                  90                  95

Phe Gly Ser Gly Thr Lys Leu Glu Ile Lys
                100                 105

<210> SEQ ID NO 31
<211> LENGTH: 113
<212> TYPE: PRT
<213> ORGANISM: Artificial Sequence
<220> FEATURE:
<223> OTHER INFORMATION: mAb KCD048 heavy chain

<400> SEQUENCE: 31

Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Ala Thr
                20                  25                  30

Tyr Met His Trp Val Arg Gln Arg Pro Glu Lys Gly Leu Glu Trp Ile
            35                  40                  45

Gly Arg Ile Asp Pro Ala Asn Gly His Thr Ile Tyr Asp Pro Gln Phe
        50                  55                  60

Gln Gly Lys Ala Thr Ile Thr Ser Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Glu Ala Met Asp Tyr Trp Gly Gln Gly Thr Ser Val Thr Val Ser
                100                 105                 110

Ser

<210> SEQ ID NO 32
<211> LENGTH: 106
<212> TYPE: PRT
<213> ORGANISM: Artificial Sequence
<220> FEATURE:
<223> OTHER INFORMATION: mAb KCD048 light chain

<400> SEQUENCE: 32

Gln Ile Val Leu Thr Gln Ser Pro Ala Ile Met Ser Ala Ser Pro Gly
1               5                   10                  15

Glu Lys Val Thr Leu Thr Cys Ser Ala Thr Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Asp Ala Thr Tyr Tyr Cys Gln Gln Trp Ser Asn Tyr Pro Phe Thr
                85                  90                  95

Phe Gly Gly Gly Thr Lys Leu Glu Ile Lys
                100                 105

<210> SEQ ID NO 33
<211> LENGTH: 118
<212> TYPE: PRT
<213> ORGANISM: Artificial Sequence
<220> FEATURE:
<223> OTHER INFORMATION: mAb KCD070 heavy chain
```

<400> SEQUENCE: 33

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Ile Leu Trp Val Lys Gln Ser His Gly Lys Ser Leu Glu Trp Ile
        35                  40                  45

Gly Asn Ile Asn Pro Tyr Tyr Asp Tyr Thr Ser Tyr Asn Leu Lys Phe
50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Asp Gly Tyr Tyr Gly Gly Asp Tyr Trp Gly Gln Gly Thr
            100                 105                 110

Ser Val Thr Val Ser Ser
            115

<210> SEQ ID NO 34
<211> LENGTH: 107
<212> TYPE: PRT
<213> ORGANISM: Artificial Sequence
<220> FEATURE:
<223> OTHER INFORMATION: mAb KCD070 light chain

<400> SEQUENCE: 34

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Thr Leu Glu Ile Lys
            100                 105

<210> SEQ ID NO 35
<211> LENGTH: 118
<212> TYPE: PRT
<213> ORGANISM: Artificial Sequence
<220> FEATURE:
<223> OTHER INFORMATION: mAb KCD101 heavy chain

<400> SEQUENCE: 35

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

```
Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Gly Arg Asn Gly Tyr Asp Gly Ser Met Asp Tyr Trp Gly Gln Gly Thr
            100                 105                 110

Ser Val Thr Val Ser Ser
        115
```

<210> SEQ ID NO 36
<211> LENGTH: 107
<212> TYPE: PRT
<213> ORGANISM: Artificial Sequence
<220> FEATURE:
<223> OTHER INFORMATION: mAb KCD101 light chain

<400> SEQUENCE: 36

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Pro Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Tyr
                 85                  90                  95

Thr Phe Gly Gly Gly Thr Lys Leu Glu Ile Lys
            100                 105
```

<210> SEQ ID NO 37
<211> LENGTH: 118
<212> TYPE: PRT
<213> ORGANISM: Artificial Sequence
<220> FEATURE:
<223> OTHER INFORMATION: mAb KCD102 heavy chain

<400> SEQUENCE: 37

```
Gln Val Gln Leu Gln Gln Pro Gly Ala Glu Leu Val Arg Pro Gly Thr
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
 50                  55                  60

Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asn Gly Tyr Asp Gly Ser Met Asp Tyr Trp Gly Gln Gly Thr
            100                 105                 110

Ser Val Thr Val Ser Ser
        115
```

-continued

<210> SEQ ID NO 38
<211> LENGTH: 107
<212> TYPE: PRT
<213> ORGANISM: Artificial Sequence
<220> FEATURE:
<223> OTHER INFORMATION: mAb KCD102 light chain

<400> SEQUENCE: 38

```
Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Pro Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105
```

<210> SEQ ID NO 39
<211> LENGTH: 118
<212> TYPE: PRT
<213> ORGANISM: Artificial Sequence
<220> FEATURE:
<223> OTHER INFORMATION: mAb KCD103 heavy chain

<400> SEQUENCE: 39

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Lys Tyr Asn Gln Lys Phe
50                  55                  60

Lys Asp Lys Ala Thr Leu Thr Val Glu Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Asn Gly Tyr Asp Gly Ser Met Asp Tyr Trp Gly Gln Gly Thr
            100                 105                 110

Ser Val Thr Val Ser Ser
        115
```

<210> SEQ ID NO 40
<211> LENGTH: 107
<212> TYPE: PRT
<213> ORGANISM: Artificial Sequence
<220> FEATURE:
<223> OTHER INFORMATION: mAb KCD103 light chain

<400> SEQUENCE: 40

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Ser
            20                  25                  30
```

```
Leu Asn Trp Tyr Gln Gln Lys Pro Asp Gly Thr Val Lys Leu Leu Ile
        35                  40                  45

Tyr Tyr Thr Ser Arg Leu His Ser Arg Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Ala Asn Thr Leu Pro Tyr
                85                  90                  95

Thr Phe Gly Gly Gly Thr Lys Leu Glu Ile Lys
            100                 105

<210> SEQ ID NO 41
<211> LENGTH: 118
<212> TYPE: PRT
<213> ORGANISM: Artificial Sequence
<220> FEATURE:
<223> OTHER INFORMATION: mAb KCD104 heavy chain

<400> SEQUENCE: 41

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Tyr Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Gly Tyr Asp Gly Ala Met Asp Tyr Trp Gly Gln Gly Thr
            100                 105                 110

Ser Val Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: mAb KCD104 light chain

<400> SEQUENCE: 42

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Pro Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Tyr
                85                  90                  95

Thr Phe Gly Gly Gly Thr Lys Leu Glu Ile Lys
```

-continued

<210> SEQ ID NO 43
<211> LENGTH: 116
<212> TYPE: PRT
<213> ORGANISM: Artificial Sequence
<220> FEATURE:
<223> OTHER INFORMATION: mAb KCD118 heavy chain

<400> SEQUENCE: 43

Glu Val Gln Leu Gln Gln Ser Gly Pro Glu Leu Val Lys Pro Gly Ala
1               5                   10                  15

Ser Val Lys Ile Ser Cys Lys Ala Phe Gly Tyr Thr Phe Thr Asp Tyr
            20                  25                  30

Tyr Lys Asn Trp Met Arg Gln Arg His Gly Glu Ser Leu Glu Trp Ile
        35                  40                  45

Gly Asp Ile Asn Pro Asn Ser Gly Asp Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly His Gly Thr Leu Val
            100                 105                 110

Thr Val Ser Ala
        115

<210> SEQ ID NO 44
<211> LENGTH: 112
<212> TYPE: PRT
<213> ORGANISM: Artificial Sequence
<220> FEATURE:
<223> OTHER INFORMATION: mAb KCD118 light chain

<400> SEQUENCE: 44

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 45
<211> LENGTH: 116
<212> TYPE: PRT
<213> ORGANISM: Artificial Sequence
<220> FEATURE:
<223> OTHER INFORMATION: mAb KCD119 heavy chain

<400> SEQUENCE: 45

Glu Val Gln Leu Gln Gln Ser Gly Pro Glu Leu Val Lys Pro Gly Ala
1               5                   10                  15

-continued

Ser Val Lys Ile Ser Cys Lys Ala Ser Gly Tyr Thr Phe Thr Asp Tyr
            20                  25                  30

Tyr Thr Asn Trp Met Arg Gln Arg His Gly Glu Ser Leu Glu Trp Ile
        35                  40                  45

Gly Asp Ile Asn Pro Asn Thr Gly Asp Thr Ser Tyr Asn Gln Lys Phe
50                  55                  60

Arg Val Lys Ala Thr Leu Thr Val Asp Lys Ser Ser Gly Thr Ala Tyr
65                  70                  75                  80

Met Gly Leu Arg Ser Leu Thr Ser Glu Asp Ser Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ala
        115

<210> SEQ ID NO 46
<211> LENGTH: 112
<212> TYPE: PRT
<213> ORGANISM: Artificial Sequence
<220> FEATURE:
<223> OTHER INFORMATION: mAb KCD119 light chain

<400> SEQUENCE: 46

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Thr Leu Glu Ile Lys
            100                 105                 110

<210> SEQ ID NO 47
<211> LENGTH: 116
<212> TYPE: PRT
<213> ORGANISM: Artificial Sequence
<220> FEATURE:
<223> OTHER INFORMATION: mAb KCD121 heavy chain

<400> SEQUENCE: 47

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Lys Asn Trp Met Arg Gln Arg His Gly Glu Ser Leu Glu Trp Ile
        35                  40                  45

Gly Asp Ile Asn Pro Asn Asn Gly Asp Thr Ser Tyr Asn Gln Lys Phe
50                  55                  60

Arg Gly Lys Ala Thr Leu Thr Val Asp Lys Ser Ser Ser Thr Ala Phe
65                  70                  75                  80

Met Glu Leu Arg Ser Leu Thr Ser Glu Asp Ser Ala Val Tyr Tyr Cys 85                  90                  95
Ala Arg Glu Gly Pro Ser Phe Ala Tyr Trp Gly Gln Gly Thr Leu Val
                100                 105                 110

Thr Val Ser Ala
        115

<210> SEQ ID NO 48
<211> LENGTH: 112
<212> TYPE: PRT
<213> ORGANISM: Artificial Sequence
<220> FEATURE:
<223> OTHER INFORMATION: mAb KCD121 light chain

<400> SEQUENCE: 48

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 49
<211> LENGTH: 116
<212> TYPE: PRT
<213> ORGANISM: Artificial Sequence
<220> FEATURE:
<223> OTHER INFORMATION: mAb KCD122 heavy chain

<400> SEQUENCE: 49

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Lys Asn Trp Met Arg Gln Arg His Gly Glu Ser Leu Glu Trp Ile
        35                  40                  45

Gly Asp Ile Asn Pro Asn Asn Gly Asp Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Glu Gly Pro Ser Phe Ala Tyr Trp Gly His Gly Thr Leu Val
                100                 105                 110

Thr Val Ser Ala
        115

<210> SEQ ID NO 50
<211> LENGTH: 112
<212> TYPE: PRT
<213> ORGANISM: Artificial Sequence
<220> FEATURE:

<223> OTHER INFORMATION: mAb KCD122 light chain

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 51
<211> LENGTH: 116
<212> TYPE: PRT
<213> ORGANISM: Artificial Sequence
<220> FEATURE:
<223> OTHER INFORMATION: mAb KCD123 heavy chain

<400> SEQUENCE: 51

Glu Val His Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Phe
            20                  25                  30

Tyr Lys Asn Trp Met Arg Gln Arg His Gly Glu Ser Leu Glu Trp Ile
        35                  40                  45

Gly Asp Ile Asn Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 52
<211> LENGTH: 112
<212> TYPE: PRT
<213> ORGANISM: Artificial Sequence
<220> FEATURE:
<223> OTHER INFORMATION: mAb KCD123 light chain

<400> SEQUENCE: 52

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                     85                  90                  95

Ser His Val Pro Pro Thr Phe Gly Gly Gly Thr Lys Leu Glu Ile Lys
                    100                 105                 110

<210> SEQ ID NO 53
<211> LENGTH: 116
<212> TYPE: PRT
<213> ORGANISM: Artificial Sequence
<220> FEATURE:
<223> OTHER INFORMATION: mAb KCD124 heavy chain

<400> SEQUENCE: 53

Glu Val Gln Leu Gln Gln Ser Gly Pro Glu Leu Val Lys Pro Gly Ala
  1               5                  10                  15

Ser Val Lys Ile Ser Cys Lys Ala Ser Gly Tyr Thr Phe Thr Asp His
                 20                  25                  30

Tyr Met Asn Trp Val Lys Gln Ser His Gly Lys Ser Leu Glu Trp Ile
             35                  40                  45

Gly Asp Ile Asn Pro Asn Asn Gly Gly Thr Ser Tyr Asn Gln Lys Phe
 50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Gly Asp Ser Ala Val Tyr Tyr Cys
                 85                  90                  95

Thr Arg Glu Gly Ala Ser Phe Ala Phe Trp Gly Gln Gly Thr Leu Val
                100                 105                 110

Thr Val Ser Ala
            115

<210> SEQ ID NO 54
<211> LENGTH: 112
<212> TYPE: PRT
<213> ORGANISM: Artificial Sequence
<220> FEATURE:
<223> OTHER INFORMATION: mAb KCD124 light chain

<400> SEQUENCE: 54

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
                 20                  25                  30

Asn Gly Asp Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
                100                 105                 110

<210> SEQ ID NO 55
<211> LENGTH: 122
```

<212> TYPE: PRT
<213> ORGANISM: Artificial Sequence
<220> FEATURE:
<223> OTHER INFORMATION: mAb KCD131 heavy chain

<400> SEQUENCE: 55

Gln Val Gln Leu Gln Gln Ser Gly Pro Glu Leu Val Lys Pro Gly Ala
1               5                   10                  15

Ser Val Lys Ile Ser Cys Lys Ala Ser Ala Tyr Thr Phe Thr Asp Tyr
            20                  25                  30

Tyr Ile Asn Trp Val Lys Gln Arg Pro Gly Gln Gly Pro Glu Trp Ile
        35                  40                  45

Gly Trp Ile Phe Pro Gly Ser Asn Ser Thr Tyr Ser Asn Glu Lys Phe
    50                  55                  60

Glu Val Lys Ala Thr Leu Thr Val Asp Glu Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Leu Gly Tyr Phe Gly Ser Ser Tyr His Ala Leu Asp Tyr Trp
            100                 105                 110

Gly Gln Gly Thr Ser Val Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: mAb KCD131 light chain

<400> SEQUENCE: 56

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser His
            20                  25                  30

Leu Ala Trp Phe Gln Gln Lys Gln Gly Lys Ser Pro Arg Leu Leu Val
        35                  40                  45

Tyr Ser Ala Thr Asn Leu Pro Asp Gly Val Pro Ser Arg Phe Ser Gly
    50                  55                  60

Ser Gly Ser Gly Thr Gln Tyr Ser Leu Lys Ile Asn Ile Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105

<210> SEQ ID NO 57
<211> LENGTH: 113
<212> TYPE: PRT
<213> ORGANISM: Artificial Sequence
<220> FEATURE:
<223> OTHER INFORMATION: mAb KCD136 heavy chain

<400> SEQUENCE: 57

Glu Val Gln Leu Gln Gln Ser Val Ala Glu Leu Val Arg Pro Gly Ala
1               5                   10                  15

Ser Val Lys Leu Ser Cys Ser Ala Ser Gly Phe Asn Ile Lys Asn Thr
            20                  25                  30

Tyr Met His Trp Val Asn Gln Arg Pro Glu Gln Gly Leu Glu Trp Ile

```
                    35                  40                  45
Gly Arg Ile Asp Pro Ala Asn Gly Ile Thr Lys Tyr Ala Pro Asn Phe
 50                  55                  60

Gln Gly Lys Ala Thr Ile Thr Ala Asp Thr Ser Ser Asn Thr Ala Tyr
 65                  70                  75                  80

Leu Gln Leu Ser Asn Leu Thr Ser Glu Asp Thr Ala Ile Tyr Tyr Cys
                 85                  90                  95

Thr Arg Ala Met Asp Tyr Trp Gly Gln Gly Thr Ser Val Thr Val Ser
            100                 105                 110

Ser

<210> SEQ ID NO 58
<211> LENGTH: 106
<212> TYPE: PRT
<213> ORGANISM: Artificial Sequence
<220> FEATURE:
<223> OTHER INFORMATION: mAb KCD136 light chain

<400> SEQUENCE: 58

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
             35                  40                  45

Asp Ile Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Asp Thr Tyr Pro Trp Thr
                 85                  90                  95

Phe Gly Gly Gly Thr Lys Leu Glu Ile Lys
            100                 105

<210> SEQ ID NO 59
<211> LENGTH: 116
<212> TYPE: PRT
<213> ORGANISM: Artificial Sequence
<220> FEATURE:
<223> OTHER INFORMATION: mAb KCD200 heavy chain

<400> SEQUENCE: 59

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Ser Tyr
                20                  25                  30

Tyr Lys Asn Trp Met Arg Gln Arg His Gly Glu Ser Leu Glu Trp Ile
             35                  40                  45

Gly Asp Ile Asn Pro Asn Ser Gly Asp Thr Ala Tyr Asn Gln Lys Phe
 50                  55                  60

Lys Gly Lys Ala Thr Leu Thr Val Asp Arg Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Gly Pro Ser Phe Ala Tyr Trp Gly Gln Gly Thr Leu Val
            100                 105                 110

Thr Val Ser Ala
```

<210> SEQ ID NO 60
<211> LENGTH: 112
<212> TYPE: PRT
<213> ORGANISM: Artificial Sequence
<220> FEATURE:
<223> OTHER INFORMATION: mAb KCD200 light chain

<400> SEQUENCE: 60

Asp Val Leu Met Thr Gln Thr Pro Leu Ser Leu Pro Val Ser Leu Gly
1               5                   10                  15

Asp Gln Val Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 61
<211> LENGTH: 115
<212> TYPE: PRT
<213> ORGANISM: Artificial Sequence
<220> FEATURE:
<223> OTHER INFORMATION: mAb KCD208 heavy chain

<400> SEQUENCE: 61

Glu Val Gln Leu Gln Gln Ser Val Ala Glu Leu Val Arg Pro Gly Ala
1               5                   10                  15

Ser Val Lys Leu Ser Cys Thr Val Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Thr Tyr Ala Pro Lys Phe
    50                  55                  60

Gln Gly Lys Ala Thr Ile Thr Ala Asp Thr Ser Ser Asn Ser Ala Tyr
65                  70                  75                  80

Leu His Leu Ser Arg Leu Thr Ser Glu Asp Thr Ala Ile Tyr Tyr Cys
                85                  90                  95

Ser Leu Tyr Asp Tyr Asp Gly Tyr Trp Gly Gln Gly Thr Thr Leu Thr
            100                 105                 110

Val Ser Ser
        115

<210> SEQ ID NO 62
<211> LENGTH: 108
<212> TYPE: PRT
<213> ORGANISM: Artificial Sequence
<220> FEATURE:
<223> OTHER INFORMATION: mAb KCD208 light chain

<400> SEQUENCE: 62

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser
                    20                  25                  30

Ser Leu His Trp Tyr Arg Gln Lys Ser Gly Thr Ser Pro Lys Pro Trp
            35                  40                  45

Ile Tyr Gly Thr Ser His Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Asp Thr Tyr Pro
                85                  90                  95

Trp Thr Phe Gly Gly Gly Thr Lys Leu Glu Ile Lys
            100                 105

<210> SEQ ID NO 63
<211> LENGTH: 115
<212> TYPE: PRT
<213> ORGANISM: Artificial Sequence
<220> FEATURE:
<223> OTHER INFORMATION: mAb KCD214 heavy chain

<400> SEQUENCE: 63

Glu Val Gln Leu Gln Gln Ser Val Ala Glu Phe Val Arg Pro Gly Ala
1               5                   10                  15

Ser Val Lys Leu Ser Cys Thr Ala Ser Gly Phe Asn Ile Lys Asn Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Glu Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Leu Tyr Asp Tyr Asp Gly Tyr Trp Gly Gln Gly Thr Thr Leu Thr
                100                 105                 110

Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: mAb KCD214 light chain

<400> SEQUENCE: 64

Glu Ile Val Leu Thr Gln Ser Pro Ala Leu Met Ala Ala Ser Pro Gly
1               5                   10                  15

Glu Lys Val Thr Ile Thr Cys Arg Val Ser Ser Ile Ser Ser Ser
                20                  25                  30

Ser Leu His Trp Tyr Gln Gln Lys Ser Gly Thr Ser Pro Lys Pro Trp
            35                  40                  45

Ile Tyr Gly Thr Ser Asn Leu Ala Ser Gly Val Pro Val Arg Phe Ser
    50                  55                  60

Gly Ser Arg Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Asp Tyr Pro

```
                     85                  90                  95

Trp Thr Phe Gly Gly Gly Thr Lys Leu Glu Ile Lys
            100                 105

<210> SEQ ID NO 65
<211> LENGTH: 119
<212> TYPE: PRT
<213> ORGANISM: Artificial Sequence
<220> FEATURE:
<223> OTHER INFORMATION: mAb KCD220 heavy chain

<400> SEQUENCE: 65

Gln Val Gln Leu Gln Gln Ser Gly Ala Glu Leu Met Glu Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Thr Leu Pro Gly Ser Asp Ser Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Asp Tyr Ser Asn Tyr Trp Tyr Phe Asp Val Trp Gly Thr Gly
            100                 105                 110

Thr Thr Val Thr Val Ser Ser
        115

<210> SEQ ID NO 66
<211> LENGTH: 106
<212> TYPE: PRT
<213> ORGANISM: Artificial Sequence
<220> FEATURE:
<223> OTHER INFORMATION: mAb KCD220 light chain

<400> SEQUENCE: 66

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Asp Ser Lys His Arg Thr
                85                  90                  95

Phe Gly Gly Gly Thr Lys Leu Glu Ile Lys
            100                 105

<210> SEQ ID NO 67
<211> LENGTH: 119
<212> TYPE: PRT
<213> ORGANISM: Artificial Sequence
<220> FEATURE:
<223> OTHER INFORMATION: mAb KCD224 heavy chain

<400> SEQUENCE: 67
```

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Ile Arg Gln Ser Pro Gly Lys Gly Leu Glu Trp Leu
        35                  40                  45

Gly Val Ile Trp Gly Val Gly Ser Thr Asn Tyr Asn Ser Ala Leu Lys
    50                  55                  60

Ser Arg Leu Ser Ile Ser Lys Asp Asn Ser Lys Ser Gln Val Phe Leu
65              70                  75                  80

Lys Met Asn Ser Leu Gln Thr Asp Thr Ala Met Tyr Tyr Cys Ala
                85                  90                  95

Arg Ser Tyr Asp Gly Ser Tyr Trp Tyr Phe Asp Val Trp Gly Thr Gly
            100                 105                 110

Thr Thr Val Thr Val Ser Ser
            115

<210> SEQ ID NO 68
<211> LENGTH: 107
<212> TYPE: PRT
<213> ORGANISM: Artificial Sequence
<220> FEATURE:
<223> OTHER INFORMATION: mAb KCD224 light chain

<400> SEQUENCE: 68

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Val Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65              70                  75                  80

Glu Asp Ile Ala Thr Tyr Tyr Cys Gln Gln Tyr Ser Lys Leu Pro Tyr
                85                  90                  95

Thr Phe Gly Ser Gly Thr Lys Leu Glu Ile Lys
            100                 105

<210> SEQ ID NO 69
<211> LENGTH: 116
<212> TYPE: PRT
<213> ORGANISM: Artificial Sequence
<220> FEATURE:
<223> OTHER INFORMATION: mAb 119_TAF heavy chain

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
        35                  40                  45

Gly Asp Ile Asn Pro Asn Thr Gly Asp Thr Ser Tyr Asn Ala Asp Phe
    50                  55                  60

Lys Arg Arg Phe Thr Phe Ser Leu Asp Thr Ser Lys Ser Thr Ala Tyr
```

```
                65                  70                  75                  80
Leu Gln Met Asn Ser Leu Arg Ala Glu Asp Thr Ala Val Tyr Tyr Cys
                    85                  90                  95

Thr Arg Glu Gly Pro Ser Phe Ala Tyr Trp Gly Gln Gly Thr Leu Val
                    100                 105                 110

Thr Val Ser Ser
            115

<210> SEQ ID NO 70
<211> LENGTH: 112
<212> TYPE: PRT
<213> ORGANISM: Artificial Sequence
<220> FEATURE:
<223> OTHER INFORMATION: mAb 119_TAF light chain

<400> SEQUENCE: 70

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
                20                  25                  30

Asn Gly Asp Thr Tyr Leu Glu Trp Tyr Gln Gln Lys Pro Gly Lys Ala
            35                  40                  45

Pro Asn Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                    85                  90                  95

Ser His Val Pro Pro Thr Phe Gly Gln Gly Thr Lys Val Glu Ile Lys
                    100                 105                 110

<210> SEQ ID NO 71
<211> LENGTH: 116
<212> TYPE: PRT
<213> ORGANISM: Artificial Sequence
<220> FEATURE:
<223> OTHER INFORMATION: mAb 119_TAF Germ heavy chain

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
                20                  25                  30

Tyr Met Ser Trp Val Arg Gln Ala Pro Gly Lys Gly Leu Glu Trp Ile
            35                  40                  45

Gly Asp Ile Asn Pro Asn Thr Gly Asp Thr Ser Tyr Asn Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                    85                  90                  95

Cys Thr Arg Glu Gly Pro Ser Phe Ala Tyr Trp Gly Gln Gly Thr Leu
                    100                 105                 110

Val Thr Val Ser
            115

<210> SEQ ID NO 72
<211> LENGTH: 112
```

```
<212> TYPE: PRT
<213> ORGANISM: Artificial Sequence
<220> FEATURE:
<223> OTHER INFORMATION: mAb 119_TAF Germ light chain

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
        35                  40                  45

Pro Asn Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Pro Thr Phe Gly Gln Gly Thr Lys Val Glu Ile Lys
            100                 105                 110

<210> SEQ ID NO 73
<211> LENGTH: 107
<212> TYPE: PRT
<213> ORGANISM: Artificial Sequence
<220> FEATURE:
<223> OTHER INFORMATION: mAb 119_Human Germ heavy chain

<400> SEQUENCE: 73

Glu Val Lys Lys Pro Gly Ala Ser Val Lys Val Ser Cys Lys Ala Ser
1               5                   10                  15

Gly Tyr Thr Phe Thr Asp Tyr Tyr Met His Trp Val Arg Gln Ala Pro
            20                  25                  30

Gly Gln Gly Leu Glu Trp Ile Gly Asp Ile Asn Pro Asn Thr Gly Asp
        35                  40                  45

Thr Ser Tyr Asn Gln Lys Phe Gln Gly Arg Val Thr Ser Thr Arg Asp
    50                  55                  60

Thr Ser Ile Ser Thr Ala Tyr Met Glu Leu Ser Arg Leu Arg Ser Asp
65                  70                  75                  80

Asp Thr Val Val Tyr Tyr Cys Thr Arg Glu Gly Pro Ser Phe Ala Tyr
                85                  90                  95

Trp Gly Gln Gly Thr Leu Val Thr Val Ser Ser
            100                 105

<210> SEQ ID NO 74
<211> LENGTH: 112
<212> TYPE: PRT
<213> ORGANISM: Artificial Sequence
<220> FEATURE:
<223> OTHER INFORMATION: mAb 119_Human Germ light chain

<400> SEQUENCE: 74

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asn Gly Asp Thr Tyr Leu Glu Trp Phe Gln Gln Arg Pro Gly Gln Ser
        35                  40                  45

Pro Asn Leu Leu Ile Tyr Lys Val Ser Asn Arg Phe Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Pro Thr Phe Gly Gly Gly Thr Lys Val Glu Ile Lys
                100                 105                 110
```

<210> SEQ ID NO 75
<211> LENGTH: 10
<212> TYPE: PRT
<213> ORGANISM: Artificial Sequence
<220> FEATURE:
<223> OTHER INFORMATION: KCD002 H1

<400> SEQUENCE: 75

```
Gly Phe Thr Phe Ser Asp Tyr Tyr Met Ala
 1               5                  10
```

<210> SEQ ID NO 76
<211> LENGTH: 16
<212> TYPE: PRT
<213> ORGANISM: Artificial Sequence
<220> FEATURE:
<223> OTHER INFORMATION: KCD002 H2

<400> SEQUENCE: 76

```
Ile Asn Tyr Asp Gly Ser Ser Thr Tyr Tyr Leu Asp Ser Leu Lys Ser
 1               5                  10                  15
```

<210> SEQ ID NO 77
<211> LENGTH: 13
<212> TYPE: PRT
<213> ORGANISM: Artificial Sequence
<220> FEATURE:
<223> OTHER INFORMATION: KCD002 H3

<400> SEQUENCE: 77

```
Ala Arg Gly Glu Asp Phe Tyr Leu Tyr Ala Met Asp Tyr
 1               5                  10
```

<210> SEQ ID NO 78
<211> LENGTH: 11
<212> TYPE: PRT
<213> ORGANISM: Artificial Sequence
<220> FEATURE:
<223> OTHER INFORMATION: KCD002 L1

<400> SEQUENCE: 78

```
Arg Ala Ser Glu Asn Ile His Ser Tyr Leu Ala
 1               5                  10
```

<210> SEQ ID NO 79
<211> LENGTH: 7
<212> TYPE: PRT
<213> ORGANISM: Artificial Sequence
<220> FEATURE:
<223> OTHER INFORMATION: KCD002 L2

<400> SEQUENCE: 79

```
Asn Thr Lys Thr Leu Ala Glu
 1               5
```

<210> SEQ ID NO 80
<211> LENGTH: 9

```
<212> TYPE: PRT
<213> ORGANISM: Artificial Sequence
<220> FEATURE:
<223> OTHER INFORMATION: KCD002 L3

<400> SEQUENCE: 80

Gln His His Tyr Gly Ile Pro Pro Thr
1               5

<210> SEQ ID NO 81
<211> LENGTH: 10
<212> TYPE: PRT
<213> ORGANISM: Artificial Sequence
<220> FEATURE:
<223> OTHER INFORMATION: KCD003 H1

<400> SEQUENCE: 81

Gly Tyr Thr Phe Thr Asp Tyr Tyr Met Asn
1               5                   10

<210> SEQ ID NO 82
<211> LENGTH: 16
<212> TYPE: PRT
<213> ORGANISM: Artificial Sequence
<220> FEATURE:
<223> OTHER INFORMATION: KCD003 H2

<400> SEQUENCE: 82

Ile Asn Pro Asn Asn Gly Asp Pro Ser Tyr Asn Gln Lys Phe Lys Asp
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: KCD003 H3

<400> SEQUENCE: 83

Ala Arg Glu Gly Pro Ser Phe Ala Tyr
1               5

<210> SEQ ID NO 84
<211> LENGTH: 16
<212> TYPE: PRT
<213> ORGANISM: Artificial Sequence
<220> FEATURE:
<223> OTHER INFORMATION: KCD003 L1

<400> SEQUENCE: 84

Arg Ser Ser Gln Thr Ile Val His Ser Asn Gly Asp Thr Tyr Leu Glu
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: KCD003 L2

<400> SEQUENCE: 85

Lys Val Ser Asn Arg Phe Ser
1               5

<210> SEQ ID NO 86
<211> LENGTH: 9
<212> TYPE: PRT
```

```
<213> ORGANISM: Artificial Sequence
<220> FEATURE:
<223> OTHER INFORMATION: KCD003 L3

<400> SEQUENCE: 86

Phe Gln Gly Ser His Val Pro Pro Thr
1               5

<210> SEQ ID NO 87
<211> LENGTH: 10
<212> TYPE: PRT
<213> ORGANISM: Artificial Sequence
<220> FEATURE:
<223> OTHER INFORMATION: KCD005 H1

<400> SEQUENCE: 87

Gly Tyr Thr Phe Thr Asp His Tyr Met Asn
1               5                   10

<210> SEQ ID NO 88
<211> LENGTH: 16
<212> TYPE: PRT
<213> ORGANISM: Artificial Sequence
<220> FEATURE:
<223> OTHER INFORMATION: KCD005 H2

<400> SEQUENCE: 88

Ile Asn Pro Asn Asn Gly Gly Thr Ser Cys Asn Gln Lys Phe Lys Gly
1               5                   10                  15

<210> SEQ ID NO 89
<211> LENGTH: 9
<212> TYPE: PRT
<213> ORGANISM: Artificial Sequence
<220> FEATURE:
<223> OTHER INFORMATION: KCD005 H3

<400> SEQUENCE: 89

Thr Arg Glu Gly Ala Ser Phe Ala Phe
1               5

<210> SEQ ID NO 90
<211> LENGTH: 16
<212> TYPE: PRT
<213> ORGANISM: Artificial Sequence
<220> FEATURE:
<223> OTHER INFORMATION: KCD005 L1

<400> SEQUENCE: 90

Arg Ser Ser Gln Ser Ile Val His Ser Asn Gly Asp Thr Tyr Leu Glu
1               5                   10                  15

<210> SEQ ID NO 91
<211> LENGTH: 7
<212> TYPE: PRT
<213> ORGANISM: Artificial Sequence
<220> FEATURE:
<223> OTHER INFORMATION: KCD005 L2

<400> SEQUENCE: 91

Lys Val Ser Asn Arg Phe Ser
1               5

<210> SEQ ID NO 92
<211> LENGTH: 9
<212> TYPE: PRT
<213> ORGANISM: Artificial Sequence
```

```
<220> FEATURE:
<223> OTHER INFORMATION: KCD005 L3

<400> SEQUENCE: 92

Phe Gln Gly Ser His Val Pro Val Thr
1               5

<210> SEQ ID NO 93
<211> LENGTH: 10
<212> TYPE: PRT
<213> ORGANISM: Artificial Sequence
<220> FEATURE:
<223> OTHER INFORMATION: KCD009 H1

<400> SEQUENCE: 93

Gly Tyr Ile Phe Arg Asn Tyr Gly Met Asn
1               5                   10

<210> SEQ ID NO 94
<211> LENGTH: 16
<212> TYPE: PRT
<213> ORGANISM: Artificial Sequence
<220> FEATURE:
<223> OTHER INFORMATION: KCD009 H2

<400> SEQUENCE: 94

Ile Asn Thr Tyr Thr Gly Glu Pro Thr Tyr Ala Asp Asp Phe Lys Gly
1               5                   10                  15

<210> SEQ ID NO 95
<211> LENGTH: 9
<212> TYPE: PRT
<213> ORGANISM: Artificial Sequence
<220> FEATURE:
<223> OTHER INFORMATION: KCD009 H3

<400> SEQUENCE: 95

Val Arg Asp Gly Pro Gly Phe Ala Tyr
1               5

<210> SEQ ID NO 96
<211> LENGTH: 16
<212> TYPE: PRT
<213> ORGANISM: Artificial Sequence
<220> FEATURE:
<223> OTHER INFORMATION: KCD009 L1

<400> SEQUENCE: 96

Arg Ser Ser Leu Ile Ile Glu His Ser Asp Gly Asn Thr Tyr Leu Glu
1               5                   10                  15

<210> SEQ ID NO 97
<211> LENGTH: 7
<212> TYPE: PRT
<213> ORGANISM: Artificial Sequence
<220> FEATURE:
<223> OTHER INFORMATION: KCD009 L2

<400> SEQUENCE: 97

Lys Val Ser Asn Arg Phe Ser
1               5

<210> SEQ ID NO 98
<211> LENGTH: 9
<212> TYPE: PRT
<213> ORGANISM: Artificial Sequence
<220> FEATURE:
```

<223> OTHER INFORMATION: KCD009 L3

<400> SEQUENCE: 98

Phe Gln Gly Ser His Val Pro Val Thr
1               5

<210> SEQ ID NO 99
<211> LENGTH: 10
<212> TYPE: PRT
<213> ORGANISM: Artificial Sequence
<220> FEATURE:
<223> OTHER INFORMATION: KCD010 H1

<400> SEQUENCE: 99

Gly Tyr Thr Phe Thr Asp Tyr Asp Met Asp
1               5                   10

<210> SEQ ID NO 100
<211> LENGTH: 16
<212> TYPE: PRT
<213> ORGANISM: Artificial Sequence
<220> FEATURE:
<223> OTHER INFORMATION: KCD010 H2

<400> SEQUENCE: 100

Ile Asn Pro Asn Asn Gly Gly Thr Ile Tyr Asn Gln Lys Phe Lys Gly
1               5                   10                  15

<210> SEQ ID NO 101
<211> LENGTH: 7
<212> TYPE: PRT
<213> ORGANISM: Artificial Sequence
<220> FEATURE:
<223> OTHER INFORMATION: KCD010 H3

<400> SEQUENCE: 101

Gly Thr Gly Asp Phe Ala Tyr
1               5

<210> SEQ ID NO 102
<211> LENGTH: 12
<212> TYPE: PRT
<213> ORGANISM: Artificial Sequence
<220> FEATURE:
<223> OTHER INFORMATION: KCD010 L1

<400> SEQUENCE: 102

Ser Ala Ser Ser Ser Val Ser Ser Ser Tyr Leu Tyr
1               5                   10

<210> SEQ ID NO 103
<211> LENGTH: 7
<212> TYPE: PRT
<213> ORGANISM: Artificial Sequence
<220> FEATURE:
<223> OTHER INFORMATION: KCD010 L2

<400> SEQUENCE: 103

Ser Thr Ser Asn Leu Ala Ser
1               5

<210> SEQ ID NO 104
<211> LENGTH: 9
<212> TYPE: PRT
<213> ORGANISM: Artificial Sequence
<220> FEATURE:
<223> OTHER INFORMATION: KCD010 L3

<400> SEQUENCE: 104

His Gln Trp Ser Ser Tyr Pro Pro Thr
1               5

<210> SEQ ID NO 105
<211> LENGTH: 10
<212> TYPE: PRT
<213> ORGANISM: Artificial Sequence
<220> FEATURE:
<223> OTHER INFORMATION: KCD023 H1

<400> SEQUENCE: 105

Gly Tyr Thr Phe Thr Asp Tyr Asn Ile Asp
1               5                   10

<210> SEQ ID NO 106
<211> LENGTH: 16
<212> TYPE: PRT
<213> ORGANISM: Artificial Sequence
<220> FEATURE:
<223> OTHER INFORMATION: KCD023 H2

<400> SEQUENCE: 106

Ile Asn Pro Asn Asn Gly Gly Ile Asn Tyr Asn Gln Lys Phe Lys Gly
1               5                   10                  15

<210> SEQ ID NO 107
<211> LENGTH: 7
<212> TYPE: PRT
<213> ORGANISM: Artificial Sequence
<220> FEATURE:
<223> OTHER INFORMATION: KCD023 H3

<400> SEQUENCE: 107

Gly Thr Gly Asp Tyr Ala Tyr
1               5

<210> SEQ ID NO 108
<211> LENGTH: 12
<212> TYPE: PRT
<213> ORGANISM: Artificial Sequence
<220> FEATURE:
<223> OTHER INFORMATION: KCD023 L1

<400> SEQUENCE: 108

Ser Ala Ser Ser Ser Val Ser Ser Ser Tyr Leu Tyr
1               5                   10

<210> SEQ ID NO 109
<211> LENGTH: 7
<212> TYPE: PRT
<213> ORGANISM: Artificial Sequence
<220> FEATURE:
<223> OTHER INFORMATION: KCD023 L2

<400> SEQUENCE: 109

Ser Thr Ser Asn Leu Ala Ser
1               5

<210> SEQ ID NO 110
<211> LENGTH: 9
<212> TYPE: PRT
<213> ORGANISM: Artificial Sequence
<220> FEATURE:
<223> OTHER INFORMATION: KCD023 L3

```
<400> SEQUENCE: 110

His Gln Trp Thr Ser Tyr Pro Pro Thr
1               5

<210> SEQ ID NO 111
<211> LENGTH: 10
<212> TYPE: PRT
<213> ORGANISM: Artificial Sequence
<220> FEATURE:
<223> OTHER INFORMATION: KCD036 H1

<400> SEQUENCE: 111

Gly Tyr Ser Phe Thr Gly Tyr Thr Met Thr
1               5                   10

<210> SEQ ID NO 112
<211> LENGTH: 16
<212> TYPE: PRT
<213> ORGANISM: Artificial Sequence
<220> FEATURE:
<223> OTHER INFORMATION: KCD036 H2

<400> SEQUENCE: 112

Ile Asn Pro Tyr Asn Gly Gly Thr Asn Tyr Asn Gln Lys Phe Lys Gly
1               5                   10                  15

<210> SEQ ID NO 113
<211> LENGTH: 11
<212> TYPE: PRT
<213> ORGANISM: Artificial Sequence
<220> FEATURE:
<223> OTHER INFORMATION: KCD036 H3

<400> SEQUENCE: 113

Ala Arg Arg His Tyr Gly Ser Ser Trp Asp Tyr
1               5                   10

<210> SEQ ID NO 114
<211> LENGTH: 11
<212> TYPE: PRT
<213> ORGANISM: Artificial Sequence
<220> FEATURE:
<223> OTHER INFORMATION: KCD036 L1

<400> SEQUENCE: 114

Lys Ala Ser Gln Asp Ile Asn Thr Tyr Leu Ser
1               5                   10

<210> SEQ ID NO 115
<211> LENGTH: 7
<212> TYPE: PRT
<213> ORGANISM: Artificial Sequence
<220> FEATURE:
<223> OTHER INFORMATION: KCD036 L2

<400> SEQUENCE: 115

Arg Ala Asn Arg Leu Val Asp
1               5

<210> SEQ ID NO 116
<211> LENGTH: 9
<212> TYPE: PRT
<213> ORGANISM: Artificial Sequence
<220> FEATURE:
<223> OTHER INFORMATION: KCD036 L3

<400> SEQUENCE: 116
```

Leu Gln Tyr Asp Glu Phe Pro Tyr Thr
1               5

<210> SEQ ID NO 117
<211> LENGTH: 10
<212> TYPE: PRT
<213> ORGANISM: Artificial Sequence
<220> FEATURE:
<223> OTHER INFORMATION: KCD040 H1

<400> SEQUENCE: 117

Asp Phe Asn Ile Lys Asp Thr Tyr Met His
1               5                   10

<210> SEQ ID NO 118
<211> LENGTH: 16
<212> TYPE: PRT
<213> ORGANISM: Artificial Sequence
<220> FEATURE:
<223> OTHER INFORMATION: KCD040 H2

<400> SEQUENCE: 118

Ile Asp Pro Ala Asn Gly Asn Thr Glu Phe Asp Pro Lys Phe Gln Gly
1               5                   10                  15

<210> SEQ ID NO 119
<211> LENGTH: 6
<212> TYPE: PRT
<213> ORGANISM: Artificial Sequence
<220> FEATURE:
<223> OTHER INFORMATION: KCD040 H3

<400> SEQUENCE: 119

Thr Arg Ala Met Asp Tyr
1               5

<210> SEQ ID NO 120
<211> LENGTH: 10
<212> TYPE: PRT
<213> ORGANISM: Artificial Sequence
<220> FEATURE:
<223> OTHER INFORMATION: KCD040 L1

<400> SEQUENCE: 120

Ser Ala Gly Ser Ser Val Ser Tyr Met Tyr
1               5                   10

<210> SEQ ID NO 121
<211> LENGTH: 7
<212> TYPE: PRT
<213> ORGANISM: Artificial Sequence
<220> FEATURE:
<223> OTHER INFORMATION: KCD040 L2

<400> SEQUENCE: 121

Asp Thr Ser Asn Leu Ala Ser
1               5

<210> SEQ ID NO 122
<211> LENGTH: 9
<212> TYPE: PRT
<213> ORGANISM: Artificial Sequence
<220> FEATURE:
<223> OTHER INFORMATION: KCD040 L3

<400> SEQUENCE: 122

-continued

Gln Gln Trp Ser Asn Tyr Pro Tyr Thr
1               5

<210> SEQ ID NO 123
<211> LENGTH: 10
<212> TYPE: PRT
<213> ORGANISM: Artificial Sequence
<220> FEATURE:
<223> OTHER INFORMATION: KCD042 H1

<400> SEQUENCE: 123

Gly Phe Asn Ile Lys His Thr Tyr Ile His
1               5                   10

<210> SEQ ID NO 124
<211> LENGTH: 16
<212> TYPE: PRT
<213> ORGANISM: Artificial Sequence
<220> FEATURE:
<223> OTHER INFORMATION: KCD042 H2

<400> SEQUENCE: 124

Ile Asp Pro Ala Asn Gly Asn Thr Lys Tyr Asp Pro Lys Phe Gln Gly
1               5                   10                  15

<210> SEQ ID NO 125
<211> LENGTH: 6
<212> TYPE: PRT
<213> ORGANISM: Artificial Sequence
<220> FEATURE:
<223> OTHER INFORMATION: KCD042 H3

<400> SEQUENCE: 125

Val Asn Ala Met Glu Tyr
1               5

<210> SEQ ID NO 126
<211> LENGTH: 10
<212> TYPE: PRT
<213> ORGANISM: Artificial Sequence
<220> FEATURE:
<223> OTHER INFORMATION: KCD042 L1

<400> SEQUENCE: 126

Ser Ala Asn Ser Ser Val Ser Asp Met Tyr
1               5                   10

<210> SEQ ID NO 127
<211> LENGTH: 7
<212> TYPE: PRT
<213> ORGANISM: Artificial Sequence
<220> FEATURE:
<223> OTHER INFORMATION: KCD042 L2

<400> SEQUENCE: 127

Asp Thr Ser Asn Leu Ala Ser
1               5

<210> SEQ ID NO 128
<211> LENGTH: 9
<212> TYPE: PRT
<213> ORGANISM: Artificial Sequence
<220> FEATURE:
<223> OTHER INFORMATION: KCD042 L3

<400> SEQUENCE: 128

Gln Gln Trp Ser Thr Tyr Pro Trp Thr

```
<210> SEQ ID NO 129
<211> LENGTH: 10
<212> TYPE: PRT
<213> ORGANISM: Artificial Sequence
<220> FEATURE:
<223> OTHER INFORMATION: KCD044 H1

<400> SEQUENCE: 129

Gly Phe Asn Ile Lys His Thr Tyr Met His
1               5                   10

<210> SEQ ID NO 130
<211> LENGTH: 16
<212> TYPE: PRT
<213> ORGANISM: Artificial Sequence
<220> FEATURE:
<223> OTHER INFORMATION: KCD044 H2

<400> SEQUENCE: 130

Ile Asp Pro Ala Asn Gly Asn Thr Lys Tyr Asp Pro Lys Phe Gln Gly
1               5                   10                  15

<210> SEQ ID NO 131
<211> LENGTH: 6
<212> TYPE: PRT
<213> ORGANISM: Artificial Sequence
<220> FEATURE:
<223> OTHER INFORMATION: KCD044 H3

<400> SEQUENCE: 131

Leu Asn Ala Met Glu Tyr
1               5

<210> SEQ ID NO 132
<211> LENGTH: 10
<212> TYPE: PRT
<213> ORGANISM: Artificial Sequence
<220> FEATURE:
<223> OTHER INFORMATION: KCD044 L1

<400> SEQUENCE: 132

Ser Ala Asn Ser Ser Val Ser Asp Met Tyr
1               5                   10

<210> SEQ ID NO 133
<211> LENGTH: 7
<212> TYPE: PRT
<213> ORGANISM: Artificial Sequence
<220> FEATURE:
<223> OTHER INFORMATION: KCD044 L2

<400> SEQUENCE: 133

Asp Thr Ser Asn Leu Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: KCD044 L3

<400> SEQUENCE: 134

Gln Gln Trp Ser Thr Tyr Pro Trp Thr
1               5
```

<210> SEQ ID NO 135
<211> LENGTH: 10
<212> TYPE: PRT
<213> ORGANISM: Artificial Sequence
<220> FEATURE:
<223> OTHER INFORMATION: KCD047 H1

<400> SEQUENCE: 135

Gly Phe Asn Ile Lys Asp Thr Tyr Met His
1               5                   10

<210> SEQ ID NO 136
<211> LENGTH: 16
<212> TYPE: PRT
<213> ORGANISM: Artificial Sequence
<220> FEATURE:
<223> OTHER INFORMATION: KCD047 H2

<400> SEQUENCE: 136

Ile Asp Pro Ala Asn Gly Tyr Thr Lys Asp Asp Pro Lys Phe Gln Gly
1               5                   10                  15

<210> SEQ ID NO 137
<211> LENGTH: 6
<212> TYPE: PRT
<213> ORGANISM: Artificial Sequence
<220> FEATURE:
<223> OTHER INFORMATION: KCD047 H3

<400> SEQUENCE: 137

Ala Ser Ala Met Asp Tyr
1               5

<210> SEQ ID NO 138
<211> LENGTH: 10
<212> TYPE: PRT
<213> ORGANISM: Artificial Sequence
<220> FEATURE:
<223> OTHER INFORMATION: KCD047 L1

<400> SEQUENCE: 138

Ser Ala Ser Ser Ser Val Thr Tyr Met Tyr
1               5                   10

<210> SEQ ID NO 139
<211> LENGTH: 7
<212> TYPE: PRT
<213> ORGANISM: Artificial Sequence
<220> FEATURE:
<223> OTHER INFORMATION: KCD047 L2

<400> SEQUENCE: 139

Asp Thr Ser Asn Leu Ala Ser
1               5

<210> SEQ ID NO 140
<211> LENGTH: 9
<212> TYPE: PRT
<213> ORGANISM: Artificial Sequence
<220> FEATURE:
<223> OTHER INFORMATION: KCD047 L3

<400> SEQUENCE: 140

Gln Gln Trp Ser Asn Tyr Pro Phe Thr
1               5

```
<210> SEQ ID NO 141
<211> LENGTH: 10
<212> TYPE: PRT
<213> ORGANISM: Artificial Sequence
<220> FEATURE:
<223> OTHER INFORMATION: KCD048 H1

<400> SEQUENCE: 141

Gly Phe Asn Ile Lys Ala Thr Tyr Met His
1               5                   10

<210> SEQ ID NO 142
<211> LENGTH: 16
<212> TYPE: PRT
<213> ORGANISM: Artificial Sequence
<220> FEATURE:
<223> OTHER INFORMATION: KCD048 H2

<400> SEQUENCE: 142

Ile Asp Pro Ala Asn Gly His Thr Ile Tyr Asp Pro Gln Phe Gln Gly
1               5                   10                  15

<210> SEQ ID NO 143
<211> LENGTH: 6
<212> TYPE: PRT
<213> ORGANISM: Artificial Sequence
<220> FEATURE:
<223> OTHER INFORMATION: KCD048 H3

<400> SEQUENCE: 143

Ala Glu Ala Met Asp Tyr
1               5

<210> SEQ ID NO 144
<211> LENGTH: 10
<212> TYPE: PRT
<213> ORGANISM: Artificial Sequence
<220> FEATURE:
<223> OTHER INFORMATION: KCD048 L1

<400> SEQUENCE: 144

Ser Ala Thr Ser Ser Val Ser Tyr Met Tyr
1               5                   10

<210> SEQ ID NO 145
<211> LENGTH: 7
<212> TYPE: PRT
<213> ORGANISM: Artificial Sequence
<220> FEATURE:
<223> OTHER INFORMATION: KCD048 L2

<400> SEQUENCE: 145

Asp Thr Ser Asn Leu Ala Ser
1               5

<210> SEQ ID NO 146
<211> LENGTH: 9
<212> TYPE: PRT
<213> ORGANISM: Artificial Sequence
<220> FEATURE:
<223> OTHER INFORMATION: KCD048 L3

<400> SEQUENCE: 146

Gln Gln Trp Ser Asn Tyr Pro Phe Thr
1               5
```

<210> SEQ ID NO 147
<211> LENGTH: 10
<212> TYPE: PRT
<213> ORGANISM: Artificial Sequence
<220> FEATURE:
<223> OTHER INFORMATION: KCD070 H1

<400> SEQUENCE: 147

Gly Tyr Ser Phe Thr Asp Tyr Ile Ile Leu
1               5                   10

<210> SEQ ID NO 148
<211> LENGTH: 16
<212> TYPE: PRT
<213> ORGANISM: Artificial Sequence
<220> FEATURE:
<223> OTHER INFORMATION: KCD070 H2

<400> SEQUENCE: 148

Ile Asn Pro Tyr Tyr Asp Tyr Thr Ser Tyr Asn Leu Lys Phe Lys Gly
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: KCD070 H3

<400> SEQUENCE: 149

Ala Arg Ser Asp Gly Tyr Tyr Gly Gly Asp Tyr
1               5                   10

<210> SEQ ID NO 150
<211> LENGTH: 11
<212> TYPE: PRT
<213> ORGANISM: Artificial Sequence
<220> FEATURE:
<223> OTHER INFORMATION: KCD070 L1

<400> SEQUENCE: 150

Lys Ala Ser Gln Asp Val Gly Thr Ala Val Ala
1               5                   10

<210> SEQ ID NO 151
<211> LENGTH: 7
<212> TYPE: PRT
<213> ORGANISM: Artificial Sequence
<220> FEATURE:
<223> OTHER INFORMATION: KCD070 L2

<400> SEQUENCE: 151

Trp Ala Ser Thr Arg His Thr
1               5

<210> SEQ ID NO 152
<211> LENGTH: 9
<212> TYPE: PRT
<213> ORGANISM: Artificial Sequence
<220> FEATURE:
<223> OTHER INFORMATION: KCD070 L3

<400> SEQUENCE: 152

Gln Gln Tyr Ser Ser Tyr Pro Trp Thr
1               5

<210> SEQ ID NO 153

```
<211> LENGTH: 10
<212> TYPE: PRT
<213> ORGANISM: Artificial Sequence
<220> FEATURE:
<223> OTHER INFORMATION: KCD101 H1

<400> SEQUENCE: 153

Gly Tyr Thr Phe Thr Ser Tyr Trp Met His
1               5                   10

<210> SEQ ID NO 154
<211> LENGTH: 16
<212> TYPE: PRT
<213> ORGANISM: Artificial Sequence
<220> FEATURE:
<223> OTHER INFORMATION: KCD101 H2

<400> SEQUENCE: 154

Ile Asp Pro Ser Asp Ser Tyr Thr Asn Tyr Asn Gln Lys Phe Lys Gly
1               5                   10                  15

<210> SEQ ID NO 155
<211> LENGTH: 11
<212> TYPE: PRT
<213> ORGANISM: Artificial Sequence
<220> FEATURE:
<223> OTHER INFORMATION: KCD101 H3

<400> SEQUENCE: 155

Gly Arg Asn Gly Tyr Asp Gly Ser Met Asp Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: KCD101 L1

<400> SEQUENCE: 156

Arg Ala Ser Gln Asp Ile Ser Asn Tyr Leu Asn
1               5                   10

<210> SEQ ID NO 157
<211> LENGTH: 7
<212> TYPE: PRT
<213> ORGANISM: Artificial Sequence
<220> FEATURE:
<223> OTHER INFORMATION: KCD101 L2

<400> SEQUENCE: 157

Tyr Pro Ser Arg Leu His Ser
1               5

<210> SEQ ID NO 158
<211> LENGTH: 9
<212> TYPE: PRT
<213> ORGANISM: Artificial Sequence
<220> FEATURE:
<223> OTHER INFORMATION: KCD101 L3

<400> SEQUENCE: 158

Gln Gln Gly Asn Thr Leu Pro Tyr Thr
1               5

<210> SEQ ID NO 159
<211> LENGTH: 10
```

```
<212> TYPE: PRT
<213> ORGANISM: Artificial Sequence
<220> FEATURE:
<223> OTHER INFORMATION: KCD102 H1

<400> SEQUENCE: 159

Gly Tyr Thr Phe Thr Ser Tyr Trp Met His
1               5                   10

<210> SEQ ID NO 160
<211> LENGTH: 16
<212> TYPE: PRT
<213> ORGANISM: Artificial Sequence
<220> FEATURE:
<223> OTHER INFORMATION: KCD102 H2

<400> SEQUENCE: 160

Ile Asp Pro Ser Asp Ser Tyr Thr Asn Tyr Asn Gln Lys Phe Lys Gly
1               5                   10                  15

<210> SEQ ID NO 161
<211> LENGTH: 11
<212> TYPE: PRT
<213> ORGANISM: Artificial Sequence
<220> FEATURE:
<223> OTHER INFORMATION: KCD102 H3

<400> SEQUENCE: 161

Ala Arg Asn Gly Tyr Asp Gly Ser Met Asp Tyr
1               5                   10

<210> SEQ ID NO 162
<211> LENGTH: 11
<212> TYPE: PRT
<213> ORGANISM: Artificial Sequence
<220> FEATURE:
<223> OTHER INFORMATION: KCD102 L1

<400> SEQUENCE: 162

Arg Ala Ser Gln Asp Ile Ser Asn Tyr Leu Asn
1               5                   10

<210> SEQ ID NO 163
<211> LENGTH: 7
<212> TYPE: PRT
<213> ORGANISM: Artificial Sequence
<220> FEATURE:
<223> OTHER INFORMATION: KCD102 L2

<400> SEQUENCE: 163

Tyr Pro Ser Arg Leu His Ser
1               5

<210> SEQ ID NO 164
<211> LENGTH: 9
<212> TYPE: PRT
<213> ORGANISM: Artificial Sequence
<220> FEATURE:
<223> OTHER INFORMATION: KCD102 L3

<400> SEQUENCE: 164

Gln Gln Gly Asn Thr Leu Pro Tyr Thr
1               5

<210> SEQ ID NO 165
<211> LENGTH: 10
<212> TYPE: PRT
```

```
<213> ORGANISM: Artificial Sequence
<220> FEATURE:
<223> OTHER INFORMATION: KCD103 H1

<400> SEQUENCE: 165

Gly Tyr Thr Phe Thr Ser Tyr Trp Met His
1               5                   10

<210> SEQ ID NO 166
<211> LENGTH: 16
<212> TYPE: PRT
<213> ORGANISM: Artificial Sequence
<220> FEATURE:
<223> OTHER INFORMATION: KCD103 H2

<400> SEQUENCE: 166

Ile Asp Pro Ser Asp Ser Tyr Thr Lys Tyr Asn Gln Lys Phe Lys Asp
1               5                   10                  15

<210> SEQ ID NO 167
<211> LENGTH: 11
<212> TYPE: PRT
<213> ORGANISM: Artificial Sequence
<220> FEATURE:
<223> OTHER INFORMATION: KCD103 H3

<400> SEQUENCE: 167

Ala Gly Asn Gly Tyr Asp Gly Ser Met Asp Tyr
1               5                   10

<210> SEQ ID NO 168
<211> LENGTH: 11
<212> TYPE: PRT
<213> ORGANISM: Artificial Sequence
<220> FEATURE:
<223> OTHER INFORMATION: KCD103 L1

<400> SEQUENCE: 168

Arg Ala Ser Gln Asp Ile Ser Asn Ser Leu Asn
1               5                   10

<210> SEQ ID NO 169
<211> LENGTH: 7
<212> TYPE: PRT
<213> ORGANISM: Artificial Sequence
<220> FEATURE:
<223> OTHER INFORMATION: KCD103 L2

<400> SEQUENCE: 169

Tyr Thr Ser Arg Leu His Ser
1               5

<210> SEQ ID NO 170
<211> LENGTH: 9
<212> TYPE: PRT
<213> ORGANISM: Artificial Sequence
<220> FEATURE:
<223> OTHER INFORMATION: KCD103 L3

<400> SEQUENCE: 170

Gln Gln Ala Asn Thr Leu Pro Tyr Thr
1               5

<210> SEQ ID NO 171
<211> LENGTH: 10
<212> TYPE: PRT
<213> ORGANISM: Artificial Sequence
```

```
<220> FEATURE:
<223> OTHER INFORMATION: KCD104 H1

<400> SEQUENCE: 171

Gly Tyr Thr Phe Thr Ser Tyr Trp Met His
1               5                   10

<210> SEQ ID NO 172
<211> LENGTH: 16
<212> TYPE: PRT
<213> ORGANISM: Artificial Sequence
<220> FEATURE:
<223> OTHER INFORMATION: KCD104 H2

<400> SEQUENCE: 172

Ile Asp Pro Ser Asp Ser Tyr Thr Tyr Tyr Asn Gln Lys Phe Lys Gly
1               5                   10                  15

<210> SEQ ID NO 173
<211> LENGTH: 11
<212> TYPE: PRT
<213> ORGANISM: Artificial Sequence
<220> FEATURE:
<223> OTHER INFORMATION: KCD104 H3

<400> SEQUENCE: 173

Ala Arg Asn Gly Tyr Asp Gly Ala Met Asp Tyr
1               5                   10

<210> SEQ ID NO 174
<211> LENGTH: 11
<212> TYPE: PRT
<213> ORGANISM: Artificial Sequence
<220> FEATURE:
<223> OTHER INFORMATION: KCD104 L1

<400> SEQUENCE: 174

Arg Ala Ser Gln Asp Ile Ser Asn Tyr Leu Asn
1               5                   10

<210> SEQ ID NO 175
<211> LENGTH: 7
<212> TYPE: PRT
<213> ORGANISM: Artificial Sequence
<220> FEATURE:
<223> OTHER INFORMATION: KCD104 L2

<400> SEQUENCE: 175

Tyr Pro Ser Arg Leu His Ser
1               5

<210> SEQ ID NO 176
<211> LENGTH: 9
<212> TYPE: PRT
<213> ORGANISM: Artificial Sequence
<220> FEATURE:
<223> OTHER INFORMATION: KCD104 L3

<400> SEQUENCE: 176

Gln Gln Gly Asn Thr Leu Pro Tyr Thr
1               5

<210> SEQ ID NO 177
<211> LENGTH: 10
<212> TYPE: PRT
<213> ORGANISM: Artificial Sequence
<220> FEATURE:
```

<223> OTHER INFORMATION: KCD118 H1

<400> SEQUENCE: 177

Gly Tyr Thr Phe Thr Asp Tyr Tyr Lys Asn
1               5                   10

<210> SEQ ID NO 178
<211> LENGTH: 16
<212> TYPE: PRT
<213> ORGANISM: Artificial Sequence
<220> FEATURE:
<223> OTHER INFORMATION: KCD118 H2

<400> SEQUENCE: 178

Ile Asn Pro Asn Ser Gly Asp Ala Asn Tyr Asn Gln Lys Phe Lys Gly
1               5                   10                  15

<210> SEQ ID NO 179
<211> LENGTH: 9
<212> TYPE: PRT
<213> ORGANISM: Artificial Sequence
<220> FEATURE:
<223> OTHER INFORMATION: KCD118 H3

<400> SEQUENCE: 179

Ala Arg Glu Gly Pro Ser Phe Ala Tyr
1               5

<210> SEQ ID NO 180
<211> LENGTH: 16
<212> TYPE: PRT
<213> ORGANISM: Artificial Sequence
<220> FEATURE:
<223> OTHER INFORMATION: KCD118 L1

<400> SEQUENCE: 180

Arg Ser Ser Gln Thr Ile Val His Ser Asn Gly Asp Thr Tyr Leu Glu
1               5                   10                  15

<210> SEQ ID NO 181
<211> LENGTH: 7
<212> TYPE: PRT
<213> ORGANISM: Artificial Sequence
<220> FEATURE:
<223> OTHER INFORMATION: KCD118 L2

<400> SEQUENCE: 181

Lys Val Ser Asn Arg Phe Ser
1               5

<210> SEQ ID NO 182
<211> LENGTH: 9
<212> TYPE: PRT
<213> ORGANISM: Artificial Sequence
<220> FEATURE:
<223> OTHER INFORMATION: KCD118 L3

<400> SEQUENCE: 182

Phe Gln Gly Ser His Val Pro Pro Thr
1               5

<210> SEQ ID NO 183
<211> LENGTH: 446
<212> TYPE: PRT
<213> ORGANISM: Artificial Sequence
<220> FEATURE:
<223> OTHER INFORMATION: Exemplary human IgG1 heavy chain

<400> SEQUENCE: 183

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15| |

Ser Leu Arg Leu Ser Cys Ala Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Gly Asp Ile Asn Pro Ile Thr Gly Asp Thr Asp Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Ser Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp

```
                    405                 410                 415
Gln Gln Gly Asn Val Phe Ser Cys Ser Val Met His Glu Ala Leu His
            420                 425                 430

Asn His Tyr Thr Gln Lys Ser Leu Ser Cys Ser Pro Gly Lys
            435                 440                 445

<210> SEQ ID NO 184
<211> LENGTH: 219
<212> TYPE: PRT
<213> ORGANISM: Artificial Sequence
<220> FEATURE:
<223> OTHER INFORMATION: Exemplary human kappa light chain

<400> SEQUENCE: 184

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
        35                  40                  45

Pro Asn Leu Leu Ile Arg Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Val Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 185
<211> LENGTH: 10
<212> TYPE: PRT
<213> ORGANISM: Artificial Sequence
<220> FEATURE:
<223> OTHER INFORMATION: KCD119 H1

<400> SEQUENCE: 185

Gly Tyr Thr Phe Thr Asp Tyr Tyr Thr Asn
1               5                   10

<210> SEQ ID NO 186
<211> LENGTH: 16
<212> TYPE: PRT
<213> ORGANISM: Artificial Sequence
<220> FEATURE:
```

```
<223> OTHER INFORMATION: KCD119 H2

<400> SEQUENCE: 186

Ile Asn Pro Asn Thr Gly Asp Thr Ser Tyr Asn Gln Lys Phe Arg Val
1               5                   10                  15

<210> SEQ ID NO 187
<211> LENGTH: 9
<212> TYPE: PRT
<213> ORGANISM: Artificial Sequence
<220> FEATURE:
<223> OTHER INFORMATION: KCD119 H3

<400> SEQUENCE: 187

Thr Arg Glu Gly Pro Ser Phe Ala Tyr
1               5

<210> SEQ ID NO 188
<211> LENGTH: 16
<212> TYPE: PRT
<213> ORGANISM: Artificial Sequence
<220> FEATURE:
<223> OTHER INFORMATION: KCD119 L1

<400> SEQUENCE: 188

Arg Ser Ser Gln Thr Ile Val His Ser Asn Gly Asp Thr Tyr Leu Glu
1               5                   10                  15

<210> SEQ ID NO 189
<211> LENGTH: 7
<212> TYPE: PRT
<213> ORGANISM: Artificial Sequence
<220> FEATURE:
<223> OTHER INFORMATION: KCD119 L2

<400> SEQUENCE: 189

Lys Val Ser Asn Arg Phe Ser
1               5

<210> SEQ ID NO 190
<211> LENGTH: 9
<212> TYPE: PRT
<213> ORGANISM: Artificial Sequence
<220> FEATURE:
<223> OTHER INFORMATION: KCD119 L3

<400> SEQUENCE: 190

Phe Gln Gly Ser His Val Pro Pro Thr
1               5

<210> SEQ ID NO 191
<211> LENGTH: 10
<212> TYPE: PRT
<213> ORGANISM: Artificial Sequence
<220> FEATURE:
<223> OTHER INFORMATION: KCD121 H1

<400> SEQUENCE: 191

Gly Tyr Thr Phe Thr Asp Tyr Tyr Lys Asn
1               5                   10

<210> SEQ ID NO 192
<211> LENGTH: 16
<212> TYPE: PRT
<213> ORGANISM: Artificial Sequence
<220> FEATURE:
<223> OTHER INFORMATION: KCD121 H2
```

<400> SEQUENCE: 192

Ile Asn Pro Asn Asn Gly Asp Thr Ser Tyr Asn Gln Lys Phe Arg Gly
1               5                   10                  15

<210> SEQ ID NO 193
<211> LENGTH: 9
<212> TYPE: PRT
<213> ORGANISM: Artificial Sequence
<220> FEATURE:
<223> OTHER INFORMATION: KCD121 H3

<400> SEQUENCE: 193

Ala Arg Glu Gly Pro Ser Phe Ala Tyr
1               5

<210> SEQ ID NO 194
<211> LENGTH: 16
<212> TYPE: PRT
<213> ORGANISM: Artificial Sequence
<220> FEATURE:
<223> OTHER INFORMATION: KCD121 L1

<400> SEQUENCE: 194

Arg Ser Asn Gln Thr Ile Val His Ser Asn Gly Asp Thr Tyr Leu Glu
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: KCD121 L2

<400> SEQUENCE: 195

Lys Val Ser Asn Arg Phe Ser
1               5

<210> SEQ ID NO 196
<211> LENGTH: 9
<212> TYPE: PRT
<213> ORGANISM: Artificial Sequence
<220> FEATURE:
<223> OTHER INFORMATION: KCD121 L3

<400> SEQUENCE: 196

Phe Gln Gly Ser His Val Pro Pro Thr
1               5

<210> SEQ ID NO 197
<211> LENGTH: 10
<212> TYPE: PRT
<213> ORGANISM: Artificial Sequence
<220> FEATURE:
<223> OTHER INFORMATION: KCD122 H1

<400> SEQUENCE: 197

Gly Tyr Thr Phe Thr Asp Tyr Tyr Lys Asn
1               5                   10

<210> SEQ ID NO 198
<211> LENGTH: 16
<212> TYPE: PRT
<213> ORGANISM: Artificial Sequence
<220> FEATURE:
<223> OTHER INFORMATION: KCD122 H2

```
<400> SEQUENCE: 198

Ile Asn Pro Asn Asn Gly Asp Ala Asn Tyr Asn Gln Lys Phe Lys Gly
1               5                   10                  15

<210> SEQ ID NO 199
<211> LENGTH: 9
<212> TYPE: PRT
<213> ORGANISM: Artificial Sequence
<220> FEATURE:
<223> OTHER INFORMATION: KCD122 H3

<400> SEQUENCE: 199

Ala Arg Glu Gly Pro Ser Phe Ala Tyr
1               5

<210> SEQ ID NO 200
<211> LENGTH: 16
<212> TYPE: PRT
<213> ORGANISM: Artificial Sequence
<220> FEATURE:
<223> OTHER INFORMATION: KCD122 L1

<400> SEQUENCE: 200

Arg Ser Ser Gln Thr Ile Val His Ser Asn Gly Asp Thr Tyr Leu Glu
1               5                   10                  15

<210> SEQ ID NO 201
<211> LENGTH: 7
<212> TYPE: PRT
<213> ORGANISM: Artificial Sequence
<220> FEATURE:
<223> OTHER INFORMATION: KCD122 L2

<400> SEQUENCE: 201

Lys Val Ser Asn Arg Phe Ser
1               5

<210> SEQ ID NO 202
<211> LENGTH: 9
<212> TYPE: PRT
<213> ORGANISM: Artificial Sequence
<220> FEATURE:
<223> OTHER INFORMATION: KCD122 L3

<400> SEQUENCE: 202

Phe Gln Gly Ser His Val Pro Pro Thr
1               5

<210> SEQ ID NO 203
<211> LENGTH: 10
<212> TYPE: PRT
<213> ORGANISM: Artificial Sequence
<220> FEATURE:
<223> OTHER INFORMATION: KCD123 H1

<400> SEQUENCE: 203

Gly Tyr Thr Phe Thr Asp Phe Tyr Lys Asn
1               5                   10

<210> SEQ ID NO 204
<211> LENGTH: 16
<212> TYPE: PRT
<213> ORGANISM: Artificial Sequence
<220> FEATURE:
<223> OTHER INFORMATION: KCD123 H2

<400> SEQUENCE: 204
```

```
Ile Asn Pro Asn Asn Gly Gly Thr Asn Tyr Asn Gln Lys Phe Lys Gly
1               5                   10                  15
```

<210> SEQ ID NO 205
<211> LENGTH: 9
<212> TYPE: PRT
<213> ORGANISM: Artificial Sequence
<220> FEATURE:
<223> OTHER INFORMATION: KCD123 H3

<400> SEQUENCE: 205

```
Ala Arg Glu Gly Pro Ser Phe Ala Tyr
1               5
```

<210> SEQ ID NO 206
<211> LENGTH: 16
<212> TYPE: PRT
<213> ORGANISM: Artificial Sequence
<220> FEATURE:
<223> OTHER INFORMATION: KCD123 L1

<400> SEQUENCE: 206

```
Arg Ser Ser Gln Thr Ile Val His Ser Asn Gly Asp Thr Tyr Leu Glu
1               5                   10                  15
```

<210> SEQ ID NO 207
<211> LENGTH: 7
<212> TYPE: PRT
<213> ORGANISM: Artificial Sequence
<220> FEATURE:
<223> OTHER INFORMATION: KCD123 L2

<400> SEQUENCE: 207

```
Lys Val Ser Asn Arg Phe Ser
1               5
```

<210> SEQ ID NO 208
<211> LENGTH: 9
<212> TYPE: PRT
<213> ORGANISM: Artificial Sequence
<220> FEATURE:
<223> OTHER INFORMATION: KCD123 L3

<400> SEQUENCE: 208

```
Phe Gln Gly Ser His Val Pro Pro Thr
1               5
```

<210> SEQ ID NO 209
<211> LENGTH: 10
<212> TYPE: PRT
<213> ORGANISM: Artificial Sequence
<220> FEATURE:
<223> OTHER INFORMATION: KCD124 H1

<400> SEQUENCE: 209

```
Gly Tyr Thr Phe Thr Asp His Tyr Met Asn
1               5                   10
```

<210> SEQ ID NO 210
<211> LENGTH: 16
<212> TYPE: PRT
<213> ORGANISM: Artificial Sequence
<220> FEATURE:
<223> OTHER INFORMATION: KCD124 H2

<400> SEQUENCE: 210

```
Ile Asn Pro Asn Asn Gly Gly Thr Ser Tyr Asn Gln Lys Phe Lys Gly
1               5                   10                  15

<210> SEQ ID NO 211
<211> LENGTH: 9
<212> TYPE: PRT
<213> ORGANISM: Artificial Sequence
<220> FEATURE:
<223> OTHER INFORMATION: KCD124 H3

<400> SEQUENCE: 211

Thr Arg Glu Gly Ala Ser Phe Ala Phe
1               5

<210> SEQ ID NO 212
<211> LENGTH: 16
<212> TYPE: PRT
<213> ORGANISM: Artificial Sequence
<220> FEATURE:
<223> OTHER INFORMATION: KCD124 L1

<400> SEQUENCE: 212

Arg Ser Ser Gln Ser Ile Val His Ser Asn Gly Asp Thr Tyr Leu Glu
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: KCD124 L2

<400> SEQUENCE: 213

Lys Val Ser Asn Arg Phe Ser
1               5

<210> SEQ ID NO 214
<211> LENGTH: 9
<212> TYPE: PRT
<213> ORGANISM: Artificial Sequence
<220> FEATURE:
<223> OTHER INFORMATION: KCD124 L3

<400> SEQUENCE: 214

Phe Gln Gly Ser His Val Pro Leu Thr
1               5

<210> SEQ ID NO 215
<211> LENGTH: 10
<212> TYPE: PRT
<213> ORGANISM: Artificial Sequence
<220> FEATURE:
<223> OTHER INFORMATION: KCD131 H1

<400> SEQUENCE: 215

Ala Tyr Thr Phe Thr Asp Tyr Tyr Ile Asn
1               5                   10

<210> SEQ ID NO 216
<211> LENGTH: 16
<212> TYPE: PRT
<213> ORGANISM: Artificial Sequence
<220> FEATURE:
<223> OTHER INFORMATION: KCD131 H2

<400> SEQUENCE: 216

Ile Phe Pro Gly Ser Asn Ser Thr Tyr Ser Asn Glu Lys Phe Glu Val
```

```
<210> SEQ ID NO 217
<211> LENGTH: 15
<212> TYPE: PRT
<213> ORGANISM: Artificial Sequence
<220> FEATURE:
<223> OTHER INFORMATION: KCD131 H3

<400> SEQUENCE: 217

Ala Arg Leu Gly Tyr Phe Gly Ser Ser Tyr His Ala Leu Asp Tyr
1               5                   10                  15

<210> SEQ ID NO 218
<211> LENGTH: 11
<212> TYPE: PRT
<213> ORGANISM: Artificial Sequence
<220> FEATURE:
<223> OTHER INFORMATION: KCD131 L1

<400> SEQUENCE: 218

Arg Ala Ser Glu Asn Ile Tyr Ser His Leu Ala
1               5                   10

<210> SEQ ID NO 219
<211> LENGTH: 7
<212> TYPE: PRT
<213> ORGANISM: Artificial Sequence
<220> FEATURE:
<223> OTHER INFORMATION: KCD131 L2

<400> SEQUENCE: 219

Ser Ala Thr Asn Leu Pro Asp
1               5

<210> SEQ ID NO 220
<211> LENGTH: 9
<212> TYPE: PRT
<213> ORGANISM: Artificial Sequence
<220> FEATURE:
<223> OTHER INFORMATION: KCD131 L3

<400> SEQUENCE: 220

Gln His Phe Trp Gly Thr Pro Trp Thr
1               5

<210> SEQ ID NO 221
<211> LENGTH: 10
<212> TYPE: PRT
<213> ORGANISM: Artificial Sequence
<220> FEATURE:
<223> OTHER INFORMATION: KCD136 H1

<400> SEQUENCE: 221

Gly Phe Asn Ile Lys Asn Thr Tyr Met His
1               5                   10

<210> SEQ ID NO 222
<211> LENGTH: 17
<212> TYPE: PRT
<213> ORGANISM: Artificial Sequence
<220> FEATURE:
<223> OTHER INFORMATION: KCD136 H2

<400> SEQUENCE: 222

Arg Ile Asp Pro Ala Asn Gly Ile Thr Lys Tyr Ala Pro Asn Phe Gln
1               5                   10                  15
```

Gly

<210> SEQ ID NO 223
<211> LENGTH: 6
<212> TYPE: PRT
<213> ORGANISM: Artificial Sequence
<220> FEATURE:
<223> OTHER INFORMATION: KCD136 H3

<400> SEQUENCE: 223

Thr Arg Ala Met Asp Tyr
1               5

<210> SEQ ID NO 224
<211> LENGTH: 10
<212> TYPE: PRT
<213> ORGANISM: Artificial Sequence
<220> FEATURE:
<223> OTHER INFORMATION: KCD136 L1

<400> SEQUENCE: 224

Ser Ala Ser Ser Ser Val Ser Tyr Met Tyr
1               5                   10

<210> SEQ ID NO 225
<211> LENGTH: 7
<212> TYPE: PRT
<213> ORGANISM: Artificial Sequence
<220> FEATURE:
<223> OTHER INFORMATION: KCD136 L2

<400> SEQUENCE: 225

Asp Ile Ser Asn Leu Ala Ser
1               5

<210> SEQ ID NO 226
<211> LENGTH: 9
<212> TYPE: PRT
<213> ORGANISM: Artificial Sequence
<220> FEATURE:
<223> OTHER INFORMATION: KCD136 L3

<400> SEQUENCE: 226

Gln Gln Trp Asp Thr Tyr Pro Trp Thr
1               5

<210> SEQ ID NO 227
<211> LENGTH: 10
<212> TYPE: PRT
<213> ORGANISM: Artificial Sequence
<220> FEATURE:
<223> OTHER INFORMATION: KCD200 H1

<400> SEQUENCE: 227

Gly Tyr Thr Phe Thr Ser Tyr Tyr Lys Asn
1               5                   10

<210> SEQ ID NO 228
<211> LENGTH: 16
<212> TYPE: PRT
<213> ORGANISM: Artificial Sequence
<220> FEATURE:
<223> OTHER INFORMATION: KCD200 H2

<400> SEQUENCE: 228

Ile Asn Pro Asn Ser Gly Asp Thr Ala Tyr Asn Gln Lys Phe Lys Gly

```
<210> SEQ ID NO 229
<211> LENGTH: 9
<212> TYPE: PRT
<213> ORGANISM: Artificial Sequence
<220> FEATURE:
<223> OTHER INFORMATION: KCD200 H3

<400> SEQUENCE: 229

Ala Arg Glu Gly Pro Ser Phe Ala Tyr
1               5

<210> SEQ ID NO 230
<211> LENGTH: 16
<212> TYPE: PRT
<213> ORGANISM: Artificial Sequence
<220> FEATURE:
<223> OTHER INFORMATION: KCD200 L1

<400> SEQUENCE: 230

Arg Ser Ser Gln Thr Ile Val His Ser Asn Gly Asp Thr Tyr Leu Glu
1               5                   10                  15

<210> SEQ ID NO 231
<211> LENGTH: 7
<212> TYPE: PRT
<213> ORGANISM: Artificial Sequence
<220> FEATURE:
<223> OTHER INFORMATION: KCD200 L2

<400> SEQUENCE: 231

Lys Val Ser Asn Arg Phe Ser
1               5

<210> SEQ ID NO 232
<211> LENGTH: 9
<212> TYPE: PRT
<213> ORGANISM: Artificial Sequence
<220> FEATURE:
<223> OTHER INFORMATION: KCD200 L3

<400> SEQUENCE: 232

Phe Gln Gly Ser His Val Pro Pro Thr
1               5

<210> SEQ ID NO 233
<211> LENGTH: 10
<212> TYPE: PRT
<213> ORGANISM: Artificial Sequence
<220> FEATURE:
<223> OTHER INFORMATION: KCD208 H1

<400> SEQUENCE: 233

Gly Phe Asn Ile Lys Asn Thr Tyr Met His
1               5                   10

<210> SEQ ID NO 234
<211> LENGTH: 17
<212> TYPE: PRT
<213> ORGANISM: Artificial Sequence
<220> FEATURE:
<223> OTHER INFORMATION: KCD208 H2

<400> SEQUENCE: 234

Arg Ile Asp Pro Ala Asn Gly Asp Thr Thr Tyr Ala Pro Lys Phe Gln
1               5                   10                  15
```

Gly

<210> SEQ ID NO 235
<211> LENGTH: 8
<212> TYPE: PRT
<213> ORGANISM: Artificial Sequence
<220> FEATURE:
<223> OTHER INFORMATION: KCD208 H3

<400> SEQUENCE: 235

Ser Leu Tyr Asp Tyr Asp Gly Tyr
1               5

<210> SEQ ID NO 236
<211> LENGTH: 12
<212> TYPE: PRT
<213> ORGANISM: Artificial Sequence
<220> FEATURE:
<223> OTHER INFORMATION: KCD208 L1

<400> SEQUENCE: 236

Ser Val Ser Ser Ser Ile Ser Ser Ser Ser Leu His
1               5                   10

<210> SEQ ID NO 237
<211> LENGTH: 7
<212> TYPE: PRT
<213> ORGANISM: Artificial Sequence
<220> FEATURE:
<223> OTHER INFORMATION: KCD208 L2

<400> SEQUENCE: 237

Gly Thr Ser His Leu Ala Ser
1               5

<210> SEQ ID NO 238
<211> LENGTH: 9
<212> TYPE: PRT
<213> ORGANISM: Artificial Sequence
<220> FEATURE:
<223> OTHER INFORMATION: KCD208 L3

<400> SEQUENCE: 238

Gln Gln Trp Asp Thr Tyr Pro Trp Thr
1               5

<210> SEQ ID NO 239
<211> LENGTH: 10
<212> TYPE: PRT
<213> ORGANISM: Artificial Sequence
<220> FEATURE:
<223> OTHER INFORMATION: KCD214 H1

<400> SEQUENCE: 239

Gly Phe Asn Ile Lys Asn Thr Tyr Met His
1               5                   10

<210> SEQ ID NO 240
<211> LENGTH: 17
<212> TYPE: PRT
<213> ORGANISM: Artificial Sequence
<220> FEATURE:
<223> OTHER INFORMATION: KCD214 H2

<400> SEQUENCE: 240

Arg Ile Asp Pro Ala Asn Gly Asp Thr Thr Tyr Ala Pro Lys Phe Gln

<210> SEQ ID NO 241
<211> LENGTH: 8
<212> TYPE: PRT
<213> ORGANISM: Artificial Sequence
<220> FEATURE:
<223> OTHER INFORMATION: KCD214 H3

<400> SEQUENCE: 241

Ala Leu Tyr Asp Tyr Asp Gly Tyr
1               5

<210> SEQ ID NO 242
<211> LENGTH: 12
<212> TYPE: PRT
<213> ORGANISM: Artificial Sequence
<220> FEATURE:
<223> OTHER INFORMATION: KCD214 L1

<400> SEQUENCE: 242

Arg Val Ser Ser Ser Ile Ser Ser Ser Ser Leu His
1               5                   10

<210> SEQ ID NO 243
<211> LENGTH: 7
<212> TYPE: PRT
<213> ORGANISM: Artificial Sequence
<220> FEATURE:
<223> OTHER INFORMATION: KCD214 L2

<400> SEQUENCE: 243

Gly Thr Ser Asn Leu Ala Ser
1               5

<210> SEQ ID NO 244
<211> LENGTH: 9
<212> TYPE: PRT
<213> ORGANISM: Artificial Sequence
<220> FEATURE:
<223> OTHER INFORMATION: KCD214 L3

<400> SEQUENCE: 244

Gln Gln Trp Ser Asp Tyr Pro Trp Thr
1               5

<210> SEQ ID NO 245
<211> LENGTH: 10
<212> TYPE: PRT
<213> ORGANISM: Artificial Sequence
<220> FEATURE:
<223> OTHER INFORMATION: KCD220 H1

<400> SEQUENCE: 245

Gly Tyr Thr Phe Thr Gly Tyr Trp Ile Glu
1               5                   10

<210> SEQ ID NO 246
<211> LENGTH: 17
<212> TYPE: PRT
<213> ORGANISM: Artificial Sequence
<220> FEATURE:
<223> OTHER INFORMATION: KCD220 H2

<400> SEQUENCE: 246

Glu Thr Leu Pro Gly Ser Asp Ser Asn Asn Tyr Asn Glu Lys Phe Lys
1               5                   10                  15
Gly

<210> SEQ ID NO 247
<211> LENGTH: 12
<212> TYPE: PRT
<213> ORGANISM: Artificial Sequence
<220> FEATURE:
<223> OTHER INFORMATION: KCD220 H3

<400> SEQUENCE: 247

Ala Arg Asp Tyr Ser Asn Tyr Trp Tyr Phe Asp Val
1               5                   10

<210> SEQ ID NO 248
<211> LENGTH: 11
<212> TYPE: PRT
<213> ORGANISM: Artificial Sequence
<220> FEATURE:
<223> OTHER INFORMATION: KCD220 L1

<400> SEQUENCE: 248

Arg Ala Ser Gln Asp Ile Ser Asn Tyr Leu Asn
1               5                   10

<210> SEQ ID NO 249
<211> LENGTH: 7
<212> TYPE: PRT
<213> ORGANISM: Artificial Sequence
<220> FEATURE:
<223> OTHER INFORMATION: KCD220 L2

<400> SEQUENCE: 249

Tyr Thr Ser Asn Leu His Ser
1               5

<210> SEQ ID NO 250
<211> LENGTH: 8
<212> TYPE: PRT
<213> ORGANISM: Artificial Sequence
<220> FEATURE:
<223> OTHER INFORMATION: KCD220 L3

<400> SEQUENCE: 250

Gln Gln Asp Ser Lys His Arg Thr
1               5

<210> SEQ ID NO 251
<211> LENGTH: 10
<212> TYPE: PRT
<213> ORGANISM: Artificial Sequence
<220> FEATURE:
<223> OTHER INFORMATION: KCD224 H1

<400> SEQUENCE: 251

Gly Phe Ser Leu Thr Ser Tyr Gly Val Asp
1               5                   10

<210> SEQ ID NO 252
<211> LENGTH: 16
<212> TYPE: PRT
<213> ORGANISM: Artificial Sequence
<220> FEATURE:
<223> OTHER INFORMATION: KCD224 H2

<400> SEQUENCE: 252

Val Ile Trp Gly Val Gly Ser Thr Asn Tyr Asn Ser Ala Leu Lys Ser
1               5                   10                  15

<210> SEQ ID NO 253
<211> LENGTH: 13
<212> TYPE: PRT
<213> ORGANISM: Artificial Sequence
<220> FEATURE:
<223> OTHER INFORMATION: KCD224 H3

<400> SEQUENCE: 253

Ala Arg Ser Tyr Asp Gly Ser Tyr Trp Tyr Phe Asp Val
1               5                   10

<210> SEQ ID NO 254
<211> LENGTH: 11
<212> TYPE: PRT
<213> ORGANISM: Artificial Sequence
<220> FEATURE:
<223> OTHER INFORMATION: KCD224 L1

<400> SEQUENCE: 254

Arg Ala Ser Gln Val Ile Ser Asn Tyr Leu Asn
1               5                   10

<210> SEQ ID NO 255
<211> LENGTH: 7
<212> TYPE: PRT
<213> ORGANISM: Artificial Sequence
<220> FEATURE:
<223> OTHER INFORMATION: KCD224 L2

<400> SEQUENCE: 255

Tyr Thr Ser Arg Leu His Ser
1               5

<210> SEQ ID NO 256
<211> LENGTH: 9
<212> TYPE: PRT
<213> ORGANISM: Artificial Sequence
<220> FEATURE:
<223> OTHER INFORMATION: KCD224 L3

<400> SEQUENCE: 256

Gln Gln Tyr Ser Lys Leu Pro Tyr Thr
1               5

<210> SEQ ID NO 257
<211> LENGTH: 420
<212> TYPE: DNA
<213> ORGANISM: Artificial Sequence
<220> FEATURE:
<223> OTHER INFORMATION: mAb KCD002 heavy chain

<400> SEQUENCE: 257
atgtatcgaa tgcaacttct cagttgtatt gcgttgtctt ggctttggt  cactaattct      60 gaggtgaaac ttgtagaatc tgaaggtggt cttgtccagc caggaagttc catgaaactg     120
agctgtaccg cttccgggtt tacgtttagt gattactata tggcctgggt gagacaagtg     180
cctgaaaagg gcctcgagtg gtaggaaac  attaactatg atgggtctag cacctattac     240
cttgatagtc ttaagtcacg attcattatt tcaagagact cagcaaagaa tatcctttat     300
ctgcagatgt cttctcttaa gagtgaggat acgccactt  acttctgtgc gagaggtgaa     360
gatttctacc tttatgctat ggattactgg ggcaaggca  ctagcgttac cgtctcctca     420

<210> SEQ ID NO 258
<211> LENGTH: 380
<212> TYPE: DNA
<213> ORGANISM: Artificial Sequence
<220> FEATURE:
<223> OTHER INFORMATION: mAb KCD002 light chain

<400> SEQUENCE: 258

| | | | | | |
|---|---|---|---|---|---|
| tgtaccgaat | gcagctcttg | tcctgcattg | ctttgtctct | cgctttggtc | acgaactccg | 60 |
| atattcaaat | gactcagagc | cccgcatctc | tctctgcttc | cgtaggcgaa | accgtaacaa | 120 |
| tcacttgtcg | agctagtgaa | aacatacact | cctatctcgc | ttggtaccaa | cagaaacagg | 180 |
| gaaagtcacc | acaacttatt | gtgtataaca | ccaagacgct | ggccgagggt | gtacctagtc | 240 |
| ggttttctgg | atccggtagc | ggtacacagt | tttctttgaa | aataaatagc | cttcaacctg | 300 |
| aagattttgg | atcctactat | tgccagcatc | actatgggat | accaccgacg | ttcggaggcg | 360 |
| gtacaaagct | tgaaattaaa | | | | | 380 |

<210> SEQ ID NO 259
<211> LENGTH: 408
<212> TYPE: DNA
<213> ORGANISM: Artificial Sequence
<220> FEATURE:
<223> OTHER INFORMATION: mAb KCD003 heavy chain

<400> SEQUENCE: 259

| | | | | | |
|---|---|---|---|---|---|
| atgtatagaa | tgcaattgtt | gtcctgtatc | gctctgagcc | ttgccttgt | cacgaatagc | 60 |
| gaagtccaac | ttcagcagtc | tcgccccgaa | ctggtgaagc | ctggggcgag | tgtaaaaatt | 120 |
| ttttgcaaag | catccggcta | tacatttacg | gactactaca | tgaattggat | gaggcagagg | 180 |
| cacggcgaga | cccttgagtg | gataggagac | atcaacccga | caacgggga | cccgtcatac | 240 |
| aatcagaagt | tcaaagataa | agcaactctt | actgttgata | atcctcaag | cactgcgagc | 300 |
| atggaactga | ggagtcttac | atccgacgat | tccgctgttt | actattgcgc | cagggaaggt | 360 |
| ccttccttcg | cttattgggg | tcaggggaca | ttggttaccg | tctccgca | | 408 |

<210> SEQ ID NO 260
<211> LENGTH: 396
<212> TYPE: DNA
<213> ORGANISM: Artificial Sequence
<220> FEATURE:
<223> OTHER INFORMATION: mAb KCD003 light chain

<400> SEQUENCE: 260

| | | | | | |
|---|---|---|---|---|---|
| atgtatcgaa | tgcagctctt | gtcatgtata | gcccttctc | tggctctcgt | tactaacagc | 60 |
| gatgtgttga | tgcacaaac | ccctctcagt | ctgcccgttt | cacttggcga | acaggcgagt | 120 |
| attagctgcc | gatcttccca | aactatagtt | cacagtaacg | gagatacgta | cctggagtgg | 180 |
| tacctgcaga | aaccgggcca | gtcacctaac | ttgctcattt | acaaagtctc | aaatagattc | 240 |
| tccggagttc | cagataggtt | ttccggtagt | ggttctggta | cggacttcac | tttgaagatt | 300 |
| agccgcgtcg | aggcggagga | ccttggggtc | tactattgct | ccaaggctc | ccatgtgcct | 360 |
| cccacgtttg | gaggaggcac | taagcttgaa | attaaa | | | 396 |

<210> SEQ ID NO 261
<211> LENGTH: 408
<212> TYPE: DNA
<213> ORGANISM: Artificial Sequence
<220> FEATURE:

<223> OTHER INFORMATION: mAb KCD005 heavy chain

<400> SEQUENCE: 261

```
atgtatcgga tgcaactgtt gagttgcatt gcacttagtc tcgcactcgt gacgaacagc    60
gaggtacaac tgcaacagtc tggccctgaa ttggtaaaac ccggtgcctc tgttaaaatc   120
agctgtaaag cgtccggcta tacatttaca gaccactata tgaattgggt caagcaatct   180
catggaaaat cccttgaatg gataggagat ataaatccga ataacggagg cactagttgt   240
aaccagaagt ttaagggaaa agctactctg actgtggata aatcatcttc cactgcctat   300
atggagctta ggtctcttac tagcggggac tctgcggtct actactgcac cgcgaaggg    360
gcatctttcg ctttctgggg tcagggaaca ctggttacag tctctgca                408
```

<210> SEQ ID NO 262
<211> LENGTH: 396
<212> TYPE: DNA
<213> ORGANISM: Artificial Sequence
<220> FEATURE:
<223> OTHER INFORMATION: mAb KCD005 light chain

<400> SEQUENCE: 262

```
atgtatagaa tgcaattgtt gtcatgtatc gcgctctcac tcgcattggt tactaactct    60
gatgtgttga tgacgcagac tcccctgtct ctcccagtgt cacttggcga tcaggcttct   120
atatcctgcc gaagctccca gagcattgtc acagtaacg gagacactta tctggaatgg    180
tacctccaaa agccgggcca gagtccaaaa ctttgatcct ataaagtcag taatagattt    240
agtggggttc cagacaggtt ctcaggcagc ggctcaggca ccgacttcac tctgaagata   300
agccgggttg aagctgagga tctcggggtg tattactgtt tccaagggtc acatgtacca   360
gttacatttg gagcaggcac taagcttgaa attaaa                             396
```

<210> SEQ ID NO 263
<211> LENGTH: 408
<212> TYPE: PRT
<213> ORGANISM: Artificial Sequence
<220> FEATURE:
<223> OTHER INFORMATION: mAb KCD009 heavy chain

<400> SEQUENCE: 263

```
Ala Thr Gly Thr Ala Cys Cys Gly Cys Ala Thr Gly Cys Ala Ala Cys
1               5                   10                  15

Thr Thr Cys Thr Thr Ala Gly Cys Thr Gly Thr Ala Thr Thr Gly Cys
                20                  25                  30

Cys Cys Thr Cys Thr Cys Cys Cys Thr Thr Gly Cys Ala Cys Thr Cys
            35                  40                  45

Gly Thr Thr Ala Cys Cys Ala Ala Thr Ala Gly Cys Cys Ala Gly Ala
        50                  55                  60

Thr Ala Cys Ala Ala Cys Thr Gly Gly Thr Gly Cys Ala Ala Ala Gly
65                  70                  75                  80

Cys Gly Gly Gly Cys Thr Gly Ala Gly Cys Thr Thr Ala Ala Ala Gly
                85                  90                  95

Ala Ala Ala Cys Cys Ala Gly Gly Ala Gly Ala Ala Cys Ala Gly
                100                 105                 110

Thr Cys Ala Ala Ala Ala Thr Thr Thr Cys Cys Thr Gly Cys Ala Ala
            115                 120                 125

Ala Gly Cys Gly Thr Cys Ala Gly Gly Cys Thr Ala Cys Ala Thr Ala
        130                 135                 140
```

```
Thr Thr Cys Ala Gly Gly Ala Ala Cys Thr Ala Cys Gly Gly Cys Ala
145                 150                 155                 160
Thr Gly Ala Ala Thr Gly Gly Thr Gly Ala Ala Gly Cys Ala
                165                 170                 175
Ala Gly Gly Thr Cys Gly Gly Cys Ala Ala Gly Gly Cys
                180                 185                 190
Cys Thr Cys Ala Ala Ala Thr Gly Gly Ala Thr Gly Gly Gly Gly Thr
                195                 200                 205
Gly Gly Ala Thr Cys Ala Ala Cys Ala Cys Ala Thr Ala Cys Ala Cys
                210                 215                 220
Gly Gly Gly Thr Gly Ala Gly Cys Cys Ala Cys Thr Thr Ala Cys
225                 230                 235                 240
Gly Cys Ala Gly Ala Cys Gly Ala Cys Thr Thr Cys Ala Ala Gly Gly
                245                 250                 255
Gly Ala Ala Gly Ala Thr Thr Thr Gly Cys Ala Thr Thr Thr Cys
                260                 265                 270
Ala Cys Thr Thr Gly Ala Ala Cys Gly Thr Cys Ala Gly Cys Cys
                275                 280                 285
Ala Gly Thr Ala Cys Ala Gly Cys Ala Thr Ala Thr Thr Thr Gly Cys
                290                 295                 300
Ala Gly Ala Thr Thr Thr Cys Cys Ala Ala Cys Cys Thr Thr Ala Ala
305                 310                 315                 320
Gly Ala Ala Cys Gly Ala Gly Gly Ala Thr Cys Ala Gly Cys Cys
                325                 330                 335
Ala Cys Thr Thr Ala Thr Thr Thr Cys Thr Gly Thr Gly Thr Thr Ala
                340                 345                 350
Gly Gly Gly Ala Thr Gly Gly Thr Cys Cys Ala Gly Gly Thr Thr Thr
                355                 360                 365
Thr Gly Cys Gly Thr Ala Cys Thr Gly Gly Gly Gly Cys Ala Ala
                370                 375                 380
Gly Gly Ala Ala Cys Thr Cys Thr Gly Gly Thr Gly Ala Cys Thr Gly
385                 390                 395                 400
Thr Ala Thr Cys Thr Gly Cys Ala
                405
```

<210> SEQ ID NO 264
<211> LENGTH: 396
<212> TYPE: DNA
<213> ORGANISM: Artificial Sequence
<220> FEATURE:
<223> OTHER INFORMATION: mAb KCD009 light chain

<400> SEQUENCE: 264

```
atgtaccgaa tgcagctcct gtcttgcatc gcccttagcc tcgctcttgt aacaaattct      60
gatgtattga tgactcagac acctctgtcc cttcctgtct cactcggaga ccaagcctca     120
atttcttgta gatccagtct tataatagag cattctgatg gtaatactta tctggagtgg     180
tatcttcaga aacccggtca gtctccgaag ttgcttatct acaaggtctc caatcggttt     240
tctggagttc cggataggtt ttctggctca gggagcggga ccgattttac cttgaaaatt     300
tcacgggtgg aagcagatga cttggtgtgt actattgtt tcaggggag ccatgtcccg      360
gtgacgttcg gcgctgggac caagcttgaa attaaa                              396
```

<210> SEQ ID NO 265
<211> LENGTH: 402
<212> TYPE: DNA

```
<213> ORGANISM: Artificial Sequence
<220> FEATURE:
<223> OTHER INFORMATION: mAb KCD010 heavy chain

<400> SEQUENCE: 265
atgtatcgaa tgcagctttt gtcctgtata gctttgtctt tggcccttgt gacaaattcc      60
gaggtcctgc ttcagcaatc aggccccgag ctggtcaagc caggagcatc tgtcaaaata     120
ccctgtaagg caagcggcta cacgtttacg gactacgata tggattgggt taagcaatca     180
cacggaaagt cattggagtg gataggccac atcaatccaa ataacggtgg cactatttat     240
aaccaaaagt tcaagggcaa agccacccctg accgtcgata gtcatcatc tactgcgtac     300
atggagttga ggtctctgac atcagaagat accgccgttt attactgtgg cactggggat     360
ttcgcatatt ggggacatgg aactctggtc acagtttcag ca                        402

<210> SEQ ID NO 266
<211> LENGTH: 384
<212> TYPE: DNA
<213> ORGANISM: Artificial Sequence
<220> FEATURE:
<223> OTHER INFORMATION: mAb KCD010 light chain

<400> SEQUENCE: 266
atgtatagga tgcaactgtt gtcctgcatt gctctttctc ttgcacttgt aacaaactcc      60
caaatcgtac tcacccaatc cccagccata atgtccgtca gtccaggaga aaaagttacc     120
ttgacctgca gcgcgagttc aagcgtgtcc tcctcttatt tgtactggta ccagaagaag     180
ccgggtagct ctcctaaaact ctggatctac tccaccagta acttggctag tggtgtccct     240
gcgagatttt cagggtctgg gagtgggaca tcctattccc tcacaataag ctcaatggaa     300
gctgaggatg cggcgagcta ttttgccat cagtggtcta gctacccacc tacatttggt     360
gctggaacga agcttgaaat taaa                                             384

<210> SEQ ID NO 267
<211> LENGTH: 402
<212> TYPE: DNA
<213> ORGANISM: Artificial Sequence
<220> FEATURE:
<223> OTHER INFORMATION: mAb KCD023 heavy chain

<400> SEQUENCE: 267
atgtaccgaa tgcagttgct ctcatgtatt gctcttagcc tcgccctcgt gaccaatagt      60
gaagtcctcc ttcaacaaag tggccctgaa ctcgttaaac cggggggcctc tgtcaagata    120
ccttgtaaag cgagtggcta tacctttaca gactataata ttgactgggt taaacaatca     180
catggaaaga gcctggaatg gatcggtgat ataaatccca acaacggtgg aattaactac     240
aatcaaaaat ttaaagggaa agccactctt actgttgaca agagtagctc aacggcgtac     300
atggaactcc ggtctctcac ttcagaggac acagccgtat attattgcgg gacaggagac     360
tatgcctatt ggggacaggg cactctggtc acagtttcag ca                        402

<210> SEQ ID NO 268
<211> LENGTH: 384
<212> TYPE: DNA
<213> ORGANISM: Artificial Sequence
<220> FEATURE:
<223> OTHER INFORMATION: mAb KCD023 light chain

<400> SEQUENCE: 268
atgtatagaa tgcagctctt gagctgcatc gctctttcct tggccctcgt gacaaactct      60
```

```
cagatcgtat tgacccagag ccccgccttc atgagcgcca gtcctggcga gaaagttact    120
ctcacctgct ccgcttcaag tagtgtgtcc agtagttacc tgtactggta tcaacaaaaa    180
cccggaagta gtcctaagtt gtggatttac tccacttcta atcttgccag cggagtgcct    240
ggaaggttta gtgggagtgg cagcggaact tcctacagtc ttacaatctc cagcatggaa    300
gccgaggatg cggcgtccta cttctgccac cagtggacat cctatccccc taccttcgga    360
gccgggacca agcttgaaat taaa                                           384

<210> SEQ ID NO 269
<211> LENGTH: 414
<212> TYPE: DNA
<213> ORGANISM: Artificial Sequence
<220> FEATURE:
<223> OTHER INFORMATION: mAb KCD036 heavy chain

<400> SEQUENCE: 269
atgtatagaa tgcaacttct gagttgcata gcgttgagtc tcgccttggt tacgaactct     60
gaggtgcaac tgcaacaatc tgggccggag cttgtgaagc caggagcatc tatgaaaata    120
agttgcaagg catctggata ctcttttaca ggatacacta tgcatgggt aaagcaaagc     180 cacgggaaaa atcttgaatg gatcggcctc atcaatcctt acaatggtgg gaccaattac    240
aatcagaaat ttaaagggaa ggcgacccttt actgtcgaca atcaagctc cactgcatat    300 atggaactct tgtcccttac gagcgaggac agcgcggtct attattgcgc caggcgacac    360
tacggaagct cttgggatta ctggggcaa gggaccacac tgacagtttc atca           414

<210> SEQ ID NO 270
<211> LENGTH: 381
<212> TYPE: DNA
<213> ORGANISM: Artificial Sequence
<220> FEATURE:
<223> OTHER INFORMATION: mAb KCD036 light chain

<400> SEQUENCE: 270
atgtaccgaa tgcagttgtt gagttgtata gctctgtcac tcgcgcttgt aaccaattca     60
gacataaagt tgacccaaag tccgagttca atgtatgcct ctcttggtga aagggtaacg    120
ataacttgca aggcgtccca ggatataaac acgtatctta gttggtttca acagaaaccg    180
ggtaaaagtc ccaaaactct tatctaccga gctaataggt tggtagatgg ggtgccgtca    240
agattcagcg gttcaggctc aggccaggac tactctttga ccatcagctc acttgaatac    300
gaggagatgg gcatatacta ttgcctgcaa tacgacgagt cccgtacac tttcggaggg    360 ggtacgaagc ttgaaattaa a                                              381

<210> SEQ ID NO 271
<211> LENGTH: 399
<212> TYPE: DNA
<213> ORGANISM: Artificial Sequence
<220> FEATURE:
<223> OTHER INFORMATION: mAb KCD040 heavy chain

<400> SEQUENCE: 271
atgtatagaa tgcagctcct ttcttgtatt gccctgagtt tggccttggt aactaatagt     60
gaggttcaac tccagcaaag tggcgcggag ctggtcaagc caggtgctag tgtaaaactt    120
tcatgcaccg cctccgactt caatatcaag gatacgtata tgcactgggt gatgcagcgg    180
ccagaacagg gtctggaatg gatcggtaaa atagacccgg cgaacggtaa cactgagttt    240
```

```
gaccctaaat ttcagggcaa ggcaaccatc acagctgaca cctccagtaa tacagcgtac      300
ctccagttga cctcactcac cagcgaggac accgcagtct attactgcac gcgagctatg      360
gactattggg gtcaagggac ttcagttaca gtgagctca                             399
```

<210> SEQ ID NO 272
<211> LENGTH: 378
<212> TYPE: DNA
<213> ORGANISM: Artificial Sequence
<220> FEATURE:
<223> OTHER INFORMATION: mAb KCD040 light chain

<400> SEQUENCE: 272

```
atgtaccgga tgcagttgtt gagctgtata gccctgagct ggcgcttgt cacaaactct       60 caaatcgtcc tcacgcaatc acctgcgatc atgtcagcta gtccggggga gaaagtcacg      120
atgacgtgct ctgccggatc ttccgtttct tatatgtatt ggtaccagca gaagccaggg     180
agttcccctc gcgtcttgat ttacgataca tctaatcttg ctagtggcgt cccggtccgg      240
ttctccgggt ccggcagcgg tacatcatat tctctgacga taagtaggat ggaggccgaa     300
gatgctgcaa catactattg ccagcagtgg agtaactatc cctacacttt tggcggaggc     360
actaagcttg aaattaaa                                                    378
```

<210> SEQ ID NO 273
<211> LENGTH: 399
<212> TYPE: DNA
<213> ORGANISM: Artificial Sequence
<220> FEATURE:
<223> OTHER INFORMATION: mAb KCD042 heavy chain

<400> SEQUENCE: 273

```
atgtaccgca tgcaattgct ttcttgtatt gctctgagtt tggcattggt aaccaactcc      60
gaggttcagc tccagcagtc aggtgcagaa cttgtcaaac cgggcgcgag tgtgcgcctc     120
tcttgtaccg cctcaggttt taacattaag catacatata ttcattgggt atcccagcgc     180
ccggaacaag gcttggagtg gatcgggaaa atagatcctg ccaatgggaa taccaaatac     240
gacccaaagt tccaggggaa ggccaccatt acggcagata cctcttctaa taccgcttat     300
ctccaactct catcacttac gtcagaagat accgcggttt attactgcgt taatgcaatg     360
gaatactggg gccaaggcac gtccgttaca gtatcttca                            399
```

<210> SEQ ID NO 274
<211> LENGTH: 378
<212> TYPE: DNA
<213> ORGANISM: Artificial Sequence
<220> FEATURE:
<223> OTHER INFORMATION: mAb KCD042 light chain

<400> SEQUENCE: 274

```
atgtatcgga tgcaattgct gtcttgtatc gcccttagcc tcgccctcgt cacgaacagc      60
cagtccgtgc tgacgcagag tccggcaatc atgtctgcga gtcccggtga gaaagtaacg     120
atgacttgct ccgctaatag ctccgtgagc gatatgtatt ggttccagca acggccagga     180
tcatccccgc gcttgttgat atacgacaca tctaatctgg cttccggtgt gccagttcga     240
ttctctgggt ctgggtccgg tacgtcatat agtctcacca ttagccggat ggaagcagaa     300
gatgcggcga cgtattattg ccagcaatgg agtacctatc catggacctt ggggggtgga     360
acgaagcttg aaattaaa                                                    378
```

```
<210> SEQ ID NO 275
<211> LENGTH: 399
<212> TYPE: DNA
<213> ORGANISM: Artificial Sequence
<220> FEATURE:
<223> OTHER INFORMATION: mAb KCD044 heavy chain

<400> SEQUENCE: 275
atgtatcgaa tgcaactttt gagttgcata gcactgagtc ttgctctggt aacaaactcc     60
gaggttcagc ttcagcaatc aggtgcagaa ctggtaaagc ctggggcatc cgttagactt    120
agttgtaccg caagtggatt caacataaaa cacacctata tgcattgggt cagccagaga    180
cccgaaaggg gtcttgaatg gattggcaaa atagacctg caaacgggaa tacgaaatat     240
gatccaaagt ttcagggtaa agcaactata acagccgata cgtcatccaa tacagtatac    300
ttgcaactta gcagccttac gtccgaagac accgctgtct actattgctt gaatgctatg    360
gaatactggg gacaggggac ttctgtaacc gtatcctca                           399

<210> SEQ ID NO 276
<211> LENGTH: 378
<212> TYPE: DNA
<213> ORGANISM: Artificial Sequence
<220> FEATURE:
<223> OTHER INFORMATION: mAb KCD044 light chain

<400> SEQUENCE: 276
atgtacagaa tgcaactcct gagttgcatc gcactgtctc tggcgctggt gacaaactca     60
cagtctgtcc tcacgcagag tcctgcgatt atgtccgcaa gcccagggga gaaggtaacg    120
atgacatgct ccgctaatag ctctgtgtct gatatgtatt ggtatcagca acgcccaggg    180
tctagtcccc ggctcctcat ttacgatacc agcaacctcg ctagtggcgt ccccgtgcga    240
ttttctggct ccgggtcagg gactagctac agcctcacta tctccagaat ggaagcggaa    300
gatgcagcga cgtattattg tcagcagtgg agcacatatc catggacctt tgggggtggg    360
actaagcttg aaattaaa                                                  378

<210> SEQ ID NO 277
<211> LENGTH: 399
<212> TYPE: DNA
<213> ORGANISM: Artificial Sequence
<220> FEATURE:
<223> OTHER INFORMATION: mAb KCD047 heavy chain

<400> SEQUENCE: 277
atgtatcgaa tgcaactgct ttcatgtatt gcgctttcat ggctcttgt tactaactcc      60 gaagttcaac ttcagcagtc tggagctgag tttgtaaagc ccggtgcctc agtaaggctg    120
tcttgcaccg cttctgggtt caatatcaag gacacgtaca tgcactgggt caagcaaagg    180
ccagagcagg gattggaatg gattggtcgg atcgatcctg cgaatggtta caccaaggat    240
gacccgaagt tccaaggcaa agctacgata acggcagaca cgtcaagcaa tacggcgtat    300
cttcagctta gtagcttgac ttctgaagac actgccgttt attactgtgc ttccgcaatg    360
gactactggg gccaagggac ttccgtgact gtatcatca                           399

<210> SEQ ID NO 278
<211> LENGTH: 378
<212> TYPE: DNA
<213> ORGANISM: Artificial Sequence
<220> FEATURE:
<223> OTHER INFORMATION: mAb KCD047 light chain
```

<400> SEQUENCE: 278

| | |
|---|---|
| atgtatagaa tgcagttgct ctcctgtatc gctctctctc tggctttggt gactaacagt | 60 |
| cagatcgtgc tcactcaatc acccgccgtt atgtctgcgt ctccagggga aaggtagcc | 120 |
| atgacctgct cagcaagtag cagcgtgacg tatatgtatt ggtatcagca aaaacctgga | 180 |
| agctccccca ggttgcttat atatgacact tctaatttgg cgagtggcgt acctgtacga | 240 |
| ttttctggca gcggttctgg cacaagttat agtctcacga ttagtcgcat ggaagccgaa | 300 |
| gacgccgcga cttactattg ccaacaatgg agcacatatc cattcccatt cggctccggc | 360 |
| acgaagcttg aaattaaa | 378 |

<210> SEQ ID NO 279
<211> LENGTH: 399
<212> TYPE: DNA
<213> ORGANISM: Artificial Sequence
<220> FEATURE:
<223> OTHER INFORMATION: mAb KCD048 heavy chain

<400> SEQUENCE: 279

| | |
|---|---|
| atgtaccgaa tgcaacttct gagttgcatt gccttgtccc tggcacttgt gactaatagt | 60 |
| gaagtgcagc tccaacaaag tggcgctgat ctggtcaagc tggtgcgag tgtgaaactt | 120 |
| agctgcacag cgagcgggtt caatatcaaa gcaacttaca tgcactgggt acggcagcga | 180 |
| ccggagaaag gcctcgaatg gataggccgc atcgaccccg ccaatggaca tacaatctat | 240 |
| gacccccagt ttcaggggaa ggctaccatt acgtccgata ctagtagcaa tacagcatac | 300 |
| ctccagttga actctctcac aagcgaggat acggcagtct actattgtgc ggaggcgatg | 360 |
| gattattggg gtcaaggtac atctgtgact gtttcctca | 399 |

<210> SEQ ID NO 280
<211> LENGTH: 378
<212> TYPE: DNA
<213> ORGANISM: Artificial Sequence
<220> FEATURE:
<223> OTHER INFORMATION: mAb KCD048 light chain

<400> SEQUENCE: 280

| | |
|---|---|
| atgtatcgga tgcagcttct ttcctgcatc gctcttagtc tcgccttggt tacaaattct | 60 |
| caaattgtgc tcactcagtc accagcgata atgtccgcct ctcccggtga aaaggtgact | 120 |
| ctgacatgca gcgctacatc cagcgtctca tacatgtact ggtatcagca gaagcctggt | 180 |
| tccagccctc ggctcctgat atacgacaca agtaacctgg cttccggcgt gccggtgagg | 240 |
| ttctctggaa gcgggagtgg cacctcttat tccttgacga tttccagaat ggaagcggag | 300 |
| gatgatgcga cctattattg tcaacaatgg agcaactatc cctttacttt tggcggtgga | 360 |
| acgaagcttg aaattaaa | 378 |

<210> SEQ ID NO 281
<211> LENGTH: 414
<212> TYPE: DNA
<213> ORGANISM: Artificial Sequence
<220> FEATURE:
<223> OTHER INFORMATION: mAb KCD070 heavy chain

<400> SEQUENCE: 281

| | |
|---|---|
| atgtacagaa tgcaactcct ctcctgtata gctctgtccc tggccctcgt aactaattcc | 60 |
| gagatacagt tgcaacaaac tggaccagaa cttgtcaagc caggtgcatc tgtcaagata | 120 |
| agctgcaaag cctccggtta cagctttaca gactacatta tcctgtgggt gaaacagtca | 180 |

```
catggtaaaa gtctggagtg gataggaaac ataaatcctt actacgatta taccagctat    240
aatctcaaat tcaaaggtaa agcgactctg actgtagaca aatccagctc taccgcctac    300
atgcagctta actcacttac ttctgaggac agtgccgtct actattgcgc ccgctccgac    360
ggctactacg aggggatta ctggggtcag ggtacgagtg taacggtttc atca           414
```

```
<210> SEQ ID NO 282
<211> LENGTH: 381
<212> TYPE: DNA
<213> ORGANISM: Artificial Sequence
<220> FEATURE:
<223> OTHER INFORMATION: mAb KCD070 light chain

<400> SEQUENCE: 282
atgtaccgaa tgcagcttct gagttgtatc gcgctgtcat ggccctggt cacgaactcc     60 gacatagtta tgacccagtc acacaaattt atgtccacgt cagtaggtga tcgcgtgagt    120
ataacgtgta aagcgagcca ggatgttggc accgccgtgg cgtggtatca acaaaagcct    180
ggccagtccc cgaagctcct catatattgg gccagtacga gacatacagg cgtgcctgac    240
cgattcactg gagtggttc cggcacagac ttcaccctca cgataaataa tgttcagtct    300
gaagacctgg ctgattactt ctgtcagcaa tattcttctt acccttggac atttggcgga    360
ggcaccaagc ttgaaattaa a                                              381
```

```
<210> SEQ ID NO 283
<211> LENGTH: 413
<212> TYPE: DNA
<213> ORGANISM: Artificial Sequence
<220> FEATURE:
<223> OTHER INFORMATION: mAb KCD101 heavy chain

<400> SEQUENCE: 283
tgtacaggat gcaactcctg tcttgcattg cactaagtct tgcacttgtc actaactcac     60
aggtccaact gcagcagcct ggggctgagc tggtgaggcc tgggacttca gtgaagttgt    120
cctgcaaggc ttctggctac accttcacca gctactggat gcactggta aagcagaggc    180 ctggacaagg ccttgagtgg atcggagtga ttgatcctc tgatagttat actaattaca    240
atcaaaagtt caagggcaag gccacattga ctgtagacac atcctccagc acagcctaca    300
tgcagctcag cagcctgaca tctgaggact ctgcggtcta ttactgtgga agaaatggtt    360
acgacgggtc tatggactac tggggtcaag gaacctcagt caccgtctcc tca           413
```

```
<210> SEQ ID NO 284
<211> LENGTH: 372
<212> TYPE: DNA
<213> ORGANISM: Artificial Sequence
<220> FEATURE:
<223> OTHER INFORMATION: mAb KCD101 light chain

<400> SEQUENCE: 284
atgtacagga tgcaactcct gtcttgcatt gcactaagtc ttgcacttgt cactaactca     60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac ccatcaagat tacactcagg agtcccatca    240
aggttcagtg gcagtgggtc tggaacagat tattctctca ccattagcaa cctggagcaa    300
gaagattttg ccacttactt ttgccaacag ggtaatacgc ttccgtacac gttcggaggg    360
```

```
gggaccaagc tt                                                      372
```

<210> SEQ ID NO 285
<211> LENGTH: 414
<212> TYPE: DNA
<213> ORGANISM: Artificial Sequence
<220> FEATURE:
<223> OTHER INFORMATION: mAb KCD102 heavy chain

<400> SEQUENCE: 285

```
atgtacagga tgcaactcct gtcttgcatt gcactaagtc ttgcacttgt cactaactca    60
caggtccaac tgcagcagcc tggggctgag ctggtgaggc ctgggacttc agtgaagttg   120
tcctgcaagg cttctggcta caccttcacc agctactgga tgcactgggt aaagcagagg   180
cctggacaag ccttgagtg gatcggagtg attgatcctt ctgatagtta tactaactac   240
aatcaaaagt tcaagggcaa ggccacattg actgtagaca catcctccag cacagcctac   300
atgcagctca gcagcctgac atctgaggac tctgcggtct attactgtgc aagaaatggt   360
tacgacgggg ctatggacta ctggggtcaa ggaacctcag tcaccgtctc ctca         414
```

<210> SEQ ID NO 286
<211> LENGTH: 372
<212> TYPE: DNA
<213> ORGANISM: Artificial Sequence
<220> FEATURE:
<223> OTHER INFORMATION: mAb KCD102 light chain

<400> SEQUENCE: 286

```
atgtacagga tgcaactcct gtcttgcatt gcactaagtc ttgcacttgt cactaactca    60
gaaatccaga tgacacagac tacatcctcc ctgtctgcct ctctgggaga cagagtcacc   120
atcagttgca gggcaagtca ggacattagc aattatttaa actggtatca gcagaaacca   180
gatggaactg ttaaactcct gatctactac ccatcaagat tacactcagg agtcccatca   240
aggttcagtg gcagtgggtc tggaacagat tattctctca ccattagcaa cctggagcaa   300
gaagattttg ccacttactt ttgccaacag gtaatacgc ttccgtacac gttcggaggg   360
gggaccaagc tt                                                      372
```

<210> SEQ ID NO 287
<211> LENGTH: 414
<212> TYPE: DNA
<213> ORGANISM: Artificial Sequence
<220> FEATURE:
<223> OTHER INFORMATION: mAb KCD103 heavy chain

<400> SEQUENCE: 287

```
atgtacagga tgcaactcct gtcttgcatt gcactaagtc ttgcacttgt cactaactca    60
caggtccaac tgcagcagcc tggggctgag ctggtgaggc ctgggacttc agtgaagttg   120
tcctgcaagg cttctggcta caccttcacc agctactgga tgcactgggt aaagcagagg   180
cctggacaag ccttgagtg gatcggagtg attgatcctt ctgatagtta tactaagtac   240
aatcaaaagt tcaaggacaa ggccacattg actgtagaga catcctccag cacagcctac   300
atgcagctca gcagcctgac atctgaggac tctgcggtct attactgtgc aggaaatggt   360
tacgacgggt ctatggacta ctggggtcaa ggaacctcag tcaccgtctc ctca         414
```

<210> SEQ ID NO 288
<211> LENGTH: 372
<212> TYPE: DNA
<213> ORGANISM: Artificial Sequence
<220> FEATURE:
<223> OTHER INFORMATION: mAb KCD103 light chain

<400> SEQUENCE: 288

```
atgtacagga tgcaactcct gtcttgcatt gcactaagtc ttgcacttgt cactaactca     60
gatatccaga tgacacagac tacatcctcc ctgtctgcct ctctgggaga cagagtcacc    120
atcagttgca gggcaagtca ggacattagc aattctttaa actggtatca gcagaaacca    180
gatggaactg ttaaactcct gatctactac acatcaagat tacactcacg agtcccatca    240
aggttcagtg gcagtgggtc tggaacagat tattctctca ccattagcaa cctggaccaa    300
gaagatattg ccacttactt tgccaacag gctaatacgc ttccgtacac gttcggaggg     360
gggaccaagc tt                                                        372
```

<210> SEQ ID NO 289
<211> LENGTH: 414
<212> TYPE: DNA
<213> ORGANISM: Artificial Sequence
<220> FEATURE:
<223> OTHER INFORMATION: mAb KCD104 heavy chain

<400> SEQUENCE: 289

```
atgtacagga tgcaactcct gtcttgcatt gcactaagtc ttgcacttgt cactaactca     60
caggtccaac tgcagcagcc tggggctgag ctggtgaggc ctgggacttc agtgaagttg    120
tcctgcaagg cttctggcta caccttcacc agctactgga tgcactgggt aaagcagagg    180
cctggacaag gccttgagtg gatcggagtg attgatcctt ctgatagtta tacttactac    240
aatcaaaagt tcaagggcaa ggccacattg actgtagaca catcctccag cacagcctac    300
atgcagctca gcagcctgac atctgaggac tctgcggtct attactgtgc aagaaatggt    360
tacgacgggg ctatggacta ctggggtcaa ggaacctcag tcaccgtctc ctca          414
```

<210> SEQ ID NO 290
<211> LENGTH: 372
<212> TYPE: DNA
<213> ORGANISM: Artificial Sequence
<220> FEATURE:
<223> OTHER INFORMATION: mAb KCD104 light chain

<400> SEQUENCE: 290

```
atgtacagga tgcaactcct gtcttgcatt gcactaagtc ttgcacttgt cactaactca     60
gaaatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac ccatcaagat tacactcagg agtcccatca    240
aggttcagtg gcagtgggtc tggaacagat tattctctca ccattagcaa cctggagcaa    300
gaagattttg ccacttactt tgccaacag gtaatacgc ttccgtacac gttcggaggg      360
gggaccaagc tt                                                        372
```

<210> SEQ ID NO 291
<211> LENGTH: 408
<212> TYPE: DNA
<213> ORGANISM: Artificial Sequence
<220> FEATURE:
<223> OTHER INFORMATION: mAb KCD118 heavy chain

<400> SEQUENCE: 291

```
atgtacagga tgcaactcct gtcttgcatt gcactaagtc ttgcacttgt cactaactca     60
```

```
gaggtccagc tgcaacagtc tggacctgaa ctggtgaagc ctggggcttc agtgaagata      120
tcctgtaagg cttttggata cacgttcact gactactaca agaactggat gaggcagaga      180
catggagaga gccttgagtg gattggagat attaatccta acagtggtga tgctaactac      240
aaccagaagt tcaagggcaa ggccacattg actgttgaca gtcctccag cacagcctac       300 atggagctcc gcagcctgac atctgaggac tctgcagtct attactgtgc aagagaggga      360
ccttcgtttg cttactgggg ccatgggact ctggtcactg tctctgca                   408
```

<210> SEQ ID NO 292
<211> LENGTH: 387
<212> TYPE: DNA
<213> ORGANISM: Artificial Sequence
<220> FEATURE:
<223> OTHER INFORMATION: mAb KCD118 light chain

<400> SEQUENCE: 292

```
atgtacagga tgcaactcct gtcttgcatt gcactaagtc ttgcacttgt cactaactca       60
gatgttttga tgacccaaac tccactctcc ctgcctgtca gtcttggaga tcaagcctcc      120
atctcttgca gatctagtca gaccattgtt catagtaatg agacaccta tttagaatgg       180 tacctgcaga aaccaggcca gtctccaaac ctcctgatct acaaagtttc caaccgattt      240
tctggggtcc cagacaggtt cagtggcagt ggatccggga cagatttcac actcaagatc      300
agcagagtgg aggctgagga tctgggaatt tattactgct ttcaaggttc acatgttcct      360
ccgacgttcg gtggaggcac caagctt                                          387
```

<210> SEQ ID NO 293
<211> LENGTH: 408
<212> TYPE: DNA
<213> ORGANISM: Artificial Sequence
<220> FEATURE:
<223> OTHER INFORMATION: mAb KCD119 heavy chain

<400> SEQUENCE: 293

```
atgtacagga tgcaactcct gtcttgcatt gcactaagtc ttgcacttgt cactaactca       60
gaggtccagc tgcaacagtc tggacctgaa ctggtgaagc ctggggcttc agtgaagata      120
tcctgtaagg cttctggata cactttcact gactactaca cgaactggat gaggcagaga      180
catggagaga gccttgagtg gattggagat attaatccta acactggtga tactagctac      240
aaccagaagt tcagggtcaa ggccacattg actgtagaca gtcctccgg cacagcctac       300 atggggctcc gcagcctgac atctgaggac tctgccgtct attactgtac aagagaggga      360
ccttcgtttg cttactgggg ccaagggact ctggtcactg tctctgca                   408
```

<210> SEQ ID NO 294
<211> LENGTH: 387
<212> TYPE: DNA
<213> ORGANISM: Artificial Sequence
<220> FEATURE:
<223> OTHER INFORMATION: mAb KCD119 light chain

<400> SEQUENCE: 294

```
atgtacagga tgcaactcct gtcttgcatt gcactaagtc ttgcacttgt cactaactca       60
gatgttttga tgacccaaac tccactctcc ctgcctgtca gtcttggaga tcaagcctcc      120
atctcttgca gatctagtca gaccattgta catagtaatg agacaccta tttagaatgg       180 tacctgcaga aaccaggcca gtctccaaac ctcctgatct ataaagtttc caaccgattt      240
tctggggtcc cagacaggtt cagtggcagt ggatccggga cagatttcac actcaagatc      300
```

```
agcagagtgg aggctgagga tctgggagtt tattactgct ttcaaggttc acatgttcct    360
ccgacgttcg gtggaggcac caagctt                                       387
```

<210> SEQ ID NO 295
<211> LENGTH: 408
<212> TYPE: DNA
<213> ORGANISM: Artificial Sequence
<220> FEATURE:
<223> OTHER INFORMATION: mAb KCD121 heavy chain

<400> SEQUENCE: 295

```
atgtacagga tgcaactcct gtcttgcatt gcactaagtc ttgcacttgt cactaactca    60
gaggtccagc tgcaacagtc tggacctgaa ctggtgaagc ctggggcttc agtgaagata   120
tcctgtaagg cttctggata cacgttcact gactactaca gaactggat gaggcagaga    180 catggagaga gccttgagtg gattggagat attaatccta acaatggtga tacttcctac   240
aaccagaagt tcaggggcaa ggccacattg actgtagaca gtcctccag cacagccttc    300 atggagctcc gcagcctgac atctgaggac tctgcagtct attactgtgc aagagaggga   360
ccttcctttg cttactgggg ccaagggact ctggtcactg tctctgca                408
```

<210> SEQ ID NO 296
<211> LENGTH: 387
<212> TYPE: DNA
<213> ORGANISM: Artificial Sequence
<220> FEATURE:
<223> OTHER INFORMATION: mAb KCD121 light chain

<400> SEQUENCE: 296

```
atgtacagga tgcaactcct gtcttgcatt gcactaagtc ttgcacttgt cactaactca    60
gatgttttga tgacccaaac tccactctcc ctgcctgtca gtcttggaga tcaagcctcc   120
atctcttgca gatctaatca gaccattgta catagtaatg gagacacgta tttagaatgg   180
tacctgcaga aaccaggcca gtctccaaac ctcctgatct acaaagtttc caaccgattt   240
tctggggtcc cagacaggtt cagtggcagt ggatccggga cagatttcac actcaggatc   300
agcagagtgg aggctgagga tctgggagtt tattactgct ttcaaggttc acatgttcct   360
ccgacgttcg gtggaggcac caagctt                                       387
```

<210> SEQ ID NO 297
<211> LENGTH: 408
<212> TYPE: DNA
<213> ORGANISM: Artificial Sequence
<220> FEATURE:
<223> OTHER INFORMATION: mAb KCD122 heavy chain

<400> SEQUENCE: 297

```
atgtacagga tgcaactcct gtcttgcatt gcactaagtc ttgcacttgt cactaactca    60
gaggtccagc tgcaacagtc tggacctgaa ctggtgaagc ctggggcttc agtgaagata   120
tcctgtaagg cttctggata cacgttcact gactactaca gaactggat gaggcagaga    180 catggagaga gccttgagtg gattggagat attaatccta acaatggtga tgctaactac   240
aaccagaagt tcaggggcaa ggccacattg actgttgaca gtcctccag cacagcctac    300 atggagctcc gcagcctgac atctgaggac tctgcagtct atttctgtgc aagagaggga   360
ccttcgtttg cttactgggg ccatgggact ctggtcactg tctctgca                408
```

<210> SEQ ID NO 298

```
<211> LENGTH: 387
<212> TYPE: DNA
<213> ORGANISM: Artificial Sequence
<220> FEATURE:
<223> OTHER INFORMATION: mAb KCD122 light chain

<400> SEQUENCE: 298
atgtacagga tgcaactcct gtcttgcatt gcactaagtc ttgcacttgt cactaactca      60
gatgttttga tgacccaaac tccactctcc ctgcctgtca gtcttggaga tcaagcctcc     120
atctcttgca gatctagtca gaccattgtt catagtaatg gagacaccta tttagaatgg     180
tacctgcaga aaccaggcca gtctccaaac ctcctgatct acaaagtttc caaccgattt     240
tctggggtcc cagacaggtt cagtggcagt ggatccggga cagatttcac actcaagatc     300
agcagagtgg aggctgagga tctgggagtt tattactgct ttcaaggttc acatgttcct     360
ccgacgttcg gtggaggcac caagctt                                         387

<210> SEQ ID NO 299
<211> LENGTH: 408
<212> TYPE: DNA
<213> ORGANISM: Artificial Sequence
<220> FEATURE:
<223> OTHER INFORMATION: mAb KCD123 heavy chain

<400> SEQUENCE: 299
atgtacagga tgcaactcct gtcttgcatt gcactaagtc ttgcacttgt cactaactca      60
gaggtccacc tgcaacagtc tggacctgaa ctggtgaagc ctggggcttc agtgaagata     120
tcctgtaagg cttctggata cacgttcact gacttctaca gaactggat gaggcagaga     180 catggagaga gccttgagtg gattggagat attaatccta acaatggtgg tactaactac     240
aaccagaagt tcaagggcaa ggccacattg actgtagaca gtcctccag cacagcctac     300 atggagctcc gcagcctgac atctgaggac tctgcagtct attactgtgc aagagaggga     360
ccttcgtttg cttactgggg ccaagggact ctggtcactg tctctgca                  408

<210> SEQ ID NO 300
<211> LENGTH: 387
<212> TYPE: DNA
<213> ORGANISM: Artificial Sequence
<220> FEATURE:
<223> OTHER INFORMATION: mAb KCD123 light chain

<400> SEQUENCE: 300
atgtacagga tgcaactcct gtcttgcatt gcactaagtc ttgcacttgt cactaactca      60
gatgttttga tgacccaaac tccactctcc ctgcctgtca gtcttggaga tcaagcctcc     120
atctcttgca gatctagtca gaccattgtt catagtaatg gagacaccta tttagaatgg     180
tacctgcaga aaccaggcca gtctccaaac ctcctgatct acaaagtttc caaccgattt     240
tctggggtcc cagacaggtt cagtggcagt ggatccggga cagatttcac actcaagatc     300
agcagagtgg aggctgagga tctgggagtt tattactgct ttcaaggttc acatgttcct     360
ccgacgttcg gtggaggcac caagctt                                         387

<210> SEQ ID NO 301
<211> LENGTH: 408
<212> TYPE: DNA
<213> ORGANISM: Artificial Sequence
<220> FEATURE:
<223> OTHER INFORMATION: mAb KCD124 heavy chain

<400> SEQUENCE: 301
```

```
atgtacagga tgcaactcct gtcttgcatt gcactaagtc ttgcacttgt cactaactca    60
gaagtccagc tccaacagtc tggacctgag ctggtgaagc ctggggcttc agtgaagata   120
tcctgtaagg cttctggata cacattcact gaccactaca tgaactgggt gaaacagagc   180
catggaaaga gccttgagtg gattggagat attaatccta caatggtgg tactagctac    240 aaccagaagt tcaagggcaa ggccacattg actgtagaca gtcctccag cacagcctac    300 atggagctcc gcagcctgac atctggggac tctgcagtct attactgtac aagagagggg   360
gcctcgtttg ctttctgggg ccaagggact ctggtcactg tctctgca               408
```

<210> SEQ ID NO 302
<211> LENGTH: 387
<212> TYPE: DNA
<213> ORGANISM: Artificial Sequence
<220> FEATURE:
<223> OTHER INFORMATION: mAb KCD124 light chain

<400> SEQUENCE: 302

```
atgtacagga tgcaactcct gtcttgcatt gcactaagtc ttgcacttgt cactaactca    60
gatgttttga tgacccaaac tccactctcc ctgcctgtca gtcttggaga tcaagcctcc   120
atctcttgca gatctagtca gagcattgta catagtaatg gagacaccta tttagagtgg   180
tacctgcaga agccaggcca gtctccaaag ctcctgatct acaaagtttc caaccgattt   240
tctggggtcc cagacaggtt cagtggcagt ggatcaggga cagatttcac actcaagatc   300
agcagagtgg aggctgagga tctgggagtt tattactgct ttcaaggttc acatgttccg   360
ctcacgttcg gtgctgggac caagctt                                      387
```

<210> SEQ ID NO 303
<211> LENGTH: 426
<212> TYPE: DNA
<213> ORGANISM: Artificial Sequence
<220> FEATURE:
<223> OTHER INFORMATION: mAb KCD131 heavy chain

<400> SEQUENCE: 303

```
atgtacagga tgcaactcct gtcttgcatt gcactaagtc ttgcacttgt cactaactca    60
caggtccagc tacagcagtc tggacctgag ctggtgaagc ctggggcttc agtgaagatc   120
tcctgcaagg cttctgccta caccttcact gactactata aaactgggt gaagcagagg    180 cctggacagg gacctgagtg gattggatgg attttcctg aagtaatag tacttattcc     240 aatgagaagt tcgaggtcaa ggccacactg actgtagacg aatcctccag cacagcctac   300
atgttgctca gcagcctgac ctctgaggac tctgcggtct atttctgtgc aagattggga   360
tacttcggta gtagttacca tgcttttgac tactggggtc aaggcacctc agtcaccgtc   420
tcctca                                                             426
```

<210> SEQ ID NO 304
<211> LENGTH: 372
<212> TYPE: DNA
<213> ORGANISM: Artificial Sequence
<220> FEATURE:
<223> OTHER INFORMATION: mAb KCD131 light chain

<400> SEQUENCE: 304

```
atgtacagga tgcaactcct gtcttgcatt gcactaagtc ttgcacttgt cactaactca    60
gacatccaga tgactcagtc tccagcctcc ctatctgtat ctgtgggaga aactgtcacc   120
```

```
atcacatgtc gagcaagtga gaatatttac agtcatttag catggtttca gcagaaacag      180
ggaaaatctc ctcggctcct ggtctattct gcaacaaact taccagatgg tgtgccatca      240
agattcagtg gcagtggatc aggcacacag tattccctca agatcaacat cctgcagtct      300
gaagattttg ggagttatta ctgtcaacat ttttggggta ctccgtggac gttcggtgga      360
ggcaccaagc tt                                                          372

<210> SEQ ID NO 305
<211> LENGTH: 399
<212> TYPE: DNA
<213> ORGANISM: Artificial Sequence
<220> FEATURE:
<223> OTHER INFORMATION: mAb KCD136 heavy chain

<400> SEQUENCE: 305
atgtacagga tgcaactcct gtcttgcatt gcactaagtc ttgcacttgt cactaactca       60
gaggttcagc tgcagcagtc tgtggcagag cttgtgaggc caggggcctc agtcaagttg      120
tcctgctcag cttctggctt caacattaaa aacacctata tgcactgggt gaaccagagg      180
cctgaacagg gcctggagtg gattggaagg attgatcctg cgaatggtat tactaaatat      240
gccccgaact tccagggcaa ggccactata actgcagaca catcttccaa cacagcctac      300
ctgcagctca gcaacctgac atctgaggac actgccatct attactgtac tagggctatg      360
gactactggg gtcaaggaac ctcagtcacc gtctcctca                             399

<210> SEQ ID NO 306
<211> LENGTH: 369
<212> TYPE: DNA
<213> ORGANISM: Artificial Sequence
<220> FEATURE:
<223> OTHER INFORMATION: mAb KCD136 light chain

<400> SEQUENCE: 306
atgtacagga tgcaactcct gtcttgcatt gcactaagtc ttgcacttgt cactaactca       60
caaattgttc tcacccagtc tccagcaatc atgtctgcat ctccagggga aaggtcacc      120 atgacctgca gtgccagctc aagtgtaagt tacatgtact ggtaccagca aaagccagga      180
tcctccccca gactcctgat ttatgacata tccaacctgg cttctggagt ccctgttcgc      240
ttcagtggca gtgggtctgg gacctcttac tctctcacaa tcagccgaat ggaggctgaa      300
gatgctgcca cttattactg ccagcagtgg gatacttacc cgtggacgtt cggtggaggc      360
accaagctt                                                              369

<210> SEQ ID NO 307
<211> LENGTH: 408
<212> TYPE: DNA
<213> ORGANISM: Artificial Sequence
<220> FEATURE:
<223> OTHER INFORMATION: mAb KCD200 heavy chain

<400> SEQUENCE: 307
atgtacagga tgcaactcct gtcttgcatt gcactaagtc ttgcacttgt cactaactca       60
gaggtccagc tgcaacagtc tggacctgaa ctggtgaagc ctggggcttc agtgaagata      120
tcctgtaagg cttccggata cacgttcacc agctactaca gaactggat gaggcagaga      180 catggagaga gccttgagtg gattggagat attaatccta acagtggtga tactgcctac      240
aaccagaagt tcaagggcaa ggccacattg actgtagaca ggtcctccag cacagcctac      300
atggagctcc gcagcctgac atctgaggac tctgcagtct attactgtgc aagagaggga      360
```

```
ccttcgtttg cttactgggg ccaagggact ctggtcactg tctctgca         408
```

```
<210> SEQ ID NO 308
<211> LENGTH: 387
<212> TYPE: DNA
<213> ORGANISM: Artificial Sequence
<220> FEATURE:
<223> OTHER INFORMATION: mAb KCD200 light chain

<400> SEQUENCE: 308
atgtacagga tgcaactcct gtcttgcatt gcactaagtc ttgcacttgt cactaactca    60
gatgttttga tgacccaaac tccactctcc ctgcctgtca gtcttggaga tcaagtctcc   120
atctcttgca gatctagtca gaccattgtt catagtaatg agacaccta tttggaatgg    180
tacctgcaga aaccaggcca gtctccaaat ctcctgatct acaaagtttc caaccgtttt   240
tctggggtcc cagacaggtt cagtggcagt ggatccggga cagatttcac actcaagatc   300
agcagagtgg aggctgagga tctgggagtg tattactgct ttcaaggttc acatgttcct   360
ccgacgttcg gtggaggcac caagctt                                       387
```

```
<210> SEQ ID NO 309
<211> LENGTH: 405
<212> TYPE: DNA
<213> ORGANISM: Artificial Sequence
<220> FEATURE:
<223> OTHER INFORMATION: mAb KCD208 heavy chain

<400> SEQUENCE: 309
atgtacagga tgcaactcct gtcttgcatt gcactaagtc ttgcacttgt cactaactca    60
gaggttcagc tgcagcagtc tgtggcagag cttgtgaggc caggggcctc agtcaagttg   120
tcctgcacag tttctggctt caacattaaa aacacctata tgcactgggt gaagcagagg   180
cctgaacagg gcctggagtg gattggaagg attgatcctg cgaatggtga tactacatat   240
gccccgaagt tccagggcaa ggccactata actgcagaca catcctccaa ctcagcctac   300
ctgcacctca gccgcctgac atctgaggac actgccatct attactgttc tctttatgat   360
tacgacggct actggggcca aggcaccact ctcacagtct cctca                   405
```

```
<210> SEQ ID NO 310
<211> LENGTH: 375
<212> TYPE: DNA
<213> ORGANISM: Artificial Sequence
<220> FEATURE:
<223> OTHER INFORMATION: mAb KCD208 light chain

<400> SEQUENCE: 310
atgtacagga tgcaactcct gtcttgcatt gcactaagtc ttgcacttgt cactaactca    60
gaaattgtgc tcacccagtc tccagcactc atggctgcat ctccagggga aaggtcacc   120
atcacctgca gtgtcagctc aagtataagt tccagctcct acactggta ccggcagaag   180
tcaggaacct cccccaaacc ctggatttat ggcacatccc accttgcttc tggagtccct   240
gttcgcttca gtggcagtgg atctgggacc tcttattctc tcacaatcag cagcatggag   300
gctgaagatg ctgccactta ttactgtcaa cagtgggata cttacccgtg gacgttcggt   360
ggaggcacca agctt                                                    375
```

```
<210> SEQ ID NO 311
<211> LENGTH: 405
<212> TYPE: DNA
```

<213> ORGANISM: Artificial Sequence
<220> FEATURE:
<223> OTHER INFORMATION: mAb KCD214 heavy chain

<400> SEQUENCE: 311

| | |
|---|---|
| atgtacagga tgcaactcct gtcttgcatt gcactaagtc ttgcacttgt cactaactca | 60 |
| gaggttcagc tgcagcagtc tgtggcagag tttgtgaggc caggggcctc agtcaagttg | 120 |
| tcctgcacag cttctggctt caacattaaa aacacctata tgcactgggt gaagcagagg | 180 |
| cctgaacagg gcctggaatg gattggaagg attgatcctg cgaatggtaa tactgaatat | 240 |
| gccccgaagt tccagggcaa ggccactata actgcagaca tcctccaa cacagcctac | 300 |
| ctgcagctca gcagcctgac atctgaggac actgccatct attactgtgc tctttatgat | 360 |
| tacgacggct actggggcca aggcaccact ctcacagtct cctca | 405 |

<210> SEQ ID NO 312
<211> LENGTH: 375
<212> TYPE: DNA
<213> ORGANISM: Artificial Sequence
<220> FEATURE:
<223> OTHER INFORMATION: mAb KCD214 light chain

<400> SEQUENCE: 312

| | |
|---|---|
| atgtacagga tgcaactcct gtcttgcatt gcactaagtc ttgcacttgt cactaactca | 60 |
| gaaattgtgc tcacccagtc tccagcactc atggctgcat ctccagggga aaggtcacc | 120 |
| atcacctgcc gtgtcagctc aagtataagt tccagcagct acactggta ccagcaaaag | 180 |
| tcaggaacct cccccaaacc ctggatttat ggcacctcca accttgcttc tggagtccct | 240 |
| gttcgcttca gtggcagtag atctgggacc tcttattctc tcacaatcag cagcatggag | 300 |
| gctgaagatg ctgccactta ttactgtcaa cagtggagtg attacccgtg gacgttcggt | 360 |
| ggaggcacca agctt | 375 |

<210> SEQ ID NO 313
<211> LENGTH: 417
<212> TYPE: DNA
<213> ORGANISM: Artificial Sequence
<220> FEATURE:
<223> OTHER INFORMATION: mAb KCD220 heavy chain

<400> SEQUENCE: 313

| | |
|---|---|
| atgtacagga tgcaactcct gtcttgcatt gcactaagtc ttgcacttgt cactaactca | 60 |
| caggttcagc tgcaacagtc tggagctgag ctgatggagc ctggggcctc agtgaagctt | 120 |
| tcctgcaagg ctactggcta cacattcact ggctactgga tagagtgggt aaagcagagg | 180 |
| cctggacatg gccttgagtg gattggagag actttacctg gaagtgatag taataattac | 240 |
| aatgagaagt tcaagggcaa ggccacattc actgcagata tcctccaa cacagcctac | 300 |
| atgcaactca gcagcctgac aactgaggac tctgccatct attactgtgc aagagactat | 360 |
| agtaactact ggtacttcga tgtctggggc acagggacca cggtcaccgt ctcctca | 417 |

<210> SEQ ID NO 314
<211> LENGTH: 369
<212> TYPE: DNA
<213> ORGANISM: Artificial Sequence
<220> FEATURE:
<223> OTHER INFORMATION: mAb KCD220 light chain

<400> SEQUENCE: 314

| | |
|---|---|
| atgtacagga tgcaactcct gtcttgcatt gcactaagtc ttgcacttgt cactaactca | 60 |

```
gatatccaga tgacacagac tacatcctcc ctgtctgcct ctctgggaga cagagtcacc      120
attagttgca gggcaagtca ggacattagc aattatttaa actggtatca gcagaaacca      180
gatggaactg ttaaactcct gatctactac acatcaaact tacactcagg agtcccatca      240
aggttcagtg gcagtgggtc tgggacagat tattctctca ctattagtaa cctggaacaa      300
gaagatattg ccacttactt ttgccaacag gatagtaagc atcggacgtt cggtggaggc      360
accaagctt                                                              369

<210> SEQ ID NO 315
<211> LENGTH: 417
<212> TYPE: DNA
<213> ORGANISM: Artificial Sequence
<220> FEATURE:
<223> OTHER INFORMATION: mAb KCD224 heavy chain

<400> SEQUENCE: 315
atgtacagga tgcaactcct gtcttgcatt gcactaagtc ttgcacttgt cactaactca       60
caggtgcagc tgaaggagtc aggacctggc ctggtggcgc cctcacagag cctgtccatc      120
acatgcactg tctctgggtt ctcattaacc agctatggtg tagactggat tcgccagtct      180
ccaggaaagg gtctggagtg gctgggagta atatgggtg ttggaagcac aaattataat       240
tcagctctca aatccagact gagcatcagc aaggacaact ccaagagcca agttttctta      300
aaaatgaaca gtctgcaaac tgatgacaca gccatgtact actgtgcccg ctcctatgat      360
ggttcctact ggtacttcga tgtctggggc acagggacca cggtcaccgt ctcctca        417

<210> SEQ ID NO 316
<211> LENGTH: 372
<212> TYPE: DNA
<213> ORGANISM: Artificial Sequence
<220> FEATURE:
<223> OTHER INFORMATION: mAb KCD224 light chain

<400> SEQUENCE: 316
atgtacagga tgcaactcct gtcttgcatt gcactaagtc ttgcacttgt cactaactca       60
gatatccaga tgacacagac tacatcctcc ctgtctgcct ctctgggaga cagagtcacc      120
atcagttgca gggcaagtca ggttattagc aattatttaa actggtatca gcagaaacca      180
gatggaactg ttaaactcct gatctactac acatcaagat tacactcagg agtcccatca      240
aggttcagtg gcagtgggtc tgggacagat tattctctca ccatcagcaa cctggaacct      300
gaagatattg ccacttacta ttgtcagcag tatagtaaac ttccgtatac gttcggatcg      360
gggaccaagc tt                                                          372

<210> SEQ ID NO 317
<211> LENGTH: 349
<212> TYPE: DNA
<213> ORGANISM: Artificial Sequence
<220> FEATURE:
<223> OTHER INFORMATION: mAb 119_TAF heavy chain

<400> SEQUENCE: 317
gaggtgcagc tggtggaatc tggcggcgga ctggtgcagc ctggcggctc cctgagactg       60
tcttgcgccg cctccggcta caccttcacc gactactaca tgaactgggt gcgacaggcc      120
cctggcaagg gcctggaatg gatcggcgac atcaacccca caccggcga caccagctac       180 aacgccgact tcaagcggcg gttcaccttc tccctgacca cctccaagtc caccgcctac      240
```

```
ctgcagatga actccctgcg ggccgaggac accgccgtgt actactgtac cagagagggc    300
ccctccttcg cctactgggg ccagggcaca ctggtgacag tgtcctccg                349
```

<210> SEQ ID NO 318
<211> LENGTH: 337
<212> TYPE: DNA
<213> ORGANISM: Artificial Sequence
<220> FEATURE:
<223> OTHER INFORMATION: mAb 119_TAF light chain

<400> SEQUENCE: 318

```
gacatccagc tgacccagag cccctccagc ctgtccgcct ctgtgggcga cagagtgacc    60
atcacctgtc ggtcctccca gaccatcgtg cactccaacg gcgacaccta cctggaatgg    120
tatcagcaga agcccggcaa ggccctaac ctgctgatct acaaggtgtc caaccggttc    180
tccggcgtgc cctccagatt ctccggctcc ggctctggca ccgacttcac cctgaccatc    240
tccagcctgc agcccgagga cttcgccacc tactactgtt ttcaaggctc ccacgtgcca    300
cccaccttcg gccagggcac caaggtggaa atcaagc                             337
```

<210> SEQ ID NO 319
<211> LENGTH: 351
<212> TYPE: DNA
<213> ORGANISM: Artificial Sequence
<220> FEATURE:
<223> OTHER INFORMATION: mAb 119_TAF Germ heavy chain

<400> SEQUENCE: 319

```
gaggtgcagc tggtggaatc tggcggcgga ctggtgcagc ctggcggctc cctgagactg    60
tcttgcgccg cctccggcta caccttcacc gactactaca tgtcctgggt gcgacaggcc    120
cctggcaagg gcctggaatg gatcggcgac atcaacccca caccggcga caccagctac    180 aacgccgact ccgtgaaggg ccggttcacc atctcccggg acaactccaa gaacaccctg    240
tacctgcaga tgaactccct gcgggccgag gacaccgccg tgtactactg taccagagag    300
ggcccctcct tcgcctactg ggggccagggc acactggtga cagtgtcctc c             351
```

<210> SEQ ID NO 320
<211> LENGTH: 336
<212> TYPE: DNA
<213> ORGANISM: Artificial Sequence
<220> FEATURE:
<223> OTHER INFORMATION: mAb 119_TAF Germ light chain

<400> SEQUENCE: 320

```
gacgtggtga tgacccagtc ccctctgtcc ctgcccgtga cctgggcca gcctgcctcc    60 atctcctgcc ggtcctccca gaccatcgtg cactccaacg gcgacaccta cctggaatgg    120
ttccagcagc ggcctggcca gtcccctaac ctgctgatct acaaggtgtc caaccggttc    180
tccggcgtgc ccgacagatt ctccggctcc ggctctggca ccgacttcac cctgaagatc    240
tcccgggtgg aagccgagga cgtgggcgtg tactactgtt ttcaaggctc ccacgtgcca    300
cccaccttcg gcggaggcac caaggtggaa atcaag                              336
```

<210> SEQ ID NO 321
<211> LENGTH: 348
<212> TYPE: DNA
<213> ORGANISM: Artificial Sequence
<220> FEATURE:
<223> OTHER INFORMATION: mAb 119_Human Germ heavy chain

<400> SEQUENCE: 321
caggtgcagc tggtgcagtc tggcgccgaa gtgaagaaac ctggcgcctc cgtgaaggtg 60
tcctgcaagg cctccggcta caccttcacc gactactaca tgcactgggt gcgacaggcc 120
ccaggccagg gcctggaatg gatcggcgac atcaacccca acaccggcga caccagctac 180

aaccagaaat tccagggcag agtgacctcc acccgggaca cctccatctc caccgcctac 240
atggaactgt cccggctgcg gagcgacgac accgtggtgt actactgtac cagagagggc 300
ccctccttcg cctactgggg ccagggcaca ctggtgacag tgtcctcc 348

<210> SEQ ID NO 322
<211> LENGTH: 336
<212> TYPE: DNA
<213> ORGANISM: Artificial Sequence
<220> FEATURE:
<223> OTHER INFORMATION: mAb 119_Human Germ light chain

<400> SEQUENCE: 322
gacatccaga tgacccagag cccctccagc ctgtccgcct ccgtgggcga cagagtgacc 60
atcacctgtc ggtcctccca gaccatcgtg cactccaacg gcgacaccta cctggaatgg 120
tatcagcaga agcccggcaa ggcccctaac ctgctgatct acaaggtgtc caaccggttc 180
tccggcgtgc cctccagatt ctccggctcc ggctctggca ccgacttcac cctgaccatc 240
tccagcctgc agcccgagga cttcgccacc tactactgtt ttcaaggctc ccacgtgcca 300
cccaccttcg gccagggcac caaggtggaa atcaag 336

<210> SEQ ID NO 323
<211> LENGTH: 13
<212> TYPE: PRT
<213> ORGANISM: Artificial Sequence
<220> FEATURE:
<223> OTHER INFORMATION: CDR1 light chain (lead)
<220> FEATURE:
<221> NAME/KEY: VARIANT
<222> LOCATION: (2)...(2)
<223> OTHER INFORMATION: Xaa = T, D, G, H, I, N, Q, R, V or W
<220> FEATURE:
<221> NAME/KEY: VARIANT
<222> LOCATION: (3)...(3)
<223> OTHER INFORMATION: Xaa = I, A or V
<220> FEATURE:
<221> NAME/KEY: VARIANT
<222> LOCATION: (4)...(4)
<223> OTHER INFORMATION: Xaa = V, A, D, E, F, I, K, L, Q, R, S, W or Y
<220> FEATURE:
<221> NAME/KEY: VARIANT
<222> LOCATION: (6)...(6)
<223> OTHER INFORMATION: Xaa = S, A, D, F, G, I, R, T, V or W
<220> FEATURE:
<221> NAME/KEY: VARIANT
<222> LOCATION: (8)...(8)
<223> OTHER INFORMATION: Xaa = G, E, F, or S
<220> FEATURE:
<221> NAME/KEY: VARIANT
<222> LOCATION: (9)...(9)
<223> OTHER INFORMATION: Xaa = D or E
<220> FEATURE:
<221> NAME/KEY: VARIANT
<222> LOCATION: (10)...(10)
<223> OTHER INFORMATION: Xaa = T, S or V
<220> FEATURE:
<221> NAME/KEY: VARIANT
<222> LOCATION: (12)...(12)
<223> OTHER INFORMATION: Xaa = L or I

<400> SEQUENCE: 323

Gln Xaa Xaa Xaa His Xaa Asn Xaa Xaa Xaa Tyr Xaa Glu
1 5 10

```
<210> SEQ ID NO 324
<211> LENGTH: 11
<212> TYPE: PRT
<213> ORGANISM: Artificial Sequence
<220> FEATURE:
<223> OTHER INFORMATION: CDR2 light chain (lead)
<220> FEATURE:
<221> NAME/KEY: VARIANT
<222> LOCATION: (1)...(1)
<223> OTHER INFORMATION: Xaa = N, D, E, R, S, V or Y
<220> FEATURE:
<221> NAME/KEY: VARIANT
<222> LOCATION: (2)...(2)
<223> OTHER INFORMATION: Xaa = L or I
<220> FEATURE:
<221> NAME/KEY: VARIANT
<222> LOCATION: (4)...(4)
<223> OTHER INFORMATION: Xaa = I or T
<220> FEATURE:
<221> NAME/KEY: VARIANT
<222> LOCATION: (5)...(5)
<223> OTHER INFORMATION: Xaa = Y, D, E, F, G, L, R, S, T or V
<220> FEATURE:
<221> NAME/KEY: VARIANT
<222> LOCATION: (7)...(7)
<223> OTHER INFORMATION: Xaa = V, A or I
<220> FEATURE:
<221> NAME/KEY: VARIANT
<222> LOCATION: (8)...(8)
<223> OTHER INFORMATION: Xaa = S, A, F, G, K, L, Q, R, T or Y
<220> FEATURE:
<221> NAME/KEY: VARIANT
<222> LOCATION: (9)...(9)
<223> OTHER INFORMATION: Xaa = N, E, G, H, I, L, Q, R, T or Y
<220> FEATURE:
<221> NAME/KEY: VARIANT
<222> LOCATION: (11)...(11)
<223> OTHER INFORMATION: Xaa = F, E, G, I, L, R or W

<400> SEQUENCE: 324

Xaa Xaa Leu Xaa Xaa Lys Xaa Xaa Xaa Arg Xaa
1               5                   10

<210> SEQ ID NO 325
<211> LENGTH: 9
<212> TYPE: PRT
<213> ORGANISM: Artificial Sequence
<220> FEATURE:
<223> OTHER INFORMATION: CDR3 light chain (lead)
<220> FEATURE:
<221> NAME/KEY: VARIANT
<222> LOCATION: (1)...(1)
<223> OTHER INFORMATION: Xaa = F or M
<220> FEATURE:
<221> NAME/KEY: VARIANT
<222> LOCATION: (5)...(5)
<223> OTHER INFORMATION: Xaa = H, A, E, F, G, L, N, Q, T, V, W or Y
<220> FEATURE:
<221> NAME/KEY: VARIANT
<222> LOCATION: (6)...(6)
<223> OTHER INFORMATION: Xaa = V, W, Q or N
<220> FEATURE:
<221> NAME/KEY: VARIANT
<222> LOCATION: (8)...(8)
<223> OTHER INFORMATION: Xaa = P or V

<400> SEQUENCE: 325

Xaa Gln Gly Ser Xaa Xaa Pro Xaa Thr
1               5

<210> SEQ ID NO 326
<211> LENGTH: 9
<212> TYPE: PRT
```

```
<213> ORGANISM: Artificial Sequence
<220> FEATURE:
<223> OTHER INFORMATION: CDR1 heavy chain (lead)
<220> FEATURE:
<221> NAME/KEY: VARIANT
<222> LOCATION: (3)...(3)
<223> OTHER INFORMATION: Xaa = T, D, E, F, H, I, K, P, R, S, W or Y
<220> FEATURE:
<221> NAME/KEY: VARIANT
<222> LOCATION: (6)...(6)
<223> OTHER INFORMATION: Xaa = D, A, F, G, S, V or Y
<220> FEATURE:
<221> NAME/KEY: VARIANT
<222> LOCATION: (7)...(7)
<223> OTHER INFORMATION: Xaa = Y or F
<220> FEATURE:
<221> NAME/KEY: VARIANT
<222> LOCATION: (8)...(8)
<223> OTHER INFORMATION: Xaa = Y or P
<220> FEATURE:
<221> NAME/KEY: VARIANT
<222> LOCATION: (9)...(9)
<223> OTHER INFORMATION: Xaa = M, H or I

<400> SEQUENCE: 326

Gly Tyr Xaa Phe Thr Xaa Xaa Xaa Xaa
1               5

<210> SEQ ID NO 327
<211> LENGTH: 14
<212> TYPE: PRT
<213> ORGANISM: Artificial Sequence
<220> FEATURE:
<223> OTHER INFORMATION: CDR2 heavy chain (lead)
<220> FEATURE:
<221> NAME/KEY: VARIANT
<222> LOCATION: (5)...(5)
<223> OTHER INFORMATION: Xaa =I, L or V
<220> FEATURE:
<221> NAME/KEY: VARIANT
<222> LOCATION: (6)...(6)
<223> OTHER INFORMATION: Xaa = N, A or G
<220> FEATURE:
<221> NAME/KEY: VARIANT
<222> LOCATION: (7)...(7)
<223> OTHER INFORMATION: Xaa = P or T
<220> FEATURE:
<221> NAME/KEY: VARIANT
<222> LOCATION: (8)...(8)
<223> OTHER INFORMATION: Xaa = N, A, D, G, H, I, L, R, T,V, W or Y
<220> FEATURE:
<221> NAME/KEY: VARIANT
<222> LOCATION: (9)...(9)
<223> OTHER INFORMATION: Xaa = T, I, K, L, Q, R, S or V
<220> FEATURE:
<221> NAME/KEY: VARIANT
<222> LOCATION: (10)...(10)
<223> OTHER INFORMATION: Xaa = G or V
<220> FEATURE:
<221> NAME/KEY: VARIANT
<222> LOCATION: (11)...(11)
<223> OTHER INFORMATION: Xaa = any amino acid
<220> FEATURE:
<221> NAME/KEY: VARIANT
<222> LOCATION: (12)...(12)
<223> OTHER INFORMATION: Xaa = any amino acid except I
<220> FEATURE:
<221> NAME/KEY: VARIANT
<222> LOCATION: (13)...(13)
<223> OTHER INFORMATION: Xaa = any amino acid except K or R
<220> FEATURE:
<221> NAME/KEY: VARIANT
<222> LOCATION: (14)...(14)
<223> OTHER INFORMATION: Xaa = any amino acid except I or W

<400> SEQUENCE: 327
```

```
Trp Ile Gly Asp Xaa Xaa Xaa Xaa Xaa Xaa Xaa Xaa Xaa
1               5                   10
```

<210> SEQ ID NO 328
<211> LENGTH: 9
<212> TYPE: PRT
<213> ORGANISM: Artificial Sequence
<220> FEATURE:
<223> OTHER INFORMATION: CDR3 heavy chain (lead)
<220> FEATURE:
<221> NAME/KEY: VARIANT
<222> LOCATION: (1)...(1)
<223> OTHER INFORMATION: Xaa = T, A or Q
<220> FEATURE:
<221> NAME/KEY: VARIANT
<222> LOCATION: (6)...(6)
<223> OTHER INFORMATION: Xaa = S or A
<220> FEATURE:
<221> NAME/KEY: VARIANT
<222> LOCATION: (8)...(8)
<223> OTHER INFORMATION: Xaa = A or R
<220> FEATURE:
<221> NAME/KEY: VARIANT
<222> LOCATION: (9)...(9)
<223> OTHER INFORMATION: Xaa = Y, A, H, F, V, Y or L

<400> SEQUENCE: 328

```
Xaa Arg Glu Gly Pro Xaa Phe Xaa Xaa
1               5
```

<210> SEQ ID NO 329
<211> LENGTH: 11
<212> TYPE: PRT
<213> ORGANISM: Artificial Sequence
<220> FEATURE:
<223> OTHER INFORMATION: CDR1 light chain (lead)
<220> FEATURE:
<221> NAME/KEY: VARIANT
<222> LOCATION: (2)...(2)
<223> OTHER INFORMATION: Xaa = T, D, G, H, I, N, Q, R, V or W
<220> FEATURE:
<221> NAME/KEY: VARIANT
<222> LOCATION: (3)...(3)
<223> OTHER INFORMATION: Xaa = I, A or V
<220> FEATURE:
<221> NAME/KEY: VARIANT
<222> LOCATION: (4)...(4)
<223> OTHER INFORMATION: Xaa = V, A, D, E, F, I, K, L, Q, R, S, W or Y
<220> FEATURE:
<221> NAME/KEY: VARIANT
<222> LOCATION: (6)...(6)
<223> OTHER INFORMATION: Xaa = S, A, D, F, G, I, R, T, V or W
<220> FEATURE:
<221> NAME/KEY: VARIANT
<222> LOCATION: (8)...(8)
<223> OTHER INFORMATION: Xaa = G, E, F or S
<220> FEATURE:
<221> NAME/KEY: VARIANT
<222> LOCATION: (9)...(9)
<223> OTHER INFORMATION: Xaa = D or E
<220> FEATURE:
<221> NAME/KEY: VARIANT
<222> LOCATION: (10)...(10)
<223> OTHER INFORMATION: Xaa = T, S or V

<400> SEQUENCE: 329

```
Gln Xaa Xaa Xaa His Xaa Asn Xaa Xaa Xaa Tyr
1               5                   10
```

<210> SEQ ID NO 330
<211> LENGTH: 3
<212> TYPE: PRT
<213> ORGANISM: Artificial Sequence
<220> FEATURE:

```
<223> OTHER INFORMATION: CDR2 light chain (lead)
<220> FEATURE:
<221> NAME/KEY: VARIANT
<222> LOCATION: (2)...(2)
<223> OTHER INFORMATION: Xaa = V, A or I
<220> FEATURE:
<221> NAME/KEY: VARIANT
<222> LOCATION: (3)...(3)
<223> OTHER INFORMATION: Xaa = S, A, F, G, K, L, Q, R, T or Y

<400> SEQUENCE: 330

Lys Xaa Xaa
1

<210> SEQ ID NO 331
<211> LENGTH: 9
<212> TYPE: PRT
<213> ORGANISM: Artificial Sequence
<220> FEATURE:
<223> OTHER INFORMATION: CDR3 light chain (lead)
<220> FEATURE:
<221> NAME/KEY: VARIANT
<222> LOCATION: (1)...(1)
<223> OTHER INFORMATION: Xaa = F or M
<220> FEATURE:
<221> NAME/KEY: VARIANT
<222> LOCATION: (5)...(5)
<223> OTHER INFORMATION: Xaa = H, A, E, F, G, L, N, Q, T, V, W or Y
<220> FEATURE:
<221> NAME/KEY: VARIANT
<222> LOCATION: (6)...(6)
<223> OTHER INFORMATION: Xaa = V, W, Q or N
<220> FEATURE:
<221> NAME/KEY: VARIANT
<222> LOCATION: (8)...(8)
<223> OTHER INFORMATION: Xaa = P or V

<400> SEQUENCE: 331

Xaa Gln Gly Ser Xaa Xaa Pro Xaa Thr
1               5

<210> SEQ ID NO 332
<211> LENGTH: 3
<212> TYPE: PRT
<213> ORGANISM: Artificial Sequence
<220> FEATURE:
<223> OTHER INFORMATION: CDR1 heavy chain (lead)
<220> FEATURE:
<221> NAME/KEY: VARIANT
<222> LOCATION: (1)...(1)
<223> OTHER INFORMATION: Xaa = D, A, F, G, S, V or Y
<220> FEATURE:
<221> NAME/KEY: VARIANT
<222> LOCATION: (2)...(2)
<223> OTHER INFORMATION: Xaa = Y or F
<220> FEATURE:
<221> NAME/KEY: VARIANT
<222> LOCATION: (3)...(3)
<223> OTHER INFORMATION: Xaa = Y or P

<400> SEQUENCE: 332

Xaa Xaa Xaa
1

<210> SEQ ID NO 333
<211> LENGTH: 8
<212> TYPE: PRT
<213> ORGANISM: Artificial Sequence
<220> FEATURE:
<223> OTHER INFORMATION: CDR2 heavy chain (lead)
<220> FEATURE:
<221> NAME/KEY: VARIANT
<222> LOCATION: (1)...(1)
```

```
<223> OTHER INFORMATION: Xaa = I, L or V
<220> FEATURE:
<221> NAME/KEY: VARIANT
<222> LOCATION: (2)...(2)
<223> OTHER INFORMATION: Xaa = N, A or G
<220> FEATURE:
<221> NAME/KEY: VARIANT
<222> LOCATION: (3)...(3)
<223> OTHER INFORMATION: Xaa = P or T
<220> FEATURE:
<221> NAME/KEY: VARIANT
<222> LOCATION: (4)...(4)
<223> OTHER INFORMATION: Xaa = N, A, D, G, H, I, L, R, T, V, W or Y
<220> FEATURE:
<221> NAME/KEY: VARIANT
<222> LOCATION: (5)...(5)
<223> OTHER INFORMATION: Xaa =T, I, K, L, Q, R, S or V
<220> FEATURE:
<221> NAME/KEY: VARIANT
<222> LOCATION: (6)...(6)
<223> OTHER INFORMATION: Xaa = G or V
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (8)...(8)
<223> OTHER INFORMATION: Xaa = any amino acid except I

<400> SEQUENCE: 333

Xaa Xaa Xaa Xaa Xaa Xaa Xaa Xaa
1               5

<210> SEQ ID NO 334
<211> LENGTH: 7
<212> TYPE: PRT
<213> ORGANISM: Artificial Sequence
<220> FEATURE:
<223> OTHER INFORMATION: CDR3 heavy chain (lead)
<220> FEATURE:
<221> NAME/KEY: VARIANT
<222> LOCATION: (4)...(4)
<223> OTHER INFORMATION: Xaa = S or A
<220> FEATURE:
<221> NAME/KEY: VARIANT
<222> LOCATION: (6)...(6)
<223> OTHER INFORMATION: Xaa = A or R
<220> FEATURE:
<221> NAME/KEY: VARIANT
<222> LOCATION: (7)...(7)
<223> OTHER INFORMATION: Xaa = Y, A, H, F, V, Y or L

<400> SEQUENCE: 334

Glu Gly Pro Xaa Phe Xaa Xaa
1               5

<210> SEQ ID NO 335
<211> LENGTH: 121
<212> TYPE: PRT
<213> ORGANISM: Artificial Sequence
<220> FEATURE:
<223> OTHER INFORMATION: KCD001 heavy chain variable region AA sequence

<400> SEQUENCE: 335

Glu Val Gln Leu Gln Gln Ser Gly Pro Glu Leu Val Lys Pro Gly Ala
1               5                   10                  15

Ser Val Lys Ile Ser Cys Lys Ala Ser Asp Asn Ser Phe Thr Gly Tyr
            20                  25                  30

Tyr Met His Trp Val Lys Gln Ser His Gly Asn Ile Leu Asp Trp Ile
        35                  40                  45
```

```
Gly Tyr Ile Asp Pro Tyr Asn Gly Val Ser Ser Tyr Asn Gln Lys Phe
    50                  55                  60

Lys Gly Lys Ala Thr Leu Thr Val Asp Lys Ser Ser Thr Ala Tyr
65              70                  75                  80

Met Glu Ile Arg Ser Leu Thr Ser Glu Asp Ser Ala Val Tyr Tyr Cys
                85                  90                  95

Ala Ser Tyr Tyr Gly Ser Ser Pro Tyr Trp Tyr Phe Asp Val Trp Gly
            100                 105                 110

Thr Gly Thr Thr Val Thr Val Ser Ser
            115                 120

<210> SEQ ID NO 336
<211> LENGTH: 106
<212> TYPE: PRT
<213> ORGANISM: Artificial Sequence
<220> FEATURE:
<223> OTHER INFORMATION: KCD001 light chain variable region AA sequence

<400> SEQUENCE: 336

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser His Phe Leu Thr Ile Ser Arg Leu Glu Ala Glu
65              70                  75                  80

Asp Ala Ala Thr Tyr Phe Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 337
<211> LENGTH: 120
<212> TYPE: PRT
<213> ORGANISM: Artificial Sequence
<220> FEATURE:
<223> OTHER INFORMATION: KCD002 heavy chain variable region AA sequence

<400> SEQUENCE: 337

Glu Val Lys Leu Val Glu Ser Glu Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Gly Asn Ile Asn Tyr Asp Gly Ser Ser Thr Tyr Tyr Leu Asp Ser Leu
        50                  55                  60

Lys Ser Arg Phe Ile Ile Ser Arg Asp Ser Ala Lys Asn Ile Leu Tyr
65              70                  75                  80

Leu Gln Met Ser Ser Leu Lys Ser Glu Asp Thr Ala Thr Tyr Phe Cys
                85                  90                  95

Ala Arg Gly Glu Asp Phe Tyr Leu Tyr Ala Met Asp Tyr Trp Gly Gln
            100                 105                 110

Gly Thr Ser Val Thr Val Ser Ser
            115                 120
```

<210> SEQ ID NO 338
<211> LENGTH: 107
<212> TYPE: PRT
<213> ORGANISM: Artificial Sequence
<220> FEATURE:
<223> OTHER INFORMATION: KCD002 light chain variable region AA sequence

<400> SEQUENCE: 338

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile His Ser Tyr
            20                  25                  30

Leu Ala Trp Tyr Gln Gln Lys Gln Gly Lys Ser Pro Gln Leu Ile Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Pro
                85                  90                  95

Thr Phe Gly Gly Gly Thr Lys Leu Glu Ile Lys
            100                 105

<210> SEQ ID NO 339
<211> LENGTH: 116
<212> TYPE: PRT
<213> ORGANISM: Artificial Sequence
<220> FEATURE:
<223> OTHER INFORMATION: KCD003 heavy chain variable region AA sequence

<400> SEQUENCE: 339

Glu Val Gln Leu Gln Gln Ser Arg Pro Glu Leu Val Lys Pro Gly Ala
1               5                   10                  15

Ser Val Lys Ile Phe Cys Lys Ala Ser Gly Tyr Thr Phe Thr Asp Tyr
            20                  25                  30

Tyr Met Asn Trp Met Arg Gln Arg His Gly Glu Thr Leu Glu Trp Ile
        35                  40                  45

Gly Asp Ile Asn Pro Asn Asn Gly Asp Pro Ser Tyr Asn Gln Lys Phe
    50                  55                  60

Lys Asp Lys Ala Thr Leu Thr Val Asp Lys Ser Ser Ser Thr Ala Ser
65                  70                  75                  80

Met Glu Leu Arg Ser Leu Thr Ser Asp Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 340
<211> LENGTH: 112
<212> TYPE: PRT
<213> ORGANISM: Artificial Sequence
<220> FEATURE:
<223> OTHER INFORMATION: KCD003 light chain variable region AA sequence

<400> SEQUENCE: 340

Asp Val Leu Met Thr Gln Thr Pro Leu Ser Leu Pro Val Ser Leu Gly
1               5                   10                  15

```
Glu Gln Ala Ser Ile Ser Cys Arg Ser Ser Gln Thr Ile Val His Ser
                20                  25                  30

Asn Gly Asp Thr Tyr Leu Glu Trp Tyr Leu Lys Pro Gly Gln Ser
            35                  40                  45

Pro Asn Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Lys Leu Glu Ile Lys
                100                 105                 110
```

<210> SEQ ID NO 341
<211> LENGTH: 119
<212> TYPE: PRT
<213> ORGANISM: Artificial Sequence
<220> FEATURE:
<223> OTHER INFORMATION: KCD004 heavy chain variable region AA sequence

<400> SEQUENCE: 341

```
Glu Val Gln Leu Gln Gln Ser Gly Ala Glu Leu Val Arg Pro Gly Ser
1               5                   10                  15

Ser Val Lys Met Ser Cys Lys Thr Ser Gly Lys Thr Phe Thr Ser His
                20                  25                  30

Gly Ile Asn Trp Val Lys Gln Arg Pro Gly Gln Gly Leu Glu Trp Ile
            35                  40                  45

Gly Tyr Ile Tyr Ile Gly Asn Gly Tyr Asn Glu Tyr Asn Glu Lys Phe
 50                  55                  60

Lys Gly Lys Ala Thr Leu Thr Ser Asp Thr Ser Ser Ser Thr Ala Tyr
65                  70                  75                  80

Met Gln Leu Ser Ser Leu Thr Phe Glu Asp Ser Ala Ile Tyr Phe Cys
                 85                  90                  95

Val Arg Lys Ala Tyr Gly Asn Tyr Gly Phe Asp Asp Trp Gly Gln Gly
                100                 105                 110

Thr Thr Leu Thr Val Ser Ser
            115
```

<210> SEQ ID NO 342
<211> LENGTH: 107
<212> TYPE: PRT
<213> ORGANISM: Artificial Sequence
<220> FEATURE:
<223> OTHER INFORMATION: KCD004 light chain variable region AA sequence

<400> SEQUENCE: 342

```
Asp Ile Gln Met Thr Gln Ser Pro Thr Ser Leu Ser Ala Ser Leu Gly
1               5                   10                  15

Glu Ser Val Ser Leu Thr Cys Arg Ala Ser Gln Glu Ile Ser Gly Tyr
                20                  25                  30

Leu Asn Trp Leu Gln Gln Lys Pro Asp Gly Ser Ile Lys Arg Leu Ile
            35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Asn Tyr Pro Phe
                 85                  90                  95
```

-continued

Thr Phe Gly Ser Gly Thr Lys Leu Glu Val Lys
                100                 105

<210> SEQ ID NO 343
<211> LENGTH: 116
<212> TYPE: PRT
<213> ORGANISM: Artificial Sequence
<220> FEATURE:
<223> OTHER INFORMATION: KCD005 heavy chain variable region AA sequence

<400> SEQUENCE: 343

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Cys Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Gly Asp Ser Ala Val Tyr Tyr Cys
                85                  90                  95

Thr Arg Glu Gly Ala Ser Phe Ala Phe Trp Gly Gln Gly Thr Leu Val
                100                 105                 110

Thr Val Ser Ala
        115

<210> SEQ ID NO 344
<211> LENGTH: 112
<212> TYPE: PRT
<213> ORGANISM: Artificial Sequence
<220> FEATURE:
<223> OTHER INFORMATION: KCD005 light chain variable region AA sequence

<400> SEQUENCE: 344

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Val Thr Phe Gly Ala Gly Thr Lys Leu Glu Leu Lys
                100                 105                 110

<210> SEQ ID NO 345
<211> LENGTH: 113
<212> TYPE: PRT
<213> ORGANISM: Artificial Sequence
<220> FEATURE:
<223> OTHER INFORMATION: KCD006 heavy chain variable region AA sequence

<400> SEQUENCE: 345

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Met His Trp Val Lys Glu Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Asn Ala Met Asp Tyr Trp Gly Gln Gly Thr Ser Val Thr Val Ser
            100                 105                 110

Ser
```

<210> SEQ ID NO 346
<211> LENGTH: 106
<212> TYPE: PRT
<213> ORGANISM: Artificial Sequence
<220> FEATURE:
<223> OTHER INFORMATION: KCD006 light chain variable region AA sequence

<400> SEQUENCE: 346

```
Gln Ile Ile Leu Thr Gln Ser Pro Ala Ile Met Ser Ala Ser Pro Gly
1               5                   10                  15

Glu Lys Val Thr Met Thr Cys Ser Ala Arg Ser Ser Val Ser Asn Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Trp Thr
                85                  90                  95

Phe Gly Gly Gly Thr Lys Leu Glu Ile Lys
            100                 105
```

<210> SEQ ID NO 347
<211> LENGTH: 113
<212> TYPE: PRT
<213> ORGANISM: Artificial Sequence
<220> FEATURE:
<223> OTHER INFORMATION: KCD007 heavy chain variable region AA sequence

<400> SEQUENCE: 347

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Met His Trp Val Lys Glu Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80
```

-continued

Leu Gln Leu Ser Ser Leu Thr Ser Glu Asp Thr Ala Val Tyr Tyr Cys
                85                  90                  95

Ala Asn Ala Met Asp Tyr Trp Gly Gln Gly Thr Ser Val Thr Val Ser
            100                 105                 110

Ser

<210> SEQ ID NO 348
<211> LENGTH: 106
<212> TYPE: PRT
<213> ORGANISM: Artificial Sequence
<220> FEATURE:
<223> OTHER INFORMATION: KCD007 light chain variable region AA sequence

<400> SEQUENCE: 348

Gln Ile Ile Leu Thr Gln Ser Pro Ala Ile Met Ser Ala Ser Pro Gly
1               5                   10                  15

Glu Arg Val Thr Met Thr Cys Ser Ala Ser Ser Ser Val Ser Asn Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Leu Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Trp Thr
                85                  90                  95

Phe Gly Gly Gly Thr Lys Leu Glu Ile Lys
            100                 105

<210> SEQ ID NO 349
<211> LENGTH: 113
<212> TYPE: PRT
<213> ORGANISM: Artificial Sequence
<220> FEATURE:
<223> OTHER INFORMATION: KCD008 heavy chain variable region AA sequence

<400> SEQUENCE: 349

Glu Val Gln Leu Gln Gln Ser Gly Pro Glu Leu Val Lys Ala Gly Ala
1               5                   10                  15

Ser Val Lys Met Ser Cys Thr Ala Ser Gly Phe Asn Ile Lys Asp Thr
            20                  25                  30

Tyr Met His Trp Val Lys Gln Arg Pro Glu Gln Gly Leu Ala Trp Ile
        35                  40                  45

Gly Arg Ile Asp Pro Ala Asn Gly Asn Ile Lys Tyr Asp Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Asp Asp Thr Ala Val Tyr Tyr Cys
                85                  90                  95

Thr Ser Ala Met Asp Tyr Trp Gly Gln Gly Thr Ser Val Thr Val Ser
            100                 105                 110

Ser

<210> SEQ ID NO 350
<211> LENGTH: 106
<212> TYPE: PRT
<213> ORGANISM: Artificial Sequence
<220> FEATURE:
<223> OTHER INFORMATION: KCD008 light chain variable region AA sequence

<400> SEQUENCE: 350

Gln Ile Val Leu Thr Gln Ser Pro Glu Ile Met Ser Ala Ser Pro Gly
1               5                   10                  15

Glu Lys Val Thr Met Thr Cys Ser Ala Arg Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Thr Glu
65                  70                  75                  80

Asp Ala Ala Thr Tyr Tyr Cys Gln Gln Trp Ser Thr Tyr Pro Phe Thr
                85                  90                  95

Phe Gly Ser Gly Thr Lys Leu Glu Ile Lys
            100                 105

<210> SEQ ID NO 351
<211> LENGTH: 116
<212> TYPE: PRT
<213> ORGANISM: Artificial Sequence
<220> FEATURE:
<223> OTHER INFORMATION: KCD009 heavy chain variable region AA sequence

<400> SEQUENCE: 351

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Arg Asn Tyr
            20                  25                  30

Gly Met Asn Trp Val Lys Gln Gly Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Val Arg Asp Gly Pro Gly Phe Ala Tyr Trp Gly Gln Gly Thr Leu Val
            100                 105                 110

Thr Val Ser Ala
        115

<210> SEQ ID NO 352
<211> LENGTH: 112
<212> TYPE: PRT
<213> ORGANISM: Artificial Sequence
<220> FEATURE:
<223> OTHER INFORMATION: KCD009 light chain variable region AA sequence

<400> SEQUENCE: 352

Asp Val Leu Met Thr Gln Thr Pro Leu Ser Leu Pro Val Ser Leu Gly
1               5                   10                  15

Asp Gln Ala Ser Ile Ser Cys Arg Ser Ser Leu Ile Ile Glu His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Gly
                85                  90                  95

Ser His Val Pro Val Thr Phe Gly Ala Gly Thr Asn Leu Glu Leu Lys
            100                 105                 110
```

<210> SEQ ID NO 353
<211> LENGTH: 114
<212> TYPE: PRT
<213> ORGANISM: Artificial Sequence
<220> FEATURE:
<223> OTHER INFORMATION: KCD010 heavy chain variable region AA sequence

<400> SEQUENCE: 353

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asp Met Asp Trp Val Lys Gln Ser His Gly Lys Ser Leu Glu Trp Ile
            35                  40                  45

Gly His Ile Asn Pro Asn Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Gly Thr Gly Asp Phe Ala Tyr Trp Gly His Gly Thr Leu Val Thr Val
            100                 105                 110

Ser Ala
```

<210> SEQ ID NO 354
<211> LENGTH: 108
<212> TYPE: PRT
<213> ORGANISM: Artificial Sequence
<220> FEATURE:
<223> OTHER INFORMATION: KCD010 light chain variable region AA sequence

<400> SEQUENCE: 354

```
Gln Ile Val Leu Thr Gln Ser Pro Ala Ile Met Ser Val Ser Pro Gly
1               5                   10                  15

Glu Lys Val Thr Leu Thr Cys Ser Ala Ser Ser Ser Val Ser Ser Ser
                20                  25                  30

Tyr Leu Tyr Trp Tyr Gln Lys Lys Pro Gly Ser Ser Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Ala Gly Thr Lys Leu Glu Leu Lys
            100                 105
```

<210> SEQ ID NO 355
<211> LENGTH: 117
<212> TYPE: PRT
<213> ORGANISM: Artificial Sequence

```
<220> FEATURE:
<223> OTHER INFORMATION: KCD011 heavy chain variable region AA sequence

<400> SEQUENCE: 355

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Asn
            20                  25                  30

Thr Met Ser Trp Val Arg Gln Thr Pro Glu Lys Arg Leu Glu Trp Val
        35                  40                  45

Ala Tyr Ile Thr Asn Gly Gly Ser Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asp Tyr Tyr Thr Met Asp Tyr Trp Gly Gln Gly Thr Ser
            100                 105                 110

Val Thr Val Ser Ser
        115

<210> SEQ ID NO 356
<211> LENGTH: 107
<212> TYPE: PRT
<213> ORGANISM: Artificial Sequence
<220> FEATURE:
<223> OTHER INFORMATION: KCD011 light chain variable region AA sequence

<400> SEQUENCE: 356

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys
            100                 105

<210> SEQ ID NO 357
<211> LENGTH: 113
<212> TYPE: PRT
<213> ORGANISM: Artificial Sequence
<220> FEATURE:
<223> OTHER INFORMATION: KCD013 heavy chain variable region AA sequence

<400> SEQUENCE: 357

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Met His Trp Val Lys Glu Arg Pro Asp Gln Gly Leu Glu Trp Ile
        35                  40                  45
```

Gly Arg Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Asn Ala Met Asp Tyr Trp Gly Gln Gly Thr Ser Val Thr Val Ser
                100                 105                 110

Ser

<210> SEQ ID NO 358
<211> LENGTH: 106
<212> TYPE: PRT
<213> ORGANISM: Artificial Sequence
<220> FEATURE:
<223> OTHER INFORMATION: KCD013 light chain variable region AA sequence

<400> SEQUENCE: 358

Gln Ile Ile Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Asn Met
                 20                  25                  30

Tyr Trp Tyr Gln Gln Lys Pro Gly Ser Ser Pro Arg Leu Leu Ile Tyr
             35                  40                  45

Asp Thr Ser Asn Leu Ala Ser Gly Val Pro Val Arg Phe Ser Gly Ser
 50                  55                  60

Gly Ser Gly Ala Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Trp Thr
                 85                  90                  95

Phe Gly Gly Gly Thr Lys Leu Glu Ile Lys
            100                 105

<210> SEQ ID NO 359
<211> LENGTH: 118
<212> TYPE: PRT
<213> ORGANISM: Artificial Sequence
<220> FEATURE:
<223> OTHER INFORMATION: KCD014 heavy chain variable region AA sequence

<400> SEQUENCE: 359

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
                 20                  25                  30

Ile Met Ser Trp Val Arg Gln Thr Pro Glu Lys Arg Leu Glu Trp Val
             35                  40                  45

Ala Tyr Ile Thr Asn Gly Gly Gly Asn Thr Tyr Tyr Pro Asp Thr Ile
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Gly Thr Gly Tyr Ala Met Asp Tyr Trp Gly Gln Gly Thr
                100                 105                 110

Ser Val Thr Val Ser Ser
            115

<210> SEQ ID NO 360
<211> LENGTH: 108
<212> TYPE: PRT
<213> ORGANISM: Artificial Sequence
<220> FEATURE:
<223> OTHER INFORMATION: KCD014 light chain variable region AA sequence

<400> SEQUENCE: 360

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys
            100                 105

<210> SEQ ID NO 361
<211> LENGTH: 113
<212> TYPE: PRT
<213> ORGANISM: Artificial Sequence
<220> FEATURE:
<223> OTHER INFORMATION: KCD015 heavy chain variable region AA sequence

<400> SEQUENCE: 361

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Glu Tyr Asp Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ser Ala Ala Tyr Tyr Cys
                85                  90                  95

Thr Ser Ala Met Glu Phe Trp Gly Gln Gly Thr Ser Val Thr Val Ser
            100                 105                 110

Ser

<210> SEQ ID NO 362
<211> LENGTH: 106
<212> TYPE: PRT
<213> ORGANISM: Artificial Sequence
<220> FEATURE:
<223> OTHER INFORMATION: KCD015 light chain variable region AA sequence

<400> SEQUENCE: 362

Gln Ile Val Leu Thr Gln Ser Pro Ala Ile Leu Ser Ala Ser Pro Gly
1               5                   10                  15

Glu Lys Val Thr Met Thr Cys Ser Ala Ser Ser Ser Val Ser Tyr Ile
            20                  25                  30

```
Tyr Trp Tyr Gln Gln Lys Pro Arg Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Phe Thr
                85                  90                  95

Phe Gly Gly Gly Thr Lys Leu Glu Val Lys
            100                 105

<210> SEQ ID NO 363
<211> LENGTH: 122
<212> TYPE: PRT
<213> ORGANISM: Artificial Sequence
<220> FEATURE:
<223> OTHER INFORMATION: KCD016 heavy chain variable region AA sequence

<400> SEQUENCE: 363

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Phe
            20                  25                  30

Trp Met His Trp Val Lys Gln Arg Pro Gly Gln Gly Leu Glu Trp Ile
        35                  40                  45

Gly Phe Phe Asn Pro Ser Thr Ala Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Leu His Leu Ser Ser Leu Thr Ser Glu Asp Ser Ala Val Tyr Tyr Cys
                85                  90                  95

Ala Arg Arg Asp Tyr Gly Ser Ser Tyr Gly Trp Tyr Phe Asp Val Trp
            100                 105                 110

Gly Ala Gly Thr Thr Val Thr Val Ser Ser
        115                 120

<210> SEQ ID NO 364
<211> LENGTH: 106
<212> TYPE: PRT
<213> ORGANISM: Artificial Sequence
<220> FEATURE:
<223> OTHER INFORMATION: KCD016 light chain variable region AA sequence

<400> SEQUENCE: 364

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Tyr Tyr Tyr Cys Gln His Phe Trp Ser Thr Pro Thr
                85                  90                  95

Phe Gly Gly Gly Thr Lys Leu Glu Ile Lys
            100                 105
```

<210> SEQ ID NO 365
<211> LENGTH: 122
<212> TYPE: PRT
<213> ORGANISM: Artificial Sequence
<220> FEATURE:
<223> OTHER INFORMATION: KCD017 heavy chain variable region AA sequence

<400> SEQUENCE: 365

Asp Val Gln Leu Gln Glu Ser Gly Pro Asp Leu Val Lys Pro Ser Gln
1               5                   10                  15

Ser Leu Ser Leu Thr Cys Thr Val Thr Asp Tyr Ser Ile Thr Ser Gly
            20                  25                  30

Tyr Ser Trp His Trp Ile Arg Gln Phe Pro Gly Asn Lys Leu Glu Trp
        35                  40                  45

Leu Gly Tyr Ile His Ser Ser Gly Asn Thr Asn Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Leu His Tyr Tyr Gly Ser Ser Phe Gly Trp Tyr Phe Asp Val Trp
            100                 105                 110

Gly Ala Gly Thr Thr Val Thr Val Ser Ser
        115                 120

<210> SEQ ID NO 366
<211> LENGTH: 107
<212> TYPE: PRT
<213> ORGANISM: Artificial Sequence
<220> FEATURE:
<223> OTHER INFORMATION: KCD017 light chain variable region AA sequence

<400> SEQUENCE: 366

Asp Ile Val Met Thr Gln Ser His Lys Phe Met Ser Thr Ser Val Gly
1               5                   10                  15

Asp Arg Val Tyr Ile Thr Cys Lys Ala Ser Gln Asp Val Gly Thr Ala
            20                  25                  30

Val Ala Trp Tyr Gln Gln Thr Ser Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Leu Ser Asn Val Gln Ser
65                  70                  75                  80

Glu Asp Leu Ala Asp Tyr Phe Cys Gln Gln Tyr Thr Ser Tyr Pro Leu
                85                  90                  95

Thr Phe Gly Ala Gly Thr Lys Leu Glu Leu Lys
            100                 105

<210> SEQ ID NO 367
<211> LENGTH: 119
<212> TYPE: PRT
<213> ORGANISM: Artificial Sequence
<220> FEATURE:
<223> OTHER INFORMATION: KCD018 heavy chain variable region AA sequence

<400> SEQUENCE: 367

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Val His Trp Val Lys Gln Arg Pro Gly Gln Gly Leu Glu Trp Ile
            35                  40                  45

Gly Tyr Ile Asn Pro Ser Ser Gly Phe Thr Asp Tyr Asn Gln Lys Phe
50                      55                  60

Lys Asp Lys Thr Thr Leu Thr Ala Asp Ile Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Arg Gly Val Asn Trp Ser Trp Phe Ala Tyr Trp Gly Gln Gly
                100                 105                 110

Thr Leu Val Thr Val Ser Ala
        115

<210> SEQ ID NO 368
<211> LENGTH: 112
<212> TYPE: PRT
<213> ORGANISM: Artificial Sequence
<220> FEATURE:
<223> OTHER INFORMATION: KCD018 light chain variable region AA sequence

<400> SEQUENCE: 368

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Gln Leu Leu Ile Tyr Trp Ala Ser Thr Arg Glu Ser Gly Val
    50                  55                  60

Pro Glu Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Trp Thr Phe Gly Gly Gly Thr Lys Leu Glu Ile Lys
                100                 105                 110

<210> SEQ ID NO 369
<211> LENGTH: 122
<212> TYPE: PRT
<213> ORGANISM: Artificial Sequence
<220> FEATURE:
<223> OTHER INFORMATION: KCD019 heavy chain variable region AA sequence

<400> SEQUENCE: 369

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Ala Thr Tyr
            20                  25                  30

Thr Ile His Trp Val Lys Gln Arg Pro Gly Gln Gly Leu Glu Trp Ile
            35                  40                  45

Gly Tyr Leu Asn Leu Arg Asn Asp Tyr Thr His Tyr Asn Gln Lys Phe
        50                  55                  60

Arg Asp Lys Ala Ala Leu Thr Ala Asp Lys Ser Ser Ser Thr Ala Tyr
65                  70                  75                  80

Met Gln Leu Ser Ser Leu Thr Ser Glu Asp Ser Ala Val Tyr Asn Cys

```
                85                  90                  95
Ala Phe Arg Leu Gly Asn Asp Arg Gln Gly Trp Tyr Phe Asp Val Trp
            100                 105                 110

Gly Ala Gly Thr Thr Val Thr Val Ser Ser
        115                 120

<210> SEQ ID NO 370
<211> LENGTH: 107
<212> TYPE: PRT
<213> ORGANISM: Artificial Sequence
<220> FEATURE:
<223> OTHER INFORMATION: KCD019 light chain variable region AA sequence

<400> SEQUENCE: 370

Asp Ile Val Met Thr Gln Ala His Arg Phe Met Ser Thr Ser Val Gly
1               5                   10                  15

Asp Arg Val Ile Ile Ser Cys Lys Ala Ser Gln Asp Val Gly Thr Ala
            20                  25                  30

Val Ala Trp Tyr Gln Gln Thr Pro Gly Gln Ser Pro Lys Ile Leu Ile
        35                  40                  45

Tyr Trp Thr Ser Thr Arg His Thr Gly Val Pro Asp Arg Phe Thr Gly
50                  55                  60

Ser Arg Ser Gly Thr Asp Phe Thr Leu Thr Ile Ser Asn Val Gln Ser
65                  70                  75                  80

Glu Asp Leu Ala Asp Tyr Phe Cys Gln Gln Tyr Thr Thr Tyr Pro Leu
                85                  90                  95

Thr Phe Gly Gly Gly Thr Lys Leu Glu Ile Lys
            100                 105

<210> SEQ ID NO 371
<211> LENGTH: 122
<212> TYPE: PRT
<213> ORGANISM: Artificial Sequence
<220> FEATURE:
<223> OTHER INFORMATION: KCD022 heavy chain variable region AA sequence

<400> SEQUENCE: 371

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Thr Leu Glu Trp
        35                  40                  45

Met Gly Tyr Ile His Tyr Ser Gly Ser Thr Asn Tyr Asn Pro Ser Leu
50                  55                  60

Glu Ser Arg Ile Ser Phe Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Leu His Phe Tyr Gly Tyr Asn Leu Gly Trp Tyr Phe Asp Val Trp
            100                 105                 110

Gly Ala Gly Thr Thr Val Thr Val Ser Ser
        115                 120

<210> SEQ ID NO 372
<211> LENGTH: 107
<212> TYPE: PRT
<213> ORGANISM: Artificial Sequence
<220> FEATURE:
```

<223> OTHER INFORMATION: KCD022 light chain variable region AA sequence

<400> SEQUENCE: 372

Asp Ile Val Met Thr Gln Ser His Lys Phe Met Thr Ser Ile Gly
1               5                   10                  15

Asp Arg Val Ile Ile Thr Cys Lys Ala Ser Gln Asp Val Gly Thr Thr
            20                  25                  30

Val Ala Trp Tyr Gln Gln Arg Pro Gly Gln Ser Pro Lys Leu Leu Ile
        35                  40                  45

Tyr Trp Ala Ser Thr Arg His Thr Ala Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Thr Ser Tyr Pro Leu
                85                  90                  95

Thr Phe Gly Ala Gly Thr Gln Leu Glu Leu Lys
            100                 105

<210> SEQ ID NO 373
<211> LENGTH: 114
<212> TYPE: PRT
<213> ORGANISM: Artificial Sequence
<220> FEATURE:
<223> OTHER INFORMATION: KCD023 heavy chain variable region AA sequence

<400> SEQUENCE: 373

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Ile Asp Trp Val Lys Gln Ser His Gly Lys Ser Leu Glu Trp Ile
        35                  40                  45

Gly Asp Ile Asn Pro Asn Asn Gly Gly Ile Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Gly Thr Gly Asp Tyr Ala Tyr Trp Gly Gln Gly Thr Leu Val Thr Val
            100                 105                 110

Ser Ala

<210> SEQ ID NO 374
<211> LENGTH: 108
<212> TYPE: PRT
<213> ORGANISM: Artificial Sequence
<220> FEATURE:
<223> OTHER INFORMATION: KCD023 light chain variable region AA sequence

<400> SEQUENCE: 374

Gln Ile Val Leu Thr Gln Ser Pro Ala Phe Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

```
Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Thr Ser Tyr Pro
                 85                  90                  95

Pro Thr Phe Gly Ala Gly Thr Lys Leu Glu Leu Lys
            100                 105
```

<210> SEQ ID NO 375
<211> LENGTH: 117
<212> TYPE: PRT
<213> ORGANISM: Artificial Sequence
<220> FEATURE:
<223> OTHER INFORMATION: KCD030 heavy chain variable region AA sequence

<400> SEQUENCE: 375

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Tyr Ile Asn Pro Ser Ile Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Phe Tyr Cys
                85                  90                  95

Ala Thr Phe Ile Tyr Tyr Ala Met Asp Tyr Trp Gly Gln Gly Thr Ser
                100                 105                 110

Val Thr Val Ser Ser
            115
```

<210> SEQ ID NO 376
<211> LENGTH: 107
<212> TYPE: PRT
<213> ORGANISM: Artificial Sequence
<220> FEATURE:
<223> OTHER INFORMATION: KCD030 light chain variable region AA sequence

<400> SEQUENCE: 376

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
                20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
                100                 105
```

<210> SEQ ID NO 377
<211> LENGTH: 118
<212> TYPE: PRT

```
<213> ORGANISM: Artificial Sequence
<220> FEATURE:
<223> OTHER INFORMATION: KCD033 heavy chain variable region AA sequence

<400> SEQUENCE: 377

Glu Val Gln Leu Gln Gln Ser Gly Pro Glu Leu Val Lys Pro Gly Ala
1               5                   10                  15

Ser Met Lys Ile Ser Cys Thr Ala Ser Gly Tyr Ser Phe Thr Gly Tyr
            20                  25                  30

Thr Met Thr Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Lys Phe
    50                  55                  60

Lys Gly Lys Ala Thr Leu Thr Val Asp Lys Ser Ser Ile Ala Tyr
65                  70                  75                  80

Met Glu Leu Leu Ser Leu Thr Ser Glu Asp Ser Ala Val Tyr Tyr Cys
                85                  90                  95

Ala Arg Arg His Tyr Gly Ser Asn Trp Asp Tyr Trp Gly Gln Gly Thr
            100                 105                 110

Thr Leu Thr Val Ser Ser
            115

<210> SEQ ID NO 378
<211> LENGTH: 107
<212> TYPE: PRT
<213> ORGANISM: Artificial Sequence
<220> FEATURE:
<223> OTHER INFORMATION: KCD033 light chain variable region AA sequence

<400> SEQUENCE: 378

Asp Ile Lys Leu Thr Gln Ser Pro Ser Ser Ile Tyr Thr Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Arg Pro Gly Lys Ser Pro Lys Thr Leu Ile
        35                  40                  45

Tyr Arg Ala Asp Arg Leu Val Asp Gly Val Pro Ser Arg Val Arg Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 379
<211> LENGTH: 118
<212> TYPE: PRT
<213> ORGANISM: Artificial Sequence
<220> FEATURE:
<223> OTHER INFORMATION: KCD036 heavy chain variable region AA sequence

<400> SEQUENCE: 379

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Thr Trp Val Lys Gln Ser His Gly Lys Asn Leu Glu Trp Ile
        35                  40                  45
```

```
Gly Leu Ile Asn Pro Tyr Asn Gly Gly Thr Asn Tyr Asn Gln Lys Phe
        50                  55                  60

Lys Gly Lys Ala Thr Phe Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                    85                  90                  95

Ala Arg Arg His Tyr Gly Ser Ser Trp Asp Tyr Trp Gly Gln Gly Thr
                100                 105                 110

Thr Leu Thr Val Ser Ser
            115

<210> SEQ ID NO 380
<211> LENGTH: 107
<212> TYPE: PRT
<213> ORGANISM: Artificial Sequence
<220> FEATURE:
<223> OTHER INFORMATION: KCD036 light chain variable region AA sequence

<400> SEQUENCE: 380

Asp Ile Lys Leu Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Thr Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Glu Met Gly Ile Tyr Tyr Cys Leu Gln Tyr Asp Glu Phe Pro Tyr
                85                  90                  95

Thr Phe Gly Gly Gly Thr Lys Leu Glu Ile Lys
                100                 105

<210> SEQ ID NO 381
<211> LENGTH: 123
<212> TYPE: PRT
<213> ORGANISM: Artificial Sequence
<220> FEATURE:
<223> OTHER INFORMATION: KCD038 heavy chain variable region AA sequence

<400> SEQUENCE: 381

Glu Val Gln Leu Gln Gln Ser Gly Pro Glu Leu Val Lys Pro Gly Thr
 1               5                  10                  15

Ser Met Lys Ile Ser Cys Lys Ala Ser Gly Tyr Ser Phe Ala Asp Tyr
                20                  25                  30

Thr Met Asn Trp Val Lys Gln Ser His Gly Lys Ser Leu Glu Trp Ile
            35                  40                  45

Gly Leu Ile Asn Pro Tyr Asn Gly Gly Thr Ser Tyr Asn Gln Lys Phe
 50                  55                  60

Met Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                85                  90                  95

Ala Arg Trp Gly Thr Tyr Ser His Asn Tyr Asp Tyr Ala Met Asp Tyr
                100                 105                 110

Trp Gly Gln Gly Thr Ser Val Thr Val Ser Ser
```

<210> SEQ ID NO 382
<211> LENGTH: 113
<212> TYPE: PRT
<213> ORGANISM: Artificial Sequence
<220> FEATURE:
<223> OTHER INFORMATION: KCD038 light chain variable region AA sequence

<400> SEQUENCE: 382

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Phe Gln Lys Pro Gly Gln Ser
        35                  40                  45

Pro Lys Phe Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Phe Thr Phe Gly Ser Gly Thr Lys Leu Glu Ile
            100                 105                 110

Lys

<210> SEQ ID NO 383
<211> LENGTH: 123
<212> TYPE: PRT
<213> ORGANISM: Artificial Sequence
<220> FEATURE:
<223> OTHER INFORMATION: KCD039 heavy chain variable region AA sequence

<400> SEQUENCE: 383

Glu Val Gln Leu Gln Gln Ser Gly Pro Glu Met Val Lys Pro Gly Ala
1               5                   10                  15

Ser Met Lys Ile Ser Cys Lys Ala Ser Gly Tyr Ser Phe Ala Asp Tyr
            20                  25                  30

Thr Leu Asn Trp Val Lys Gln Ser His Gly Lys Ser Leu Glu Trp Ile
        35                  40                  45

Gly Leu Ile Asn Pro Tyr Asn Gly Gly Thr Ser Tyr Asn Gln Lys Phe
    50                  55                  60

Met Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Thr Arg Trp Gly Thr Tyr Ser His Asn Tyr Asp Tyr Ala Met Asp Tyr
            100                 105                 110

Trp Gly Gln Gly Thr Ser Val Thr Val Ser Ser
        115                 120

<210> SEQ ID NO 384
<211> LENGTH: 113
<212> TYPE: PRT
<213> ORGANISM: Artificial Sequence
<220> FEATURE:
<223> OTHER INFORMATION: KCD039 light chain variable region AA sequence

<400> SEQUENCE: 384

```
Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Lys Val Ser Asn Arg Phe Ser Gly Ile Thr
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Phe Thr Phe Gly Ser Gly Thr Lys Leu Glu Ile
                100                 105                 110

Lys
```

<210> SEQ ID NO 385
<211> LENGTH: 113
<212> TYPE: PRT
<213> ORGANISM: Artificial Sequence
<220> FEATURE:
<223> OTHER INFORMATION: KCD040 heavy chain variable region AA sequence

<400> SEQUENCE: 385

```
Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Lys Asp Thr
            20                  25                  30

Tyr Met His Trp Val Met Gln Arg Pro Glu Gln Gly Leu Glu Trp Ile
        35                  40                  45

Gly Lys Ile Asp Pro Ala Asn Gly Asn Thr Glu Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Thr Arg Ala Met Asp Tyr Trp Gly Gln Gly Thr Ser Val Thr Val Ser
                100                 105                 110

Ser
```

<210> SEQ ID NO 386
<211> LENGTH: 106
<212> TYPE: PRT
<213> ORGANISM: Artificial Sequence
<220> FEATURE:
<223> OTHER INFORMATION: KCD040 light chain variable region AA sequence

<400> SEQUENCE: 386

```
Gln Ile Val Leu Thr Gln Ser Pro Ala Ile Met Ser Ala Ser Pro Gly
1               5                   10                  15

Glu Lys Val Thr Met Thr Cys Ser Ala Gly Ser Ser Val Ser Tyr Met
            20                  25                  30

Tyr Trp Tyr Gln Gln Lys Pro Gly Ser Ser Pro Arg Val Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
```

```
                65                  70                  75                  80
Asp Ala Ala Thr Tyr Tyr Cys Gln Gln Trp Ser Asn Tyr Pro Tyr Thr
                    85                  90                  95

Phe Gly Gly Gly Thr Lys Leu Glu Ile Lys
                100                 105
```

<210> SEQ ID NO 387
<211> LENGTH: 113
<212> TYPE: PRT
<213> ORGANISM: Artificial Sequence
<220> FEATURE:
<223> OTHER INFORMATION: KCD042 heavy chain variable region AA sequence

<400> SEQUENCE: 387

```
Glu Val Gln Leu Gln Gln Ser Gly Ala Glu Leu Val Lys Pro Gly Ala
1               5                   10                  15

Ser Val Arg Leu Ser Cys Thr Ala Ser Gly Phe Asn Ile Lys His Thr
                20                  25                  30

Tyr Ile His Trp Val Ser Gln Arg Pro Glu Gln Gly Leu Glu Trp Ile
            35                  40                  45

Gly Lys Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Asn Ala Met Glu Tyr Trp Gly Gln Gly Thr Ser Val Thr Val Ser
                100                 105                 110

Ser
```

<210> SEQ ID NO 388
<211> LENGTH: 106
<212> TYPE: PRT
<213> ORGANISM: Artificial Sequence
<220> FEATURE:
<223> OTHER INFORMATION: KCD042 light chain variable region AA sequence

<400> SEQUENCE: 388

```
Gln Ser Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Asp Met
                20                  25                  30

Tyr Trp Phe Gln Gln Arg Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Trp Thr
                85                  90                  95

Phe Gly Gly Gly Thr Lys Leu Glu Ile Lys
                100                 105
```

<210> SEQ ID NO 389
<211> LENGTH: 113
<212> TYPE: PRT
<213> ORGANISM: Artificial Sequence
<220> FEATURE:
<223> OTHER INFORMATION: KCD044 heavy chain variable region AA sequence

<400> SEQUENCE: 389

Glu Val Gln Leu Gln Gln Ser Gly Ala Glu Leu Val Lys Pro Gly Ala
1               5                   10                  15

Ser Val Arg Leu Ser Cys Thr Ala Ser Gly Phe Asn Ile Lys His Thr
            20                  25                  30

Tyr Met His Trp Val Ser Gln Arg Pro Glu Arg Gly Leu Glu Trp Ile
        35                  40                  45

Gly Lys Ile Asp Pro Ala Asn Gly Asn Thr Lys Tyr Asp Pro Lys Phe
50                  55                  60

Gln Gly Lys Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Leu Asn Ala Met Glu Tyr Trp Gly Gln Gly Thr Ser Val Thr Val Ser
            100                 105                 110

Ser

<210> SEQ ID NO 390
<211> LENGTH: 106
<212> TYPE: PRT
<213> ORGANISM: Artificial Sequence
<220> FEATURE:
<223> OTHER INFORMATION: KCD044 light chain variable region AA sequence

<400> SEQUENCE: 390

Gln Ser Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Asp Met
            20                  25                  30

Tyr Trp Tyr Gln Gln Arg Pro Gly Ser Ser Pro Arg Leu Leu Ile Tyr
        35                  40                  45

Asp Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Trp Thr
                85                  90                  95

Phe Gly Gly Gly Thr Lys Leu Glu Ile Lys
            100                 105

<210> SEQ ID NO 391
<211> LENGTH: 113
<212> TYPE: PRT
<213> ORGANISM: Artificial Sequence
<220> FEATURE:
<223> OTHER INFORMATION: KCD047 heavy chain variable region AA sequence

<400> SEQUENCE: 391

Glu Val Gln Leu Gln Gln Ser Gly Ala Glu Phe Val Lys Pro Gly Ala
1               5                   10                  15

Ser Val Arg Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Lys Asp Asp Pro Lys Phe
50                  55                  60

```
Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Ala Met Asp Tyr Trp Gly Gln Gly Thr Ser Val Thr Val Ser
            100                 105                 110

Ser
```

<210> SEQ ID NO 392
<211> LENGTH: 106
<212> TYPE: PRT
<213> ORGANISM: Artificial Sequence
<220> FEATURE:
<223> OTHER INFORMATION: KCD047 light chain variable region AA sequence

<400> SEQUENCE: 392

```
Gln Ile Val Leu Thr Gln Ser Pro Ala Val Met Ser Ala Ser Pro Gly
1               5                   10                  15

Glu Lys Val Ala Met Thr Cys Ser Ala Ser Ser Val Thr Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Phe Pro
                85                  90                  95

Phe Gly Ser Gly Thr Lys Leu Glu Ile Lys
            100                 105
```

<210> SEQ ID NO 393
<211> LENGTH: 113
<212> TYPE: PRT
<213> ORGANISM: Artificial Sequence
<220> FEATURE:
<223> OTHER INFORMATION: KCD048 heavy chain variable region AA sequence

<400> SEQUENCE: 393

```
Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Ala Thr
                20                  25                  30

Tyr Met His Trp Val Arg Gln Arg Pro Glu Lys Gly Leu Glu Trp Ile
            35                  40                  45

Gly Arg Ile Asp Pro Ala Asn Gly His Thr Ile Tyr Asp Pro Gln Phe
        50                  55                  60

Gln Gly Lys Ala Thr Ile Thr Ser Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Glu Ala Met Asp Tyr Trp Gly Gln Gly Thr Ser Val Thr Val Ser
            100                 105                 110

Ser
```

<210> SEQ ID NO 394
<211> LENGTH: 106
<212> TYPE: PRT

```
<213> ORGANISM: Artificial Sequence
<220> FEATURE:
<223> OTHER INFORMATION: KCD048 light chain variable region AA sequence

<400> SEQUENCE: 394

Gln Ile Val Leu Thr Gln Ser Pro Ala Ile Met Ser Ala Ser Pro Gly
1               5                   10                  15

Glu Lys Val Thr Leu Thr Cys Ser Ala Thr Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Asp Ala Thr Tyr Tyr Cys Gln Gln Trp Ser Asn Tyr Pro Phe Thr
                85                  90                  95

Phe Gly Gly Gly Thr Lys Leu Glu Ile Lys
            100                 105

<210> SEQ ID NO 395
<211> LENGTH: 122
<212> TYPE: PRT
<213> ORGANISM: Artificial Sequence
<220> FEATURE:
<223> OTHER INFORMATION: KCD049 heavy chain variable region AA sequence

<400> SEQUENCE: 395

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Gln Trp Val Arg Gln Pro Pro Gly Gln Gly Leu Glu Trp Leu
        35                  40                  45

Val Val Ile Trp Arg Asp Gly Ser Ile Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Gly
                85                  90                  95

Arg Thr Ser His Tyr Gly Asn Tyr Asn Tyr Tyr Val Met Asp Tyr Trp
            100                 105                 110

Gly Gln Gly Thr Ala Val Thr Val Ser Ser
        115                 120

<210> SEQ ID NO 396
<211> LENGTH: 111
<212> TYPE: PRT
<213> ORGANISM: Artificial Sequence
<220> FEATURE:
<223> OTHER INFORMATION: KCD049 light chain variable region AA sequence

<400> SEQUENCE: 396

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Lys Tyr
            20                  25                  30

Gly Ile Ser Phe Leu Asn Trp Phe Gln Gln Lys Pro Gly Gln Pro Pro
        35                  40                  45
```

```
Lys Leu Leu Ile Tyr Ala Ala Ser Asn Gln Gly Ser Gly Val Pro Ala
         50                  55                  60

Arg Phe Ser Gly Ser Gly Ser Gly Thr Asp Phe Ser Leu Asn Ile His
 65                  70                  75                  80

Pro Met Glu Glu Asp Asp Pro Ala Met Tyr Phe Cys Gln Gln Gly Lys
                 85                  90                  95

Glu Val Pro Trp Thr Phe Gly Gly Gly Thr Lys Leu Glu Ile Lys
            100                 105                 110

<210> SEQ ID NO 397
<211> LENGTH: 122
<212> TYPE: PRT
<213> ORGANISM: Artificial Sequence
<220> FEATURE:
<223> OTHER INFORMATION: KCD050 heavy chain variable region AA sequence

<400> SEQUENCE: 397

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Asn Ser Tyr
                20                  25                  30

Gly Val Gln Trp Val Arg Gln Pro Pro Gly Gln Gly Leu Glu Trp Leu
             35                  40                  45

Val Val Ile Trp Arg Asp Gly Thr Ile Thr Tyr Asn Ser Ala Leu Lys
         50                  55                  60

Ser Arg Leu Ser Ile Asn Lys Asp Asn Ser Lys Ser Gln Val Phe Leu
 65                  70                  75                  80

Lys Met Asn Ser Leu Gln Thr Asp Asp Thr Ala Met Tyr Tyr Cys Gly
                 85                  90                  95

Arg Thr Ser His Tyr Gly Asn Phe Asn Tyr Tyr Val Met Asp Tyr Trp
            100                 105                 110

Gly Gln Gly Thr Ala Val Thr Val Ser Ser
            115                 120

<210> SEQ ID NO 398
<211> LENGTH: 111
<212> TYPE: PRT
<213> ORGANISM: Artificial Sequence
<220> FEATURE:
<223> OTHER INFORMATION: KCD050 light chain variable region AA sequence

<400> SEQUENCE: 398

Asp Ile Val Met Thr Gln Ser Pro Thr Ser Leu Ala Val Ser Leu Gly
 1               5                  10                  15

Gln Arg Ala Thr Ile Ser Cys Arg Ala Ser Glu Ser Val Asp Lys Tyr
                20                  25                  30

Gly Ile Ser Phe Leu Asn Trp Phe Gln Gln Lys Pro Gly Gln Pro Pro
             35                  40                  45

Arg Leu Leu Ile Tyr Ala Ala Ser Asn Gln Gly Ser Gly Val Pro Ala
         50                  55                  60

Arg Phe Ser Gly Ser Gly Ser Gly Thr Asp Phe Ser Leu Asn Ile His
 65                  70                  75                  80

Pro Met Glu Glu Asp Asp Pro Ala Val Tyr Phe Cys Gln Gln Gly Lys
                 85                  90                  95

Glu Phe Pro Trp Thr Phe Gly Gly Gly Thr Lys Leu Glu Ile Lys
            100                 105                 110
```

```
<210> SEQ ID NO 399
<211> LENGTH: 122
<212> TYPE: PRT
<213> ORGANISM: Artificial Sequence
<220> FEATURE:
<223> OTHER INFORMATION: KCD052 heavy chain variable region AA sequence

<400> SEQUENCE: 399

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asn Ser Tyr
            20                  25                  30

Gly Val Gln Trp Val Arg Gln Pro Pro Gly Gln Gly Leu Glu Trp Leu
        35                  40                  45

Gly Val Ile Trp Arg Asp Gly Ser Ile Thr Tyr Asn Ser Ala Leu Lys
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Gly
                85                  90                  95

Arg Thr Ser His Tyr Gly Asn Tyr Asn Tyr Tyr Val Met Asp Tyr Trp
            100                 105                 110

Gly Gln Gly Thr Ala Val Thr Val Ser Ser
        115                 120

<210> SEQ ID NO 400
<211> LENGTH: 111
<212> TYPE: PRT
<213> ORGANISM: Artificial Sequence
<220> FEATURE:
<223> OTHER INFORMATION: KCD052 light chain variable region AA sequence

<400> SEQUENCE: 400

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Lys Tyr
            20                  25                  30

Gly Ile Ser Phe Leu Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Pro Ala Ile Tyr Phe Cys Gln Gln Gly Lys
                85                  90                  95

Glu Val Pro Trp Thr Phe Gly Gly Gly Thr Lys Leu Glu Ile Lys
            100                 105                 110

<210> SEQ ID NO 401
<211> LENGTH: 117
<212> TYPE: PRT
<213> ORGANISM: Artificial Sequence
<220> FEATURE:
<223> OTHER INFORMATION: KCD056 heavy chain variable region AA sequence

<400> SEQUENCE: 401

Glu Val Lys Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Thr Tyr
            20                  25                  30
```

Thr Met Ser Trp Val Arg Gln Thr Pro Glu Lys Arg Leu Glu Trp Val
            35                  40                  45

Ala Tyr Ile Thr Asn Gly Gly Ser Thr Tyr Tyr Pro Asp Thr Glu
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg His Asp Tyr Tyr Ala Met Asp Tyr Trp Gly Gln Gly Thr Ser
            100                 105                 110

Val Thr Val Ser Ser
        115

<210> SEQ ID NO 402
<211> LENGTH: 107
<212> TYPE: PRT
<213> ORGANISM: Artificial Sequence
<220> FEATURE:
<223> OTHER INFORMATION: KCD056 light chain variable region AA sequence

<400> SEQUENCE: 402

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Thr Leu Glu Ile Lys
            100                 105

<210> SEQ ID NO 403
<211> LENGTH: 117
<212> TYPE: PRT
<213> ORGANISM: Artificial Sequence
<220> FEATURE:
<223> OTHER INFORMATION: KCD057 heavy chain variable region AA sequence

<400> SEQUENCE: 403

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Ile Met Ser Trp Val Arg Gln Thr Pro Glu Lys Arg Leu Glu Trp Val
            35                  40                  45

Ala Tyr Ile Thr Asn Gly Gly Gly Ala Thr Tyr Tyr Pro Asp Thr Val
        50                  55                  60

Lys Gly Gln Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg His Asp Phe Tyr Ala Leu Asp Phe Trp Gly Gln Gly Thr Ser

<210> SEQ ID NO 404
<211> LENGTH: 107
<212> TYPE: PRT
<213> ORGANISM: Artificial Sequence
<220> FEATURE:
<223> OTHER INFORMATION: KCD057 light chain variable region AA sequence

<400> SEQUENCE: 404

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Lys Tyr Asp Asn Leu Leu Tyr
                85                  90                  95

Thr Phe Gly Gly Gly Thr Lys Leu Glu Ile Lys
            100                 105

<210> SEQ ID NO 405
<211> LENGTH: 117
<212> TYPE: PRT
<213> ORGANISM: Artificial Sequence
<220> FEATURE:
<223> OTHER INFORMATION: KCD058 heavy chain variable region AA sequence

<400> SEQUENCE: 405

Glu Val Lys Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Arg Tyr
            20                  25                  30

Ile Met Ser Trp Val Arg Leu Thr Pro Glu Lys Arg Leu Glu Trp Val
        35                  40                  45

Ala Phe Ile Thr Asn Gly Gly Asn Thr Tyr His Pro Asp Thr Val
    50                  55                  60

Lys Gly Arg Phe Thr Ile Ser Arg Asp Asn Ala Asn Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg His Asp Tyr Tyr Ala Leu Asp Tyr Trp Gly Gln Gly Thr Ser
            100                 105                 110

Val Thr Val Ser Ser
        115

<210> SEQ ID NO 406
<211> LENGTH: 107
<212> TYPE: PRT
<213> ORGANISM: Artificial Sequence
<220> FEATURE:
<223> OTHER INFORMATION: KCD058 light chain variable region AA sequence

<400> SEQUENCE: 406

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys
            100                 105

<210> SEQ ID NO 407
<211> LENGTH: 118
<212> TYPE: PRT
<213> ORGANISM: Artificial Sequence
<220> FEATURE:
<223> OTHER INFORMATION: KCD062 heavy chain variable region AA sequence

<400> SEQUENCE: 407

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ile Met Ser Trp Val Arg Gln Thr Pro Glu Lys Arg Leu Glu Trp Val
        35                  40                  45

Ala Tyr Ile Thr Ser Gly Gly Ser Thr Tyr Tyr Pro Asp Thr Val
50                  55                  60

Lys Gly Arg Phe Thr Ile Ser Arg Asp Asn Ala Lys Ser Thr Leu Tyr
65                  70                  75                  80

Leu Gln Met Ser Ser Leu Lys Ser Glu Asp Thr Ala Met Tyr Tyr Cys
                85                  90                  95

Ala Arg His Ala His Phe Tyr Ala Met Asp Tyr Trp Gly Gln Gly Thr
            100                 105                 110

Ser Val Thr Val Ser Ser
            115

<210> SEQ ID NO 408
<211> LENGTH: 107
<212> TYPE: PRT
<213> ORGANISM: Artificial Sequence
<220> FEATURE:
<223> OTHER INFORMATION: KCD062 light chain variable region AA sequence

<400> SEQUENCE: 408

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
50                  55                  60

Ser Gly Ser Gly Arg Asp Tyr Ser Phe Ser Ile Ser Asn Leu Glu Pro
```

65              70              75              80

Glu Asp Ile Ala Thr Tyr Tyr Cys Leu Gln Tyr Asp Asn Leu Leu Tyr
                85              90              95

Thr Phe Gly Gly Gly Thr Lys Leu Glu Ile Lys
            100             105

<210> SEQ ID NO 409
<211> LENGTH: 118
<212> TYPE: PRT
<213> ORGANISM: Artificial Sequence
<220> FEATURE:
<223> OTHER INFORMATION: KCD063 heavy chain variable region AA sequence

<400> SEQUENCE: 409

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
                20                  25                  30

Ile Met Ser Trp Val Arg Gln Thr Pro Glu Lys Arg Leu Glu Trp Val
            35                  40                  45

Ala Tyr Ile Thr Asn Gly Gly Ser Thr Tyr Tyr Pro Asp Thr Val
        50                  55                  60

Lys Gly Arg Leu Thr Ile Ser Arg Asp Asn Ala Lys Asn Thr Leu Tyr
65              70                  75                  80

Leu Gln Met Ser Ser Leu Lys Ser Glu Asp Thr Ala Met Tyr Tyr Cys
                85                  90                  95

Val Arg His Ala His Tyr Tyr Ala Met Asp Tyr Trp Gly Gln Gly Thr
            100                 105                 110

Ser Val Thr Val Ser Ser
        115

<210> SEQ ID NO 410
<211> LENGTH: 107
<212> TYPE: PRT
<213> ORGANISM: Artificial Sequence
<220> FEATURE:
<223> OTHER INFORMATION: KCD063 light chain variable region AA sequence

<400> SEQUENCE: 410

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Thr Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65              70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys
            100                 105

<210> SEQ ID NO 411
<211> LENGTH: 118
<212> TYPE: PRT
<213> ORGANISM: Artificial Sequence
<220> FEATURE:

-continued

<223> OTHER INFORMATION: KCD064 heavy chain variable region AA sequence

<400> SEQUENCE: 411

Glu Val Lys Leu Val Glu Ser Gly Gly Gly Leu Val Gln Pro Gly
1               5                   10                  15

Ser Leu Lys Leu Ser Cys Ala Ala Ser Gly Phe Thr Phe Ser Ser Tyr
            20                  25                  30

Ile Met Ser Trp Val Arg Gln Thr Pro Glu Lys Arg Leu Gly Trp Val
        35                  40                  45

Ala Tyr Ile Thr Ser Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Thr Gly Tyr Ala Met Asp Tyr Trp Gly Gln Gly Thr
            100                 105                 110

Ser Val Thr Val Ser Ser
        115

<210> SEQ ID NO 412
<211> LENGTH: 107
<212> TYPE: PRT
<213> ORGANISM: Artificial Sequence
<220> FEATURE:
<223> OTHER INFORMATION: KCD064 light chain variable region AA sequence

<400> SEQUENCE: 412

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Glu Leu Glu Ile Lys
            100                 105

<210> SEQ ID NO 413
<211> LENGTH: 122
<212> TYPE: PRT
<213> ORGANISM: Artificial Sequence
<220> FEATURE:
<223> OTHER INFORMATION: KCD065 heavy chain variable region AA sequence

<400> SEQUENCE: 413

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Lys Gln Arg Pro Gly Gln Gly Leu Glu Trp Ile
        35                  40                  45

Gly Tyr Ile Asn Pro Ser Ser Asp Phe Thr Asn Tyr Asn Gln Asn Phe

```
                    50                  55                  60

Ala Asp Lys Ala Thr Leu Thr Ala Asp Arg Ser Ser Thr Ala Tyr
 65                  70                  75                  80

Met Gln Leu Ser Ser Leu Thr Ser Glu Glu Ser Ala Val Tyr Tyr Cys
                    85                  90                  95

Ala Ile Arg Leu Gly Tyr Asp Arg Gln Gly Trp Tyr Phe Asp Val Trp
                100                 105                 110

Gly Ala Gly Thr Thr Val Thr Val Ser Ser
            115                 120

<210> SEQ ID NO 414
<211> LENGTH: 107
<212> TYPE: PRT
<213> ORGANISM: Artificial Sequence
<220> FEATURE:
<223> OTHER INFORMATION: KCD065 light chain variable region AA sequence

<400> SEQUENCE: 414

Asp Ile Val Met Thr Gln Ser His Lys Phe Leu Ser Thr Ser Leu Gly
  1               5                  10                  15

Asp Arg Val Ser Ile Thr Cys Lys Ala Ser Gln Asp Val Gly Ser Ala
                 20                  25                  30

Val Ala Trp Tyr Gln Gln Lys Pro Gly Gln Ser Pro Asp Leu Leu Ile
             35                  40                  45

Tyr Trp Thr Phe Thr Arg His Thr Gly Val Pro Asp Arg Phe Thr Gly
 50                  55                  60

Ser Arg Ser Gly Thr Asp Phe Thr Leu Thr Ile Ser Asn Val Gln Ser
 65                  70                  75                  80

Gly Asp Leu Ala Asp Tyr Phe Cys Gln Gln Tyr Ser Asn Tyr Pro Leu
                 85                  90                  95

Thr Phe Gly Gly Gly Thr Lys Leu Glu Ile Lys
                100                 105

<210> SEQ ID NO 415
<211> LENGTH: 117
<212> TYPE: PRT
<213> ORGANISM: Artificial Sequence
<220> FEATURE:
<223> OTHER INFORMATION: KCD066 heavy chain variable region AA sequence

<400> SEQUENCE: 415

Gln Val Gln Leu Gln Gln Ser Ala Ala Glu Leu Ala Arg Pro Gly Ala
  1               5                  10                  15

Ser Val Lys Met Ser Cys Lys Ala Ser Gly Tyr Thr Phe Thr Asp Tyr
                 20                  25                  30

Thr Met His Trp Val Lys Gln Arg Pro Gly Gln Gly Leu Glu Trp Ile
             35                  40                  45

Gly Tyr Ile Asn Pro Ser Gly Gly Tyr Thr Asp Tyr Asn Gln Lys Phe
 50                  55                  60

Lys Asp Lys Thr Ala Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Arg Asp Tyr Trp Phe Ala Tyr Trp Gly Gln Gly Thr Leu
                100                 105                 110

Val Thr Val Ser Ala
            115
```

<210> SEQ ID NO 416
<211> LENGTH: 112
<212> TYPE: PRT
<213> ORGANISM: Artificial Sequence
<220> FEATURE:
<223> OTHER INFORMATION: KCD066 light chain variable region AA sequence

<400> SEQUENCE: 416

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Gly Asn Gln Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Leu Thr Phe Gly Ala Gly Thr Lys Leu Glu Leu Lys
            100                 105                 110
```

<210> SEQ ID NO 417
<211> LENGTH: 118
<212> TYPE: PRT
<213> ORGANISM: Artificial Sequence
<220> FEATURE:
<223> OTHER INFORMATION: KCD070 heavy chain variable region AA sequence

<400> SEQUENCE: 417

```
Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
                20                  25                  30

Ile Ile Leu Trp Val Lys Gln Ser His Gly Lys Ser Leu Glu Trp Ile
            35                  40                  45

Gly Asn Ile Asn Pro Tyr Tyr Asp Tyr Thr Ser Tyr Asn Leu Lys Phe
        50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Asp Gly Tyr Tyr Gly Gly Asp Tyr Trp Gly Gln Gly Thr
            100                 105                 110

Ser Val Thr Val Ser Ser
        115
```

<210> SEQ ID NO 418
<211> LENGTH: 107
<212> TYPE: PRT
<213> ORGANISM: Artificial Sequence
<220> FEATURE:
<223> OTHER INFORMATION: KCD070 light chain variable region AA sequence

<400> SEQUENCE: 418

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
```

```
                20                  25                  30
Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Asn Asn Val Gln Ser
 65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Thr Leu Glu Ile Lys
                100                 105
```

<210> SEQ ID NO 419
<211> LENGTH: 116
<212> TYPE: PRT
<213> ORGANISM: Artificial Sequence
<220> FEATURE:
<223> OTHER INFORMATION: KCD075 heavy chain variable region AA sequence

<400> SEQUENCE: 419

```
Gln Val Gln Leu Leu Gln Pro Gly Ala Glu Leu Val Arg Pro Gly Thr
 1               5                  10                  15

Ser Val Lys Leu Ser Cys Lys Ala Ser Gly Tyr Thr Phe Ser Asn Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Ser Ile Asn Tyr Asn Gln Lys Phe
 50                  55                  60

Lys Asp Lys Ala Thr Leu Thr Val Asp Lys Ser Ser Thr Thr Ala Tyr
 65                  70                  75                  80

Met Gln Leu Ser Ser Pro Thr Ser Glu Asp Ser Ala Val Tyr Tyr Cys
                85                  90                  95

Thr Gly Thr Asp Trp Tyr Phe Asp Val Trp Gly Ala Gly Thr Thr Val
                100                 105                 110

Thr Val Ser Ser
            115
```

<210> SEQ ID NO 420
<211> LENGTH: 107
<212> TYPE: PRT
<213> ORGANISM: Artificial Sequence
<220> FEATURE:
<223> OTHER INFORMATION: KCD075 light chain variable region AA sequence

<400> SEQUENCE: 420

```
Asp Ile Gln Met Thr Gln Thr Ser Ser Leu Ser Ala Ser Leu Gly
 1               5                  10                  15

Asp Arg Val Thr Ile Ser Cys Ser Gly Gly Gln Gly Ile Ser Asn Tyr
                20                  25                  30

Leu Asn Trp Tyr Gln Gln Lys Pro Asp Gly Thr Phe Lys Leu Leu Ile
            35                  40                  45

Tyr Tyr Thr Ser Thr Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Val Ala Thr Tyr Tyr Cys Gln Gln Tyr Ser Lys Leu Pro Tyr
                85                  90                  95
```

Thr Phe Gly Gly Gly Thr Lys Leu Glu Ile Lys
            100                 105

<210> SEQ ID NO 421
<211> LENGTH: 116
<212> TYPE: PRT
<213> ORGANISM: Artificial Sequence
<220> FEATURE:
<223> OTHER INFORMATION: KCD077 heavy chain variable region AA sequence

<400> SEQUENCE: 421

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly His Thr Ile Tyr Asp Pro Arg Phe
    50                  55                  60

Gln Gly Lys Ala Thr Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Gly Leu Leu Gly Phe Ala Tyr Trp Gly Gln Gly Thr Leu Val
            100                 105                 110

Thr Val Ser Ala
        115

<210> SEQ ID NO 422
<211> LENGTH: 109
<212> TYPE: PRT
<213> ORGANISM: Artificial Sequence
<220> FEATURE:
<223> OTHER INFORMATION: KCD077 light chain variable region AA sequence

<400> SEQUENCE: 422

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Thr Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Met Tyr Thr Phe Gly Gly Gly Thr Lys Leu Glu Ile Lys
            100                 105

<210> SEQ ID NO 423
<211> LENGTH: 118
<212> TYPE: PRT
<213> ORGANISM: Artificial Sequence
<220> FEATURE:
<223> OTHER INFORMATION: KCD101 heavy chain variable region AA sequence

<400> SEQUENCE: 423

Gln Val Gln Leu Gln Gln Pro Gly Ala Glu Leu Val Arg Pro Gly Thr

-continued

```
                1               5                  10                  15
Ser Val Lys Leu Ser Cys Lys Ala Ser Gly Tyr Thr Phe Thr Ser Tyr
                        20                  25                  30

Trp Met His Trp Val Lys Gln Arg Pro Gly Gln Gly Leu Glu Trp Ile
                        35                  40                  45

Gly Val Ile Asp Pro Ser Ser Tyr Thr Asn Tyr Asn Gln Lys Phe
            50                  55                  60

Lys Gly Lys Ala Thr Leu Thr Val Asp Thr Ser Ser Ser Thr Ala Tyr
 65                     70                  75                  80

Met Gln Leu Ser Ser Leu Thr Ser Glu Asp Ser Ala Val Tyr Tyr Cys
                        85                  90                  95

Gly Arg Asn Gly Tyr Asp Gly Ser Met Asp Tyr Trp Gly Gln Gly Thr
                        100                 105                 110

Ser Val Thr Val Ser Ser
            115
```

<210> SEQ ID NO 424
<211> LENGTH: 107
<212> TYPE: PRT
<213> ORGANISM: Artificial Sequence
<220> FEATURE:
<223> OTHER INFORMATION: KCD101 light chain variable region AA sequence

<400> SEQUENCE: 424

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
                35                  40                  45

Tyr Tyr Pro Ser Arg Leu His Ser Gly Val Pro Ser Arg Phe Ser Gly
            50                  55                  60

Ser Gly Ser Gly Thr Asp Tyr Ser Leu Thr Ile Ser Asn Leu Glu Gln
 65                     70                  75                  80

Glu Asp Phe Ala Thr Tyr Phe Cys Gln Gln Gly Asn Thr Leu Pro Tyr
                        85                  90                  95

Thr Phe Gly Gly Gly Thr Lys Leu Glu Ile Lys
                100                 105
```

<210> SEQ ID NO 425
<211> LENGTH: 121
<212> TYPE: PRT
<213> ORGANISM: Artificial Sequence
<220> FEATURE:
<223> OTHER INFORMATION: KCD110 heavy chain variable region AA sequence

<400> SEQUENCE: 425

```
Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Asn Ile Leu Asp Trp Ile
                35                  40                  45

Gly Tyr Ile Asp Pro Asp Asn Gly Val Ser Ser Lys Asn Gln Lys Phe
            50                  55                  60

Thr Gly Lys Ala Thr Val Thr Ala Asp Lys Ser Ser Ser Thr Ala Tyr
 65                     70                  75                  80
```

Met Glu Leu Arg Ser Leu Thr Ser Glu Asp Ser Ala Val Tyr Tyr Cys
                85                  90                  95

Ala Gly Tyr Tyr Gly Ser Ser Trp Tyr Trp Tyr Phe Asp Val Trp Gly
            100                 105                 110

Thr Gly Thr Thr Val Thr Val Ser Ser
        115                 120

<210> SEQ ID NO 426
<211> LENGTH: 106
<212> TYPE: PRT
<213> ORGANISM: Artificial Sequence
<220> FEATURE:
<223> OTHER INFORMATION: KCD110 light chain variable region AA sequence

<400> SEQUENCE: 426

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 427
<211> LENGTH: 121
<212> TYPE: PRT
<213> ORGANISM: Artificial Sequence
<220> FEATURE:
<223> OTHER INFORMATION: KCD111 heavy chain variable region AA sequence

<400> SEQUENCE: 427

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met His Trp Val Lys Gln Ser His Gly Asn Ile Leu Asp Trp Ile
        35                  40                  45

Gly Tyr Ile Asp Pro Tyr Asn Gly Val Ser Ser Tyr Asn Gln Lys Phe
    50                  55                  60

Lys Gly Lys Ala Thr Leu Ser Val Asp Gln Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Ser Tyr Tyr Gly Ser Ser Pro Tyr Trp Tyr Phe Asp Val Trp Gly
            100                 105                 110

Thr Gly Thr Arg Val Thr Val Ser Ser
        115                 120

<210> SEQ ID NO 428
<211> LENGTH: 106
<212> TYPE: PRT
<213> ORGANISM: Artificial Sequence

```
<220> FEATURE:
<223> OTHER INFORMATION: KCD111 light chain variable region AA sequence

<400> SEQUENCE: 428

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Ser
    50                  55                  60

Gly Ser Gly Thr Ser Tyr Ser Leu Thr Ile Ser Lys Leu Glu Ala Glu
65                  70                  75                  80

Asp Ala Ala Thr Tyr Tyr Cys Gln Gln Trp Ser Asn Pro Tyr Thr
                85                  90                  95

Phe Gly Gly Gly Thr Lys Leu Glu Ile Lys
            100                 105

<210> SEQ ID NO 429
<211> LENGTH: 122
<212> TYPE: PRT
<213> ORGANISM: Artificial Sequence
<220> FEATURE:
<223> OTHER INFORMATION: KCD112 heavy chain variable region AA sequence

<400> SEQUENCE: 429

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Tyr Met Asn Trp Val Lys His Ser Pro Glu Lys Ser Leu Glu Trp Ile
        35                  40                  45

Gly Asp Ile Asn Pro Ser Thr Gly Gly Thr Thr Tyr Asn Gln Lys Phe
    50                  55                  60

Lys Ala Arg Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Thr Thr Tyr Tyr Ser Gly Asn Ser Tyr Val Gly Phe Ala Tyr Trp
            100                 105                 110

Gly Gln Gly Thr Leu Val Thr Val Ser Ala
        115                 120

<210> SEQ ID NO 430
<211> LENGTH: 107
<212> TYPE: PRT
<213> ORGANISM: Artificial Sequence
<220> FEATURE:
<223> OTHER INFORMATION: KCD112 light chain variable region AA sequence

<400> SEQUENCE: 430

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45
```

```
Phe Trp Thr Ser Thr Arg His Thr Gly Val Pro Asp Arg Phe Thr Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Thr Thr Pro Trp
                 85                  90                  95

Thr Phe Gly Gly Gly Thr Lys Leu Glu Ile Lys
            100                 105
```

<210> SEQ ID NO 431
<211> LENGTH: 122
<212> TYPE: PRT
<213> ORGANISM: Artificial Sequence
<220> FEATURE:
<223> OTHER INFORMATION: KCD114 heavy chain variable region AA sequence

<400> SEQUENCE: 431

```
Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Ala Tyr
                 20                  25                  30

Tyr Met Asn Trp Val Lys Gln Ser Pro Glu Lys Ser Leu Glu Trp Ile
             35                  40                  45

Gly Asp Ile Asn Pro Ser Thr Gly Gly Thr Thr Tyr Asn Gln Asn Phe
 50                  55                  60

Lys Ala Lys Ala Thr Leu Thr Val Asp Lys Ser Ser Ser Thr Ala Tyr
 65                  70                  75                  80

Met His Leu Lys Ser Leu Thr Ser Glu Asp Ser Ala Val Tyr Tyr Cys
                 85                  90                  95

Ala Thr Thr Tyr Tyr Ser Gly Asn Ser Tyr Val Gly Phe Ala Tyr Trp
                100                 105                 110

Gly Gln Gly Thr Leu Val Thr Val Ser Ala
            115                 120
```

<210> SEQ ID NO 432
<211> LENGTH: 107
<212> TYPE: PRT
<213> ORGANISM: Artificial Sequence
<220> FEATURE:
<223> OTHER INFORMATION: KCD114 light chain variable region AA sequence

<400> SEQUENCE: 432

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
             35                  40                  45

Phe Trp Ala Ser Thr Arg His Thr Gly Val Pro Asp Arg Phe Thr Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Thr Pro Trp
                 85                  90                  95

Thr Phe Gly Gly Gly Thr Lys Leu Glu Ile Lys
            100                 105
```

<210> SEQ ID NO 433

```
<211> LENGTH: 122
<212> TYPE: PRT
<213> ORGANISM: Artificial Sequence
<220> FEATURE:
<223> OTHER INFORMATION: KCD115 heavy chain variable region AA sequence

<400> SEQUENCE: 433

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Asp Ile Asn Pro Ser Thr Gly Gly Thr Thr Tyr Asn Gln Lys Phe
    50                  55                  60

Lys Ala Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Thr Pro Tyr Tyr Tyr Gly Ser Ser Tyr Val Gly Phe Ala Tyr Trp
            100                 105                 110

Gly Gln Gly Thr Leu Val Thr Val Ser Ala
            115                 120

<210> SEQ ID NO 434
<211> LENGTH: 107
<212> TYPE: PRT
<213> ORGANISM: Artificial Sequence
<220> FEATURE:
<223> OTHER INFORMATION: KCD115 light chain variable region AA sequence

<400> SEQUENCE: 434

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 435
<211> LENGTH: 116
<212> TYPE: PRT
<213> ORGANISM: Artificial Sequence
<220> FEATURE:
<223> OTHER INFORMATION: KCD118 heavy chain variable region AA sequence

<400> SEQUENCE: 435

Glu Val Gln Leu Gln Gln Ser Gly Pro Glu Leu Val Lys Pro Gly Ala
1               5                   10                  15

Ser Val Lys Ile Ser Cys Lys Ala Phe Gly Tyr Thr Phe Thr Asp Tyr
            20                  25                  30
```

```
Tyr Lys Asn Trp Met Arg Gln Arg His Gly Glu Ser Leu Glu Trp Ile
            35                  40                  45

Gly Asp Ile Asn Pro Asn Ser Gly Asp Ala Asn Tyr Asn Gln Lys Phe
 50                  55                  60

Lys Gly Lys Ala Thr Leu Thr Val Asp Lys Ser Ser Ser Thr Ala Tyr
65                   70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly His Gly Thr Leu Val
                100                 105                 110

Thr Val Ser Ala
        115

<210> SEQ ID NO 436
<211> LENGTH: 112
<212> TYPE: PRT
<213> ORGANISM: Artificial Sequence
<220> FEATURE:
<223> OTHER INFORMATION: KCD118 light chain variable region AA sequence

<400> SEQUENCE: 436

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
                20                  25                  30

Asn Gly Asp Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                   70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 437
<211> LENGTH: 116
<212> TYPE: PRT
<213> ORGANISM: Artificial Sequence
<220> FEATURE:
<223> OTHER INFORMATION: KCD119 heavy chain variable region AA sequence

<400> SEQUENCE: 437

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Thr Asn Trp Met Arg Gln Arg His Gly Glu Ser Leu Glu Trp Ile
            35                  40                  45

Gly Asp Ile Asn Pro Asn Thr Gly Asp Thr Tyr Asn Gln Lys Phe
 50                  55                  60

Arg Val Lys Ala Thr Leu Thr Val Asp Lys Ser Ser Gly Thr Ala Tyr
65                   70                  75                  80

Met Gly Leu Arg Ser Leu Thr Ser Glu Asp Ser Ala Val Tyr Tyr Cys
                85                  90                  95

Thr Arg Glu Gly Pro Ser Phe Ala Tyr Trp Gly Gln Gly Thr Leu Val
                100                 105                 110
```

```
Thr Val Ser Ala
        115

<210> SEQ ID NO 438
<211> LENGTH: 112
<212> TYPE: PRT
<213> ORGANISM: Artificial Sequence
<220> FEATURE:
<223> OTHER INFORMATION: KCD119 light chain variable region AA sequence

<400> SEQUENCE: 438

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Thr Leu Glu Ile Lys
            100                 105                 110

<210> SEQ ID NO 439
<211> LENGTH: 118
<212> TYPE: PRT
<213> ORGANISM: Artificial Sequence
<220> FEATURE:
<223> OTHER INFORMATION: KCD102 heavy chain variable region AA sequence

<400> SEQUENCE: 439

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Gly Tyr Asp Gly Ser Met Asp Tyr Trp Gly Gln Gly Thr
            100                 105                 110

Ser Val Thr Val Ser Ser
        115

<210> SEQ ID NO 440
<211> LENGTH: 107
<212> TYPE: PRT
<213> ORGANISM: Artificial Sequence
<220> FEATURE:
<223> OTHER INFORMATION: KCD102 light chain variable region AA sequence

<400> SEQUENCE: 440
```

-continued

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Pro Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 441
<211> LENGTH: 116
<212> TYPE: PRT
<213> ORGANISM: Artificial Sequence
<220> FEATURE:
<223> OTHER INFORMATION: KCD121 heavy chain variable region AA sequence

<400> SEQUENCE: 441

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Lys Asn Trp Met Arg Gln Arg His Gly Glu Ser Leu Glu Trp Ile
        35                  40                  45

Gly Asp Ile Asn Pro Asn Asn Gly Asp Thr Ser Tyr Asn Gln Lys Phe
50                  55                  60

Arg Gly Lys Ala Thr Leu Thr Val Asp Lys Ser Ser Thr Ala Phe
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 442
<211> LENGTH: 112
<212> TYPE: PRT
<213> ORGANISM: Artificial Sequence
<220> FEATURE:
<223> OTHER INFORMATION: KCD121 light chain variable region AA sequence

<400> SEQUENCE: 442

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Arg Ile
65                  70                  75                  80

```
Ser Arg Val Glu Ala Glu Asp Leu Gly Val Tyr Tyr Cys Phe Gln Gly
            85                  90                  95

Ser His Val Pro Pro Thr Phe Gly Gly Gly Thr Lys Leu Glu Ile Lys
            100                 105                 110

<210> SEQ ID NO 443
<211> LENGTH: 116
<212> TYPE: PRT
<213> ORGANISM: Artificial Sequence
<220> FEATURE:
<223> OTHER INFORMATION: KCD122 heavy chain variable region AA sequence

<400> SEQUENCE: 443

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Lys Asn Trp Met Arg Gln Arg His Gly Glu Ser Leu Glu Trp Ile
            35                  40                  45

Gly Asp Ile Asn Pro Asn Asn Gly Asp Ala Asn Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Glu Gly Pro Ser Phe Ala Tyr Trp Gly His Gly Thr Leu Val
            100                 105                 110

Thr Val Ser Ala
        115

<210> SEQ ID NO 444
<211> LENGTH: 112
<212> TYPE: PRT
<213> ORGANISM: Artificial Sequence
<220> FEATURE:
<223> OTHER INFORMATION: KCD122 light chain variable region AA sequence

<400> SEQUENCE: 444

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
                20                  25                  30

Asn Gly Asp Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 445
<211> LENGTH: 116
<212> TYPE: PRT
<213> ORGANISM: Artificial Sequence
<220> FEATURE:
<223> OTHER INFORMATION: KCD123 heavy chain variable region AA sequence
```

<400> SEQUENCE: 445

Glu Val His Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Phe
            20                  25                  30

Tyr Lys Asn Trp Met Arg Gln Arg His Gly Glu Ser Leu Glu Trp Ile
        35                  40                  45

Gly Asp Ile Asn Pro Asn Gly Gly Thr Asn Tyr Asn Gln Lys Phe
50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
            115

<210> SEQ ID NO 446
<211> LENGTH: 112
<212> TYPE: PRT
<213> ORGANISM: Artificial Sequence
<220> FEATURE:
<223> OTHER INFORMATION: KCD123 light chain variable region AA sequence

<400> SEQUENCE: 446

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 447
<211> LENGTH: 116
<212> TYPE: PRT
<213> ORGANISM: Artificial Sequence
<220> FEATURE:
<223> OTHER INFORMATION: KCD124 heavy chain variable region AA sequence

<400> SEQUENCE: 447

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
50                  55                  60

```
Lys Gly Lys Ala Thr Leu Thr Val Asp Lys Ser Ser Thr Ala Tyr
 65                  70                  75                  80

Met Glu Leu Arg Ser Leu Thr Ser Gly Asp Ser Ala Val Tyr Tyr Cys
                 85                  90                  95

Thr Arg Glu Gly Ala Ser Phe Ala Phe Trp Gly Gln Gly Thr Leu Val
            100                 105                 110

Thr Val Ser Ala
        115

<210> SEQ ID NO 448
<211> LENGTH: 112
<212> TYPE: PRT
<213> ORGANISM: Artificial Sequence
<220> FEATURE:
<223> OTHER INFORMATION: KCD124 light chain variable region AA sequence

<400> SEQUENCE: 448

Asp Val Leu Met Thr Gln Thr Pro Leu Ser Leu Pro Val Ser Leu Gly
  1               5                  10                  15

Asp Gln Ala Ser Ile Ser Cys Arg Ser Gln Ser Ile Val His Ser
                 20                  25                  30

Asn Gly Asp Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
            100                 105                 110

<210> SEQ ID NO 449
<211> LENGTH: 119
<212> TYPE: PRT
<213> ORGANISM: Artificial Sequence
<220> FEATURE:
<223> OTHER INFORMATION: KCD125 heavy chain variable region AA sequence

<400> SEQUENCE: 449

Glu Val Gln Leu Gln Gln Ser Gly Ala Glu Leu Val Arg Pro Gly Ser
  1               5                  10                  15

Ser Val Lys Met Ser Cys Lys Thr Ser Gly Asn Thr Phe Thr Ser Tyr
                 20                  25                  30

Gly Ile Asn Trp Val Lys Gln Arg Pro Gly Gln Gly Leu Glu Trp Ile
             35                  40                  45

Gly Tyr Ile Tyr Ile Gly Thr Gly Tyr Thr Glu Tyr Asn Glu Lys Phe
 50                  55                  60

Lys Gly Lys Ala Thr Leu Thr Ser Asp Thr Ser Ser Ser Thr Ala Tyr
 65                  70                  75                  80

Met Gln Leu Ser Ser Leu Thr Ser Glu Asp Ser Ala Ile Tyr Phe Cys
                 85                  90                  95

Val Arg Lys Ala Tyr Gly Asn Tyr Gly Phe Asp Tyr Trp Gly Gln Gly
            100                 105                 110

Thr Thr Leu Thr Val Ser Ser
        115
```

```
<210> SEQ ID NO 450
<211> LENGTH: 107
<212> TYPE: PRT
<213> ORGANISM: Artificial Sequence
<220> FEATURE:
<223> OTHER INFORMATION: KCD125 light chain variable region AA sequence

<400> SEQUENCE: 450

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 451
<211> LENGTH: 119
<212> TYPE: PRT
<213> ORGANISM: Artificial Sequence
<220> FEATURE:
<223> OTHER INFORMATION: KCD126 heavy chain variable region AA sequence

<400> SEQUENCE: 451

Glu Val Gln Leu Gln Gln Ser Gly Ala Glu Leu Val Arg Pro Gly Ser
1               5                   10                  15

Ser Val Lys Met Ser Cys Lys Thr Ser Gly Lys Thr Phe Thr Ser His
            20                  25                  30

Gly Ile Asn Trp Val Lys Gln Arg Pro Gly Gln Gly Leu Glu Trp Ile
        35                  40                  45

Gly Tyr Ile Tyr Ile Gly Asn Gly Tyr Asn Glu Tyr Asn Glu Lys Phe
    50                  55                  60

Lys Gly Lys Ala Thr Leu Thr Ser Asp Thr Ser Ser Ser Thr Ala Tyr
65                  70                  75                  80

Met Gln Leu Ser Ser Leu Thr Phe Glu Asp Ser Ala Ile Tyr Phe Cys
                85                  90                  95

Val Arg Lys Ala Tyr Gly Asn Tyr Gly Phe Asp Asp Trp Gly Gln Gly
            100                 105                 110

Thr Thr Leu Thr Val Ser Ser
        115

<210> SEQ ID NO 452
<211> LENGTH: 107
<212> TYPE: PRT
<213> ORGANISM: Artificial Sequence
<220> FEATURE:
<223> OTHER INFORMATION: KCD126 light chain variable region AA sequence

<400> SEQUENCE: 452

Asp Ile Gln Met Thr Gln Ser Pro Thr Ser Leu Ser Ala Ser Leu Gly
1               5                   10                  15

Glu Ser Val Ser Leu Thr Cys Arg Ala Ser Gln Glu Ile Ser Gly Asn
            20                  25                  30
```

```
Leu Asn Trp Leu Gln Gln Lys Pro Asp Gly Ser Ile Lys Arg Leu Ile
        35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Asn Tyr Pro Phe
                 85                  90                  95

Thr Phe Gly Ser Gly Thr Lys Leu Glu Val Lys
            100                 105
```

<210> SEQ ID NO 453
<211> LENGTH: 123
<212> TYPE: PRT
<213> ORGANISM: Artificial Sequence
<220> FEATURE:
<223> OTHER INFORMATION: KCD127 heavy chain variable region AA sequence

<400> SEQUENCE: 453

```
Gln Val Gln Leu Gln Gln Pro Gly Ala Glu Leu Val Arg Pro Glu Ser
 1               5                  10                  15

Ser Val Lys Leu Ser Cys Lys Ala Ser Gly Tyr Thr Phe Thr Asn Phe
             20                  25                  30

Trp Met Asp Trp Val Lys Gln Arg Pro Gly Gln Gly Leu Glu Trp Ile
         35                  40                  45

Gly Asn Ile Tyr Pro Ser Gly Ser Glu Thr His Tyr Asn Gln Lys Phe
 50                  55                  60

Lys Asp Lys Ala Thr Leu Thr Val Asp Lys Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Gly Tyr Tyr Gly Ser Arg Tyr Leu Tyr Tyr Phe Asp Tyr
            100                 105                 110

Trp Gly Gln Gly Thr Thr Leu Thr Val Ser Ser
        115                 120
```

<210> SEQ ID NO 454
<211> LENGTH: 107
<212> TYPE: PRT
<213> ORGANISM: Artificial Sequence
<220> FEATURE:
<223> OTHER INFORMATION: KCD127 light chain variable region AA sequence

<400> SEQUENCE: 454

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Tyr Ser Ala Ser Tyr Arg Ser Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Arg
            100                 105
```

<210> SEQ ID NO 455
<211> LENGTH: 123
<212> TYPE: PRT
<213> ORGANISM: Artificial Sequence
<220> FEATURE:
<223> OTHER INFORMATION: KCD128 heavy chain variable region AA sequence

<400> SEQUENCE: 455

Gln Val Gln Leu Gln Gln Pro Gly Ala Glu Leu Val Arg Pro Glu Ser
1               5                   10                  15

Ser Val Lys Leu Ser Cys Lys Ala Ser Gly Tyr Thr Phe Thr Ser Tyr
            20                  25                  30

Trp Met Asp Trp Val Met Gln Arg Pro Gly Gln Gly Leu Glu Trp Ile
        35                  40                  45

Gly Asn Ile Tyr Pro Ser Gly Ser Glu Thr His Tyr Asn Gln Lys Phe
    50                  55                  60

Lys Asp Lys Ala Thr Leu Thr Val Asp Lys Ser Ser Thr Thr Ala Tyr
65                  70                  75                  80

Met Gln Leu Ser Ser Leu Thr Phe Glu Asp Ser Ala Val Tyr Tyr Cys
                85                  90                  95

Ala Arg Ser Gly Phe Ile Gly Ser Arg Tyr Leu Tyr Tyr Phe Asp Tyr
            100                 105                 110

Trp Gly Gln Gly Thr Thr Leu Thr Val Ser Ser
        115                 120

<210> SEQ ID NO 456
<211> LENGTH: 107
<212> TYPE: PRT
<213> ORGANISM: Artificial Sequence
<220> FEATURE:
<223> OTHER INFORMATION: KCD128 light chain variable region AA sequence

<400> SEQUENCE: 456

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Ser Asn Ala
            20                  25                  30

Val Ala Trp Tyr Gln Leu Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Ala Asp Leu Ala Val Tyr Tyr Cys Gln Gln His Tyr Ile Thr Pro Tyr
                85                  90                  95

Thr Phe Gly Gly Gly Thr Lys Leu Glu Ile Lys
            100                 105

<210> SEQ ID NO 457
<211> LENGTH: 120
<212> TYPE: PRT
<213> ORGANISM: Artificial Sequence
<220> FEATURE:
<223> OTHER INFORMATION: KCD129 heavy chain variable region AA sequence

<400> SEQUENCE: 457

Glu Val Gln Leu Val Glu Ser Gly Gly Gly Leu Val Gln Pro Lys Gly
1               5                   10                  15

```
Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
50                  55                  60

Ser Val Lys Asp Arg Phe Thr Ile Ser Arg Asp Asp Ser Glu Ser Met
65                  70                  75                  80

Val Tyr Leu Gln Met Asn Asn Leu Lys Thr Glu Asp Thr Ala Met Tyr
                85                  90                  95

Tyr Cys Val Arg His Gly Tyr Tyr Trp Tyr Phe Asp Val Trp Gly Thr
            100                 105                 110

Gly Thr Thr Val Thr Val Ser Ser
            115                 120

<210> SEQ ID NO 458
<211> LENGTH: 112
<212> TYPE: PRT
<213> ORGANISM: Artificial Sequence
<220> FEATURE:
<223> OTHER INFORMATION: KCD129 light chain variable region AA sequence

<400> SEQUENCE: 458

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Met Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 459
<211> LENGTH: 118
<212> TYPE: PRT
<213> ORGANISM: Artificial Sequence
<220> FEATURE:
<223> OTHER INFORMATION: KCD103 heavy chain variable region AA sequence

<400> SEQUENCE: 459

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Lys Tyr Asn Gln Lys Phe
50                  55                  60

Lys Asp Lys Ala Thr Leu Thr Val Glu Thr Ser Ser Ser Thr Ala Tyr
65                  70                  75                  80

Met Gln Leu Ser Ser Leu Thr Ser Glu Asp Ser Ala Val Tyr Tyr Cys
```

85                  90                  95

Ala Gly Asn Gly Tyr Asp Gly Ser Met Asp Tyr Trp Gly Gln Gly Thr
                100                 105                 110

Ser Val Thr Val Ser Ser
        115

<210> SEQ ID NO 460
<211> LENGTH: 107
<212> TYPE: PRT
<213> ORGANISM: Artificial Sequence
<220> FEATURE:
<223> OTHER INFORMATION: KCD103 light chain variable region AA sequence

<400> SEQUENCE: 460

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Ser
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Arg Val Pro Ser Arg Phe Ser Gly
50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Ala Asn Thr Leu Pro Tyr
                85                  90                  95

Thr Phe Gly Gly Gly Thr Lys Leu Glu Ile Lys
            100                 105

<210> SEQ ID NO 461
<211> LENGTH: 122
<212> TYPE: PRT
<213> ORGANISM: Artificial Sequence
<220> FEATURE:
<223> OTHER INFORMATION: KCD131 heavy chain variable region AA sequence

<400> SEQUENCE: 461

Gln Val Gln Leu Gln Gln Ser Gly Pro Glu Leu Val Lys Pro Gly Ala
1               5                   10                  15

Ser Val Lys Ile Ser Cys Lys Ala Ser Ala Tyr Thr Phe Thr Asp Tyr
                20                  25                  30

Tyr Ile Asn Trp Val Lys Gln Arg Pro Gly Gln Gly Pro Glu Trp Ile
            35                  40                  45

Gly Trp Ile Phe Pro Gly Ser Asn Ser Thr Tyr Ser Asn Glu Lys Phe
50                  55                  60

Glu Val Lys Ala Thr Leu Thr Val Asp Glu Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Leu Gly Tyr Phe Gly Ser Ser Tyr His Ala Leu Asp Tyr Trp
            100                 105                 110

Gly Gln Gly Thr Ser Val Thr Val Ser Ser
        115                 120

<210> SEQ ID NO 462
<211> LENGTH: 107
<212> TYPE: PRT
<213> ORGANISM: Artificial Sequence
<220> FEATURE:

<223> OTHER INFORMATION: KCD131 light chain variable region AA sequence

<400> SEQUENCE: 462

```
Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser His
            20                  25                  30
Leu Ala Trp Phe Gln Gln Lys Gln Gly Lys Ser Pro Arg Leu Leu Val
        35                  40                  45
Tyr Ser Ala Thr Asn Leu Pro Asp Gly Val Pro Ser Arg Phe Ser Gly
    50                  55                  60
Ser Gly Ser Gly Thr Gln Tyr Ser Leu Lys Ile Asn Ile Leu Gln Ser
65                  70                  75                  80
Glu Asp Phe Gly Ser Tyr Tyr Cys Gln His Phe Trp Gly Thr Pro Trp
                85                  90                  95
Thr Phe Gly Gly Gly Thr Lys Leu Glu Ile Lys
            100                 105
```

<210> SEQ ID NO 463
<211> LENGTH: 121
<212> TYPE: PRT
<213> ORGANISM: Artificial Sequence
<220> FEATURE:
<223> OTHER INFORMATION: KCD132 heavy chain variable region AA sequence

<400> SEQUENCE: 463

```
Gln Val Gln Leu Gln Gln Ser Gly Pro Glu Leu Val Lys Pro Gly Ala
1               5                   10                  15
Ser Val Lys Ile Ser Cys Lys Ala Ser Gly Tyr Ser Phe Thr Asp Tyr
            20                  25                  30
Tyr Ile Asn Trp Val Lys Gln Arg Pro Gly Gln Gly Leu Glu Trp Ile
        35                  40                  45
Gly Trp Ile Phe Pro Gly Ser Gly Ser Thr Tyr Tyr Asn Glu Lys Phe
    50                  55                  60
Lys Gly Lys Ala Thr Leu Thr Val Asp Lys Ser Ser Ser Thr Ala Tyr
65                  70                  75                  80
Met Leu Leu Ser Ser Leu Thr Ser Glu Asp Ser Ala Val Tyr Phe Cys
                85                  90                  95
Ala Arg Thr Gly Tyr Tyr Ser Asn Leu Tyr Ala Val Asp Tyr Trp Gly
            100                 105                 110
Gln Gly Thr Ser Val Thr Val Ser Ser
        115                 120
```

<210> SEQ ID NO 464
<211> LENGTH: 107
<212> TYPE: PRT
<213> ORGANISM: Artificial Sequence
<220> FEATURE:
<223> OTHER INFORMATION: KCD132 light chain variable region AA sequence

<400> SEQUENCE: 464

```
Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser Asn
            20                  25                  30
Leu Ala Trp Tyr Gln Gln Lys Gln Gly Lys Ser Pro Gln Leu Leu Val
        35                  40                  45
Tyr Val Ala Thr Asn Leu Ala Asp Gly Val Pro Ser Arg Phe Ser Gly
```

```
                    50                  55                  60

Ser Gly Ser Gly Thr Gln Tyr Ser Leu Lys Ile Asn Ser Leu Gln Ser
 65                  70                  75                  80

Glu Asp Phe Gly Asn Tyr Tyr Cys Gln His Phe Trp Gly Thr Pro Tyr
                     85                  90                  95

Thr Phe Gly Gly Gly Thr Lys Leu Glu Met Arg
                100                 105
```

<210> SEQ ID NO 465
<211> LENGTH: 121
<212> TYPE: PRT
<213> ORGANISM: Artificial Sequence
<220> FEATURE:
<223> OTHER INFORMATION: KCD133 heavy chain variable region AA sequence

<400> SEQUENCE: 465

```
Glu Val Gln Leu Val Glu Ser Gly Gly Gly Leu Leu Gln Pro Lys Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
             35                  40                  45

Ala Arg Ile Arg Ser Lys Ser Ser Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Phe Tyr Leu Glu Met Asn Asn Leu Lys Thr Glu Asp Thr Ala Met Tyr
                 85                  90                  95

Tyr Cys Val Arg Asp Arg Gly Tyr Tyr Tyr Val Met Asp Tyr Trp Gly
                100                 105                 110

Gln Gly Thr Ser Val Thr Val Ser Ser
            115                 120
```

<210> SEQ ID NO 466
<211> LENGTH: 111
<212> TYPE: PRT
<213> ORGANISM: Artificial Sequence
<220> FEATURE:
<223> OTHER INFORMATION: KCD133 light chain variable region AA sequence

<400> SEQUENCE: 466

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
             35                  40                  45

Lys Leu Leu Ile Asn Ala Ala Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Trp Thr Phe Gly Gly Gly Thr Lys Leu Glu Ile Lys
                100                 105                 110
```

<210> SEQ ID NO 467
<211> LENGTH: 121

-continued

```
<212> TYPE: PRT
<213> ORGANISM: Artificial Sequence
<220> FEATURE:
<223> OTHER INFORMATION: KCD134 heavy chain variable region AA sequence

<400> SEQUENCE: 467
```

Glu Val Gln Leu Gln Gln Ser Gly Pro Glu Met Val Lys Pro Gly Ala
1               5                   10                  15

Ser Val Lys Met Ser Cys Gln Ala Ser Gly Tyr Thr Phe Thr Asp Tyr
            20                  25                  30

Tyr Met Asn Trp Val Lys Gln Ser His Gly Glu Thr Leu Glu Trp Ile
        35                  40                  45

Gly Asp Ile Tyr Pro His Asn Gly Tyr Thr Ala Tyr Asn Gln Lys Phe
50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Arg Gly Gly Gln Leu Arg Leu Pro Ala Trp Phe Ala Tyr Trp Gly
        100                 105                 110

Gln Gly Thr Leu Val Thr Val Ser Ala
        115                 120

```
<210> SEQ ID NO 468
<211> LENGTH: 107
<212> TYPE: PRT
<213> ORGANISM: Artificial Sequence
<220> FEATURE:
<223> OTHER INFORMATION: KCD134 light chain variable region AA sequence

<400> SEQUENCE: 468
```

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Ser Leu Arg Pro Gly Val Pro Ser Arg Phe Ser Ser
50                  55                  60

Ser Gly Tyr Gly Thr Asp Phe Val Phe Thr Ile Glu Asp Met Phe Ser
65                  70                  75                  80

Glu Asp Val Ala Asp Tyr His Cys Leu Gln Ser Asp Asn Leu Pro Tyr
            85                  90                  95

Thr Phe Gly Gly Gly Thr Lys Leu Glu Ile Lys
        100                 105

```
<210> SEQ ID NO 469
<211> LENGTH: 117
<212> TYPE: PRT
<213> ORGANISM: Artificial Sequence
<220> FEATURE:
<223> OTHER INFORMATION: KCD135 heavy chain variable region AA sequence

<400> SEQUENCE: 469
```

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Ile Phe Thr Asp Tyr
            20                  25                  30

Ser Ile His Trp Val Lys Gln Ser His Gly Lys Ser Leu Glu Trp Ile

```
                35                  40                  45
Gly Tyr Ile Asn Pro Asn Asn Gly Gly Thr Ser Tyr Asn Gln Lys Phe
 50                  55                  60

Lys Gly Lys Ala Thr Leu Thr Val Asn Lys Ser Ser Thr Thr Ala Tyr
 65                  70                  75                  80

Met Glu Leu Arg Ser Leu Thr Ser Glu Asp Ser Ala Val Tyr Phe Cys
                 85                  90                  95

Ala Arg Asp Thr Thr Ile Val Gly Asp Tyr Trp Gly Gln Gly Thr Thr
                100                 105                 110

Leu Thr Val Ser Ser
        115

<210> SEQ ID NO 470
<211> LENGTH: 107
<212> TYPE: PRT
<213> ORGANISM: Artificial Sequence
<220> FEATURE:
<223> OTHER INFORMATION: KCD135 light chain variable region AA sequence

<400> SEQUENCE: 470

Asp Ile Val Met Thr Gln Ser Gln Lys Phe Met Ser Thr Ser Val Gly
 1               5                  10                  15

Asp Arg Val Ser Val Thr Cys Lys Ala Ser Gln His Val Gly Thr Asn
                20                  25                  30

Val Val Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Ser Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Phe Asn Ser Tyr Pro Leu
                 85                  90                  95

Thr Phe Gly Gly Gly Thr Lys Leu Glu Ile Lys
                100                 105

<210> SEQ ID NO 471
<211> LENGTH: 113
<212> TYPE: PRT
<213> ORGANISM: Artificial Sequence
<220> FEATURE:
<223> OTHER INFORMATION: KCD136 heavy chain variable region AA sequence

<400> SEQUENCE: 471

Glu Val Gln Leu Gln Gln Ser Val Ala Glu Leu Val Arg Pro Gly Ala
 1               5                  10                  15

Ser Val Lys Leu Ser Cys Ser Ala Ser Gly Phe Asn Ile Lys Asn Thr
                20                  25                  30

Tyr Met His Trp Val Asn Gln Arg Pro Glu Gln Gly Leu Glu Trp Ile
            35                  40                  45

Gly Arg Ile Asp Pro Ala Asn Gly Ile Thr Lys Tyr Ala Pro Asn Phe
 50                  55                  60

Gln Gly Lys Ala Thr Ile Thr Ala Asp Thr Ser Ser Asn Thr Ala Tyr
 65                  70                  75                  80

Leu Gln Leu Ser Asn Leu Thr Ser Glu Asp Thr Ala Ile Tyr Tyr Cys
                 85                  90                  95

Thr Arg Ala Met Asp Tyr Trp Gly Gln Gly Thr Ser Val Thr Val Ser
                100                 105                 110
```

Ser

<210> SEQ ID NO 472
<211> LENGTH: 106
<212> TYPE: PRT
<213> ORGANISM: Artificial Sequence
<220> FEATURE:
<223> OTHER INFORMATION: KCD136 light chain variable region AA sequence

<400> SEQUENCE: 472

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Ile Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Asp Thr Tyr Pro Trp Thr
                85                  90                  95

Phe Gly Gly Gly Thr Lys Leu Glu Ile Lys
            100                 105

<210> SEQ ID NO 473
<211> LENGTH: 122
<212> TYPE: PRT
<213> ORGANISM: Artificial Sequence
<220> FEATURE:
<223> OTHER INFORMATION: KCD137 heavy chain variable region AA sequence

<400> SEQUENCE: 473

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Ile Pro Asp Lys Arg Leu Glu Trp Val
        35                  40                  45

Ala Ile Ser Ser Arg Asp Asn Ser Phe Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Phe Cys
                85                  90                  95

Thr Arg His Pro Tyr Leu Pro Thr Gly Gly Tyr Val Met Asp Tyr Trp
            100                 105                 110

Gly Gln Gly Thr Ser Val Thr Val Ser Ser
        115                 120

<210> SEQ ID NO 474
<211> LENGTH: 107
<212> TYPE: PRT
<213> ORGANISM: Artificial Sequence
<220> FEATURE:
<223> OTHER INFORMATION: KCD137 light chain variable region AA sequence

<400> SEQUENCE: 474

Asp Ile Val Met Thr Gln Ser His Lys Phe Met Ser Thr Ser Val Gly
1               5                   10                  15

```
Asp Arg Val Ser Ile Thr Cys Lys Ala Ser Gln Asp Val Gly Thr Ala
            20                  25                  30

Val Ala Trp Tyr Gln Gln Arg Pro Gly Gln Ser Pro Lys Leu Leu Ile
        35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Val Ser Asn Val Gln Ser
65                  70                  75                  80

Glu Asp Leu Ala Asp Tyr Phe Cys Gln Gln Tyr Thr Ser Tyr Pro Leu
                85                  90                  95

Thr Phe Gly Ala Gly Thr Lys Leu Glu Leu Lys
            100                 105

<210> SEQ ID NO 475
<211> LENGTH: 119
<212> TYPE: PRT
<213> ORGANISM: Artificial Sequence
<220> FEATURE:
<223> OTHER INFORMATION: KCD139 heavy chain variable region AA sequence

<400> SEQUENCE: 475

Glu Val Gln Leu Gln Gln Ser Gly Ala Glu Leu Val Arg Pro Gly Ser
1               5                   10                  15

Ser Val Lys Met Ser Cys Lys Thr Ser Gly Tyr Thr Phe Thr Ser Tyr
            20                  25                  30

Gly Ile Asn Trp Val Lys Gln Arg Pro Gly Gln Gly Leu Glu Trp Ile
        35                  40                  45

Gly Tyr Ile Tyr Ile Ala Asn Gly Tyr Thr Glu Asn Asn Glu Lys Phe
 50                  55                  60

Lys Gly Lys Ala Lys Leu Thr Ser Asp Ile Ser Ser Thr Ala Tyr
65                  70                  75                  80

Met Gln Leu Ser Ser Leu Thr Ser Glu Asp Ser Ala Ile Tyr Phe Cys
                85                  90                  95

Ala Arg Arg Phe Asp Tyr Ala Gly Ala Leu Asp Tyr Trp Gly Gln Gly
            100                 105                 110

Thr Ser Val Thr Val Ser Ser
        115

<210> SEQ ID NO 476
<211> LENGTH: 111
<212> TYPE: PRT
<213> ORGANISM: Artificial Sequence
<220> FEATURE:
<223> OTHER INFORMATION: KCD139 light chain variable region AA sequence

<400> SEQUENCE: 476

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile His Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Ile Tyr Tyr Cys Gln Gln Thr Asn
```

```
                    85                  90                  95

Asp Asp Pro Tyr Thr Phe Gly Gly Thr Asn Leu Glu Ile Lys
                100                 105                 110
```

<210> SEQ ID NO 477
<211> LENGTH: 118
<212> TYPE: PRT
<213> ORGANISM: Artificial Sequence
<220> FEATURE:
<223> OTHER INFORMATION: KCD104 heavy chain variable region AA sequence

<400> SEQUENCE: 477

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Tyr Tyr Asn Gln Lys Phe
50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Gly Tyr Asp Gly Ala Met Asp Tyr Trp Gly Gln Gly Thr
                100                 105                 110

Ser Val Thr Val Ser Ser
            115
```

<210> SEQ ID NO 478
<211> LENGTH: 107
<212> TYPE: PRT
<213> ORGANISM: Artificial Sequence
<220> FEATURE:
<223> OTHER INFORMATION: KCD104 light chain variable region AA sequence

<400> SEQUENCE: 478

```
Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Pro Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Tyr
                85                  90                  95

Thr Phe Gly Gly Gly Thr Lys Leu Glu Ile Lys
                100                 105
```

<210> SEQ ID NO 479
<211> LENGTH: 116
<212> TYPE: PRT
<213> ORGANISM: Artificial Sequence
<220> FEATURE:
<223> OTHER INFORMATION: KCD200 heavy chain variable region AA sequence

<400> SEQUENCE: 479

-continued

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
            20                  25                  30

Tyr Lys Asn Trp Met Arg Gln Arg His Gly Glu Ser Leu Glu Trp Ile
        35                  40                  45

Gly Asp Ile Asn Pro Asn Ser Gly Asp Thr Ala Tyr Asn Gln Lys Phe
    50                  55                  60

Lys Gly Lys Ala Thr Leu Thr Val Asp Arg Ser Ser Thr Ala Tyr
65              70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 480
<211> LENGTH: 112
<212> TYPE: PRT
<213> ORGANISM: Artificial Sequence
<220> FEATURE:
<223> OTHER INFORMATION: KCD200 light chain variable region AA sequence

<400> SEQUENCE: 480

Asp Val Leu Met Thr Gln Thr Pro Leu Ser Leu Pro Val Ser Leu Gly
1               5                   10                  15

Asp Gln Val Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 481
<211> LENGTH: 119
<212> TYPE: PRT
<213> ORGANISM: Artificial Sequence
<220> FEATURE:
<223> OTHER INFORMATION: KCD210 heavy chain variable region AA sequence

<400> SEQUENCE: 481

Glu Val Gln Leu Gln Gln Ser Gly Pro Val Leu Val Lys Pro Gly Ala
1               5                   10                  15

Ser Val Thr Met Ser Cys Lys Ala Ser Gly Tyr Thr Phe Thr Glu Tyr
            20                  25                  30

Tyr Met Asn Trp Val Lys Gln Ser His Gly Lys Ser Leu Asp Trp Ile
        35                  40                  45

Gly Val Ile Asn Pro Tyr Ser Gly Gly Thr Ser Tyr Lys Gln Lys Phe
    50                  55                  60

Lys Asp Lys Ala Thr Leu Thr Val Asp Lys Ser Ser Ser Thr Ala Tyr

```
                65                  70                  75                  80
Met Glu Leu Asn Gly Leu Thr Ser Glu Asp Ser Ala Val Tyr Phe Cys
                    85                  90                  95

Val Arg Gly Gly Leu Arg Arg Asn Tyr Phe Asp Tyr Trp Gly Gln Gly
            100                 105                 110

Thr Thr Leu Thr Val Ser Ser
        115

<210> SEQ ID NO 482
<211> LENGTH: 108
<212> TYPE: PRT
<213> ORGANISM: Artificial Sequence
<220> FEATURE:
<223> OTHER INFORMATION: KCD210 light chain variable region AA sequence

<400> SEQUENCE: 482

Glu Ile Val Leu Thr Gln Ser Pro Ala Leu Met Thr Ala Ser Pro Gly
1               5                   10                  15

Glu Lys Val Thr Ile Thr Cys Ser Val Ser Ser Ser Ile Ser Ser Thr
            20                  25                  30

Asn Leu His Trp Tyr Gln Gln Lys Ser Gly Thr Ser Pro Lys Pro Trp
        35                  40                  45

Ile Phe Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Asn Met Glu
65                  70                  75                  80

Ala Glu Asp Ala Ala Thr Tyr Tyr Cys Gln Gln Trp Asn Ser Tyr Pro
                85                  90                  95

Phe Thr Phe Gly Thr Gly Thr Lys Leu Glu Ile Lys
            100                 105

<210> SEQ ID NO 483
<211> LENGTH: 121
<212> TYPE: PRT
<213> ORGANISM: Artificial Sequence
<220> FEATURE:
<223> OTHER INFORMATION: KCD212 heavy chain variable region AA sequence

<400> SEQUENCE: 483

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Ala Gly Ser Tyr Thr Tyr Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Lys Ser Glu Asp Thr Ala Met Tyr Tyr Cys
                85                  90                  95

Ala Arg Pro Leu Asn Tyr Tyr Gly Thr Ser Ser Phe Asp Tyr Trp Gly
            100                 105                 110

Gln Gly Thr Thr Leu Thr Val Ser Ser
        115                 120

<210> SEQ ID NO 484
<211> LENGTH: 108
```

```
<212> TYPE: PRT
<213> ORGANISM: Artificial Sequence
<220> FEATURE:
<223> OTHER INFORMATION: KCD212 light chain variable region AA sequence

<400> SEQUENCE: 484

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Val Ser Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Pro Arg Phe Ser
50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Asn Thr Phe Gly Ala Gly Thr Lys Leu Glu Leu Lys
            100                 105

<210> SEQ ID NO 485
<211> LENGTH: 115
<212> TYPE: PRT
<213> ORGANISM: Artificial Sequence
<220> FEATURE:
<223> OTHER INFORMATION: KCD214 heavy chain variable region AA sequence

<400> SEQUENCE: 485

Glu Val Gln Leu Gln Gln Ser Val Ala Glu Phe Val Arg Pro Gly Ala
1               5                   10                  15

Ser Val Lys Leu Ser Cys Thr Ala Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Glu Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Leu Tyr Asp Tyr Asp Gly Tyr Trp Gly Gln Gly Thr Thr Leu Thr
            100                 105                 110

Val Ser Ser
        115

<210> SEQ ID NO 486
<211> LENGTH: 108
<212> TYPE: PRT
<213> ORGANISM: Artificial Sequence
<220> FEATURE:
<223> OTHER INFORMATION: KCD214 light chain variable region AA sequence

<400> SEQUENCE: 486

Glu Ile Val Leu Thr Gln Ser Pro Ala Leu Met Ala Ala Ser Pro Gly
1               5                   10                  15

Glu Lys Val Thr Ile Thr Cys Arg Val Ser Ser Ser Ile Ser Ser Ser
            20                  25                  30

Ser Leu His Trp Tyr Gln Gln Lys Ser Gly Thr Ser Pro Lys Pro Trp
```

```
                35                  40                  45
Ile Tyr Gly Thr Ser Asn Leu Ala Ser Gly Val Pro Val Arg Phe Ser
         50                  55                  60
Gly Ser Arg Ser Gly Thr Ser Tyr Ser Leu Thr Ile Ser Ser Met Glu
 65                  70                  75                  80
Ala Glu Asp Ala Ala Thr Tyr Tyr Cys Gln Gln Trp Ser Asp Tyr Pro
                 85                  90                  95
Trp Thr Phe Gly Gly Gly Thr Lys Leu Glu Ile Lys
            100                 105
```

<210> SEQ ID NO 487
<211> LENGTH: 122
<212> TYPE: PRT
<213> ORGANISM: Artificial Sequence
<220> FEATURE:
<223> OTHER INFORMATION: KCD216 heavy chain variable region AA sequence

<400> SEQUENCE: 487

```
Gln Val His Leu Gln Gln Ser Gly Pro Glu Leu Val Lys Pro Gly Ala
 1               5                  10                  15
Ser Val Lys Ile Ser Cys Lys Ala Ser Gly Tyr Thr Phe Ile Asp Tyr
             20                  25                  30
Tyr Ile Asn Trp Val Lys Gln Arg Pro Gly Gln Gly Leu Glu Trp Ile
         35                  40                  45
Gly Trp Ile Phe Pro Gly Ser Asp Ser Thr Tyr Tyr Asn Glu Lys Phe
     50                  55                  60
Lys Gly Lys Ala Thr Leu Thr Val Asp Lys Ser Ser Ser Thr Ala Tyr
 65                  70                  75                  80
Met Leu Leu Ser Ser Leu Thr Ser Glu Asp Ser Ala Val Tyr Phe Cys
                 85                  90                  95
Ala Arg Tyr Gly Tyr Tyr Gly Ser Ser Phe Tyr Ala Met Asp Tyr Trp
            100                 105                 110
Gly Gln Gly Thr Ser Val Thr Val Ser Ser
            115                 120
```

<210> SEQ ID NO 488
<211> LENGTH: 107
<212> TYPE: PRT
<213> ORGANISM: Artificial Sequence
<220> FEATURE:
<223> OTHER INFORMATION: KCD216 light chain variable region AA sequence

<400> SEQUENCE: 488

```
Asp Ile Gln Met Thr Gln Ser Pro Ala Ser Leu Ser Val Ser Val Gly
 1               5                  10                  15
Glu Thr Val Thr Ile Thr Cys Arg Ala Ser Glu Asn Ile Tyr Ser Asn
             20                  25                  30
Leu Ala Trp Tyr Gln Gln Lys Gln Gly Lys Ser Pro Gln Leu Leu Val
         35                  40                  45
Tyr Ala Ala Thr Asn Leu Ala Asp Gly Val Pro Ser Arg Phe Ser Gly
     50                  55                  60
Ser Gly Ser Gly Thr Gln Tyr Ser Leu Lys Ile Asn Ser Leu Gln Ser
 65                  70                  75                  80
Glu Asp Phe Gly Ser Tyr Tyr Cys Gln His Phe Trp Gly Thr Pro Pro
                 85                  90                  95
Thr Phe Gly Gly Gly Ser Lys Leu Glu Ile Lys
            100                 105
```

-continued

<210> SEQ ID NO 489
<211> LENGTH: 118
<212> TYPE: PRT
<213> ORGANISM: Artificial Sequence
<220> FEATURE:
<223> OTHER INFORMATION: KCD217 heavy chain variable region AA sequence

<400> SEQUENCE: 489

Gln Val Gln Val Gln Gln Pro Gly Ala Glu Phe Val Lys Thr Gly Ala
1               5                   10                  15

Ser Val Lys Leu Ser Cys Lys Thr Ser Gly Tyr Thr Phe Ile Asp Tyr
            20                  25                  30

Trp Ile His Trp Val Lys Gln Arg Pro Gly His Gly Leu Glu Trp Ile
        35                  40                  45

Gly Arg Ile Asp Pro Asn Thr Gly Gly Ser Lys Tyr Tyr Glu Lys Phe
    50                  55                  60

Lys Arg Lys Ala Thr Leu Thr Val Asp Lys Pro Ser Arg Thr Val Tyr
65                  70                  75                  80

Met Gln Leu Ser Ser Leu Thr Ser Glu Asp Ser Ala Val Tyr Tyr Cys
                85                  90                  95

Thr Arg Glu Tyr Asp Tyr Gly Trp Phe Gly Tyr Trp Gly Gln Gly Thr
            100                 105                 110

Leu Val Thr Val Ser Glu
        115

<210> SEQ ID NO 490
<211> LENGTH: 107
<212> TYPE: PRT
<213> ORGANISM: Artificial Sequence
<220> FEATURE:
<223> OTHER INFORMATION: KCD217 light chain variable region AA sequence

<400> SEQUENCE: 490

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Trp
                85                  90                  95

Thr Phe Gly Gly Gly Thr Lys Leu Glu Ile Lys
            100                 105

<210> SEQ ID NO 491
<211> LENGTH: 122
<212> TYPE: PRT
<213> ORGANISM: Artificial Sequence
<220> FEATURE:
<223> OTHER INFORMATION: KCD219 heavy chain variable region AA sequence

<400> SEQUENCE: 491

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr

```
                20                  25                  30

Tyr Ile Asn Trp Val Lys Gln Arg Pro Gly Gln Gly Leu Glu Trp Ile
            35                  40                  45

Gly Trp Ile Phe Pro Gly Ser Gly Ser Thr Tyr Tyr Asn Glu Lys Phe
        50                  55                  60

Lys Gly Lys Ala Thr Leu Thr Val Asp Lys Ser Ser Thr Ala Tyr
65                  70                  75                  80

Met Leu Leu Ser Ser Leu Pro Ser Glu Asp Ser Ala Val Tyr Phe Cys
                85                  90                  95

Ala Arg Tyr Gly Tyr Tyr Gly Ser Ser Phe Tyr Ala Met Asp Tyr Trp
            100                 105                 110

Gly Gln Gly Thr Ser Val Thr Val Ser Ser
            115                 120

<210> SEQ ID NO 492
<211> LENGTH: 107
<212> TYPE: PRT
<213> ORGANISM: Artificial Sequence
<220> FEATURE:
<223> OTHER INFORMATION: KCD219 light chain variable region AA sequence

<400> SEQUENCE: 492

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30

Leu Ala Trp Tyr Gln Gly Lys Gln Gly Lys Ser Pro Gln Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Ser Pro Pro
                85                  90                  95

Thr Phe Gly Gly Gly Thr Lys Leu Glu Ile Lys
            100                 105

<210> SEQ ID NO 493
<211> LENGTH: 119
<212> TYPE: PRT
<213> ORGANISM: Artificial Sequence
<220> FEATURE:
<223> OTHER INFORMATION: KCD220 heavy chain variable region AA sequence

<400> SEQUENCE: 493

Gln Val Gln Leu Gln Gln Ser Gly Ala Glu Leu Met Glu Pro Gly Ala
1               5                   10                  15

Ser Val Lys Leu Ser Cys Lys Ala Thr Gly Tyr Thr Phe Thr Gly Tyr
                20                  25                  30

Trp Ile Glu Trp Val Lys Gln Arg Pro Gly His Gly Leu Glu Trp Ile
            35                  40                  45

Gly Glu Thr Leu Pro Gly Ser Asp Ser Asn Asn Tyr Asn Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95
```

Ala Arg Asp Tyr Ser Asn Tyr Trp Tyr Phe Asp Val Trp Gly Thr Gly
            100                 105                 110

Thr Thr Val Thr Val Ser Ser
        115

<210> SEQ ID NO 494
<211> LENGTH: 106
<212> TYPE: PRT
<213> ORGANISM: Artificial Sequence
<220> FEATURE:
<223> OTHER INFORMATION: KCD220 light chain variable region AA sequence

<400> SEQUENCE: 494

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Asp Ser Lys His Arg Thr
                85                  90                  95

Phe Gly Gly Gly Thr Lys Leu Glu Ile Lys
            100                 105

<210> SEQ ID NO 495
<211> LENGTH: 119
<212> TYPE: PRT
<213> ORGANISM: Artificial Sequence
<220> FEATURE:
<223> OTHER INFORMATION: KCD224 heavy chain variable region AA sequence

<400> SEQUENCE: 495

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Ile Arg Gln Ser Pro Gly Lys Gly Leu Glu Trp Leu
        35                  40                  45

Gly Val Ile Trp Gly Val Gly Ser Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ser Tyr Asp Gly Ser Tyr Trp Tyr Phe Asp Val Trp Gly Thr Gly
            100                 105                 110

Thr Thr Val Thr Val Ser Ser
        115

<210> SEQ ID NO 496
<211> LENGTH: 107
<212> TYPE: PRT
<213> ORGANISM: Artificial Sequence
<220> FEATURE:
<223> OTHER INFORMATION: KCD224 light chain variable region AA sequence

```
<400> SEQUENCE: 496

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Val Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Ser Gly Thr Lys Leu Glu Ile Lys
            100                 105

<210> SEQ ID NO 497
<211> LENGTH: 122
<212> TYPE: PRT
<213> ORGANISM: Artificial Sequence
<220> FEATURE:
<223> OTHER INFORMATION: KCD225 heavy chain variable region AA sequence

<400> SEQUENCE: 497

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Met Lys Gln Arg Pro Gly Gln Gly Leu Glu Trp Ile
        35                  40                  45

Gly Trp Ile Phe Pro Gly Ser Asp Ser Thr Tyr Tyr Asn Glu Lys Phe
50                  55                  60

Lys Gly Lys Ala Thr Leu Thr Val Asp Lys Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Leu Gly Tyr Tyr Ser His Ser Tyr Tyr Ala Met Asp Tyr Trp
            100                 105                 110

Gly Gln Gly Thr Ser Val Thr Val Ser Ser
        115                 120

<210> SEQ ID NO 498
<211> LENGTH: 107
<212> TYPE: PRT
<213> ORGANISM: Artificial Sequence
<220> FEATURE:
<223> OTHER INFORMATION: KCD225 light chain variable region AA sequence

<400> SEQUENCE: 498

Asp Ile Gln Met Thr Gln Ser Pro Ala Ser Leu Ser Val Ser Thr Gly
1               5                   10                  15

Glu Thr Val Thr Ile Thr Cys Arg Ala Ser Glu Asn Ile Tyr Ser Asn
            20                  25                  30

Leu Ala Trp Phe Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
50                  55                  60
```

Ser Gly Ser Gly Thr Gln Tyr Ser Leu Lys Ile Thr Ser Leu Gln Ser
65                  70                  75                  80

Glu Asp Phe Gly Ser Tyr Tyr Cys Gln His Phe Trp Gly Thr Pro Leu
                85                  90                  95

Thr Phe Gly Ala Gly Thr Lys Leu Asp Leu Lys
            100                 105

<210> SEQ ID NO 499
<211> LENGTH: 120
<212> TYPE: PRT
<213> ORGANISM: Artificial Sequence
<220> FEATURE:
<223> OTHER INFORMATION: KCD229 heavy chain variable region AA sequence

<400> SEQUENCE: 499

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Phe Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg His Gly Tyr Tyr Trp Tyr Phe Asp Val Trp Gly Thr
            100                 105                 110

Gly Thr Thr Val Thr Val Ser Ser
        115                 120

<210> SEQ ID NO 500
<211> LENGTH: 112
<212> TYPE: PRT
<213> ORGANISM: Artificial Sequence
<220> FEATURE:
<223> OTHER INFORMATION: KCD229 light chain variable region AA sequence

<400> SEQUENCE: 500

Asp Val Leu Met Thr Gln Asn Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Asn Leu Leu Ile Tyr Asn Val Phe Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Ser Gly Thr Lys Leu Glu Ile Lys
            100                 105                 110

<210> SEQ ID NO 501
<211> LENGTH: 118
<212> TYPE: PRT
<213> ORGANISM: Artificial Sequence

```
<220> FEATURE:
<223> OTHER INFORMATION: KCD230 heavy chain variable region AA sequence

<400> SEQUENCE: 501

Gln Val Gln Leu Gln Gln Pro Gly Thr Glu Leu Val Lys Pro Gly Ala
1               5                   10                  15

Ser Val Lys Leu Pro Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Thr Tyr Ile Asn Tyr Asn Gln Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Thr Thr Ile Met Ala Ser Asp Tyr Trp Gly Gln Gly Thr
            100                 105                 110

Thr Leu Thr Val Ser Ser
        115

<210> SEQ ID NO 502
<211> LENGTH: 107
<212> TYPE: PRT
<213> ORGANISM: Artificial Sequence
<220> FEATURE:
<223> OTHER INFORMATION: KCD230 light chain variable region AA sequence

<400> SEQUENCE: 502

Asp Ile Gln Met Thr Gln Thr Thr Ser Ser Leu Ser Val Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 503
<211> LENGTH: 120
<212> TYPE: PRT
<213> ORGANISM: Artificial Sequence
<220> FEATURE:
<223> OTHER INFORMATION: KCD232 heavy chain variable region AA sequence

<400> SEQUENCE: 503

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Ser Asn Asn Tyr Ala Thr Tyr Tyr Ala Asp
 50                  55                  60
Ser Val Lys Asp Arg Phe Thr Ile Ser Arg Asp Asp Ser Glu Ser Met
 65                  70                  75                  80
Val Tyr Leu Gln Met Asn Asn Leu Lys Thr Glu Asp Thr Ala Met Tyr
                 85                  90                  95
Tyr Cys Val Arg His Gly Tyr Tyr Trp Tyr Phe Asp Val Trp Gly Thr
                100                 105                 110
Gly Thr Thr Val Thr Val Ser Ser
                115                 120

<210> SEQ ID NO 504
<211> LENGTH: 112
<212> TYPE: PRT
<213> ORGANISM: Artificial Sequence
<220> FEATURE:
<223> OTHER INFORMATION: KCD232 light chain variable region AA sequence

<400> SEQUENCE: 504

Asp Val Leu Met Thr Gln Thr Pro Leu Ser Leu Pro Val Ser Leu Gly
 1               5                  10                  15
Asp Gln Ala Ser Ile Ser Cys Arg Ser Ser Gln Ser Ile Val His Ser
                 20                  25                  30
Asp Gly Asn Thr Tyr Leu Glu Trp Tyr Leu Gln Lys Pro Gly Gln Ser
             35                  40                  45
Pro Lys Leu Leu Ile Tyr Arg Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Met Glu Ala Glu Asp Leu Gly Val Tyr Tyr Cys Phe Gln Gly
                 85                  90                  95
Ser His Val Pro Tyr Thr Phe Gly Gly Gly Thr Lys Leu Glu Ile Lys
                100                 105                 110

<210> SEQ ID NO 505
<211> LENGTH: 119
<212> TYPE: PRT
<213> ORGANISM: Artificial Sequence
<220> FEATURE:
<223> OTHER INFORMATION: KCD205 heavy chain variable region AA sequence

<400> SEQUENCE: 505

Glu Val Gln Leu Gln Gln Ser Gly Ala Glu Leu Val Arg Pro Gly Ser
 1               5                  10                  15
Ser Val Lys Met Ser Cys Lys Thr Ser Gly Asn Thr Phe Thr Ser His
                 20                  25                  30
Gly Ile Asn Trp Val Lys Gln Arg Pro Gly Gln Gly Leu Glu Trp Ile
             35                  40                  45
Gly Tyr Ile Tyr Ile Gly Asn Gly Tyr Asn Glu Tyr Asn Glu Lys Phe
 50                  55                  60
Lys Gly Lys Ala Thr Leu Thr Ser Asp Thr Ser Ser Ser Thr Ala Tyr
 65                  70                  75                  80
Met Gln Leu Ser Ser Leu Thr Ser Glu Asp Ser Ala Ile Tyr Phe Cys
                 85                  90                  95
Val Arg Lys Ala Tyr Gly Asn Tyr Gly Phe Asp Asp Trp Gly Gln Gly
                100                 105                 110
Thr Thr Leu Thr Val Ser Ser
            115
```

```
<210> SEQ ID NO 506
<211> LENGTH: 107
<212> TYPE: PRT
<213> ORGANISM: Artificial Sequence
<220> FEATURE:
<223> OTHER INFORMATION: KCD205 light chain variable region AA sequence

<400> SEQUENCE: 506

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Ser Ser Gly Ser Asp Tyr Ser Leu Thr Ile Ser Ser Leu Glu Ser
65                  70                  75                  80

Asp Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 507
<211> LENGTH: 120
<212> TYPE: PRT
<213> ORGANISM: Artificial Sequence
<220> FEATURE:
<223> OTHER INFORMATION: KCD207 heavy chain variable region AA sequence

<400> SEQUENCE: 507

Ala Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Leu Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Gly Phe Tyr Trp Tyr Phe Asp Val Trp Gly Thr
            100                 105                 110

Gly Thr Thr Val Thr Val Ser Ser
            115                 120

<210> SEQ ID NO 508
<211> LENGTH: 112
<212> TYPE: PRT
<213> ORGANISM: Artificial Sequence
<220> FEATURE:
<223> OTHER INFORMATION: KCD207 light chain variable region AA sequence

<400> SEQUENCE: 508

Asp Val Leu Met Thr Gln Thr Pro Leu Ser Leu Pro Val Ser Leu Gly
1               5                   10                  15
```

```
Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Ser Gly Gln Ser
            35                  40                  45

Pro Lys Leu Leu Ile Tyr Asn Val Ser Asn Arg Phe Ser Gly Val Pro
        50                  55                  60

Asp Arg Phe Arg Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Ser Gly Thr Lys Leu Glu Ile Lys
            100                 105                 110

<210> SEQ ID NO 509
<211> LENGTH: 115
<212> TYPE: PRT
<213> ORGANISM: Artificial Sequence
<220> FEATURE:
<223> OTHER INFORMATION: KCD208 heavy chain variable region AA sequence

<400> SEQUENCE: 509

Glu Val Gln Leu Gln Gln Ser Val Ala Glu Leu Val Arg Pro Gly Ala
1               5                   10                  15

Ser Val Lys Leu Ser Cys Thr Val Ser Gly Phe Asn Ile Lys Asn Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asp Thr Thr Tyr Ala Pro Lys Phe
        50                  55                  60

Gln Gly Lys Ala Thr Ile Thr Ala Asp Thr Ser Ser Asn Ser Ala Tyr
65                  70                  75                  80

Leu His Leu Ser Arg Leu Thr Ser Glu Asp Thr Ala Ile Tyr Tyr Cys
                85                  90                  95

Ser Leu Tyr Asp Tyr Asp Gly Tyr Trp Gly Gln Gly Thr Thr Leu Thr
            100                 105                 110

Val Ser Ser
        115

<210> SEQ ID NO 510
<211> LENGTH: 108
<212> TYPE: PRT
<213> ORGANISM: Artificial Sequence
<220> FEATURE:
<223> OTHER INFORMATION: KCD208 light chain variable region AA sequence

<400> SEQUENCE: 510

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
                20                  25                  30

Ser Leu His Trp Tyr Arg Gln Lys Ser Gly Thr Ser Pro Lys Pro Trp
            35                  40                  45

Ile Tyr Gly Thr Ser His Leu Ala Ser Gly Val Pro Val Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Asp Thr Tyr Pro
                85                  90                  95
```

```
Trp Thr Phe Gly Gly Gly Thr Lys Leu Glu Ile Lys
            100                 105
```

<210> SEQ ID NO 511
<211> LENGTH: 29
<212> TYPE: DNA
<213> ORGANISM: Artificial Sequence
<220> FEATURE:
<223> OTHER INFORMATION: Primer RDJ121

<400> SEQUENCE: 511
gatcgaattc ggaggtgcag ctggtggaa                                      29

<210> SEQ ID NO 512
<211> LENGTH: 22
<212> TYPE: DNA
<213> ORGANISM: Artificial Sequence
<220> FEATURE:
<223> OTHER INFORMATION: Primer RDJ122

<400> SEQUENCE: 512
gatcggagga cactgtcacc ag                                             22

<210> SEQ ID NO 513
<211> LENGTH: 116
<212> TYPE: PRT
<213> ORGANISM: Artificial Sequence
<220> FEATURE:
<223> OTHER INFORMATION: KCD119 TAF heavy chain

<400> SEQUENCE: 513

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
        35                  40                  45

Gly Asp Ile Asn Pro Asn Thr Gly Asp Thr Ser Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
        115
```

<210> SEQ ID NO 514
<211> LENGTH: 116
<212> TYPE: PRT
<213> ORGANISM: Artificial Sequence
<220> FEATURE:
<223> OTHER INFORMATION: 54V heavy chain

<400> SEQUENCE: 514

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
```

35                  40                  45

Gly Asp Ile Asn Pro Val Thr Gly Asp Thr Ser Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
            115

<210> SEQ ID NO 515
<211> LENGTH: 116
<212> TYPE: PRT
<213> ORGANISM: Artificial Sequence
<220> FEATURE:
<223> OTHER INFORMATION: 54I heavy chain

<400> SEQUENCE: 515

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
        35                  40                  45

Gly Asp Ile Asn Pro Ile Thr Gly Asp Thr Ser Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
            115

<210> SEQ ID NO 516
<211> LENGTH: 116
<212> TYPE: PRT
<213> ORGANISM: Artificial Sequence
<220> FEATURE:
<223> OTHER INFORMATION: 54V59D heavy chain

<400> SEQUENCE: 516

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
        35                  40                  45

Gly Asp Ile Asn Pro Val Thr Gly Asp Thr Asp Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

-continued

```
Thr Arg Glu Gly Pro Ser Phe Ala Tyr Trp Gly Gln Gly Thr Leu Val
            100                 105                 110
Thr Val Ser Ser
        115

<210> SEQ ID NO 517
<211> LENGTH: 116
<212> TYPE: PRT
<213> ORGANISM: Artificial Sequence
<220> FEATURE:
<223> OTHER INFORMATION: 54I59D heavy chain

<400> SEQUENCE: 517

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Met Asn Trp Val Arg Gln Ala Pro Gly Lys Gly Leu Glu Trp Ile
        35                  40                  45

Gly Asp Ile Asn Pro Ile Thr Gly Asp Thr Asp Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
        115

<210> SEQ ID NO 518
<211> LENGTH: 116
<212> TYPE: PRT
<213> ORGANISM: Artificial Sequence
<220> FEATURE:
<223> OTHER INFORMATION: 34I54I59D heavy chain

<400> SEQUENCE: 518

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Gly Asp Ile Asn Pro Ile Thr Gly Asp Thr Asp Tyr Asn Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
        115

<210> SEQ ID NO 519
<211> LENGTH: 116
<212> TYPE: PRT
<213> ORGANISM: Artificial Sequence
```

<220> FEATURE:
<223> OTHER INFORMATION: 31S34I54I59D heavy chain

<400> SEQUENCE: 519

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Tyr Ile Asn Trp Val Arg Gln Ala Pro Gly Lys Gly Leu Glu Trp Ile
        35                  40                  45

Gly Asp Ile Asn Pro Ile Thr Gly Asp Thr Asp Tyr Asn Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
            115

<210> SEQ ID NO 520
<211> LENGTH: 116
<212> TYPE: PRT
<213> ORGANISM: Artificial Sequence
<220> FEATURE:
<223> OTHER INFORMATION: 34I54I59D84S heavy chain

<400> SEQUENCE: 520

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Gly Asp Ile Asn Pro Ile Thr Gly Asp Thr Asp Tyr Asn Ala Asp Phe
50                  55                  60

Lys Arg Arg Phe Thr Phe Ser Leu Asp Thr Ser Lys Ser Thr Ala Tyr
65                  70                  75                  80

Leu Gln Met Ser Ser Leu Arg Ala Glu Asp Thr Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ser
            115

<210> SEQ ID NO 521
<211> LENGTH: 116
<212> TYPE: PRT
<213> ORGANISM: Artificial Sequence
<220> FEATURE:
<223> OTHER INFORMATION: 31S34I54I59D84S heavy chain

<400> SEQUENCE: 521

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

-continued

Tyr Ile Asn Trp Val Arg Gln Ala Pro Gly Lys Gly Leu Glu Trp Ile
         35                  40                  45

Gly Asp Ile Asn Pro Ile Thr Gly Asp Thr Tyr Asn Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Ser Ser Leu Arg Ala Glu Asp Thr Ala Val Tyr Tyr Cys
                 85                  90                  95

Thr Arg Glu Gly Pro Ser Phe Ala Tyr Trp Gly Gln Gly Thr Leu Val
                100                 105                 110

Thr Val Ser Ser
        115

<210> SEQ ID NO 522
<211> LENGTH: 112
<212> TYPE: PRT
<213> ORGANISM: Artificial Sequence
<220> FEATURE:
<223> OTHER INFORMATION: KCD119 TAF light chain

<400> SEQUENCE: 522

Asp Ile Gln Leu Thr Gln Ser Pro Ser Ser Leu Ser Ala Ser Val Gly
 1               5                  10                  15

Asp Arg Val Thr Ile Thr Cys Arg Ser Ser Gln Thr Ile Val His Ser
                 20                  25                  30

Asn Gly Asp Thr Tyr Leu Glu Trp Tyr Gln Gln Lys Pro Gly Lys Ala
                 35                  40                  45

Pro Asn Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser His Val Pro Pro Thr Phe Gly Gln Gly Thr Lys Val Glu Ile Lys
                100                 105                 110

<210> SEQ ID NO 523
<211> LENGTH: 112
<212> TYPE: PRT
<213> ORGANISM: Artificial Sequence
<220> FEATURE:
<223> OTHER INFORMATION: 54R light chain

<400> SEQUENCE: 523

Asp Ile Gln Leu Thr Gln Ser Pro Ser Ser Leu Ser Ala Ser Val Gly
 1               5                  10                  15

Asp Arg Val Thr Ile Thr Cys Arg Ser Ser Gln Thr Ile Val His Ser
                 20                  25                  30

Asn Gly Asp Thr Tyr Leu Glu Trp Tyr Gln Gln Lys Pro Gly Lys Ala
                 35                  40                  45

Pro Asn Leu Leu Ile Arg Lys Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser His Val Pro Pro Thr Phe Gly Gln Gly Thr Lys Val Glu Ile Lys
                100                 105                 110

<210> SEQ ID NO 524
<211> LENGTH: 112
<212> TYPE: PRT
<213> ORGANISM: Artificial Sequence
<220> FEATURE:
<223> OTHER INFORMATION: 101V light chain

<400> SEQUENCE: 524

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
        35                  40                  45

Pro Asn Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Val Thr Phe Gly Gln Gly Thr Lys Val Glu Ile Lys
            100                 105                 110

<210> SEQ ID NO 525
<211> LENGTH: 112
<212> TYPE: PRT
<213> ORGANISM: Artificial Sequence
<220> FEATURE:
<223> OTHER INFORMATION: 54R101V light chain

<400> SEQUENCE: 525

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
        35                  40                  45

Pro Asn Leu Leu Ile Arg Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Val Thr Phe Gly Gln Gly Thr Lys Val Glu Ile Lys
            100                 105                 110

<210> SEQ ID NO 526
<211> LENGTH: 112
<212> TYPE: PRT
<213> ORGANISM: Artificial Sequence
<220> FEATURE:
<223> OTHER INFORMATION: 54G101V light chain

<400> SEQUENCE: 526

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
            35                  40                  45

Pro Asn Leu Leu Ile Gly Lys Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser His Val Pro Val Thr Phe Gly Gln Gly Thr Lys Val Glu Ile Lys
            100                 105                 110

<210> SEQ ID NO 527
<211> LENGTH: 348
<212> TYPE: DNA
<213> ORGANISM: Artificial Sequence
<220> FEATURE:
<223> OTHER INFORMATION: KCD119 Taf heavy chain

<400> SEQUENCE: 527
gaggtgcagc tggtggaatc tggcggcgga ctggtgcagc ctggcggctc cctgagactg    60
tcttgcgccg cctccggcta caccttcacc gactactaca tgaactgggt gcgacaggcc   120
cctggcaagg gcctggaatg gatcggcgac atcaaccccc acaccggcga caccagctac   180
aacgccgact tcaagcggcg gttcaccttc tccctggaca cctccaagtc caccgcctac   240
ctgcagatga actccctgcg ggccgaggac accgccgtgt actactgtac cagagagggc   300
ccctccttcg cctactgggg ccagggcaca ctggtgacag tgtcctcc              348

<210> SEQ ID NO 528
<211> LENGTH: 348
<212> TYPE: DNA
<213> ORGANISM: Artificial Sequence
<220> FEATURE:
<223> OTHER INFORMATION: 54V heavy chain

<400> SEQUENCE: 528
gaggtgcagc tggtggaatc tggcggcgga ctggtgcagc ctggcggctc cctgagactg    60
tcttgcgccg cctccggcta caccttcacc gactactaca tgaactgggt gcgacaggcc   120
cctggcaagg gcctggaatg gatcggcgac atcaaccccg tcaccggcga caccagctac   180
aacgccgact tcaagcggcg gttcaccttc tccctggaca cctccaagtc caccgcctac   240
ctgcagatga actccctgcg ggccgaggac accgccgtgt actactgtac cagagagggc   300
ccctccttcg cctactgggg ccagggcaca ctggtgacag tgtcctcc              348

<210> SEQ ID NO 529
<211> LENGTH: 348
<212> TYPE: DNA
<213> ORGANISM: Artificial Sequence
<220> FEATURE:
<223> OTHER INFORMATION: 54I heavy chain

<400> SEQUENCE: 529
gaggtgcagc tggtggaatc tggcggcgga ctggtgcagc ctggcggctc cctgagactg    60
tcttgcgccg cctccggcta caccttcacc gactactaca tgaactgggt gcgacaggcc   120
cctggcaagg gcctggaatg gatcggcgac atcaaccccca tcaccggcga caccagctac   180
aacgccgact tcaagcggcg gttcaccttc tccctggaca cctccaagtc caccgcctac   240
ctgcagatga actccctgcg ggccgaggac accgccgtgt actactgtac cagagagggc   300 cctccttcg cctactgggg ccagggcaca ctggtgacag tgtcctcc    348

<210> SEQ ID NO 530
<211> LENGTH: 348
<212> TYPE: DNA
<213> ORGANISM: Artificial Sequence
<220> FEATURE:
<223> OTHER INFORMATION: 54V59D heavy chain

<400> SEQUENCE: 530
gaggtgcagc tggtggaatc tggcggcgga ctggtgcagc ctggcggctc cctgagactg    60
tcttgcgccg cctccggcta caccttcacc gactactaca tgaactgggt gcgacaggcc    120
cctggcaagg gcctggaatg gatcggcgac atcaaccccg tcaccggcga caccgactac    180
aacgccgact tcaagcggcg gttcaccttc tccctggaca cctccaagtc caccgcctac    240
ctgcagatga actccctgcg ggccgaggac accgccgtgt actactgtac cagagagggc    300
ccctccttcg cctactgggg ccagggcaca ctggtgacag tgtcctcc    348

<210> SEQ ID NO 531
<211> LENGTH: 348
<212> TYPE: DNA
<213> ORGANISM: Artificial Sequence
<220> FEATURE:
<223> OTHER INFORMATION: 54I59D heavy chain

<400> SEQUENCE: 531
gaggtgcagc tggtggaatc tggcggcgga ctggtgcagc ctggcggctc cctgagactg    60
tcttgcgccg cctccggcta caccttcacc gactactaca tgaactgggt gcgacaggcc    120
cctggcaagg gcctggaatg gatcggcgac atcaaccca tcaccggcga caccgactac    180
aacgccgact tcaagcggcg gttcaccttc tccctggaca cctccaagtc caccgcctac    240
ctgcagatga actccctgcg ggccgaggac accgccgtgt actactgtac cagagagggc    300
ccctccttcg cctactgggg ccagggcaca ctggtgacag tgtcctcc    348

<210> SEQ ID NO 532
<211> LENGTH: 348
<212> TYPE: DNA
<213> ORGANISM: Artificial Sequence
<220> FEATURE:
<223> OTHER INFORMATION: 34I54I59D heavy chain

<400> SEQUENCE: 532
gaggtgcagc tggtggaatc tggcggcgga ctggtgcagc ctggcggctc cctgagactg    60
tcttgcgccg cctccggcta caccttcacc gactactaca tcaactgggt gcgacaggcc    120
cctggcaagg gcctggaatg gatcggcgac atcaaccca tcaccggcga caccgactac    180
aacgccgact tcaagcggcg gttcaccttc tccctggaca cctccaagtc caccgcctac    240
ctgcagatga actccctgcg ggccgaggac accgccgtgt actactgtac cagagagggc    300
ccctccttcg cctactgggg ccagggcaca ctggtgacag tgtcctcc    348

<210> SEQ ID NO 533
<211> LENGTH: 348
<212> TYPE: DNA
<213> ORGANISM: Artificial Sequence
<220> FEATURE:
<223> OTHER INFORMATION: 31S34I54I59D heavy chain

<400> SEQUENCE: 533
gaggtgcagc tggtggaatc tggcggcgga ctggtgcagc ctggcggctc cctgagactg    60

```
tcttgcgccg cctccggcta caccttcacc agctactaca tcaactgggt gcgacaggcc    120
cctggcaagg gcctggaatg gatcggcgac atcaaccca tcaccggcga caccgactac     180
aacgccgact tcaagcggcg gttcaccttc tccctggaca cctccaagtc caccgcctac    240
ctgcagatga actccctgcg ggccgaggac accgccgtgt actactgtac cagagagggc    300
ccctccttcg cctactgggg ccagggcaca ctggtgacag tgtcctcc                 348
```

<210> SEQ ID NO 534
<211> LENGTH: 348
<212> TYPE: DNA
<213> ORGANISM: Artificial Sequence
<220> FEATURE:
<223> OTHER INFORMATION: 34I54I59D84S heavy chain

<400> SEQUENCE: 534

```
gaggtgcagc tggtggaatc tggcggcgga ctggtgcagc ctggcggctc cctgagactg     60
tcttgcgccg cctccggcta caccttcacc gactactaca tcaactgggt gcgacaggcc    120
cctggcaagg gcctggaatg gatcggcgac atcaaccca tcaccggcga caccgactac     180
aacgccgact tcaagcggcg gttcaccttc tccctggaca cctccaagtc caccgcctac    240
ctgcagatga gctccctgcg ggccgaggac accgccgtgt actactgtac cagagagggc    300
ccctccttcg cctactgggg ccagggcaca ctggtgacag tgtcctcc                 348
```

<210> SEQ ID NO 535
<211> LENGTH: 348
<212> TYPE: DNA
<213> ORGANISM: Artificial Sequence
<220> FEATURE:
<223> OTHER INFORMATION: 31S34I54I59D84S heavy chain

<400> SEQUENCE: 535

```
gaggtgcagc tggtggaatc tggcggcgga ctggtgcagc ctggcggctc cctgagactg     60
tcttgcgccg cctccggcta caccttcacc agctactaca tcaactgggt gcgacaggcc    120
cctggcaagg gcctggaatg gatcggcgac atcaaccca tcaccggcga caccgactac     180
aacgccgact tcaagcggcg gttcaccttc tccctggaca cctccaagtc caccgcctac    240
ctgcagatga gctccctgcg ggccgaggac accgccgtgt actactgtac cagagagggc    300
ccctccttcg cctactgggg ccagggcaca ctggtgacag tgtcctcc                 348
```

<210> SEQ ID NO 536
<211> LENGTH: 336
<212> TYPE: DNA
<213> ORGANISM: Artificial Sequence
<220> FEATURE:
<223> OTHER INFORMATION: KCD119 Taf light chain

<400> SEQUENCE: 536

```
gacatccagc tgacccagag cccctccagc ctgtccgcct ctgtgggcga cagagtgacc     60
atcacctgtc ggtcctccca gaccatcgtg cactccaacg gcgacaccta cctggaatgg    120
tatcagcaga gcccggcaa ggcccctaac ctgctgatct acaaggtgtc caaccggttc     180
tccggcgtgc cctccagatt ctccggctcc ggctctggca ccgacttcac cctgaccatc    240
tccagcctgc agcccgagga cttcgccacc tactactgtt ttcaaggctc ccacgtgcca    300
cccaccttcg gccagggcac caaggtggaa atcaag                               336
```

<210> SEQ ID NO 537

```
<211> LENGTH: 335
<212> TYPE: DNA
<213> ORGANISM: Artificial Sequence
<220> FEATURE:
<223> OTHER INFORMATION: 54R light chain

<400> SEQUENCE: 537
gacatccagc tgacccagag cccctccagc ctgtccgcct ctgtgggcga cagagtgacc      60
atcacctgtc ggtcctccca gaccatcgtg cactccaacg gcgacaccta cctggaatgg     120
tatcagcaga agcccggcaa ggcccctaac ctgctgatcc gcaaggtgtc caaccggttc     180
tccggcgtgc cctccagatt ctccggctcc ggctctggca ccgacttcac cctgaccatc     240
tccagcctgc agcccgagga cttcgccacc tactactgtt ttcaaggctc ccacgtgcca     300
cccaccttcg gccagggcac caaggtggaa atcaa                                335

<210> SEQ ID NO 538
<211> LENGTH: 336
<212> TYPE: DNA
<213> ORGANISM: Artificial Sequence
<220> FEATURE:
<223> OTHER INFORMATION: 101V light chain

<400> SEQUENCE: 538
gacatccagc tgacccagag cccctccagc ctgtccgcct ctgtgggcga cagagtgacc      60
atcacctgtc ggtcctccca gaccatcgtg cactccaacg gcgacaccta cctggaatgg     120
tatcagcaga agcccggcaa ggcccctaac ctgctgatct acaaggtgtc caaccggttc     180
tccggcgtgc cctccagatt ctccggctcc ggctctggca ccgacttcac cctgaccatc     240
tccagcctgc agcccgagga cttcgccacc tactactgtt ttcaaggctc ccacgtgcca     300
gtcaccttcg gccagggcac caaggtggaa atcaag                               336

<210> SEQ ID NO 539
<211> LENGTH: 336
<212> TYPE: DNA
<213> ORGANISM: Artificial Sequence
<220> FEATURE:
<223> OTHER INFORMATION: 54R101V light chain

<400> SEQUENCE: 539
gacatccagc tgacccagag cccctccagc ctgtccgcct ctgtgggcga cagagtgacc      60
atcacctgtc ggtcctccca gaccatcgtg cactccaacg gcgacaccta cctggaatgg     120
tatcagcaga agcccggcaa ggcccctaac ctgctgatcc gcaaggtgtc caaccggttc     180
tccggcgtgc cctccagatt ctccggctcc ggctctggca ccgacttcac cctgaccatc     240
tccagcctgc agcccgagga cttcgccacc tactactgtt ttcaaggctc ccacgtgcca     300
gtcaccttcg gccagggcac caaggtggaa atcaag                               336

<210> SEQ ID NO 540
<211> LENGTH: 336
<212> TYPE: DNA
<213> ORGANISM: Artificial Sequence
<220> FEATURE:
<223> OTHER INFORMATION: 54G101V light chain

<400> SEQUENCE: 540
gacatccagc tgacccagag cccctccagc ctgtccgcct ctgtgggcga cagagtgacc      60
atcacctgtc ggtcctccca gaccatcgtg cactccaacg gcgacaccta cctggaatgg     120
tatcagcaga agcccggcaa ggcccctaac ctgctgatcg gaaaggtgtc caaccggttc     180
```

```
tccggcgtgc ctccagatt ctccggctcc ggctctggca ccgacttcac cctgaccatc    240
tccagcctgc agcccgagga cttcgccacc tactactgtt ttcaaggctc ccacgtgcca    300
gtcaccttcg gccagggcac caaggtggaa atcaag                             336
```

```
<210> SEQ ID NO 541
<211> LENGTH: 3
<212> TYPE: PRT
<213> ORGANISM: Artificial Sequence
<220> FEATURE:
<223> OTHER INFORMATION: HCDR1

<400> SEQUENCE: 541

Asp Tyr Tyr
1

<210> SEQ ID NO 542
<211> LENGTH: 8
<212> TYPE: PRT
<213> ORGANISM: Artificial Sequence
<220> FEATURE:
<223> OTHER INFORMATION: HCDR2

<400> SEQUENCE: 542

Ile Asn Pro Ile Thr Gly Asp Thr
1               5

<210> SEQ ID NO 543
<211> LENGTH: 7
<212> TYPE: PRT
<213> ORGANISM: Artificial Sequence
<220> FEATURE:
<223> OTHER INFORMATION: HCDR3

<400> SEQUENCE: 543

Glu Gly Pro Ser Phe Ala Tyr
1               5

<210> SEQ ID NO 544
<211> LENGTH: 10
<212> TYPE: PRT
<213> ORGANISM: Artificial Sequence
<220> FEATURE:
<223> OTHER INFORMATION: LCDR1

<400> SEQUENCE: 544

Gln Thr Ile Val His Ser Asn Gly Asp Thr
1               5                   10

<210> SEQ ID NO 545
<211> LENGTH: 3
<212> TYPE: PRT
<213> ORGANISM: Artificial Sequence
<220> FEATURE:
<223> OTHER INFORMATION: LCDR2

<400> SEQUENCE: 545

Lys Val Ser
1

<210> SEQ ID NO 546
<211> LENGTH: 9
<212> TYPE: PRT
<213> ORGANISM: Artificial Sequence
<220> FEATURE:
<223> OTHER INFORMATION: LCDR3
```

<400> SEQUENCE: 546

Phe Gln Gly Ser His Val Pro Val Thr
1               5

<210> SEQ ID NO 547
<211> LENGTH: 49
<212> TYPE: PRT
<213> ORGANISM: Artificial Sequence
<220> FEATURE:
<223> OTHER INFORMATION: KCD119 heavy chain

<400> SEQUENCE: 547

Asp Thr Gln Pro Leu Gly Ile Cys Gln Tyr Trp Gln Pro Gly Pro Leu
1               5                   10                  15
Ile Ser Ser Gly Val Pro Arg Phe Ser Gly Ser Gly Ser Gly Thr Phe
            20                  25                  30
Thr Leu Ile Ser Glu Asp Tyr Tyr Cys Gln Pro Thr Phe Gly Gly Thr
        35                  40                  45
Lys

<210> SEQ ID NO 548
<211> LENGTH: 112
<212> TYPE: PRT
<213> ORGANISM: Artificial Sequence
<220> FEATURE:
<223> OTHER INFORMATION: KCD119

<400> SEQUENCE: 548

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Thr Ile Val His Ser
            20                  25                  30
Asn Gly Asp Thr Tyr Leu Glu Trp Tyr Leu Gln Lys Pro Gly Gln Ser
        35                  40                  45
Pro Asn Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Ile Tyr Tyr Cys Phe Gln Gly
                85                  90                  95
Ser His Val Pro Pro Thr Phe Gly Gly Gly Thr Lys Leu Glu Ile Lys
            100                 105                 110

<210> SEQ ID NO 549
<211> LENGTH: 112
<212> TYPE: PRT
<213> ORGANISM: Artificial Sequence
<220> FEATURE:
<223> OTHER INFORMATION: KCD200

<400> SEQUENCE: 549

Asp Val Leu Met Thr Gln Thr Pro Leu Ser Leu Pro Val Ser Leu Gly
1               5                   10                  15
Asp Gln Val Ser Ile Ser Cys Arg Ser Ser Gln Thr Ile Val His Ser
            20                  25                  30
Asn Gly Asp Thr Tyr Leu Glu Trp Tyr Leu Gln Lys Pro Gly Gln Ser
        35                  40                  45
Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 550
<211> LENGTH: 112
<212> TYPE: PRT
<213> ORGANISM: Artificial Sequence
<220> FEATURE:
<223> OTHER INFORMATION: KCD118

<400> SEQUENCE: 550

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 551
<211> LENGTH: 112
<212> TYPE: PRT
<213> ORGANISM: Artificial Sequence
<220> FEATURE:
<223> OTHER INFORMATION: KCD120

<400> SEQUENCE: 551

Asp Val Leu Met Thr Gln Thr Pro Leu Ser Leu Pro Val Ser Leu Gly
1               5                   10                  15

Asp Gln Val Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 552
<211> LENGTH: 112
<212> TYPE: PRT
<213> ORGANISM: Artificial Sequence
<220> FEATURE:
<223> OTHER INFORMATION: KCD121

<400> SEQUENCE: 552

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 553
<211> LENGTH: 112
<212> TYPE: PRT
<213> ORGANISM: Artificial Sequence
<220> FEATURE:
<223> OTHER INFORMATION: KCD122

<400> SEQUENCE: 553

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 554
<211> LENGTH: 112
<212> TYPE: PRT
<213> ORGANISM: Artificial Sequence
<220> FEATURE:
<223> OTHER INFORMATION: KCD123

<400> SEQUENCE: 554

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Tyr Cys Phe Gln Gly
            85                  90                  95

Ser His Val Pro Pro Thr Phe Gly Gly Gly Thr Lys Leu Glu Ile Lys
            100                 105                 110

<210> SEQ ID NO 555
<211> LENGTH: 112
<212> TYPE: PRT
<213> ORGANISM: Artificial Sequence
<220> FEATURE:
<223> OTHER INFORMATION: KCD124

<400> SEQUENCE: 555

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110

<210> SEQ ID NO 556
<211> LENGTH: 109
<212> TYPE: PRT
<213> ORGANISM: Artificial Sequence
<220> FEATURE:
<223> OTHER INFORMATION: KCD003

<400> SEQUENCE: 556

Asp Val Leu Met Thr Gln Thr Pro Leu Ser Leu Pro Val Ser Leu Gly
1               5                   10                  15

Glu Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Pro Thr Phe Gly Gly Gly Thr Lys Leu
            100                 105

<210> SEQ ID NO 557
<211> LENGTH: 109
<212> TYPE: PRT
<213> ORGANISM: Artificial Sequence
<220> FEATURE:
<223> OTHER INFORMATION: KCD005

<400> SEQUENCE: 557
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Val Thr Phe Gly Ala Gly Thr Lys Leu
            100                 105
```

<210> SEQ ID NO 558
<211> LENGTH: 112
<212> TYPE: PRT
<213> ORGANISM: Artificial Sequence
<220> FEATURE:
<223> OTHER INFORMATION: IGKV2-30

<400> SEQUENCE: 558

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110
```

<210> SEQ ID NO 559
<211> LENGTH: 110
<212> TYPE: PRT
<213> ORGANISM: Artificial Sequence
<220> FEATURE:
<223> OTHER INFORMATION: Mouse Germline

<400> SEQUENCE: 559

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Phe Thr Leu Lys Ile Ser
65                  70                  75                  80

Arg Val Glu Ala Glu Asp Leu Gly Val Tyr Tyr Cys Phe Gln Gly Ser
                85                  90                  95
```

His Val Pro Pro Thr Phe Gly Gly Gly Thr Lys Leu Glu Ile
            100                 105                 110

<210> SEQ ID NO 560
<211> LENGTH: 107
<212> TYPE: PRT
<213> ORGANISM: Artificial Sequence
<220> FEATURE:
<223> OTHER INFORMATION: IGKVD1-39

<400> SEQUENCE: 560

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 561
<211> LENGTH: 107
<212> TYPE: PRT
<213> ORGANISM: Artificial Sequence
<220> FEATURE:
<223> OTHER INFORMATION: TAF

<400> SEQUENCE: 561

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 562
<211> LENGTH: 116
<212> TYPE: PRT
<213> ORGANISM: Artificial Sequence
<220> FEATURE:
<223> OTHER INFORMATION: KCD119 light chain

<400> SEQUENCE: 562

Glu Val Gln Leu Gln Gln Ser Gly Pro Glu Leu Val Lys Pro Gly Ala
1               5                   10                  15

```
Ser Val Lys Ile Ser Cys Lys Ala Ser Gly Tyr Thr Phe Thr Asp Tyr
            20                  25                  30

Tyr Met Asn Trp Met Arg Gln Arg His Gly Glu Ser Leu Glu Trp Ile
        35                  40                  45

Gly Asp Ile Asn Pro Asn Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 563
<211> LENGTH: 116
<212> TYPE: PRT
<213> ORGANISM: Artificial Sequence
<220> FEATURE:
<223> OTHER INFORMATION: KCD119

<400> SEQUENCE: 563

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Thr Asn Trp Met Arg Gln Arg His Gly Glu Ser Leu Glu Trp Ile
        35                  40                  45

Gly Asp Ile Asn Pro Asn Thr Gly Asp Thr Ser Tyr Asn Gln Lys Phe
    50                  55                  60

Arg Val Lys Ala Thr Leu Thr Val Asp Lys Ser Ser Gly Thr Ala Tyr
65                  70                  75                  80

Met Gly Leu Arg Ser Leu Thr Ser Glu Asp Ser Ala Val Tyr Tyr Cys
                85                  90                  95

Thr Arg Glu Gly Pro Ser Phe Ala Tyr Trp Gly Gln Gly Thr Leu Val
            100                 105                 110

Thr Val Ser Ala
        115

<210> SEQ ID NO 564
<211> LENGTH: 116
<212> TYPE: PRT
<213> ORGANISM: Artificial Sequence
<220> FEATURE:
<223> OTHER INFORMATION: KCD200

<400> SEQUENCE: 564

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
            20                  25                  30

Tyr Lys Asn Trp Met Arg Gln Arg His Gly Glu Ser Leu Glu Trp Ile
        35                  40                  45

Gly Asp Ile Asn Pro Asn Ser Gly Asp Thr Ala Tyr Asn Gln Lys Phe
    50                  55                  60

Lys Gly Lys Ala Thr Leu Thr Val Asp Arg Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 565
<211> LENGTH: 116
<212> TYPE: PRT
<213> ORGANISM: Artificial Sequence
<220> FEATURE:
<223> OTHER INFORMATION: KCD118

<400> SEQUENCE: 565

Glu Val Gln Leu Gln Gln Ser Gly Pro Glu Leu Val Lys Pro Gly Ala
1               5                   10                  15

Ser Val Lys Ile Ser Cys Lys Ala Phe Gly Tyr Thr Phe Thr Asp Tyr
                20                  25                  30

Tyr Lys Asn Trp Met Arg Gln Arg His Gly Glu Ser Leu Glu Trp Ile
            35                  40                  45

Gly Asp Ile Asn Pro Asn Ser Gly Asp Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly His Gly Thr Leu Val
            100                 105                 110

Thr Val Ser Ala
        115

<210> SEQ ID NO 566
<211> LENGTH: 116
<212> TYPE: PRT
<213> ORGANISM: Artificial Sequence
<220> FEATURE:
<223> OTHER INFORMATION: KCD120

<400> SEQUENCE: 566

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
                20                  25                  30

Tyr Lys Asn Trp Met Arg Gln Arg His Gly Glu Ser Leu Glu Trp Ile
            35                  40                  45

Gly Asp Ile Asn Pro Asn Ser Gly Asp Thr Ala Tyr Asn Gln Lys Phe
    50                  55                  60

Lys Gly Lys Ala Thr Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115
```

```
<210> SEQ ID NO 567
<211> LENGTH: 116
<212> TYPE: PRT
<213> ORGANISM: Artificial Sequence
<220> FEATURE:
<223> OTHER INFORMATION: KCD121

<400> SEQUENCE: 567
```

| Glu | Val | Gln | Leu | Gln | Gln | Ser | Gly | Pro | Glu | Leu | Val | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Ile | Ser | Cys | Lys | Ala | Ser | Gly | Tyr | Thr | Phe | Thr | Asp | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Lys | Asn | Trp | Met | Arg | Gln | Arg | His | Gly | Glu | Ser | Leu | Glu | Trp | Ile |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gly | Asp | Ile | Asn | Pro | Asn | Asn | Gly | Asp | Thr | Ser | Tyr | Asn | Gln | Lys | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Gly | Lys | Ala | Thr | Leu | Thr | Val | Asp | Lys | Ser | Ser | Ser | Thr | Ala | Phe |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Glu | Leu | Arg | Ser | Leu | Thr | Ser | Glu | Asp | Ser | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Glu | Gly | Pro | Ser | Phe | Ala | Tyr | Trp | Gly | Gln | Gly | Thr | Leu | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Val | Ser | Ala |
|-----|-----|-----|-----|
|     |     | 115 |     |

```
<210> SEQ ID NO 568
<211> LENGTH: 116
<212> TYPE: PRT
<213> ORGANISM: Artificial Sequence
<220> FEATURE:
<223> OTHER INFORMATION: KCD122

<400> SEQUENCE: 568
```

| Glu | Val | Gln | Leu | Gln | Gln | Ser | Gly | Pro | Glu | Leu | Val | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Ile | Ser | Cys | Lys | Ala | Ser | Gly | Tyr | Thr | Phe | Thr | Asp | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Lys | Asn | Trp | Met | Arg | Gln | Arg | His | Gly | Glu | Ser | Leu | Glu | Trp | Ile |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gly | Asp | Ile | Asn | Pro | Asn | Asn | Gly | Asp | Ala | Asn | Tyr | Asn | Gln | Lys | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Gly | Lys | Ala | Thr | Leu | Thr | Val | Asp | Lys | Ser | Ser | Ser | Thr | Ala | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Glu | Leu | Arg | Ser | Leu | Thr | Ser | Glu | Asp | Ser | Ala | Val | Tyr | Phe | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Glu | Gly | Pro | Ser | Phe | Ala | Tyr | Trp | Gly | His | Gly | Thr | Leu | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Val | Ser | Ala |
|-----|-----|-----|-----|
|     |     | 115 |     |

```
<210> SEQ ID NO 569
<211> LENGTH: 116
<212> TYPE: PRT
<213> ORGANISM: Artificial Sequence
<220> FEATURE:
<223> OTHER INFORMATION: KCD123

<400> SEQUENCE: 569
```

| Glu | Val | His | Leu | Gln | Gln | Ser | Gly | Pro | Glu | Leu | Val | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Val Lys Ile Ser Cys Lys Ala Ser Gly Tyr Thr Phe Thr Asp Phe
            20                  25                  30

Tyr Lys Asn Trp Met Arg Gln Arg His Gly Glu Ser Leu Glu Trp Ile
        35                  40                  45

Gly Asp Ile Asn Pro Asn Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 570
<211> LENGTH: 116
<212> TYPE: PRT
<213> ORGANISM: Artificial Sequence
<220> FEATURE:
<223> OTHER INFORMATION: KCD124

<400> SEQUENCE: 570

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Gly Asp Ser Ala Val Tyr Tyr Cys
                85                  90                  95

Thr Arg Glu Gly Ala Ser Phe Ala Phe Trp Gly Gln Gly Thr Leu Val
            100                 105                 110

Thr Val Ser Ala
        115

<210> SEQ ID NO 571
<211> LENGTH: 116
<212> TYPE: PRT
<213> ORGANISM: Artificial Sequence
<220> FEATURE:
<223> OTHER INFORMATION: KCD003

<400> SEQUENCE: 571

Glu Val Gln Leu Gln Gln Ser Arg Pro Glu Leu Val Lys Pro Gly Ala
1               5                   10                  15

Ser Val Lys Ile Phe Cys Lys Ala Ser Gly Tyr Thr Phe Thr Asp Tyr
            20                  25                  30

Tyr Met Asn Trp Met Arg Gln Arg His Gly Glu Thr Leu Glu Trp Ile
        35                  40                  45

Gly Asp Ile Asn Pro Asn Asn Gly Asp Pro Ser Tyr Asn Gln Lys Phe
    50                  55                  60

Lys Asp Lys Ala Thr Leu Thr Val Asp Lys Ser Ser Ser Thr Ala Ser

```
                65                  70                  75                  80
Met Glu Leu Arg Ser Leu Thr Ser Asp Ser Ala Val Tyr Tyr Cys
                    85                  90                  95

Ala Arg Glu Gly Pro Ser Phe Ala Tyr Trp Gly Gln Gly Thr Leu Val
            100                 105                 110

Thr Val Ser Ala
        115

<210> SEQ ID NO 572
<211> LENGTH: 116
<212> TYPE: PRT
<213> ORGANISM: Artificial Sequence
<220> FEATURE:
<223> OTHER INFORMATION: KCD005

<400> SEQUENCE: 572

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Cys Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Gly Asp Ser Ala Val Tyr Tyr Cys
                    85                  90                  95

Thr Arg Glu Gly Ala Ser Phe Ala Phe Trp Gly Gln Gly Thr Leu Val
            100                 105                 110

Thr Val Ser Ala
        115

<210> SEQ ID NO 573
<211> LENGTH: 115
<212> TYPE: PRT
<213> ORGANISM: Artificial Sequence
<220> FEATURE:
<223> OTHER INFORMATION: IGHV3-66

<400> SEQUENCE: 573

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                    85                  90                  95

Cys Ala Arg Asp Ala Phe Asp Val Trp Gly Gln Gly Thr Met Val Thr
            100                 105                 110

Val Ser Ser
        115
```

<210> SEQ ID NO 574
<211> LENGTH: 113
<212> TYPE: PRT
<213> ORGANISM: Artificial Sequence
<220> FEATURE:
<223> OTHER INFORMATION: IGHV1-2

<400> SEQUENCE: 574

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Tyr Phe Asp Tyr Trp Gly Gln Gly Thr Leu Val Thr Val Ser
            100                 105                 110
Ser
```

<210> SEQ ID NO 575
<211> LENGTH: 113
<212> TYPE: PRT
<213> ORGANISM: Artificial Sequence
<220> FEATURE:
<223> OTHER INFORMATION: Mouse Germline

<400> SEQUENCE: 575

```
Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
                20                  25                  30
Tyr Met Asn Trp Val Lys Gln Ser His Gly Lys Ser Leu Glu Trp Ile
            35                  40                  45
Gly Asp Ile Asn Pro Asn Asn Gly Gly Thr Ser Tyr Asn Gln Lys Phe
        50                  55                  60
Lys Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Trp Phe Ala Tyr Trp Gly Gln Gly Thr Leu Val Thr Val Ser
            100                 105                 110
Ala
```

<210> SEQ ID NO 576
<211> LENGTH: 123
<212> TYPE: PRT
<213> ORGANISM: Artificial Sequence
<220> FEATURE:
<223> OTHER INFORMATION: TAF

<400> SEQUENCE: 576

```
Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 577
<211> LENGTH: 10
<212> TYPE: PRT
<213> ORGANISM: Artificial Sequence
<220> FEATURE:
<223> OTHER INFORMATION: CDR sequence

<400> SEQUENCE: 577

Gly Tyr Thr Phe Thr Asp Tyr Tyr Ile Asn
1               5                   10

<210> SEQ ID NO 578
<211> LENGTH: 16
<212> TYPE: PRT
<213> ORGANISM: Artificial Sequence
<220> FEATURE:
<223> OTHER INFORMATION: CDR sequence

<400> SEQUENCE: 578

Ile Asn Pro Ile Thr Gly Asp Thr Asp Tyr Asn Ala Asp Phe Lys Arg
1               5                   10                  15

<210> SEQ ID NO 579
<211> LENGTH: 9
<212> TYPE: PRT
<213> ORGANISM: Artificial Sequence
<220> FEATURE:
<223> OTHER INFORMATION: CDR sequence

<400> SEQUENCE: 579

Thr Arg Glu Gly Pro Ser Phe Ala Tyr
1               5

<210> SEQ ID NO 580
<211> LENGTH: 16
<212> TYPE: PRT
<213> ORGANISM: Artificial Sequence
<220> FEATURE:
<223> OTHER INFORMATION: CDR sequence

<400> SEQUENCE: 580

Arg Ser Ser Gln Thr Ile Val His Ser Asn Gly Asp Thr Tyr Leu Glu
1               5                   10                  15

<210> SEQ ID NO 581
<211> LENGTH: 11
<212> TYPE: PRT
<213> ORGANISM: Artificial Sequence
<220> FEATURE:

```
<223> OTHER INFORMATION: CDR sequence

<400> SEQUENCE: 581

Leu Leu Ile Arg Lys Val Ser Asn Arg Phe Ser
1               5                   10

<210> SEQ ID NO 582
<211> LENGTH: 9
<212> TYPE: PRT
<213> ORGANISM: Artificial Sequence
<220> FEATURE:
<223> OTHER INFORMATION: CDR sequence

<400> SEQUENCE: 582

Phe Gln Gly Ser His Val Pro Val Thr
1               5

<210> SEQ ID NO 583
<211> LENGTH: 113
<212> TYPE: PRT
<213> ORGANISM: Artificial Sequence
<220> FEATURE:
<223> OTHER INFORMATION: IGHV3-66*01; IGHJ3*01

<400> SEQUENCE: 583

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Phe Asp Val Trp Gly Gln Gly Thr Met Val Thr Val Ser
            100                 105                 110

Ser

<210> SEQ ID NO 584
<211> LENGTH: 110
<212> TYPE: PRT
<213> ORGANISM: Artificial Sequence
<220> FEATURE:
<223> OTHER INFORMATION: IGKV2-30*02; IGKJ1*01

<400> SEQUENCE: 584

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
```

```
                    85                  90                  95

Thr His Trp Pro Phe Gly Gln Gly Thr Lys Val Glu Ile Lys
                100                 105                 110

<210> SEQ ID NO 585
<211> LENGTH: 113
<212> TYPE: PRT
<213> ORGANISM: Artificial Sequence
<220> FEATURE:
<223> OTHER INFORMATION: IGHV1-2*02; IGHJ4*01

<400> SEQUENCE: 585

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser

<210> SEQ ID NO 586
<211> LENGTH: 110
<212> TYPE: PRT
<213> ORGANISM: Mus musculus

<400> SEQUENCE: 586

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Leu Ser Gly Val Pro
        50                  55                  60

Asp Arg Phe Ser Gly Ser Gly Ser Gly Thr Phe Thr Leu Lys Ile Ser
65                  70                  75                  80

Arg Val Glu Ala Glu Asp Leu Gly Val Tyr Tyr Cys Phe Gln Gly Ser
                85                  90                  95

His Val Pro Pro Thr Phe Gly Gly Gly Thr Lys Leu Glu Ile
                100                 105                 110

<210> SEQ ID NO 587
<211> LENGTH: 113
<212> TYPE: PRT
<213> ORGANISM: Mus musculus

<400> SEQUENCE: 587

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
```

```
                    20                  25                  30
Tyr Met Asn Trp Val Lys Gln Ser His Gly Lys Ser Leu Glu Trp Ile
                35                  40                  45
Gly Asp Ile Asn Pro Asn Asn Gly Gly Thr Ser Tyr Asn Gln Lys Phe
            50                  55                  60
Lys Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Trp Phe Ala Tyr Trp Gly Gln Gly Thr Leu Val Thr Val Ser
                100                 105                 110
Ala

<210> SEQ ID NO 588
<211> LENGTH: 107
<212> TYPE: PRT
<213> ORGANISM: Artificial Sequence
<220> FEATURE:
<223> OTHER INFORMATION: IGKV1D-39; IGKJ1*01

<400> SEQUENCE: 588

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
                35                  40                  45
Tyr Ala Ala Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Trp
                85                  90                  95
Thr Phe Gly Gln Gly Thr Lys Val Glu Ile Lys
                100                 105

<210> SEQ ID NO 589
<211> LENGTH: 123
<212> TYPE: PRT
<213> ORGANISM: Artificial Sequence
<220> FEATURE:
<223> OTHER INFORMATION: TAF HC

<400> SEQUENCE: 589

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Asp Phe Thr His Tyr
                20                  25                  30
Gly Met Asn Trp Val Arg Gln Ala Pro Gly Lys Gly Leu Glu Trp Val
                35                  40                  45
Gly Trp Ile Asn Thr Tyr Thr Gly Glu Pro Thr Tyr Ala Ala Asp Phe
            50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro Tyr Tyr Tyr Gly Thr Ser His Trp Tyr Phe Asp Val
```

```
                    100             105             110
Trp Gly Gln Gly Thr Leu Val Thr Val Ser Ser
            115             120

<210> SEQ ID NO 590
<211> LENGTH: 112
<212> TYPE: PRT
<213> ORGANISM: Artificial Sequence
<220> FEATURE:
<223> OTHER INFORMATION: TAF LC

<400> SEQUENCE: 590

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Thr Ile Val His Ser
            20                  25                  30

Asn Gly Asp Thr Tyr Leu Glu Trp Tyr Gln Gln Lys Pro Gly Lys Ala
        35                  40                  45

Pro Asn Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Pro Thr Phe Gly Gln Gly Thr Lys Val Glu Ile Lys
            100                 105                 110
```

COMPLEMENT FACTOR D ANTAGONIST ANTIBODIES AND CONJUGATES THEREOF

CROSS REFERENCE TO RELATED APPLICATION

This application claims the benefit of U.S. Provisional Application No. 62/485,718, filed on Apr. 14, 2017, the entirety of which is hereby incorporated by reference.

SEQUENCE LISTING AND ELECTRONIC TABLE

The present application is being filed along with a Sequence Listing in electronic format. The Sequence Listing is provided in an ASCII txt file designated KDIAK001A.txt of 413,159 bytes, created May 9, 2018. The information in the electronic format of the Sequence Listing is incorporated herein by reference in its entirety. The present application is being filed along with a Table in electronic format. The Table is provided as a file entitled CTKDK001A.txt, created and last saved on Apr. 12, 2018, which is 819,316 bytes in size. The information in the electronic format of the Table is incorporated herein by reference in its entirety.

BIOLOGICAL SAMPLE DEPOSIT STATEMENT

In some embodiments, anti-CFD antagonistic antibodies and conjugates thereof are provided, which were deposited in the American Type Culture Collection (ATCC), in accordance with the Budapest Treaty, under the numbers PTA-123800 and PTA-123801, on Jan. 31, 2017.

These deposits were made under the provisions of the Budapest Treaty on the International Recognition of the Deposit of Microorganisms for the Purposes of Patent Procedure and the Regulations thereunder (Budapest Treaty). This assures maintenance of the deposit for 30 years from date of deposit. The deposit will be made available by the ATCC under the terms of the Budapest Treaty, and subject to an agreement between Applicant and the ATCC, which assures permanent and unrestricted availability of the deposit to the public upon issuance of the pertinent U.S. patent or upon laying open to the public of any U.S. or foreign patent application, whichever comes first, and assures availability of the deposit to one determined by the U.S. Commissioner of Patents and Trademarks to be entitled thereto according to 35 U.S.C. § 122 and the Commissioner's Rules pursuant thereto (including 37 C.F.R. § 1.14). Availability of the deposited biological material is not to be construed as a license to practice the invention in contravention of the rights granted under the authority of any Government in accordance with its Patent Laws.

FIELD

The present invention relates generally to constructs, including conjugates thereof, that bind complement factor D (CFD).

BACKGROUND

Age related macular degeneration (AMD) is a leading cause of vision loss and blindness in the elderly. About ten million Americans are afflicted with AMD. The prevalence of AMD in the population increases steadily with age: at 40 years of age only about 2% of the population is affected by AMD but by the age of 80 it is about 25%. Friedman D S et al. 2004. Prevalence of age-related macular degeneration in the United States. Arch Ophthalmol. 122:564-572.

AMD is a progressive disease that evolves over time through various stages eventually resulting in severe central vision loss. One of the hallmarks of AMD are extracellular deposits called drusen. Drusen are subretinal deposits of oxidized lipids and proteins that appear beneath the retinal pigment epithelium (RPE). Also often seen in early AMD are visible clumps of pigment in the macula. As AMD progresses, drusen become larger and pigment changes in the macula become more pronounced. Subsequently, some 10 to 15% of patients will develop subretinal choroidal neovascularization (CNV), typically called wet AMD. CNV is characterized by the presence of new immature blood vessels which grow towards the outer retina from the choroid. These immature blood vessels leak fluid below and in the retina, causing vision loss and blindness. Other patients will develop non-neovascular or dry AMD.

Advanced cases of dry AMD are characterized by sharply demarcated uni- or multi-focal regions of dysfunctional macula, termed geographic atrophy (GA). Over time, GA patches enlarge and involve the RPE and corresponding neurosensory retina and the choriocapillary layer of the choroid. These changes to the eye are progressive and irreversible, resulting in permanent loss visual function. GA occurs bilaterally in over 50% of patients. Binder S, Stanzel B V, Krebs I, Glittenberg C. 2007. Transplantation of the RPE in AMD. Prog Retn Eye Res. 26:516-554. GA accounts for some 20-25% of patients with severe visual loss secondary to AMD (i.e. legal blindness related to AMD). Klein R, Klein B E, Jensen S C, Meuer S M. 1997. The five-year incidence and progression of age-related maculopathy: The Beaver Dam Eye Study. Ophthal. 104:7-21. Forms of dry AMD less severe than GA are responsible for a much larger percentage of moderate visual function loss.

SUMMARY

In some embodiments, an isolated antagonist antibody is provided that specifically binds to complement factor D (CFD) and directly inhibits a proteolytic activity of CFD.

In some embodiments, an isolated antagonist antibody is provided that specifically binds to complement factor D (CFD), inhibits a proteolytic activity of CFD, and inhibits CFD binding to C3bB complex.

In some embodiments, an isolated antagonist antibody is provided that specifically binds to complement factor D (CFD), wherein the antibody does not bind a human CFD mutant comprising mutations R157A and R207A.

In some embodiments, an isolated antagonist antibody is provided that binds an epitope on human CFD, wherein the epitope excludes positions R157 and R207.

In some embodiments, an isolated antagonistic antibody is provided. The antibody comprises a heavy chain amino acid variable region that comprises SEQ ID NO 183; and a light chain amino acid variable region that comprises SEQ ID NO. 184.

In some embodiments, an isolated antagonist antibody is provided that comprises: a heavy chain variable region (VH) comprising a VH complementarity determining region one (CDR1), VH CDR2, and VH CDR3 of the VH having an amino acid sequence selected group the group consisting of SEQ ID NO: 541, SEQ ID NO: 542; and SEQ ID NO: 543; and a light chain variable region (VL) comprising a VL CDR1, VL CDR2, and VL CDR3 of the VL having an amino acid sequence selected from the group consisting of SEQ ID NO: 544; SEQ ID NO: 545; and SEQ ID NO: 546.

In some embodiments, an isolated antagonist antibody that specifically binds to CFD is provided that comprises a heavy chain variable region (VH); and a light chain variable region (VL), wherein the antibody comprises the following mutations: L234A, L235A, and G237A.

In some embodiments, an isolated antagonist antibody is provided. The antibody binds an epitope on human CFD that is the same as or overlaps with the epitope recognized by an antibody comprising the amino acid sequences shown in SEQ ID NO: 61 and SEQ ID NO: 62. In some embodiments, an isolated antagonist antibody is provided. The antibody binds an epitope on human CFD that is the same as or overlaps with the epitope recognized by an antibody comprising the amino acid sequences shown in SEQ ID NO: 45 and SEQ ID NO: 46.

In some embodiments, an isolated antagonist antibody that binds to CFD is provided. The antibody comprises: a heavy chain comprising the amino acid sequence shown in SEQ ID NO: 183, with or without the C-terminal lysine; and a light chain comprising the amino acid sequence shown in SEQ ID NO: 184.

In some embodiments, an isolated antagonist antibody that binds to CFD is provided. The antibody comprises a VH comprising the amino acid sequence shown in SEQ ID NO: 520, or a sequence that is at least 90% identical thereto, having amino acid substitutions in residues that are not within a CDR of SEQ ID NO: 520 and 525.

In some embodiments, an isolated antagonistic antibody that binds to CFD is provided. The antibody comprises a $CDR_H1$ that is the $CDR_H1$ in SEQ ID NO: 520; a $CDR_H2$ that is the $CDR_H2$ in SEQ ID NO: 520; a $CDR_H3$ that is the $CDR_H3$ in SEQ ID NO: 520; a $CDR_L1$ that is the $CDR_L1$ in SEQ ID NO: 525; a $CDR_L2$ that is the $CDR_L2$ in SEQ ID NO: 525; a $CDR_L3$ that is the $CDR_L3$ in SEQ ID NO: 525; at least one of the following mutations (EU numbering): L234A, L235A, and G237A; and at least one of the following mutations (EU numbering): Q347C or L443C.

In some embodiments, an isolated antagonist antibody that specifically binds to complement factor D (CFD) is provided. The antibody is configured to provide a reduced complement reaction, wherein the antibody specifically binds to complement factor D (CFD), and wherein the antibody at least inhibits a proteolytic activity of CFD or inhibits CFD binding to C3bB complex.

In some embodiments, a conjugate is provided that comprises: a) any of the isolated antagonistic antibodies provided herein; and b) a polymer, wherein the polymer is covalently attached to the antibody.

In some embodiments, a conjugate is provided that comprises: a) an isolated antagonist antibody that specifically binds to complement factor D (CFD); and b) a phosphorylcholine containing polymer, wherein the polymer is covalently bonded to the antibody.

In some embodiments, a conjugate is provided that comprises: a) an isolated antagonist antibody that specifically binds to complement factor D (CFD); and b) a polymer comprising a zwitterionic monomer, wherein the zwitterionic monomer is selected from the group consisting of HEMA-phosphorylcholine, PEG, biocompatible fatty acids and derivatives thereof, Hydroxy Alkyl Starch (HAS), Hydroxy Ethyl Starch (HES), Poly Ethylene Glycol (PEG), Poly $(Gly_x\text{-}Ser_y)$ (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, and FcRn binding peptides.

In some embodiments, a conjugate comprising an anti-CFD antibody and a polymer that is capable of blocking at least 80% of an interaction between CFD and C3bB is provided.

In some embodiments, a conjugate comprising (1) an anti-CFD antibody and (2) a phosphorylcholine containing polymer is provided. The polymer is covalently bonded to the antibody at a cysteine outside a variable region of the antibody wherein said cysteine has been added via recombinant DNA technology.

In some embodiments of the conjugate, the conjugate the polymer has 9 arms; and the polymer has a molecular weight of between about 600,000 to about 900,000 Da.

In some embodiments of the conjugate, the conjugate has the following structure:

Formula (17)

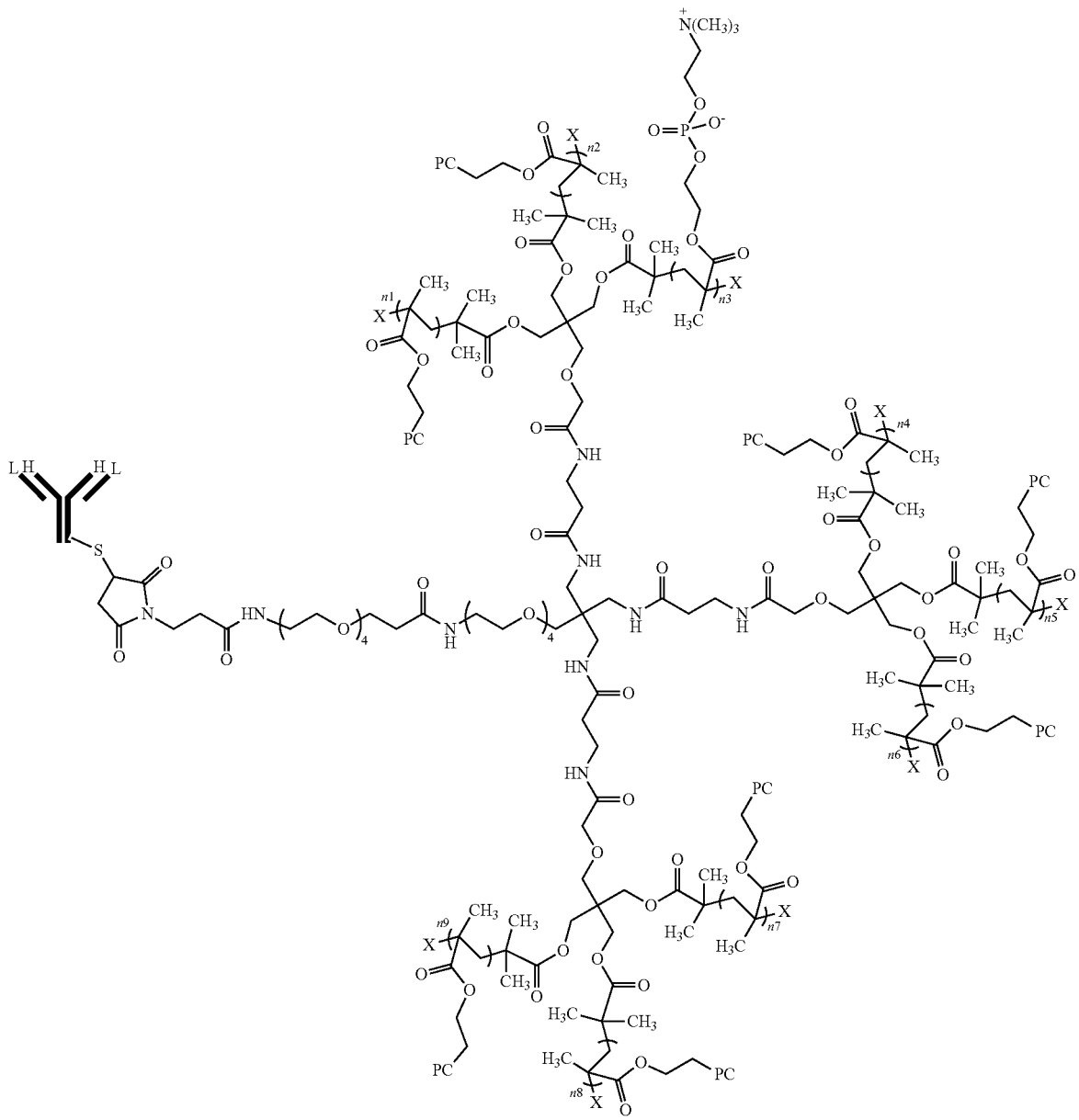

wherein:
each heavy chain of the antibody is denoted by the letter H, and each light chain of the anti-CFD antibody is denoted by the letter L;
the polymer is bonded to the antibody through the sulfhydryl of C443 (EU numbering), which bond is depicted on one of the heavy chains;
PC is

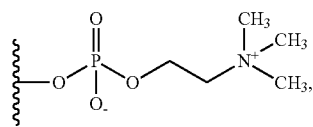

where the curvy line indicates the point of attachment to the rest of the polymer, where X=a) OR where R=H, methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n7, n8 and n9 is 2500 plus or minus 15%.

In some embodiments, an isolated cell line is provided that produces an isolated antagonistic antibody provided herein.

In some embodiments, an isolated nucleic acid is provided that encodes an isolated antagonistic antibody as provided herein.

In some embodiments, a recombinant expression vector is provided that comprises the nucleic acid.

In some embodiments, a host cell is provided that comprises the expression vector.

In some embodiments, a method of producing a CFD antagonist antibody is provided. The method comprises: culturing a cell line that recombinantly produces an isolated antagonistic antibody of as provided herein under conditions wherein the antibody is produced; and recovering the antibody.

In some embodiments, a method of producing a CFD antagonist antibody is provided. The method comprises: culturing a cell line comprising nucleic acid encoding an antibody comprising a heavy chain comprising the amino acid sequence shown in SEQ ID NO: 520 and a light chain comprising the amino acid sequence shown in SEQ ID NO: 525 under conditions wherein the antibody is produced; and recovering the antibody.

In some embodiments, a pharmaceutical composition is provided. The composition comprises an isolated antagonistic antibody as provided herein and/or a conjugate as provided herein, and a pharmaceutically acceptable carrier.

In some embodiments, a method for the treatment or prophylaxis of a disease in a patient in need thereof is provided. The method comprises administering to the patient an isolated antagonist antibody as provided herein, and/or a conjugate as provided herein.

In some embodiments, a method for the treatment or prophylaxis of a disease in a patient in need thereof is provided. The method comprises: identifying a patient having hyperactive CFD activity; and administering to the patient an isolated antagonist antibody as provided herein and/or a conjugate as provided herein.

In some embodiments, a method for the treatment or prophylaxis of a disease in a patient in need thereof is provided. The method comprises administering to the patient a conjugate as provided herein, and/or a composition as provided herein.

In some embodiments, an isolated antagonist antibody is provided. The antibody binds an epitope on human CFD that is the same as or overlaps with the epitope recognized by an antibody comprising the amino acid sequences shown in SEQ ID NO: 520 and SEQ ID NO: 525.

In some embodiments, an isolated antagonist antibody that binds to CFD is provided. The antibody does not increase an enzymatic activity of CFD when bound thereto.

In some embodiments, an isolated antagonist antibody is provided. The antibody competes for binding to human CFD with an antibody comprising the amino acid sequences shown in SEQ ID NO: 520 and SEQ ID NO: 525.

In some embodiments, an isolated antagonist antibody that binds to CFD is provided. The antibody does not maintain an enzymatic activity of CFD when bound thereto.

In some embodiments, an isolated antagonist antibody that specifically binds to complement factor D (CFD) is provided. When bound, the antibody is within 3A of residue 209 of SEQ ID NO: 1 of CFD.

In some embodiments, an isolated antagonist antibody that specifically binds to complement factor D (CFD) is provided. When bound, the antibody is within 3A of residue 156 of SEQ ID NO: 1 of CFD.

In some embodiments, an isolated antagonist antibody that specifically binds to complement factor D (CFD) is provided. The antibody binds to one or more of residues 156 or 209 of SEQ ID NO: 1 of CFD.

In some embodiments, an isolated antagonist antibody that specifically binds to complement factor D (CFD) is provided. The antibody binds to both of residues 156 and 209 of SEQ ID NO: 1 of CFD.

In some embodiments, an isolated antagonist antibody that specifically binds to complement factor D (CFD) is provided. The antibody, when bound to CFD, is not within 6 angstroms of at least one of 117, 118, and 156 of SEQ ID NO: 1.

In some embodiments, an isolated antagonist antibody that specifically binds to complement factor D (CFD) is provided. The antibody binds to CFD as described in Tables: 1.1, 0.1A, 0.1B, 0.1D, and/or 11.3.

In some embodiments, a crystallized CFD-antibody complex is provided, wherein the antibody comprises any one or more of the CDRs within SEQ ID NO:s 183 or 520 and 184 or 525.

BRIEF DESCRIPTION OF THE DRAWINGS

FIG. 1 Depicts a sequence of CFD.
FIG. 2C shows the synthesis of OG1802 from R3707.
FIG. 2H shows the synthesis of OG 1785 from OG1405.
FIG. 2I shows the synthesis of OG1786 from OG1785.
FIG. 2J shows OG1801.
FIG. 2K shows OG1802.

FIG. 20 shows the binding affinity of OG1965 and its bio-conjugate (OG1970) to purified human CFD.

FIG. 27 illustrates a biacore complex assembly assay showing that both OG1965 and OG1970 inhibit CFD from binding to C3bB. KCD004 is used as a positive control.

DETAILED DESCRIPTION

Figure 2A:
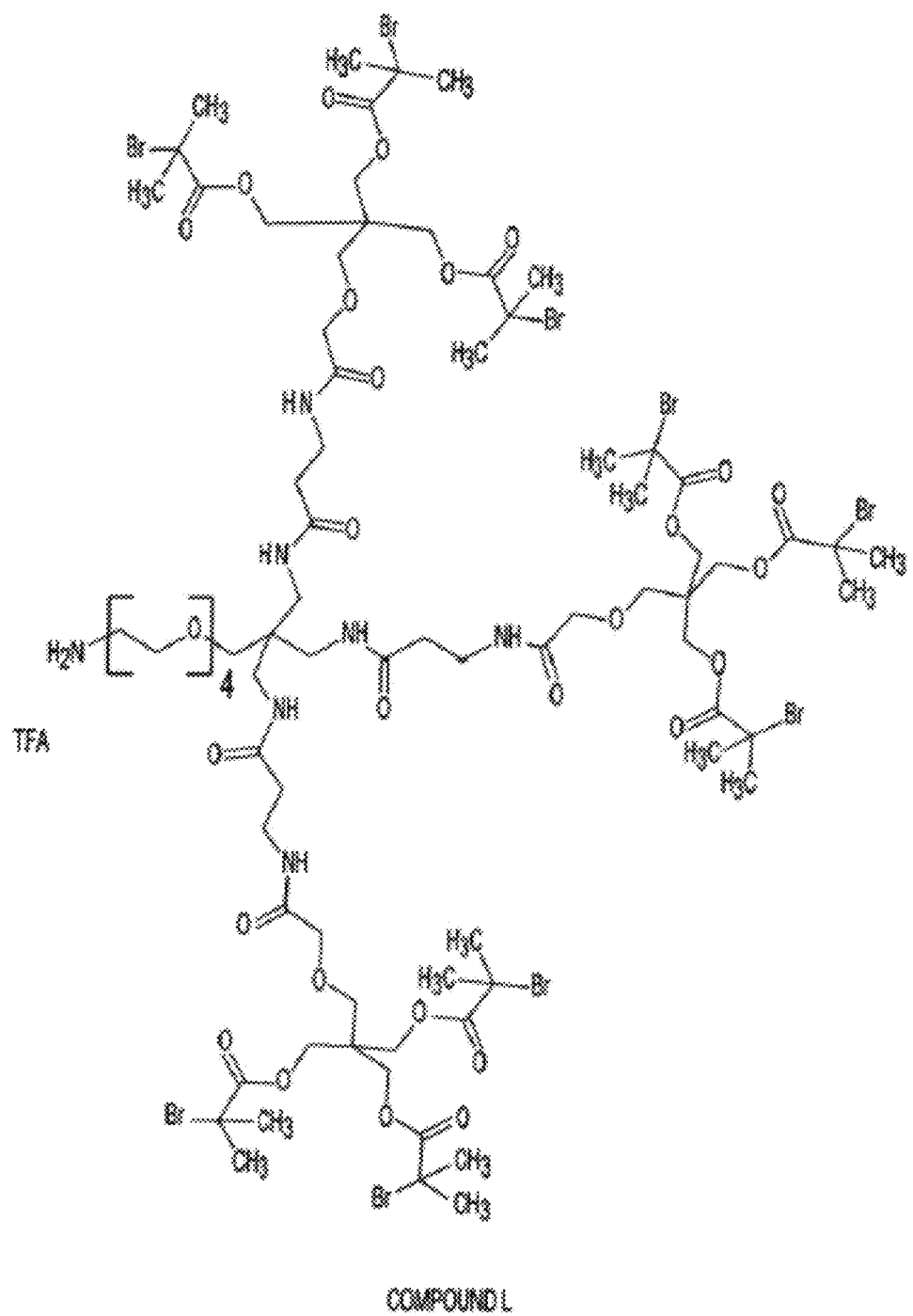
FIG. 2A shows Compound L.

Although progress had been made toward treatment of wet AMD, presently, there is no corresponding treatment for dry AMD or GA. There are also no available treatments to halt GA patch enlargement or slow vision loss. Because of the rapidly aging population and that dry AMD remains an untreated source of morbidity, there is a need for treatments for dry AMD.

There is also a need for dry AMD therapeutics and therapy regimes which will lead to good patient compliance. Currently, Roche's lampalizumab is in phase III clinical trials for treatment of GA. Lampalizumab is administered by intravitreal injection. While phase II results indicate some positive efficacy, efficacy was only seen for the monthly dosage of lampalizumab. In the study, bimonthly injections of lampalizumab were found to be no better than sham injections.

From the view point of both patients and treating physicians, intravitreal injections are not trivial. Many patients experience pain and discomfort from the injection and patient compliance is a serious issue. Common side effects of intravitreal injections include conjunctival hemorrhage, eye pain, vitreous floaters, increased intraocular pressure, and intraocular inflammation. Intravitreal injections are associated with relatively rare serious adverse events, including endophthalmitis, retinal detachment and traumatic cataracts.

There is, thus, also a need in the art for therapies that can be effectively administered less frequently, e.g., less than once a month.

Disclosed herein are antibodies that specifically bind to complement factor D (CFD), and conjugates thereof. Methods of making anti-CFD antibodies, anti-CFD antibody conjugates, compositions comprising these antibodies and/ or antibody conjugates, and methods of using these antibodies and/or antibody conjugates as a medicament are also provided. Anti-CFD antibodies and anti-CFD antibody conjugates provided herein can be used in the prevention and/or treatment of age related macular degeneration and/or other diseases.

OG1965 is a high affinity antagonistic humanized antibody against complement factor D (CFD). In some embodiments, it can be covalently conjugated to a high molecular weight biopolymer to result in OG1970, for intravitreal injection for the treatment of intermediate dry AMD and Geographic Atrophy (GA), as well as other indications. OG1970 is expected to have a longer resident half-life in the eye for potent efficacy and superior dosing intervals.

In some embodiments, the estimated Q12w or Q16w dosing interval of OG1970 can allow treatment of broad set of patients with increasingly earlier and less advanced forms of dry AMD Various embodiments provided herein can employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule 8purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "CFD," "complement factor D," "factor D," or "FD," as used interchangeably herein, refers to any form of CFD and variants thereof that retain at least part of the activity of CFD. Unless indicated differently, such as by specific reference to human CFD, CFD includes all mammalian species of native sequence CFD, e.g., human, canine, feline, equine, and bovine. One exemplary human CFD is found as UniProt Accession Number P00746, which displayed sequence is further processed into a mature form, as shown in (SEQ ID NO: 1).

Anti-CFD antibodies or other biologics described herein are typically provided in isolated form. This means that an antibody is typically at least 50% w/w pure of interfering proteins and other contaminants arising from its production or purification but does not exclude the possibility that the antibody is combined with a pharmaceutically acceptable excipient intended to facilitate its use. Sometimes antibodies are at least 60, 70, 80, 90, 95 or 99% w/w pure of interfering proteins and contaminants from production or purification. Often an antibody (or antibody conjugate) is the predominant macromolecular species remaining after its purification. In some embodiments, no other protein material is present in at meaningful (functioning) level and/or detectable level.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the IMGT approach (Lefranc et al., 2003) Dev Comp Immunol. 27:55-77), computational programs such as Paratome (Kunik et al., 2012, Nucl Acids Res. W521-4), the AbM definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, IMGT, Paratome, AbM, and/or conformational definitions, or a combination of any of the foregoing.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues. A human antibody can be modified to provide altered (including superior) binding.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to CFD, e.g., the antibodies compete for binding to the antigen.

The term "compete," as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, an antibody "interacts with" CFD when the equilibrium dissociation constant is equal to or less than 20 nM, preferably less than about 6 nM, more preferably less than about 1 nM, most preferably less than about 0.2 nM, as measured by the methods disclosed herein in Example 8.

A CFD antagonist antibody encompasses antibodies that block, antagonize, suppress or reduce (to any degree including significantly) a CFD biological activity such as, e.g., substrate (including but not limited to, synthetic peptides or Factor B pre-bound to C3b) binding and/or cleavage, C3bB (a complex of factor B, magnesium ions, and complement component 3b) binding, and/or downstream pathways mediated by CFD signaling, such as elicitation of a cellular response to CFD activation. For purpose of the present invention, it will be explicitly understood that the term "CFD antagonist antibody" encompasses all the previously identified terms, titles, and functional states and characteristics whereby the CFD itself, a CFD biological activity (including but not limited to its ability to mediate any aspect of interaction with the C3bB, and downregulation of the alternative complement cascade), or the consequences of the biological activity, are substantially nullified, decreased, or neutralized in any meaningful degree. In some embodiments, a CFD antagonist antibody binds CFD and substantially blocks CFD catalysis. Examples of CFD antagonist antibodies are provided herein.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, and/or more rapidly, and/or with greater duration and/or with greater affinity with a particular cell or substance than it does with alternative cells or substances. An antibody "specifically binds" or "preferentially binds" to a target if it binds with greater affinity, and/or avidity, and/or more readily, and/or with greater duration than it binds to other substances. For example, an antibody that specifically or preferentially binds to a CFD epitope is an antibody that binds this epitope with greater affinity, and/or avidity, and/or more readily, and/or with greater duration than it binds to other CFD epitopes or non-CFD epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results.

As used herein, "CFD related disorders" include, for example, inflammatory disorders and disorders of the Complement cascade in patients. Inflammatory disorders include eye inflammatory disorders such as dry and wet age-related macular degeneration (including geographic strophy GA), glaucoma, diabetic retinopathy, corneal disease (e.g. chemical insults, acute bacterial infection, pseudophakic bullous keratopathy, HSV-1 keratitis, and herpes Zoster scleritis), and uveitis. Inflammatory disorders also include sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, and vasculitis.

Benefits can also be obtained from applying the methods and compositions provided herein to slowing the rate of deposition of drusen, decreasing the rate of atrophy and/or thinning of the RPE or conversely the rate of hypertrophy/hyperpigmentation of the RPE, decreasing the rate of formation of new abnormal blood vessels or rate of growth of existing abnormal blood vessels and magnitude of associated leakage of fluid and/or blood, slowing or reversing the deterioration in visual function loss as well as other symptoms resulting from dry and/or wet AMD, decreasing the frequency of administration and or dose of other medications required to treat dry and/or wet AMD, and in general slowing the progression of dry and/or wet AMD, curing dry and/or wet AMD.

As used herein, "Ameliorating" means a lessening or improvement of one or more symptoms as compared to not administering an CFD antibody. "Ameliorating" also includes shortening or reduction in duration of a symptom.

As used herein, "Antagonistic antibody" denotes an antibody that blocks one or more function or activity of the molecule that the antibody binds to.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, AMD including, for example without limitation, dry AMD and wet AMD, decreasing the dose of other medications required to treat the disease, enhancing the effect of another medication, and/or delaying the progression of AMD in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

Anti-CFD antibodies are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The "biological half-life" of a substance is a pharmacokinetic parameter which specifies the time required for one half of the substance to be removed from an organism following introduction of the substance into the organism.

The term "preventing" or "prevent" refers to (a) keeping a disorder from occurring (b) delaying the onset of a disorder or onset of symptoms of a disorder, and/or (c) slowing the progression of an existing condition. Unless denoted otherwise, "preventing" does not require the absolute prohibition of the event from occurring.

An "individual" or a "subject" is a mammal or bird, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, various types of wetting agents, detergents such as polysorbate 20 to prevent aggregation, and sugars such as sucrose as cryoprotectant. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody (or bioconjugate) to an antigen. Specifically, the rate constants ($k_{on}$ and $k_{off}$) and equilibrium dissociation constants are measured using full-length antibodies and/or Fab antibody fragments (i.e. univalent) and CFD.

The term "$k_{off}$", as used herein, refers to the rate constant for dissociation of an antibody (or bioconjugate) from the antibody/antigen complex.

The term "$K_D$", as used herein, refers to the equilibrium dissociation constant of an antibody-antigen (or bioconjugate-antigen) interaction.

Reference to "about" a value or parameter herein includes (and describes) embodiments that are directed to that value or parameter per se. For example, description referring to "about X" includes description of "X." Numeric ranges are inclusive of the numbers defining the range.

The term "patient" includes human and other subjects (including mammals) that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

A humanized antibody is a genetically engineered antibody in which the CDRs from a non-human "donor" antibody are grafted into a human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al, J. Immunol. 169:3076, 2002; Vajdos et al., Journal of Molecular Biology, 320: 415-428, 2002; Iwahashi et al., Mol. Immunol. 36: 1079-1091, 1999; Tamura et al, Journal of Immunology, 164: 1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332.

A "polymer" is a molecule composed of many repeating subunits. The subunits, also sometimes referred to as "monomers" can be the same or different. There are both natural and synthetic polymers. DNA, protein and complex carbohydrates are examples of natural polymers. Poly-styrene and poly-acrylamide are examples of synthetic polymers. A polymer composed of repeating units of a single monomer is called a homopolymer. A polymer composed of two or more monomers is called a copolymer or sometimes a heteropolymer. A copolymer in which certain monomer types are clustered together are sometimes called block copolymers. Polymers can be linear or branched. When the polymer is branched, polymer chains having a common origin are sometimes referred to as a polymer arm(s).

An "initiator" is a compound capable of serving as a substrate on which one or more polymerizations can take place using monomers or comonomers as described herein. The polymerization can be a conventional free radical polymerization or preferably a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. Initiators suitable for ATRP contain one or more labile bonds which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments of the present invention, the initiator contains one or more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolysable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

As used herein, "phosphorylcholine," also denoted as "PC," refers to the following:

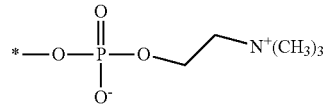

where * denotes the point of attachment. The phosphorylcholine is a zwitterionic group and includes salts (such as inner salts), and protonated and deprotonated forms thereof.

As used herein, "phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy) ethyl-2-(trimethylammonium)ethyl phosphate as monomer.

Poly(methacryloyloxyethyl phosphorylcholine) containing polymer refers to a polymer containing 2-(methacryloyloxy)ethyl-2-(trimethylammonium)ethyl phosphate as monomer.

As used herein, "molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography-multi angle light scattering). The polymeric reagents of the invention are typically polydisperse (i.e., number average molecular weight and weight average molecular weight of the polymers are not equal). The Poly Dispersity Index (PDI) provides a measure for the dispersity of polymers in a mixture. PDI is given by the formula Mw/Mn. In this regard a homogenous protein will have a PDI of 1.0 (Mn is the same as Mw). Typically, the PDI for polymers will be above 1.0. Polymers in accordance with the present invention preferably have relatively low polydispersity (PDI) values of, for example, less than about 1.5, as judged, for example, by SEC-MALS. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

As used herein, "protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," 3$^{rd}$ Edition, John Wiley and Sons, Inc., New York, 1999.

As used herein, "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6 carbons.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl, alkenyl, alkylene, heteroalkyl, heteroalkylene, heteroalkenyl, alkynyl, cycloalkyl, heterocycloalkyl, cycloalkenyl, and heterocycloalkenyl radicals can be one or more of a variety of groups selected from, but not limited to: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR"", —N R—C(NR'R")=NR''', —S(O)R', —S(O)$_2$R', —S(O)$_2$NR'R", —$NRSO_2$R', —CN and —$NO_2$ in a number ranging from 1 to (2m'+1), where m' is the total number of carbon atoms in such radical. Each of R', R", R''' and R"" independently refers to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl.

As used herein, "alkoxy" refers to alkyl group attached to an oxygen atom and forms radical —O—R, wherein R is alkyl. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described herein. For example, the alkoxy groups can be substituted with halogens to form a "halo-alkoxy" group.

As used herein, "carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

As used herein, "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy. Haloalkyl can also be referred to as halo-substitute alkyl, such as fluoro-substituted alkyl.

As used herein, "cytokine" in the context of this invention is a member of a group of protein signaling molecules that may participate in cell-cell communication in immune and inflammatory responses. Cytokines are typically small, water-soluble glycoproteins that have a mass of about 8-35 kDa.

As used herein, "cycloalkyl" refers to a saturated mono- or multi-cyclic aliphatic ring system that contains from about 3 to 12, from 3 to 10, from 3 to 7, or from 3 to 6 carbon atoms. When cycloalkyl group is composed of two or more rings, the rings may be joined together with a fused ring or a spiro ring structure. When cycloalkyl group is composed of three or more rings, the rings may also join together forming a bridged ring structure. Monocyclic rings include, for example, cyclopropyl, cyclobutyl, cyclopentyl, cyclohexyl, and cyclooctyl. Bicyclic and polycyclic rings include, for example, bicyclo[1.1.1]pentane, bicyclco[2.1.1]heptane, norbornane, decahydronaphthalene and adamantane. For example, $C_{3-8}$ cycloalkyl includes cyclopropyl, cyclobutyl, cyclopentyl, cyclohexyl, cyclooctyl, and norbornane.

As used herein, "endocyclic" refers to an atom or group of atoms which comprise part of a cyclic ring structure.

As used herein, "exocyclic" refers to an atom or group of atoms which are attached but do not define the cyclic ring structure.

As used herein, "cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

As used herein, "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons.

As used herein, "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons.

As used herein, "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

As used herein, "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, "heterocycloalkylene" refers to a heterocyclalkyl group, as defined above, linking at least two other groups. The two moieties linked to the heterocycloalkylene can be linked to the same atom or different atoms of the heterocycloalkylene.

As used herein, "aryl" refers to a monocyclic or multicyclic (e.g., fused bicyclic, tricyclic or greater) aromatic ring assembly containing 6 to 16 carbon atoms. For example, aryl may be phenyl, benzyl or naphthyl, preferably phenyl. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, "arylene" refers to an aryl group, as defined above, linking at least two other groups. The two moieties linked to the arylene are linked to different atoms of the arylene. Arylene groups include, but are not limited to, phenylene.

As used herein, "arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

As used herein, "electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

As used herein, "nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

As used herein, "maleimido" refers to a pyrrole-2,5-dione-1-yl group having the structure:

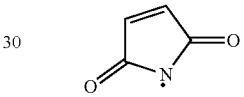

which upon reaction with a sulfhydryl (e.g., a thio alkyl) forms an —S-maleimido group having the structure

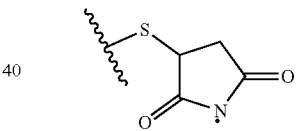

where "•" indicates the point of attachment for the maleimido group and "⚡" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

As used herein, "linear" in reference to the geometry, architecture or overall structure of a polymer, refers to polymer having a single polymer arm.

As used herein, "branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

As used herein, "pharmaceutically acceptable excipient" refer to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Figure 2B:
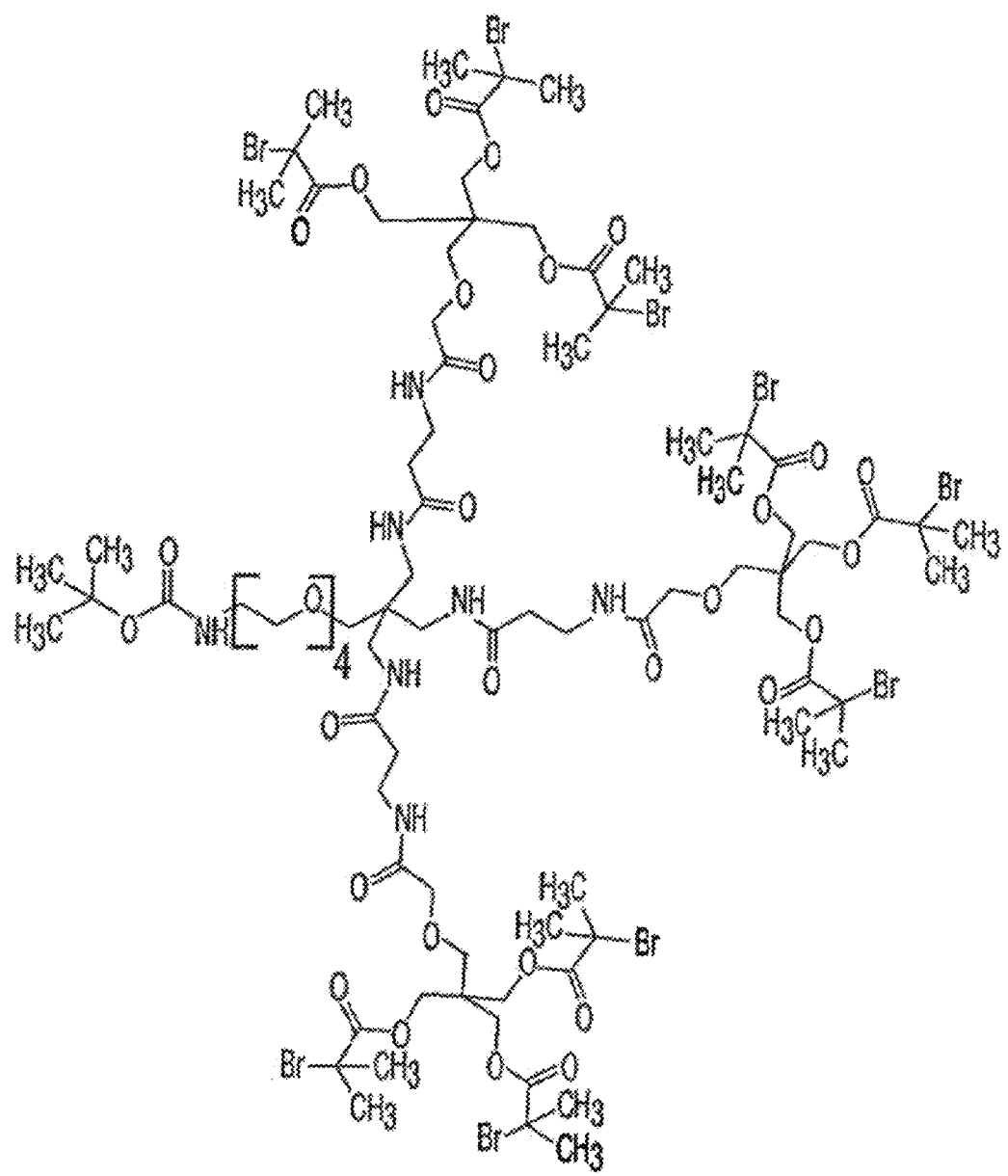
FIG. 2B shows Compound K.
Figure 2D:
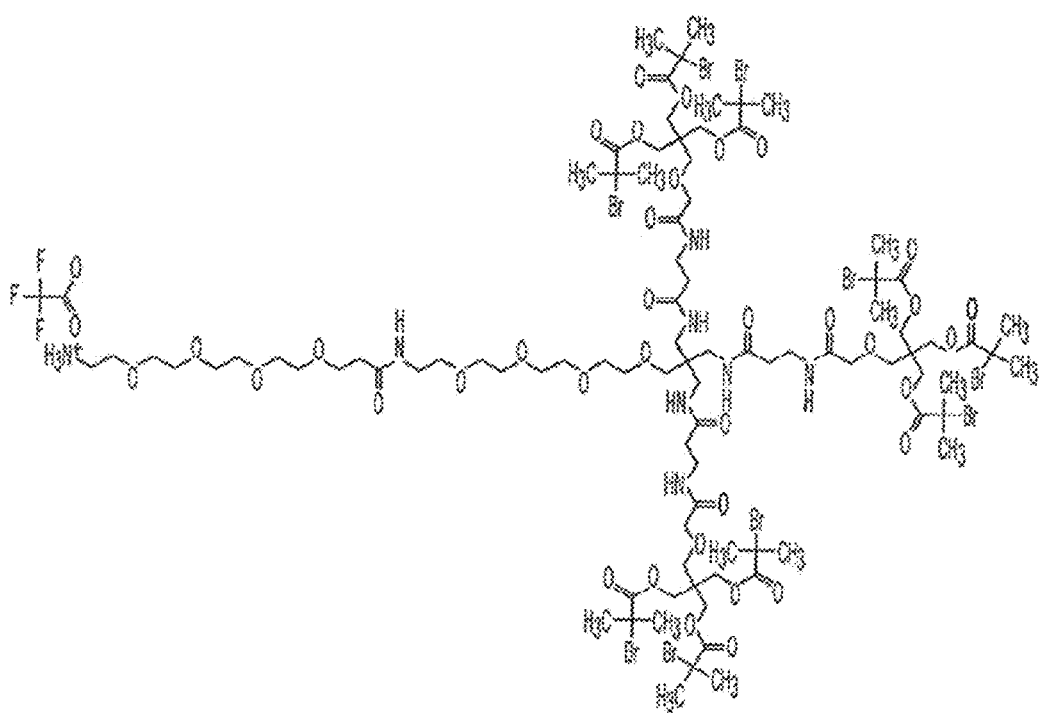
FIG. 2D shows OG1786.

As used herein, "OG1786" is a 9-arm initiator used for polymer synthesis with the structure shown in FIG. 2D, which depicts that salt form of OG1786 with trifluororacetic acid. OG1786 may be used in accordance with the present invention as other salts or as the free base.

As used herein, "OG1801" is an approximately (+/−15%) 750 kDa polymer (either by Mn or Mp) made using OG1786 as an initiator for ATRP synthesis using the monomer HEMA-PC. The structure of OG1801 is shown in FIG. 2J.

As used herein, "OG1802" is OG1801 with a maleimide functionality added, and it has the structure shown in FIG. 2K, wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% Daltons.

By "directly inhibit", "direct inhibitor", or other similar phrase in regard to the proteolytic activity of CFD, it is meant that the antibody reduces the enzymatic activity of CFD itself, rather than reducing a downstream activity of CFD or by some other mechanism of action. Thus, for example, an antibody that reduces CFD proteolytic activity indirectly, by altering an activity or function of CFD that occurs as a result of (e.g., downstream of) the proteolytic activity, would not "directly inhibit" proteolytic activity. Similarly, an antibody that binds to CFD and does not reduce the proteolytic activity of CFD, would not "directly inhibit" the proteolytic activity, even if it also blocked other aspects (for example, preventing a substrate from accessing the enzymatic binding location of CFD or from leaving the enzymatic location of CFD. A direct inhibitor of proteolytic activity of CFD will decrease the enzymatic activity of CFD. While not expressly stated, all disclosure in the present specification that is directed to inhibiting proteolytic activity of CFD, contemplates both the direct inhibition of CFD and the indirect inhibition of CFD, unless stated otherwise (e.g., through data or a statement). Thus, each disclosure provides support for both forms of inhibition, unless expressly stated otherwise (this does not apply for the claims.) The term "directly inhibits" proteolytic processing excludes the mechanism of action by which lampalizumab functions, as lampalizumab allows CFD to maintain proteolytic processing, even while bound to CFD. While lampalizumab may "block" some activity of CFD by preventing the binding of CFD to its substrate, lampalizumab does not appear to actually reduce or prevent CFD enzymatic activity itself. In some embodiments, this can be assayed for by using a small peptide substrate, for example, N-carbobenzyloxy-Lys-ThioBenzyl ester. Lampalizumab will not block CFD processing of N-carbobenzyloxy-Lys-ThioBenzyl ester, while various embodiments provided herein can reduce CFD processing of N-carbobenzyloxy-Lys-ThioBenzyl ester, thereby serving as direct inhibitors of proteolytic processing by CFD.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The phrase "a" or "an" entity refers to one or more of that entity; for example, a compound refers to one or more compounds or at least one compound. As such, the terms "a" (or "an"), "one or more", and "at least one" can be used interchangeably herein.

As used herein, "about" means variation one might see in measurements taken among different instruments, samples, and sample preparations.

Multi-angle light scattering (MALS) is a technique of analyzing macromolecules where the laser light impinges on the molecule, the oscillating electric field of the light induces an oscillating dipole within it. This oscillating dipole will re-radiate light and can be measured using a MALS detector such as Wyatt miniDawn TREOS. The intensity of the radiated light depends on the magnitude of the dipole induced in the macromolecule which in turn is proportional to the polarizability of the macromolecule, the larger the induced dipole, and hence, the greater the intensity of the scattered light. Therefore, in order to analyze the scattering from a solution of such macromolecules, one should know their polarizability relative to the surrounding medium (e.g., the solvent). This may be determined from a measurement of the change, $\Delta n$, of the solution's refractive index n with the molecular concentration change, $\Delta c$, by measuring the dn/dc ($=\Delta n/\Delta c$) value using a Wyatt Optilab T-rEX differential refractometer. Two molar weight parameters that MALS determination employ are number average molecular weight (Mn) and weight average molecular weight (Mw) where the polydispersity index (PDI) equals Mw divided by Mn. SEC also allows another average molecular weight determination of the peak molecular weight Mp which is defined as the molecular weight of the highest peak at the SEC.

The PDI is used as a measure of the broadness of a molecular weight distribution of a polymer and bioconjugate which is derived from conjugation of a discrete protein to a polydisperse biopolymer (e.g., OG1802). For a protein sample, its polydispersity is close to 1.0 due to the fact that it is a product of translation where every protein molecule in a solution is expected to have almost the same length and molar mass. In contrast, due to the polydisperse nature of the biopolymer where the various length of polymer chains are synthesized during the polymerization process, it is very important to determine the PDI of the sample as one of its quality attribute for narrow distribution of molecular weight.

Size exclusion chromatography (SEC) is a chromatography technique in which molecules in solution are separated by their size. Typically an aqueous solution is applied to transport the sample through the column which is packed with resins of various pore sizes. The resin is expected to be inert to the analyte when passing through the column and the analytes separate from each other based on their unique size and the pore size characteristics of the selected column.

Coupling the SEC with MALS or SEC/MALS provides accurate distribution of molar mass and size (root mean square radius) as opposed to relying on a set of SEC calibration standards. This type of arrangement has many advantages over traditional column calibration methods. Since the light scattering and concentration are measured for each eluting fraction, the molar mass and size can be determined independently of the elution position. This is particularly relevant for species with non-globular shaped macromolecules such as the biopolymers (OG1802) or bioconjugates; such species typically do not elute in a manner that might be described by a set of column calibration standards.

In some embodiments, a SEC/MALS analysis includes a Waters HPLC system with Alliance 2695 solvent delivery module and Waters 2996 Photodiole Array Detector equipped with a Shodex SEC-HPLC column (7.8×300 mm). This is connected online with a Wyatt miniDawn TREOS and Wyatt Optilab T-rEX differential refractometer. The Empower software from Waters can be used to control the Waters HPLC system and the ASTRA V 6.1.7.16 software from Wyatt can be used to acquire the MALS data from the Wyatt miniDawn TREOS, dn/dc data from the T-rEX detector and the mass recovery data using the A280 absorbance signal from the Waters 2996 Photodiole Array detector. SEC can be carried out at 1 ml/min in 1×PBS pH 7.4, upon sample injection, the MALS and RI signals can be analyzed by the ASTRA software for determination of absolute molar mass (Mp, Mw, Mn) and polydisperse index (PDI). In addition, the calculation also involves the input dn/dc values for polymer and protein as 0.142 and 0.183, respectively. For OG1970 bioconjugates dn/dc value, the dn/dc is calculated based on the weighted MW of the polymer and the protein to be about 0.148 using the formula below:

$$\text{Conjugate } dn/dc = 0.142 \times [MWpolymer/(MWpolymer+MWprotein)] + 0.183 \times [MWprotein/(MWpolymer+MWprotein)]$$

Where MWpolyme.r for OG1802 measured by SEC-MALS is about 800 kDa and the MWprotein for OG1965 measured by SEC-MALS is about 145 kDa, the expected total molecular weight of OG1970 bioconjugate measured by SEC-MALS is about 1000 kDa Exemplary methods and materials are described herein, although methods and materials similar or equivalent to those described herein can also be used in the practice or testing of the present invention. The materials, methods, and examples are illustrative only and not intended to be limiting.

CFD Antagonist Antibodies and Conjugates Thereof

Provided herein are anti-CFD antibodies that block, suppress or reduce (including significantly reduces) CFD biological activity, including downstream events mediated by CFD. In some embodiments, a CFD antagonist antibody can exhibit any one or more of the following characteristics: (a) bind to CFD and block downstream signaling events; (b) block C3bB (a complex of factor B, magnesium ions, and complement component 3b) binding to CFD; (c) directly inhibit proteolytic activity of CFD; and (d) block the alternative complement cascade. In some embodiments, the CFD antagonist antibody will have one or more of the CDR sequences provided herein.

In some embodiments, the isolated antagonist antibody specifically binds to complement factor D (CFD). In some embodiments, the isolated antagonist antibody specifically inhibits a proteolytic activity of CFD. In some embodiments, the isolated antagonist antibody specifically inhibits CFD binding to C3bB complex. In some embodiments, the isolated antagonist antibody specifically binds to complement factor D (CFD) and specifically inhibits a proteolytic activity of CFD. In some embodiments, the isolated antagonist antibody directly inhibits the proteolytic activity of CFD.

In some embodiments, the isolated antagonist antibody specifically binds to complement factor D (CFD) and specifically inhibits CFD binding to C3bB complex. In some embodiments, the isolated antagonist antibody specifically inhibits a proteolytic activity of CFD and specifically inhibits CFD binding to C3bB complex. In some embodiments, the isolated antagonist antibody specifically binds to complement factor D (CFD), specifically inhibits a proteolytic activity of CFD and specifically inhibits CFD binding to C3bB complex.

In some embodiments, the isolated antagonist antibody specifically binds to complement factor D (CFD) but does not bind a human CFD mutant comprising mutations R157A and R207A. In some embodiments, the isolated antagonist antibody binds an epitope on human CFD, wherein the epitope excludes positions R157 and R207. In some embodiments, the isolated antagonist antibody does not bind a human CFD mutant comprising the mutations R157A and R207A. In some embodiments, the isolated antagonist antibody binds a human CFD mutant comprising mutations R157A and R207A.

In some embodiments, the antibody preferably reacts with CFD in a manner that inhibits CFD signaling function. In some embodiments, the CFD antagonist antibody specifically binds primate CFD.

In some embodiments, the isolated antagonist anti-CFD antibody blocks the alternative complement cascade. In some embodiments, the isolated antagonist anti-CFD antibody blocks C3bB binding to CFD. In some embodiments, the isolated antagonist anti-CFD antibody blocks the alternative complement cascade by blocking C3bB binding to CFD.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the CFD antagonist antibody is a monoclonal antibody. In some embodiments, the antibody is a human or humanized antibody.

In some embodiments, the antibody comprises a heavy chain amino acid variable region that comprises SEQ ID NO: 520 and a light chain amino acid variable region that comprises SEQ ID NO. 184. In some embodiments, an isolated antagonist antibody comprises a heavy chain variable region (VH) comprising a VH complementarity determining region one (CDR1), VH CDR2, and VH CDR3 of the VH having an amino acid sequence of SEQ ID NO: 520, and a light chain variable region (VL) comprising a VL CDR1, VL CDR2, and VL CDR3 of the VL having an amino acid sequence of SEQ ID NO: 525.

In some embodiments, an isolated antagonist anti-CFD antibody is provided. The antibody comprises a heavy chain constant domain comprising one or more mutations to reduce effector function. In some embodiments, the one or more mutations reduce effector functions of the antibody related to the complement cascade, for example, a reduced activation of the complement cascade. In some embodiments, the reduction in effector function is at least about 50%.

In some embodiments, an isolated antagonist antibody that specifically binds to CFD comprising a heavy chain variable region (VH) and a light chain variable region (VL), wherein the antibody comprises the mutations L234A, L235A, and G237A (based on EU numbering) is provided. In some embodiments, the isolated antagonist antibody comprises the mutations L234A, L235A, and G237A. In some embodiments, the isolated antagonist antibody with mutations has minimized binding to FC gamma receptors or C1q. In some embodiments, the isolated antagonist antibody with mutations L234A, L235A, and G237A has minimized binding to FC gamma receptors or C1q. In some embodiments, an isolated antagonist anti-CFD antibody is provided, wherein the mutation(s) is located at one or more of the following amino acid positions (EU numbering): E233, L234, L235, G236, G237, A327, A330, and P331. In some embodiments, an isolated antagonist anti-CFD antibody is provided, wherein the mutation (s) is selected from the group consisting of E233P, L234V, L234A, L235A, G237A, A327G, A330S, and P331S.

In some embodiments, an isolated antagonist anti-CFD antibody is provided. The heavy chain constant domain further comprises a cysteine residue introduced by recombinant DNA technology. In some embodiments, the cysteine residue is selected from the group consisting of Q347C and L443C (EU numbering). In some embodiments, the cysteine residue is L443C (EU numbering).

In some embodiments, the isolated antagonist antibody specifically binds to complement factor D (CFD). The antibody is configured to provide a reduced complement reaction. The antibody specifically binds to complement factor D (CFD), and the antibody at least inhibits a proteolytic activity of CFD or inhibits CFD binding to C3bB complex. In some embodiments, the antibody comprises all three of the following mutations (EU numbering) L234A, L235A, and G237A, and the antibody comprises L443C (EU numbering). In some embodiments, the antibody is a human IgG1, and a heavy chain constant domain of the antibody comprises one or more mutations that reduce an immune-mediated effector function.

In some embodiments, an isolated antagonist antibody is provided that binds an epitope on human CFD that is the same as or overlaps with the epitope recognized by an antibody comprising the amino acid sequences in SEQ ID NO: 61 and SEQ ID NO: 62. In some embodiments, an isolated antagonist antibody is provided that binds an epitope on human CFD that is the same as or overlaps with the epitope recognized by an antibody comprising the amino acid sequences in SEQ ID NO: 45 and SEQ ID NO: 46.

In some embodiments, an isolated antagonist antibody is provided that binds an epitope on human CFD that is the same as or overlaps with the epitope recognized by an antibody comprising the amino acid sequences in SEQ ID NO: 520 and SEQ ID NO: 525. In some embodiments, an isolated antagonist antibody is provided that binds an epitope on human CFD that is the same as or overlaps with the epitope recognized by an antibody comprising the amino acid sequences in any one or more of Tables: 1.1, 0.1A, 0.1B, 0.1D, and/or 11.3. In some embodiments, the isolated antibody is one that comprises the amino acid sequences of the heavy and/or light chain sequences within deposited material PTA-123800 and/or PTA-123801. In some embodiments, the antibody is one that competes for binding with an antibody that comprises the heavy and/or light chain sequences within PTA-123800 (light chain) and/or PTA-123801 (heavy chain). In some embodiments, the antibody is one that is encoded by a nucleic acid sequence that hybridizes to the plasmid sequences provided in PTA-123800 (light chain) and/or PTA-123801 (heavy chain) under moderate to stringent conditions.

In some embodiments, an isolated antagonist antibody that binds to CFD is provided. In some embodiments, the isolated antagonist antibody that binds to CFD comprises a heavy chain comprising the amino acid sequence shown in SEQ ID NO: 183, with or without the C-terminal lysine and a light chain comprising the amino acid sequence shown in SEQ ID NO: 184.

In some embodiments, an isolated antagonist antibody that binds to CFD is provided. The antibody comprises a VH comprising the amino acid sequence shown in SEQ ID NO: 520, or a sequence that is at least 90% identical thereto, having amino acid substitutions in residues that are not within a CDR. In some embodiments, the antibody comprises one or more of: HCDR1: DYY (SEQ ID NO: 541), HCDR2: INPITGDT (SEQ ID NO: 542), HCDR3: EGPS-FAY (SEQ ID NO: 543); LCDR1: QTIVHSNGDT (SEQ ID NO: 544), LCDR2: KVS (SEQ ID NO: 545), LCDR3: FQGSHVPVT (SEQ ID NO: 546), for example, 1, 2, 3, 4, 5, or all 6 CDRs. In some embodiments, the antibody includes HCDR3.

In some embodiments, an antibody that binds to CFD is provided, wherein the antibody comprises a CDRH1 that is the CDRH1 in SEQ ID NO: 520, a CDRH2 that is the CDRH2 in SEQ ID NO: 520, a CDRH3 that is the CDRH3 in SEQ ID NO: 520, a CDRL1 that is the CDRL1 in SEQ ID NO: 525, a CDRL2 that is the CDRL2 in SEQ ID NO: 525, a CDRL3 that is the CDRL3 in SEQ ID NO: 525, at least one of the following mutations: L234A, L235A, and G237A based on EU numbering, or L233A, L234A, and G236A in SEQ ID NO 183, and at least one of the following mutations: Q347C or L443C based on EU numbering, or Q346C or L442C in SEQ ID NO 183.

In some embodiments, an isolated antagonist anti-CFD antibody is provided. The heavy chain variable region of the antibody comprises three complementarity determining regions (CDRs) comprising the amino acid sequences shown in SEQ ID NO: 541, 542, and 543. In some embodiments, an isolated antagonist anti-CFD antibody is provided, wherein the light chain variable region of the antibody comprises three complementarity determining regions (CDRs) comprising the amino acid sequences shown in SEQ ID NO: 544, 545, and 546.

In some embodiments, an isolated antagonist anti-CFD antibody comprises a heavy chain variable region (VH) that comprises three CDRs comprising the amino acid sequences shown in SEQ ID NO: 541, SEQ ID NO: 542, and SEQ ID NO: 543, and the light chain variable region (VL) of the antibody comprises three CDRs comprising the amino acid sequences shown in SEQ ID NO: 544, SEQ ID NO: 545, and SEQ ID NO: 546.

In some embodiments, an isolated antagonist anti-CFD antibody is provided. The VH comprises the amino acid sequences shown in SEQ ID NO: 520 and the light chain variable region of the antibody comprises three CDRs comprising the amino acid sequences shown in SEQ ID NO: 544, SEQ ID NO: 545, and SEQ ID NO: 546.

In some embodiments, an isolated antagonist anti-CFD antibody is provided, wherein the antibody comprises a VL comprising the amino acid sequence shown in SEQ ID NO: 525, or a variant thereof with one amino acid substitution in amino acids that are not within a CDR. In some embodiments, an isolated antagonist anti-CFD antibody is provided, wherein the antibody comprises a VH comprising the amino acid sequence shown in SEQ ID NO: 520, or a variant thereof with several amino acid substitutions in amino acids that are not within a CDR.

In some embodiments, an isolated antagonist antibody is provided, wherein the antibody comprises a heavy chain comprising the amino acid sequence shown in SEQ ID NO: 183, with a C-terminal lysine, and a light chain comprising the amino acid sequence shown in SEQ ID NO: 184. In some embodiments, an isolated antagonist antibody is provided, wherein the antibody comprises a heavy chain comprising the amino acid sequence shown in SEQ ID NO: 183, without a C-terminal lysine, and a light chain comprising the amino acid sequence shown in SEQ ID NO: 184.

The CFD antagonist antibodies may be made by any method known in the art. General techniques for production of human and mouse antibodies are known in the art and/or are described herein.

CFD antagonist antibodies can be identified or characterized using methods known in the art, whereby reduction, amelioration, or neutralization of CFD biological activity is detected and/or measured. In some embodiments, an CFD antagonist antibody is identified by incubating a candidate agent with CFD and monitoring binding and/or attendant reduction or neutralization of a biological activity of CFD. The binding assay may be performed with, e.g., purified CFD polypeptide(s), or with cells naturally expressing (e.g., various strains), or transfected to express, CFD polypeptide(s). In one embodiment, the binding assay is a competitive binding assay, where the ability of a candidate antibody to compete with a known CFD antagonist antibody for CFD binding is evaluated. The assay may be performed in various formats, including the ELISA format. In some embodiments, an CFD antagonist antibody is identified by incubating a candidate antibody with CFD and monitoring binding.

Following initial identification, the activity of a candidate CFD antagonist antibody can be further confirmed and refined by bioassays, known to test the targeted biological activities. In some embodiments, an in vitro cell assay is used to further characterize a candidate CFD antagonist antibody. For example, a direct functional assay based on human alternative complement-mediated rabbit red blood cell lysis assay (hemolysis assay) can be used to characterize a candidate anti-CFD antibody. In this assay, human serum complement components are activated, triggering the alternative complement cascade and resulting in lysis of rabbit blood cells. Anti-CFD antibodies that block the enzyme active site may block the alternative complement cascade, thus preventing lysis of the red blood cells. Greater than 50% inhibition of red blood cell lysis is the standard measure for successful antibody-mediated blockade of the alternative complement cascade.

A candidate anti-CFD antibody can be evaluated for its ability to affect the proteolytic activity of human CFD for the synthetic substrate Z-L-Lys-SBzl hydrochloride. Alternatively, bioassays can be used to screen candidates directly.

The CFD antagonist antibodies of the invention exhibit one or more of the following characteristics: (a) bind to CFD and block downstream signaling events; (b) block C3bB (a complex of factor B, magnesium ions, and complement component 3b) binding to CFD; (c) block C3bB cleavage by CFD; (d) block the alternative complement cascade; and e) directly inhibit CFD proteolytic activity. In some embodiments, the CFD antagonist antibodies have two or more of these features. In some embodiments, the CFD antagonist antibodies have three or more of these features. In some embodiments, the CFD antagonist antibodies have four or more of these features. In some embodiments, the antibodies have all five characteristics. In some embodiments, the CFD antagonist antibodies of the invention can inhibit the ability of human serum to lyse rabbit red blood cells in a hemolytic assay. In preferred embodiments, CFD antagonist antibodies of the invention can inhibit the proteolytic activity of CFD. In some embodiments, CFD antagonist antibodies of the invention can directly inhibit the proteolytic activity of CFD. In some embodiments, CFD antagonist antibodies of the invention can increase the proteolytic activity of CFD. In some embodiments, CFD antagonist antibodies are provided which have little to no direct effect on the proteolytic activity of CFD.

CFD antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an CFD antagonist antibody binds. CFD antagonist antibody Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an CFD antagonist antibody. In another example, the epitope to which the CFD antagonist antibody binds can be determined in a systematic screening by using overlapping peptides derived from the CFD sequence and determining binding by the CFD antagonist antibody. According to the gene fragment expression assays, the open reading frame encoding CFD is fragmented either randomly or by specific genetic constructions and the reactivity of the expressed fragments of CFD with the antibody to be tested is determined. The gene fragments may, for example, be produced by PCR and then transcribed and translated into protein in vitro, in the presence of radioactive amino acids. The binding of the antibody to the radioactively labeled CFD fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant CFD in which various residues of the CFD polypeptide have been replaced with alanine. By assessing binding of the antibody to the mutant CFD, the importance of the particular CFD residues to antibody binding can be assessed.

In some embodiments, the antibody binds to one or more of residues R157 and R207 on CFD, and does not increase the activity of CFD in the proteolytic processing of a small peptide substrate N-carbobenzyloxy-Lys-ThioBenzyl.

In some embodiments, the antibody binds to CFD with an interaction involving one or more of R157, K209, D150, T153, R156, R157, and D161 (of SEQ ID NO: 1) at 3 angstroms or less. In some embodiments, the antibody binds to CFD with an interaction involving one or more of R157, T158, H159, D161, R207, K208, K209, D116, P119, D150, R151, A152, T153, N155, R156, G162, I164, or E166 (of SEQ ID NO: 1) at 5 angstroms or less. In some embodiments, the antibody binds to CFD with an interaction involving one or more of R157, T158, H159, D161, N206, R207, K208, K209, D116, P119, D150, R151, A152, T153, N155, R156, R157, T158, or D161, G162, A163, I164, T165, E166 (of SEQ ID NO: 1) at 6 angstroms or less.

In some embodiments, the antibody binds to CFD with an interaction involving one or more of 157, 209, 150, 153, 156, 157, and 161 (of SEQ ID NO: 1) at 3 angstroms or less. In some embodiments, the antibody binds to CFD with an interaction involving one or more of 157, 158, 159, 161, 207, 208, 209; 116, 119, 150, 151, 152, 153, 155, 156, 162, 164, or 166 (of SEQ ID NO: 1) at 5 angstroms or less. In some embodiments, the antibody binds to CFD with an interaction involving one or more of 157-159, 161; 206-209; 116, 119, 150-153, 155-158; or 161-166 (of SEQ ID NO: 1) at 6 angstroms or less.

In some embodiments, the antibody binds to CFD at R157, K209, D150, T153, R156, R157, and D161 (of SEQ ID NO: 1). In some embodiments, the antibody binds to CFD at one or more of R157, T158, H159, D161, R207, K208, K209, D116, P119, D150, R151, A152, T153, N155, R156, G162, I164, or E166 (of SEQ ID NO: 1). In some embodiments, the antibody binds to CFD at one or more of R157, T158, H159, D161, N206, R207, K208, K209, D116, P119, D150, R151, A152, T153, N155, R156, R157, T158, or D161, G162, A163, I164, T165, E166 (of SEQ ID NO: 1).

In some embodiments, the antibody binds to CFD and is no more than 3 angstroms from one or more of 157, 209, 150, 153, 156, 157, and 161 (of SEQ ID NO: 1). In some embodiments, the antibody is no more than this distance from 2, 3, 4, 5, 6, or 7 of these residues. In some embodiments, the antibody binds to CFD and is no more than 5 angstroms from one or more of 157, 158, 159, 161, 207, 208, 209, 116, 119, 150, 151, 152, 153, 155, 156, 162, 164, or 166 (of SEQ ID NO: 1). In some embodiments, the antibody is no more than this distance from 2, 3, 4, 5, 6, 7, 8, 9, 10, 11, 12, 13, 14, 15, 16, 17, or 18 of these residues. In some embodiments, the antibody binds to CFD and is no more than 6 angstroms from one or more of 157-159, 161; 206-209; 116, 119, 150-153, 155-158; or 161-166 (of SEQ ID NO: 1). In some embodiments, the antibody is no more than this distance from 2, 3, 4, 5, 6, 7, 8, 9, 10, 11, 12, 13, 14, 15, 16, 17, 18, 19, 20, 21, 22, 23, or 24 of these residues.

In some embodiments, the antibody interacts with CFD at 2, 3, 4, 5, 6 or 7 of 157, 209, 150, 153, 156, 157, and 161 (of SEQ ID NO: 1) at 3 angstroms or less. In some embodiments, the antibody interacts with CFD at 2, 3, 4, 5, 6, 7, 8, 9, 10, 11, 12, 13, 14, 15, 16, 17, or 18 of 157, 158, 159, 161, 207, 208, 209; 116, 119, 150, 151, 152, 153, 155, 156, 162, 164, or 166 (of SEQ ID NO: 1) at 5 angstroms or less.

In some embodiments, the antibody interacts with CFD at one or more of 157, 158, 159, 161, 206, 207, 208, 209, 116, 119, 150, 151, 152, 153, 155, 156, 162, 163, 164, 165, or 166 of SEQ ID NO: 1. In some embodiments, the antibody interacts with CFD 2, 3, 4, 5, 6, 7, 8, 9, 10, 11, 12, 13, 14, 15, 16, 17, 18, 19, 20 or more of 157, 158, 159, 161, 206, 207, 208, 209, 116, 119, 150, 151, 152, 153, 155, 156, 162, 163, 164, 165, or 166 of SEQ ID NO: 1.

In some embodiments, an isolated antagonist antibody that specifically binds to complement factor D (CFD) is provided. When bound, the antibody is within 3 angstroms of residue 209 of SEQ ID NO: 1 of CFD.

In some embodiments, an isolated antagonist antibody that specifically binds to complement factor D (CFD) is provided. When bound, the antibody is within 3A of residue 156 of SEQ ID NO: 1 of CFD.

In some embodiments, an isolated antagonist antibody that specifically binds to complement factor D (CFD) is provided. The antibody binds to one or more of residues 156 or 209 of SEQ ID NO: 1 of CFD. In some embodiments, an isolated antagonist antibody that specifically binds to complement factor D (CFD) is provided. The antibody binds to both of residues 156 and 209 of SEQ ID NO: 1 of CFD. In some embodiments, an isolated antagonist antibody that specifically binds to complement factor D (CFD) is provided. The antibody, when bound to CFD, is not within 6 angstroms of at least one of 117, 118, and 156. In some embodiments, an isolated antagonist antibody that specifically binds to complement factor D (CFD) is provided. The antibody binds to CFD as described in any one or more of Tables: 1.1, 0.1A, 0.1B, 0.1D, and/or 11.3 (e.g., binds in the same manner as the designated antibodies in the noted tables).

In some embodiments, the antibody has the same or similar paratope as the antibody in the crystal structure provided herewith (in CTKDK001A.txt). In some embodiments, the paratope is the same as that shown in FIGS. 24A-26C (or the residues designated therein). In some embodiments, the paratope allows for an interaction with one or more of the residues designated in Table 38.1. In some embodiments, the paratope allows for an interaction with one or more of the residues designated in Table 38.2. In some embodiments, the paratope allows for an interaction with one or more of the residues designated in Table 38.3. In some embodiments, any antibody with the same paratope as KCD119 can be used in any of the method provided herein. In some embodiments, the paratope of the antibody includes one or more of: N52, D50, E99, and S103 on one chain (e.g., heavy chain) and E39, and D35 on the other chain (e.g., light chain). In some embodiments, 1, 2, 3, or 4 of the residues on the heavy chain are part of the paratope. In some embodiments, 1 or 2 of the residues on the light chain are part of the paratope. In some embodiments, 1, 2, 3, 4, 5, or 6 of N52, D50, E99, and S103 on the heavy chain and E39, and D35 on the light chain are the paratope. In some embodiments, this is the paratope of KCD119, involving SEQ ID NOs: 183 and 184 for the antibody. In some embodiments, the antibody's paratope includes residues positions 52, 50, 99, and 103 on the heavy chain and 39 and 35 on the light chain. In some embodiments, 1, 2, 3, 4, 5, or 6 of the paratope residues are maintained, while the rest of the heavy and/or light chain can be 80, 85, 90, 95, 98, 99, or 100% identical to a starting sequence, e.g., SEQ ID NOs; 183/184 or 520/525. In some embodiments, the paratope includes one or more of the antibody residues in Tables 38.1, 38.2, and 38.3.

In some embodiments, a crystallized CFD-antibody complex is provided. The antibody within the crystal comprises any one or more of the CDRs within SEQ ID NO:s 183 and 184, or any of the CDRs within any of Tables: 1.1, 0.1A, 0.1B, 0.1D, 11.3.

In some embodiments, the antibody is any antibody that binds to a same residues as any of the antibodies provided in Tables: 1.1, 0.1A, 0.1B, 0.1D, and/or 11.3. This can be identified through alanine scanning or other scanning mutagenesis studies. This can also be identified through solved crystal structures, in which residues that are less than 8, for example less than 5, angstroms from one another can be characterized as binding to one another. Thus, for any crystal structure produced, when a residue in the CDR of the antibody is less than 5 Angstroms from a particular residue on CFD, then that antibody can be characterized as binding to said residue. Antibodies that bind to the same residues as those antibodies provided herein are contemplated for all of the various embodiments provided herein, as appropriate (e.g., compositions, methods, etc.)

Yet another method which can be used to characterize a CFD antagonist antibody is to use competition assays with other antibodies known to bind to the same antigen, i.e., various fragments of CFD, to determine if the CFD antagonist antibody binds to the same epitope as other antibodies. Competition assays are well known to those of skill in the art, including in an ELISA format, and SPR (Surface Plasmon Resonance) biosensor.

In some embodiments, an isolated antagonist anti-CFD antibody is provided, wherein the antibody binds human CFD with an affinity of between about 0.01 pM to about 100 pM. In some embodiments, an isolated antagonist anti-CFD antibody is provided, wherein the antibody binds human CFD with an affinity of between about 0.1 pM to about 20 pM. In some embodiments, an isolated antagonist anti-CFD antibody is provided, wherein the antibody binds human CFD with an affinity of about 0.01, 0.05, 0.1, 0.5, 1, 5, 10, 15, 20, 25, 30, 35, 40, 45, 50, 55, 60, 65, 70, 75, 80, 85, 90, 95 or 100 pM.

The binding affinity ($K_D$) of an CFD antagonist antibody to CFD can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, about 2 pM, about 1 pM, about 0.5 pM, about 0.1 pM, about 0.05 pM, about 0.01 pM, about 0.005 pM, or about 0.001 pM.

In some embodiments, an isolated antagonist anti-CFD antibody is provided, wherein the antibody binds human CFD with a koff that is at least 5.0E-03 at 37 degrees. In some embodiments the koff is 5E-04. In some embodiments, an isolated antagonist anti-CFD antibody is provided, wherein the antibody binds human CFD with a koff that is better than 5.0E-04 at 37 degrees.

In some embodiments, binding affinity can be defined in terms of one or more of association constant ($k_a$), dissociation constant ($k_d$), and analyte concentration that achieves half-maximum binding capacity (KD). In some embodiments, $k_a$ can range from about 0.50E+05 to about 5.00E+08. In some embodiments, $k_d$ can range from about 0.50E-06 to about 5.00E-03. In some embodiments, $K_D$ can range from about 0.50E-12 to about 0.50E-07.

In some embodiments, a pharmaceutical composition comprising any of the antibodies disclosed herein is provided. In some embodiments, a pharmaceutical composition comprising any of the conjugates disclosed herein is provided. In some embodiments, the pharmaceutical composition comprises one or more pharmaceutically acceptable carriers. In some embodiments, the pharmaceutical composition is a liquid. In some embodiments, the pharmaceutical composition has an endotoxin level less than about 0.2 EU/ml. In some embodiments, the pharmaceutical composition is a liquid and has an endotoxin level less than about 0.2 EU/ml. In some embodiments, the pharmaceutical composition is a liquid and has an endotoxin level less than about 2.0, 1, 0.5, 0.2 EU/ml. In some embodiments, for example in intravitreal injection, the endotoxin limit is 0.01-0.02 EU/injection/eye.

Some embodiments provide any of the following, or compositions (including pharmaceutical compositions) comprising an antibody having a partial light chain sequence and a partial heavy chain sequence as found in Tables 1.1, 0.1A, and 11.3, or variants thereof. In Table 0.1A, the underlined sequences are some embodiments of CDR sequences as provided herein. In some embodiments, a composition as disclosed herein comprises an antibody having a partial or complete light chain sequence and a partial or complete heavy chain sequence from any of the options provided in Tables 1.1, 0.1A, and 11.3 and SEQ ID NO:s 184 and 183, or variants thereof. In some embodiments, the antibody (or binding fragment thereof) can include any one or more of the CDRs provided in Tables: 1.1, 0.1A, 0.1B, 0.1D, 11.3. In some embodiments, the antibody (or binding fragment thereof) can include any three or more of the CDRs provided in Tables: 1.1, 0.1A, 0.1B, 0.1D, 11.3. In some embodiments, the antibody (or binding fragment thereof) can include any all six of the CDRs provided in Tables 1.1, 0.1A, 0.1B, 0.1D, 11.3. CDR sequences for various constructs are also found in Tables 1.1, 0.1A, 0.1B, 0.1D, 11.3, and Table 1C depicts the nucleic acid sequences for a variety of the identified antibodies in the other tables.

TABLE 0.1A

Variable Regions Sequences of anti-CFD Antagonist monoclonal Antibodies (CDRs are underlined).

| mAb | Heavy Chain | Light Chain |
|---|---|---|
| KCD002 | EVKLVESEGGLVQPGSSMKLSCTASGFTFS<u>DYY MAW</u>VRQPEKGLEWVGN<u>INYDGSSTYYLDSL KS</u>RFIISRDSAKNILYLQMSSLKSEDTATYFCAR <u>GEDFYLYAMDY</u>WGQGTSVTVSS (SEQ ID NO: 2) | DIQMTQSPASLSASVGETVTITCRAS<u>ENIHSYLA WY</u>QQKQGKSPQLIVY<u>NTKT</u>LAEGVPSRFSGSG SGTQFSLKINSLQPEDEGSYYC<u>QHHYGIPPTEG </u>GGTKLEIK (SEQ ID NO: 4) |
| KCD003 | EVQLQQSRPELVKPGASVKIECKASGYTFT<u>DYY MNW</u>MRQRHGETLEWIG<u>DINPNNGDPSYNQKF K</u>DKATLTVDKSSSTASMELRSLTSDDSAVYYCA <u>REGPSFAY</u>WGQGTLVTVSA (SEQ ID NO: 5) | DVLMTQTPLSLPVSLGEQASICRSS<u>QTIVHSNG DTYLEW</u>YLQKPGQSPNLLIY<u>KVS</u>NRFSGVPDRF SGSGSGTDFTLKISRVEAEDLGVYYC<u>FQGSHVP PT</u>FGGGTKLEIK (SEQ ID NO: 6) |
| KCD005 | EVQLQQSGPELVKPGASVKISCKASGYTFT<u>DHY MNW</u>VKQSHGKSLEWGD<u>INPNNGGTS</u>CNQKF KGKATLTVDKSSSTAYMELRSLTSGDSAVYYC T<u>REGASFAF</u>WGQGTLVTVSA (SEQ ID NO: 7) | DVLMTQTPLSLPVSLGDQASICRSS<u>QSIVHSNG DTYLEW</u>YLQKPGQSPKLLIY<u>KVS</u>NRFSGVPDRF SGSGSGTDFTLKISRVEAEDLGVYYC<u>FQGSHVP VT</u>FGAGTKLELK (SEQ ID NO: 8) |
| KCD009 | QIQLVQSGPELKKPGETVKISCKASGYIFR<u>NYG MNW</u>VKQPGKGLKWMGW<u>INTYTGEPT</u>YADD FKGRFAFSLETSASTAYLQISNLKNEDTATYFC V<u>RDGPGFAY</u>WGQGTLVTVSA (SEQ ID NO: 15) | DVLMTQTPLSLPVSLGDQASICRSS<u>LIIEHSDG NTYLEW</u>YLQKPGQSPKLLIY<u>KVS</u>NRFSGVPDRF SGSGSGTDFTLKISRVEADDLGVYYC<u>FQGSHVP VT</u>FGAGTNLELK (SEQ ID NO: 16) |
| KCD010 | EVLLQQSGPELVKPGASVKIPCKASGYTFT<u>DYD MDW</u>VKQSHGKSLEWIGH<u>INPNNGGTI</u>YNQKF KGKATLTVDKSSSTAYMELRSLTSEDTAVYYC GT<u>GDFAY</u>WGHGTLVTVSA (SEQ ID NO: 17) | QIVLTQSPAIMSVSPGEKVTLTCSASS<u>SVSSSYLY WY</u>QKKPGSSPKLWIY<u>STS</u>NLASGVPARFSGSGS GTSYSLTISSMEAEDAASYFC<u>HQWSSYPPT</u>FGA GTKLELK (SEQ ID NO: 18) |
| KCD023 | EVLLQQSGPELVKPGASVKIPCKASGYTFT<u>DYN IDW</u>VKQSHGKSLEWIGD<u>INPNNGGIN</u>YNQKFK GKATLTVDKSSSTAYMERSLTSEDTAVYYCG T<u>GDYAY</u>WGQGTLVTVSA (SEQ ID NO: 19) | QIVLTQSPAFMSASPGEKVTLTCSASS<u>SVSSSYL YW</u>YQQKPGSSPKLWIY<u>STS</u>NLASGVPGRFSGSG SGTSYSLTISSMEAEDAASYFC<u>HQWTSYPPTEG</u> AGTKLELK (SEQ ID NO: 20) |
| KCD036 | EVQLQQSGPELVKPGASMKISCKASGYSFT<u>GYT MTW</u>VKQSHGKNLEWIGL<u>INPYNGGT</u>NYNQKF KGKATFTVDKSSSTAYMELLSLTSEDSAVYYCA <u>RRHYGSSWDY</u>WGQGTTLTVSS (SEQ ID NO: 21) | DIKLTQSPSSMYASLGERVTITCKAS<u>QDINTYLS WF</u>QQKPGKSPKTLIY<u>RANR</u>LVDGVPSRFSGSGS GQDYSLTISSLEYEEMGIYYC<u>LQYDEFPYT</u>EGG GTKLEIK (SEQ ID NO: 22) |
| KCD040 | EVQLQQSGAELVKPGASVKLSCTASDFNIK<u>DTY MHW</u>VMQRPEQGLEWIG<u>KIDPANGNTE</u>FDPKF QGKATITADTSSNTAYLQLTSLTSEDTAVYYCT <u>RAMDY</u>WGQGTSVTVSS (SEQ ID NO: 23) | QIVLTQSPAIMSASPGEKVTMTCSAGS<u>SVSYMY WY</u>QQKPGSSPRVLIY<u>DTS</u>NLASGVPVRFSGSGS GTSYSLTISRMEAEDAATYYC<u>QQWSNYPYT</u>EG GGTKLEIK (SEQ ID NO: 24) |
| KCD042 | EVQLQQSGAELVKPGASVRLSCTASGFNIK<u>HTY IHW</u>VSQRPEQGLEWIG<u>KIDPANGNTK</u>YDPKFQ GKATITADTSSNTAYLQLSSLTSEDTAVYYCVN <u>AMEY</u>WGQGTSVTVSS (SEQ ID NO: 25) | QSVLTQSPAIMSASPGEKVTMTCSANS<u>SVSDMY WF</u>QQRPGSSPRLLIY<u>DTS</u>NLASGVPVRFSGSGS GTSYSLTISRMEAEDAATYYC<u>QQWSTYPWT</u>FG GGTKLEIK (SEQ ID NO: 26) |
| KCD044 | EVQLQQSGAELVKPGASVRLSCTASGFNIK<u>HTY MHW</u>VSQRPERGLEWIG<u>KIDPANGNTK</u>YDPKF QGKATITADTSSNTVYLQLSSLTSEDTAVYYCL N<u>AMEY</u>WGQGTSVTVSS (SEQ ID NO: 27) | QSVLTQSPAIMSASPGEKVTMTCSANS<u>SVSDMY WY</u>QQRPGSSPRLLIY<u>DTS</u>NLASGVPVRFSGSGS GTSYSLTISRMEAEDAATYYC<u>QQWSTYPWT</u>FG GGTKLEIK (SEQ ID NO: 28) |
| KCD047 | EVQLQQSGAEFVKPGASVRLSCTASGFNIK<u>DTY MHW</u>VKQRPEQGLEWIG<u>RIDPANGYTK</u>DDPKF QGKATITADTSSNTAYLQLSSLTSEDTAVYYCA <u>SAMDY</u>WGQGTSVTVSS (SEQ ID NO: 29) | QIVLTQSPAVMSASPGEKVAMTCSASS<u>SVTYMY WY</u>QQKPGSSPRLLIY<u>DTS</u>NLASGVPVRFSGSGS GTSYSLTISRMEAEDAATYYC<u>QQWSTYPFPF</u>GS GTKLEIK (SEQ ID NO: 30) |
| KCD048 | EVQLQQSGADLVKPGASVKLSCTASGFNIK<u>ATY MHW</u>VRQRPEKGLEWIG<u>RIDPANGHTI</u>YDPQFQ GKATITSDTSSNTAYLQLNSLTSEDTAVYYCAE <u>AMDY</u>WGQGTSVTVSS (SEQ ID NO: 31) | QIVLTQSPAIMSASPGEKVTLTCSATS<u>SVSYMY WY</u>QQKPGSSPRLLIY<u>DTS</u>NLASGVPVRFSGSGS GTSYSLTISRMEAEDDATYYC<u>QQWSNYPFT</u>FG GGTKLEIK (SEQ ID NO: 32) |
| KCD070 | EIQLQQTGPELVKPGASVKISCKASGYSFT<u>DYII LWV</u>KQSHGKSLEWIGN<u>INPYYDYTS</u>YNLKFKG KATLTVDKSSSTAYMQLNSLTSEDSAVYYCAR<u>S DGYYGGDY</u>WGQGTSVTVSS (SEQ ID NO: 33) | DIVMTQSHKFMSTSVGDRVSITCKAS<u>QDVGTA VAW</u>YQQKPGQSPKLLIY<u>WAS</u>TRHTGVPDRFTG SGSGTDFTLTINNVQSEDLADYFC<u>QQYSSYPWT</u> FGGGTTLEIK (SEQ ID NO: 34) |
| KCD101 | QVQLQQPGAELVRPGTSVKLSCKASGYTFT<u>SY WMHW</u>VKQRPGQGLEWIG<u>VIDPSDSYT</u>NYNQK FKGKATLTVDTSSSTAYMQLSSLTSEDSAVYYC GR<u>NGYDGSMDY</u>WGQGTSVTVSS (SEQ ID NO: 35) | DIQMTQTTSSLSASLGDRVTISCRAS<u>QDISNYLN WY</u>QQKPDGTVKLLIY<u>YPS</u>RLHSGVPSRFSGSGS GTDYSLTISNLEQEDFATYFC<u>QQGNTLPYT</u>FGG GTKLEIK (SEQ ID NO: 36) |

TABLE 0.1A-continued

Variable Regions Sequences of anti-CFD Antagonist monoclonal Antibodies (CDRs are underlined).

| mAb | Heavy Chain | Light Chain |
|---|---|---|
| KCD102 | QVQLQQPGAELVRPGTSVKLSCKASGYTFT<u>SY WMH</u>WVKQRPGQGLEWIGV<u>IDPSDSYTNYNQK FKG</u>KATLTVDTSSSTAYMQLSSLTSEDSAVYYC AR<u>NGYDGSMDY</u>WGQGTSVTVSS (SEQ ID NO: 37) | EIQMTQTTSSLSASLGDRVTISCRAS<u>QDISNYLN</u> WYQQKPDGTVKLLIY<u>YPS</u>RLHSGVPSRFSGSGS GTDYSLTISNLEQEDFATYFC<u>QQGNTLPYT</u>EGG GTKLEIK (SEQ ID NO: 38) |
| KCD103 | QVQLQQPGAELVRPGTSVKLSCKASGYTFT<u>SY WMH</u>WVKQRPGQGLEWIGV<u>IDPSDSYTKYNQK FKD</u>KATLTVETSSSTAYMQLSSLTSEDSAVYYC AG<u>NGYDGSMDY</u>WGQGTSVTVSS (SEQ ID NO: 39) | DIQMTQTTSSLSASLGDRVTISCRAS<u>QDISNSLN</u> WYQQKPDGTVKLLIY<u>YTS</u>RLHSRVPSRFSGSGS GTDYSLTISNLDQEDIATYFC<u>QQANTLPYT</u>FGG GTKLEIK (SEQ ID NO: 40) |
| KCD104 | QVQLQQPGAELVRPGTSVKLSCKASGYTFT<u>SY WMH</u>WVKQRPGQGLEWIGV<u>IDPSDSYTYYNQK FKG</u>KATLTVDTSSSTAYMQLSSLTSEDSAVYYC AR<u>NGYDGAMDY</u>WGQGTSVTVSS (SEQ ID NO: 41) | EIQMTQTTSSLSASLGDRVTISCRAS<u>QDISNYLN</u> WYQQKPDGTVKLLIY<u>YPS</u>RLHSGVPSRFSGSGS GTDYSLTISNLEQEDFATYFC<u>QQGNTLPYT</u>EGG GTKLEIK (SEQ ID NO: 42) |
| KCD118 | EVQLQQSGPELVKPGASVKISCKAFGYTFT<u>DYY KN</u>WMRQRHGESLEWIG<u>DINPNSGDANYNQKF KG</u>KATLTVDKSSSTAYMELRSLTSEDSAVYYCA R<u>EGPSFAY</u>WGHGTLVTVSA (SEQ ID NO: 43) | DVLMTQTPLSLPVSLGDQASISCRSS<u>QTIVHSNG DTYLE</u>WYLQKPGQSPNLLIY<u>KVS</u>NRFSGVPDRF SGSGSGTDFTLKISRVEAEDLGIYYC<u>FQGSHVPP T</u>FGGGTKLEIK (SEQ ID NO: 44) |
| KCD119 | EVQLQQSGPELVKPGASVKISCKASGYTFT<u>DYY TN</u>WMRQRHGESLEWIG<u>DINPNTGDTSYNQKFR V</u>KATLTVDKSSGTAYMGLRSLTSEDSAVYYCT R<u>EGPSFAY</u>WGQGTLVTVSA (SEQ ID NO: 45) | DVLMTQTPLSLPVSLGDQASISCRSS<u>QTIVHSNG DTYLE</u>WYLQKPGQSPNLLIY<u>KVS</u>NRFSGVPDRF SGSGSGTDFTLKISRVEAEDLGVYYC<u>FQGSHVP PT</u>FGGGTTLEIK (SEQ ID NO: 46) |
| KCD121 | EVQLQQSGPELVKPGASVKISCKASGYTFT<u>DYY KN</u>WMRQRHGESLEWIG<u>DINPNNGDTSYNQKF RG</u>KATLTVDKSSSTAFMELRSLTSEDSAVYYCA R<u>EGPSFAY</u>WGQGTLVTVSA (SEQ ID NO: 47) | DVLMTQTPLSLPVSLGDQASISCRSN<u>QTIVHSN GDTYLE</u>WYLQKPGQSPNLLIY<u>KVS</u>NRFSGVPD RFSGSGSGTDFTLRISRVEADLGVYYC<u>FQGSH VPPT</u>FGGGTKLEIK (SEQ ID NO: 48) |
| KCD122 | EVQLQQSGPELVKPGASVKISCKASGYTFT<u>DYY KN</u>WMRQRHGESLEWIG<u>DINPNNGDANYNQKF KG</u>KATLTVDKSSSTAYMELRSLTSEDSAVYFCA R<u>EGPSFAY</u>WGHGTLVTVSA (SEQ ID NO: 49) | DVLMTQTPLSLPVSLGDQASISCRSS<u>QTIVHSNG DTYLE</u>WYLQKPGQSPNLLIY<u>KVS</u>NRFSGVPDRF SGSGSGTDFTLKISRVEAEDLGVYYC<u>FQGSHVP PT</u>FGGGTKLEIK (SEQ ID NO: 50) |
| KCD123 | EVHLQQSGPELVKPGASVKISCKASGYTFT<u>DFY KN</u>WMRQRHGESLEWIG<u>DINPNNGGTNYNQKF KG</u>KATLTVDKSSSTAYMELRSLTSEDSAVYYCA R<u>EGPSFAY</u>WGQGTLVTVSA (SEQ ID NO: 51) | DVLMTQTPLSLPVSLGDQASISCRSS<u>QTIVHSNG DTYLE</u>WYLQKPGQSPNLLIY<u>KVS</u>NRFSGVPDRF SGSGSGTDFTLKISRVEAEDLGVYYC<u>FQGSHVP PT</u>FGGGTKLEIK (SEQ ID NO: 52) |
| KCD124 | EVQLQQSGPELVKPGASVKISCKASGYTFT<u>DHY MN</u>WVKQSHGKLEWIG<u>DINPNNGGTSYNQKF KG</u>KATLTVDKSSSTAYMELRSLTSGDSAVYYC TR<u>EGASPAFW</u>GQGTLVTVSA (SEQ ID NO: 53) | DVLMTQTPLSLPVSLGDQASISCRSS<u>QSIVHSNG DTYLE</u>WYLQKPGQSPKLLIY<u>KVS</u>NRFSGVPDRF SGSGSGTDFTLKISRVEAEDLGVYYC<u>FQGSHVP LT</u>FGAGTKLELK (SEQ ID NO: 54) |
| KCD131 | QVQLQQSGPELVKPGASVKISCKASAYTFT<u>DYY IN</u>WVKQRPGQGPEWIGW<u>IFPGSNSTYSNEKFE V</u>KATLTVDESSSTAYMLLSSLTSEDSAVYFCAR <u>LGYFGSSYHALDY</u>WGQGTSVTVSS (SEQ ID NO: 55) | DIQMTQSPASLSVSVGETVTITCRAS<u>ENIYSHLA</u> WFQQKQGKSPRLLVY<u>SATN</u>LPDGVPSRFSGSG SGTQYSLKINILQSEDEGSYYC<u>QHFWGTPWT</u>FG GGTKLEIK (SEQ ID NO: 56) |
| KCD136 | EVQLQQSVAELVRPGASVKLSCSASGFNIK<u>NTY MH</u>WVNQRPEQGLEWIG<u>RIDPANGITKYAPNFQ G</u>KATITADTSSNTAYLQLSNLTSEDTAIYYCTR<u>A MDY</u>WGQGTSVTVSS (SEQ ID NO: 57) | QIVLTQSPAIMSASPGEKVTMTCSAS<u>SSVSYMY</u> WYQQKPGSSPRLLIY<u>DISN</u>LASGVPVRFSGSGS GTSYSLTISRMEAEDAATYYC<u>QQWDTYPWT</u>FG GGTKLEIK (SEQ ID NO: 58) |
| KCD200 | EVQLQQSGPELVKPGASVKISCKASGYTFT<u>SYY KN</u>WMRQRHGESLEWIG<u>DINPNSGDTAYNQKF KG</u>KATLTVDRSSSTAYMELRSLTSEDSAVYYCA R<u>EGPSFAY</u>WGQGTLVTVSA (SEQ ID NO: 59) | DVLMTQTPLSLPVSLGDQVSISCRSS<u>QTIVHSNG DTYLE</u>WYLQKPGQSPNLLIY<u>KVS</u>NRFSGVPDRF SGSGSGTDFTLKISRVEAEDLGVYYC<u>FQGSHVP PT</u>FGGGTKLEIK (SEQ ID NO: 60) |
| KCD208 | EVQLQQSVAELVRPGASVKLSCTVSGFNIK<u>NTY MH</u>WVKQRPEQGLEWIG<u>RIDPANGDTTYAPKF QG</u>KATITADTSSNSAYLHLSRLTSEDTAIYYCSL <u>YDYDGY</u>WGQGTTLTVSS (SEQ ID NO: 61) | EIVLTQSPALMAASPGEKVTITCSVS<u>SSISSSSLH</u> WYRQKSGTSPKPWIY<u>GTS</u>HLASGVPVRFSGSGS GTSYSLTISSMEAEDAATYYC<u>QQWDTYPWT</u>FG GGTKLEIK (SEQ ID NO: 62) |
| KCD214 | EVQLQQSVAEFVRPGASVKLSCTASGFNIK<u>NTY MH</u>WVKQRPEQGLEWIG<u>RIDPANGNTEYAPKF QG</u>KATITADTSSNTAYLQLSSLTSEDTAIYYCAL <u>YDYDGY</u>WGQGTTLTVSS (SEQ ID NO: 63) | EIVLTQSPALMAASPGEKVTITCRVS<u>SSISSSSLH</u> WYQQKSGTSPKPWIY<u>GTS</u>NLASGVPVRFSGSRS GTSYSLTISSMEAEDAATYYC<u>QQWSDYPWT</u>FG GGTKLEIK (SEQ ID NO: 64) |

TABLE 0.1A-continued

Variable Regions Sequences of anti-CFD Antagonist monoclonal Antibodies (CDRs are underlined).

| mAb | Heavy Chain | Light Chain |
|---|---|---|
| KCD220 | QVQLQQSGAELMEPGASVKLSCKATGYTF<u>TGY</u><br><u>WIEWV</u>KQRPGHGLEWIGE<u>TLPGSDSNNYNEKF</u><br><u>KG</u>KATFTADTSSNTAYMQLSSLTTEDSAIYYCA<br><u>RDYSNYWYFDV</u>WGTGTTVTVSS (SEQ ID NO: 65) | DIQMTQTTSSLSASLGDRVTISCRAS<u>QDISNYLN</u><br>WYQQKPDGTVKLLIY<u>YTS</u>NLHSGVPSRFSGSGS<br>GTDYSLTISNLEQEDIATYFC<u>QQDSKHRT</u>FGGG<br>TKLEIK (SEQ ID NO: 66) |
| KCD224 | QVQLKESGPGLVAPSQSLSITCTVSGFSLT<u>SYGV</u><br><u>DWIR</u>QSPGKGLEWLGV<u>IWGVGSTNYNSALKSR</u><br>LSISKDNSKSQVFLKMNSLQTDDTAMYYCARS<br><u>YDGSYWYFDV</u>WGTGTTVTVSS (SEQ ID NO: 67) | DIQMTQTTSSLSASLGDRVTISCRAS<u>QVISNYLN</u><br>WYQQKPDGTVKLLIY<u>YTS</u>RLHSGVPSRFSGSGS<br>GTDYSLTISNLEPEDIATYYC<u>QQYSKLPYT</u>EGSG<br>TKLEIK (SEQ ID NO: 68) |
| 119_TAF | EVQLVESGGGLVQPGGSLRLSCAASGYTFTDY<br>YMNWVRQAPGKGLEWIGDINPNTGDTSYNAD<br>FKRRFTFSLDTSKSTAYLQMNSLRAEDTAVYYC<br>TREGPSFAYWGQGTLVTVSS (SEQ ID NO: 69) | DIQLTQSPSSLSASVGDRVTITCRSSQTIVHSNG<br>DTYLEWYQQKPGKAPNLLIYKVSNRFSGVPSR<br>FSGSGSGTDFTLTISSLQPEDFATYYCFQGSHVP<br>PTFGQGTKVEIK (SEQ ID NO: 70) |
| 119_TAF Germ | EVQLVESGGGLVQPGGSLRLSCAASGYTFTDY<br>YMSWVRQAPGKGLEWIGDINPNTGDTSYNADS<br>VKGRFTISRDNSKNTLYLQMNSLRAEDTAVYY<br>CTREGPSFAYWGQGTLVTVSS (SEQ ID NO: 71) | DIQMTQSPSSLSASVGDRVTITCRSSQTIVHSNG<br>DTYLEWYQQKPGKAPNLLIYKVSNRFSGVPSR<br>FSGSGSGTDFTLTISSLQPEDFATYYCFQGSHVP<br>PTFGQGTKVEIK (SEQ ID NO: 72) |
| 119_Human Germ | EVKKPGASVKVSCKASGYTFTDYYMHWVRQA<br>PGQGLEWIGDINPNTGDTSYNQKFQGRVTSTR<br>DTSISTAYMELSRLRSDDTVVYYCTREGPSFAY<br>WGQGTLVTVSS (SEQ ID NO: 73) | DVVMTQSPLSLPVTLGQPASISCRSSQTIVHSNG<br>DTYLEWFQQRPGQSPNLLIYKVSNRFSGVPDRF<br>SGSGSGTDFTLKISRVEAEDVGVYYCFQGSHVP<br>PTFGGGTKVEIK (SEQ ID NO: 74) |

TABLE 0.1B

CDRs of anti-CFD Antagonist monoclonal Antibodies based on a broad CDR definition

| | H1 | H2 | H3 | L1 | L2 | L3 |
|---|---|---|---|---|---|---|
| KCD002 | GFTFSDYYMA (SEQ ID NO: 75) | INYDGSSTYY LDSLKS (SEQ ID NO: 76) | ARGEDFYLY AMDY (SEQ ID NO: 77) | RASENIHSYL A (SEQ ID NO: 78) | NTKTLAE (SEQ ID NO: 79) | QHHYGIPPT (SEQ ID NO: 80) |
| KCD003 | GYTFTDYM N (SEQ ID NO: 81) | INPNNGDPSY NQKFKD (SEQ ID NO: 82) | AREGPSFAY (SEQ ID NO: 83) | RSSQTIVHSN GDTYLE (SEQ ID NO: 84) | KVSNRFS (SEQ ID NO: 85) | FQGSHVPPT (SEQ ID NO: 86) |
| KCD005 | GYTFTDHYM N (SEQ ID NO: 87) | INPNNGGTSC NQKFKG (SEQ ID NO: 88) | TREGASFAF (SEQ ID NO: 89) | RSSQSIVHSN GDTYLE (SEQ ID NO: 90) | KVSNRFS (SEQ ID NO: 91) | FQGSHVPVT (SEQ ID NO: 92) |
| KCD009 | GYIFRNYGMN (SEQ ID NO: 93) | INTYTGEPTY ADDFKG (SEQ ID NO: 94) | VRDGPGFAY (SEQ ID NO: 95) | RSSLILEHSDG NTYLE (SEQ ID NO: 96) | KVSNRFS (SEQ ID NO: 97) | FQGSHVPVT (SEQ ID NO: 98) |
| KCD010 | GYTFTDYDM D (SEQ ID NO: 99) | INPNNGGTIY NQKFKG (SEQ ID NO: 100) | GTGDFAY (SEQ ID NO: 101) | SASSSVSSSYL Y (SEQ ID NO: 102) | STSNLAS (SEQ ID NO: 103) | HQWSSYPPT (SEQ ID NO: 104) |
| KCD023 | GYTFTDYNID (SEQ ID NO: 105) | INPNNGGINY NQKFKG (SEQ ID NO: 106) | GTGDYAY (SEQ ID NO: 107) | SASSSVSSSYL Y (SEQ ID NO: 108) | STSNLAS (SEQ ID NO: 109) | HQWTSYPPT (SEQ ID NO: 110) |
| KCD036 | GYSFTGYTMT (SEQ ID NO: 111) | INPYNGGTNY NQKFKG (SEQ ID NO: 112) | ARRHYGSSW DY (SEQ ID NO: 113) | KASQDINTYL S (SEQ ID NO: 114) | RANRLVD (SEQ ID NO: 115) | LQYDEFPYT (SEQ ID NO: 116) |
| KCD040 | DFNIKDTYMH (SEQ ID NO: 117) | IDPANGNTEF DPKFQG (SEQ ID NO: 118) | TRAMDY (SEQ ID NO: 119) | SAGSSVSYMY (SEQ ID NO: 120) | DTSNLAS (SEQ ID NO: 121) | QQWSNYPYT (SEQ ID NO: 122) |
| KCD042 | GFNIKHTYIH (SEQ ID NO: 123) | IDPANGNTKY DPKFQG (SEQ ID NO: 124) | VNAMEY (SEQ ID NO: 125) | SANSSVSDMY (SEQ ID NO: 126) | DTSNLAS (SEQ ID NO: 127) | QQWSTYPWT (SEQ ID NO: 128) |
| KCD044 | GFNIKHTYMH (SEQ ID NO: 129) | IDPANGNTKY DPKFQG (SEQ ID NO: 130) | LNAMEY (SEQ ID NO: 131) | SANSSVSDMY (SEQ ID NO: 133) | DTSNLAS (SEQ ID NO: 134) | QQWSTYPWT (SEQ ID NO: 132) |

TABLE 0.1B-continued

CDRs of anti-CFD Antagonist monoclonal Antibodies based on a broad CDR definition

| | H1 | H2 | H3 | L1 | L2 | L3 |
|---|---|---|---|---|---|---|
| KCD047 | GFNIKDTYMH (SEQ ID NO: 135) | IDPANGYTKD DPKFQG (SEQ ID NO: 136) | ASAMDY (SEQ ID NO: 137) | SASSSVTYMY (SEQ ID NO: 138) | DTSNLAS (SEQ ID NO: 139) | QQWSNYPFT (SEQ ID NO: 140) |
| KCD048 | GFNIKATYMH (SEQ ID NO: 141) | IDPANGHTIY DPQFQG (SEQ ID NO: 142) | AEAMDY (SEQ ID NO: 143) | SATSSVSYMY (SEQ ID NO: 144) | DTSNLAS (SEQ ID NO: 145) | QQWSNYPFT (SEQ ID NO: 146) |
| KCD070 | GYSFTDYIIL (SEQ ID NO: 147) | INPYYDYTSY NLKFKG (SEQ ID NO: 148) | ARSDGYYGG DY (SEQ ID NO: 149) | KASQDVGTA VA (SEQ ID NO: 150) | WASTRHT (SEQ ID NO: 151) | QQYSSYPWT (SEQ ID NO: 152) |
| KCD101 | GYTFTSYWM H (SEQ ID NO: 153) | IDPSDSYTNY NQKFKG (SEQ ID NO: 154) | GRNGYDGSM DY (SEQ ID NO: 155) | RASQDISNYL N (SEQ ID NO: 156) | YPSRLHS (SEQ ID NO: 157) | QQGNTLPYT (SEQ ID NO: 158) |
| KCD102 | GYTFTSYWM H (SEQ ID NO: 159) | IDPSDSYTNY NQKFKG (SEQ ID NO: 160) | ARNGYDGSM DY (SEQ ID NO: 161) | RASQDISNYL N (SEQ ID NO: 162) | YPSRLHS (SEQ ID NO: 163) | QQGNTLPYT (SEQ ID NO: 164) |
| KCD103 | GYTFTSYWM H (SEQ ID NO: 165) | IDPSDSYTKY NQKFKD (SEQ ID NO: 166) | AGNGYDGSM DY (SEQ ID NO: 167) | RASQDISNSL N (SEQ ID NO: 168) | YTSRLHS (SEQ ID NO: 169) | QQANTLPYT (SEQ ID NO: 170) |
| KCD104 | GYTFTSYWM H (SEQ ID NO: 171) | IDPSDSYTYY NQKFKG (SEQ ID NO: 172) | ARNGYDGAM DY (SEQ ID NO: 173) | RASQDISNYL N (SEQ ID NO: 174) | YPSRLHS (SEQ ID NO: 175) | QQGNTLPYT (SEQ ID NO: 176) |
| KCD118 | GYTFTDYYKN (SEQ ID NO: 177) | INPNSGDANY NQKFKG (SEQ ID NO: 178) | AREGPSFAY (SEQ ID NO: 179) | RSSQTIVHSN GDTYLE (SEQ ID NO: 180) | KVSNRFS (SEQ ID NO: 181) | FQGSHVPPT (SEQ ID NO: 182) |
| KCD119 | GYTFTDYYTN (SEQ ID NO: 185) | INPNTGDTSY NQKFRV (SEQ ID NO: 186) | TREGPSFAY (SEQ ID NO: 187) | RSSQTIVHSN GDTYLE (SEQ ID NO: 188) | KVSNRFS (SEQ ID NO: 189) | FQGSHVPPT (SEQ ID NO: 190) |
| KCD121 | GYTFTDYYKN (SEQ ID NO: 191) | INPNNGDTSY NQKFRG (SEQ ID NO: 192) | AREGPSFAY (SEQ ID NO: 193) | RSNQTIVHSN GDTYLE (SEQ ID NO: 194) | KVSNRFS (SEQ ID NO: 195) | FQGSHVPPT (SEQ ID NO: 196) |
| KCD122 | GYTFTDYYKN (SEQ ID NO: 197) | INPNNGDANY NQKFKG (SEQ ID NO: 198) | AREGPSFAY (SEQ ID NO: 199) | RSSQTIVHSN GDTYLE (SEQ ID NO: 200) | KVSNRFS (SEQ ID NO: 201) | FQGSHVPPT (SEQ ID NO: 202) |
| KCD123 | GYTFTDFYKN (SEQ ID NO: 203) | INPNNGGTNY NQKFKG (SEQ ID NO: 204) | AREGPSFAY (SEQ ID NO: 205) | RSSQTIVHSN GDTYLE (SEQ ID NO: 206) | KVSNRFS (SEQ ID NO: 207) | FQGSHVPPT (SEQ ID NO: 208) |
| KCD124 | GYTFTDHYM N (SEQ ID NO: 209) | INPNNGGTSY NQKFKG (SEQ ID NO: 210) | TREGASFAF (SEQ ID NO: 211) | RSSQSIVHSN GDTYLE (SEQ ID NO: 212) | KVSNRFS (SEQ ID NO: 213) | FQGSHVPLT (SEQ ID NO: 214) |
| KCD131 | AYTFTDYYIN (SEQ ID NO: 215) | IFPGSNSTYSN EKFEV (SEQ ID NO: 216) | ARLGYFGSSY HALDY (SEQ ID NO: 217) | RASENIYSHL A (SEQ ID NO: 218) | SATNLPD (SEQ ID NO: 219) | QHFWGTPWT (SEQ ID NO: 220) |
| KCD136 | GFNIKNTYMH (SEQ ID NO: 221) | RIDPANGITK YAPNFQG (SEQ ID NO: 222) | TRAMDY (SEQ ID NO: 223) | SASSSVSYMY (SEQ ID NO: 224) | DISNLAS (SEQ ID NO: 225) | QQWDTYPWT (SEQ ID NO: 226) |
| KCD200 | GYTFTSYYKN (SEQ ID NO: 227) | INPNSGDTAY NQKFKG (SEQ ID NO: 228) | AREGPSFAY (SEQ ID NO: 229) | RSSQTIVHSN GDTYLE (SEQ ID NO: 230) | KVSNRFS (SEQ ID NO: 231) | FQGSHVPPT (SEQ ID NO: 232) |
| KCD208 | GFNIKNTYMH (SEQ ID NO: 233) | RIDPANGDTT YAPKFQG (SEQ ID NO: 234) | SLYDYDGY (SEQ ID NO: 235) | SVSSSISSSL H (SEQ ID NO: 236) | GTSHLAS (SEQ ID NO: 237) | QQWDTYPWT (SEQ ID NO: 238) |
| KCD214 | GFNIKNTYMH (SEQ ID NO: 239) | RIDPANGDTT YAPKFQG (SEQ ID NO: 240) | ALYDYDGY (SEQ ID NO: 241) | RVSSSISSSL H (SEQ ID NO: 242) | GTSNLAS (SEQ ID NO: 243) | QQWSDYPWT (SEQ ID NO: 244) |

TABLE 0.1B-continued

CDRs of anti-CFD Antagonist monoclonal Antibodies based on a broad CDR definition

| | H1 | H2 | H3 | L1 | L2 | L3 |
|---|---|---|---|---|---|---|
| KCD220 | GYTFTGYWIE (SEQ ID NO: 245) | ETLPGSDSNN YNEKFKG (SEQ ID NO: 246) | ARDYSNYWY FDV (SEQ ID NO: 247) | RASQDISNYL N (SEQ ID NO: 248) | YTSNLHS (SEQ ID NO: 249) | QQDSKHRT (SEQ ID NO: 250) |
| KCD224 | GFSLTSYGVD (SEQ ID NO: 251) | VIWGVGSTNY NSALKS (SEQ ID NO: 252) | ARSYDGSYW YFDV (SEQ ID NO: 253) | RASQVISNYL N (SEQ ID NO: 254) | YTSRLHS (SEQ ID NO: 255) | QQYSKLPYT (SEQ ID NO: 256) |

TABLE 0.1C

Nucleotide sequences of variable domains of anti-CFD Antagonist monoclonal Antibodies

| mAb | Heavy Chain | Light Chain |
|---|---|---|
| KCD002 | ATGTATCGAATGCAACTTCTCAGTTGTATT GCGTTGTCTTTGGCTTTGGTCACTAATTCT GAGGTGAAACTTGTAGAATCTGAAGGTGGT CTTGTCCAGCCAGGAAGTTCCATGAAACTG AGCTGTACCGCTTCCGGGTTTACGTTTAGT GATTACTATATGGCCTGGGTGAGACAAGTG CCTGAAAAGGGCCTCGAGTGGGTAGGAAA CATTAACTATGATGGGTCTAGCACCTATTA CCTTGATAGTCTTAAGTCACGATTCATTATT TCAAGAGACTCAGCAAAGAATATCCTTTAT CTGCAGATGTCTTCTCTTAAGAGTGAGGAT ACGGCCACTTACTTCTGTGCGAGAGGTGAA GATTTCTACCTTTATGCTATGGATTACTGG GGGCAAGGCACTAGCGTTACCGTCTCCTCA (SEQ ID NO: 257) | ATGTACCGAATGCAGCTCTTGTCCTGCATT GCTTTGTCTCTCGCTTTGGTCACGAACTCC GATATTCAAATGACTCAGAGCCCCGCATCT CTCTCTGCTTCCGTAGGCGAAACCGTAACA ATCACTTGTCGAGCTAGTGAAAACATACAC TCCTATCTCGCTTGGTACCAACAGAAACAG GGAAAGTCACCACAACTTATTGTGTATAAC ACCAAGACGCTGGCCGAGGGTGTACCTAGT CGGTTTTCTGGATCCGGTAGCGGTACACAG TTTTCTTTGAAAATAAATAGCCTTCAACCTG AAGATTTTGGATCCTACTATTGCCAGCATC ACTATGGGATACCACCGACGTTCGGAGGCG GTACAAAGCTTGAAATTAAA (SEQ ID NO: 258) |
| KCD003 | ATGTATAGAATGCAATTGTTGTCCTGTATC GCTCTGAGCCTTGCCCTTGTCACGAATAGC GAAGTCCAACTTCAGCAGTCTCGCCCCGAA CTGGTGAAGCCTGGGGCGAGTGTAAAAATT TTTTGCAAAGCATCCGGCTATACATTTACG GACTACTACATGAATTGGATGAGGCAGAGG CACGGCGAGACCCTTGAGTGGATAGGAGA CATCAACCCGAACAACGGGGACCCGTCATA CAATCAGAAGTTCAAAGATAAAGCAACTCT TACTGTTGATAAATCCTCAAGCACTGCGAG CATGGAACTGAGGAGTCTTACATCCGACGA TTCCGCTGTTTACTATTGCGCCAGGGAAGG TCCTTCCTTCGCTTATTGGGGTCAGGGGAC ATTGGTTACCGTCTCCGCA (SEQ ID NO: 259) | ATGTATCGAATGCAGCTCTTGTCATGTATA GCCCTTTCTCTGGCTCTCGTTACTAACAGC GATGTGTTGATGACACAAACCCCTCTCAGT CTGCCCGTTTCACTTGGCGAACAGGCGAGT ATTAGCTGCCGATCTTCCCAAACTATAGTT CACAGTAACGGAGATACGTACCTGGAGTGG TACCTGCAGAAACCGGGCCAGTCACCTAAC TTGCTCATTTACAAAGTCTCAAATAGATTCT CCGGAGTTCCAGATAGGTTTTCCGGTAGTG GTTCTGGTACGGACTTCACTTTGAAGATTA GCCGCGTCGAGGCGGAGGACCTTGGGGTC TACTATTGCTTCCAAGGCTCCCATGTGCCT CCCACGTTTGGAGGAGGCACTAAGCTTGAA ATTAAA (SEQ ID NO: 260) |
| KCD005 | ATGTATCGGATGCAACTGTTGAGTTGCATT GCACTTAGTCTCGCACTCGTGACGAACAGC GAGGTACAACTGCAACAGTCTGGCCCTGAA TTGGTAAAACCCGGTGCCTCTGTTAAAATC AGCTGTAAAGCGTCCGGCTATACATTTACA GACCACTATATGAATTGGGTCAAGCAATCT CATGGAAAATCCCTTGAATGGATAGGAGAT ATAAATCCGAATAACGGAGGCACTAGTTGT AACCAGAAGTTTAAGGGAAAAGCTACTCTG ACTGTGGATAAATCATCTTCCACTGCCTAT ATGGAGCTTAGGTCTCTTACTAGCGGGGAC TCTGCGGTCTACTACTGCACCCGCGAAGGG GCATCTTTCGCTTTCTGGGGTCAGGGAACA CTGGTTACAGTCTCTGCA (SEQ ID NO: 261) | ATGTATAGAATGCAATTGTTGTCATGTATC GCGCTCTCACTCGCATTGGTTACTAACTCT GATGTGTTGATGACGCAGACTCCCCTGTCT CTCCCAGTGTCACTTGGCGATCAGGCTTCT ATATCCTGCCGAAGCTCCCAGAGCATTGTC CACAGTAACGGAGACACTTATCTGGAATGG TACCTCCAAAAGCGGGCCAGAGTCCAAAA CTTTTGATCTATAAAGTCAGTAATAGATTTA GTGGGGTTCCAGACAGGTTCTCAGGCAGC GGCTCAGGCACCGACTTCACTCTGAAGATA AGCCGGGTTGAAGCTGAGGATCTCGGGGT GTATTACTGTTTCAAGGGTCACATGTACC AGTTACATTTGGAGCAGGCACTAAGCTTGA AATTAAA (SEQ ID NO: 262) |
| KCD009 | ATGTACCGCATGCAACTTCTTAGCTGTATT GCCCTCTCCCTTGCACTCGTTACCAATAGC CAGATACAACTGGTGCAAAGCGGGCCTGA GCTTAAGAAACCAGGAGAAACAGTCAAAAT TTCCTGCAAAGCGTCAGGCTACATATTCAG GAACTACGGCATGAATTGGGTGAAGCAAG GTCCGGGCAAAGGCCTCAAATGGATGGGG | ATGTACCGAATGCAGCTCCTGTCTTGCATC GCCCTTAGCCTCGCTCTTGTAACAATTCT CTTCCTGTCTCACTCGGGAGACCAAGCCTCA ATTTCTTGTAGATCCAGTCTTATAATAGAG CATTCTGATGGTAATACTTATCTGGAGTGG TATCTTCAGAAACCCGGTCAGTCTCCGAAG |

TABLE 0.1C-continued

Nucleotide sequences of variable domains of anti-CFD Antagonist monoclonal Antibodies

| mAb | Heavy Chain | Light Chain |
|---|---|---|
| | TGGATCAACACATACACGGGTGAGCCCACT<br>TACGCAGACGACTTCAAGGGAAGATTTGCA<br>TTTTCACTTGAAACGTCAGCCAGTACAGCA<br>TATTTGCAGATTTCCAACCTTAAGAACGAG<br>GATACAGCCACTTATTTCTGTGTTAGGGAT<br>GGTCCAGGTTTTGCGTACTGGGGGCAAGG<br>AACTCTGGTGACTGTATCTGCA<br>(SEQ ID NO: 263) | TTGCTTATCTACAAGGTCTCCAATCGGTTTT<br>CTGGAGTTCCGGATAGGTTTTCTGGCTCAG<br>GGAGCGGGACCGATTTTACCTTGAAAATTT<br>CACGGGTGGAAGCAGATGACTTGGGTGTG<br>TACTATTGTTTTCAGGGGAGCCATGTCCCG<br>GTGACGTTCGGCGCTGGGACCAAGCTTGAA<br>ATTAAA (SEQ ID NO: 264) |
| KCD010 | ATGTATCGAATGCAGCTTTTGTCCTGTATA<br>GCTTTGTCTTTGGCCCTTGTGACAAATTCC<br>GAGGTCCTGCTTCAGCAATCAGGCCCCGAG<br>CTGGTCAAGCCAGGAGCATCTGTCAAAATA<br>CCCTGTAAGGCAAGCGGCTACACGTTTACG<br>GACTACGATATGGATTGGGTTAAGCAATCA<br>CACGGAAAGTCATTGGAGTGGATAGGCCAC<br>ATCAATCCAAATAACGGTGGCACTATTTAT<br>AACCCAAAAGTTCAAGGGCAAAGCCACCCTG<br>ACCGTCGATAAGTCATCATCTACTGCGTAC<br>ATGGAGTTGAGGTCTCTGACATCAGAAGAT<br>ACCGCCGTTTATTACTGTGGCACTGGGGAT<br>TTCGCATATTGGGGACATGGAACTCTGGTC<br>ACAGTTTCAGCA (SEQ ID NO: 265) | ATGTATAGGATGCAACTGTTGTCCTGCATT<br>GCTCTTTCTCTTGCACTTGTAACAAACTCCC<br>AAATCGTACTCACCCAATCCCCAGCCATAA<br>TGTCCGTCAGTCCAGGAGAAAAAGTTACCT<br>TGACCTGCAGCGCGAGTTCAAGCGTGTCCT<br>CCTCTTATTTGTACTGGTACCAGAAGAAGC<br>CGGGTAGCTCTCCTAAACTCTGGATCTACT<br>CCACCAGTAACTTGGCTAGTGGTGTCCCTG<br>CGAGATTTTCAGGGTCTGGGAGTGGGACAT<br>CCTATTCCCTCACAATAAGCTCAATGGAAG<br>CTGAGGATGCGGCGACGTATTTTTGCCATC<br>AGTGGTCTAGCTACCCACCTACATTTGGTG<br>CTGGAACGAAGCTTGAAATTAAA<br>(SEQ ID NO: 266) |
| KCD023 | ATGTACCGAATGCAGTTGCTCTCATGTATT<br>GCTCTTAGCCTCGCCCTCGTGACCAATAGT<br>GAAGTCCTCCTTCAACAAAGTGGCCCTGAA<br>CTCGTTAAACCGGGGGCCTCTGTCAAGATA<br>CCTTGTAAAGCGAGTGGCTATACCTTTACA<br>GACTATAATATTGACTGGGTTAAACAATCA<br>CATGGAAAGAGCCTGGAATGGATCGGTGAT<br>ATAAATCCCAACAACGGTGGAATTAACTAC<br>AATCAAAAATTTAAAGGGAAAGCCACTCTT<br>ACTGTTGACAAGAGTAGCTCAACGGCGTAC<br>ATGGAACTCCGGTCTCTCACTTCAGAGGAC<br>ACAGCCGTATATTATTGCGGGACAGGAGAC<br>TATGCCTATTGGGACAGGGCACTCTGGTC<br>ACAGTTTCAGCA (SEQ ID NO: 267) | ATGTATAGAATGCAGCTCTTGAGCTGCATC<br>GCTCTTTCCTTGGCCCTCGTGACAAACTCT<br>CAGATCGTATTGACCCAGAGCCCCGCCTTC<br>ATGAGCGCCAGTCCTGGCGAGAAAGTTACT<br>CTCACCTGCTCCGCTTCAAGTAGTGTGTCC<br>AGTAGTTACCTGTACTGGTATCAACAAAAA<br>CCCGGAAGTAGTCCTAAGTTGTGGATTTAC<br>TCCACTTCTAATCTTGCCAGCGGAGTGCCT<br>GGAAGGTTTAGTGGGAGTGGCAGCGGAGC<br>TTCCTACAGTCTTACAATCTCCAGCATGGA<br>AGCCGAGGATGCGGCGTCCTACTTCTGCCA<br>CCAGTGGACATCCTATCCCCCTACCTTCGG<br>AGCCGGGACCAAGCTTGAAATTAAA<br>(SEQ ID NO: 268) |
| KCD036 | ATGTATAGAATGCAACTTCTGAGTTGCATA<br>GCGTTGAGTCTCGCCTTGGTTACGAACTCT<br>GAGGTGCAACTGCAACAATCTGGGCCGGA<br>GCTTGTGAAGCAGGAGCATCTATGAAAAT<br>AAGTTGCAAGGCATCTGGATACTCTTTTAC<br>AGGATACACTATGCATGGGTAAAGCAAAG<br>CCACGGGAAAAATCTTGAATGGATCGGCCT<br>CATCAATCCTTACAATGGTGGGACCAATTA<br>CAATCAGAAATTTAAAGGGAAGGCGACCTT<br>TACTGTCGACAAATCAAGCTCCACTGCATA<br>TATGGAACTCTTGTCCCTTACGAGCGAGGA<br>CAGCGCGGTCTATTATTGCGCCAGGCGACA<br>CTACGGAAGCTCTTGGGATTACTGGGGCA<br>AGGGACCACACTGACAGTTTCATCA (SEQ ID NO: 269) | ATGTACCGAATGCAGTTGTTGAGTTGTATA<br>GCTCTGTCACTCGCGCTTGTAACCAATTCA<br>GACATAAAGTTGACCCAAAGTCCGAGTTCA<br>ATGTATGCCTCTCTTGGTGAAAGGGTAACG<br>ATAACTTGCAAGGCGTCCCAGGATATAAAC<br>ACGTATCTTAGTTGGTTTCAACAGAAACCG<br>GGTAAAAGTCCCAAAACTCTTATCTACCGA<br>GCTAATAGGTTGGTAGATGGGTGCCGTCA<br>AGATTCAGCGGTTCAGGCTCAGGCCAGGAC<br>TACTCTTTGACCATCAGCTCACTTGAATAC<br>GAGGAGATGGGCATATACTATTGCCTGCAA<br>TACGACGAGTTCCCGTACACTTTCGGAGGG<br>GGTACGAAGCTTGAAATTAAA<br>(SEQ ID NO: 270) |
| KCD040 | ATGTATAGAATGCAGCTCCTTTCTTGTATT<br>GCCCTGAGTTTGGCCTTGGTAACTAATAGT<br>GAGGTTCAACTCCAGCAAAGTGGCGCGGA<br>GCTGGTCAAGCCAGGTGCTAGTGTAAAACT<br>TTCATGCACCGCCTCCGACTTCAATATCAA<br>GGATACGTATATGCACTGGGTGATGCAGCG<br>GCCAGAACAGGGTCTGGAATGGATCGGTA<br>AAATAGACCCGGCGAACGGTAACACTGAGT<br>TTGACCCTAAATTTCAGGGCAAGGCAACCA<br>TCACAGCTGACACCTCCAGTAATACAGCGT<br>ACCTCCAGTTGACCTCACTCACCAGCGAGG<br>ACACCGCAGTCTATTACTGCACGCGAGCTA<br>TGGACTATTGGGGTCAAGGGACTTCAGTTA<br>CAGTGAGCTCA (SEQ ID NO: 271) | ATGTACCGGATGCAGTTGTTGAGCTGTATA<br>GCCCTGAGCTTGGCGCTTGTCACAAACTCT<br>CAAATCGTCCTCACGCAATCACCTGCGATC<br>ATGTCAGCTAGTCCGGGGGAGAAAGTCAC<br>GATGACGTGCTCTGCCGGATCTTCCGTTTC<br>TTATATGTATTGGTACCAGCAGAAGCCAGG<br>GAGTTCCCCTGCGTCTTGATTTACGATAC<br>ATCTAATCTTGCTAGTGGCGTCCCGGTCCG<br>GTTCTCCGGGTCCGGCAGCGGTACATCATA<br>TTCTCTGACGATAAGTAGGATGGAGGCCGA<br>AGATGCTGCAACATACTATTGCTACAGCAGTG<br>GAGTAACTATCCCTACACTTTTGGCGGAGG<br>CACTAAGCTTGAAATTAAA<br>(SEQ ID NO: 272) |
| KCD042 | ATGTACCGCATGCAATTGCTTTCTTGTATT<br>GCTCTGAGTTTGGCATTGGTAACCAACTCC<br>GAGGTTCAGCTCCAGCAGTCAGGTGCAGAA<br>CTTGTCAAACCGGGCGCGAGTGTGCGCCTC<br>TCTTGTACCGCCTCAGGTTTTAACATTAAG | ATGTATCGGATGCAATTGCTGTCTTGTATC<br>GCCCTTAGCCTCGCCCTCGTCACGAACAGC<br>CAGTCCGTGCTGACGCAGAGTCCGGCAATC<br>ATGTCTGCGAGTCCCGGTGAGAAAGTAACG<br>ATGACTTGCTCCGCTAATAGCTCCGTGAGC |

TABLE 0.1C-continued

Nucleotide sequences of variable domains of anti-CFD Antagonist monoclonal Antibodies

| mAb | Heavy Chain | Light Chain |
|---|---|---|
|  | CATACATATATTCATTGGGTATCCCAGCGC CCGGAACAAGGCTTGGAGTGGATCGGGAA AATAGATCCTGCCAATGGGAATACCAAATA CGACCCAAAGTTCCAGGGGAAGGCCACCAT TACGGCAGATACCTCTTCTAATACCGCTTA TCTCCAACTCTCATCACTTACGTCAGAAGA TACCGCGGTTTATTACTGCGTTAATGCAAT GGAATACTGGGGCCAAGGCACGTCCGTTAC AGTATCTTCA (SEQ ID NO: 273) | GATATGTATTGGTTCCAGCAACGGCCAGGA TCATCCCCGCGCTTGTTGATATACGACACA TCTAATCTGGCTTCCGGTGTGCCAGTTCGA TTCTCTGGGTCTGGGTCCGGTACGTCATAT AGTCTCACCATTAGCCGGATGGAAGCAGAA GATGCGGCGACGTATTATTGCCAGCAATGG AGTACCTATCCATGGACCTTTGGGGGTGGA ACGAAGCTTGAAATTAAA (SEQ ID NO: 274) |
| KCD044 | ATGTATCGAATGCAACTTTTGAGTTGCATA GCACTGAGTCTTGCTCTGGTAACAAACTCC GAGGTTCAGCTTCAGCAATCAGGTGCAGAA CTGGTAAAGCCTGGGGCATCCGTTAGACTT AGTTGTACCGCAAGTGGATTCAACATAAAA CACACCTATATGCATTGGGTCAGCCAGAGA CCCGAAAGGGGTCTTGAATGGATTGGCAAA ATAGACCCTGCAAACGGGAATACGAAATAT GATCCAAAGTTTCAGGGTAAAGCAACTATA ACAGCCGATACGTCATCCAATACAGTATAC TTGCAACTTAGCAGCCTTACGTCCGAAGAC ACCGCTGTCTACTATTGCTTGAATGCTATG GAATACTGGGGACAGGGGACTTCTGTAACC GTATCCTCA (SEQ ID NO: 275) | ATGTACAGAATGCAACTCCTGAGTTGCATC GCACTGTCTCTGGCGCTGGTGACAAACTCA CAGTCTGTCCTCACGCAGAGTCCTGCGATT ATGTCCGCAAGCCCAGGGGAGAAGGTAAC GATGACATGCTCCGCTAATAGCTCTGTGTC TGATATGTATTGGTATCAGCAACGCCCAGG GTCTAGTCCCCGGCTCCTCATTTACGATAC CAGCAACCTCGCTAGTGGCGTCCCCGTGCG ATTTTCTGGCTCCGGGTCAGGGACTAGCTA CAGCCTCACTATCTCCAGAATGGAAGCGGA AGATGCAGCGACGTATTATTGTCAGCAGTG GAGCACATATCCATGGACCTTTGGGGGTGG GACTAAGCTTGAAATTAAA (SEQ ID NO: 276) |
| KCD047 | ATGTATCGAATGCAACTGCTTTCATGTATT GCGCTTTCATTGGCTCTTGTTACTAACTCC GAAGTTCAACTTCAGCAGTCTGGAGCTGAG TTTGTAAAGCCCGGTGCCTCAGTAAGGCTG TCTTGCACCGCTTCTGGGTTCAATATCAAG GACACGTACATGCACTGGGTCAAGCAAAGG CCAGAGCAGGGATTGGAATGGATTGGTCG GATCGATCCTGCGAATGGTTACACCAAGGA TGACCCGAAGTTCCAAGGCAAAGCTACGAT AACGGCAGACACGTCAAGCAATACGGCGTA TCTTCAGCTTAGTAGCTTGACTTCTGAAGA CACTGCCGTTTATTACTGTGCTTCCGCAAT GGACTACTGGGGCCAAGGGACTTCCGTGA CTGTATCATCA (SEQ ID NO: 277) | ATGTATAGAATGCAGTTGCTCTCCTGTATC GCTCTCTCTCTGGCTTTGGTGACTAACAGT CAGATCGTGCTCACTCAATCACCCGCCGTT ATGTCTGCGTCTCCAGGGGAGAAGGTAGCC ATGACCTGCTCAGCAAGTAGCAGCGTGACG TATATGTATTGGTATCAGCAAAAACCTGGA AGCTCCCCCAGGTTGCTTATATATGACACT TCTAATTTGGCGAGTGGCGTACCTGTACGA TTTTCTGGCAGCGGTTCTGGCACAAGTTAT AGTCTCACGATTAGTCGCATGGAAGCCGAA GACGCCGCGACTTACTATTGCCAACAATGG AGCACATATCCATTCCCATTCGGCTCCGGC ACGAAGCTTGAAATTAAA (SEQ ID NO: 278) |
| KCD048 | ATGTACCGAATGCAACTTCTGAGTTGCATT GCCTTGTCCCTGGCACTTGTGACTAATAGT GAAGTGCAGCTCCAACAAAGTGGCGCTGAT CTGGTCAAGCCTGGTGCGAGTGTGAAACTT AGCTGCACAGCGAGCGGGTTCAATATCAAA GCAACTTACATGCACTGGGTACGGCAGCGA CCGGAGAAAGGCCTCGAATGGATAGGCCG CATCGACCCCGCCAATGGACATACAATCTA TGACCCCCAGTTTCAGGGGAAGGCTACCAT TACGTCCGATACTAGTAGCAATACAGCATA CCTCCAGTTGAACTCTCTCACAAGCGAGGA TACGGCAGTCTACTATTGTGCGGAGGCGAT GGATTATTGGGTCAAGGTACATCTGTGAC TGTTTCCTCA (SEQ ID NO: 279) | ATGTATCGGATGCAGCTTCTTTCCTGCATC GCTCTTAGTCTCGCCTTGGTTACAAATTCT CAAATTGTGCTCACTCAGTCACCAGCGATA ATGTCCGCCTCTCCCGGTGAAAAGGTGACT CTGACATGCAGCGCTACATCCAGCGTCTCA TACATGTACTGGTATCAGCAGAAGCCTGGT TCCAGCCCTCGGCTCCTGATATACGACACA AGTAACCTGGCTTCCGGCGTGCCGGTGAG GTTCTCTGGAAGCGGGAGTGGCACCTCTTA TTCCTTGACGATTTCCAGAATGGAAGCGGA GGATGATGCGACCTATTATTGTCAACAATG GAGCAACTATCCCTTTACTTTTGGCGGTGG AACGAAGCTTGAAATTAAA (SEQ ID NO: 280) |
| KCD070 | ATGTACAGAATGCAACTCCTCTCCTGTATA GCTCTGTCCCTGGCCCTCGTAACTAATTCC GAGATACAGTTGCAACAAACTGGACCAGAA CTTGTCAAGCCAGGTGCATCTGTCAAGATA AGCTGCAAAGCCTCCGGTTACAGCTTTACA GACTACATTATCCTGTGGGTGAAACAGTCA CATGGTAAAAGTCTGGAGTGGATAGGAAAC ATAAATCCTTACTACGATTATACCAGCTATA ATCTCAAATTCAAAGGTAAAGCGACTCTGA CTGTAGACAAATCCAGCTCTACCGCCTACA TGCAGCTTAACTCACTTACTTCTGAGGACA GTGCCGTCTACTATTGCGCCCGCTCCGACG GCTACTACGAGGGGATTACTGGGGTCAG GGTACGAGTGTAACGGTTTCATCA (SEQ ID NO: 281) | ATGTACCGAATGCAGCTTCTGAGTTGTATC GCGCTGTCATTGGCCCTGGTCACGAACTCC GACATAGTTATGACCCAGTCACACAAATTT ATGTCCACGTCAGTAGGTGATCGCGTGAGT ATAACGTGTAAAGCGAGCCAGGATGTTGGC ACCGCCGTGGCGTGGTATCAACAAAAGCCT GGCCAGTCCCCGAAGCTCCTCATATATTGG GCCAGTACGAGACATACAGGCGTGCCTGAC CGATTCACTGGGAGTGGTTCCGGCACAGAC TTCACCCTCACGATAAATAATGTTCAGTCT GAAGACCTCGCTGATTACTTCTGTCAGCAA TATTCTTCTTACCCTTGGACATTTGGCGGA GGCACCAAGCTTGAAATTAAA (SEQ ID NO: 282) |
| KCD101 | ATGTACAGGATGCAACTCCTGTCTTGCATT GCACTAAGTCTTGCACTTGTCACTAACTCA CAGGTCCAACTGCAGCAGCCTGGGGCTGA GCTGGTGAGGCCTGGGACTTCAGTGAAGTT | ATGTACAGGATGCAACTCCTGTCTTGCATT GCACTAAGTCTTGCACTTGTCACTAACTCA GATATCCAGATGACACAGACTACATCCTCC CTGTCTGCCTCTCTGGGAGACAGAGTCACC |

TABLE 0.1C-continued

Nucleotide sequences of variable domains
of anti-CFD Antagonist monoclonal Antibodies

| mAb | Heavy Chain | Light Chain |
|---|---|---|
|  | GTCCTGCAAGGCTTCTGGCTACACCTTCAC<br>CAGCTACTGGATGCACTGGGTAAAGCAGAG<br>GCCTGGACAAGGCCTTGAGTGGATCGGAG<br>TGATTGATCCTTCTGATAGTTATACTAATTA<br>CAATCAAAAGTTCAAGGGCAAGGCCACATT<br>GACTGTAGACACATCCTCCAGCACAGCCTA<br>CATGCAGCTCAGCAGCCTGACATCTGAGGA<br>CTCTGCGGTCTATTACTGTGGAAGAAATGG<br>TTACGACGGGTCTATGGACTACTGGGGTCA<br>AGGAACCTCAGTCACCGTCTCCTCA<br>(SEQ ID NO: 283) | ATCAGTTGCAGGGCAAGTCAGGACATTAGC<br>AATTATTTAAACTGGTATCAGCAGAAACCA<br>GATGGAACTGTTAAACTCCTGATCTACTAC<br>CCATCAAGATTACACTCAGGAGTCCCATCA<br>AGGTTCAGTGGCAGTGGGTCTGGAACAGAT<br>TATTCTCTCACCATTAGCAACCTGGAGCAA<br>GAAGATTTTGCCACTTACTTTTGCCAACAG<br>GGTAATACGCTTCCGTACACGTTCGGAGGG<br>GGGACCAAGCTT (SEQ ID NO: 284) |
| KCD102 | ATGTACAGGATGCAACTCCTGTCTTGCATT<br>GCACTAAGTCTTGCACTTGTCACTAACTCA<br>CAGGTCCAACTGCAGCAGCCTGGGGCTGA<br>GCTGGTGAGGCCTGGGACTTCAGTGAAGTT<br>GTCCTGCAAGGCTTCTGGCTACACCTTCAC<br>CAGCTACTGGATGCACTGGGTAAAGCAGAG<br>GCCTGGACAAGGCCTTGAGTGGATCGGAG<br>TGATTGATCCTTCTGATAGTTATACTAACTA<br>CAATCAAAAGTTCAAGGGCAAGGCCACATT<br>GACTGTAGACACATCCTCCAGCACAGCCTA<br>CATGCAGCTCAGCAGCCTGACATCTGAGGA<br>CTCTGCGGTCTATTACTGTGCAAGAAATGG<br>TTACGACGGGTCTATGGACTACTGGGGTCA<br>AGGAACCTCAGTCACCGTCTCCTCA<br>(SEQ ID NO: 285) | ATGTACAGGATGCAACTCCTGTCTTGCATT<br>GCACTAAGTCTTGCACTTGTCACTAACTCA<br>GAAATCCAGATGACACAGACTACATCCTCC<br>CTGTCTGCCTCTCTGGGAGACAGAGTCACC<br>ATCAGTTGCAGGGCAAGTCAGGACATTAGC<br>AATTATTTAAACTGGTATCAGCAGAAACCA<br>GATGGAACTGTTAAACTCCTGATCTACTAC<br>CCATCAAGATTACACTCAGGAGTCCCATCA<br>AGGTTCAGTGGCAGTGGGTCTGGAACAGAT<br>TATTCTCTCACCATTAGCAACCTGGAGCAA<br>GAAGATTTTGCCACTTACTTTTGCCAACAG<br>GGTAATACGCTTCCGTACACGTTCGGAGGG<br>GGGACCAAGCTT (SEQ ID NO: 286) |
| KCD103 | ATGTACAGGATGCAACTCCTGTCTTGCATT<br>GCACTAAGTCTTGCACTTGTCACTAACTCA<br>CAGGTCCAACTGCAGCAGCCTGGGGCTGA<br>GCTGGTGAGGCCTGGGACTTCAGTGAAGTT<br>GTCCTGCAAGGCTTCTGGCTACACCTTCAC<br>CAGCTACTGGATGCACTGGGTAAAGCAGAG<br>GCCTGGACAAGGCCTTGAGTGGATCGGAG<br>TGATTGATCCTTCTGATAGTTATACTAAGTA<br>CAATCAAAAGTTCAAGGGCAACAAGGCCACATT<br>GACTGTAGAGACATCCTCCAGCACAGCCTA<br>CATGCAGCTCAGCAGCCTGACATCTGAGGA<br>CTCTGCGGTCTATTACTGTGCAGGAAATGG<br>TTACGACGGGTCTATGGACTACTGGGGTCA<br>AGGAACCTCAGTCACCGTCTCCTCA<br>(SEQ ID NO: 287) | ATGTACAGGATGCAACTCCTGTCTTGCATT<br>GCACTAAGTCTTGCACTTGTCACTAACTCA<br>GATATCCAGATGACACAGACTACATCCTCC<br>CTGTCTGCCTCTCTGGGAGACAGAGTCACC<br>ATCAGTTGCAGGGCAAGTCAGGACATTAGC<br>AATTCTTTAAACTGGTATCAGCAGAAACCA<br>GATGGAACTGTTAAACTCCTGATCTACTAC<br>ACATCAAGATTACACTCACGAGTCCCATCA<br>AGGTTCAGTGGCAGTGGGTCTGGAACAGAT<br>TATTCTCTCACCATTAGCAACCTGGACCAA<br>GAAGATATTGCCACTTACTTTTGCCAACAG<br>GCTAATACGCTTCCGTACACGTTCGGAGGG<br>GGGACCAAGCTT (SEQ ID NO: 288) |
| KCD104 | ATGTACAGGATGCAACTCCTGTCTTGCATT<br>GCACTAAGTCTTGCACTTGTCACTAACTCA<br>CAGGTCCAACTGCAGCAGCCTGGGGCTGA<br>GCTGGTGAGGCCTGGGACTTCAGTGAAGTT<br>GTCCTGCAAGGCTTCTGGCTACACCTTCAC<br>CAGCTACTGGATGCACTGGGTAAAGCAGAG<br>GCCTGGACAAGGCCTTGAGTGGATCGGAG<br>TGATTGATCCTTCTGATAGTTATACTTACTA<br>CAATCAAAAGTTCAAGGGCAAGGCCACATT<br>GACTGTAGACACATCCTCCAGCACAGCCTA<br>CATGCAGCTCAGCAGCCTGACATCTGAGGA<br>CTCTGCGGTCTATTACTGTGCAAGAAATGG<br>TTACGACGGGGCTATGGACTACTGGGGTCA<br>AGGAACCTCAGTCACCGTCTCCTCA<br>(SEQ ID NO: 289) | ATGTACAGGATGCAACTCCTGTCTTGCATT<br>GCACTAAGTCTTGCACTTGTCACTAACTCA<br>GAAATCCAGATGACACAGACTACATCCTCC<br>CTGTCTGCCTCTCTGGGAGACAGAGTCACC<br>ATCAGTTGCAGGGCAAGTCAGGACATTAGC<br>AATTATTTAAACTGGTATCAGCAGAAACCA<br>GATGGAACTGTTAAACTCCTGATCTACTAC<br>CCATCAAGATTACACTCAGGAGTCCCATCA<br>AGGTTCAGTGGCAGTGGGTCTGGAACAGAT<br>TATTCTCTCACCATTAGCAACCTGGAGCAA<br>GAAGATTTTGCCACTTACTTTTGCCAACAG<br>GGTAATACGCTTCCGTACACGTTCGGAGGG<br>GGGACCAAGCTT (SEQ ID NO: 290) |
| KCD118 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTTTGGATACACGTTCACT<br>GACTACTACAAGAACTGGATGAGGCAGAGA<br>CATGGAGAGAGCCTTGAGTGGATTGGAGAT<br>ATTAATCCTAACAGTGGTGATGCTAACTAC<br>AACCAGAAGTTCAAGGGCAAGGCCACATTG<br>ACTGTTGACAAGTCCTCCAGCACAGCCTAC<br>ATGGAGCTCCGCAGCCTGACATCTGAGGAC<br>TCTGCAGTCTATTACTGTCAAGAGAGGGA<br>CCTTCGTTTGCTTACTGGGGCCATGGGACT<br>CTGGTCACTGTCTCTGCA<br>(SEQ ID NO: 291) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTT<br>CATAGTAATGGAGACACCTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAAT<br>TTATTACTGCTTTCAAGGTTCACATGTTCCT<br>CCGACGTTCGGTGGAGGCACCAAGCTT<br>(SEQ ID NO: 292) |

TABLE 0.1C-continued

Nucleotide sequences of variable domains
of anti-CFD Antagonist monoclonal Antibodies

| mAb | Heavy Chain | Light Chain |
|---|---|---|
| KCD119 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACTTTCACT<br>GACTACTACACGAACTGGATGAGGCAGAGA<br>CATGGAGAGAGCCTTGAGTGGATTGGAGAT<br>ATTAATCCTAACACTGGTGATACTAGCTAC<br>AACCAGAAGTTCAGGGTCAAGGCCACATTG<br>ACTGTAGACAAGTCCTCCGGCACAGCCTAC<br>ATGGGGCTCCGCAGCCTGACATCTGAGGAC<br>TCTGCCGTCTATTACTGTACAAGAGAGGGA<br>CCTTCGTTTGCTTACTGGGGCCAAGGGACT<br>CTGGTCACTGTCTCTGCA<br>(SEQ ID NO: 293) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTA<br>CATAGTAATGGAGACACCTATTTAGAATGG<br>TACCTGCAGAAACCAGGCCAGTCTCCAAAC<br>CTCCTGATCTATAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 294) |
| KCD121 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACGTTCACT<br>GACTACTACAAGAACTGGATGAGGCAGAGA<br>CATGGAGAGAGCCTTGAGTGGATTGGAGAT<br>ATTAATCCTAACAATGGTGATACTTCCTAC<br>AACCAGAAGTTCAGGGGCAAGGCCACATTG<br>ACTGTAGACAAGTCCTCCAGCACAGCCTTC<br>ATGGAGCTCCGCAGCCTGACATCTGAGGAC<br>TCTGCAGTCTATTACTGTGCAAGAGAGGGA<br>CCTTCCTTTGCTTACTGGGGCCAAGGGACT<br>CTGGTCACTGTCTCTGCA<br>(SEQ ID NO: 295) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAATCAGACCATTGTA<br>CATAGTAATGGAGACACGTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 296) |
| KCD122 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACGTTCACT<br>GACTACTACAAGAACTGGATGAGGCAGAGA<br>CATGGAGAGAGCCTTGAGTGGATTGGAGAT<br>ATTAATCCTAACAATGGTGATGCTAACTAC<br>AACCAGAAGTTCAAGGGCAAGGCCACATTG<br>ACTGTTGACAAGTCCTCCAGCACAGCCTAC<br>ATGGAGCTCCGCAGCCTGACATCTGAGGAC<br>TCTGCAGTCTATTTCTGTGCAAGAGAGGGA<br>CCTTCGTTTGCTTACTGGGGCCATGGGACT<br>CTGGTCACTGTCTCTGCA<br>(SEQ ID NO: 297) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTT<br>CATAGTAATGGAGACACCTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 298) |
| KCD123 | ATGTACAGGATGCAACTCCTGTCTTGCATT<br>GCACTAAGTCTTGCACTTGTCACTAACTCA<br>GAGGTCCACCTGCAACAGTCTGGACCTGAA<br>CTGGTGAAGCCTGGGGCTTCAGTGAAGATA<br>TCCTGTAAGGCTTCTGGATACACGTTCACT<br>GACTTCTACAAGAACTGGATGAGGCAGAGA<br>CATGGAGAGAGCCTTGAGTGGATTGGAGAT<br>ATTAATCCTAACAATGGTGGTACTAACTAC<br>AACCAGAAGTTCAAGGGCAAGGCCACATTG<br>ACTGTAGACAAGTCCTCCAGCACAGCCTAC<br>ATGGAGCTCCGCAGCCTGACATCTGAGGAC<br>TCTGCAGTCTATTACTGTGCAAGAGAGGGA<br>CCTTCGTTTGCTTACTGGGGCCAAGGGACT<br>CTGGTCACTGTCTCTGCA<br>(SEQ ID NO: 299) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTT<br>CATAGTAATGGAGACACCTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 300) |
| KCD124 | ATGTACAGGATGCAACTCCTGTCTTGCATT<br>GCACTAAGTCTTGCACTTGTCACTAACTCA<br>GAAGTCCAGCTCCAACAGTCTGGACCTGAG<br>CTGGTGAAGCCTGGGGCTTCAGTGAAGATA<br>TCCTGTAAGGCTTCTGGATACACATTCACT<br>GACCACTACATGAACTGGGTGAAACAGAGC<br>CATGGAAAGAGCCTTGAGTGGATTGGAGAT<br>ATTAATCCTAACAATGGTGGTACTAGCTAC<br>AACCAGAAGTTCAAGGGCAAGGCCACATTG<br>ACTGTAGACAAGTCCTCCAGCACAGCCTAC | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGAGCATTGTA<br>CATAGTAATGGAGACACCTATTTAGAGTGG<br>TACCTGCAGAAGCCAGGCCAGTCTCCAAAG<br>CTCCTGATCTACAAAGTTTCCAACCGATTTT<br>CTGGGGTCCCAGACAGGTTCAGTGGCAGT<br>GGATCAGGGACAGATTTCACACTCAAGATC |

TABLE 0.1C-continued

Nucleotide sequences of variable domains of anti-CFD Antagonist monoclonal Antibodies

| mAb | Heavy Chain | Light Chain |
|---|---|---|
|  | ATGGAGCTCCGCAGCCTGACATCTGGGGAC<br>TCTGCAGTCTATTACTGTACAAGAGAGGGG<br>GCCTCGTTTGCTTTCTGGGGCCAAGGGACT<br>CTGGTCACTGTCTCTGCA<br>(SEQ ID NO: 301) | AGCAGAGTGGAGGCTGAGGATCTGGGAGT<br>TTATTACTGCTTTCAAGGTTCACATGTTCCG<br>CTCACGTTCGGTGCTGGGACCAAGCTT<br>(SEQ ID NO: 302) |
| KCD131 | ATGTACAGGATGCAACTCCTGTCTTGCATT<br>GCACTAAGTCTTGCACTTGTCACTAACTCA<br>CAGGTCCAGCTACAGCAGTCTGGACCTGAG<br>CTGGTGAAGCCTGGGGCTTCAGTGAAGATC<br>TCCTGCAAGGCTTCTGCCTACACCTTCACT<br>GACTACTATATAAACTGGGTGAAGCAGAGG<br>CCTGGACAGGGACCTGAGTGGATTGGATG<br>GATTTTTCCTGGAAGTAATAGTACTTATTCC<br>AATGAGAAGTTCGAGGTCAAGGCCACACTG<br>ACTGTAGACGAATCCTCCAGCACAGCCTAC<br>ATGTTGCTCAGCAGCCTGACCTCTGAGGAC<br>TCTGCGGTCTATTTCTGTGCAAGATTGGGA<br>TACTTCGGTAGTAGTTACCATGCTTTGGAC<br>TACTGGGGTCAAGGCACCTCAGTCACCGTC<br>TCCTCA (SEQ ID NO: 303) | ATGTACAGGATGCAACTCCTGTCTTGCATT<br>GCACTAAGTCTTGCACTTGTCACTAACTCA<br>GACATCCAGATGACTCAGTCTCCAGCCTCC<br>CTATCTGTATCTGTGGGAGAAACTGTCACC<br>ATCACATGTCGAGCAAGTGAGAATATTTAC<br>AGTCATTTAGCATGGTTTCAGCAGAAACAG<br>GGAAAATCTCCTCGGCTCCTGGTCTATTCT<br>GCAACAAACTTACCAGATGGTGTGCCATCA<br>AGATTCAGTGGCAGTGGATCAGGCACACAG<br>TATTCCCTCAAGATCAACATCCTGCAGTCT<br>GAAGATTTTGGGAGTTATTACTGTCAACAT<br>TTTTGGGGTACTCCGTGGACGTTCGGTGGA<br>GGCACCAAGCTT (SEQ ID NO: 304) |
| KCD136 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GCTTGTGAGGCCAGGGGCCTCAGTCAAGTT<br>GTCCTGCTCAGCTTCTGGCTTCAACATTAA<br>AAACACCTATATGCACTGGGTGAACCAGAG<br>GCCTGAACAGGGCCTGGAGTGGATTGGAA<br>GGATTGATCCTGCGAATGGTATTACTAAAT<br>ATGCCCCGAACTTCCAGGGCAAGGCCACTA<br>TAACTGCAGACACATCTTCCAACACAGCCT<br>ACCTGCAGCTCAGCAACCTGACATCTGAGG<br>ACACTGCCATCTATTACTGTACTAGGGCTA<br>TGGACTACTGGGGTCAAGGAACCTCAGTCA<br>CCGTCTCCTCA (SEQ ID NO: 305) | ATGTACAGGATGCAACTCCTGTCTTGCATT<br>GCACTAAGTCTTGCACTTGTCACTAACTCA<br>CAAATTGTTCTCACCCAGTCTCCAGCAATC<br>ATGTCTGCATCTCCAGGGGAGAAGGTCACC<br>ATGACCTGCAGTGCCAGCTCAAGTGTAAGT<br>TACATGTACTGGTACCAGCAGAAGCCAGGA<br>TCCTCCCCCAGACTCCTGATTTATGACATA<br>TCCAACCTGGCTTCTGGAGTCCCTGTTCGC<br>TTCAGTGGCAGTGGGTCTGGGACCTCTTAC<br>TCTCTCACAATCAGCCGAATGGAGGCTGAA<br>GATGCTGCCACTTATTACTGCCAGCAGTGG<br>GATACTTACCCGTGGACGTTCGGTGGAGGC<br>ACCAAGCTT (SEQ ID NO: 306) |
| KCD200 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCCGGATACACGTTCACC<br>AGCTACTACAAGAACTGGATGAGGCAGAGA<br>CATGGAGAGAGCCTTGAGTGGATTGGAGAT<br>ATTAATCCTAACAGTGGTGATACTGCCTAC<br>AACCAGAAGTTCAAGGGCAAGGCCACATTG<br>ACTGTAGACAGGTCCTCCAGCACAGCCTAC<br>ATGGAGCTCCGCAGCCTGACATCTGAGGAC<br>TCTGCAGTCTATTACTGTGCAAGAGAGGGA<br>CCTTCGTTTGCTTACTGGGGCCAAGGGACT<br>CTGGTCACTGTCTCTGCA<br>(SEQ ID NO: 307) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGTCTCC<br>ATCTCTTGCAGATCTAGTCAGACCATTGTT<br>CATAGTAATGGAGACACCTATTTGGAATGG<br>TACCTGCAGAAACCAGGCCAGTCTCCAAAT<br>CTCCTGATCTACAAAGTTTCCAACCGTTTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>GTATTACTGCTTTCAAGGTTCACATGTTCCT<br>CCGACGTTCGGTGGAGGCACCAAGCTT<br>(SEQ ID NO: 308) |
| KCD208 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GCTTGTGAGGCCAGGGGCCTCAGTCAAGTT<br>GTCCTGCACAGTTTCTGGCTTCAACATTAA<br>AAACACCTATATGCACTGGGTGAAGCAGAG<br>GCCTGAACAGGGCCTGGAGTGGATTGGAA<br>GGATTGATCCTGCGAATGGTGATACTACAT<br>ATGCCCCGAAGTTCCAGGGCAAGGCCACTA<br>TAACTGCAGACACATCCTCCAACTCAGCCT<br>ACCTGCACCTCAGCCGCCTGACATCTGAGG<br>ACACTGCCATCTATTACTGTTCTCTTTATGA<br>TTACGACGGCTACTGGGGCCAAGGCACCAC<br>TCTCACAGTCTCCTCA<br>(SEQ ID NO: 309) | ATGTACAGGATGCAACTCCTGTCTTGCATT<br>GCACTAAGTCTTGCACTTGTCACTAACTCA<br>GAAATTGTGCTCACCCAGTCTCCAGCACTC<br>ATGGCTGCATCTCCAGGGGAGAAGGTCACC<br>ATCACCTGCAGTGTCAGCTCAAGTATAAGT<br>TCCAGCTCCTTACACTGGTACCGGCAGAAG<br>TCAGGAACCTCCCCCAAACCCTGGATTTAT<br>GGCACATCCCACCTTGCTTCTGGAGTCCCT<br>GTTCGCTTCAGTGGCAGTGGATCTGGGACC<br>TCTTATTCTCTCACAATCAGCAGCATGGAG<br>GCTGAAGATGCTGCCACTTATTACTGTCAA<br>CAGTGGGATACTTACCCGTGGACGTTCGGT<br>GGAGGCACCAAGCTT<br>(SEQ ID NO: 310) |
| KCD214 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GTTTGTGAGGCCAGGGGCCTCAGTCAAGTT<br>GTCCTGCACAGCTTCTGGCTTCAACATTAA<br>AAACACCTATATGCACTGGGTGAAGCAGAG | ATGTACAGGATGCAACTCCTGTCTTGCATT<br>GCACTAAGTCTTGCACTTGTCACTAACTCA<br>GAAATTGTGCTCACCCAGTCTCCAGCACTC<br>ATGGCTGCATCTCCAGGGGAGAAGGTCACC<br>ATCACCTGCCGTGTCAGCTCAAGTATAAGT<br>TCCAGCAGCTTACACTGGTACCAGCAAAAG |

TABLE 0.1C-continued

Nucleotide sequences of variable domains of anti-CFD Antagonist monoclonal Antibodies

| mAb | Heavy Chain | Light Chain |
|---|---|---|
| | GCCTGAACAGGGCCTGGAATGGATTGGAA GGATTGATCCTGCGAATGGTAATACTGAAT ATGCCCCGAAGTTCCAGGGCAAGGCCACTA TAACTGCAGACACATCCTCCAACACAGCCT ACCTGCAGCTCAGCAGCCTGACATCTGAGG ACACTGCCATCTATTACTGTGCTCTTTATGA TTACGACGGCTACTGGGGCCAAGGCACCAC TCTCACAGTCTCCTCA (SEQ ID NO: 311) | TCAGGAACCTCCCCCAAACCCTGGATTTAT GGCACCTCCAACCTTGCTTCTGGAGTCCCT GTTCGCTTCAGTGGCAGTAGATCTGGGACC TCTTATTCTCTCACAATCAGCAGCATGGAG GCTGAAGATGCTGCCACTTATTACTGTCAA CAGTGGAGTGATTACCCGTGGACGTTCGGT GGAGGCACCAAGCTT (SEQ ID NO: 312) |
| KCD220 | ATGTACAGGATGCAACTCCTGTCTTGCATT GCACTAAGTCTTGCACTTGTCACTAACTCA CAGGTTCAGCTGCAACAGTCTGGAGCTGAG CTGATGGAGCCTGGGGCCTCAGTGAAGCTT TCCTGCAAGGCTACTGGCTACACATTCACT GGCTACTGGATAGAGTGGGTAAAGCAGAG GCCTGGACATGGCCTTGAGTGGATTGGAGA GACTTTACCTGGAAGTGATAGTAATAATTA CAATGAGAAGTTCAAGGGCAAGGCCACATT CACTGCAGATACATCCTCCAACACAGCCTA CATGCAACTCAGCAGCCTGACAACTGAGGA CTCTGCCATCTATTACTGTGCAAGAGACTA TAGTAACTACTGGTACTTCGATGTCTGGGG CACAGGGACCACGGTCACCGTCTCCTCA (SEQ ID NO: 313) | ATGTACAGGATGCAACTCCTGTCTTGCATT GCACTAAGTCTTGCACTTGTCACTAACTCA GATATCCAGATGACACAGACTACATCCTCC CTGTCTGCCTCTCTGGGAGACAGAGTCACC ATTAGTTGCAGGGCAAGTCAGGACATTAGC AATTATTTAAACTGGTATCAGCAGAAACCA GATGGAACTGTTAAACTCCTGATCTACTAC ACATCAAACTTACACTCAGGAGTCCCATCA AGGTTCAGTGGCAGTGGGTCTGGGACAGA TTATTCTCTCACTATTAGTAACCTGGAACAA GAAGATATTGCCACTTACTTTTGCCAACAG GATAGTAAGCATCGGACGTTCGGTGGAGG CACCAAGCTT (SEQ ID NO: 314) |
| KCD224 | ATGTACAGGATGCAACTCCTGTCTTGCATT GCACTAAGTCTTGCACTTGTCACTAACTCA CAGGTGCAGCTGAAGGAGTCAGGACCTGG CCTGGTGGCGCCCTCACAGAGCCTGTCCAT CACATGCACTGTCTCTGGGTTCTCATTAAC CAGCTATGGTGTAGACTGGATTCGCCAGTC TCCAGGAAAGGGTCTGGAGTGGCTGGGAG TAATATGGGGTGTTGGAAGCACAAATTATA ATTCAGCTCTCAAATCCAGACTGAGCATCA GCAAGGACAACTCCAAGAGCCAAGTTTTCT TAAAAATGAACAGTCTGCAAACTGATGACA CAGCCATGTACTACTGTGCCCGCTCCTATG ATGGTTCCTACTGGTACTTCGATGTCTGGG GCACAGGGACCACGGTCACCGTCTCCTCA (SEQ ID NO: 315) | ATGTACAGGATGCAACTCCTGTCTTGCATT GCACTAAGTCTTGCACTTGTCACTAACTCA GATATCCAGATGACACAGACTACATCCTCC CTGTCTGCCTCTCTGGGAGACAGAGTCACC ATCAGTTGCAGGGCAAGTCAGGTTATTAGC AATTATTTAAACTGGTATCAGCAGAAACCA GATGGAACTGTTAAACTCCTGATCTACTAC ACATCAAGATTACACTCAGGAGTCCCATCA AGGTTCAGTGGCAGTGGGTCTGGGACAGA TTATTCTCTCACCATCAGCAACCTGGAACC TGAAGATATTGCCACTTACTATTGTCAGCA GTATAGTAAACTTCCGTATACGTTCGGATC GGGGACCAAGCTT (SEQ ID NO: 316) |
| 119_TAF | GAGGTGCAGCTGGTGGAATCTGGCGGCGG ACTGGTGCAGCCTGGCGGCTCCCTGAGACT GTCTTGCGCCGCCTCCGGCTACACCTTCAC CGACTACTACATGAACTGGGTGCGACAGGC CCCTGGCAAGGGCCTGGAATGGATCGGCG ACATCAACCCCAACACCGGCGACACCAGCT ACAACGCCGACTTCAAGCGGCGGTTCACCT TCTCCCTGGACACCTCCAAGTCCACCGCCT ACCTGCAGATGAACTCCCTGCGGGCCGAG GACACCGCCGTGTACTACTGTACCAGAGAG GGCCCCTCCTTCGCCTACTGGGGCCAGGGC ACACTGGTGACAGTGTCCTCCG (SEQ ID NO: 317) | GACATCCAGCTGACCCAGAGCCCCTCCAGC CTGTCCGCCTCTGTGGGCGACAGAGTGACC ATCACCTGTCGGTCCTCCCAGACCATCGTG CACTCCAACGGCGACACCTACCTGGAATGG TATCAGCAGAAGCCCGGCAAGGCCCCTAAC CTGCTGATCTACAAGGTGTCCAACCGGTTC TCCGGCGTGCCCTCCAGATTCTCCGGCTCC GGCTCTGGCACCGACTTCACCCTGACCATC TCCAGCCTGCAGCCCGAGGACTTCGCCACC TACTACTGTTTTCAAGGCTCCCACGTGCCA CCCACCTTCGGCCAGGGCACCAAGGTGGA AATCAAGC (SEQ ID NO: 318) |
| 119_TAF Germ | GAGGTGCAGCTGGTGGAATCTGGCGGCGG ACTGGTGCAGCCTGGCGGCTCCCTGAGACT GTCTTGCGCCGCCTCCGGCTACACCTTCAC CGACTACTACATGTCCTGGGTGCGACAGGC CCCTGGCAAGGGCCTGGAATGGATCGGCG ACATCAACCCCAACACCGGCGACACCTCA ACAACGCCGACTCCGTGAAGGGCCGGTTCA CCATCTCCCGGGACAACTCCAAGAACACCC TGTACCTGCAGATGAACTCCCTGCGGGCC AGGACACCGCCGTGTACTACTGTACCAGAG AGGGCCCCTCCTTCGCCTACTGGGGCCAGG GCACACTGGTGACAGTGTCCTCC (SEQ ID NO: 319) | GACGTGGTGATGACCCAGTCCCCTCTGTCC CTGCCCGTGACCCTGGGCCAGCCTGCCTCC ATCTCCTGCCGGTCCTCCCAGACCATCGTG CACTCCAACGGCGACACCTACCTGGAATGG TTCCAGCAGCGGCCTGGCCAGTCCCCTAAC CTGCTGATCTACAAGGTGTCCAACCGGTTC TCCGGCGTGCCCGACAGATTCTCCGGCTCC GGCTCTGGCACCGACTTCACCCTGAAGATC TCCCGGGTGGAAGCCGAGGACGTGGGCGT GTACTACTGTTTTCAAGGCTCCCACGTGCC ACCCACCTTCGGCGGAGGCACCAAGGTGG AAATCAAG (SEQ ID NO: 320) |
| 119_Human Germ | CAGGTGCAGCTGGTGCAGTCTGGCGCCGA AGTGAAGAAACCTGGCGCCTCCGTGAAGGT GTCCTGCAAGGCCTCCGGCTACACCTTCAC CGACTACTACATGCACTGGGTGCGACAGGC CCCAGGCCAGGGCCTGGAATGGATCGGCG | GACATCCAGATGACCCAGAGCCCCTCCAGC CTGTCCGCCTCCGTGGGCGACAGAGTGACC ATCACCTGTCGGTCCTCCCAGACCATCGTG CACTCCAACGGCGACACCTACCTGGAATGG TATCAGCAGAAGCCCGGCAAGGCCCCTAAC |

TABLE 0.1C-continued

Nucleotide sequences of variable domains
of anti-CFD Antagonist monoclonal Antibodies

| mAb | Heavy Chain | Light Chain |
|---|---|---|
| | ACATCAACCCCAACACCGGCGACACCAGCT<br>ACAACCAGAAATTCCAGGGCAGAGTGACCT<br>CCACCCGGGACACCTCCATCTCCACCGCCT<br>ACATGGAACTGTCCCGGCTGCGGAGCGAC<br>GACACCGTGGTGTACTACTGTACCAGAGAG<br>GGCCCCTCCTTCGCCTACTGGGGCCAGGGC<br>ACACTGGTGACAGTGTCCTCC<br>(SEQ ID NO: 321) | CTGCTGATCTACAAGGTGTCCAACCGGTTC<br>TCCGGCGTGCCCTCCAGATTCTCCGGCTCC<br>GGCTCTGGCACCGACTTCACCCTGACCATC<br>TCCAGCCTGCAGCCCGAGGACTTCGCCACC<br>TACTACTGTTTTCAAGGCTCCCACGTGCCA<br>CCCACCTTCGGCCAGGGCACCAAGGTGGA<br>AATCAAG (SEQ ID NO: 322) |

In some embodiments, a composition as disclosed herein comprises an antibody having a partial or complete light chain sequence and a partial or complete heavy chain sequence from any of the options provided in Table 0.1D, or variants thereof. In Table 0.1D, the underlined sequences are some embodiments of CDR sequences.

TABLE 0.1D

Variable Regions Sequences of Variant Humanized
CFD Antagonist Antibodies based on a CDR definition

| | CDR1 | CDR2 | CDR3 |
|---|---|---|---|
| | | Table with CDR sequences | |
| Light chain | QX$_1$X$_2$X$_3$HX$_4$NX$_5$X$_6$X$_7$YX$_8$E, wherein X$_1$ is T, D, G, H, I, N, Q, R, V, or W; X$_2$ is I, A, or V; X$_3$ is V, A, D, E, F, I, K, L, Q, R, S, W, or Y; X$_4$ is S, A, D, F, G, I, R, T, V, or W; X$_5$ is G, E, F, or S; X$_6$ is D or E; X$_7$ is T, S, or V; X$_8$ is L or I (SEQ ID NO: 323) | X$_1$X$_2$LX$_3$X$_4$KX$_5$X$_6$X$_7$RX$_8$; wherein X$_1$ is N, D, E, R, S, V, or Y; X$_2$ is L or I; X$_3$ is I or T; X$_4$ is Y, D, E, F, G, L, R, S, T, or V; X$_5$ is V, A, or I; X$_6$ is S, A, F, G, K, L, Q, R, T, or Y; X$_7$ is N, E, G, H, I, L, Q, R, T, or Y; X$_8$ is F, E, G, I, L, R or W (SEQ ID NO: 324) | X$_1$QGSX$_2$X$_3$PX$_4$T, wherein X$_1$ is F or M; X$_2$ is H, A, E, F, G, L, N, Q, T, V, W, or Y; X$_3$ is V, W, Q or N; and X$_4$ is P or V (SEQ ID NO: 325) |
| Heavy chain | GYX$_1$FTX$_2$X$_3$X$_4$X$_5$, wherein X$_1$ is T, D, E, F, H, I, K, P, R, S, W, or Y; X$_2$ is D, A, F, G, S, V, or Y; X$_3$ is Y or F; X$_4$ is Y or P; X$_5$ is M, H, or I (SEQ ID NO: 326) | WIGDX$_1$X$_2$X$_3$X$_4$XE X$_6$X$_7$X$_8$X$_9$X$_{10}$, wherein X$_1$ is I, L, OR V; X$_2$ is N, A, or G; X$_3$ is P, or T; X$_4$ is N, A, D, G, H, I, L, R, T, V, W, OR Y; X$_5$ is T, I, K, L, Q, R, S, or V X$_6$ is G or V; X$_7$ is any amino acid; X$_8$ is any amino acid except I; X$_9$ is any amino acid except K or R; X$_{10}$ is any amino acid except I or W. (SEQ ID NO: 327) | X$_1$REGPX$_2$FX$_3$X$_4$, wherein X$_1$ is T, A, or Q; X$_2$ is S or A; X$_3$ is A or R; and X$_4$ is Y, A, H, F, V, Y, or L (SEQ ID NO: 328) |
| | | CDRs (streamlined CDR defined sequence): | |
| Light Chain | QX$_1$X$_2$X$_3$HX$_4$NX$_5$X$_6$X$_7$Y, wherein X$_1$ is T, D, G, H, I, N, Q, R, V, or W; X$_2$ is I, A, or V; X$_3$ is V, A, D, E, F, I, K, L, Q, R, S, W, or Y; X$_4$ is S, A, D, F, G, I, R, T, V, or W; X$_5$ is G, E, F, or S; X$_6$ is D or E; X$_7$ is T, S, or V (SEQ ID NO: 329) | KX$_1$X$_2$; wherein X$_1$ is V, A, or I; X$_2$ is S, A, F, G, K, L, Q, R, T, or Y (SEQ ID NO: 330) | X$_1$QGSX$_2$X$_3$PX$_4$T, wherein X$_1$ is F or M; X$_2$ is H, A, E, F, G, L, N, Q, T, V, W, or Y; X$_3$ is V, W, Q or N; and X$_4$ is P or V (SEQ ID NO: 331) |
| Heavy Chain | X$_1$X$_2$X$_3$, wherein X$_1$ is D, A, F, G, S, V, or Y; X$_2$ is Y or F; X$_3$ is Y or P (SEQ ID NO: 332) | X$_1$X$_2$X$_3$X$_4$X$_5$X$_6$X$_7$X$_8$, wherein X$_1$ is I, L, OR V; X$_2$ is N, A, or G; X$_3$ is P, or T; X$_4$ is N, A, D, G, H, I, L, R, T, V, W, OR Y; X$_5$ is T, I, K, L, Q, R, S, or V X$_6$ is G or V; X$_7$ is any amino acid; X$_8$ is any amino acid except I (SEQ ID NO: 333) | EGPX$_1$FX$_2$X$_3$, wherein X$_1$ is S or A; X$_2$ is A or R; and X$_3$ is Y, A, H, F, V, Y, or L (SEQ ID NO: 334) |

In some embodiments, a composition as disclosed herein comprises an antibody having a partial or complete light chain CDR sequence and a partial or complete heavy chain CDR sequence from any of the options provided in Tables 1.1, 0.1A, 0.1B, 0.1D, 11.3, or variants thereof. Tables 1.1, 0.1A, 0.1B, 0.1D, 11.3 provides examples of CDR sequences of variant CFD antagonist antibodies provided herein.

In some embodiments, CDR portions of CFD antagonist antibodies are also provided. Determination of CDR regions is well within the skill of the art. It is understood that in some embodiments, CDRs can be a combination of the IMGT and Paratome CDRs (also termed "combined CDRs" or "extended CDRs"). Determination of CDRs is well within the skill of the art. In some embodiments, the CDRs are the IMGT CDRs. In other embodiments, the CDRs are the Paratome CDRs. In other embodiments, the CDRs are the extended, AbM, conformational, Kabat, or Chothia CDRs. In embodiments with more than one CDR, the CDRs may be any of IMGT, Paratome, extended, Kabat, Chothia, AbM, conformational CDRs, or combinations thereof. In some embodiments, other CDR definitions may also be used. In some embodiments, only residues that are in common between 2, 3, 4, 5, 6, or 7 of the above definitions are used (resulting in a shorter sequence). In some embodiments, any residue in any of 2, 3, 4, 5, 6, or 7 of the above definitions can be used (resulting in a longer sequence).

In some embodiments, a CFD antagonist antibody comprises three CDRs of any one of the heavy chain variable regions shown in Tables 1.1, 0.1A, 0.1B, 0.1D, or 11.3. In some embodiments, the antibody comprises three CDRs of any one of the light chain variable regions shown in Tables 1.1, 0.1A, 0.1B, 0.1D, or 11.3. In some embodiments, the antibody comprises three CDRs of any one of the heavy chain variable regions shown in Tables 1.1, 0.1A, 0.1B, 0.1D, or 11.3, and three CDRs of any one of the light chain variable regions shown in Tables 1.1, 0.1A, 0.1B, 0.1D, or 11.3.

In some embodiments, the antibody used for binding to CFD can be one that includes one or more of the sequences in Tables: 1.1, 0.1A, 0.1B, 0.1D, and/or 11.3. In some embodiments, the antibody used for binding to CFD can be one that includes three or more of the sequences in Tables: 1.1, 0.1A, 0.1B, 0.1D, and/or 11.3. In some embodiments, the antibody used for binding to CFD can be one that includes six of the sequences in any one of Tables: 1.1, 0.1A, 0.1B, 0.1D, and/or 11.3. In some embodiments, the antibody that binds to CFD can be one that competes for binding with an antibody that includes 6 of the specified CDRs in any one of Tables: 1.1, 0.1A, 0.1B, 0.1D, 11.3.

To express the anti-CFD antibodies of the present invention, DNA fragments encoding VH and VL regions described can first be obtained. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Tables: 1.1, 0.1A, and 11.3. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to CFD. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 0.4 under the heading of "conservative substitutions." If such substitutions result in a change in biological activity, then more substantial changes, denominated "exemplary substitutions" in Table 0.4, or as further described below in reference to amino acid classes, may be introduced and the products screened.

TABLE 0.4

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for CFD, to increase or decrease $k_{off}$ or to alter the binding specificity of the antibody. Techniques in site-directed mutagenesis are well-known in the art. See, e.g., Sambrook et al. and Ausubel et al., supra.

According to an aspect of the present invention, the IgG domain of a CFD antagonist antibody can be IgG1, IgG2, IgG3 or IgG4. According to another aspect of the invention, the IgG domain can be a composite in which a constant regions is formed from more than one of the above isotypes (e.g., CH$_1$ region from IgG2 or IgG4, hinge, CH$_2$ and CH$_3$ regions from IgG1). In choosing an isotype, it is known in the art that human isotypes IgG1 and IgG3 have complement-mediated cytotoxicity whereas human isotypes IgG2 and IgG4 have poor or no complement-mediated cytotoxicity. In some embodiments the CFD antagonist antibody isotype is IgG1. An exemplary human IgG1 heavy chain has the sequence (SEQ ID NO: 183):

(SEQ ID NO: 183)
EVQLVESGGGLVQPGGSLRLSCAASGYTFTDYYINWVRQAPGKGLEWI

GDINPITGDTDYNADFKRRFTFSLDTSKSTAYLQMSSLRAEDTAVYYC

TREGPSFAYWGQGTLVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTCPPCPAPEAAGAPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNG

-continued

QPENNYKTTPPVLDSDGSFFLYSKLTVDKSRWQQGNVFSCSVMHEALH

NHYTQKSLSCSPGK

The light chain constant region can be either human lambda or kappa. In some embodiments, the CFD antagonist antibody has a human kappa light chain constant region.

An exemplary human kappa light chain has the sequence (SEQ ID NO: 184):

(SEQ ID NO: 184)
DIQLTQSPSSLSASVGDRVTITCRSSQTIVHSNGDTYLEWYQQKPGKA

PNLLIRKVSNRFSGVPSRFSGSGSGTDFTLTISSLQPEDFATYYCFQG

SHVPVTFGQGTKVEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chains such as the C-terminal lysine of the heavy chain, may be missing or derivatized in a proportion or all of the molecules.

Substitutions can be made in the constant regions to reduce or increase effector function such as complement-mediated cytotoxicity (CDC), antibody-dependent cell-mediated cytotoxicity (ADCC) (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

In some embodiments, the CFD antagonist antibodies provided herein include one more substitutions that reduce complement mediated cytotoxicity. Reduction in complement mediated cytotoxicity can be accomplished with or without reduction in Fc receptor binding depending on the nature of the mutation(s). Antibodies with reduced complement mediated cytotoxicity but little or no reduction in Fc receptor allow a desired effect of Fc-mediated phagocytosis of iC3b without activating complement, which may contribute to side effects. Exemplary mutations known to reduce complement-mediated cytotoxicity in human constant regions include mutations at positions 241, 264, 265, 270, 296, 297, 322, 329 and 331 by EU numbering. Mutations in positions 318, 320, and 322 have been reported to reduce complement activation in mouse antibodies. Alanine is a preferred residue to occupy these positions in a mutated constant region. Some exemplary human mutations that have been used include F241A, V264A, D265A, V296A, N297A, K322A, and P331S in human IgG3 and D270A or E, N297Q, K322A, P329A, and P331S in human IgG1 (EU numbering).

Here, as elsewhere, the EU numbering scheme is used for numbering amino acids in the constant region of an antibody. When a residue in a variable region is referenced herein (unless designated otherwise) the residue numbering is according to the variable domain (or, if designated, the SEQ ID NO). Substitution at any or all of positions 234, 235, 236 and/or 237 reduce affinity for Fcγ receptors, particularly FcγRI receptor and also reduces complement binding and activation (see, e.g., U.S. Pat. No. 6,624,821 WO/2009/052439). An alanine substitution at positions 234, 235 and 237 reduces effector functions, particularly in the context of human IgG1. Optionally, positions 234, 236 and/or 237 in human IgG2 are substituted with alanine and position 235 with glutamine. (See, e.g., U.S. Pat. No. 5,624,821) to reduce Fc receptor binding. Exemplary substitutions for increasing half-life include a Gln at position 250 and/or a Leu at position 428. In accordance with an aspect of the present invention, where the anti-CFD antibody presented has a human IgG1 isotype, it is preferred that the antibody has at least one mutation in the constant region. Preferably, the mutation reduces complement fixation or activation by the constant region. In particularly preferred aspects of the present invention, the antibody has one or more mutations at positions E233, L234, L235, G236, G237, A327, A330 and P331 by EU numbering. Still more preferably, the mutations constitute one or more of the following E233P, L234V, L234A, L235A, G237A, A327G, A330S and P331S by EU numbering. In the most preferred embodiments the human IgG1 has the following mutations L234A, L235A and G237A by EU numbering.

Conjugates

The half-life of CFD antagonist antibodies can be extended by attachment of a "half-life extending moieties" or "half-life extending groups," which terms are herein used interchangeably to refer to one or more chemical groups attached to one or more amino acid site chain functionalities such as —SH, —OH, —COOH, —CONH2, —NH2, or one or more N- and/or O-glycan structures and that can increase in vivo circulatory half-life of proteins/peptides when conjugated to these proteins/peptides. Examples of half-life extending moieties include polymers described herein, particularly those of zwitterionic monomers, such as HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Gly$_x$-Ser$_y$) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, FcRn binding peptides and any combination thereof.

In some embodiments, the antibody is conjugated with a phosphorylcholine containing polymer. In some embodiments, the antibody is conjugated with a poly(acryloyloxyethyl phosphorylcholine) containing polymer, such as a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

In some embodiments, the antibody is conjugated with a water-soluble polymer, which refers to a polymer that is soluble in water. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

In one embodiment a half-life extending moiety can be conjugated to a CFD antagonist antibody via free amino groups of the protein using N-hydroxysuccinimide (NHS) esters. Reagents targeting conjugation to amine groups can randomly react to ε-amine group of lysines, α-amine group of N-terminal amino acids, and δ-amine group of histidines.

However, CFD antagonist antibodies of the present invention have many amine groups available for polymer conjugation. Conjugation of polymers to free amino groups, thus, might negatively impact the ability of the antibody to bind to the epitope.

In another embodiment, a half-life extending moiety is coupled to one or more free SH groups using any appropriate thiol-reactive chemistry including, without limitation, maleimide chemistry, or the coupling of polymer hydrazides or polymer amines to carbohydrate moieties of the CFD antagonist antibody after prior oxidation. The use of maleimide coupling is a particularly preferred embodiment of the present invention. Coupling preferably occurs at cysteines naturally present or introduced via genetic engineering.

In some embodiments, polymers are covalently attached to cysteine residues introduced into CFD antagonist antibodies by site directed mutagenesis. In some embodiments, the cysteine residues in the Fc portion of the CFD antagonist antibody can be used. In some embodiments, sites to introduce cysteine residues into an Fc region are provided in WO 2013/093809, U.S. Pat. No. 7,521,541, WO 2008/020827, U.S. Pat. Nos. 8,008,453, 8,455,622 and US2012/0213705, incorporated herein by reference for all purposes. In some embodiments, cysteine mutations are Q347C and L443C referring to the human IgG heavy chain by the EU index of Kabat. In some embodiments, the cysteine added by directed mutagenesis for subsequent polymer attachment is L443C. In some embodiments, the stoichiometry of CFD antagonist antibody to polymer is 1:1; in other words, a conjugate consists essentially of molecules each comprising one molecule of CFD antagonist antibody conjugated to one molecule of polymer. In some embodiments, coupling can occur at one or more lysines.

In some embodiments, a conjugate comprises an isolated antagonist antibody that specifically binds to complement factor D (CFD) conjugated to a polymer. In some embodiments, the polymer comprises a zwitterionic monomer. In some embodiments, the zwitterionic monomer, without limitations, is HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Glyx-Sery) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, or FcRn binding peptides. In some embodiments, the polymer comprising a zwitterionic monomer is a half-life extending moiety.

In some embodiments, the CFD antagonist antibody can have a half-life extending moiety attached. In some embodiments, the half-life extending moiety is a zwitterionic polymer but PEG or other half-life extenders discussed below can alternatively be used. In some embodiments, the zwitterionic polymer is formed of monomers having a phosphorylcholine group. In some embodiments, the monomer is 2-(acryloyloxyethyl)-2'-(trimethylammoniumethyl) phosphate. In some embodiments, the monomer is 2-(methacryloyloxyethyl)-2'-(trimethylammoniumethyl) phosphate (HEMA-PC).

In some embodiments, the polymer conjugated to the CFD antagonist antibody has at least 2 or 3 or more arms. Some polymers have 2, 3, 4, 5, 6, 7, 8, 9, 10, 11 or 12 arms. In some embodiments, the polymer has 3, 6 or 9 arms. In some embodiments, the polymer has 9 arms. In some embodiments, the polymer peak molecular weight is between 300,000 and 1,750,000 Da. In some embodiments, the polymer has a peak molecular weight between 500,000 and 1,000,000 Da. In some embodiments, the polymer has a peak molecular weight between 600,000 to 800,000 Da.

In some embodiments, a conjugate of antagonistic anti-CFD antibody and a polymer is provided. In some embodiments, the polymer has a peak molecular weight between 300,000 and 1,750,000 Daltons as measured by size exclusion chromatography—multi angle light scattering (hereinafter "SEC-MALS"). In some embodiments, the polymer has a peak molecular weight between 500,000 and 1,000,000 Daltons as measured by SEC-MALS. In some embodiments, the polymer has a peak molecular weight between 600,000 to 800,000 Daltons as measured by SEC-MALS.

In some embodiments, a half-life extending moiety may be conjugated to a naturally occurring cysteine residue of a CFD antagonist antibody provided herein. In some embodiments, the half-life extending moiety is conjugated added to a cysteine that is added via site directed mutagenesis. In some embodiments, the cysteine is added by using recombinant DNA technology to add the peptide SGGGC or CAA to the C-terminus of either the light or heavy chain. In some embodiments, the peptide is added to the heavy chain. In some embodiments, the cysteine residue introduced via recombinant DNA technology is selected from the group consisting of (EU numbering) Q347C and L443C.

In accordance with another aspect of the present invention, a pharmaceutical composition is presented having a CFD antagonist antibody and a pharmaceutically acceptable excipient.

CFD antagonist antibodies of the present invention can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing anti-CFD antibodies, e.g. constitutively or on induction, and (v) isolating the anti-CFD antibody, e.g. from the culture medium or by harvesting the transformed cells, in order to (vi) obtain purified anti-CFD antibody.

In some embodiments, a conjugate comprising an anti-CFD antibody and a polymer is provided. The antibody is any one of the antibodies disclosed herein. In some embodiments, the antibody is an IgG. In some embodiments, the antibody is IgA, IgE, IgD or IgM. In some embodiments, the polymer is covalently bonded to a sulfhydryl group. In some embodiments, the polymer is covalently bonded to a sulfhydryl group from a cysteine residue. In some embodiments, the polymer is covalently bonded to a sulfhydryl group from a cysteine residue on the heavy chain. In some embodiments, the polymer is covalently bonded to a sulfhydryl group from a cysteine residue on the heavy chain of the IgG. In some embodiments, the antibody comprises a cysteine residue at position 347 or 443 (EU numbering). In some embodiments, the polymer is covalently bonded to a sulfhydryl group from a cysteine residue at position 347 or 443 (EU numbering).

CFD antagonist antibodies can be produced by expression in a suitable prokaryotic or eukaryotic host system characterized by producing a pharmacologically acceptable anti-CFD antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells. In some embodiments, an isolated cell line that produces any of the antibodies disclosed herein is provided. In some embodiments, the isolated cell line is selected, without limitations, from one or more of CHO, k1SV, XCeed, CHOK1SV, GS-KO.

In some embodiments, an isolated nucleic acid encoding any of the antibodies disclosed herein is provided. In some embodiments, a recombinant expression vector comprising the isolated nucleic acid is provided. In some embodiments, a host cell comprises the expression vector.

A wide variety of vectors can be used for the preparation of the CFD antagonist antibodies and may be selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include, without limitation: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

In some embodiments, a method of producing a CFD antagonist antibody is provided. In some embodiments, the method comprises culturing a cell line that recombinantly produces any of the antibodies disclosed herein under conditions wherein the antibody is produced and recovered. In some embodiments, a method of producing a CFD antagonist antibody is provided. In some embodiments, the method comprises culturing a cell line comprising nucleic acid encoding an antibody comprising a heavy chain comprising the amino acid sequence shown in SEQ ID NO: 520 and a light chain comprising the amino acid sequence shown in SEQ ID NO: 525 under conditions wherein the antibody is produced and recovered. In some embodiments, the heavy and light chains of the antibody are encoded on separate vectors. In some embodiments, the heavy and light chains of the antibody are encoded on the same vector.

In accordance with another aspect of the present invention, provided are methods for synthesizing a zwitterionic polymer-CFD antagonist antibody conjugate, the conjugate having one or more functional agents and one or more polymer arms wherein each of the polymer arms has one or more monomer units wherein at least one of the units has a zwitterion. For example, such a method can have the steps of:
  a. providing an initiator having one or more sites for monomer polymerization and a first linker having an amine group wherein the initiator is a trifluoro acetic acid salt;

b. providing one or more monomers suitable for polymerization wherein at least one of the monomers is zwitterionic;
c. reacting the monomers with the initiator to form one or more polymer arms each corresponding to the sites for monomer polymerization to provide an initiator-polymer conjugate having the first linker with the amine group;
d. providing a second linker having at least second and third reactive groups;
e. coupling one of the second and third reactive groups of the second linker to the amine group of the first linker of the initiator-polymer conjugate to provide a linker-initiator-polymer conjugate having one or more reactive groups that were not used in the coupling step; and
f. coupling one or more functional agents to one or more of the unreacted reactive groups of the linker-initiator-polymer moiety to provide the polymer-functional agent conjugate.

In some embodiments, a conjugate comprising an isolated antagonist antibody that specifically binds to CFD and a phosphorylcholine-containing polymer is provided. In some embodiments, the polymer is covalently bonded to the antibody. In some embodiments, the polymer is non-covalently bonded to the antibody.

In some embodiments, a conjugate comprising an anti-CFD antibody and a polymer that is capable of blocking of an interaction between CFD and C3bB is provided. In some embodiments, the conjugate comprising an anti-CFD antibody and a polymer is capable of blocking at least 80% of an interaction between CFD and C3bB. In some embodiments, the conjugate comprises an anti-CFD antibody and a polymer that is capable of blocking about 80% to about 100% of an interaction between CFD and C3bB. In some embodiments, the conjugate comprising an anti-CFD antibody and a polymer is capable of blocking about 80, 85, 90, 91, 92, 93, 94, 95, 96, 97, 98, 99 or 100% of an interaction between CFD and C3bB.

In some embodiments, a conjugate comprising an anti-CFD antibody and a phosphorylcholine containing polymer is provided. The polymer is covalently bonded to the antibody outside a variable region of the antibody. In some embodiments, a conjugate comprising an anti-CFD antibody and a phosphorylcholine containing polymer is provided. The polymer is covalently bonded to the antibody at a cysteine outside a variable region of the antibody. In some embodiments, a conjugate comprising an anti-CFD antibody and a phosphorylcholine containing polymer is provided, wherein the polymer is covalently bonded to the antibody at a cysteine outside a variable region of the antibody wherein said cysteine has been added via recombinant DNA technology. In some embodiments of the conjugate, the polymer comprises 2(methacryloyloxy)ethyl (2-(trimethylammonio) ethyl) phosphate (MPC) monomers.

In accordance with another aspect of the present invention, a method is provided where the conjugation group (e.g. maleimide) is added after polymer synthesis. This is sometimes referred to as a "snap-on strategy" or "universal polymer strategy". See, e.g., U.S. patent application Ser. No. 14/916,180 (published as U.S. Patent Application Publication No. 20160199501), hereby incorporated by reference in its entirety. In some embodiments, a single initiator moiety can be used for large scale polymer synthesis. Thus, conditions can be developed for scaled up optimal polymer synthesis. Such polymers can then be adapted to various types of functional agents by "snapping-on" various types of linkers. For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In some embodiments of the methods, the initiator has about 1, 2, 3, 4, 5, 6, 7, 8, 9, 10, 11, or 12 sites for polymer initiation. In some embodiments, the initiator has about 3, about 6, or about 9 sites for polymer initiation.

In accordance with another aspect of the present invention, a second linker has second, third, fourth, fifth, and sixth reactive groups. More preferably, a second linker has just second and third reactive groups.

In accordance with an aspect of the present invention, each polymer arm has from about 20 to about 2000 monomer units. Preferably, each arm has from about 100 to 500 monomer units or from about 500 to 1000 monomer units or from about 1000 to 1500 monomer units or from about 1500 to 2000 monomer units.

In accordance with an aspect of the present invention, the peak molecular weight of the polymer-functional agent conjugate is about 100,000 to 1,500,000 Da. Preferably, the peak molecular weight of the polymer-functional agent conjugate is about 200,000 to about 300,000 Da, about 400,000 to about 600,000 Da or about 650,000 to about 850,000 Da.

In accordance with another aspect of the present invention, the first linker is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. More preferably, the first linker has the formula:

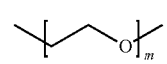

Formula (1)

wherein m is 1 to 10. In some embodiments, the first linker has the above formula (Formula (1)) and m is 4.

In some embodiments, the initiator preferably includes a structure selected from group consisting of

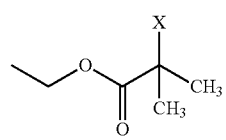

Formula (2)

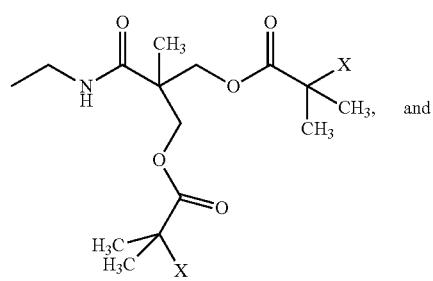

Formula (3)

and

Formula (4)

[Structure showing ethylamine-amide-amide-CH2-O-CH2-C(CH2-O-C(O)-C(CH3)2-X)3]

wherein X is selected from the group consisting of NCS, F, Cl, Br and I. More preferably, X in Formula (2), Formula (3) and/or Formula (4) is Br.

In some embodiments, the monomer is selected from the group consisting of

Formula (5)

[H2C=C(R7)-C(O)-O-(CH2)t-ZW]

Formula (6)

[H2C=C(R7)-C(O)-NH-(CH2)t-ZW]

Formula (7)

[H2C=C(R7)-phenyl-(CH2)t-ZW]

Formula (8)

[H2C=C(R7)-pyridyl-(CH2)t-ZW], and

Formula (9)

[H2C=C(R7)-N-pyrrolidinone with (CH2)t-ZW]

wherein R7 is H or C1-6 alkyl and t is 1 to 6.

More preferably, the monomer is selected from the group consisting of 2-(methacryloyloxyethyl)-2'-(trimethylammoniumethyl) phosphate (HEMA-PC) and 2-(acryloyloxyethyl)-2'-(trimethylammoniumethyl) phosphate.

Most preferably, the monomer is 2-(methacryloyloxyethyl)-2'-(trimethylammoniumethyl) phosphate.

The second linker moiety preferably comprises an activated ester having the structure Formula (10)

[R9-C(O)-O-R8]

wherein R8 is selected from the group consisting of

[pentafluorophenyl] and [N-succinimidyl]

and R9 is

Formula (11)

[maleimide-CH2CH2-C(O)-NH-CH2CH2-(O-CH2CH2)p-O-CH2CH3]

wherein p is 1 to 12.

In more preferred embodiments of the present invention, the polymer has 9 arms, m is 2-4, R9 is

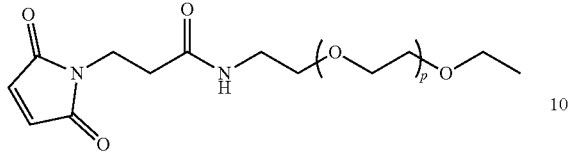
Formula (11)

wherein p is 4 to 15. Still more preferably, m is 4 and p is 12.

In some embodiments, the radically polymerizable monomer is

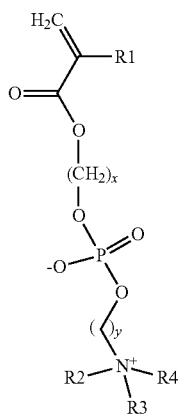
Formula (12)

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

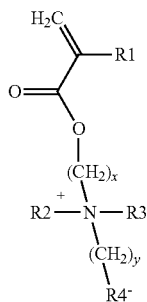
Formula (13)

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

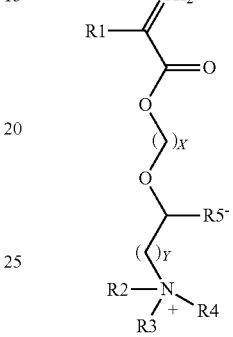
Formula (14)

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

When a polymer is the to be conjugated via a cysteine (or other specified residue), the polymer can be linked directly or indirectly to the residue (e.g., with an intervening initiator, and or spacer or the like).

In some embodiments, the phosphorylcholine containing polymer comprises 2-(methacryloyloxyethyl)-2'-(trimethylammonium)ethyl phosphate (MPC) monomers as set forth below:

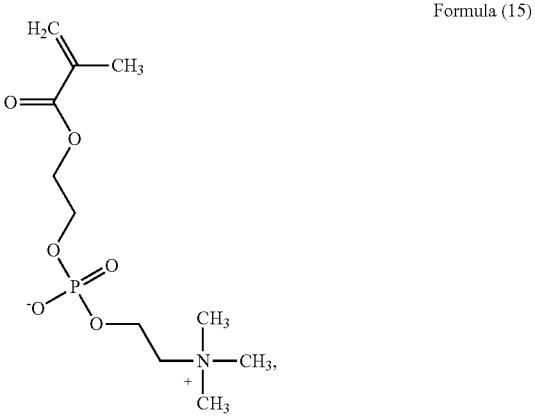
Formula (15)

such that the polymer comprises the following repeating units:

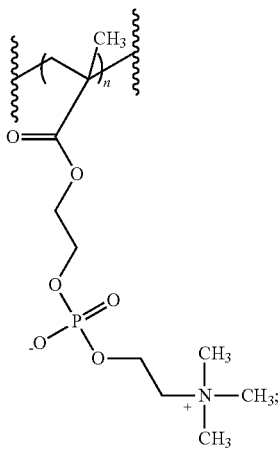

Formula (16)

where n is an integer from 1 to 3000 and the wavy lines indicate the points of attachment between monomer units in the polymer.

In some embodiments, the polymer has three or more arms, or is synthesized with an initiator comprising 3 or more polymer initiation sites. In some embodiments, the polymer has 2, 3, 4, 5, 6, 7, 8, 9, 10, 11 or 12 arms, or is synthesized with an initiator comprising 2, 3, 4, 5, 6, 7, 8, 9, 10, 11, or 12 polymer initiation sites. More preferably, the polymer has 3, 6, or 9 arms, or is synthesized with an initiator comprising 3, 6, or 9 polymer initiation sites. In some embodiments, the polymer has 9 arms, or is synthesized with an initiator comprising 9 polymer initiation sites.

In some embodiments, the polymer that is added has a molecular weight between about 300,000 and about 1,750,000 Da (SEC-MALs). In some embodiments, the polymer has a molecular weight between about 500,000 and about 1,000,000 Da. In some embodiments, the polymer has a molecular weight of between about 600,000 to about 900,000 Da. In some embodiments, the polymer has a molecular weight of between about 750,000 to about 850,000 Da. In some embodiments, the polymer has a molecular weight of between about 800,000 to about 850,000 Da. In some embodiments, the polymer has a molecular weight of between about 750,000 to about 800,000 Da.

In some embodiments, any of the antibodies described herein can be further conjugated to a polymer to form a bioconjugate. The molecular weight of the bioconjugate (in total, SEC-MALs) can be between about 350,000 and 2,000,000 Daltons, for example, between about 450,000 and 1,900,000 Daltons, between about 550,000 and 1,800,000 Daltons, between about 650,000 and 1,700,000 Daltons, between about 750,000 and 1,600,000 Daltons, between about 850,000 and 1,500,000 Daltons, between about 900,000 and 1,400,000 Daltons, between about 950,000 and 1,300,000 Daltons, between about 900,000 and 1,000,000 Daltons, between about 1,000,000 and 1,300,000 Daltons, between about 850,000 and 1,300,000 Daltons, between about 850,000 and 1,000,000 Daltons, and between about 1,000,000 and 1,200,000 Daltons. In some embodiments, the bioconjugate has a molecular weight between about 350,000 and 1,900,000 Daltons.

In some embodiments, the antibody conjugate is purified. In some embodiments, the polymer in aspect of the antibody conjugate is polydisperse, i.e. the polymer PDI is not 1.0. In some embodiments, the PDI is less than 1.5. In some embodiments, the PDI is less than 1.4. In some embodiments, the PDI is less than 1.3. In some embodiments the PDI is less than 1.2. In some embodiments the PDI is less than 1.1. In some embodiments, the conjugate PDI is equal to or less than 1.5.

In some embodiments, the antibody conjugate has an anti-CFD immunoglobulin G (IgG) bonded to a polymer, which polymer comprises MPC monomers, wherein the sequence of the anti-CFD heavy chain is SEQ ID NO. 183, and the sequence of the anti-CFD light chain is SEQ ID NO. 184, and wherein the antibody is bonded only at C442 of SEQ ID NO 183 to the polymer. In some embodiments, the polymer has 9 arms and has a molecular weight of between about 600,000 to about 1,000,000 Da.

In some embodiments, the antibody conjugate has an anti-CFD immunoglobulin G (IgG) bonded to a polymer, which polymer comprises MPC monomers, wherein the sequence of the anti-CFD heavy chain comprises SEQ ID NO. 183, and the sequence of the anti-CFD light chain comprises SEQ ID NO. 184, and wherein the antibody is bonded only at C443 (EU numbering, or 442C in SEQ ID NO 183) to the polymer. In some embodiments, the polymer has 9 arms and has a molecular weight of between about 600,000 to about 1,000,000 Da. In some embodiments, the conjugate comprises a polymer that has 9 arms and the polymer has a molecular weight of between about 600,000 to about 900,000 Da.

In some embodiments, the antibody conjugate has the following structure:

Formula (17)

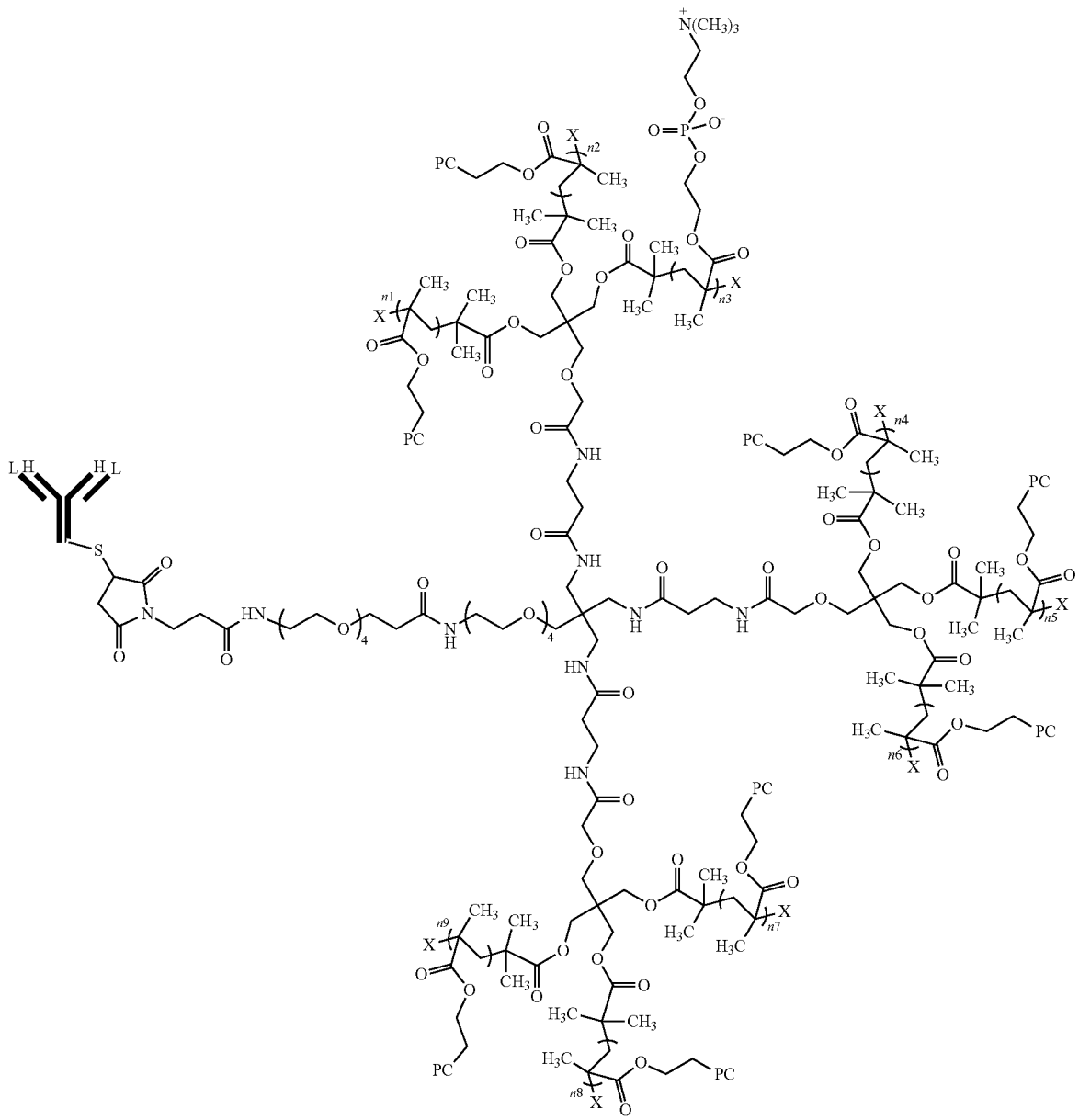

wherein: each heavy chain of the anti-CFD antibody is denoted by the letter H, and each light chain of the anti-CFD antibody is denoted by the letter L;

the polymer is bonded to the anti-CFD antibody through the sulfhydryl of C443 (EU numbering, or 442C in SEQ ID NO: 183), which bond is depicted on one of the heavy chains; PC is,

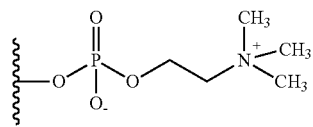

where the curvy line indicates the point of attachment to the rest of the polymer; wherein X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 10%. In some embodiments, n1, n2, n3, n4, n5, n6, n7, n8 and n9 are the same or different and are integers from 0 to 3000. In some embodiments, n1, n2, n3, n4, n5, n6, n7, n8 and n9 are the same or different and are integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—R$_7$, carbonyl —CCO—R$_7$, —CO—NR$_8$R$_9$, —(CH$_2$)$_n$—COOR$_7$, —CO—(CH)$_n$—COOR$_7$, —(CH$_2$)$_n$—NR$_8$R$_9$, ester, alkoxycarbonyl, aryloxycarbonyl, wherein n is an integer from 1 to 6, wherein each R$_7$, R$_8$ and R$_9$ is separately selected from the group consisting of a hydrogen atom, halogen atom, mono-substituted, poly-substituted or unsubstituted variants of the following residues: saturated C$_1$-C$_{24}$ alkyl, unsaturated C$_2$-C$_{24}$ alkenyl or C$_2$-C$_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

In some embodiments, the antibody conjugate has the following structure:

Formula (17)

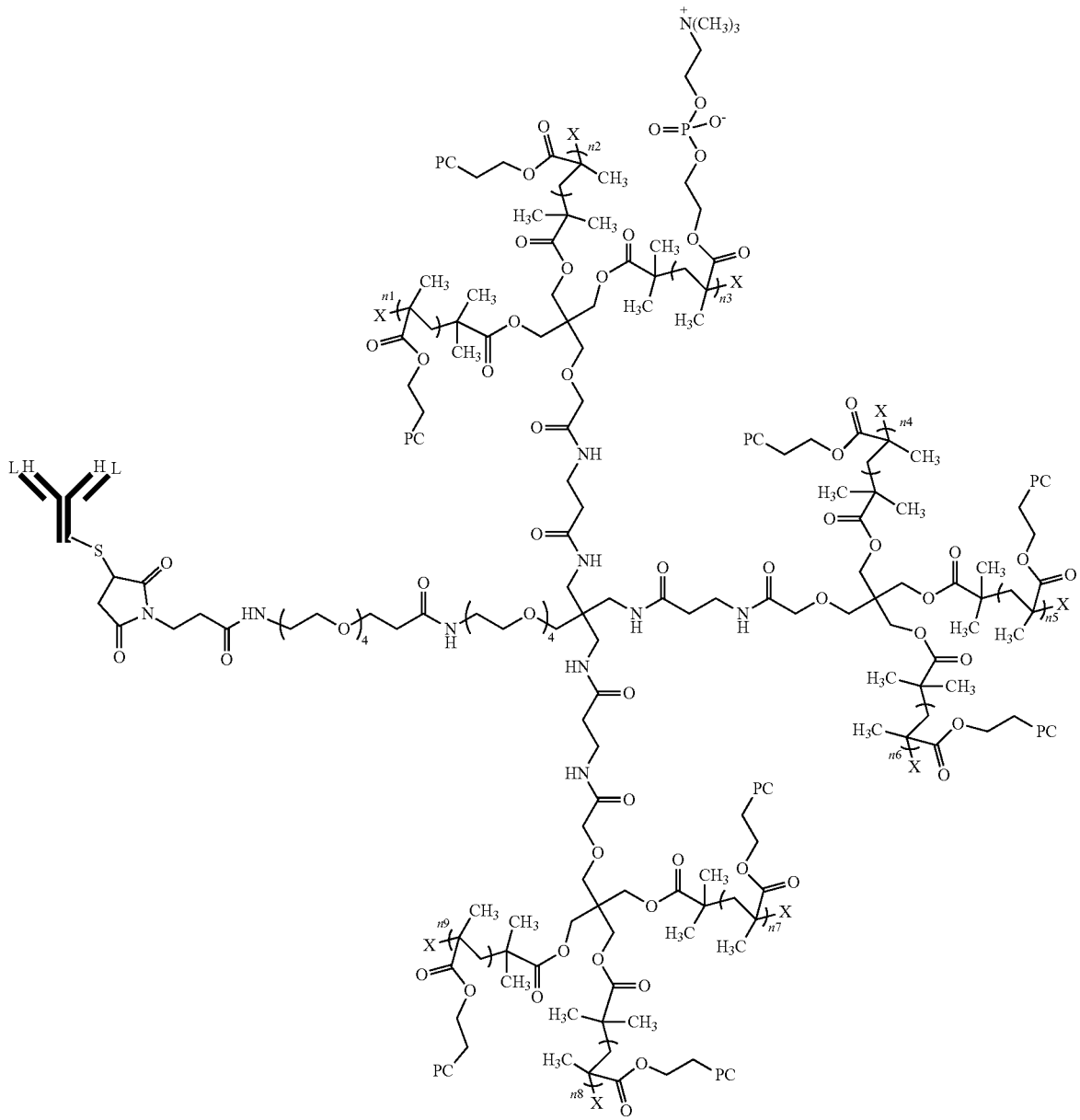

wherein:

each heavy chain of the antibody is denoted by the letter H, and each light chain of the anti-CFD antibody is denoted by the letter L;

the polymer is bonded to the antibody through the sulfhydryl of C443 (EU numbering), which bond is depicted on one of the heavy chains;

PC is

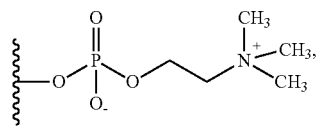

where the curvy line indicates the point of attachment to the rest of the polymer, where X=a) OR where R=H, methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 15%. In some embodiments, the sum of n1, n2, n3, n4, n5, n6, n6, n7, n8 and n9 is about 1500 to about 3500 plus or minus about 10% to about 20%.

In some embodiments, the antibody conjugate is present in a liquid formulation. In some embodiments, the antibody conjugate is combined with a pharmaceutically acceptable carrier.

In some embodiments, an anti-CFD antibody is presented. The anti-CFD antibody heavy chain has at least the following CDR sequences: $CDR_H1$: SEQ ID NO: 541, $CDR_H2$: SEQ ID NO: 542, and $CDR_H3$: SEQ ID NO: 543. In some embodiments, the anti-CFD light chain has at least the following CDRs: $CDR_L1$: SEQ ID NO: 544, $CDR_L2$: SEQ ID NO: 545 and $CDR_L3$: SEQ ID NO: 546. In some embodiments, the anti-CFD antibody heavy chain has at least the following CDR sequences: $CDR_H1$: SEQ ID NO: 326, $CDR_H2$: SEQ ID NO: 327, and $CDR_H3$: SEQ ID NO: 328. In some embodiments, the anti-CFD light chain has at least the following CDRs: $CDR_L1$: SEQ ID NO: 323, $CDR_L2$: SEQ ID NO: 324 and $CDR_L3$: SEQ ID NO: 325. In some embodiments, the anti-CFD antibody heavy chain has at least the following CDR sequences: $CDR_H1$: SEQ ID NO: 332, $CDR_H2$: SEQ ID NO: 333, and $CDR_H3$: SEQ ID NO: 334. In some embodiments, the anti-CFD light chain has at least the following CDRs: $CDR_L1$: SEQ ID NO: 329, $CDR_L2$: SEQ ID NO: 330 and $CDR_L3$: SEQ ID NO: 331.

In some embodiments, the anti-CFD antibody heavy chain has at least the following CDR sequences: HCDR1: SEQ ID NO: 577: GYTFTDYYIN, HCDR2: SEQ ID NO: 578: INPITGDTDYNADFKR, and HCDR3: SEQ ID NO: 579: TREGPSFAY. In some embodiments, the anti-CFD light chain has at least the following CDRs: LCDR1: SEQ ID NO: 580: RSSQTIVHSNGDTYLE, LCDR2: SEQ ID NO: 581: LLIRKVSNRFS, and LCDR3: SEQ ID NO: 582: FQGSHVPVT. In some embodiments, the anti-CFD antibody has at least the following CDR sequences: HCDR1: SEQ ID NO: 577: GYTFTDYYIN, HCDR2: SEQ ID NO: 578: INPITGDTDYNADFKR, HCDR3: SEQ ID NO: 579: TREGPSFAY, LCDR1: SEQ ID NO: 580: RSSQTIVHSNGDTYLE, LCDR2: SEQ ID NO: 581: LLIRKVSNRFS, and LCDR3: SEQ ID NO: 582: FQGSHVPVT.

In some embodiments, the isotype of the anti-CFD antibody heavy chain, is IgG1 and has a $CH_1$, hinge, $CH_2$ and $CH_3$ domains. In some embodiments the light chain isotype is kappa.

In some embodiments, the IgG1 domain of the anti-CFD antibody has one or more mutations to modulate effector function, such as ADCC, ADCP, and CDC. In some embodiments, the IgG1 mutations reduce effector function. In some embodiments the amino acids to use for effector function mutations include (EU numbering) E233X, L234X, L235X, G236X, G237X, G236X, D270X, K322X, A327X, P329X, A330X, A330X, P331X, and P331X, in which X is any natural or non-natural amino acid. In some embodiments, the mutations include one or more of the following: E233P, L234V, L234A, L235A, G237A, A327G, A330S and P331S (EU numbering). In some embodiments, the anti-CFD heavy chain has the following mutations (EU numbering): L234A, L235A and G237A. In some embodiments, the number of effector function mutations relative to a natural human IgG1 sequence is no more than 10. In some embodiments the number of effector function mutations relative to a natural human IgG1 sequence is no more than 5, 4, 3, 2 or 1. In some embodiments, the antibody has decreased Fc gamma binding and/or complement C1q binding, such that the antibody's ability to result in an effector function is decreased. This can be especially advantageous for ophthalmic indications/disorders.

In some embodiments, the anti-CFD antibody comprises one or more of the following amino acid mutations: L234A, L235A, G237A, and L443C (EU numbering, or 233A, 234A, 236A, and 442C in SEQ ID NO: 183).

In some embodiments, the anti-CFD antibody is or is part of a human immunoglobulin G (IgG1).

In some embodiments, the CFD antibody comprises a heavy chain constant domain that comprises one or more mutations that reduce an immune-mediated effector function.

In some embodiments an anti-CFD antibody is provided. The anti-CFD antibody comprises a heavy chain that comprises a $CDR_H1$ comprising the sequence of any one of SEQ ID NOs: 541, 326, 332, or 577, a $CDR_H2$ comprising the sequence of any one of SEQ ID NOs: 542, 327, 333, or 578, a $CDR_H3$ comprising the sequence of any one of SEQ ID NOs: 543, 328, 334, or 579 a $CDR_L1$ comprising the sequence of any one of SEQ ID NOs: 544, 323, 329, or 580, a $CDR_L2$ comprising the sequence of any one of SEQ ID NOs: 545, 324, 330, or 581, and a $CDR_L3$ comprising the sequence of any one of SEQ ID NOs: 546, 325, 331, or 582.

Alternatively, the IgG domain can be IgG2, IgG3 or IgG4 or a composite in which a constant regions is formed from more than one of these isotypes (e.g., CH1 region from IgG2 or IgG4, hinge, CH2 and CH3 regions from IgG). Such domains can contain mutations to reduce and/or modulate effector function at one or more of the EU position mentioned for IgG1. Human IgG2 and IgG4 have reduced effector functions relative to human IgG1 and IgG3.

In some embodiments, the anti-CFD heavy chain has a cysteine residue added as a mutation by recombinant DNA technology which can be used to conjugate a half-life extending moiety. In some embodiments, the mutation is Q347C (EU numbering, or 346C in SEQ ID NO 183)) and/or L443C (EU numbering, or 442C in SEQ ID NO: 183). In some embodiments, the mutation is L443C (EU numbering, or 442C in SEQ ID NO: 183). In some embodiments, the stoichiometry of antibody to polymer is 1:1; in other words, a conjugate has one molecule of antibody conjugated to one molecule of polymer.

The half-life of the anti-CFD antibodies can be extended by attachment of a "half-life ("half life") extending moieties" or "half-life ("half life") extending groups". Half-life extending moieties include peptides and proteins which can be expressed in frame with the biological drug of issue (or conjugated chemically depending on the situation) and various polymers which can be attached or conjugated to one or more amino acid side chain or end functionalities such as —SH, —OH, —COOH, —CONH2, —NH2, or one or more N- and/or O-glycan structures. Half-life extending moieties generally act to increase the in vivo circulatory half-life of biologic drugs.

Examples of peptide/protein half-life extending moieties include Fc fusion (Capon D J, Chamow S M, Mordenti J, et al. Designing CD4 immunoadhesions for AIDS therapy. Nature. 1989. 337:525-31), human serum albumin (HAS) fusion (Yeh P, Landais D, Lemaitre M, et al. Design of yeast-secreted albumin derivatives for human therapy: biological and antiviral properties of a serum albumin-CD4 genetic conjugate. Proc Natl Acad Sci USA. 1992. 89:1904-08), carboxy terminal peptide (CTP) fusion (Fares F A, Suganuma N. Nishimori K, et al. Design of a long-acting follitropin agonist by fusing the C-terminal sequence of the chorionic gonadotropin beta subunit to the follitropin beta subunit. Proc Natl Acad Sci USA. 1992. 89:4304-08), genetic fusion of non-exact repeat peptide sequence (XTEN) fusion (Schellenberger V, Wang C W, Geething N C, et al. A recombinant polypeptide extends the in vivo half-life of peptides and proteins in a tunable manner. Nat Biotechnol. 2009. 27:1186-90), elastin like peptide (ELPylation) (MCpherson D T, Morrow C, Minehan D S, et al. Production and purification of a recombinant elastomeric polypeptide, G(VPGVG19-VPGV, from *Escheriachia coli*. Biotechnol Prog. 1992. 8:347-52), human transferrin fusion (Prior C P, Lai C-H, Sadeghi H et al. Modified transferrin fusion proteins. Patent WO2004/020405. 2004), proline-alanine-serine (PASylation) (Skerra A, Theobald I, Schlapsky M. Biological active proteins having increased in vivo and/or vitro stability. Patent WO2008/155134 A1. 2008), homo-amino acid polymer (HAPylation) (Schlapschy M, Theobald I, Mack H, et al. Fusion of a recombinant antibody fragment with a homo-amino acid polymer: effects on biophysical properties and prolonged plasma half-life. Protein Eng Des Sel. 2007. 20:273-84) and gelatin like protein (GLK) fusion (Huang Y-S, Wen X-F, Zaro J L, et al. Engineering a pharmacologically superior form of granulocyte-colony-stimulating-factor by fusion with gelatin-like protein polymer. Eur J. Pharm Biopharm. 2010. 72:435-41).

Examples of polymer half-life extending moieties include polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising MPC, Poly (Gly$_x$-Ser$_y$), Hyaluronic acid (HA), Heparosan polymers (HEP), Fleximers, Dextran, and Poly-sialic acids (PSA).

In one embodiment a half-life extending moiety can be conjugated to an antibody via free amino groups of the protein using N-hydroxysuccinimide (NHS) esters. Reagents targeting conjugation to amine groups can randomly react to ϵ-amine group of lysines, α-amine group of N-terminal amino acids, and δ-amine group of histidines.

However, the anti-CFD antibodies disclosed herein can have many amine groups available for polymer conjugation. Conjugation of polymers to free amino groups, thus, might negatively impact the ability of the antibody proteins to bind to CFD.

In some embodiments, a half-life extending moiety is coupled to one or more free SH groups using any appropriate thiol-reactive chemistry including, without limitation, maleimide chemistry, or the coupling of polymer hydrazides or polymer amines to carbohydrate moieties of the antibody after prior oxidation. In some embodiments maleimide coupling is used In some embodiments, coupling occurs at cysteines naturally present or introduced via genetic engineering.

In some embodiments, conjugates of antibody and high MW polymers serving as half-life extenders are provided. In some embodiments, a conjugate comprises an antibody that is coupled to a zwitterionic polymer wherein the polymer is formed from one or more monomer units and wherein at least one monomer unit has a zwitterionic group is provided. In some embodiments, the zwitterionic group is phosphorylcholine.

In some embodiments, one of the monomer units is HEMA-PC. In some embodiments, a polymer is synthesized from a single monomer which is HEMA-PC.

In some embodiments, some antibody conjugates have 2, 3, or more polymer arms wherein the monomer is HEMA-PC. In some embodiments, the conjugates have 2, 3, 4, 5, 6, 7, 8, 9, 10, 11, or 12 polymer arms wherein the monomer is HEMA-PC. In some embodiments, the conjugates have 3, 6 or 9 arms. In some embodiments, the conjugate has 9 arms.

In some embodiments, polymer-antibody conjugates have a polymer portion with a molecular weight of between 100,000 and 1,500,000 Da. In some embodiments, the conjugate has a polymer portion with a molecular weight between 500,000 and 1,000,000 Da. In some embodiments, the conjugate has a polymer portion with a molecular weight between 600,000 to 800,000 Da. In some embodiments, the conjugate has a polymer portion with a molecular weight between 600,000 and 850,000 Da and has 9 arms. When a molecular weight is given for an antibody conjugated to a polymer, the molecular weight will be the addition of the molecular weight of the protein, including any carbohydrate moieties associated therewith, and the molecular weight of the polymer.

In some embodiments, an anti-CFD antibody has a HEMA-PC polymer which has a molecular weight measured by Mw of between about 100 kDa and 1650 kDa is provided. In some embodiments, the molecular weight of the polymer as measured by Mw is between about 500 kDa and 1000 kDa. In some embodiments, the molecular weight of the polymer as measured by Mw is between about 600 kDa to about 900 kDa. In some embodiments, the polymer molecular weight as measured by Mw is 750 or 800 kDa plus or minus 15%.

In some embodiments, the polymer is made from an initiator suitable for ATRP having one or more polymer initiation sites. In some embodiments, the polymer initiation site has a 2-bromoisobutyrate site. In some embodiments, the initiator has 3 or more polymer initiation sites. In some embodiments, the initiator has 3, 4, 5, 6, 7, 8, 9, 10, 11 or 12 polymer initiation sites. In some embodiments, the initiator has 3, 6 or 9 polymer initiation sites. In some embodiments, the initiator has 9 polymer initiation sites. In some embodiments, the initiator is OG1786.

The anti-CFD antibodies can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing antibody, e.g. constitutively or on induction, and (v) isolating the antibody, e.g. from the culture medium or by harvesting the transformed cells, in order to (vi) obtain purified antibody.

The anti-CFD antibodies can be produced by expression in a suitable prokaryotic or eukaryotic host system characterized by producing a pharmacologically acceptable antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the antibodies disclosed herein and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

Method of Conjugating Proteins to Polymers

In some embodiments, a method is presented of preparing a therapeutic protein-half life extending moiety conjugate having the step of conjugating a therapeutic protein which has a cysteine residue added via recombinant DNA technology to a half-life extending moiety having a sulfhydryl specific reacting group selected from the group consisting of maleimide, vinylsulfones, orthopyridyl-disulfides, and iodoacetamides to provide the therapeutic protein-half life extending moiety conjugate.

Figure 17:
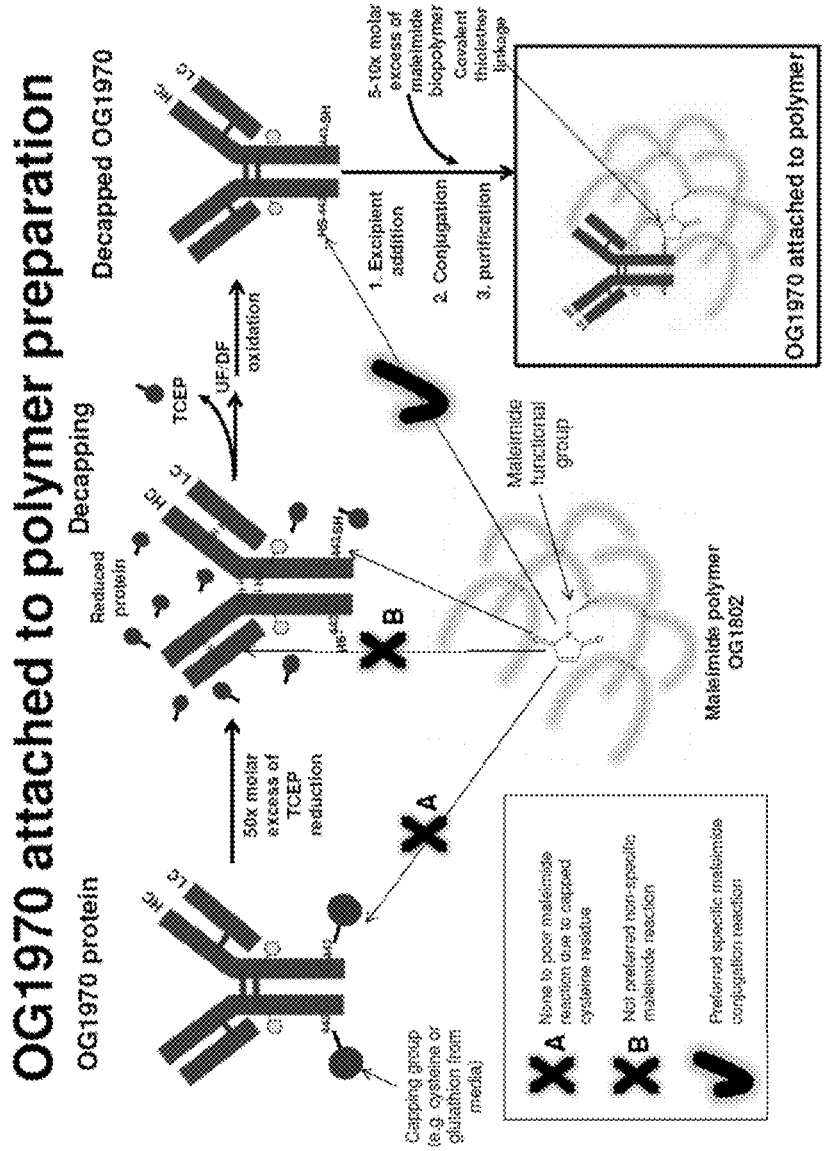
FIG. 17 depicts some embodiments of a method for preparing an antibody conjugate.

In some embodiments a method of preparing the antibody conjugate is provided. As shown in FIG. 17, the method comprises reducing the protein with a 30× molar excess of the TCEP reducing agent (FIG. 17). After reduction, the antibody is oxidized to produce a decapped antibody where the inter- and intra-light and heavy chain disulfide bonds naturally occurring in the antibody are formed, but the engineered Cysteine on the heavy chain position L443C (EU numbering, or 442C in SEQ ID NO: 183) remains to be decapped (FIG. 17). The antibody is then conjugated by adding an excipient and adding 2-10× molar excess of a maleimide biopolymer. (FIG. 17). The biopolymer links to the antibody through a covalent thioether linkage (FIG. 17). After conjugation, the antibody conjugate is purified with both unconjugated antibody and polymer removed (FIG. 17).

The protein and process described above can be varied as well. Thus, in some embodiments, a process for preparing a conjugated protein (which need not be an antibody or an anti-CFD antibody) is provided. The process includes reducing one or more cysteines in a protein to form a decapped protein in a solution. After reducing the one or more cysteines the decapped protein is reoxidized to restore at least one disulfide linkage in the reduced protein while ensuring that an engineered cysteine residue in the protein remains in a free thiol form to form a reoxidized decapped protein in the solution. At least one excipient is then added to the solution. The excipient reduces a polymer induced protein precipitation. After the excipient is added, a polymer is added to the solution, which is conjugated to the reoxidized decapped protein at the engineered cysteine residue to form a conjugated protein.

In some embodiments, the molar excess of the reducing agent can be altered to any amount that functions. In some embodiments 10, 20, 30, 40, 50, 60, 70, 80, 90× molar excess of the reducing agent (which need not be TCEP in all embodiments) can be employed. In some embodiments, any antibody (therapeutic or otherwise) can be employed. In some embodiments, 1, 2, 3, 4, 5, 6, 7, 8, 9, 10, 11, 12, 13, 14, 15× molar excess of a maleimide biopolymer can be employed. In some embodiments, there is an excess of decapped protein to polymer. In some embodiments, the amount of the reduced protein is less than the amount of the polymer. In some embodiments, the amount of the reduced protein is 90%, 80%, 70%, 60%, 50%, 40%, 30%, 20%, 10%, 5%, 4%, 3%, 2%, 1% of the amount of the polymer. In some embodiments, 10-15 times as much polymer is used as protein. In some embodiments the amount of the reduced antibody is greater than the amount of the polymer. In some embodiments the amount of the polymer is greater than the amount of the reduced antibody.

In some embodiments, the purification step is optional.

In some embodiments, the method of making an antibody conjugate comprises conjugating an anti-CFD antibody to a phosphorylcholine containing polymer. In some embodiments the method comprises the steps of conjugating an anti-CFD antibody to a phosphorylcholine containing polymer. The anti-CFD antibody comprises an amino residue added via recombinant DNA technology. In some embodiments, the added amino acid residue is a cysteine residue. In some embodiments, the cysteine residue is added outside a variable region of the antibody. The cysteine residue can be added to either the heavy chain or light chain of the antibody.

In some embodiments, the polymer comprises or consists of a phosphorylcholine containing polymer. In some embodiments, the phosphorylcholine containing polymer comprises a sulfhydryl specific reacting group selected from the group consisting of a maleimide, a vinylsulfone, an orthopyridyl-disulfide, and an iodoacetamide. In some embodiments, the sulfhydryl specific reacting group on the phosphorylcholine containing polymer reacts with the cysteine residue on the anti-CFD antibody to make the antibody conjugate.

In some embodiments, the protein to be conjugated can be an antibody, an antibody protein fusion, or a binding fragment thereof. In some embodiments, the protein is not an antibody but is an enzyme, a ligand, a receptor, or other protein or mutants or variants thereof. In some embodiments, the native protein contains at least one disulfide bond and at least one non-native cysteine.

In some embodiments, the excipient can be an acid or a base. In some embodiments, the excipient is a detergent, a sugar, or a charged amino acid. In some embodiments, the excipient assists in keeping the protein in solution during the conjugation to the polymer. In some embodiments, the excipient is added to the solution containing the protein, prior to the addition of the polymer to the solution that contains the protein.

In some embodiments, the reaction occurs under aqueous conditions between about pH 5 to about pH 9. In some embodiments, the reaction occurs between 6.0 and 8.5, between 6.5 and 8.0 or between 7.0 and 7.5.

In some embodiments, the polymer is conjugated to the protein at 2-37 degrees Celsius. In some embodiments, the conjugation occurs at 0-40 degrees Celsius, 5-35 degrees Celsius, 10-30 degrees Celsius, and 15-25 degrees Celsius.

In some embodiments, the conjugated proteins described herein can be contacted to an ion exchange medium or hydrophobic interaction chromatography or affinity chromatography medium for purification (to remove the conjugated from the unconjugated). In some embodiments, the ion exchange medium, hydrophobic interaction chromatography, and/or affinity chromatography medium separates the conjugated protein from the unconjugated free polymer and from the unconjugated reoxidized decapped protein.

In some embodiments, the processes described herein and outlined in FIG. 17 involves an excipient that is capable of facilitating and/or maintaining a solubility system. In some embodiments, the process allows the solution to maintain the solubility of the two components meant to interact. This can include the solubility of the protein and the polymer and then the end conjugate as well. In some embodiments, without the excipient approach, the issue can be that while the protein it is soluble, when the biopolymer is added, the solubility of the solution (e.g., protein) drops and it crashes/precipitates out of solution. Of course, when the protein crashes out, it is not available to conjugate efficiently with the biopolymer. Thus, an excipient can be employed to maintain the solubility of the protein in the presence of the biopolymer so the two can couple to form the protein conjugate (or as depicted in FIG. 17, an antibody conjugate). This also allows for the solubility of the conjugate to be maintained.

In some embodiments, the polymers disclosed herein can comprise one or more of the following: a zwitterion, a phosphorylcholine, or a PEG linker bridging a center of a polymer branching point to the maleimide functional group. In some embodiments, any of the polymers provided herein can be added to a protein via the methods provided herein.

In some embodiments, any of the proteins provided herein can be conjugated to any of the polymers provided herein via one or more of the methods provided herein.

In some embodiments, the process(es) provided herein allow(s) for larger scale processing to make and purify protein and/or antibody conjugates. In some embodiments, the volume employed is at least 1 liter, for example 1, 10, 100, 1,000, 5,000, 10,000, liters or more. In some embodiments, the amount of the antibody conjugate produced and/or purified can be 0.1, 1, 10, 100, 1000, or more grams.

In some embodiments, the therapeutic protein may be any of the anti-CFD antibodies described herein having a cysteine residue added via recombinant DNA technology. In some embodiments, the anti-CFD antibody heavy chain has the following CDRs: HCDR1: DYY (SEQ ID NO: 541), HCDR2: INPITGDT (SEQ ID NO: 542), HCDR3: EGPSFAY (SEQ ID NO: 543); LCDR1: QTIVHSNGDT (SEQ ID NO: 544), LCDR2: KVS (SEQ ID NO: 545), LCDR3: FQGSHVPVT (SEQ ID NO: 546), for example, 1, 2, 3, 4, 5, or all 6 CDRs. In some embodiments, the antibody includes HCDR3.

In some embodiments, the anti-CFD antibody is IgG. In some embodiments, the heavy chain has one or more mutations to modulate effector function. In some embodiments, the mutations are to one or more of the following amino acid positions (EU numbering): E233, L234, L235, G236, G237, A327, A330, and P331. In some embodiments, the mutations are selected from the group consisting of: E233P, L234V, L234A, L235A, G237A, A327A, A330S and P331S (EU numbering). In some embodiments, the mutations are (EU numbering) L234A, L235A and G237A.

In some embodiments, the cysteine residue added to the therapeutic protein via recombinant DNA technology should not be involved in Cys-Cys disulfide bond pairing. In this regard, therapeutic proteins may be dimeric. So for example, an intact anti-CFD antibody has two light chains and two heavy chains. If a Cys residue is introduced into the heavy chain for instance, the intact antibody will have two such introduced cysteines at identical positions and the possibility exists that these cysteine residues will form intra-chain disulfide bonds. If the introduced cysteine residues form Cys-Cys disulfide bonds or have a propensity to do so, that introduced Cys residue will not be useful for conjugation. It is known in the art how to avoid positions in the heavy and light chains that will give rise to intra-chain disulfide pairing. See, e.g., U.S. Patent Application No. 2015/0158952.

In some embodiments, the cysteine residue introduced via recombinant DNA technology is selected from the group consisting of (EU numbering) Q347C and L443C. In some embodiments, the cysteine residue is L443C (EU numbering, or 442C in SEQ ID NO: 183). In some embodiments, the heavy chain the antibody has the amino acid sequence set forth in SEQ ID NO. 1 and the light chain has the amino acid sequence of SEQ ID NO. 2.

In some embodiments, the sulfhydral specific reacting group is maleimide.

In some embodiments, the half-life extending moiety is selected from the group consisting of polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising 2-methacryloyloxy-2'-ethyltrimethylammoniumphosphate (MPC).

In some embodiments, the half-life extending moiety is a zwitterionic polymer. In some embodiments, the zwitterion is phosphorylcholine, i.e. a phosphorylcholine containing polymer. In some embodiments, the polymer is composed of MPC units.

In some embodiments, the MPC polymer has three or more arms. In some embodiments, the MPC polymer has 2, 3, 4, 5, 6, 7, 8, 9, 10, 11 or 12 arms. In some embodiments, the MPC polymer has 3, 6, or 9 arms. In some embodiments, the MPC polymer has 9 arms. In some embodiments, the polymer is synthesized with an initiator comprising 2, 3, 4, 5, 6, 7, 8, 9, 10, 11, 12, or more polymer initiation sites In some embodiments, the MPC polymer has a molecular weight between about 300,000 and 1,750,000 Da. In some embodiments, the MPC polymer has a molecular weight between about 500,000 and 1,000,000 Da or between about 600,000 to 900,000 Da.

In some embodiments, the method of preparing a therapeutic protein-half life extending moiety conjugate has an additional step of contacting the therapeutic protein with a thiol reductant under conditions that produce a reduced cysteine sulfhydryl group. As discussed above, it is preferable that the cysteine residue added via recombinant DNA technology are unpaired, i.e. are not involved in Cys-Cys intra chain disulfide bonds or are not substantially involved in such bonding. However, Cys residues which are not involved in such Cys-Cys disulfide bonding and are free for conjugation are known to react with with free cysteine in the culture media to form disulfide adducts. See, e.g., WO 2009/052249. A cysteine so derivatized will not be available for conjugation. To free the newly added cysteine from the disulfide adduct, the protein after purification is treated with a reducing agent, e.g., dithiothreitol. However, such treatment with a reducing agent will reduce all of the cysteine residues in the therapeutic protein, including native cysteines many of which are involved in inter and intra chain Cys-Cys disulfides bonds. The native Cys-Cys disulfides are generally crucial to protein stability and activity and they should be reformed. In some embodiments, all native (e.g., inter and intra) Cys-Cys disulfides are reformed.

To reform native inter and intra-chain disulfide residues, after reduction to remove the cysteine disulfide adducts, the therapeutic protein is exposed to oxidizing conditions and/or oxidizing agents for a prescribed period of time, e.g., overnight. In some embodiments, ambient air exposure overnight can be used to achieve reformation of the native disulfide bonds. In some embodiments, an oxidizing agent is employed to restore the native disulfides. In some embodiments, the oxidizing agent is selected from the group consisting of acqueous CuSO4 and dehydroascorbic acid (DHAA). In some embodiments, the oxidizing agent is DHAA. In some embodiments, the range of DHAA used is in the range of 5-30 equivalents. In some embodiments, the range is 10-30 equivalents. In some embodiments, the range is 15 equivalents.

In some embodiments, the thiol reductant is selected from the group consisting of: Tris[2-carboxyethyl]phosphine hydrochloride (TCEP), dithiothreitol (DTT), dithioerythritol (DTE), sodium borohydride (NaBH$_4$), sodium cyanoborohydride (NaCNBH3), β-mercaptoethanol (BME), cysteine hydrochloride and cysteine. In some embodiments, the thiol reductant is TCEP.

In some embodiments, the thiol reductant concentration is between 1 and 100 fold molar excess relative to the therapeutic protein concentration. In some embodiments, the thiol reductant concentration is between 20 to 50 fold molar excess relative to the therapeutic protein concentration. In some embodiments, the thiol reductant is removed following incubation with the therapeutic protein prior to oxidation of the therapeutic protein.

In some embodiments, the method for conjugating a therapeutic protein to a half-life extending moiety has a further step of purifying the therapeutic protein conjugate after conjugation. In some embodiments, the therapeutic protein conjugate is purified using a technique selected from the group consisting of ion exchange chromatography, hydrophobic interaction chromatography, size exclusion chromatography, and affinity chromatography or combinations thereof.

In some embodiments, the therapeutic protein conjugate retains at least 20% biological activity relative to unconjugated therapeutic protein. In some embodiments, the therapeutic protein conjugate retains at least 50% biological activity relative to unconjugated therapeutic protein. In some embodiments, the therapeutic protein conjugate retains at least 90% biological activity relative to native therapeutic protein.

In some embodiments, the therapeutic protein conjugate has an increased half-life relative to unconjugated therapeutic protein. In some embodiments, the therapeutic protein conjugate has at least a 1.5 fold increase in half-life relative to unconjugated therapeutic protein. In some embodiments, the therapeutic protein conjugate has at least a 1.5, 2, 2.5, 3, 3.5, 4, 4.5 or 5 fold increase in half-life relative to unconjugated therapeutic protein.

In some embodiments, the zwitterionic polymer of the method of conjugating a therapeutic protein to a half-life extending moiety is a radically polymerizable monomer having a zwitterionic group and the method has a further step of polymerizing the free radically polymerizable zwitterionic monomer in a polymerization medium to provide a polymer, the medium comprising: the radically polymerizable zwitterionic monomer; a transition metal catalyst $M_t^{(q-1)+}$ wherein $M_t$ is a transition metal, q is a higher oxidation state of the metal and q−1 is a lower oxidation state of the metal, wherein the metal catalyst is supplied as a salt of the form $Mt^{(q-1)+}X'_{(q-1)}$ wherein X' is a counterion or group or the transition metal catalyst is supplied in situ by providing the inactive metal salt at its higher oxidation state $M_t^{q+}X'_q$ together with a reducing agent that is capable of reducing the transition metal from the oxidized inactive state to the reduced active state; a ligand; and an initiator.

To function as an ATRP transition metal catalyst, the transition metal should have at least two readily accessible oxidation states separated by one electron, a higher oxidation state and a lower oxidation state. In ATRP, a reversible redox reaction results in the transition metal catalyst cycling between the higher oxidation state and the lower oxidation state while the polymer chains cycle between having propagating chain ends and dormant chain ends. See, e.g., U.S. Pat. No. 7,893,173.

In some embodiments, the radically polymerizable zwitterionic monomer is selected from the group consisting of

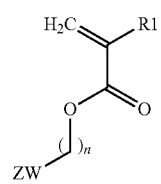

Formula (18)

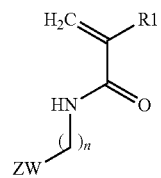

Formula (19)

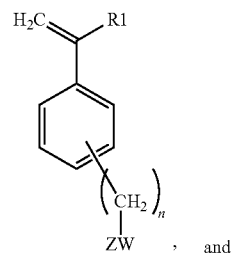

Formula (20)

, and

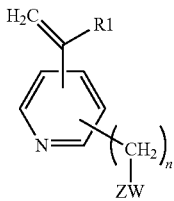

Formula (21)

wherein R1 is H or C1-6 alkyl, ZW is a zwitterion and n is an integer from 1-6.

In some embodiments, the radically polymerizable monomer is

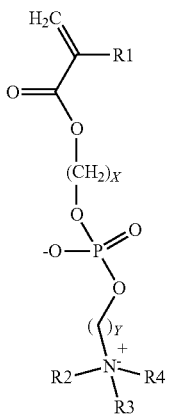

Formula (12)

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

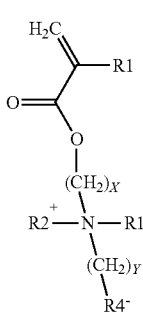

Formula (13)

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

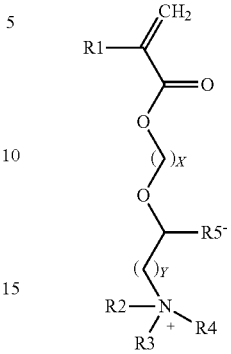

Formula (14)

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

In some embodiments, the transition metal Mt is selected from the group consisting of Cu, Fe, Ru, Cr, Mo, W, Mn, Rh, Re, Co, V, Zn, Au, and Ag. In some embodiments, the metal catalyst is supplied as a salt of the form $Mt^{(q-1)+}X'_{(q-1)}$. $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^+$, $V^{2+}$, $Zn^+$, $Au^+$, and $Ag^+$ and X' is selected from the group consisting of halogen, $C_{1-6}$ alkoxy, $(SO_4)_{1/2}$, $(PO_4)_{1/3}$, $(R7PO_4)_{1/2}$, $(R7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. In some embodiments, $M_t^{(q-1)+}$ is $Cu^{1+}$ and X' is Br.

In some embodiments, $M_t^{(q-1)+}$ is supplied in situ. In some embodiments, $M_t^{q+}X_q$ is $CuBr_2$. In some embodiments, the reducing agent is an inorganic compound. In some embodiments, the reducing agent is selected from the group consisting of a sulfur compound of a low oxidation level, sodium hydrogen sulfite, an inorganic salt comprising a metal ion, a metal, hydrazine hydrate and derivatives of such compounds. In some embodiments, the reducing agent is a metal. In some embodiments, the reducing agent is $Cu^0$.

In some embodiments, the reducing agent is an organic compound. In some embodiments, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

In some embodiments, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, —N,N,N',N',N"-Pentamethyldiethylenetriamine, 1,1,4,7,10,10-Hexamethyltriethylenetetramine, Tris(2-dimethylaminoethyl)amine, —N,N-bis(2-pyridylmethyl)octadecylamine, —N,N,N',N'-tetra[(2-pyridal)methyl] ethylenediamine, tris[(2-pyridyl)methyl]amine, tris(2-aminoethyl)amine, tris(2-bis(3-butoxy-3-oxopropyl) aminoethyl)amine, tris(2-bis(3-(2-ethylhexoxy)-3-oxopropyl)aminoethyl)amine and Tris(2-bis(3-dodecoxy-3-oxopropyl)aminoethyl)amine. In some embodiments, the ligand is 2,2'-bipyridine.

In some embodiments the initiator has the structure:

R1-R2-(-R3)$_s$   Formula (22)

wherein R1 is a nucleophilic reactive group, R2 comprises a linker, and R3 comprises a polymer synthesis initiator moiety having the structure

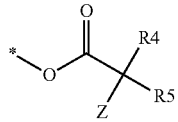
Formula (23)

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof; Z is a halogen or CN; and s is an integer between 1 and 20.

In some embodiments, Z in Formula (23) is Br and R4 and R5 are each methyl. In some embodiments, R1 in Formula (22) is selected from the group consisting of NH$_2$—, OH—, and SH—.

In some embodiments R2 in Formula (22) is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. In some embodiments, R2 in Formula (22) is

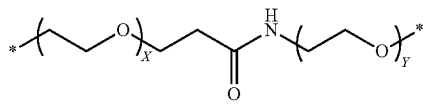
Formula (24)

wherein X and Y are the same or different and are integers from 1-20. In some embodiments, X and Y are each 4.

In some embodiments, R3 in Formula (22) is

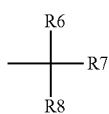
Formula (25)

wherein R6, R7 and R8 are the same or different and are selected from the group consisting of

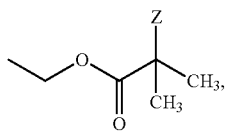
Formula (26)

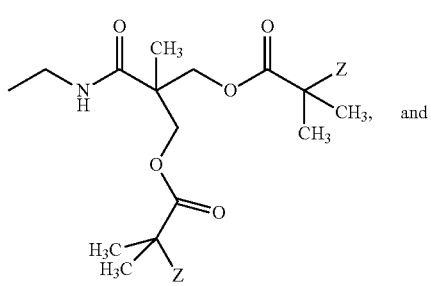
Formula (27)

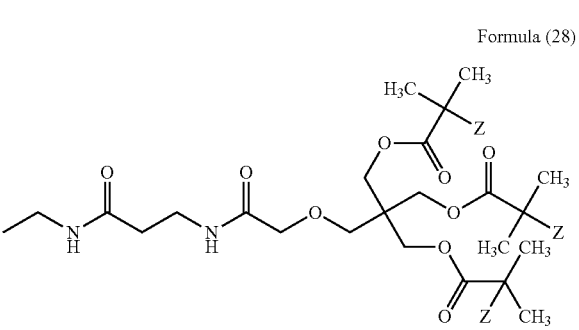
Formula (28)

wherein Z is NCS, F, Cl, Br or I. In some embodiments, Z in Formula (26), Formula (27) and/or Formula (28) is Br and R6, R7 and R8 in Formula (25) are each

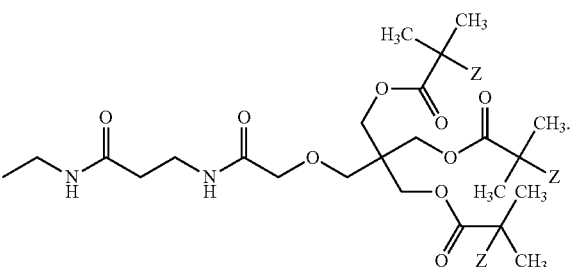
Formula (29)

In some embodiments, the initiator has the structure:

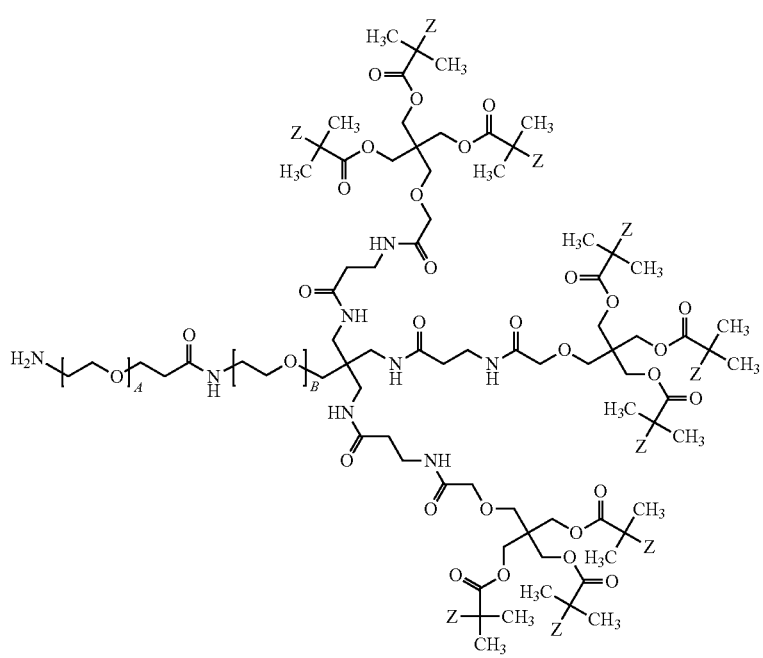

Formula (30)

wherein A and B are the same or different and are integers from 2 to 12 and Z is any halide, for example Br. In some embodiments, A and B are each 4 in Formula (30).

In some embodiments, the method further has the step of reacting the polymer with a maleimide reagent to provide a polymer having a terminal maleimide. In some embodiments, the maleimide compound is

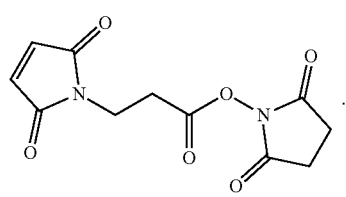

Formula (31)

A modification or mutation may also be made in a framework region or constant region to increase the half-life of a CFD antagonist antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the CFD antagonists antibodies provided herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to CFD is effected by an immunoassay or FACS. A cell overexpressing the antibody or protein of interest can be identified.

An expression vector can be used to direct expression of a CFD antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of a CFD antagonist antibody conjugate described herein. Examples of such compositions, as well as how to formulate, are also described herein. In some embodiments, the composition comprises one or more CFD antagonist antibodies and/or antibody conjugates. In other embodiments, the CFD antagonist antibody recognizes human CFD. In other embodiments, the CFD antagonist antibody is a human antibody. In other embodiments, the CFD antagonist antibody is a humanized antibody. In some embodiments, the CFD antagonist antibody comprises a constant region that does not trigger an unwanted or undesirable immune response, such as antibody-mediated lysis or ADCC. In other embodiments, the CFD antagonist comprises one or more CDR(s) of the antibody (such as one, two, three, four, five, or, in some embodiments, all six CDRs).

It is understood that the compositions can comprise more than one CFD antagonist antibody (e.g., a mixture of CFD antibodies that recognize different epitopes of CFD). Other exemplary compositions comprise more than one CFD antagonist antibody that recognize the same epitope(s), or different species of CFD antagonist antibodies that bind to different epitopes of CFD. In some embodiments, the compositions comprise a mixture of CFD antagonist antibodies that recognize different variants of CFD.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Polysorbate, PLURONICS™ or polyethylene glycol (PEG). Pharmaceutically acceptable excipients are further described herein.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerin and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-350 mOsm/kg water.

The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The CFD antagonist antibodies, CFD antagonist antibody conjugates, and pharmaceutical compositions of the invention can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

Methods for Preventing or Treating Ophthalmic Disorders

In some embodiments, the antibodies and the antibody conjugates are useful in various applications including, but are not limited to, therapeutic treatment methods.

In some embodiments, the CFD antagonist antibodies can be used to treat (and/or effect prophylaxis) complement mediated disorders via appropriate administration of an effective regime of the antibody. In general, complement mediated disorders are those associated with or characterized by excessive, unregulated or under regulated complement activation. Complement mediated disorders include: complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease in which there is an inflammatory event or condition such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. There is a strong correlation shown between complement activation and ocular diseases such as age-related macular degeneration, including dry AMD and wet AMD, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In particularly preferred aspects of the present invention, a method is presented for treating or effecting prophylaxis of dry AMD by administering an effective regime of an anti-CFD antibody presented in accordance with the present invention.

In some embodiments, a method for treating ocular disease, such as for example AMD is provided. In some embodiments, the method of treating AMD in a subject comprises administering to the subject in need thereof an effective amount of a composition (e.g., pharmaceutical composition) comprising any of the anti-CFD antibodies as described herein. As used herein, AMD includes dry AMD and wet AMD. In some embodiments, provided is a method of treating AMD in a subject, comprising administering to the subject in need thereof an effective amount of a composition comprising CFD antagonist antibodies or the CFD antagonist antibody conjugates as described herein.

In some embodiments, the methods described herein further comprise a step of treating a subject with one or more additional form(s) of therapy. In some embodiments, the additional form of therapy is an additional AMD therapy including, but not limited to, VISUDYNE®, laser photocoagulation or intravitreal injection of, e.g., LUCENTIS®, MACUGEN®, EYLEA®, OZURDEX®, ILUVIEN®, TRIESENCE®, or TRIVARIS®.

With respect to all methods described herein, reference to CFD antagonist antibodies also includes compositions comprising one or more additional agents. These compositions may further comprise suitable excipients, such as pharmaceutically acceptable excipients including buffers, which are well known in the art. The present invention can be used alone or in combination with other methods of treatment.

In some embodiments, a method for the treatment or prophylaxis of a disease in a patient in need thereof is provided. In some embodiments, the method comprises administering to the patient any of the isolated antagonist antibodies disclosed herein. In some embodiments, the method comprises administering to the patient any of the conjugates disclosed herein. In some embodiments, the method comprises administering to the patient any of the compositions disclosed herein. In some embodiments, the method comprises identifying a patient having hyperactive CFD activity and administering to the patient any of the isolated antagonist antibodies disclosed herein. In some embodiments, the method comprises identifying a patient having hyperactive CFD activity and administering to the patient any of the conjugates disclosed herein. In some embodiments, the method comprises identifying a patient having hyperactive CFD activity and administering to the patient any of the compositions disclosed herein.

In some embodiments, the patient has a mutation in a complement pathway. In some embodiments, the disease is an ocular disorder. In some embodiments, the ocular disorder is dry age related macular degeneration (dry AMD). In some embodiments, the disorder is selected from the group consisting of Wet AMD, Dry AMD, geographic atrophy. In some embodiments, the disease is maternally inherited diabetes and deafness (MIDD).

In some embodiments, the isolated antibody, conjugate, composition or a combination thereof is administered no more frequently than once a month. In some embodiments, the isolated antibody, conjugate, composition or a combination thereof is administered no more frequently than once every two months. In some embodiments, the isolated antibody, conjugate, composition or a combination thereof is administered no more frequently than once every three months. In some embodiments, the isolated antibody, conjugate, composition or a combination thereof is administered with a frequency between once a year and once every two months. In some embodiments, the treatment can be a single application of the antibody. In some embodiments, the treatment can be as many applications of the antibody as needed or desired for an outcome.

In some embodiments, the subject has one or more risk factors selected from the group of cigarette smoking, exposure to hydroquinone (HQ), hypertension, atherosclerosis, high cholesterol, obesity, and fat intake.

In some embodiments, the antibody binds an epitope on human CFD that is the same as or overlaps with the epitope recognized by an antibody comprising the amino acid sequences shown in SEQ ID NO: 520 and SEQ ID NO: 525. In some embodiments, the antibody is one that prevents or reduces an ability of an antibody to bind to CFD, as shown through a competition assay with any one of the antibodies in Tables: 1.1, 0.1A, 0.1B, 0.1D, and/or 11.3. In some embodiments, the antibody binds to CFD and does not increase an enzymatic activity of CFD when bound thereto. In some embodiments, the antibody does not maintain an enzymatic activity of CFD when bound thereto. For example, the enzymatic activity of CFD decreases for all CFD substrates, including smaller substrates. In some embodiments, the antibody binds to the binding area and/or proteolytic site of CFD and decreases CFD's activity to proteolytically process a small molecule substrate, such as N-carbobenzyloxy-Lys-ThioBenzyl ester.

The CFD antagonist antibody can be administered to a subject via any suitable route. It should be apparent to a person skilled in the art that the examples described herein are not intended to be limiting but to be illustrative of the techniques available. Accordingly, in some embodiments, the CFD antagonist antibody is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, CFD antagonist antibody can be aerosolized using a fluorocarbon formulation and a metered dose inhaler, or inhaled as a lyophilized and milled powder.

In some embodiments, the CFD antagonist antibodies, CFD antagonist antibody conjugates, and pharmaceutical compositions disclosed herein are used for prophylaxis or treatment of an ocular disease or condition. So used, the conjugates are typically formulated for and administered by ocular, intraocular, and/or intravitreal injection, and/or juxtascleral injection, and/or subtenon injection, and/or suprachoroidal injection and/or topical administration in the form of eye drops and/or ointment. Such CFD antagonist antibodies, CFD antagonist antibody conjugates, and compositions can be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a minimum and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). In therapy or as a prophylactic, the active agent may be administered to an individual as an injectable composition, for example as a sterile aqueous dispersion, preferably isotonic or substantially isotonic.

Formulations for ocular, intraocular or intravitreal administration can be prepared by methods and using ingredients known in the art. Proper penetration into the eye is desirable for efficient treatment. Unlike diseases of the front of the eye, where drugs can be delivered topically, retinal diseases merit a more site-specific approach. Eye drops and ointments rarely penetrate the back of the eye, and the blood-ocular barrier hinders penetration of systemically administered drugs into ocular tissue. In some embodiments, the method of choice for drug delivery to treat retinal disease, such as AMD and CNV, is direct intravitreal injection. In some embodiments, intravitreal injections are repeated at intervals which depend on the patient's condition, and the properties and half-life of the drug delivered.

For administration to mammals, and particularly humans, it is expected that the dosage of the active agent is from 0.01 mg/kg body weight, to typically around 1 mg/kg, for systemic administrations. For ocular diseases that require local administration (for example, intravitreal, supracoroidal, peri-ocular etc), dosage is typically 0.1 mg/eye/dose to 10 mg/eye/dose or more. In some embodiments, the dosage is 100 ul/dose/eye. In some embodiments, a needle can be used to administer the dosage. The needle can be, for example, a 30 gauge ½ inch needle or a ½ inch needle that is 27 G or 29 G. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited.

This dosage may be repeated as often as appropriate (e.g., weekly, fortnightly, monthly, quarterly). If side effects develop the amount and/or frequency of the dosage can be reduced, in accordance with normal clinical practice. In one embodiment, the pharmaceutical composition may be administered once every one to thirty days.

The CFD antagonist antibodies of the present invention may be employed in accordance with the instant invention by expression of such polypeptides in vivo in a patient, i.e., gene therapy. There are two major approaches to getting the nucleic acid (optionally contained in a vector) into the patient's cells: in vivo and ex vivo. For in vivo delivery the nucleic acid is injected directly into the patient, usually at the sites where the therapeutic protein is required, i.e., where biological activity of the therapeutic protein is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinison et al., Cancer Investigation, 14(1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the therapeutic protein, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO polypeptide from a host cell in which it is placed. Preferably the signal sequence for this purpose is a mammalian signal sequence, most preferably the native signal sequence for the therapeutic protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414 (1990). For a review of the currently known gene marking and gene therapy protocols, see, Anderson et al., Science, 256: 808-813 (1992). See also WO 93/25673 and the references cited therein.

Suitable gene therapy and methods for making retroviral particles and structural proteins can be found in, e.g., U.S. Pat. No. 5,681,746.

In accordance some aspects, a method for treatment or prophylaxis of an ocular disease in a mammal is presented in which a nucleic acid molecule that encodes an CFD antagonist antibody is administered.

In some embodiments, the composition can be used as a complement pathway inhibitor, and can comprise administering the composition to an animal, a mammal, or a human, for treating a ocular disease, disorder, or condition involving complement pathway activation. The animal or subject may be an animal in need of a particular treatment, such as an animal having been diagnosed with a particular disorder, e.g., one relating to complement. Antibodies directed against Factor D are useful for inhibiting the alternative complement pathway and thus inhibiting complement pathway related disorders or conditions. In some embodiments, the composition can be used for the treatment of AMD, diabetic retinopathy, and/or choroidal neovascularization.

Formulations

Therapeutic formulations of the CFD antagonist antibodies and CFD antagonist antibody conjugates used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the CFD antagonist antibody and/or CFD antagonist antibody conjugate are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic CFD antagonist antibody and/or antibody conjugate compositions are generally placed into a container having a sterile access port, for example, an intravenous solution bag or vial having a stopper pierceable by a hypodermic injection needle. In some embodiments, the antibody and/or antibody conjugate compositions are placed into a syringe to provide a prefilled syringe.

In some embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. For systemic injection such as IV or IP, the Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In some embodiments, the compositions or methods provided herein allow for 0.1 EU/eye/injection. In some embodiments, the compositions or methods provided herein allow for 0.05EU/eye/injection. In some embodiments, the compositions or methods provided herein allow for 0.02EU/eye/injection. In some embodiments, the compositions or methods provided herein allow for 0.01EU/eye/injection.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as Polysorbate or polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.01%, and 5% surface-active agent, and can be between 0.01 and 0.02% or 0.1 and 2.5% (polysorbate 20 or 80). It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 m, particularly 0.1 and 0.5 µm, and have a pH in the range of 5.5 to 8.0.

The emulsion compositions can be those prepared by mixing an CFD antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the antibodies described herein. Kits of the invention include one or more containers comprising an CFD antagonist antibody or conjugate described herein and instructions for use in accordance with any of the methods of the invention described herein. Generally, these instructions comprise a description of administration of the CFD antagonist antibody or conjugate for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an CFD antagonist antibody or conjugate generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as prefilled syringe, an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an CFD antagonist antibody or conjugate. The container may further comprise a second pharmaceutically active agent.

Kits may optionally provide additional components such as buffers and interpretive information. In some embodiments, the kits can include an additional syringe and needle used for back fill of the dosing syringe. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1—Initial Antibody Generation and Screening

Antibodies against human Complement Factor D (CFD) was generated and screened for binding by AbCellera Biologics. Briefly, rodents were immunized with CFD purified from human serum, and single antibody-secreting cells were enriched and isolated into nanoliter-volume chambers and used in bead-based binding assays to identify antibodies against CFD with diverse epitope binding.

414 cells expressing antibodies exhibiting diverse binding phenotypes were selected for sequencing to recover the heavy and light chain sequences. 146 unique pairs of heavy and light chains were identified.

TABLE 1.1

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| FKCD001 | EVQLQQSGPELVKPGASVKISCKASDNSFTGYYMHWVKQSHGNILDWIGYIDPYNGVSSYNQKFKGKATLTVDKSSSTAYMEIRSLTSEDSAVYYCASYYGSSPYWYFDVWGTGTTVTVSS (SEQ ID NO: 335) | KCD001 | QIVLSQSPAILSASPGEKVTMTCRASSSVSYMHWYQQKPGSSPKPWIYATSNLASGVPARFSGSGSGTSHFLTISRLEAEDAATYFCQQWSSNPYTFGGGTKLEIK (SEQ ID NO: 336) |
| KCD002 | EVKLVESEGGLVQPGSSMKLSCTASGFTFSDYYMAWVRQVPEKGLEWVGNINYDGSSTYYLDSLKSRFIISRDSAKNILYLQMSSLKSEDTATYFCARGEDFYLYAMDYWGQGTSVTVSS (SEQ ID NO: 337) | KCD002 | DIQMTQSPASLSASVGETVTITCRASENIHSYLAWYQQKQGKSPQLIVYNTKTLAEGVPSRFSGSGSGTQFSLKINSLQPEDFGSYYCQHHYGIPPTFGGGTKLEIK (SEQ ID NO: 338) |
| KCD003 | EVQLQQSRPELVKPGASVKIFCKASGYTFTDYYMNWMRQRHGETLEWIGDINPNNGDPSYNQKFKDKATLTVDKSSSTASMELRSLTSDDSAVYYCAREGPSFAYWGQGTLVTVSA (SEQ ID NO: 339) | KCD003 | DVLMTQTPLSLPVSLGEQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 340) |
| KCD004 | EVQLQQSGAELVRPGSSVKMSCKTSGKTFTSHGINWVKQRPGQGLEWIGYIYIGNGYNEYNEKFKGKATLTSDTSSSTAYMQLSSLTFEDSAIYFCVRKAYGNYGFDDWGQGTTLTVSS (SEQ ID NO: 341) | KCD004 | DIQMTQSPTSLSASLGESVSLTCRASQEISGYLNWLQQKPDGSIKRLIYAASTLDSGVPKRFSGSRSGSDYSLTISSLESEDFADYYCLQYANYPFTFGSGTKLEVK (SEQ ID NO: 342) |
| KCD005 | EVQLQQSGPELVKPGASVKISCKASGYTFTDHYMNWVKQSHGKSLEWIGDINPNNGGTSCNQKFKGKATLTVDKSSSTAYMELRSLTSGDSAVYYCTREGASFAFWGQGTLVTVSA (SEQ ID NO: 343) | KCD005 | DVLMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPVTFGAGTKLELK (SEQ ID NO: 344) |
| KCD006 | EVQLQQSGAELVKPGASVKLSCTASGFKIKDTYMHWVKERPEQGL | KCD006 | QIILTQSPAIMSASPGEKVTMTCSARSSVSNMYWYQQKPGSSPRLLI |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | EWIGRIDPANGNTKYDPKFQGKA TITADTSSNTAYLQLSSLTSEDTA VYYCANAMDYWGQGTSVTVSS (SEQ ID NO: 345) | | YDTSNLASGVPVRFSGSGSGTSYS LTISRMEAEDAATYYCQQWSSYP WTFGGGTKLEIK (SEQ ID NO: 346) |
| KCD007 | EVQLQQSGAELVKPGASVKLSCT ASGFKIKDTYMHWVKERPEQGL EWIGRIDPANGNTKYDPKFQGKA TITADTSSNTAYLQLSSLTSEDTA VYYCANAMDYWGQGTSVTVSS (SEQ ID NO: 347) | KCD007 | QIILTQSPAIMSASPGERVTMTCS ASSSVSNMYWYQQKPGSSPRLLIY DTSNLASGVPLRFSGSGSGTSYSL TISRMEAEDAATYYCQQWSSYPW TFGGGTKLEIK (SEQ ID NO: 348) |
| KCD008 | EVQLQQSGPELVKAGASVKMSCT ASGFNIKDTYMHWVKQRPEQGL AWIGRIDPANGNIKYDPKFQGKA TITADTSSNTAYLQLSSLTSDDTA VYYCTSAMDYWGQGTSVTVSS (SEQ ID NO: 349) | KCD008 | QIVLTQSPEIMSASPGEKVTMTCS ARSSVSYMYWYQQKPGSSPRLLIY DTSNLASGVPVRFSGSGSGTSYSL TISRMETEDAATYYCQQWSTYPF TFGSGTKLEIK (SEQ ID NO: 350) |
| KCD009 | QIQLVQSGPELKKPGETVKISCKA SGYIFRNYGMNWVKQGPGKGLK WMGWINTYTGEPTYADDFKGRF AFSLETSASTAYLQISNLKNEDTA TYFCVRDGPGFAYWGQGTLVTV SA (SEQ ID NO: 351) | KCD009 | DVLMTQTPLSLPVSLGDQASISCR SSLIIEHSDGNTYLEWYLQKPGQS PKLLIYKVSNRFSGVPDRFSGSGS GTDFTLKISRVEADDLGVYYCFQ GSHVPVTFGAGTNLELK (SEQ ID NO: 352) |
| KCD010 | EVLLQQSGPELVKPGASVKIPCK ASGYTFTDYDMDWVKQSHGKSL EWIGHINPNNGGTIYNQKFKGKA TLTVDKSSSTAYMELRSLTSEDTA VYYCGTGDFAYWGHGTLVTVSA (SEQ ID NO: 353) | KCD010 | QIVLTQSPAIMSVSPGEKVTLTCS ASSSVSSSYLYWYQKKPGSSPKLW IYSTSNLASGVPARFSGSGSGTSY SLTISSMEAEDAASYFCHQWSSY PPTFGAGTKLELK (SEQ ID NO: 354) |
| KCD011 | EVKLVESGGGLVQPGGSLKLSCA ASGFTFSSNTMSWVRQTPEKRLE WVAYITNGGGSTYYPDTVKGRFT ISRDNARNTLYLQMSSLKSEDTA MYYCARHDYYTMDYWGQGTSVT VSS (SEQ ID NO: 355) | KCD011 | DIQMTQSPSSLSASLGGKVTITCK ASQDINKYIAWYQHKPGKGPRLL IHYTSTLQPGIPSRFSGSGSGRDY SFSISNLEPEDIATYYCLQYDNLL YTFGGGTKLEIK (SEQ ID NO: 356) |
| KCD013 | EVQLQQSGAELVKPGASVKLSCT ASGFKIKDTYMHWVKERPDQGL EWIGRIDPANGNTKYDPKFQGKA TITADTSSNTAYLQLSSLTSEDTA VYYCANAMDYWGQGTSVTVSS (SEQ ID NO: 357) | KCD013 | QIILTQSPAIMSASPGEKVTMTCS ASSSVSNMYWYQQKPGSSPRLLIY DTSNLASGVPVRFSGSGSGASYSL TISRMEAEDAATYYCQQWSSYPW TFGGGTKLEIK (SEQ ID NO: 358) |
| KCD014 | EVKLVESGGGLVQPGGSLKLSCA ASGFTFSSYIMSWVRQTPEKRLE WVAYITNGGGNTYYPDTIKGRFTI SRDNAKNTLYLQMSSLKSEDTAM YYCARHGTGYAMDYWGQGTSVT VSS (SEQ ID NO: 359) | KCD014 | EIVLTQSPTTMAASPGEKITITCS ASSSISSNYLHWYQQKPGFSPKLL IYRTSNLASGVPARFSGSGSGTSY SLTIGTMEAEDVATYYCQQGSSIP LTFGAGTKLELK (SEQ ID NO: 360) |
| KCD015 | EVQLQQSGAELVKPGASVKLSCT ASGFNIKDTYMHWVKQRPEQGL EWIGRIDPANGYTEYDPKFQGKA TITADTSSNTAYLQLSSLTSEDSA AYYCTSAMEFWGQGTSVTVSS (SEQ ID NO: 361) | KCD015 | QIVLTQSPAILSASPGEKVTMTCS ASSSVSYIYWYQQKPRSSPRLLIY DTSNLASGVPVRFSGSGSGTSYSL TISRMEAEDAATYYCQQWSSYPF TFGGGTKLEVK (SEQ ID NO: 362) |
| KCD016 | QVQLQQSGAELAKPGASVKMSC KASGYTFTNFWMHWVKQRPGQ GLEWIGFFNPSTAYTEYNQKFKD KATLTADKSSSTAYLHLSSLTSED SAVYYCARRDYGSSYGWYFDVW GAGTTVTSS (SEQ ID NO: 363) | KCD016 | DIQMTQSPASLSASVGETVTITCR ASGNIHNYLAWYQQKQGKSPQLL VYNAKTLADGVPSRFSGSGSGTQ YSLKINSLQPEDFGYYYCQHFWS TPTFGGGTKLEIK (SEQ ID NO: 364) |
| KCD017 | DVQLQESGPDLVKPSQSLSLTCT VTDYSITSGYSWHWIRQFPGNKL EWLGYIHSSGNTNYNPSLKSRFSI TRDTSKNQFFLQLNSVTSEDTAT YYCALHYYGSSFGWYFDVWGAG TTVTVSS (SEQ ID NO: 365) | KCD017 | DIVMTQSHKFMSTSVGDRVYITC KASQDVGTAVAWYQQTSGQSPKL LIYWASTRHTGVPDRFTGSGSGT DFTLTLSNVQSEDLADYFCQQYT SYPLTFGAGTKLELK (SEQ ID NO: 366) |
| KCD018 | QVQLQQSAAELARPGASVKMSCK ASGYTFTSYTVHWVKQRPGQGLE WIGYINPSSGFTDYNQKFKDKTT LTADISSSTAYIQLSSLTSEDSAVY YCARRGVNWSWFAYWGQGTLVT VSA (SEQ ID NO: 367) | KCD018 | NIMMTQSPSSLAVSAGEKVTMSC KSSQSVLYSSNQKNYLAWYQQKP GQSPQLLIYWASTRESGVPERFT GSGSGTDFTLTISSVQAEDLAVYY CHQYLSSWTFGGGTKLEIK (SEQ ID NO: 368) |
| KCD019 | QVQLQQSGAELARPGASVKMSC KASGYTFATYTIHWVKQRPGQGL EWIGYLNLRNDYTHYNQKFRDK AALTADKSSSTAYMQLSSLTSEDS | KCD019 | DIVMTQAHRFMSTSVGDRVHSC KASQDVGTAVAWYQQTPGQSPKI LIYWTSTRHTGVPDRFTGSRSGT DFTLTISNVQSEDLADYFCQQYT |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | AVYNCAFRLGNDRQGWYFDVW GAGTTVTVSS (SEQ ID NO: 369) | | TYPLTFGGGTKLEIK (SEQ ID NO: 370) |
| KCD022 | DVQLQESGPDLVKPSQSLSLTCT VTGYSITSGYSWHWIRQFPGNTL EWMGYIHYSGSTNYNPSLESRISF TRDTSKNQFFLQLNSVTTEDTAT YYCALHFYGYNLGWYFDVWGAG TTVTVSS (SEQ ID NO: 371) | KCD022 | DIVMTQSHKFMSTSIGDRVHTCK ASQDVGTTVAWYQQRPGQSPKLL IYWASTRHTAVPDRFTGSGSGTD FTLTISNVQSEDLADYFCQQYTSY PLTFGAGTQLELK (SEQ ID NO: 372) |
| KCD023 | EVLLQQSGPELVKPGASVKIPCK ASGYTFTDYNIDWVKQSHGKSLE WIGDINPNNGGINYNQKFKGKAT LTVDKSSSTAYMELRSLTSEDTAV YYCGTGDYAYWGQGTLVTVSA (SEQ ID NO: 373) | KCD023 | QIVLTQSPAFMSASPGEKVTLTCS ASSSVSSSYLYWYQQKPGSSPKLW IYSTSNLASGVPGRFSGSGSGTSY SLTISSMEAEDAASYFCHQWTSY PPTFGAGTKLELK (SEQ ID NO: 374) |
| KCD030 | QVQLQQSGAELAKPGASVKMSC KASGYTFTNYWMHWVKQRPGQ GLEWIGYINPSIGYTEYNQKFKDK ATLTADKSSSTAYMQLSSLTSEDS AVFYCATFIYYAMDYWGQGTSVT VSS (SEQ ID NO: 375) | KCD030 | DIQMNQSPSSLSASLGDTITITCH ASQNINVWLSWYQQKPGNIPKLL IYKASNLHTGVPSRFSGSGSGTGF TLTISSLQPEDIATYYCQQGQSYP YTFGGGTKLEIK (SEQ ID NO: 376) |
| KCD033 | EVQLQQSGPELVKPGASMKISCT ASGYSFTGYTMTWVKQSHGKNL EWIGLINPYNGGTNYNQKFKGKA TLTVDKSSSIAYMELLSLTSEDSA VYYCARRHYGSNWDYWGQGTTL TVSS (SEQ ID NO: 377) | KCD033 | DIKLTQSPSSIYTSLGERVTITCKA SQDINTYLSWFQQRPGKSPKTLIY RADRLVDGVPSRVRGSGSGQDYS LTISSLEYEDMGIYYCLQYDEFPY TFGGGTKLEIK (SEQ ID NO: 378) |
| KCD036 | EVQLQQSGPELVKPGASMKISCK ASGYSFTGYTMTWVKQSHGKNL EWIGLINPYNGGTNYNQKFKGKA TFTVDKSSSTAYMELLSLTSEDSA VYYCARRHYGSSWDYWGQGTTL TVSS (SEQ ID NO: 379) | KCD036 | DIKLTQSPSSMYASLGERVTITCK ASQDINTYLSWFQQKPGKSPKTLI YRANRLVDGVPSRFSGSGSGQDY SLTISSLEYEEMGIYYCLQYDEFP YTFGGGTKLEIK (SEQ ID NO: 380) |
| KCD038 | EVQLQQSGPELVKPGTSMKISCK ASGYSFADYTMNWVKQSHGKSL EWIGLINPYNGGTSYNQKFMGKA TLTVDKSSSTAYMELLSLTSEDSA VYYCARWGTYSHNYDYAMDYWG QGTSVTVSS (SEQ ID NO: 381) | KCD038 | DVVMTQTPLSLPVSLGDQASISC RSSQSLVHSNGNTYLYWYFQKPG QSPKFLIYKVSNRFSGISDRFSGS GSGTDFTLKISRVEAEDLGVYFC SQSTHVPPFTFGSGTKLEIK (SEQ ID NO: 382) |
| KCD039 | EVQLQQSGPEMVKPGASMKISCK ASGYSFADYTLNWVKQSHGKSLE WIGLINPYNGGTSYNQKFMGKAT LTVDKSSSTAYMELLSLTSEDSAV YYCTRWGTYSHNYDYAMDYWGQ GTSVTVSS (SEQ ID NO: 383) | KCD039 | DVVMTQTPLSLSVSLGDQASISCR SSQSLVHSNGNTYLYWYLQKPGQ SPKLLIYKVSNRFSGITDRFSGSG SGTDFTLKISRVEAEDLGVYFCS QSTHVPPFTFGSGTKLEIK (SEQ ID NO: 384) |
| KCD040 | EVQLQQSGAELVKPGASVKLSCT ASDFNIKDTYMHWVMQRPEQGL EWIGKIDPANGNTEFDPKFQGKA TITADTSSNTAYLQLTSLTSEDTA VYYCTRAMDYWGQGTSVTVSS (SEQ ID NO: 385) | KCD040 | QIVLTQSPAIMSASPGEKVTMTCS AGSSVSYMYWYQQKPGSSPRVLI YDTSNLASGVPVRFSGSGSGTSYS LTISRMEAEDAATYYCQQWSNYP YTFGGGTKLEIK (SEQ ID NO: 386) |
| KCD042 | EVQLQQSGAELVKPGASVRLSCT ASGFNIKHTYIHWVSQRPEQGLE WIGKIDPANGNTKYDPKFQGKAT ITADTSSNTAYLQLSSLTSEDTAV YYCVNAMEYWGQGTSVTVSS (SEQ ID NO: 387) | KCD042 | QSVLTQSPAIMSASPGEKVTMTC SANSSVSDMYWFQQRPGSSPRLL IYDTSNLASGVPVRFSGSGSGTSY SLTISRMEAEDAAYYCQQWSTY PWTFGGGTKLEIK (SEQ ID NO: 388) |
| KCD044 | EVQLQQSGAELVKPGASVRLSCT ASGFNIKHTYMHWVSQRPERGL EWIGKIDPANGNTKYDPKFQGKA TITADTSSNTVYLQLSSLTSEDTA VYYCLNAMEYWGQGTSVTVSS (SEQ ID NO: 389) | KCD044 | QSVLTQSPAIMSASPGEKVTMTC SANSSVSDMYWYQQRPGSSPRLL IYDTSNLASGVPVRFSGSGSGTSY SLTISRMEAEDAATYYCQQWSTY PWTFGGGTKLEIK (SEQ ID NO: 390) |
| KCD047 | EVQLQQSGAEFVKPGASVRLSCT ASGFNIKDTYMHWVKQRPEQGL EWIGRIDPANGYTKDDPKFQGKA TITADTSSNTAYLQLSSLTSEDTA VYYCASAMDYWGQGTSVTVSS (SEQ ID NO: 391) | KCD047 | QIVLTQSPAVMSASPGEKVAMTC SASSSVTYMYWYQQKPGSSPRLLI YDTSNLASGVPVRFSGSGSGTSYS LTISRMEAEDAATYYCQQWSTYP FTPGSGTKLEIK (SEQ ID NO: 392) |
| KCD048 | EVQLQQSGADLVKPGASVKLSCT ASGFNIKATYMHWVRQRPEKGL EWIGRIDPANGHTIYDPQFQGKA TITSDTSSNTAYLQLNSLTSEDTA VYYCAEAMDYWGQGTSVTVSS (SEQ ID NO: 393) | KCD048 | QIVLTQSPAIMSASPGEKVTLTCS ATSSVSYMYWYQQKPGSSPRLLIY DTSNLASGVPVRFSGSGSGTSYSL TISRMEAEDDATYYCQQWSNYPF TFGGGTKLEIK (SEQ ID NO: 394) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD049 | QVQLKESGPGLVAPSQSLSITCTVSGFSLSSYGVQWVRQPPGQGLEWLVVIWRDGSITYNSALKSRLSISKDNSKSQVFLKMNSLQTDDTAMYYCGRTSHYGNYNYYVMDYWGQGTAVTVSS (SEQ ID NO: 395) | KCD049 | DIVMTQSPASLAVSLGQRATISCRASESVDKYGISFLNWFQQKPGQPKLLIYAASNQGSGVPARFSGSGSGTDFSLNIHPMEEDDPAMYFCQQGKEVPWTFGGGTKLEIK (SEQ ID NO: 396) |
| KCD050 | QVQLKESGPGLVAPSQSLSITCTVSGFSLNSYGVQWVRQPPGQGLEWLVVIWRDGTITYNSALKSRLSINKDNSKSQVFLKMNSLQTDDTAMYYCGRTSHYGNFNYYVMDYWGQGTAVTVSS (SEQ ID NO: 397) | KCD050 | DIVMTQSPTSLAVSLGQRATISCRASESVDKYGISFLNWFQQKPGQPPRLLIYAASNQGSGVPARFSGSGSGTDFSLNIHPMEEDDPAVYFCQQGKEFPWTFGGGTKLEIK (SEQ ID NO: 398) |
| KCD052 | QVQLKESGPGLVAPSQSLSITCTVSGFSLNSYGVQWVRQPPGQGLEWLGVIWRDGSITYNSALKSRLSIRKDNSKSQVFLKMNSLQTDDTAMYYCGRTSHYGNYNYYVMDYWGQGTAVTVSS (SEQ ID NO: 399) | KCD052 | DIVMTQSPASLAVSLGQRATISCRASESVDKYGISFLNWFQQKPGQPKLLIYAASNQGSGVPARFSGSGSGTDFSLNIHPMEEDDPAIYFCQQGKEVPWTFGGGTKLEIK (SEQ ID NO: 400) |
| KCD056 | EVKLVESGGGLVQPGGSLKVSCAASGFTFSTYTMSWVRQTPEKRLEWVAYITNGGGSTYYPDTEKGRFTISRDNAKNTLYLQMSSLKSEDTAMYYCVRHDYYAMDYWGQGTSVTVSS (SEQ ID NO: 401) | KCD056 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTTLEIK (SEQ ID NO: 402) |
| KCD057 | EVKLVESGGGLVQPGGSLKLSCAASGFTFSNYIMSWVRQTPEKRLEWVAYITNGGGATYYPDTVKGQFTISRDNAKNTLYLQMSSLKSEDTAIYYCARHDFYALDFWGQGTSVTVSS (SEQ ID NO: 403) | KCD057 | DIQMTQSPSSLSASLGGKVTITCKASQDINKYIAWYQHKPGKGPRLLIHYTSTLQPGIPSRFSGSGSGRDYSFSISNLEPEDIATYYCLKYDNLLYTFGGGTKLEIK (SEQ ID NO: 404) |
| KCD058 | EVKLVESGGDLVQPGGSLKLSCAASGFTFSRYIMSWVRLTPEKRLEWVAFITNGGGNTYHPDTVKGRFTISRDNANNTLYLQMSSLKSEDTAIYYCARHDYYALDYWGQGTSVTVSS (SEQ ID NO: 405) | KCD058 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTKLEIK (SEQ ID NO: 406) |
| KCD062 | EVKLVESGGGLVQPGGSLKLSCAASGFTFSTYIMSWVRQTPEKRLEWVAYITSGGSSTYYPDTVKGRFTISRDNAKSTLYLQMSSLKSEDTAMYYCARHAHFYAMDYWGQGTSVTVSS (SEQ ID NO: 407) | KCD062 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTKLEIK (SEQ ID NO: 408) |
| KCD063 | EVKLVESGGGLVQPGGSLKLSCAASGFIFSSYIMSWVRQTPEKRLEWVAYITNGGGSTYYPDTVKGRLTISRDNAKNTLYLQMSSLKSEDTAMYYCVRHAHYYAMDYWGQGTSVTVSS (SEQ ID NO: 409) | KCD063 | DIQMTQSPSSLSASLGGKVTITCKASQDINKYITWYQHKPGKGPRLLIHYTSTLQPGIPSRFSGSGSGRDYSFSISNLEPEDIATYYCLQYDNLLYTFGGGTKLEIK (SEQ ID NO: 410) |
| KCD064 | EVKLVESGGGLVQPGGSLKLSCAASGFTFSSYIMSWVRQTPEKRLGWVAYITSGGGSTYYPDTVKGRFTISRDNAKNTLYLQMSSLKSEDTAMYYCARHGTGYAMDYWGQGTSVTVSS (SEQ ID NO: 411) | KCD064 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTELEIK (SEQ ID NO: 412) |
| KCD065 | QVQLQQSGAELARPGASVKMSCKASGYTFTTYTIHWVKQRPGQGLEWIGYINPSSDFTNYNQNFADKATLTADRSSSTAYMQLSSLTSEESAVYYCAIRLGYDRQGWYFDVWGAGTTVTVSS (SEQ ID NO: 413) | KCD065 | DIVMTQSHKFLSTSLGDRVSITCKASQDVGSAVAWYQQKPGQSPDLLIYWTFTRHTGVPDRFTGSRSGTDFTLTISNVQSGDLADYFCQQYSNYPLTFGGGTKLEIK (SEQ ID NO: 414) |
| KCD066 | QVQLQQSAAELARPGASVKMSCKASGYTFTDYTMHWVKQRPGQGLEWIGYINPSGGYTDYNQKFKDKTALTADKSSSTAYMQLSSLTSEDSAVYYCARRRDYWFAYWGQGTLVTVSA (SEQ ID NO: 415) | KCD066 | DIVMSQSPSSLAVSVGEKVTMSCKSSQSLLYSGNQKNYLAWYQQKPGQSPKLLIYWASTRESGVPDRFTGSGSGTDFTLTISSVKAEDLAVYYCHQYYSYLTFGAGTKLELK (SEQ ID NO: 416) |
| KCD070 | EIQLQQTGPELVKPGASVKISCKASGYSFTDYIILWVKQSHGKSLEWIGNINPYYDYTSYNLKFKGKATLTVDKSSSTAYMQLNSLTSEDSAVYYCARSDGYYGGDYWGQGTSVTVSS (SEQ ID NO: 417) | KCD070 | DIVMTQSHKFMSTSVGDRVSITCKASQDVGTAVAWYQQKPGQSPKLLIYWASTRHTGVPDRFTGSGSGTDFTLTINNVQSEDLADYFCQQYSSYPWTFGGGTTLEIK (SEQ ID NO: 418) |
| KCD075 | QVQLLQPGAELVRPGTSVKLSCKASGYTFSNYWINWVKQRPGQGL | KCD075 | DIQMTQTTSSLSASLGDRVTISCSGGQGISNYLNWYQQKPDGTFKLL |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | EWIGNIYPSDSSINYNQKFKDKAT LTVDKSSTTAYMQLSSPTSEDSAV YYCTGTDWYFDVWGAGTTVTVS S (SEQ ID NO: 419) | | IYYTSTLHSGVPSRFSGSGSGTDY SLTISNLEPEDVATYYCQQYSKLP YTFGGGTKLEIK (SEQ ID NO: 420) |
| KCD077 | EVQLQQSGAELVRPGALVKLSCK ASGFNIKDYYMHWVKQRPEQGL EWIGWIDPENGHTYDPRFQGKA TITADTSSNTAYLQLSSLTSEDTA VYYCSRGLLGFAYWGQGTLVTVS A (SEQ ID NO: 421) | KCD077 | DIVMTQSQKFMSTSVGDRVSVTC KASQNVGTNVAWYQQKPGQSPK ALIYTASYRYSGVPDRFTGSGSGT DFTLTISNVQSEDLAEYFCQQYN SYPHMYTFGGGTKLEIK (SEQ ID NO: 422) |
| KCD101 | QVQLQQPGAELVRPGTSVKLSCK ASGYTFTSYWMHWVKQRPGQGL EWIGVIDPSDSYTNYNQKFKGKA TLTVDTSSSTAYMQLSSLTSEDSA VYYCGRNGYDGSMDYWGQGTSV TVSS (SEQ ID NO: 423) | KCD101 | DIQMTQTTSSLSASLGDRVTISCR ASQDISNYLNWYQQKPDGTVKLL IYYPSRLHSGVPSRFSGSGSGTDY SLTISNLEQEDFATYFCQQGNTL PYTFGGGTKLEIK (SEQ ID NO: 424) |
| KCD102 | QVQLQQPGAELVRPGTSVKLSCK ASGYTFTSYWMHWVKQRPGQGL EWIGVIDPSDSYTNYNQKFKGKA TLTVDTSSSTAYMQLSSLTSEDSA VYYCARNGYDGSMDYWGQGTSV TVSS (SEQ ID NO: 439) | KCD102 | EIQMTQTTSSLSASLGDRVTISCR ASQDISNYLNWYQQKPDGTVKLL IYYPSRLHSGVPSRFSGSGSGTDY SLTISNLEQEDFATYFCQQGNTL PYTFGGGTKLEIK (SEQ ID NO: 440) |
| KCD103 | QVQLQQPGAELVRPGTSVKLSCK ASGYTFTSYWMHWVKQRPGQGL EWIGVIDPSDSYTKYNQKFKDKA TLTVETSSSTAYMQLSSLTSEDSA VYYCAGNGYDGSMDYWGQGTSV TVSS (SEQ ID NO: 459) | KCD103 | DIQMTQTTSSLSASLGDRVTISCR ASQDISNSLNWYQQKPDGTVKLL IYYTSRLHSRVPSRFSGSGSGTDY SLTISNLDQEDIATYFCQQANTLP YTFGGGTKLEIK (SEQ ID NO: 460) |
| KCD104 | QVQLQQPGAELVRPGTSVKLSCK ASGYTFTSYWMHWVKQRPGQGL EWIGVIDPSDSYTYYNQKFKGKA TLTVDTSSSTAYMQLSSLTSEDSA VYYCARNGYDGAMDYWGQGTSV TVSS (SEQ ID NO: 477) | KCD104 | EIQMTQTTSSLSASLGDRVTISCR ASQDISNYLNWYQQKPDGTVKLL IYYPSRLHSGVPSRFSGSGSGTDY SLTISNLEQEDFATYFCQQGNTL PYTFGGGTKLEIK (SEQ ID NO: 478) |
| KCD110 | EVQLQQSGPELVKPGASVKISCK ASGYSFTGYYMHWVKQSHGNIL DWIGYIDPDNGVSSKNQKFTGKA TVTADKSSSTAYMELRSLTSEDSA VYYCAGYYGSSWYWYFDVWGTG TTVTVSS (SEQ ID NO: 425) | KCD110 | QIVLSQSPAILSASPGEKVTMTCR ASSSVSYMHWYQQKPGSSPKPWI YATSNLASGVPARFSGSGSGTSYS LTISRVEAEDAATYYCQQWSSNP YTFGGGTKLEIK (SEQ ID NO: 426) |
| KCD111 | EVQLQQSGPELVKPGASVKISCK ASGYSFTDYYMHWVKQSHGNIL DWIGYIDPYNGVSSYNQKFKGKA TLSVDQSSSTAYMELRSLTSEDSA VYYCSSYYGSSPYWYFDVWGTGT RVTVSS (SEQ ID NO: 427) | KCD111 | QIVLSQSPAILSASPGEKVTMTCR ASSSVSYMHWYQQKPGSSPKPWI YATSNLASGVPTRFSGSGSGTSYS LTISKLEAEDAATYYCQQWSSNP YTFGGGTKLEIK (SEQ ID NO: 428) |
| KCD112 | EVQLQQSGPELVKPGASVKISCK ASGYSFTAYYMNWVKHSPEKSLE WIGDINPSTGGTTYNQKFKARAT LTVDKSSSTAYMQLKSLTSEDSAV YYCATTYYSGNSYVGFAYWGQGT LVTVSA (SEQ ID NO: 429) | KCD112 | DIVMTQSHKFMSTSVGDRVSITC KASQDVSTAVAWYQQKPGQSPKL LIFWTSTRHTGVPDRFTGSGSGT DYTLTISSVQAEDLALYYCQQHYT TPWTFGGGTKLEIK (SEQ ID NO: 430) |
| KCD114 | EVQLQQSGPELVKPGASVKISCK ASGYSFTAYYMNWVKQSPEKSLE WIGDINPSTGGTTYNQNFKAKAT LTVDKSSSTAYMHLKSLTSEDSA VYYCATTYYSGNSYVGFAYWGQG TLVTVSA (SEQ ID NO: 431) | KCD114 | DIVMTQSHKFMSTSVGDRVSITC KASQDVSTAVAWYQQKPGQSPKL LIFWASTRHTGVPDRFTGSGSGT DYTLTISSVQAEDLALYYCQQHYS TPWTFGGGTKLEIK (SEQ ID NO: 432) |
| KCD115 | EVQLQQSGPELVKPGASVKISCK ASGYSFTGYYMNWVKQSPEKSLE WIGDINPSTGGTTYNQKFKAKAT LTVDKSSSTAYMQLKSLTSEDSAV YYCATPYYYGSSYVGFAYWGQGT LVTVSA (SEQ ID NO: 433) | KCD115 | DIVMTQSHKFMSTSVGDRVSITC KASQDVSTAVDWYQQKPGQSPKL LIYWASTRHTGVPDRFTGSGSGT DYTLTISSVQAEDLALYYCQQHYS TPWTFGGGTKLEIK (SEQ ID NO: 434) |
| KCD118 | EVQLQQSGPELVKPGASVKISCK AFGYTFTDYYKNWMRQRHGESL EWIGDINPNSGDANYNQKFKGKA TLTVDKSSTAYMELRSLTSEDSA VYYCAREGPSFAYWGHGTLVTVS A (SEQ ID NO: 435) | KCD118 | DVLMTQTPLSLPVSLGDQASISCR SSQTIVHSNGDTYLEWYLQKPGQ SPNLLIYKVSNRFSGVPDRFSGSG SGTDFTLKISRVEAEDLGIYYC GSHVPPTFGGGTKLEIK (SEQ ID NO: 436) |
| KCD119 | EVQLQQSGPELVKPGASVKISCK ASGYTFTDYYTNWMRQRHGESL EWIGDINPNTGDTSYNQKFRVKA TLTVDKSSGTAYMGLRSLTSEDS | KCD119 | DVLMTQTPLSLPVSLGDQASISCR SSQTIVHSNGDTYLEWYLQKPGQ SPNLLIYKVSNRFSGVPDRFSGSG SGTDFTLKISRVEAEDLGVYYCF |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | AVYYC<u>TREGPSFAY</u>WGQGTLVTVSA (SEQ ID NO: 437) | | <u>QGSHVPPT</u>FGGGTTLEIK (SEQ ID NO: 438) |
| KCD121 | EVQLQQSGPELVKPGASVKISCKASG<u>YTFTDYYKN</u>WMRQRHGESLEWIG<u>DINPNNGDTSYNQKFRG</u>KATLTVDKSSSTAFMELRSLTSEDSAVYYC<u>AREGPSFAY</u>WGQGTLVTVSA (SEQ ID NO: 441) | KCD121 | DVLMTQTPLSLPVSLGDQASISCR<u>SNQTIVHSNGDTYLE</u>WYLQKPGQSPNLLIY<u>KVSNRFS</u>GVPDRFSGSGSGTDFTLRISRVEAEDLGVYYC<u>FQGSHVPPT</u>FGGGTKLEIK (SEQ ID NO: 442) |
| KCD122 | EVQLQQSGPELVKPGASVKISCKASG<u>YTFTDYYKN</u>WMRQRHGESLEWIG<u>DINPNNGDANYNQKFKG</u>KATLTVDKSSSTAYMELRSLTSEDSAVYFC<u>AREGPSFAY</u>WGHGTLVTVSA (SEQ ID NO: 443) | KCD122 | DVLMTQTPLSLPVSLGDQASISCR<u>SSQTIVHSNGDTYLE</u>WYLQKPGQSPNLLIY<u>KVSNRFS</u>GVPDRFSGSGSGTDFTLKISRVEAEDLGVYYC<u>FQGSHVPPT</u>FGGGTKLEIK (SEQ ID NO: 444) |
| KCD123 | EVHLQQSGPELVKPGASVKISCKASG<u>YTFTDFYKN</u>WMRQRHGESLEWIG<u>DINPNNGGTNYNQKFKG</u>KATLTVDKSSSTAYMELRSLTSEDSAVYYC<u>AREGPSFAY</u>WGQGTLVTVSA (SEQ ID NO: 445) | KCD123 | DVLMTQTPLSLPVSLGDQASISCR<u>SSQTIVHSNGDTYLE</u>WYLQKPGQSPNLLIY<u>KVSNRFS</u>GVPDRFSGSGSGTDFTLKISRVEAEDLGVYYCF<u>QGSHVPPT</u>FGGGTKLEIK (SEQ ID NO: 446) |
| KCD124 | EVQLQQSGPELVKPGASVKISCKASG<u>YTFTDHYMN</u>WVKQSHGKSLEWIG<u>DINPNNGGTSYNQKFKG</u>KATLTVDKSSSTAYMELRSLTSGDSAVYYC<u>TREGASFAF</u>WGQGTLVTVSA (SEQ ID NO: 447) | KCD124 | DVLMTQTPLSLPVSLGDQASISCR<u>SSQSIVHSNGDTYLE</u>WYLQKPGQSPKLLIY<u>KVSNRFS</u>GVPDRFSGSGSGTDFTLKISRVEAEDLGVYYC<u>FQGSHVPLT</u>FGAGTKLELK (SEQ ID NO: 448) |
| KCD125 | EVQLQQSGAELVRPGSSVKMSCKTSG<u>NTFTSYGIN</u>WVKQRPGQGLEWIG<u>YIYIGTGYTEYNEKFKG</u>KATLTSDTSSSTAYMQLSSLTSEDSAIYFC<u>VRKAYGNYGFDY</u>WGQTTLTVSS (SEQ ID NO: 449) | KCD125 | DIQMTQSPSSLSASLGERVSLTCRASQ<u>EISGYL</u>SWLQQKPDGTIKRLIY<u>AAS</u>TLDSGVPKRFSGSRSGSDYSLTISSLESEDFADYYC<u>LQYASYPF</u>TFGSGTKLEIK (SEQ ID NO: 450) |
| KCD126 | EVQLQQSGAELVRPGSSVKMSCKTSG<u>KTFTSHGIN</u>WVKQRPGQGLEWIG<u>YIYIGNGYNEYNEKFKG</u>KATLTSDTSSSTAYMQLSSLTFEDSAIYFC<u>VRKAYGNYGFDD</u>WGQTTLTVSS (SEQ ID NO: 451) | KCD126 | DIQMTQSPTSLSASLGESVSLTCRASQ<u>EISGNL</u>NWLQQKPDGSIKRLIY<u>AAS</u>TLDSGVPKRFSGSRSGSDYSLTISSLESEDFADYYC<u>LQYANYPF</u>TFGSGTKLEVK (SEQ ID NO: 452) |
| KCD127 | QVQLQQPGAELVRPESSVKLSCKASG<u>YTFTNFWMD</u>WVKQRPGQGLEWIG<u>NIYPSGSETHYNQKFKD</u>KATLTVDKSSTTAYMQLSSLTSEDSAVYYC<u>ARSGYYGSRYLYYFDY</u>WGQGTTLTVSS (SEQ ID NO: 453) | KCD127 | DIVMTQSHKFMSTSVGDRVSITCKASQ<u>DVSTA</u>VAWYQQKPGQSPKLLIY<u>SAS</u>YRSTGVPDRFTGSGSGTDFTFTISSVQAEDLAVYYC<u>QQHYSTPYT</u>FGGGTKLEIR (SEQ ID NO: 454) |
| KCD128 | QVQLQQPGAELVRPESSVKLSCKASG<u>YTFTSYWMD</u>WVMQRPGQGLEWIG<u>NIYPSGSETHYNQKFKD</u>KATLTVDKSSTTAYMQLSSLTFEDSAVYYC<u>ARSGFIGSRYLYYFDY</u>WGQGTTLTVSS (SEQ ID NO: 455) | KCD128 | DIVMTQSHKFMSTSVGDRVTITCKASQ<u>DVSNA</u>VAWYQLKPGQSPKLLIY<u>SAS</u>YRYTGVPDRFTGSGSGTDFTFTISSVQAADLAVYYC<u>QQHYITPYT</u>FGGGTKLEIK (SEQ ID NO: 456) |
| KCD129 | EVQLVESGGGLVQPKGSLKLSCAASG<u>FSFNTYAMN</u>WVRQAPGKGLEWVA<u>RIRSKSNNYAT</u>YYADSVKDRFTISRDDSESMVYLQMNNLKTEDTAMYYC<u>VRHGYYWYFDV</u>WGTGTTVTVSS (SEQ ID NO: 457) | KCD129 | DVLMTQTPLSLPVSLGDQASISCR<u>SSQSIVHSDGNTYLE</u>WYLQKPGQSPKLLIY<u>RVSNRFS</u>GVPDRFSGSGSGTDFTLKISRMEAEDLGVYYC<u>FQGSHVPYT</u>FGGGTKLEIK (SEQ ID NO: 458) |
| KCD131 | QVQLQQSGPELVKPGASVKISCKAS<u>AYTFTDYYIN</u>WVKQRPGQGPEWIGW<u>IFPGSNSTYSNEKFEV</u>KATLTVDESSSTAYMLLSSLTSEDSAVYFC<u>ARLGYFGSSYHALDY</u>WGQGTSVTVSS (SEQ ID NO: 461) | KCD131 | DIQMTQSPASLSVSVGETVTITCR<u>ASENIYSHLA</u>WFQQKQGKSPRLLVY<u>SATNLPD</u>GVPSRFSGSGSGTQYSLKINILQSEDFGSYYC<u>QHFWGTPWT</u>FGGGTKLEIK (SEQ ID NO: 462) |
| KCD132 | QVQLQQSGPELVKPGASVKISCKASG<u>YSFTDYYIN</u>WVKQRPGQGLEWIGWIFPGSGSTYYNEKFKGKATLTVDKSSSTAYMLLSSLTSEDSAVYFC<u>ARTGYYSNLYAVDY</u>WGQGTSVTVSS (SEQ ID NO: 463) | KCD132 | DIQMTQSPASLSVSVGETVTITCR<u>ASENIYSNLA</u>WYQQKQGKSPQLLVY<u>VATNLAD</u>GVPSRFSGSGSGTQYSLKINSLQSEDFGNYYC<u>QHFWGTPYT</u>FGGGTKLEMR (SEQ ID NO: 464) |
| KCD133 | EVQLVESGGGLLQPKGSLKLSCAASG<u>FTFNTYAMN</u>WVRQAPGKGLEWVA<u>RIRSKSSNYAT</u>YYADSVKDRFTISRDDSQSMFYLEMNNLKTEDTAMYYC<u>VRDRGYYYVMDY</u>WGQGTSVTVSS (SEQ ID NO: 465) | KCD133 | DIVLTQSPASLAVSLGQRATISCR<u>ASESVEYYGTSLMQ</u>WYQQKPGQPPKLLIN<u>AAS</u>NVESGVPARFSGSGSGTDFSLNIHPVEEDDIAMYFC<u>QQSRKVPWT</u>FGGGTKLEIK (SEQ ID NO: 466) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD134 | EVQLQQSGPEMVKPGASVKMSCQAS<u>GYTFTDYYMN</u>WVKQSHGETLEWIGD<u>IYPHNGYT</u>AYNQKFKGKATLTVDKSSSTAYMELRSLTSEDSAVYYC<u>ARGGQLRLPAWFAY</u>WGQGTLVTVSA (SEQ ID NO: 467) | KCD134 | ETTVTQSPASLSMAIGEKVTIRCI<u>TSTDIDDDMN</u>WYQQKPGEPPKLLIS<u>EGNSLRP</u>GVPSRFSSSGYGTDFVFTIEDMFSEDVADYHC<u>LQSDNLPYT</u>FGGGTKLEIK (SEQ ID NO: 468) |
| KCD135 | EVQLQQSGPELVKPGASVRMSCKAS<u>GYIFTDYSIH</u>WVKQSHGKSLEWIGY<u>INPNNGGT</u>SYNQKFKGKATLTVNKSSTTAYMELRSLTSEDSAVYFC<u>ARDTTIVGDY</u>WGQGTTLTVSS (SEQ ID NO: 469) | KCD135 | DIVMTQSQKFMSTSVGDRVSVTCKAS<u>QHVGTNV</u>VWYQQKPGQSPKALIY<u>SASYRYS</u>GVPDRFSGSGSGTDFTLTISNVQSEDLAEYFC<u>QQFNSYPLT</u>FGGGTKLEIK (SEQ ID NO: 470) |
| KCD136 | EVQLQQSVAELVRPGASVKLSCSAS<u>GFNIKNTYMH</u>WVNQRPEQGLEWIG<u>RIDPANGITKYAPNF</u>QGKATITADTSSNTAYLQLSNLTSEDTAIYYC<u>TRAMDY</u>WGQGTSVTVSS (SEQ ID NO: 471) | KCD136 | QIVLTQSPAIMSASPGEKVTMTCS<u>ASSSVSYMY</u>WYQQKPGSSPRLLIY<u>DISNLAS</u>GVPVRFSGSGSTSYSLTISRMEAEDAATYYC<u>QQWDTYPWT</u>FGGGTKLEIK (SEQ ID NO: 472) |
| KCD137 | EVQLVESGGDLVKPGGSLKLSCAAS<u>GFTFSGYGMS</u>WVRQIPDKRLEWVA<u>ISSRDNSFT</u>YYPDSVKGRFTISRDNAKNTLYLQMSSLKSEDTALYFC<u>TRHPYLPTGGYVMDY</u>WGQGTSVTVSS (SEQ ID NO: 473) | KCD137 | DIVMTQSHKFMSTSVGDRVSITCKAS<u>QDVGTAVA</u>WYQQRPGQSPKLLIY<u>WAST</u>RHTGVPDRFTGSGSGTDFTLTVSNVQSEDLADYFC<u>QQYTSYPLT</u>FGAGTKLELK (SEQ ID NO: 474) |
| KCD139 | EVQLQQSGAELVRPGSSVKMSCKTS<u>GYTFTSYGIN</u>WVKQRPGQGLEWIGY<u>IYIANGYTENNEKF</u>KGKAKLTSDISSSTAYMQLSSLTSEDSAIYFC<u>ARRFDYAGALDY</u>WGQGTSVTVSS (SEQ ID NO: 475) | KCD139 | DIVLTQSPASLAVSLGQRATISCRAS<u>ESVDSYGNSFMH</u>WYQQKPGQPPKLLIH<u>RASNLES</u>GIPARFSGSGSRTDFTLTINPVEADDVAIYYC <u>QQTNDDPYT</u>FGGGTNLEIK (SEQ ID NO: 476) |
| KCD200 | EVQLQQSGPELVKPGASVKISCKAS<u>GYTFTSYYKN</u>WMRQRHGESLEWIGD<u>INPNSGDT</u>AYNQKFKGKATLTVDRSSSTAYMELRSLTSEDSAVYYC<u>AREGPSFAY</u>WGQGTLVTVSA (SEQ ID NO: 479) | KCD200 | DVLMTQTPLSLPVSLGDQVSISCR<u>SSQTIVHSNGDTYLE</u>WYLQKPGQSPNLLIY<u>KVSNRFS</u>GVPDRFSGSGSGTDFTLKISRVEAEDLGVYYC<u>FQGSHVPPT</u>FGGGTKLEIK (SEQ ID NO: 480) |
| KCD205 | EVQLQQSGAELVRPGSSVKMSCKTS<u>GNTFTSHGIN</u>WVKQRPGQGLEWIGY<u>IYIGNGYNEYNEKF</u>KGKATLTSDTSSSTAYMQLSSLTSEDSAIYFC<u>VRKAYGNYGFDD</u>WGQGTTLTVSS (SEQ ID NO: 505) | KCD205 | DIQMTQSPSSLSASLGERVSLTCRAS<u>QEISGYLS</u>WLQQKPDGTIKRLIY<u>AAST</u>LDSGVPKRFSGSSSGSDYSLTISSLESDDFADYYC<u>LQYASYPF</u>TFGSGTKLEIK (SEQ ID NO: 506) |
| KCD207 | AVQLVESGGGLVQPKGSLKLSCAAS<u>GFSFNTYAMN</u>WVRQAPGKGLEWVA<u>RIRSKSNNYAT</u>YYADSVKDRFTLSRDDSESMLYLQMNNLKTEDTAMYYC<u>VRQGFYWYFDV</u>WGTGTTVTVSS (SEQ ID NO: 507) | KCD207 | DVLMTQTPLSLPVSLGDQASISCR<u>SSQTIVHSNGNTYLE</u>WYLQKSGQSPKLLIY<u>NVSNRFS</u>GVPDRFRGSGSGTDFTLKISRVEAEDLGVYYC<u>FQGSHVPYT</u>FGSGTKLEIK (SEQ ID NO: 508) |
| KCD208 | EVQLQQSVAELVRPGASVKLSCTVS<u>GFNIKNTYMH</u>WVKQRPEQGLEWIG<u>RIDPANGDTTYAPKF</u>QGKATITADTSSNSAYLHLSRLTSEDTAIYYC<u>SLYDYDGY</u>WGQGTTLTVSS (SEQ ID NO: 509) | KCD208 | EIVLTQSPALMAASPGEKVTITCS<u>VSSSISSSSLH</u>WYRQKSGTSPKPWIY<u>GTSHLAS</u>GVPVRFSGSGSGTSYSLTISSMEAEDAATYYC<u>QQWDTYPWT</u>FGGGTKLEIK (SEQ ID NO: 510) |
| KCD210 | EVQLQQSGPVLVKPGASVTMSCKAS<u>GYTFTEYYMN</u>WVKQSHGKSLDWIG<u>INPYSGGTS</u>YKQKFKDKATLTVDKSSSTAYMELNGLTSEDSAVYFC<u>VRGGLRRNYFDY</u>WGQGTTLTVSS (SEQ ID NO: 481) | KCD210 | EIVLTQSPALMTASPGEKVTITCS<u>VSSSISSTNLH</u>WYQQKSGTSPKPWIF<u>GTSNLAS</u>GVPVRFSGSGSGTSYSLTISNMEAEDAATYYC<u>QQWNSYPFT</u>FGTGTKLEIK (SEQ ID NO: 482) |
| KCD212 | EVHLVESGGDLVKPGGSLKLSCAAS<u>GFTFSRYGMS</u>WVRQTPDKRLEWVAT<u>ISSAGSYT</u>YYPDSVKGRFTISRDNAKNTLFLQMSSLKSEDTAMYYC<u>ARPLNYYGTSSFDY</u>WGQGTTLTVSS (SEQ ID NO: 483) | KCD212 | QIVLTQSPAIMSASPGEKVTMTCRAS<u>SSVSSTYLH</u>WYQQKPGSSPKLWIY<u>STSNLAS</u>GVPVRFSGSGSGTSYSLTISSVEAEDAATYYC<u>QQYDSSPNT</u>FGAGTKLELK (SEQ ID NO: 484) |
| KCD214 | EVQLQQSVAEFVRPGASVKLSCTAS<u>GFNIKNTYMH</u>WVKQRPEQGLEWIG<u>RIDPANGNTEYAPKF</u>QGKATITADTSSNTAYLQLSSLTSEDTAIYYC<u>ALYDYDGY</u>WGQGTTLTVSS (SEQ ID NO: 485) | KCD214 | EIVLTQSPALMAASPGEKVTITCR<u>VSSSISSSSLH</u>WYQQKSGTSPKPWIY<u>GTSNLAS</u>GVPVRFSGSRSGTSYSLTISSMEAEDAATYYC<u>QQWSDYPWT</u>FGGGTKLEIK (SEQ ID NO: 486) |
| KCD216 | QVHLQQSGPELVKPGASVKISCKAS<u>GYTFIDYYIN</u>WVKQRPGQGLE | KCD216 | DIQMTQSPASLSVSVGETVTITCR<u>ASENIYSNLA</u>WYQQKQGKSPQLL |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | WIGW<u>IFPGSDSTYYNEKFKGK</u>AT LTVDKSSSTAYMLLSSLTSEDSAV YFC<u>ARYGYYGSSFYAMDY</u>WGQG TSVTVSS (SEQ ID NO: 487) | | VY<u>AAT</u>NLADGVPSRFSGSGSGTQ YSLKINSLQSEDFGSYYC<u>QHFWG TPPT</u>FGGGSKLEIK (SEQ ID NO: 488) |
| KCD217 | QVQVQQPGAEFVKTGASVKLSCK TS<u>GYTFIDY</u>WIHWVKQRPGHGLE WIGR<u>IDPNTGGSK</u>YYEKFKRKAT LTVDKPSRTVYMQLSSLTSEDSA VYYC<u>TREYDYGWFGY</u>WGQGTLV TVSE (SEQ ID NO: 489) | KCD217 | DIQMTQSPASLSASVGETVTITCG AS<u>ENIYGA</u>LNWYQRKQGKSPQLL IY<u>GAT</u>NLADGMSSRFSGSGSGRQ YSLKISSLHPDDVATYYC<u>QNVLST PWT</u>FGGGTKLEIK (SEQ ID NO: 490) |
| KCD219 | QVQLQQSGPELVKPGASVKISCK AS<u>GYTFTDYYIN</u>WVKQRPGQGLE WIGW<u>IFPGSGSTY</u>YNEKFKGKAT LTVDKSSSTAYMLLSSLPSEDSAV YFC<u>ARYGYYGSSFYAMDY</u>WGQG TSVTVSS (SEQ ID NO: 491) | KCD219 | DIQMTQSPASLSVSVGETVTITCR AS<u>ENIYSN</u>LAWYQQKQGKSPQLL VY<u>AAT</u>NLADGVPSRFSGSGSGTQ YSLKINSLQSEDFGSYYC<u>QHFWG SPPT</u>FGGGTKLEIK (SEQ ID NO: 492) |
| KCD220 | QVQLQQSGAELMEPGASVKLSCK AT<u>GYTFTGYWIE</u>WVKQRPGHGL EWIG<u>ETLPGSDSNNYNEKFKGK</u>A TFTADTSSNTAYMQLSSLTTEDS AIYYC<u>ARDYSNYWYFDV</u>WGTGTT VTVSS (SEQ ID NO: 493) | KCD220 | DIQMTQTTSSLSASLGDRVTISC<u>R AS<u>QDISNYLN</u>WYQQKPDGTVKLL IY<u>YTSNL</u>HSGVPSRFSGSGSGTDY SLTISNLEQEDIATYFC<u>QQDSKHR T</u>FGGGTKLEIK (SEQ ID NO: 494) |
| KCD224 | QVQLKESGPGLVAPSQSLSITCTV SG<u>FSLTSYGVD</u>WIRQSPGKGLEW LG<u>VIWGVGSTNYNSALKS</u>RLSISK DNSKSQVFLKMNSLQTDDTAMY YC<u>ARSYDGSYWYFDV</u>WGTGTTV TVSS (SEQ ID NO: 495) | KCD224 | DIQMTQTTSSLSASLGDRVTISC<u>R AS<u>QVISNYLN</u>WYQQKPDGTVKLL IY<u>YTSRL</u>HSGVPSRFSGSGSGTDY SLTISNLEPEDIATYYC<u>QQYSKLP YT</u>FGSGTKLEIK (SEQ ID NO: 496) |
| KCD225 | QVQLQQSGPELVKPGASVKISCK AS<u>GYTFTDYYIN</u>WMKQRPGQGL EWIGW<u>IFPGSDSTY</u>YNEKFKGKA TLTVDKSSSTAYMLLSSLTSEDSA VYFC<u>ARLGYYSHSYYAMDY</u>WGQ GTSVTVSS (SEQ ID NO: 497) | KCD225 | DIQMTQSPASLSVSTGETVTITC<u>R AS<u>ENIYSN</u>LAWFQQKQGKSPQLL VY<u>AAT</u>NLADGVPSRFSGSGSGTQ YSLKITSLQSEDFGSYYC<u>QHFWG TPLT</u>FGAGTKLDLK (SEQ ID NO: 498) |
| KCD229 | EVQLVESGGGLVQPKGSLKLSCA AS<u>GFSFNTY</u>AMNWVRQAPGKGL EWVA<u>RIRSKSNNYAT</u>YYADSVKD RFTIFRDDSESMLYLQMNNLKTE DTAMYYC<u>VRHGYYWYFDV</u>WGTG TTVTVSS (SEQ ID NO: 499) | KCD229 | DVLMTQNPLSLPVSLGDQASISC R<u>SSQSIVHSNGNTY</u>LEWYLQKPG QSPNLLIY<u>NVF</u>NRFSGVPDRFSG SGSGTDFTLKISRVEAEDLGVYYC <u>FQGSHVPYT</u>FGSGTKLEIK (SEQ ID NO: 500) |
| KCD230 | QVQLQQPGTELVKPGASVKLPCK AS<u>GYTFTSYWMQ</u>WVKQRPGQGL EWIG<u>EIDPSDTYINYNQKFKGK</u>A TLTVDTSSTTAYMQLSSLTSEDSA VYYC<u>ARYTTIMASDY</u>WGQGTTLT VSS (SEQ ID NO: 501) | KCD230 | DIQMTQTTSSLSVSLGDRVTISCR AS<u>QDITNYLN</u>WYQQKPDGTVKLL IY<u>FTSRL</u>HSGVPSRFSGSGSGTDY SLTISNLEPEDIATYYC<u>QQYSKLP WT</u>FGGGTKLEIK (SEQ ID NO: 502) |
| KCD232 | EVQLVESGGGLVQPKGSLKLSCA AS<u>GFSFNTY</u>AMNWVRQAPGKGL EWVA<u>RIRSKSNNYAT</u>YYADSVKD RFTISRDDSESMVYLQMNNLKTE DTAMYYC<u>VRHGYYWYFDV</u>WGTG TTVTVSS (SEQ ID NO: 503) | KCD232 | DVLMTQTPLSLPVSLGDQASISCR SS<u>QSIVHSDGNTY</u>LEWYLQKPG SPKLLIY<u>RVS</u>NRFSGVPDRFSGSG SGTDFTLKISRMEAEDLGVYYC<u>F QGSHVPYT</u>FGGGTKLEIK (SEQ ID NO: 504) |

Example 2—Binding of Chimeric Anti-CFD Antibodies to Human and Cynomolgus CFD 100 out of the 146 unique anti-CFD mouse antibodies sequences were chosen to be recombinantly expressed in Expi293 cells and purified using mAb select for further validation. The antibodies were selected based on the robustness of the sequencing data, distance from germline sequences, and to maximize immunoglobin heavy chain CDR3 diversity. 91 antibodies were successfully expressed and evaluated further.

A kinetic screen of all of 91 antibodies binding to serum purified CFD was performed by Wasatch Microfluidics on a MX96 SPR machine, by injecting CFD at varying concentrations over an array of 96 amine coupled antibodies. Binding kinetics and affinity of the antibodies were also determined for CFD-Mutant 1, recombinant human CFD, and recombinant Cyno-CFD. Data of the kinetic screen are shown in Table 2.1 and Table 2.2. 88 out of 91 anti-CFD mouse antibodies tested showed binding to human CFD. Variable domain sequences of these 88 mouse antibodies with confirmed binding to human CFD are listed in table 1.1.

TABLE 2.1

Binding affinities of recombinantly expressed anti-CFD antibodies to human CFD.

| | ka | kd | Rmax | KD | | ka | kd | Rmax | KD |
|---|---|---|---|---|---|---|---|---|---|
| KCDKCD000 | 6.94E+05 | 1.75E-04 | 201.8 | 2.52E-10 | KCD004 | 4.44E+05 | 1.57E-04 | 97.1 | 3.53E-10 |
| KCD009 | 3.12E+05 | 1.74E-03 | 51.96 | 5.57E-09 | KCD014 | 3.77E+05 | 8.21E-03 | 8.28 | 2.18E-08 |
| KCD019 | 1.90E+05 | 1.37E-03 | 52.6 | 7.24E-09 | KCD033 | 2.38E+05 | 2.60E-03 | 101.34 | 1.09E-08 |
| KCD040 | 2.21E+05 | 4.27E-04 | 384.58 | 1.93E-09 | KCD047 | 2.94E+05 | 1.29E-03 | 324.83 | 4.37E-09 |
| KCD056 | 2.17E+05 | 1.30E-02 | 84.43 | 6.02E-08 | KCD062 | 2.19E+05 | 5.26E-03 | 90.54 | 2.40E-08 |
| KCD066 | 2.42E+05 | 6.97E-04 | 23.43 | 2.88E-09 | KCD075 | 2.65E+05 | 9.94E-04 | 309.99 | 3.75E-09 |
| KCD103 | 3.30E+05 | 1.44E-03 | 179.72 | 4.37E-09 | KCD110 | 2.41E+05 | 8.93E-04 | 121.2 | 3.71E-09 |
| KCD115 | 2.18E+05 | 2.77E-03 | 74.25 | 1.27E-08 | KCD122 | 3.59E+05 | 5.16E-04 | 174.65 | 1.44E-09 |
| KCD126 | 4.35E+05 | 1.48E-04 | 62.33 | 3.40E-10 | KCD131 | 3.46E+05 | 4.85E-05 | 164.28 | 1.40E-10 |
| KCD136 | 3.62E+05 | 1.61E-03 | 194.38 | 4.46E-09 | KCD205 | 2.76E+05 | 8.23E-04 | 138.87 | 2.98E-09 |
| KCD212 | 5.93E+05 | 2.78E-04 | 52.41 | 4.69E-10 | KCD219 | 1.94E+05 | 8.33E-04 | 242.08 | 4.30E-09 |
| KCD225 | 3.19E+05 | 2.77E-03 | 118.29 | 8.67E-09 | KCD48-2 | 2.90E+05 | 5.78E-04 | 300.35 | 1.99E-09 |
| KCD001 | 4.25E+05 | 9.56E-05 | 124.66 | 2.25E-10 | KCD005 | 5.37E+05 | 7.48E-04 | 109.08 | 1.39E-09 |
| KCD010 | 6.01E+05 | 1.84E-03 | 154.28 | 3.05E-09 | KCD015 | 2.90E+05 | 1.80E-03 | 422.7 | 6.23E-09 |
| KCD022 | 1.27E+05 | 7.21E-03 | 103.5 | 5.68E-08 | KCD036 | 1.56E+05 | 3.98E-03 | 69.76 | 2.55E-08 |
| KCD042 | 6.85E+05 | 9.81E-04 | 72.1 | 1.43E-09 | KCD048 | 3.01E+05 | 5.62E-04 | 297.54 | 1.87E-09 |
| KCD057 | 3.94E+05 | 1.07E-03 | 66.47 | 2.71E-09 | KCD063 | 1.49E+05 | 4.97E-03 | 43.25 | 3.33E-08 |
| KCD068 | 0.00E+00*** | 0.00E+00*** | 0.00E+00*** | 0.00E+00*** | KCD077 | 2.88E+05 | 4.87E-03 | 116.48 | 1.69E-08 |
| KCD104 | 4.81E+05 | 7.60E-04 | 211.38 | 1.58E-09 | KCD111 | 2.96E+05 | 1.95E-03 | 260.3 | 6.58E-09 |
| KCD118 | 5.71E+05 | 4.32E-04 | 95.9 | 7.57E-10 | KCD123 | 2.85E+05 | 7.87E-04 | 134.7 | 2.77E-09 |
| KCD128 | 1.19E+05 | 1.68E-03 | 79.94 | 1.40E-08 | KCD132 | 1.77E+05 | 4.63E-04 | 277.7 | 2.61E-09 |
| KCD137 | 1.34E+05 | 6.74E-05 | 140.51 | 5.04E-10 | KCD207 | 1.85E+05 | 1.44E-04 | 53.42 | 7.81E-10 |
| KCD214 | 1.46E+05 | 2.27E-04 | 224 | 1.56E-09 | KCD220 | 4.69E+05 | 2.51E-05 | 161.1 | 5.35E-11 |
| KCD229 | 1.39E+05 | 1.70E-04 | 48.61 | 1.22E-09 | OG1931 | 2.93E+05 | 1.46E-04 | 406.9 | 4.97E-10 |
| KCD002 | 1.26E+06 | 1.67E-04 | 92.4 | 1.32E-10 | KCD006 | 4.00E+05 | 2.52E-03 | 181 | 6.30E-09 |
| KCD011 | 1.95E+05 | 1.51E-02 | 84.2 | 7.75E-08 | KCD017 | 1.73E+05 | 1.35E-03 | 146.58 | 7.85E-09 |
| KCD023 | 5.24E+05 | 2.77E-03 | 234.44 | 5.29E-09 | KCD038 | 2.02E+05 | 7.53E-03 | 80.56 | 3.72E-08 |
| KCD044 | 6.13E+05 | 1.61E-03 | 58.32 | 2.62E-09 | KCD050 | 2.49E+05 | 4.88E-04 | 107.09 | 1.96E-09 |
| KCD058 | 2.07E+05 | 2.05E-03 | 48.32 | 9.91E-09 | KCD064 | 2.21E+05 | 4.49E-03 | 87.19 | 2.03E-08 |
| KCD070 | 7.03E+05 | 2.69E-03 | 67.47 | 3.83E-09 | KCD101 | 3.46E+05 | 1.31E-03 | 321.4 | 3.78E-09 |
| KCD107 | 0.00E+00*** | 0.00E+00*** | 0.00E+00*** | 0.00E+00*** | KCD112 | 2.08E+05 | 1.67E-03 | 142.45 | 8.05E-09 |
| KCD119 | 4.88E+05 | 1.83E-04 | 148.79 | 3.75E-10 | KCD124 | 4.26E+05 | 1.84E-03 | 111.24 | 4.32E-09 |
| KCD129 | 1.47E+05 | 4.26E-04 | 30.07 | 2.90E-09 | KCD133 | 3.41E+05 | 3.92E-03 | 94.19 | 1.15E-08 |
| KCD138 | 0.00E+00*** | 0.00E+00*** | 0.00E+00*** | 0.00E+00*** | KCD208 | 1.86E+05 | 4.73E-04 | 213.44 | 2.55E-09 |
| KCD215 | 0.00E+00*** | 0.00E+00*** | 0.00E+00*** | 0.00E+00*** | KCD221 | 0.00E+00*** | 0.00E+00*** | 0.00E+00*** | 0.00E+00*** |
| KCD230 | 3.55E+05 | 8.80E-04 | 231.63 | 2.48E-09 | KCD119 | 3.68E+05 | 3.16E-04 | 237.05 | 8.57E-10 |
| KCD003 | 6.64E+05 | 7.00E-04 | 154.22 | 1.05E-09 | KCD008 | 3.40E+05 | 1.49E-03 | 291.8 | 4.38E-09 |
| KCD013 | 4.49E+05 | 3.29E-03 | 117.5 | 7.32E-09 | KCD018 | 1.78E+05 | 7.24E-03 | 109 | 4.08E-08 |

TABLE 2.1-continued

Binding affinities of recombinantly expressed anti-CFD antibodies to human CFD.

| | ka | kd | Rmax | KD | | ka | kd | Rmax | KD |
|---|---|---|---|---|---|---|---|---|---|
| KCD030 | 2.16E+05 | 9.02E-04 | 76 | 4.17E-09 | KCD039 | 1.46E+05 | 7.69E-03 | 96.59 | 5.25E-08 |
| KCD045 | 0.00E+00*** | 0.00E+00*** | 0.00E+00*** | 0.00E+00*** | KCD052 | 2.09E+05 | 6.43E-04 | 89.82 | 3.07E-09 |
| KCD060 | 0.00E+00*** | 0.00E+00*** | 0.00E+00*** | 0.00E+00*** | KCD065 | 1.97E+05 | 6.45E-04 | 287 | 3.28E-09 |
| KCD073 | 0.00E+00*** | 0.00E+00*** | 0.00E+00*** | 0.00E+00*** | KCD102 | 3.15E+05 | 1.12E-03 | 338.4 | 3.56E-09 |
| KCD109 | 0.00E+00*** | 0.00E+00*** | 0.00E+00*** | 0.00E+00*** | KCD114 | 2.31E+05 | 1.86E-03 | 156.55 | 8.06E-09 |
| KCD121 | 5.52E+05 | 9.95E-04 | 178.49 | 1.80E-09 | KCD125 | 3.06E+05 | 1.15E-03 | 173.9 | 3.75E-09 |
| KCD130 | 0.00E+00*** | 0.00E+00*** | 0.00E+00*** | 0.00E+00*** | KCD135 | 1.65E+05 | 3.49E-03 | 132.92 | 2.12E-08 |
| KCD139 | 3.63E+05 | 1.92E-03 | 96.98 | 5.28E-09 | KCD210 | 2.76E+05 | 9.72E-04 | 122.29 | 3.52E-09 |
| KCD216 | 4.46E+05 | 1.37E-03 | 124.99 | 3.07E-09 | KCD224 | 7.92E+04 | 9.27E-05 | 146.74 | 1.17E-09 |
| KCD232 | 1.51E+05 | 4.20E-04 | 25.82 | 2.79E-09 | Isotype Control | 0.00E+00*** | 0.00E+00*** | 0.00E+00*** | 0.00E+00*** |

*Antibodies with values in grey did not bind CFD under these conditions
*Antibodies with values marked with *** did not bind CFD under these conditions

TABLE 2.2

Binding affinities of 91 recombinantly expressed anti-CFD antibodies to various human and cyno CFD proteins.

| | hCFD-Comptech | rcyCFD-His | rhCFD-His | rhCFD-mut1-His |
|---|---|---|---|---|
| KCD000 | 2.5E-10 | 4.2E-10 | 2.1E-10 | na |
| KCD009 | 5.6E-09 | 9.9E-09 | 4.0E-09 | na |
| KCD019 | 7.2E-09 | 4.7E-08 | 6.1E-08 | 1.8E-07 |
| KCD040 | 1.9E-09 | 1.7E-07 | 1.4E-09 | 7.5E-10 |
| KCD056 | 6.0E-08 | 3.1E-08 | 5.2E-08 | 8.4E-08 |
| KCD066 | 2.9E-09 | 4.0E-09 | 1.9E-09 | 1.2E-09 |
| KCD103 | 4.4E-09 | 6.3E-08 | 3.1E-09 | 2.5E-09 |
| KCD115 | 1.3E-08 | 1.8E-08 | 6.2E-09 | 7.8E-09 |
| KCD126 | 3.4E-10 | 9.3E-10 | 2.9E-10 | 1.8E-10 |
| KCD136 | 4.5E-09 | 2.7E-08 | 3.4E-09 | 1.4E-09 |
| KCD212 | 4.7E-10 | 3.8E-09 | 2.1E-10 | 2.0E-10 |
| KCD225 | 8.7E-09 | 4.6E-08 | 5.0E-09 | 6.2E-09 |
| KCD001 | 2.2E-10 | 6.3E-10 | 2.2E-10 | 1.9E-10 |
| KCD010 | 3.1E-09 | 2.9E-09 | 2.5E-09 | na |
| KCD022 | 5.7E-08 | 5.4E-08 | 8.3E-08 | 1.1E-07 |
| KCD042 | 1.4E-09 | 3.0E-09 | 1.0E-09 | 4.2E-10 |
| KCD057 | 2.7E-09 | 3.1E-09 | 2.7E-09 | 2.5E-09 |
| KCD068 | na | na | na | na |
| KCD104 | 1.6E-09 | 7.2E-08 | 1.2E-09 | 8.2E-10 |
| KCD118 | 7.6E-10 | 1.3E-09 | 5.4E-10 | na |
| KCD128 | 1.4E-08 | 3.3E-09 | 1.4E-08 | 1.3E-08 |
| KCD137 | 5.0E-10 | 5.9E-09 | 5.5E-09 | 4.6E-09 |
| KCD214 | 1.6E-09 | 2.6E-08 | 1.1E-09 | 1.3E-09 |
| KCD229 | 1.2E-09 | 1.6E-09 | 1.2E-09 | 2.4E-09 |
| KCD002 | 1.3E-10 | 4.1E-10 | 1.1E-10 | 8.0E-11 |
| KCD011 | 7.7E-08 | 3.8E-08 | 5.9E-08 | 1.1E-07 |
| KCD023 | 5.3E-09 | 6.0E-09 | 4.1E-09 | na |
| KCD044 | 2.6E-09 | 6.0E-09 | 1.8E-09 | 9.6E-10 |
| KCD058 | 9.9E-09 | 1.1E-08 | 9.4E-09 | 7.6E-09 |
| KCD070 | 3.8E-09 | 4.9E-09 | 3.3E-09 | 7.0E-10 |
| KCD107 | na | na | na | na |
| KCD119 | 3.7E-10 | 7.0E-10 | 2.8E-10 | na |
| KCD129 | 2.9E-09 | 6.0E-09 | 2.1E-09 | 2.7E-09 |
| KCD138 | na | 1.1E-08 | na | na |
| KCD215 | na | na | na | na |
| KCD230 | 2.5E-09 | 2.7E-09 | 1.6E-09 | 8.8E-10 |
| KCD003 | 1.1E-09 | 1.8E-09 | 8.1E-10 | na |
| KCD013 | 7.3E-09 | 9.3E-08 | 1.1E-08 | 1.9E-08 |
| KCD030 | 4.2E-09 | na | 3.8E-09 | 1.3E-09 |
| KCD045 | na | na | na | na |
| KCD060 | na | na | na | na |
| KCD073 | na | na | na | na |
| KCD109 | na | na | na | na |
| KCD121 | 1.8E-09 | 2.9E-09 | 1.3E-09 | na |
| KCD130 | na | na | na | na |
| KCD139 | 5.3E-09 | 3.8E-09 | 3.3E-09 | 3.5E-09 |
| KCD216 | 3.1E-09 | 1.3E-08 | 2.0E-09 | 1.9E-09 |
| KCD232 | 2.8E-09 | 5.5E-09 | 2.4E-09 | 4.4E-09 |
| KCD004 | 3.5E-10 | 9.2E-10 | 2.4E-10 | 1.4E-10 |
| KCD014 | 2.2E-08 | na | 2.0E-08 | na |
| KCD033 | 1.1E-08 | 9.3E-08 | 1.9E-08 | 2.8E-08 |
| KCD047 | 4.4E-08 | 1.6E-07 | 3.4E-09 | 2.9E-09 |
| KCD062 | 2.4E-08 | 1.9E-08 | 3.2E-08 | 6.2E-08 |
| KCD075 | 3.7E-09 | 3.2E-09 | 2.5E-09 | 3.4E-09 |
| KCD110 | 3.7E-09 | 5.3E-09 | 2.0E-09 | 4.1E-09 |
| KCD122 | 1.4E-09 | 1.9E-09 | 9.5E-10 | na |
| KCD131 | 1.4E-10 | 9.9E-10 | 4.7E-11 | 4.5E-11 |
| KCD205 | 3.0E-09 | 3.3E-09 | 1.9E-09 | 1.8E-09 |
| KCD219 | 4.3E-09 | 1.2E-08 | 3.0E-09 | 3.6E-09 |
| KCD48-2 | 2.0E-09 | 2.1E-08 | 1.4E-09 | 8.6E-10 |
| KCD005 | 1.4E-09 | 2.3E-09 | 1.2E-09 | na |
| KCD015 | 6.2E-09 | 2.5E-07 | 4.5E-09 | 3.7E-09 |
| KCD036 | 2.6E-08 | 6.4E-08 | 2.9E-08 | 8.0E-08 |
| KCD048 | 1.9E-09 | 2.1E-08 | na | 8.3E-10 |
| KCD063 | 3.3E-08 | 2.4E-08 | na | na |
| KCD077 | 1.7E-08 | 1.4E-08 | na | 1.3E-08 |
| KCD111 | 6.6E-09 | 7.2E-09 | 4.2E-09 | 7.8E-09 |
| KCD123 | 2.8E-09 | 2.9E-09 | 1.3E-09 | na |
| KCD132 | 2.6E-09 | 8.0E-09 | 1.6E-09 | 1.4E-09 |
| KCD207 | 7.8E-10 | 1.4E-09 | 3.2E-10 | 3.1E-11 |
| KCD220 | 5.4E-11 | 2.8E-10 | 7.4E-11 | 2.9E-11 |
| OG1931 | 5.0E-10 | 6.4E-10 | 2.9E-10 | na |
| KCD006 | 6.3E-09 | 1.5E-07 | 5.8E-09 | 1.1E-08 |
| KCD017 | 7.8E-09 | 1.1E-08 | 1.3E-08 | 1.0E-08 |
| KCD038 | 3.7E-08 | 4.5E-08 | 4.8E-08 | 8.4E-08 |
| KCD050 | 2.0E-09 | 8.2E-09 | 3.1E-09 | 1.9E-09 |
| KCD064 | 2.0E-08 | 1.5E-08 | 2.0E-08 | 3.7E-08 |
| KCD101 | 3.8E-09 | 2.4E-07 | 2.7E-09 | 2.8E-09 |
| KCD112 | 8.0E-09 | 9.1E-09 | 4.3E-09 | 7.1E-09 |
| KCD124 | 4.3E-09 | 5.2E-09 | 3.3E-09 | na |
| KCD133 | 1.2E-08 | 8.4E-08 | 1.4E-08 | 1.3E-08 |
| KCD208 | 2.5E-09 | 5.2E-08 | 1.9E-09 | 1.8E-09 |
| KCD221 | na | na | na | na |
| KCD119 | 8.6E-10 | 1.1E-09 | 5.6E-10 | na |

TABLE 2.2-continued

Binding affinities of 91 recombinantly expressed anti-CFD antibodies to various human and cyno CFD proteins.

| | hCFD-Comptech | rcyCFD-His | rhCFD-His | rhCFD-mut1-His |
|---|---|---|---|---|
| KCD008 | 4.4E−09 | 6.6E−08 | 3.2E−09 | 5.7E−09 |
| KCD018 | 4.1E−08 | 5.2E−08 | 4.1E−08 | 9.9E−08 |
| KCD039 | 5.3E−08 | 3.9E−08 | 4.3E−08 | 7.0E−08 |
| KCD052 | 3.1E−09 | 1.0E−08 | 3.7E−09 | 2.5E−09 |
| KCD065 | 3.3E−09 | 2.5E−08 | 1.7E−08 | 2.5E−08 |
| KCD102 | 3.6E−09 | 2.3E−07 | 2.5E−09 | 2.5E−09 |
| KCD114 | 8.1E−09 | 8.4E−09 | 3.8E−09 | 8.4E−09 |
| KCD125 | 3.8E−09 | 4.1E−09 | 2.5E−09 | 2.7E−09 | array in a pair-wise, competition format. For each cycle, the target (serum purified CFD, rhCFD, or rcyCFD) was injected over the array and immediately followed by one of the sandwiching species. The array surface was regenerated between each cycle.

Example 4—Group Network Based on Binding Characteristics

Anti-CFD antibodies were grouped in discreet bins (Table 4.1) depending on their blocking/sandwiching behavior for binding to serum CFD, rhCFD, and rcyCFD, using the Scrubber software (BioLogic Software, LLC) and the Binning Tool (Wasatch Microfluidics Inc.).

TABLE 4.1

Binning result using Washatch 96 × 96 antibody competition binding to CFD.

| Group 1 | Group 2 | Group 3 | Group 4 | Group 5 | Group 6 | Group 7 | Group 8 | Group 9 | Group 10 | Group 11 |
|---|---|---|---|---|---|---|---|---|---|---|
| KCD023 | KCD036 | KCD017 | KCD112 | KCD225 | KCD220 | KCD230 | KCD210 | KCD224 | KCD062 | KCD038 |
| KCD010 | KCD212 | KCD050 | KCD115 | KCD030 | KCD004 | KCD135 | | KCD047 | KCD056 | KCD039 |
| KCD119 | KCD073 | KCD052 | KCD114 | KCD001 | KCD077 | | | KCD104 | KCD058 | |
| KCD122 | KCD207 | KCD065 | | KCD219 | KCD126 | | | KCD040 | KCD063 | |
| KCD119 | KCD107 | KCD019 | | KCD216 | KCD139 | | | KCD214 | KCD011 | |
| KCD003 | KCD068 | KCD128 | | KCD132 | KCD205 | | | KCD48-2 | KCD064 | |
| KCD121 | KCD033 | KCD137 | | KCD111 | KCD125 | | | KCD015 | KCD057 | |
| KCD123 | KCD133 | KCD022 | | KCD131 | KCD075 | | | KCD103 | | |
| OG1931 | KCD129 | | | KCD002 | KCD060 | | | KCD102 | | |
| KCD118 | KCD229 | | | KCD110 | KCD066 | | | KCD136 | | |
| KCD124 | KCD109 | | | | KCD018 | | | KCD101 | | |
| KCD005 | | | | | | | | KCD006 | | |
| KCD000 | | | | | | | | KCD008 | | |
| KCD009 | | | | | | | | KCD013 | | |
| | | | | | | | | KCD048 | | |
| | | | | | | | | KCD042 | | |
| | | | | | | | | KCD044 | | |
| | | | | | | | | KCD208 | | |

TABLE 2.2-continued

Binding affinities of 91 recombinantly expressed anti-CFD antibodies to various human and cyno CFD proteins.

| | hCFD-Comptech | rcyCFD-His | rhCFD-His | rhCFD-mut1-His |
|---|---|---|---|---|
| KCD135 | 2.1E−08 | 1.8E−08 | 1.3E−08 | 1.5E−08 |
| KCD210 | 3.5E−09 | 3.6E−09 | 2.9E−09 | 2.9E−09 |
| KCD224 | 1.2E−09 | 1.0E−07 | 5.4E−10 | 1.1E−09 |
| Isotype Control | na | 3.9E−08 | na | na |

Example 3—Epitope Binning of Anti-CFD Antibodies Using Competition Binding Assay (Classical Binning)

Epitope binning of the 91 newly identified and recombinantly expressed anti-CFD antibodies together with a known anti-CFD antibody OG1931 were done by Wasatch Microfluidics using the MX96 SPR machine. In this classical binning assay, a competition cycle for each mAb was configured such that each ligand is immobilized on the surface and loaded with the target during the first phase, followed by injection of one of the competing species to test whether is binds or is blocked by the surface species.

Since the target CFD is monomeric, the classical binning configuration was used where the antibodies are amine-coupled to a 96-cell array. Each mAb was binned by testing its ability to block and sandwich with every other mAb in the

Example 5. Identification and Characterization of Antagonistic Anti-CFD Antibodies Amongst 91 antibody synthesized and expressed in 293 cells, 29 blocked alternative pathway dependent hemolysis of rabbit red blood cells (RBC) by human plasma. Table 0.1A shows the variable domain sequences of these 29 antibodies. All 29 blocking antibodies blocked CFD binding to C3bB. These 29 antibodies were grouped into 6 phenotypic bins based on their effect on CFD enzymatic activity using a small synthetic peptide substrate, and if they can sandwich with the anti-CFD positive control antibody OG1931 (tables 5.3-5.9).

Hemolysis Assay: Hemolysis Assay—

For the hemolysis assay, rabbit red blood cells ("RBCs", CompTech #B301) are diluted or re-suspended and washed with GVB⁰ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Proteolysis Assay—

Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog

D-8130, 100 mM stock in DMSO)2. 50 µL of the diluted CFD is loaded into a 96 well clear plate, and 50 uls of AFD is added. The reaction is started by adding 100 µL of substrate/DTNB mixture to wells. A substrate blank containing 100 µL assay buffer and 100 µL substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/µg)=Adjusted Vmax*(OD/min)×well volume (L)×$10^{12}$ pmol/mol. ext. coeff($M^{-1}cm^{-1}$)×path corr.*(cm)×amount of enzyme (µg). *Adjusted for substrate blank, Using the extinction coefficient 13,260 $M^{-1}cm^{-1}$, *Using the path correction 0.320 cm.

Binding Characterization

ELISA (enzyme-linked immunosorbent assay) assays were used to characterize binding of anti-CFD antibodies ("AFDs") to CFD or a mutant of CFD (CFD mutant 1). CFD mutant 1 was generated that does not bind its substrate C3bB, but retains CFD enzymatic activity. CFD mutant 1 has the mutations R157A and R207A (positions based on linear positions in mature protein; using the canonical sequence based on chymotrypsin, the mutations are positions R177A and R227A. Katschke et al. 2012, Supplemental Materials Fig. S6).

Competition Assay—

To determine whether anti-CFD antibodies (AFDs) block binding of CFD to Factor B (FB), a competition assay was used. Purified human C3b (CompTech) was immobilized onto a CM5 biosensor chip (GE). Recombinant C3b was diluted to 40 ug/ml in acetate buffer (pH 4.5) and immobilized via amine coupling to the CM5 chip by following the immobilization wizard software (Biacore™ T200) with a 7 minute contact time. C3b was immobilized at 14000 resonance units (RU) on a Biacore T200 (GE Healthcare). HBS buffer (no EDTA) with 2 mM $MgCl_2$ was used as running buffer to assess binding of (a) FB, (b) CFD, or (c) FB+CFD to immobilized C3b in the presence and absence of AFDs. 3 M $MgCl_2$ was used as a regeneration buffer to remove all bound proteins after processing each sample.

A confirmed AFD non-blocker, antibody KCD004, was used as a control for maximal binding of a FB/CFD/AFD complex to C3b, while FB alone was used to set to lower limit of binding to C3b, such as would be the case with a full AFD-blocking antibody.

The anti-CFD antibodies were sorted into six different bins based on binding specificity, ability to inhibit complement-activated hemolysis, and effect on enzymatic activity of human CFD for the synthetic substrate Z-L-Lys-SBzl hydrochloride.

Table 5.3 summarizes the six bins and their characteristics, Tables 5.4 through 5.9 provides examples of anti-CFD antibodies belonging to each bin.

TABLE 5.3

29 Blocking Antibodies Belong to 6 Phenotype Bins

|  | Rabbit RBC Hemolysis | CFD Enzymatic activity | CFD Binding to C3bB | Sandwich with OG1931 | Group Network Groups |
|---|---|---|---|---|---|
| Bin 1 (OG1931) | Inhibit | increase | inhibit | No | Group 1 |
| Bin 2 | Inhibit | inhibit | inhibit | No | Group 1 |
| Bin 3 | Inhibit | no effect | inhibit | No | Group 1 |
| Bin 4 | Inhibit | increase | inhibit | Yes | Group 9 |
| Bin 5 | Inhibit | inhibit | inhibit | Yes | Group 9 |
| Bin 6 | Inhibit | no effect | inhibit | Yes | Group 9, 5 |

Table 5.4-Table 5.9 show Bin 1-Bin 6.

TABLE 5.4

Bin 1

| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
|---|---|---|---|---|---|---|---|
| Bin 1 OG1931 | Inhibit +++ | Increase 211.08 | 7.52E-12 | No 7.01 | No No | Bin A | N/A |

TABLE 5.5

Bin 2

| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
|---|---|---|---|---|---|---|---|
| Bin 2 | Inhibit | Inhibit |  | No | No |  |  |
| KCD010 | +++ | 49.38 | 1.46E-09 | 3.77 | No | Bin A | Balb/c #2 |
| KCD003 | +++ | 19.62 | 3.18E-10 | 1.53 | No | Bin A | C57BL#1 or #2 |
| KCD005 | +++ | 49.23 | 7.26E-10 | 1.79 | No | Bin A | C57BL #1 or #2 |
| KCD118 | +++ | 13.96526 | 8.83E-11 | 0.762389 | No | Bin A | C57BL#2 |
| KCD119 | +++ | 15.69617 | 3.58E-11 | 13.58885 | No | Bin A | C57BL#2 |
| KCD121 | +++ | 16.67982 | 2.93E-10 | 0.602107 | No | Bin A | C57BL#2 |
| KCD122 | +++ | 17.31039 | 1.62E-10 | 2.247191 | No | Bin A | C57BL#2 |

TABLE 5.5-continued

| | | Bin 2 | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| KCD123 | +++ | 18.74613 | 2.77E−10 | 2.910053 | No | Bin A | C57BL#2 |
| KCD124 | +++ | 19.69798 | 7.80E−10 | −0.6435 | No | Bin A | C57BL#2 |

TABLE 5.6

| | | Bin 3 | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 3 | Inhibit | No Effect | | No | No | | |
| KCD009 | +++ | 148.39 | 3.47E−09 | 5.15 | No | Bin A | Balb/C #2 |
| KCD023 | +++ | 71.84 | 1.77E−06 | 7.64 | No | Bin A | Balb/C #2 |

TABLE 5.7

| | | Bin 4 | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 4 | Inhibit | Increase | | Yes | Yes | | |
| KCD048 | +++ | 333.2908 | 9.97E−10 | 62.32239 | Yes | Bin B | Balb/C #2 |
| KCD070 | +++ | 169.2659 | 1.77E−09 | 84.61538 | Yes | N/A | Balb/C #2 |

TABLE 5.8

| | | Bin 5 | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 5 | Inhibit | Inhibit | | Yes | Yes | | |
| KCD042 | +++ | 6.797026 | 1.09E−09 | 65.55184 | Yes | Bin B | Balbc #2 |
| KCD040 | +++ | 13.6563 | 7.91E−08 | 62.1775 | Yes | Bin B | Balbc #2 |
| KCD044 | +++ | 8.801277 | 1.02E−09 | 62.54489 | Yes | Bin B | Balbc #2 |
| KCD047 | +++ | 47.29286 | 6.62E−09 | 58.8909 | Yes | Bin B | Balbc #2 |
| KCD208 | +++ | 0 | 4.51E−10 | 56.70651 | Yes | Bin B | Swiss webster #2 |
| KCD214 | +++ | 12.77884 | 2.45E−10 | 44.29379 | Yes | Bin B | Swiss webster #2 |
| KCD224 | +++ | 36.31433 | 1.56E−11 | 121.4383 | Yes | Bin B | Swiss webster #2 |
| KCD136 | +++ | 11.81753 | 5.87E−10 | 78.3358 | Yes | Bin B | C57BL#2 |

TABLE 5.9

| | | | Bin 6 | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 6 | Inhibit | No effect | | Yes | Yes | | |
| KCD002 | +++ | 143.72 | 3.07E−11 | 71.24 | Yes | Bin D | C57BL#1 or #2 |
| KCD101 | +++ | 93.15411 | 1.45E−09 | 65.79151 | Yes | Bin B | C57BL#2 |
| KCD102 | +++ | 92.27025 | 6.98E−09 | 64.26183 | Yes | Bin B | C57BL#2 |
| KCD103 | +++ | 126.4488 | 1.48E−09 | 65.2 | Yes | Bin B | C57BL#2 |
| KCD104 | +++ | 92.28768 | 1.32E−09 | 68.27279 | Yes | Bin B | C57BL#2 |
| KCD131 | +++ | 65.91077 | 3.42E−11 | 80.71025 | Yes | Bin D | C57BL#2 |
| KCD220 | +++ | 88.10648 | 6.39E−11 | 74.10941 | Yes | Bin G | Swiss Webster #2 |

Example 6

Figure 3:
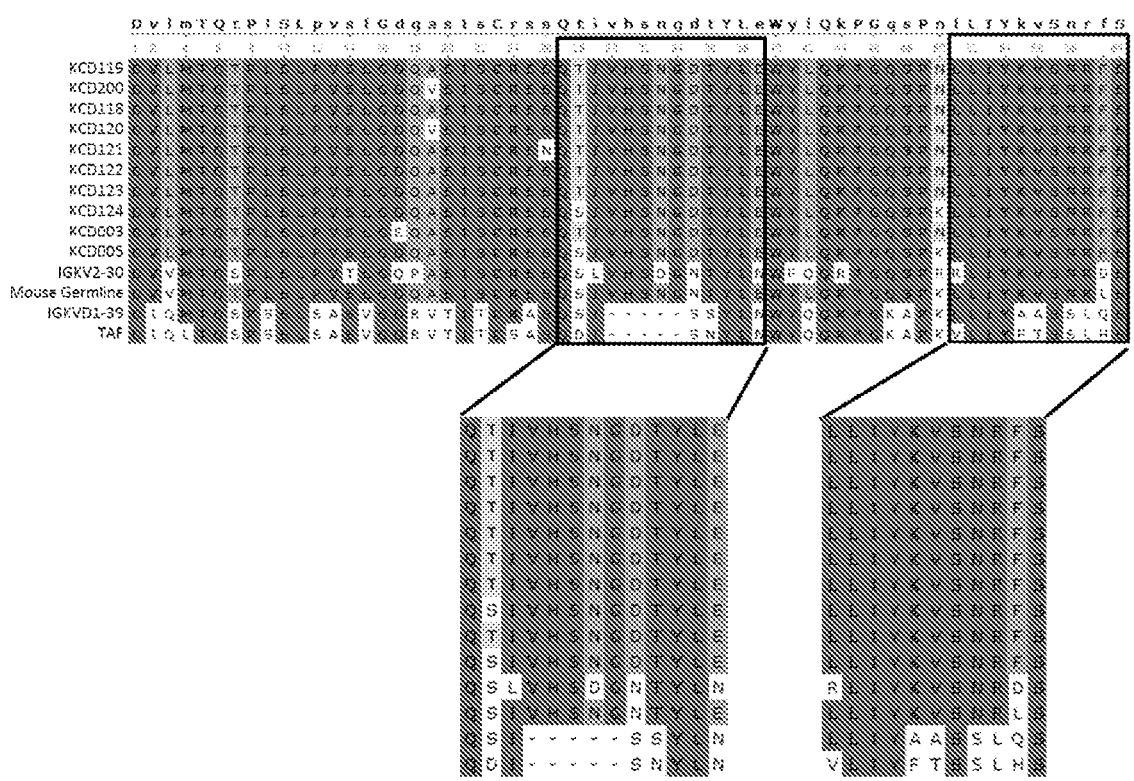
FIG. 3 shows KCD119 Family light chain alignment with human frameworks.
Figure 3:
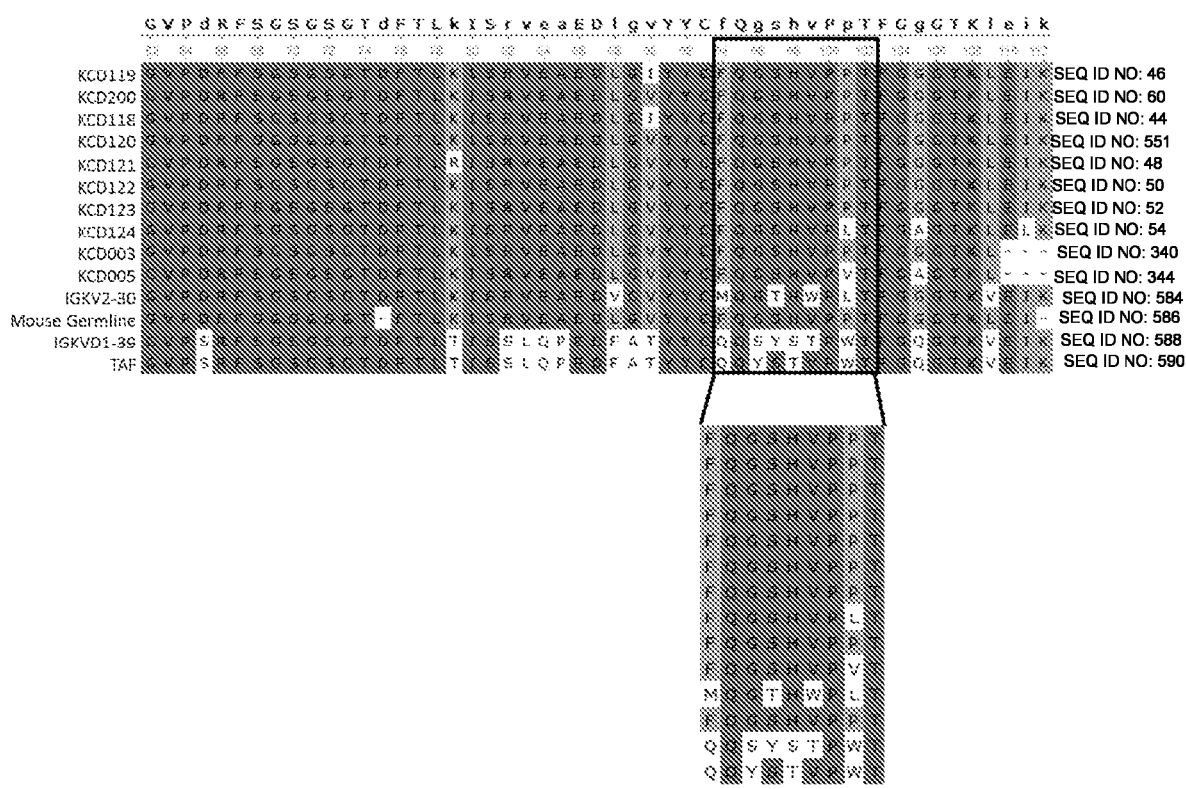
Figure 4:
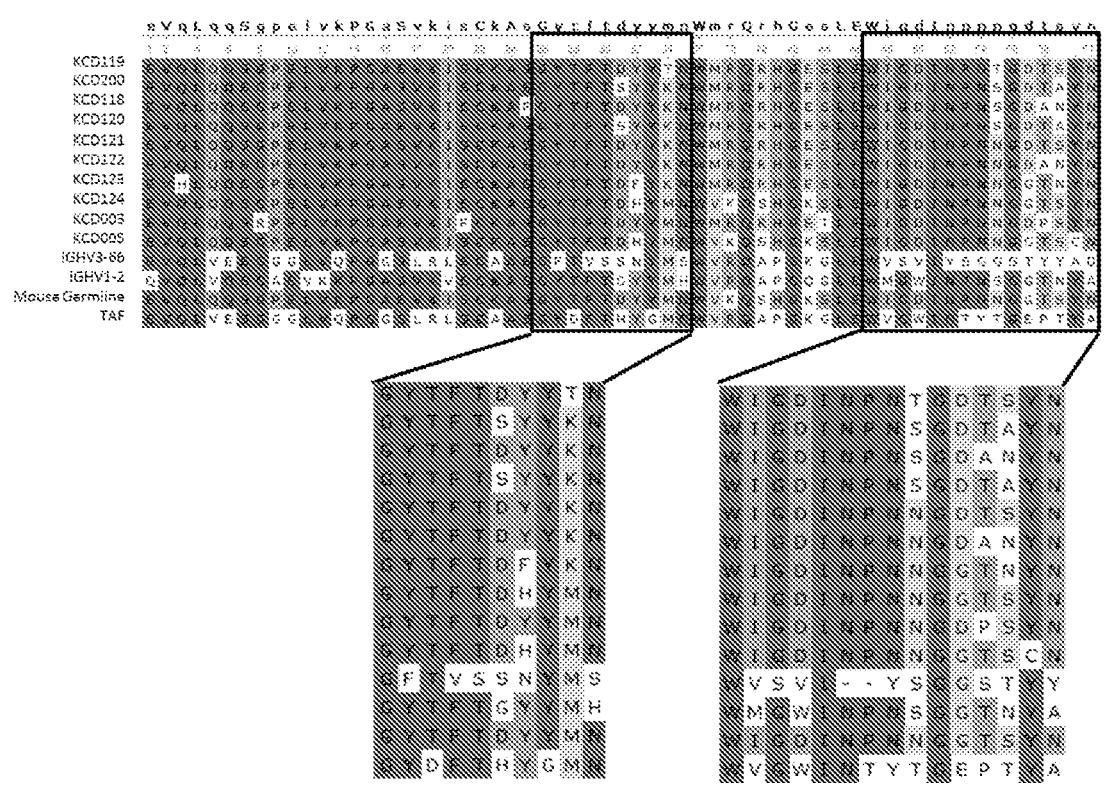
FIG. 4 shows KCD119 Family heavy chain alignment with human frameworks.
Figure 4:
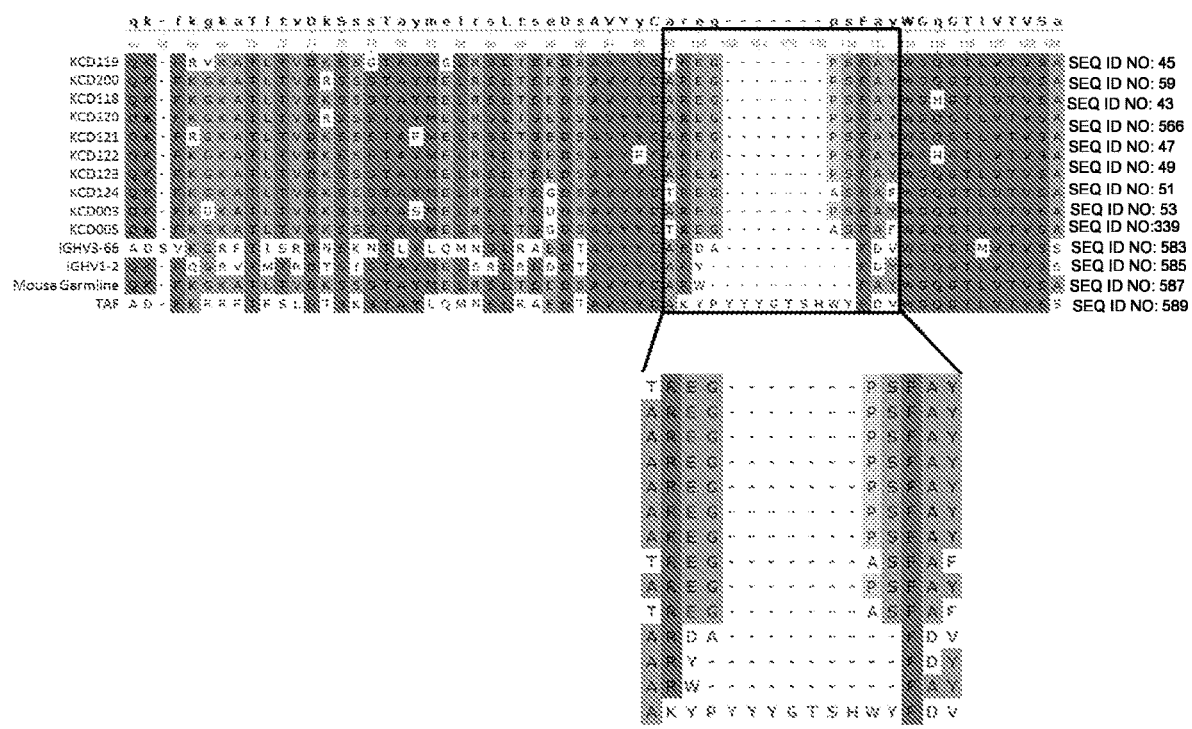

FIG. 3 shows light chain alignment of a representative bin 2 antibody KCD119, and other antibodies obtained during screening that show high sequence identity to KCD119 (KCD119 family), along with representative human frameworks that KCD19 was grafted on. FIG. 4 shows KCD119 Family heavy chain alignment.

Example 7—Humanization of KCD119

Binding kinetics were determined by measuring serum purified complement factor D binding to full-length IgG captured on protein A chip or Fab captured on CM5 chip coated with anti-Fab (Biacore Human Fab Capture Kit) according to manufacturer's instructions.

Figure 5A:
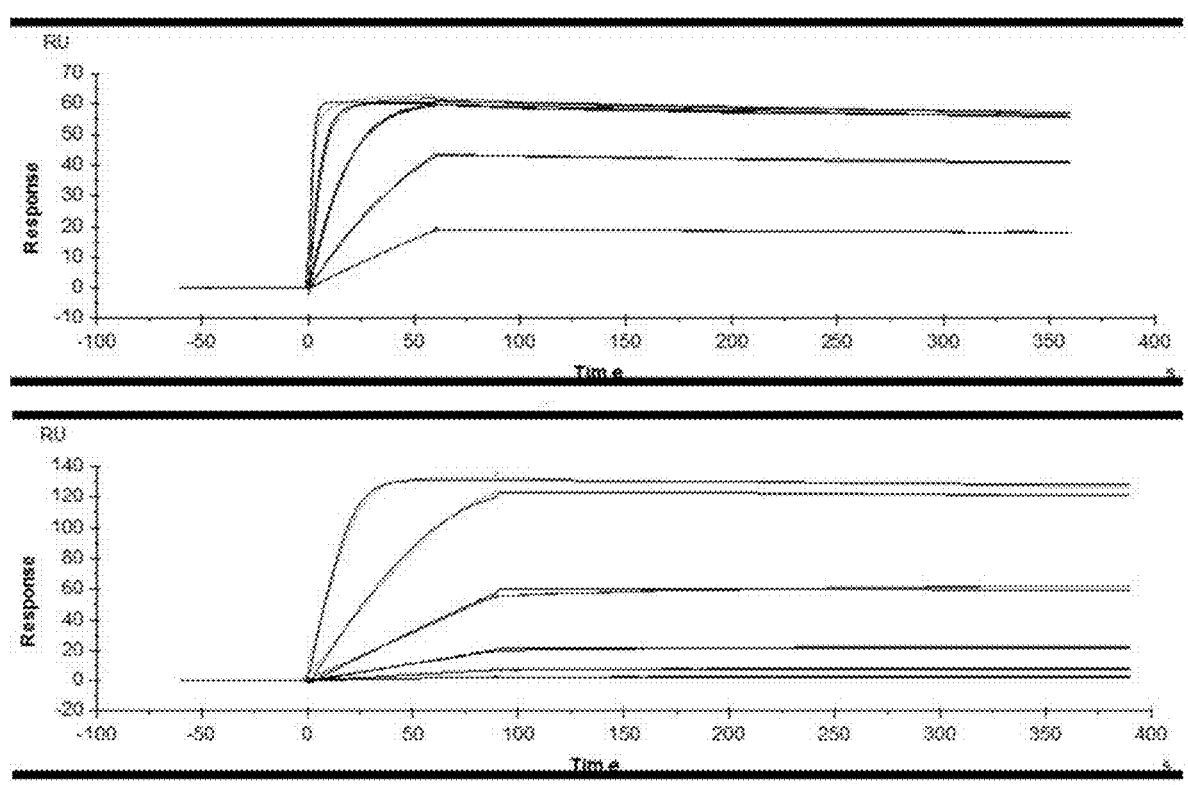
FIG. 5A shows binding affinity of KCD119-mouse monoclonal antibody to purified human CFD measured on Biacore T2000. Top panel shows binding and disassociation curve of full IgG (capture on Protein A chip). Bottom panel shows binding and disassociation curve of Fab (capture on CM5 chip immobilized with anti-human Fab capture kit).
Figure 5B:
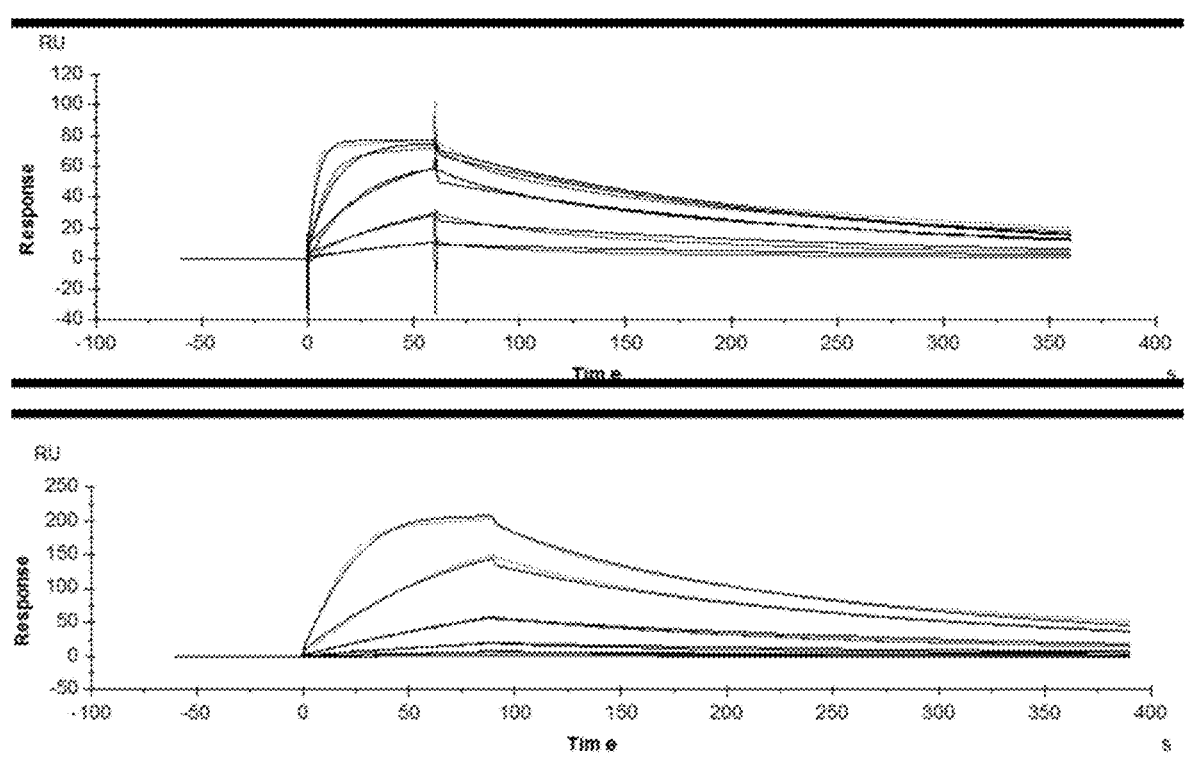
FIG. 5B shows binding affinity of KCD119-3-66 (KCD119 CDRs grafted onto human germlines IGHV3-66. and IGKVD1-39) binding affinity to purified human CFD measured on Biacore T2000 Top panel shows binding and disassociation curve of full IgG (capture on Protein A chip). Bottom panel shows binding and disassociation curve of Fab (capture on CM5 chip immobilized with anti-human Fab capture kit).
Figure 5C:
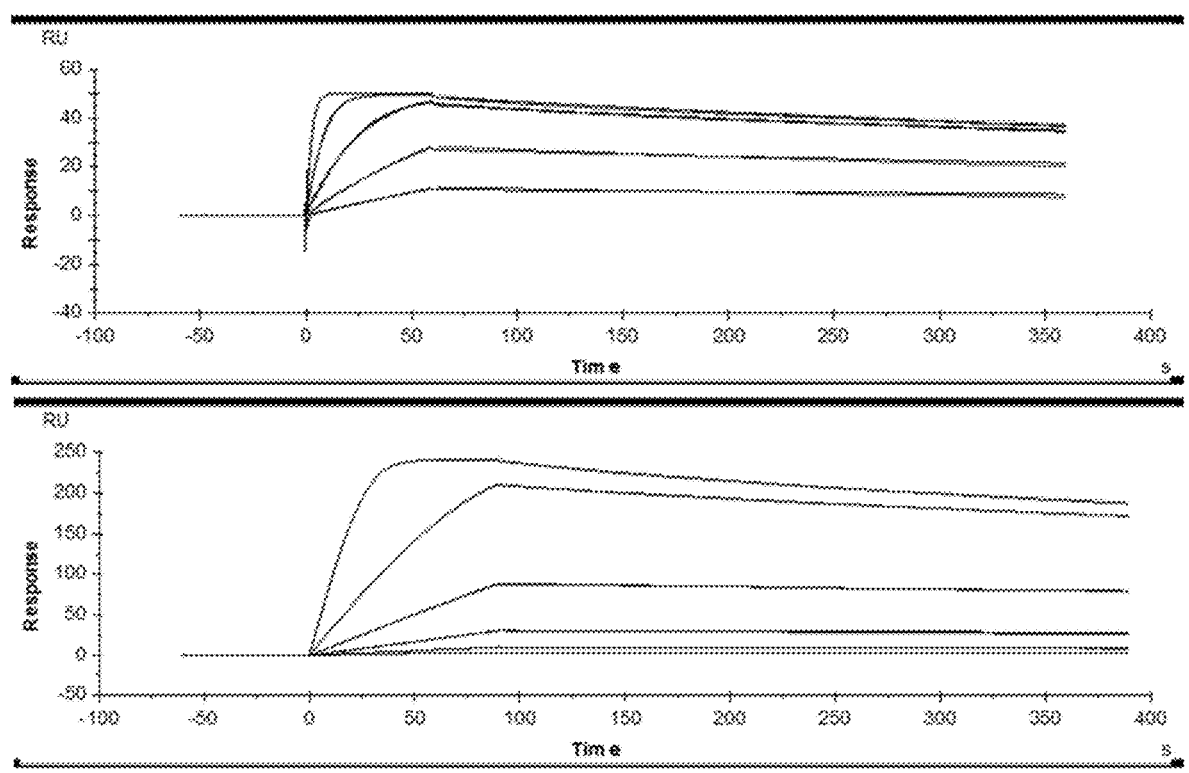
FIG. 5C shows binding affinity of KCD119-TAF to purified human CFD measured on Biacore 2000. Top panel shows binding and disassociation curve of full IgG (capture on Protein A chip). Bottom panel shows binding and disassociation curve of Fab (capture on CM5 chip immobilized with anti-human Fab capture kit).
Figure 6A:
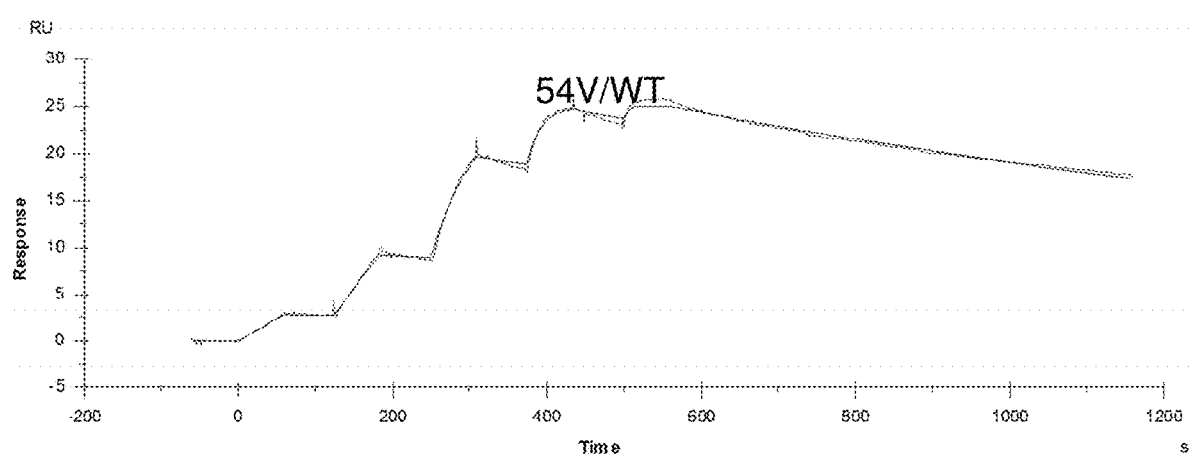
FIG. 6A shows Factor D binding kinetics data for an embodiment of a combination of both heavy and light chain mutations that corresponded with positive changes in affinity.
Figure 6B:
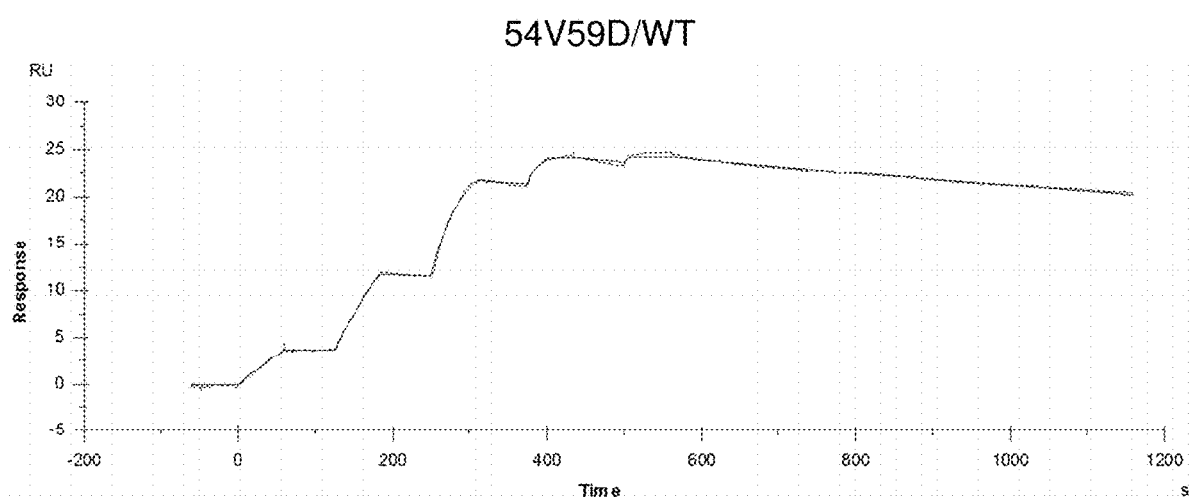
FIG. 6B shows Factor D binding kinetics data for an embodiment of a combination of both heavy and light chain mutations that corresponded with positive changes in affinity.
Figure 6C:
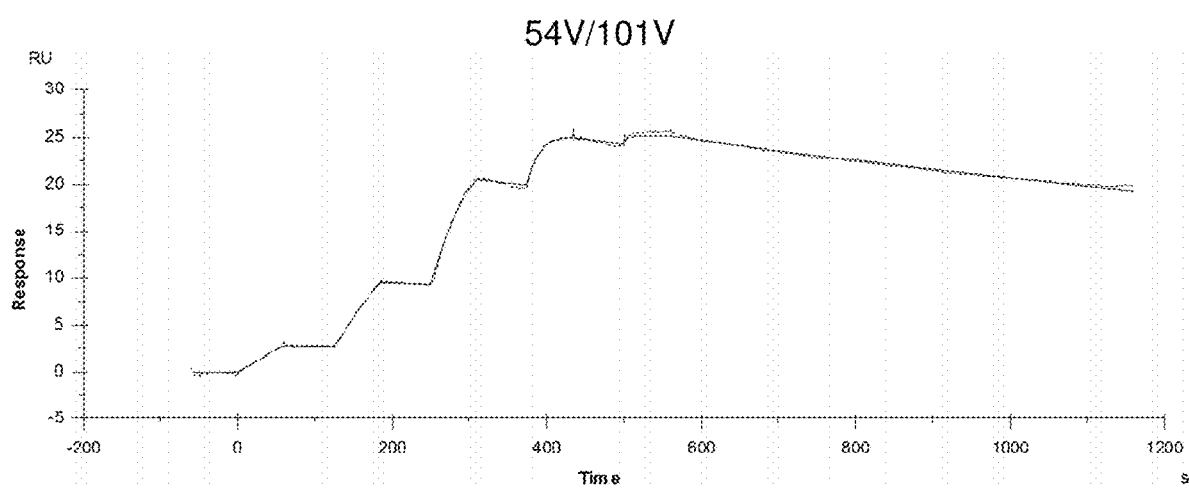
FIG. 6C shows Factor D binding kinetics data for an embodiment of a combination of both heavy and light chain mutations that corresponded with positive changes in affinity.
Figure 6D:
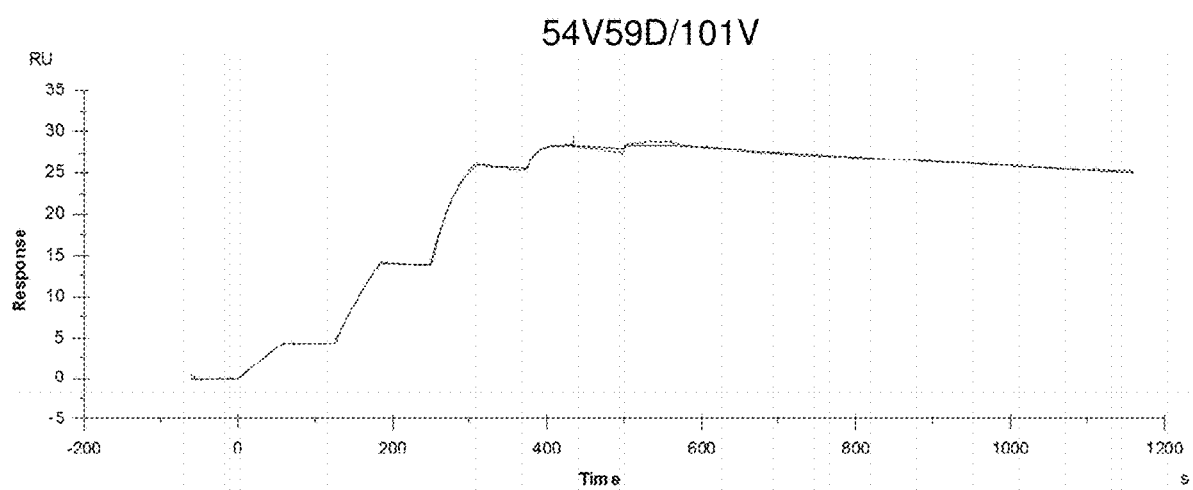
FIG. 6D shows Factor D binding kinetics data for an embodiment of a combination of both heavy and light chain mutations that corresponded with positive changes in affinity.

KCD119 CDR1, CDR2, and CDR3 for both the heavy and light chains were grafted into human variable domain frameworks IGHV 3-66 and IGK1-39, or "TAF" (IGHV 3-66 and IGK1-39 with some framework mutations), or IGHV1-2 and IGKv2-30. KCD119 CDRs with the original mouse framework (FIG. 5A) has a kD for human Complement Factor D of 40 pM, while KCD1119 CDRs grafted into the TAF framework has kD of 230 pM (FIG. 5C), and KCD119 CDRs grafted into IGHV 3-66/IGK1-39 framework has a kD of 2.60 nM (FIG. 5B). KCD119 CDRs grafted into IGHV 1-2/IGKV2-30 framework did not express sufficient antibody. The affinities for Fab were roughly equivalent to the full IgG for each framework.

KCD119 TAF (FIG. 5C) has the highest binding affinity to human CFD post grafting and is therefore chosen as the template to further affinity mature.

Example 8—Screening Results for Light Chain CDRs for Affinity Maturation of TAF KCD119 Molecule To increase the binding affinity of the humanized molecule TAF KCD119, all three CDRs in both light and heavy chain were subjected to mutagenesis to identify favorable point mutations in the CDRs.

Each residue in the light chain CDRs was mutated following manufacturer's instructions for the NEB site directed mutagenesis kit and using a mixture of mutagenic primers encoding 16 amino acids (excluding parent, C, M, and N, with a few exceptions as noted in the table). Mutants were selected by sequencing, and plasmids encoding unique heavy and light chain antibody sequences were identified and co-transfected into Expi293™ cells. After 5 days, the supernatants from the cells containing secreted antibody were diluted 1:10 in HBS-EP plus running buffer and captured on a protein A chip on a Biacore™ T200 system (GE). 45 nM, 15 nM, 5 nM, and 1.7 nM serum purified human CFD was then flowed over the captured antibody to determine affinity by single cycle kinetics using BIAevaluation software (GE).

Affinity Fold Changes Caused by Light Chain CDR Mutations was assessed. Affinity results were from Biacore testing of un-purified supernatant from Expi293 cells transfected with mutagenized KCD119 plasmid DNA. Mutant residues may have been screened on a background of other mutations.

Data are presented in Table 8.1 for CDR1, Table 8.2 for CDR2 and Table 8.3 for CDR3. Increase in fold change (>1.0) indicates loss of affinity, while decrease in fold change (<1.0) indicates increased affinity. Boxes are marked with * when the aa substitution has similar or better affinity. Boxes are marked with *** when aa substitution has worse affinity. "XX" indicates no sufficient antibody expression.

TABLE 8.1

| Affinity Fold Changes Caused by Light Chain CDR Mutations in CDR1 | | | | | | | | | | | | |
|---|---|---|---|---|---|---|---|---|---|---|---|---|
| | 28T | 29I | 30V | 31H | 32S | 33N | 34G | 35D | 36T | 37Y | 38L | 39E |
| A | | 0.3* | 1.8* | | 0.5* | 12.5*** | 13.7*** | 6.2*** | 3.6*** | | 11.4*** | 9.6*** |
| C | | | | | | | | | | | | |
| D | 0.3* | | 0.7* | 7.9*** | 0.4* | 17.9*** | 6.9*** | | 21.9*** | 550.0*** | | 733.6*** |
| E | | 78.9*** | 0.3* | 9.0*** | | 18.7*** | 1.6* | 0.5* | | 145.5*** | 7.2*** | |
| F | | 16.6*** | 0.5* | | 0.8* | 16.6*** | 2.0* | | 11.9*** | 4.3*** | 3.5*** | |
| G | 0.1* | 53.6*** | 2.3*** | 46.7*** | 0.5* | 2.7*** | | 4.8*** | 18.8*** | 2022.7*** | | xx*** |
| H | 0.9* | | | | | | 4.8*** | | 4.3*** | | 10.9*** | 8.8*** |
| I | 0.9* | | 0.6* | | 0.9* | 61.3*** | 62.8*** | | 3.8*** | 37.4*** | 1.2* | |
| K | | 133.6*** | 0.9* | 83.4*** | | 183.6*** | 19.0*** | | | | 50.6*** | xx*** |
| L | | 0.0 | 1.7* | 13.8*** | | 22.7*** | 3.2*** | | 6.9*** | 4.1*** | | |

TABLE 8.1-continued

Affinity Fold Changes Caused by Light Chain CDR Mutations in CDR1

|   | 28T | 29I | 30V | 31H | 32S | 33N | 34G | 35D | 36T | 37Y | 38L | 39E |
|---|---|---|---|---|---|---|---|---|---|---|---|---|
| M |  |  |  |  |  | 22.2*** | 18.8*** |  |  |  |  |  |
| N | 0.4* |  |  |  |  |  |  |  |  |  |  |  |
| P |  |  |  | 33.7*** |  | 47.6*** | 16.3*** |  | 27.2*** |  | 117.4*** | xx*** |
| Q | 0.9* |  | 0.3* | 18.4*** |  | 32.1*** |  |  |  |  | 11.5*** | 3.9*** |
| R | 1.3* | 47.4*** | 1.1* | 124.6*** | 0.7* | 83.4*** | 5.8*** | 52.6*** | 10.3*** | 252.3*** | 252.3*** |  |
| S | 0.0 | XX*** | 0.5* | 8.5*** |  | 13.2*** | 1.9* | 408.3*** | 2.0* | 571.2*** | 34.3*** | 9.6*** |
| T |  | 2.9*** |  | 12.0*** | 0.9* | 4.1*** | 8.6*** |  |  |  | 10.7*** | xx*** |
| V | 0.2* | 0.2* |  | 10.7*** | 0.7* | 21.3*** | 24.2*** | 12.9*** | 1.1* | 271.2*** |  | xx*** |
| W | 0.2* |  | 1.5* |  | 0.3* | 8.5*** | 3.3*** | 14.3*** | 11.2*** | 704.5*** |  |  |
| Y |  |  | 0.3* |  |  | 11.1*** | 4.9*** |  | 7.5*** |  |  |  |

TABLE 8.2

Affinity Fold Changes Caused by Light Chain CDR Mutations in CDR2

| 50N | 51L | 52L | 53I | 54Y | 55K | 56V | 57S | 58N | 60F |
|---|---|---|---|---|---|---|---|---|---|
|  | 54.2*** |  | 3.2*** |  | 7.9*** | 1.2* | 0.8* |  |  |
| 0.9* | 38.3*** | 12.0*** | 70.7*** | 1.3* | 137.0*** | 18.0*** | 10.9*** | 2.7*** | 2.8*** |
| 0.6* | 25.2*** | 19.8*** | 11.7*** | 1.1* | 16.9*** | 6.5*** |  | 0.9* | 1.5* |
|  |  |  | 3.3*** | 0.5* |  | 14.6*** | 1.2* |  |  |
|  | 69.5*** | 15.1*** | 13.5*** | 0.4* | 7.6*** | 6.8*** | 1.1* | 1.1* | 0.8* |
|  |  | 20.8*** | 5.6*** |  | 13.1*** | 13.3*** |  | 0.2* |  |
| 0.0 | 1.9* |  |  | 2.8*** |  | 1.2* |  | 1.9* | 0.3* |
|  |  | 6.2*** | 7.6*** |  |  |  | 0.6* |  |  |
|  |  |  |  | 1.9* | 6.6*** | 5.5*** | 1.0* | 1.9* | 1.2* |
|  | 48.6*** | 16.1*** | 40.4*** | 32.9*** | 14.3*** | 67.4*** |  |  |  |
|  | 28.2*** | 17.1*** | 7.7*** |  | 2.9*** | 3.8*** | 1.0* | 0.8* |  |
| 0.8* | 623.5*** | 18.0*** | 36.9*** | 0.1* | 3.7*** | 2.8*** | 0.7* |  | 1.5* |
| 0.8* | 176.5*** | 14.5*** | 5.9*** | 0.2* | 9.2*** | 3.3*** |  | 0.8* | 2.1*** |
| 4.3*** |  | 13.3*** | 1.9* | 0.4* | 10.9*** | 6.4*** | 1.0* | 1.6* | 8.7*** |
| 0.5* | 7.1*** | 10.2*** | 2.6*** | 1.1* | 11.2*** |  | 15.8*** | 1.8* | 2.2*** |
|  | 32.4*** | 18.0*** |  | 2.3*** |  | 34.9*** |  | 2.8*** | 0.4* |
| 0.7* | 43.1*** |  |  |  | 10.4*** | 13.0*** | 1.4* |  |  |

TABLE 8.3

Affinity Fold Changes Caused by Light Chain CDR Mutations in CDR3

| 94F | 95Q | 96G | 97S | 98H | 99V | 100P | 101P |
|---|---|---|---|---|---|---|---|
| 33.5*** | 38.0*** | 3.3*** | 7.3*** | 0.8* | 2.8*** | 8.4*** | 3.6*** |
|  |  | 134.2*** | 143.3*** |  | 2.7*** |  | 2.7*** |
|  |  | 12.4*** | 352.9*** | 288.1*** | 0.7* | 9.2*** |  | 23.8*** |
|  |  | 127.7*** | 75.3*** | 126.8*** | 0.7* | 3.6*** |  |  |
| 6.5*** | 118.4*** |  | 5.9*** | 1.1* | 8.4*** | 12.6*** | 3.1*** |
|  | 125.8*** | 53.9*** | 286.2*** |  |  |  | 37.7*** |
| 8.7*** |  | 21.4*** |  | X*** | 2.9*** |  | 4.8*** |
|  | 1189.0*** |  |  | X*** | 8.8*** |  | 129.9*** |
| 5.3*** | 701.5*** | 98.1*** | 110.8*** | 1.4* | 4.9*** | 8.3*** | 4.3*** |
| 1.0* |  | 224.9*** |  |  | 2.7 |  |  |
| 137.1*** |  |  | 42.0*** | 1.2* | 1.4* |  |  |
| 9.2*** | 206.8*** |  | 146.7*** | 56.7*** | 6.7*** |  |  |
|  |  |  |  | 0.7* | 2.0* |  | 15.8*** |
| 295.6*** | 562.4*** | 20.6*** | 221.2*** | X*** | 6.6*** | 9.7*** | 332.7*** |
| 153.4*** | 28.8*** | 78.6*** |  |  | 2.2*** | 14.8*** | 8.4*** |
| 12.4*** | 58.8*** | 286.2*** |  | 1.2* |  |  | 15.3*** |
|  | 6.9*** | 54.2*** | 64.5*** | 32.0*** | 0.7* |  | 8.8*** | 1.6* |
|  | 248.9*** |  | 250.9*** | 0.7* | 1.1* | 10.7*** | 13.8*** |
| 19.2*** | 219.9*** | 260.2*** | 136.4*** | 0.7* | 4.9*** |  |  |

Example 9—Screening Results for Heavy Chain CDR1 and CDR2 of TAF KCD119 Molecule Heavy chain CDR1 and CDR2 were mutagenized and screened similarly as the light chain CDRs.

Affinity Fold Changes Caused by Heavy Chain CDR Mutations was assessed. Affinity results were from Biacore testing of un-purified supernatant from Expi293 cells transfected with mutagenized KCD119 plasmid DNA. Mutant residues may have been screened on a background of other mutations. H3 was screened in *E. coli* first to determine tolerant residues (Example 10; Table 9.1).

Data are presented in Table 9.1 for CDR1 and Table 9.2 for CDR2. Increase in fold change (>1.0) indicates loss of affinity, while decrease in fold change (<1.0) indicates increased affinity. Boxes are marked with * when the aa substitution has similar or better affinity. Boxes are marked with *** when aa substitution has worse affinity. "XX" indicates no sufficient antibody expression.

TABLE 9.1

Affinity Fold Changes Caused by Heavy Chain CDR Mutations in CDR1

|   | 28T | 29F | 31D | 32Y | 33Y | 34M |
|---|-----|-----|-----|-----|-----|-----|
| A | 1.2* | 19.2*** | 0.6* | 17.0*** | 51.6*** | 9.0*** |
| C |  |  |  |  |  |  |
| D | 1.8* | 48.8*** |  | 266.1*** | 111.8*** | 4.5*** |
| E | 1.1* | 140.1*** | 37.7*** | 108.7*** |  | 2.8*** |
| F | 0.6* | 4.0*** | 0.3* | 0.7* | 3.7*** | 14.0*** |
| G | 2.9*** | 100.0*** | 0.6* | 542.6*** | 7.5*** | 8.0*** |
| H | 0.8* | 12.5*** |  |  |  | 1.3* |
| I | 0.6* | 4.1*** |  | 246.1*** | 267.1*** | 0.7* |
| K | 0.8* |  |  | 647.0*** |  | 4.2*** |
| L | 2.2*** |  |  |  | 29.4*** |  |
| M |  |  |  |  |  |  |
| N |  |  |  |  |  |  |
| P | 1.1* |  | 35.2*** | 34.3*** | 0.9* |  |
| Q | XX*** |  |  | 24.4*** | 301.4*** | 4.9*** |
| R | 0.9* | 50.2*** | 3.5*** | 11.7*** | 36.0*** |  |
| S | 0.5* | 34.6*** | 0.2* | 42.4*** | 8.4*** | 11.8*** |
| T | 2.3*** | 18.2*** | 7.5*** | 93.0*** | 2.8*** |  |
| V |  | 1.2* | 1.0* |  | 219.0*** | 5.7*** |
| W | 0.0* |  |  |  | 491.3*** |  |
| Y | 0.8* | 4.1*** | 0.6* |  | 1.6* | 9.6*** |

TABLE 9.2

Affinity Fold Changes Caused by Heavy Chain CDR Mutations in CDR2

|   | 49G | 50D | 51I | 52N | 53P | 54N | 55T | 56G | 57D | 58T | 59S | 61N |
|---|-----|-----|-----|-----|-----|-----|-----|-----|-----|-----|-----|-----|
| A | 5.5*** | 2.4*** |  | 1.1* |  | 1.3* | 6.1*** | 0.8* | 1.1* | 0.5* | 0.7* | 1.2* |
| C |  |  |  |  |  |  |  |  |  |  | 0.7* | 2.0* |
| D | 25.0*** |  | 14.7*** |  | 35.4*** | 1.7* | 8.1*** | 2.3*** |  | 0.7* | 0.4* | 1.7* |
| E | 23.5*** | 6.0*** | 5.1*** |  |  | 3.4*** | 5.4*** |  | 1.0* | 0.7* | 0.8* | 1.5* |
| F | 14.9*** |  | 2.8*** | 16.3*** | 19.5*** | 2.5*** | 4.5*** |  | 1.3* | 1.4* | 0.6* |  |
| G |  | 30.9*** | 3.9*** | 1.1* |  | 1.5* | 2.6*** |  | 1.2* | 0.7* | 0.7* | 1.2* |
| H | 26.1*** |  |  |  |  | 0.5* |  |  | 1.1* | 0.7* |  |  |
| I | 14.0*** |  |  | 64.5*** |  | 0.2* | 0.9* |  |  | 2.1*** |  | 2.2*** |
| K | 17.6*** | 1295.7*** |  | 37269.8*** |  | 3.3*** | 1.5* |  | 1.0* | 0.5* | 5.0*** | 0.8* |
| L | 24.8*** | 26.4*** | 0.4* | 55254.6*** | 43.6*** | 1.5* | 0.4* |  | 1.9* | 1.0* | 1.4* | 0.9* |
| M |  | 11.7*** |  |  |  | XX*** |  |  | 1.2* |  | 0.8* | 1.4* |
| N |  |  |  |  |  |  |  |  | 1.8* | 0.6* | 0.8* |  |
| P | 11.3*** | 18.5*** |  |  |  |  | 7.3*** |  |  | 0.9* |  |  |
| Q | 19.2*** | 41.3*** |  | 44745.4*** |  | XX*** | 1.0* |  | 1.0* | 0.6* | 1.3* | 1.2* |
| R | 18.0*** | 297.4*** | 14.0*** |  | 6.7*** | 1.8* | 1.1* |  | 1.2* | 0.5* | 42.1*** | 0.8* |
| S | 9.0*** | 11.3*** | 2.2*** | 6.4*** | 21.9*** | 3.3*** | 1.2* | 2.5*** | 1.4* | 0.5* | 0.6* | 1.0* |
| T | 30.9*** |  | 2.3*** |  | 1.8* | 0.3* |  |  | 1.2* | 0.5* | 1.2* | 1.5* |
| V |  | 172.2*** | 1.4* | 71.5*** | 30.9*** | 0.5* | 1.0* | 0.5* | 1.1* | 0.5* | 1.0* | 1.7* |
| W | 16.2*** | 5.6*** |  | 11.6*** |  | 0.7* |  |  |  | 0.7* | 1.1* | 2.5*** |
| Y | 16.1*** |  | 4.0*** | 1571.0*** |  | 0.3* | 6.1*** |  | 1.4* | 0.7* | 1.0* | 1.1* |

Example 10—Screen Result for Heavy Chain CDR3 of TAF KCD119 Molecule

Heavy Chain CDR3 was screened in E. coli before looking at expression and binding in the Expi293 system (Table 10.1). Fab fragment of KCD119 was mutagenized using degenerate oligos at each residue independently across heavy chain CDR3. Site directed mutagenesis of heavy chain KCD119 TAF Fab (cloned into pCDisplay-4 with the KCD119 TAF light chain dually expressed) using NEB Q5 Site Directed mutagenesis kit and primers RDJ63&66 (residue 1). 95 colonies were picked into a 96-well plate, reserving WT for well A1. 1.5 ml cultures were grown overnight at 30 degrees (LB+50 ug/ml Amp, 1% glucose). Cultures were diluted back to 0.2OD (600 nm) and allowed to grow for 1.5 hours. IPTG was added to 0.5 mM final concentration to induce expression for 5 hours. Cultures were spun down for 15 minutes and resuspended in 400 uls of 20% sucrose, 100 mM Hepes to osmotically stress the cells. After a 15 minute incubation at RT, cells were spun for 10 minutes. The pellet was resuspended in 200 uls of 4 mM MgCl2 and incubated on ice for 20 minutes. Samples were spun down and 180 uls of the resulting supernatant was removed (periplasmic fraction). 20 uls of 10×HBS-EP buffer and filtered through a 2 um filter plate before running on Biacore T200. Plates were screened on Biacore T200 for binding to CFD by capturing CFD on a CM5 chip coated with KCD004. Lysates were flowed over captured CFD for 1.5 minutes, and allowed to dissociate for 2 minutes. Any hits with off-rates comparable or better than WT KCD119 were sequenced and cloned into pCDNA3.3 by PCR amplifying the variable region with primers RDJ121 (gatc gaattcgGAGGTGCAGCTGGTGGAA) (SEQ ID NO: 511) (the underlined section is a restriction site) and RDJ122 (gatcGGAGGACACTGTCACCAG) (SEQ ID NO: 512). Resulting PCR fragments were cloned into a pCDNA3.3 vector between an IL2-SS and huGl Fc domain. Transfected positive clones with KCD119 TAF LC into Hek293 cells and check for binding to CFD on Biacore T200 using Protein A chip and single cycle kinetics.

The results are shown in Table 10.1. Boxes are marked with * when the aa substitution has similar or better affinity. Boxes are marked with *** when aa substitution has worse affinity. Positive hits were sequenced and cloned into mammalian expression vector. Mutations with "XX" or numerical values were tested in Expi293 cells for expression and Factor D binding. XX indicates no sufficient antibody expression.

TABLE 10.1

Affinity Fold Changes Caused by Heavy Chain CDR Mutations in CDR3

|   | 97T | 98R | 99E | 100G | 101P | 102S | 103F | 104A | 105Y |
|---|---|---|---|---|---|---|---|---|---|
| A | 15.0* | *** | *** | *** | *** | 1.6* | *** | *** | 4.4* |
| C | *** | *** | *** | *** | *** | 10.0* | *** | *** | *** |
| D | 6.0* | *** | *** | *** | *** | *** | *** | *** | *** |
| E | XX* | *** | *** | *** | *** | *** | *** | *** | *** |
| F | *** | *** | 23.3* | *** | *** | *** | *** | 9.6* | 3.8* |
| G | *** | *** | *** | *** | *** | 20.9* | *** | *** | *** |
| H | *** | *** | *** | *** | *** | *** | *** | *** | 1.5* |
| I | *** | *** | *** | *** | XX* | *** | *** | 18.0* | *** |
| K | *** | *** | *** | *** | *** | *** | *** | *** | *** |
| L | *** | *** | 18.6* | *** | 5.0* | *** | *** | *** | 2.7* |
| M | *** | *** | XX* | *** | *** | *** | *** | *** | *** |
| N | *** | *** | *** | *** | *** | 15.0* | *** | *** | *** |
| P | *** | *** | *** | *** | *** | *** | *** | *** | *** |
| Q | 5.0* | *** | *** | *** | *** | *** | *** | *** | *** |
| R | *** | *** | *** | XX* | *** | *** | *** | 2.5* | *** |
| S | 208.0* | *** | *** | *** | *** | *** | *** | *** | *** |
| T | *** | *** | *** | *** | *** | *** | *** | 19.8* | *** |
| V | *** | *** | *** | *** | *** | *** | *** | *** | 3.8* |
| W | *** | *** | *** | *** | *** | XX* | *** | *** | *** |
| Y | *** | *** | *** | *** | *** | *** | *** | *** | 1.9* |

Example 11—Identifying Additive or Synergistic Mutation Combos of TAF KCD119

Mutations that corresponded with positive changes in affinity were combined for both heavy and light chains, and various heavy and light chain pairings were tested for expression and Factor D binding kinetics.

313 unique heavy chain mutants and 451 unique light chain mutants, for a total of 764 mutants were designed and engineered within the 6 CDRs of KCD119. The tolerability of each residue within each of the 6 CDRs was assessed for various amino acid substitutions while determining functional pairings between various heavy and light chain mutants. A total of 865 mutant combinations were tested. The 865 pairings were designed in an iterative process, where light chain mutants that increased affinity were combined with heavy chain mutants that increased affinity until single digit pM affinity was achieved.

During the combination screening, each antibody containing a unique light and heavy chain combo was transfected and the resulting conditioned media was used for initial screening on Biacore. Combos that are additive were purified from Expi293 supernatants following a standard protocol. Antibodies were diluted to 0.5 ug/ml in HBS-EP+ buffer and captured on a protein A chip for 25 seconds to reach approximately 70 resonance units. 45 nM, 15 nM, 5 nM, 1.67 nM, and 0.56 nM serum purified Complement Factor D (diluted in HBS-EP+ buffer) was flowed over the captured antibodies for 60 seconds in a single cycle kinetics method, and dissociated for 30 minutes at both 25 and 37 degrees. Binding kinetic information was obtained by the BIAevaluation software (GE). Representative data are presented in FIG. 6A-FIG. 6D, and Table 11.1 and Table 11.2.

TABLE 11.1

Identifying Additive or Synergistic Mutation Combinations

| Heavy Chain | Light Chain | ka (1/Ms) | kd (1/s) | KD (M) |
|---|---|---|---|---|
| KCD119 TAF | KCD119 TAF | 4.46E6 | 1.03E−3 | 2.30E−10 |
| 54V | KCD119 TAF | 4.09E6 | 6.27E−4 | 1.53E−10 |
| 54V | 101V | 4.88E6 | 4.63E−4 | 9.49E−11 |
| 54V59D | KCD119 TAF | 5.85E6 | 3.07E−4 | 5.26E−11 |
| 54V59D | 101V | 6.64E6 | 2.13E−4 | 3.21E−11 |

TABLE 11.2

Affinity results of mutant combinations

| Heavy Chain | Light Chain | 25 Degrees | | | | 37 Degrees | | | |
|---|---|---|---|---|---|---|---|---|---|
| | | ka (1/Ms) | kd (1/s) | KD (M) | Rmax (RU) | ka (1/Ms) | kd (1/s) | KD (M) | Rmax (RU) |
| 28Q31S54V59D | 101V | 7.15E+06 | 1.64E−04 | 2.30E−11 | 17.3 | 1.35E+07 | 1.03E−03 | 7.57E−11 | 21.2 |
| 28S31S54V59D | 101V | 7.64E+06 | 1.66E−04 | 2.17E−11 | 17.3 | 1.26E+07 | 9.18E−04 | 7.27E−11 | 21.7 |
| 28V31S54V59D | 101V | 7.91E+06 | 4.76E−05 | 6.01E−12 | 16 | 1.66E+07 | 8.50E−04 | 5.10E−11 | 19.8 |
| 28H31S54V59D | 101V | 6.65E+06 | 1.67E−04 | 2.51E−11 | 18.9 | 1.72E+07 | 4.43E−04 | 2.57E−11 | 24.8 |
| 28I31S54V59D | 101V | 7.59E+06 | 1.34E−04 | 1.77E−11 | 17.5 | 2.00E+07 | 3.90E−04 | 1.95E−11 | 24 |
| 28K31S54V59D | 101V | 7.30E+06 | 1.63E−04 | 2.24E−11 | 16.6 | | | | |
| 54V56V | 101V | 5.44E+06 | 3.51E−04 | 6.45E−11 | 19.4 | 9.69E+06 | 1.04E−03 | 1.07E−10 | 22.5 |
| 54V59D | 101V | 6.94E+06 | 2.58E−04 | 3.71E−11 | 19.6 | | | | |
| 31S48V54V59D | 101V | 5.98E+06 | 1.01E−04 | 1.69E−11 | 15.9 | | | | |
| 31S54V59D | 101V | 6.95E+06 | 1.31E−04 | 1.88E−11 | 18.2 | | | | |
| 54I59D | 101V | 7.43E+06 | 1.52E−04 | 2.04E−11 | 18.7 | | | | |
| 54V59D | 32W60W101V | 7.88E+06 | 4.79E−05 | 6.07E−12 | 13.6 | | | | |
| 48V54V59D | 32W60W101V | 5.96E+06 | 9.50E−05 | 1.59E−11 | 16.4 | 1.31E+07 | 2.78E−04 | 2.12E−11 | 18.6 |
| 31S54V59D | 32W60W101V | 5.58E+06 | 8.84E−05 | 1.58E−11 | 16.3 | 1.29E+07 | 2.93E−04 | 2.27E−11 | 18.3 |
| 54I59D | 32W60W101V | 7.57E+06 | 3.50E−05 | 4.62E−12 | 14 | 1.50E+07 | 1.97E−04 | 1.31E−11 | 16.8 |
| 54V59D | 32W50I101V | 6.64E+06 | 1.05E−04 | 1.58E−11 | 16.7 | 1.37E+07 | 3.05E−04 | 2.23E−11 | 18.9 |
| 54V59D | 32D50I101V | 8.11E+06 | 1.60E−04 | 1.97E−11 | 17.3 | 1.50E+07 | 4.10E−04 | 2.74E−11 | 20.2 |
| 54V59D | 32D60W101V | 1.25E+07 | 1.28E−04 | 1.02E−11 | 14 | 8.93E+06 | 3.71E−04 | 4.15E−11 | 16.9 |
| 54V59D | 34D60W101V | 8.80E+06 | 1.87E−04 | 2.13E−11 | 15.8 | 1.56E+07 | 8.30E−04 | 5.31E−11 | 18.7 |
| 54V59D | 34D50V101V | 7.26E+06 | 1.87E−04 | 2.57E−11 | 17.8 | 1.34E+07 | 7.90E−04 | 5.91E−11 | 20.8 |
| 54V | 101V | 7.14E+06 | 4.91E−04 | 6.88E−11 | 16.6 | 1.11E+07 | 1.58E−03 | 1.42E−10 | 20.4 |
| OG1931 | OG1931 | 3.83E+07 | 1.64E−04 | 4.27E−12 | 13.3 | 2.65E+07 | 4.35E−04 | 1.64E−11 | 15 |
| 54I59D | 50I60W101V | 5.53E+06 | 6.67E−05 | 1.21E−11 | 15.6 | 1.04E+07 | 3.29E−04 | 3.18E−11 | 18 |
| 54I59D | 32W60W101V | 4.91E+06 | 8.32E−05 | 1.69E−11 | 14 | 6.86E+06 | 6.67E−05 | 9.72E−12 | 17.2 |
| 54I59D | 54R101V (SEQ ID NO: 184) | 1.10E+07 | 7.04E−05 | 6.42E−12 | 15.1 | 2.64E+07 | 1.87E−04 | 7.10E−12 | 17.1 |
| 54I59D | 54G101V | 1.15E+07 | 9.56E−05 | 8.33E−12 | 14.8 | 2.78E+07 | 2.15E−04 | 7.74E−12 | 17.1 |
| 54I59D | 101V | 5.78E+06 | 1.54E−04 | 2.67E−11 | 13.5 | 9.19E+06 | 4.37E−04 | 4.75E−11 | 16.4 |
| 31S54I59D | 50I60W101V | 5.14E+06 | 3.98E−05 | 7.74E−12 | 13.6 | 9.26E+06 | 2.56E−04 | 2.76E−11 | 16.7 |
| 31S54I59D | 32W60W101V | 3.83E+06 | 6.30E−05 | 1.65E−11 | 13.5 | 6.55E+06 | 2.25E−04 | 3.43E−11 | 14.4 |
| 31S54I59D | 54R101V (SEQ ID NO: 184) | 1.02E+07 | 7.94E−05 | 7.79E−12 | 13.8 | 3.48E+07 | 2.10E−04 | 6.05E−12 | 15.4 |
| 31S54I59D | 54G101V | 1.20E+07 | 8.25E−05 | 6.89E−12 | 13.2 | 2.38E+07 | 2.22E−04 | 9.31E−12 | 15.2 |
| 31S54V59D | 101V | 5.71E+06 | 1.01E−04 | 1.76E−11 | 15.4 | 9.08E+06 | 3.73E−04 | 4.11E−11 | 17.6 |
| 31S34I54I59D | 32W60W101V | 3.31E+06 | 5.69E−05 | 1.72E−11 | 13.2 | 6.67E+06 | 2.08E−04 | 3.12E−11 | 15.1 |
| 31S54I59D84T | 32W60W101V | 3.83E+06 | 6.01E−05 | 1.57E−11 | 12.9 | 7.79E+06 | 2.24E−04 | 2.88E−11 | 14.3 |
| 31S54I59D84S | 32W60W101V | 3.83E+06 | 7.76E−05 | 2.03E−11 | 11.1 | 8.90E+06 | 2.09E−04 | 2.35E−11 | 12.4 |
| 54I59D84T | 32W60W101V | 4.99E+06 | 8.43E−05 | 1.69E−11 | 11.2 | 1.41E+07 | 3.65E−04 | 2.58E−11 | 12.7 |
| 54V59D | 54R101V (SEQ ID NO: 184) | 1.19E+07 | 1.41E−04 | 1.19E−11 | 11.7 | 2.40E+07 | 3.70E−04 | 1.54E−11 | 13.3 |
| OG1931 | | 2.24E+07 | 6.83E−05 | 3.05E−12 | 14 | 1.41E+08 | 4.72E−04 | 3.34E−12 | 15.5 |
| 54I59D | 101V | 6.32E+06 | 5.74E−05 | 9.08E−12 | 25 | 1.21E+07 | 2.22E−04 | 1.84E−11 | 29.7 |
| 54I59D | 32W60W101V | 5.83E+06 | 6.85E−05 | 1.18E−11 | 20.9 | 1.17E+07 | 5.83E−05 | 5.01E−12 | 25.4 |
| 54I59D | 4G101V 5 | 5.91E+06 | 9.41E−08 | 1.59E−14 | 21 | 1.36E+07 | 4.08E−07 | 2.99E−14 | 25.3 |
| 31S54V59D | 54R101V (SEQ ID NO: 184) | 1.39E+07 | 5.48E−05 | 3.94E−12 | 22.3 | 3.33E+07 | 2.42E−04 | 7.25E−12 | 25.3 |
| 31S54I59D | 54R101V (SEQ ID NO: 184) | 1.40E+07 | 5.12E−05 | 3.66E−12 | 23.2 | 3.09E+07 | 2.14E−04 | 6.91E−12 | 26.7 |
| 54I59D | 54R101V (SEQ ID NO: 184) | 2.02E+07 | 5.95E−05 | 2.94E−12 | 21.3 | 4.74E+07 | 2.57E−04 | 5.43E−12 | 24.6 |
| 31S34I54I59D | 54R101V (SEQ ID NO: 184) | 1.39E+07 | 1.06E−04 | 7.60E−12 | 23.2 | 2.69E+07 | 1.57E−04 | 5.83E−12 | 26.6 |
| 31S54I59D84S | 54R101V (SEQ ID NO: 184) | 1.49E+07 | 9.14E−05 | 6.13E−12 | 22.2 | 2.84E+07 | 1.74E−04 | 6.13E−12 | 25.9 |
| 54I59D | 32W33G60W101V | 7.78E+06 | 4.00E−04 | 5.14E−11 | 17.1 | 1.14E+07 | 1.20E−03 | 1.05E−10 | 20.9 |
| 54I59D | 32W33G60W101V | 6.14E+06 | 3.28E−04 | 5.34E−11 | 21.2 | 1.51E+07 | 1.48E−03 | 9.79E−11 | 23 |
| 54I59D | 32W33G60W101V | 4.53E+06 | 3.52E−04 | 7.78E−11 | 20.7 | 8.69E+06 | 1.17E−03 | 1.35E−10 | 23.3 |
| 54I59D | 32W54S101V | 7.69E+06 | 7.29E−05 | 9.48E−12 | 18.7 | 1.41E+07 | 1.55E−04 | 1.10E−11 | 21.4 |
| 54I59D | 54S60W101V | 7.19E+06 | 7.08E−05 | 9.85E−12 | 19.5 | 1.24E+07 | 1.48E−04 | 1.19E−11 | 23.4 |
| 54I59D | 32W54S60W101V | 6.25E+06 | 5.37E−05 | 8.58E−12 | 14.4 | 1.10E+07 | 1.36E−04 | 1.24E−11 | 17.2 |
| 54I59D | 54G60W101 | 6.83E+06 | 8.54E−05 | 1.25E−11 | 17.5 | 1.19E+07 | 1.18E−04 | 9.89E−12 | 19.5 |
| 54I59D | 54R101V (SEQ ID NO: 184) | 1.71E+07 | 9.80E−05 | 5.72E−12 | 20.7 | 3.09E+07 | 2.05E−04 | 6.63E−12 | 23.7 |
| 34I54I59D | 54R101V (SEQ ID NO: 184) | 1.80E+07 | 1.01E−04 | 5.62E−12 | 15.9 | 3.27E+07 | 2.64E−04 | 8.08E−12 | 18.4 |
| 31S34I54I59D | 54R101V (SEQ ID NO: 184) | 1.32E+07 | 7.84E−05 | 5.96E−12 | 18.7 | 2.46E+07 | 2.37E−04 | 9.61E−12 | 20.6 |
| 31S54I59D | 54R101V (SEQ ID NO: 184) | 1.44E+07 | 1.20E−04 | 8.36E−12 | 18 | 2.78E+07 | 2.27E−04 | 8.17E−12 | 19.9 |
| 34I54I59D | 32W60W101V | 6.45E+06 | 1.36E−04 | 2.11E−11 | 13.3 | 1.29E+07 | 2.79E−04 | 2.17E−11 | 15.1 |
| 54I59D | 54R101V (SEQ ID NO: 184) | 1.82E+07 | 9.50E−05 | 5.23E−12 | 18.5 | 3.78E+07 | 3.00E−04 | 7.92E−12 | 20.8 |

TABLE 11.2-continued

Affinity results of mutant combinations

| Heavy Chain | Light Chain | 25 Degrees | | | | 37 Degrees | | | |
|---|---|---|---|---|---|---|---|---|---|
| | | ka (1/Ms) | kd (1/s) | KD (M) | Rmax (RU) | ka (1/Ms) | kd (1/s) | KD (M) | Rmax (RU) |
| OG1931 | | 3.48E+07 | 1.15E−04 | 3.29E−12 | 18.6 | 2.17E+08 | 8.96E−04 | 4.13E−12 | 20.6 |
| OG1931 | OG1931 | 3.11E+07 | 1.36E−05 | 4.37E−13 | 18.1 | 2.94E+08 | 9.10E−04 | 3.10E−12 | 21 |
| 31S34I54I59D84S | 54R101V (SEQ ID NO: 184) | 1.66E+07 | 1.69E−08 | 1.02E−15 | 21 | 3.50E+07 | 1.37E−04 | 3.92E−12 | 24.4 |
| 34I54I59D84S (SEQ ID NO: 183) | 54R101V (SEQ ID NO: 184) | 2.06E+07 | 9.02E−05 | 4.37E−13 | 18.2 | 4.00E+07 | 2.02E−04 | 5.04E−12 | 21.1 |
| 31S34I54I59D84S | 54G101V | 4.42E+06 | 1.81E−10 | 4.10E−17 | 19.8 | 1.21E+07 | 7.36E−05 | 6.11E−12 | 22.3 |
| 34I54I59D84S (SEQ ID NO: 183) | 54G101V | 7.59E+06 | 5.18E−05 | 6.83E−12 | 19.5 | 1.45E+07 | 1.12E−04 | 7.74E−12 | 24.1 |
| KCD119 TAF | KCD119TAF | 1.38E+07 | 1.55E−03 | 1.13E−10 | 20.5 | 1.26E+07 | 6.28E−03 | 4.99E−10 | 26.1 |

*kD values <1E−12 are outside of the limits of the Biacore T200.

Heavy and light chain sequence of high-affinity anti-CFD antibodies and their representative variants are shown in Table 11.3.

TABLE 11.3

Amino acid sequences of final heavy and light chain candidates and their variants (KCD119 Variant Sequences; a CDR embodiment is underlined.)

Heavy Chain

| KCD119 TAF | EVQLVESGGGLVQPGGSLRLSCAASGYTFT<u>DYYMN</u>WVRQAPGKGLEWIGD<u>INPNTGDTSYNADFKRRF</u>TFSLDTSKSTAYLQMNSLRAEDTAVYYCTR<u>EGPSFAY</u>WGQGTLVTVSS (SEQ ID NO: 513) |
|---|---|
| 54V | EVQLVESGGGLVQPGGSLRLSCAASGYTFT<u>DYYMN</u>WVRQAPGKGLEWIGD<u>INPVTGDTSYNADFKRRF</u>TFSLDTSKSTAYLQMNSLRAEDTAVYYCTR<u>EGPSFAY</u>WGQGTLVTVSS (SEQ ID NO: 514) |
| 54I | EVQLVESGGGLVQPGGSLRLSCAASGYTFT<u>DYYMN</u>WVRQAPGKGLEWIGD<u>INPITGDTSYNADFKRRF</u>TFSLDTSKSTAYLQMNSLRAEDTAVYYCTR<u>EGPSFAY</u>WGQGTLVTVSS (SEQ ID NO: 515) |
| 54V59D | EVQLVESGGGLVQPGGSLRLSCAASGYTFT<u>DYYMN</u>WVRQAPGKGLEWIGD<u>INPVTGDTDYNADFKRRF</u>TFSLDTSKSTAYLQMNSLRAEDTAVYYCTR<u>EGPSFAY</u>WGQGTLVTVSS (SEQ ID NO: 516) |
| 54I59D | EVQLVESGGGLVQPGGSLRLSCAASGYTFT<u>DYYMN</u>WVRQAPGKGLEWIGD<u>INPITGDTDYNADFKRRF</u>TFSLDTSKSTAYLQMNSLRAEDTAVYYCTR<u>EGPSFAY</u>WGQGTLVTVSS (SEQ ID NO: 517) |
| 34I54I59D | EVQLVESGGGLVQPGGSLRLSCAASGYTFT<u>DYYIN</u>WVRQAPGKGLEWIGD<u>INPITGDTDYNADFKRRF</u>TFSLDTSKSTAYLQMNSLRAEDTAVYYCTR<u>EGPSFAY</u>WGQGTLVTVSS (SEQ ID NO: 518) |
| 31S34I54I59D | EVQLVESGGGLVQPGGSLRLSCAASGYTFT<u>SYYIN</u>WVRQAPGKGLEWIGD<u>INPITGDTDYNADFKRRF</u>TFSLDTSKSTAYLQMNSLRAEDTAVYYCTR<u>EGPSFAY</u>WGQGTLVTVSS (SEQ ID NO: 519) |
| 34I54I59D84S | EVQLVESGGGLVQPGGSLRLSCAASGYTFT<u>DYYIN</u>WVRQAPGKGLEWIGD<u>INPITGDTDYNADFKRRF</u>TFSLDTSKSTAYLQMSSLRAEDTAVYYCTR<u>EGPSFAY</u>WGQGTLVTVSS (SEQ ID NO: 520) |
| 31S34I54I59D84S | EVQLVESGGGLVQPGGSLRLSCAASGYTFT<u>SYYIN</u>WVRQAPGKGLEWIGD<u>INPITGDTDYNADFKRRF</u>TFSLDTSKSTAYLQMSSLRAEDTAVYYCTR<u>EGPSFAY</u>WGQGTLVTVSS (SEQ ID NO: 521) |

Light Chain

| KCD119 TAF | DIQLTQSPSSLSASVGDRVTITCRSS<u>QTIVHSNGDTYLE</u>WYQQKPGKAPNLLIY<u>KVS</u>NRFSGVPSRFSGSGSGTDFTLTISSLQPEDFATYYC<u>FQGSHVPPT</u>FGQGTKVEIK (SEQ ID NO: 522) |
|---|---|
| 54R | DIQLTQSPSSLSASVGDRVTITCRSS<u>QTIVHSNGDTYLE</u>WYQQKPGKAPNLLIR<u>KVS</u>NRFSGVPSRFSGSGSGTDFTLTISSLQPEDFATYYC<u>FQGSHVPPT</u>FGQGTKVEIK (SEQ ID NO: 523) |
| 101V | DIQLTQSPSSLSASVGDRVTITCRSS<u>QTIVHSNGDTYLE</u>WYQQKPGKAPNLLIY<u>KVS</u>NRFSGVPSRFSGSGSGTDFTLTISSLQPEDFATYYC<u>FQGSHVPVT</u>FGQGTKVEIK (SEQ ID NO: 524) |
| 54R101V | DIQLTQSPSSLSASVGDRVTITCRSS<u>QTIVHSNGDTYLE</u>WYQQKPGKAPNLLIR<u>KVS</u>NRFSGVPSRFSGSGSGTDFTLTISSLQPEDFATYYC<u>FQGSHVPVT</u>FGQGTKVEIK (SEQ ID NO: 525) |
| 54G101V | DIQLTQSPSSLSASVGDRVTITCRSS<u>QTIVHSNGDTYLE</u>WYQQKPGKAPNLLIG<u>KVS</u>NRFSGVPSRFSGSGSGTDFTLTISSLQPEDFATYYC<u>FQGSHVPVT</u>FGQGTKVEIK (SEQ ID NO: 526) |

TABLE 11.4

Heavy and light chain nucleotide sequences of high-affinity anti-CFD antibodies and their variants Heavy Chain

| KCD119 Taf | GAGGTGCAGCTGGTGGAATCTGGCGGCGGACTGGTGCAGCCTGGCGGCTCCCTGAGACTGTCTTGCGCCGCCTCCGGCTACACCTTCACCGACTACTACATGAACTGGGTGCGACAGGCCCCTGGCAAGGGCCTGGAATGGATCGGCGACATCAACCCCAACACCGGCGACACCAGCTACAACGCCGACTTCAAGCGG |

TABLE 11.4-continued

Heavy and light chain nucleotide sequences of
high-affinity anti-CFD antibodies and their variants

|  |  |
|---|---|
|  | CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 527) |
| 54V | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCTGGCAAGGGC<br>CTGGAATGGATCGGCGACATCAACCCCGTCACCGGCGACACCAGCTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 528) |
| 54I | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCTGGCAAGGGC<br>CTGGAATGGATCGGCGACATCAACCCCATCACCGGCGACACCAGCTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 529) |
| 54V<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCTGGCAAGGGC<br>CTGGAATGGATCGGCGACATCAACCCCGTCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 530) |
| 54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 531) |
| 34I<br>54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATCAACTGGGTGCGACAGGCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 532) |
| 31S<br>34I<br>54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCAGCTACTACATCAACTGGGTGCGACAGGCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 533) |
| 34I<br>54I<br>59D<br>84S | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATCAACTGGGTGCGACAGGCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAGCTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 534) |
| 31S<br>34I<br>54I<br>59D<br>84S | GAGGTGCAGCTGGTGGAATCTGGCGGCGGACTGGTGCAGCCTGGCGGCTCCCTGAGACTGTCTTGC<br>GCCGCCTCCGGCTACACCTTCACCAGCTACTACATCAACTGGGTGCGACAGGCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAGCTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 535) |

Light Chain

|  |  |
|---|---|
| KC<br>D119<br>Taf | GACATCCAGCTGACCCAGAGCCCCTCCAGCCTGTCCGCCTCTGTGGGCGACAGAGTGACCATCACCT<br>GTCGGTCCTCCCAGACCATCGTGCACTCCAACGGCGACACCTACCTGGAATGGTATCAGCAGAAGCC<br>CGGCAAGGCCCCTAACCTGCTGATCTACAAGGTGTCCAACCGGTTCTCCGGCGTGCCCTCCAGATTC<br>TCCGGCTCCGGCTCTGGCACCGACTTCACCCTGACCATCTCCAGCCTGCAGCCCGAGGACTTCGCCA<br>CCTACTACTGTTTTCAAGGCTCCCACGTGCCACCCACCTTCGGCCAGGGCACCAAGGTGGAAATCAA<br>G (SEQ ID NO: 536) |
| 54R | GACATCCAGCTGACCCAGAGCCCCTCCAGCCTGTCCGCCTCTGTGGGCGACAGAGTGACCATCACCT<br>GTCGGTCCTCCCAGACCATCGTGCACTCCAACGGCGACACCTACCTGGAATGGTATCAGCAGAAGCC<br>CGGCAAGGCCCCTAACCTGCTGATCCGCAAGGTGTCCAACCGGTTCTCCGGCGTGCCCTCCAGATTC<br>TCCGGCTCCGGCTCTGGCACCGACTTCACCCTGACCATCTCCAGCCTGCAGCCCGAGGACTTCGCCA<br>CCTACTACTGTTTTCAAGGCTCCCACGTGCCACCCACCTTCGGCCAGGGCACCAAGGTGGAAATCAA<br>G (SEQ ID NO: 537) |

TABLE 11.4-continued

Heavy and light chain nucleotide sequences of
high-affinity anti-CFD antibodies and their variants

```
101V    GACATCCAGCTGACCCAGAGCCCCTCCAGCCTGTCCGCCTCTGTGGGCGACAGAGTGACCATCACCT
        GTCGGTCCTCCCAGACCATCGTGCACTCCAACGGCGACACCTACCTGGAATGGTATCAGCAGAAGCC
        CGGCAAGGCCCCTAACCTGCTGATCTACAAGGTGTCCAACCGGTTCTCCGGCGTGCCCTCCAGATTC
        TCCGGCTCCGGCTCTGGCACCGACTTCACCCTGACCATCTCCAGCCTGCAGCCCGAGGACTTCGCCA
        CCTACTACTGTTTTCAAGGCTCCCACGTGCCAGTCACCTTCGGCCAGGGCACCAAGGTGGAAATCAA
        G (SEQ ID NO: 538)

54R     GACATCCAGCTGACCCAGAGCCCCTCCAGCCTGTCCGCCTCTGTGGGCGACAGAGTGACCATCACCT
101V    GTCGGTCCTCCCAGACCATCGTGCACTCCAACGGCGACACCTACCTGGAATGGTATCAGCAGAAGCC
        CGGCAAGGCCCCTAACCTGCTGATCCGCAAGGTGTCCAACCGGTTCTCCGGCGTGCCCTCCAGATTC
        TCCGGCTCCGGCTCTGGCACCGACTTCACCCTGACCATCTCCAGCCTGCAGCCCGAGGACTTCGCCA
        CCTACTACTGTTTTCAAGGCTCCCACGTGCCAGTCACCTTCGGCCAGGGCACCAAGGTGGAAATCAA
        G (SEQ ID NO: 539)

54G     GACATCCAGCTGACCCAGAGCCCCTCCAGCCTGTCCGCCTCTGTGGGCGACAGAGTGACCATCACCT
101V    GTCGGTCCTCCCAGACCATCGTGCACTCCAACGGCGACACCTACCTGGAATGGTATCAGCAGAAGCC
        CGGCAAGGCCCCTAACCTGCTGATCGGAAAGGTGTCCAACCGGTTCTCCGGCGTGCCCTCCAGATTC
        TCCGGCTCCGGCTCTGGCACCGACTTCACCCTGACCATCTCCAGCCTGCAGCCCGAGGACTTCGCCA
        CCTACTACTGTTTTCAAGGCTCCCACGTGCCAGTCACCTTCGGCCAGGGCACCAAGGTGGAAATCAA
        G (SEQ ID NO: 540)
```

Example 12—Removal of Sequence Liability for Manufacturability

Sequence in heavy chain TAF KCD119 CDR2 contain potential deamidation site 'NPNT'. Mutagenesis of NPNT reveal N54V or N54I enhanced affinity. Resulting molecule (54V/wt) was tested in Mass Spec under oxidation or temperature/high pH stress to look for additional glycosylation, oxidation and deamidation sites.

No N- or O-glycosylation sites were found in CDRs by mass spectrometry analysis (Example 13.2).

One Methionine oxidation was found in Heavy chain CDR1 (M34) by mass spectrometry analysis (Example 13.3).

One deamidation site in heavy chain FW3 that was increasingly deamidated in a high temperature/high pH stressed sample (2 weeks at 40 degree pH9) in 54V/wt was identified by mass spectrometry analysis (Example 13.4).

Example 13.1—Glycosylation Sites 54 v/wt sample was deglycosylated to remove N-linked glycans with only PNGase F (New England BioLabs, P/N P0705L). The sample was denatured with 8 M urea in 100 mM Tris (pH 8.0), buffer exchanged, deglycosylated at 37° C. overnight (16 hours), buffer exchanged, reduced with 25 mM DTT, and alkylated with 50 mM IAA. The sample was then digested in tandem with first endoproteinase Lys-C (2 hours) and then trypsin overnight (16 hours).

54 v/wt sample was deglycosylated to remove N-linked and O-linked glycans using the deglycosylase mix (New England BioLabs, P/N P6039). The sample was denatured with 8 M urea in 100 mM Tris (pH 8.0), buffer exchanged, deglycosylated at 37° C. overnight (16 hours), buffer exchanged, reduced with 25 mM DTT and alkylated with 50 mM IAA. The sample was digested in tandem by first adding the endoproteinase Lys-C for 2 hours at 37° C. and then adding trypsin before allowing the digestion to proceed overnight (16 hours) at 37° C.

The glycosylated sample was denatured with 8 M urea in 100 mM Tris (pH 8.0), reduced with 25 mM DTT and alkylated with 50 mM IAA. The sample was digested in tandem by first adding the endoproteinase Lys-C for 2 hours at 37° C. and then adding trypsin before allowing the digestion to proceed overnight (16 hours) at 37° C.

Peptide sequence coverage from Mass Spec analysis was compared amongst glycosylated and deglycosylated samples. No additional N- or O-glycosylation sites were found in CDRs.

Example 13.2—Oxidation Sites

Two 54 v/wt samples were stressed in a light chamber at 765 W/m2 over a 24 hour period. One sample was removed and frozen (−20° C.) at 8 hours. The remaining material was removed after 24 hours. The stressed samples were treated with the deglycosylase mix to remove N-linked and O-linked glycans as described in the previous slide.

Peptide sequence coverage from Mass Spec analysis was compared amongst UV stressed and non-stressed samples. One Methionine oxidation was found in Heavy chain CDR1 (M34).

For removal of M34 oxidation site, substitutions at residue 34 were screened. Looked for residues to improve or have no effect on affinity, and found that M34I did not affect affinity of 54 v/wt. M34I was then engineered into the high affinity variants 31S54I59D/54R101V or 54I59D/54R101V to determine its effects on binding affinity at 25 and 37 degrees (Table 13.2.1 and Table 13.2.2).

TABLE 13.2.1

Screening substitutions for removal of M34 oxidation site at 25 C.

| Heavy Chain | Light Chain | ka (1/Ms) | kd (1/s) | KD (M) |
|---|---|---|---|---|
| 31S54I59D | 54R101V (SEQ ID NO: 184) | 1.44E+07 | 1.20E−04 | 8.36E−12 |
| 54I59D | 54R101V (SEQ ID NO: 184) | 1.71E+07 | 9.80E−05 | 5.72E−12 |
| 34I54I59D | 54R101V (SEQ ID NO: 184) | 1.80E+07 | 1.01E−04 | 5.62E−12 |
| 31S34I54I59D | 54R101V (SEQ ID NO: 184) | 1.32E+07 | 7.84E−05 | 5.96E−12 |

TABLE 13.2.2

Screening substitutions for removal of M34 oxidation site at 37 C.

| Heavy Chain | Light Chain | ka (1/Ms) | kd (1/s) | KD (M) |
|---|---|---|---|---|
| 31S54I59D | 54R101V (SEQ ID NO: 184) | 2.78E+07 | 2.27E−04 | 8.17E−12 |
| 54I59D | 54R101V (SEQ ID NO: 184) | 3.09E+07 | 2.05E−04 | 6.63E−12 |
| 34I54I59D | 54R101V (SEQ ID NO: 184) | 3.27E+07 | 2.64E−04 | 8.08E−12 |
| 31S34I54I59D | 54R101V (SEQ ID NO: 184) | 2.46E+07 | 2.37E−04 | 9.61E−12 |

Example 13.3—Deamidation Sites 54 v/wt samples were adjusted to pH9 and incubated at 40 degrees for 2 weeks. The stressed samples were treated with the deglycosylase mix to remove N-linked and O-linked glycans. Deamidation of residue 84N in HFW3 was found to be significantly increased in the 54 v/wt sample that was incubated at 40 degree and pH9 for 2 weeks as compared to a sample that did not go through the temperature and pH stress (22.5% vs. 7.5%).

For removal of 84N Deamidation site, 84N was substituted with S or T (the second and third commonly occurring amino acids at 84 position with 25% and 7% frequency, respectively). 84S did not affect affinity (Table 13.3.1 and Table 13.3.2).

TABLE 13.3.1

Screening substitutions for removal of 84N deamidation site at 25 C.

| Heavy Chain | Light Chain | ka (1/Ms) | kd (1/s) | KD (M) |
|---|---|---|---|---|
| 31S54I59D | 54R101V (SEQ ID NO: 184) | 1.40E+07 | 5.12E−05 | 3.66E−12 |
| 31S54I59D84S | 54R101V (SEQ ID NO: 184) | 1.49E+07 | 9.14E−05 | 6.13E−12 |

TABLE 13.3.2

Screening substitutions for removal of 84N deamidation site at 37 C.

| Heavy Chain | Light Chain | ka (1/Ms) | kd (1/s) | KD (M) |
|---|---|---|---|---|
| 31S54I59D | 54R101V (SEQ ID NO: 184) | 3.09E+07 | 2.14E−04 | 6.91E−12 |
| 31S54I59D84S | 54R101V (SEQ ID NO: 184) | 2.84E+07 | 1.74E−04 | 6.13E−12 |

Example 14—Polyreactivity

Figure 7A:
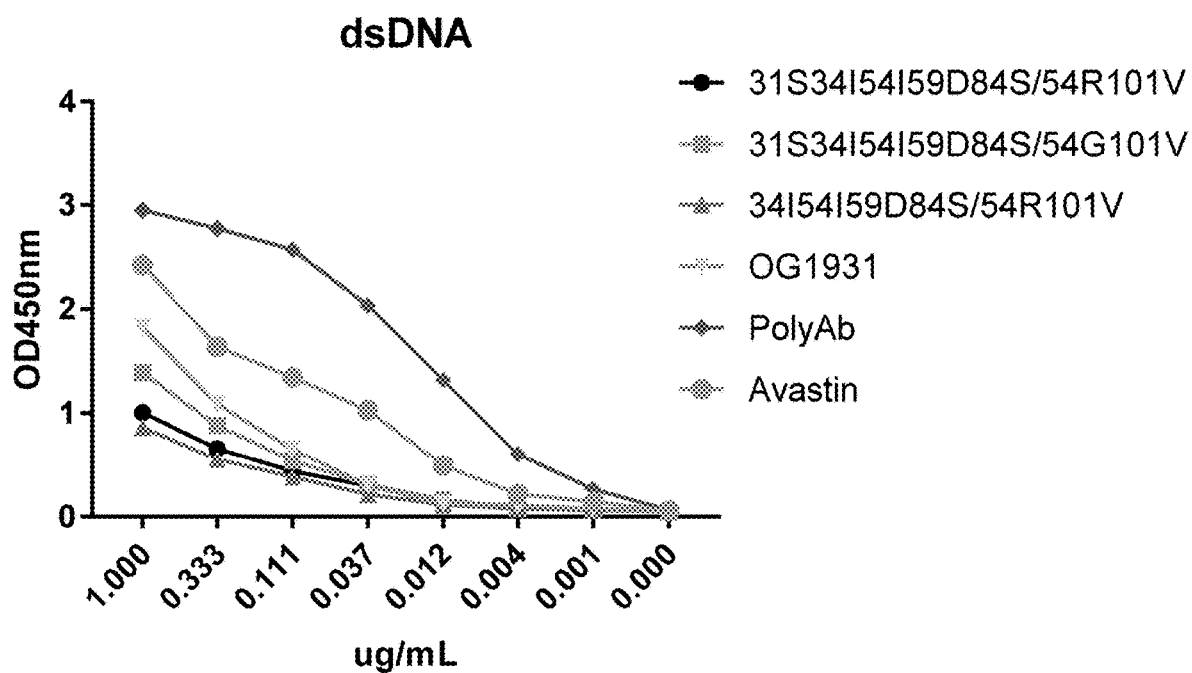
FIG. 7A shows polyreactivity profile of a panel of antibodies tested by ELISA against dsDNA antigen.
Figure 7B:
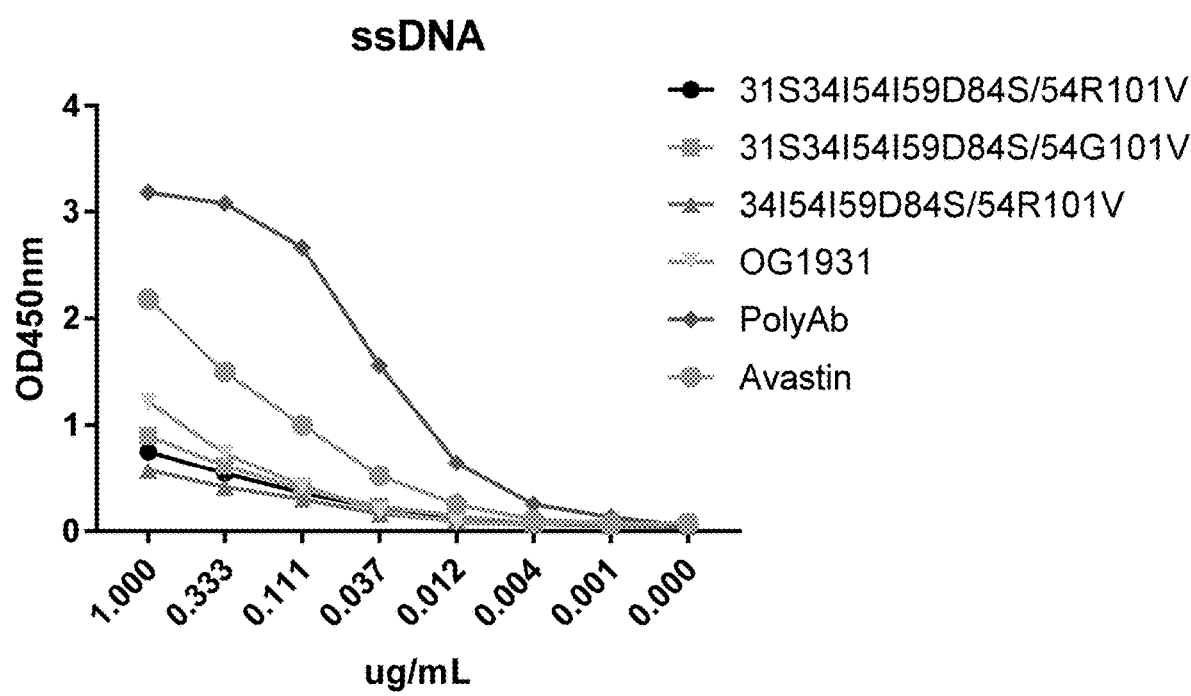
FIG. 7B shows polyreactivity profile of a panel of antibodies tested by ELISA against ssDNA antigen.
Figure 7C:
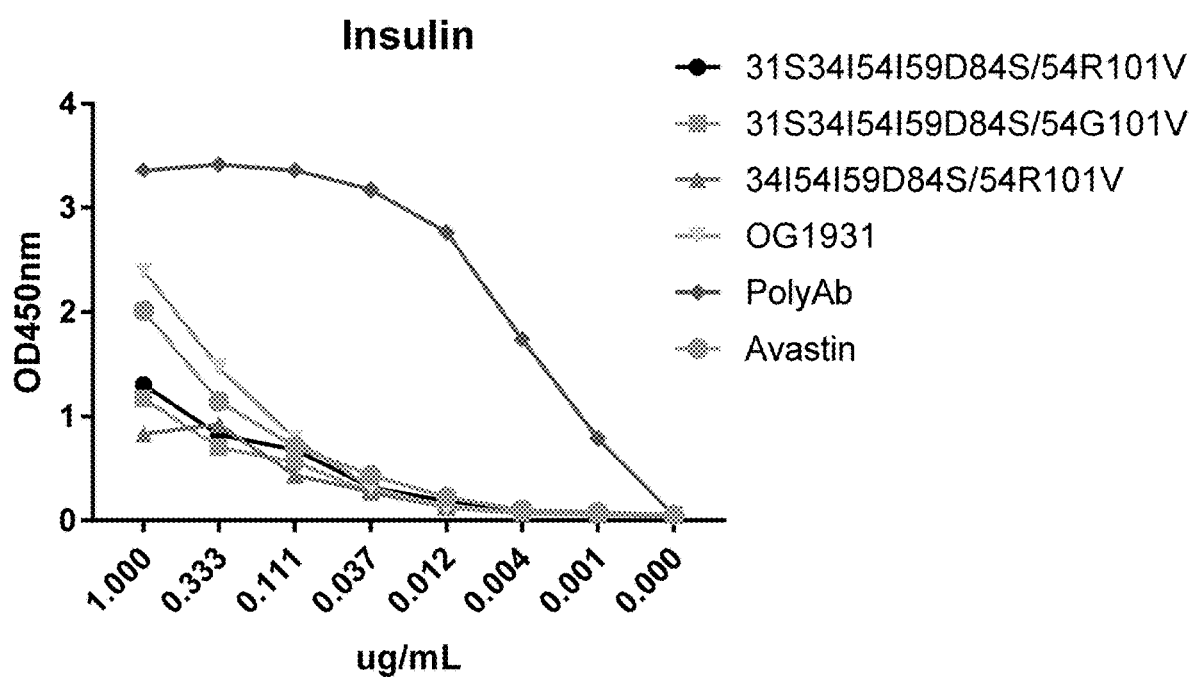
FIG. 7C shows polyreactivity profile of a panel of antibodies tested by ELISA against insulin antigen.
Figure 7D:
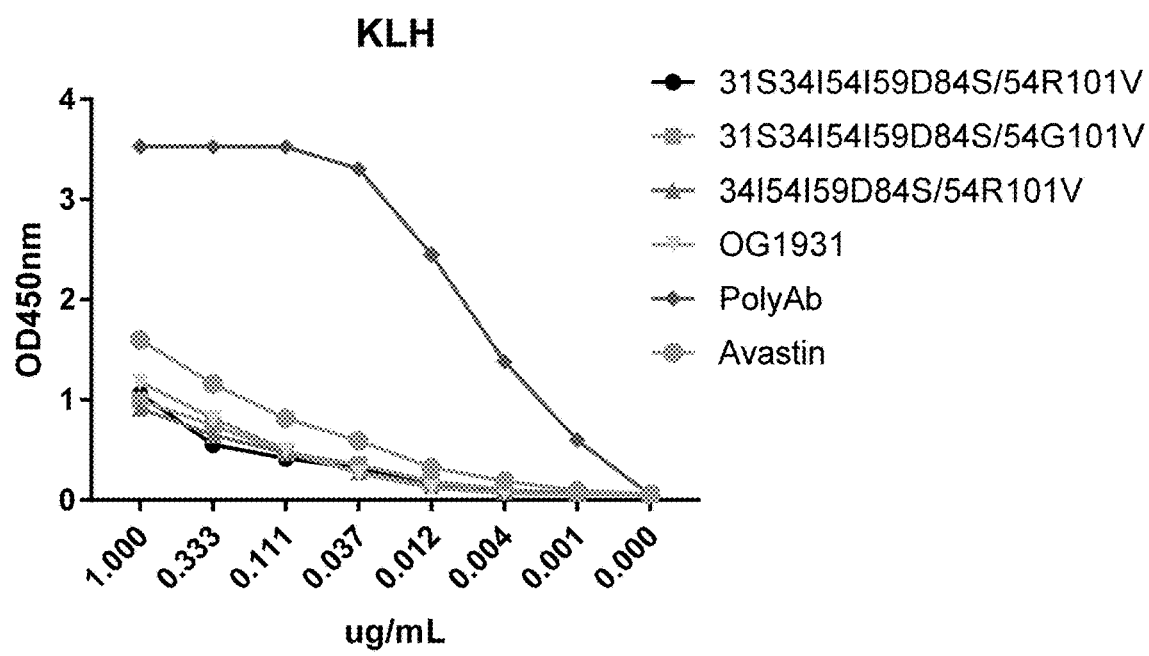
FIG. 7D shows polyreactivity profile of a panel of antibodies tested by ELISA against KLH antigen.
Figure 7E:
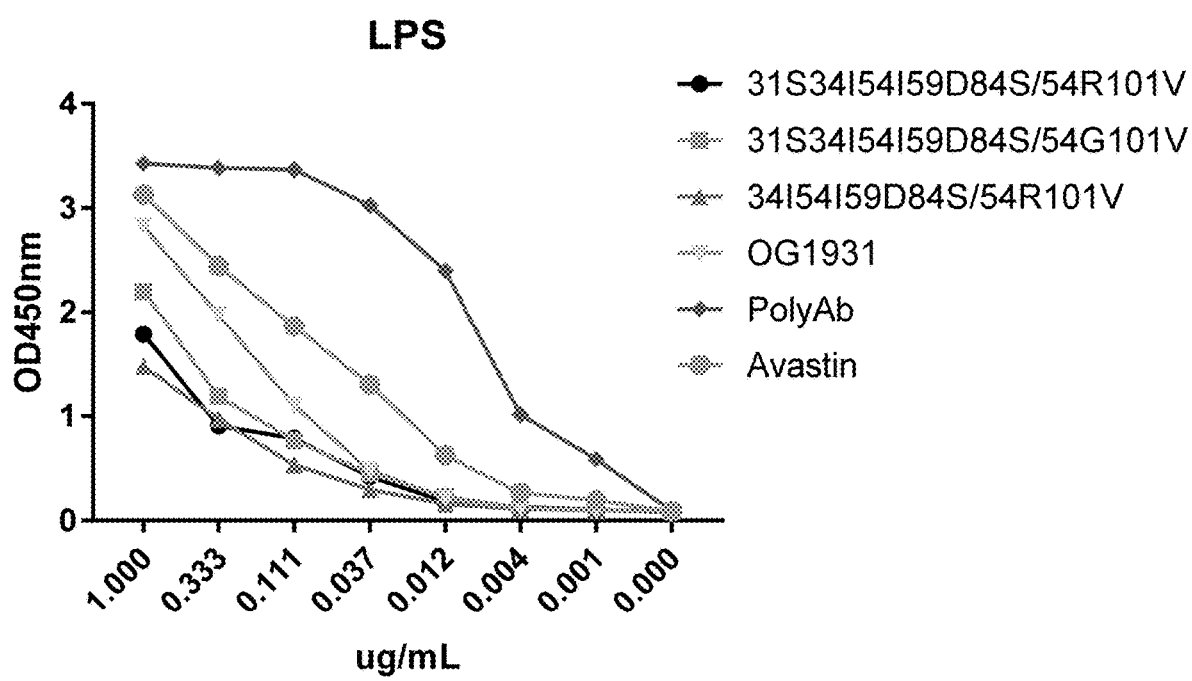
FIG. 7E shows polyreactivity profile of a panel of antibodies tested by ELISA against LPS antigen.
Figure 7F:
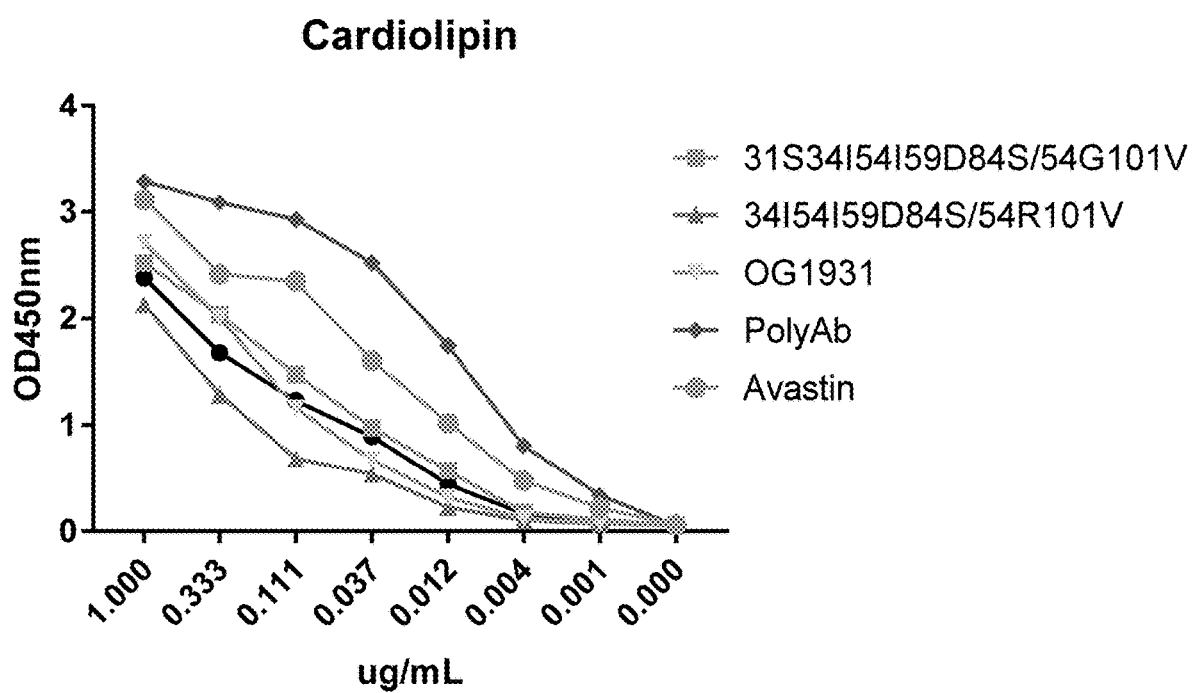
FIG. 7F shows polyreactivity profile of a panel of antibodies tested by ELISA against cardiolipin antigen.

The polyreactivity profile of a panel of high-affinity humanized anti-CFD antibodies were tested by ELISA. Briefly, various antigens (dsDNA (FIG. 7A), ssDNA (FIG. 7B), insulin (FIG. 7C), KLH (FIG. 7D), LPS (FIG. 7E) and cardiolipin (FIG. 7F)) were coated overnight at room temperature at 5 ug/mL; except for insulin at 2.5 ug/mL. Plates were washed in water then blocked in ELISA buffer (1 mM EDTA, 0.05% Tween 20) for 2 hours at room temperature. Antibody panel was titrated 1:3 from a top concentration of 1 ug/mL in 1×PBS and incubated for 2 hours at room temperature, followed by 3 washes in water and incubation with an HRP conjugated anti-human Fc antibody in ELISA buffer for 1 hour at room temperature. Lastly, plates were washed in water, incubated in ELISA buffer for 5 min at room temperature followed by a final wash in water prior to TMB development.

Example 15—Manufacturability

Representative high affinity anti-CFD antibodies and their variants have excellent expression in Mammalian Cells Table as determined by antibody expression levels in the supernatant of transiently transfected HEK293 and CHO cells. Data are presented in Table 15.1.

TABLE 15.1

Antibody expression levels in the supernatant of transiently transfected HEK293 and CHO cells

| Heavy | Light | Expi293 Expression (3 ml) (mg/L) | CHO Expression (1 L) (mg/L) |
|---|---|---|---|
| OG1931 | OG1931 | 140 | 13.6 |
| 31S34I54I59D84S | 54R101V (SEQ ID NO: 184) | 124 | 228.3 |
| 34I54I59D84S (SEQ ID NO: 183) | 54R101V (SEQ ID NO: 184) | 86 | 206.1 |
| 31S34I54I59D84S | 54G101V | 35 | 248.7 |
| 34I54I59D84S (SEQ ID NO: 183) | 54G101V | 123 | NA |
| KCD119 TAF | KCD119TAF | 84 | |

Example 16

One embodiment of the antibody included the point mutations of 34I54I59D84S (heavy, SEQ ID NO: 183 or 520)/54R101V (light, SEQ ID NO: 184 or 525), also called OG1965.

Example 17.1—FB Cleavage Assay for Anti-CFD Antibodies

Factor B Cleavage Assay—

Figure 8:
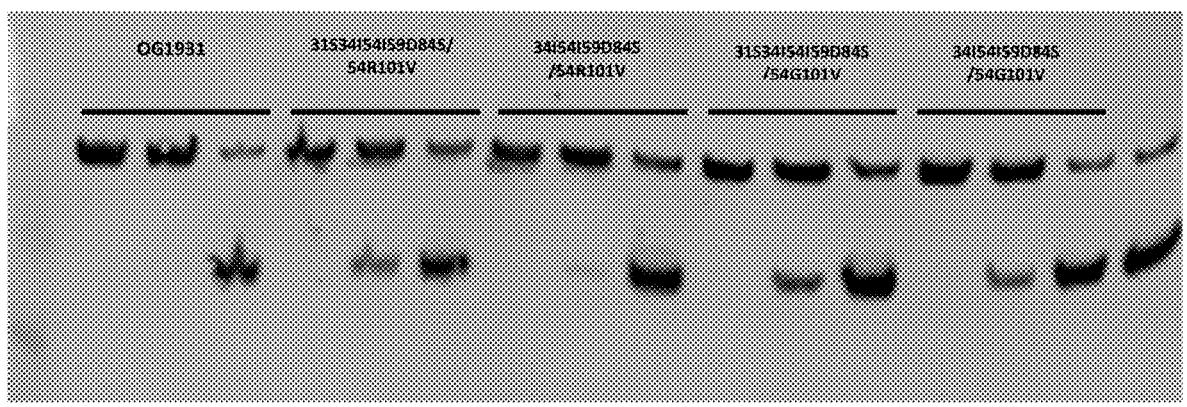
FIG. 8 shows an image of a Western blot of an FB cleavage assay for anti-CFD antibodies.
Figure 9:
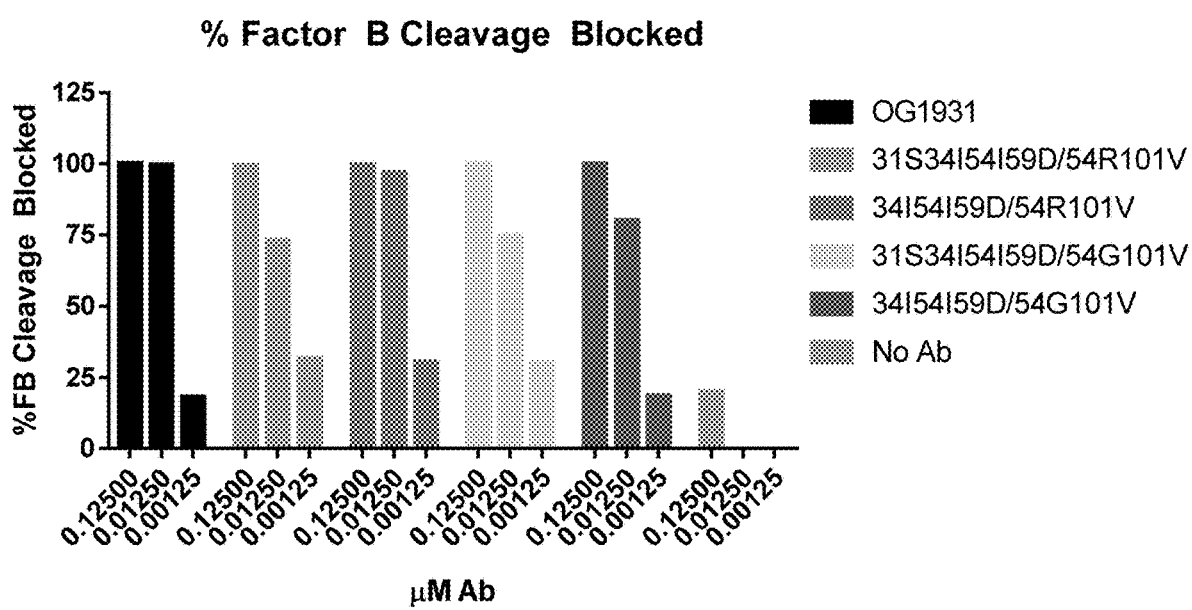
FIG. 9 shows a graph of the % of FB cleavage blocked in the FB cleavage assay for anti-CFD antibodies.

To determine whether anti-CFD antibodies (AFDs) block factor B (FB) cleavage, a FB cleavage assay was used. For the assay, 0.15 uM CFD (serum purified; CompTech cat. no. A136) was mixed with varying concentrations of AFDs (0.5 uM down to 0.005 uM) in a final volume of 10 uls. The complexes were incubated at room temperature for 45 minutes. 0.5 uM of Factor B (FB; serum purified; A135 CompTech) and 0.5 uM C3b (serum purified; CompTech cat. no. A114) were combined and incubated for 15 minutes at room temperature in a final volume of 10 uls for each sample. 10 uls of FB/C3b complex was added to 10 uls of CFD/AFD so that the final concentrations of FB/C3b were 0.25 uM and CFD was 0.0375 uM in a final volume of 20 uls. The proteins were then incubated at 37° C. for 45 minutes. Following incubation, sample buffer with reducing agent was added to samples and run on a 4-12% Bis-Tris gel before being transferred to a nitrocellulose membrane for western blot analysis. Membranes were blocked for 1 hour in Odyssey® Blocking Buffer (LI-COR®) and then incubated with 1:1000 dilution of anti-Factor B antibody (Rabbit monoclonal antibody; EPR9288(B) Abcam) overnight. The blot was washed 3 times with PBS with 0.5% Tween®, and incubated with 1:10000 dilution of goat anti-Rabbit 800 secondary antibody (LI-COR®). The blot was then washed 3 times with PBS, once with water, and imaged on a LI-COR® Odyssey® Fc scanner. Factor B cleavage was quantified using Image Studio® Western Blot analysis software. The blocking ability of each antibody was calculated by taking the percentage of cleaved Factor B of the total Factor B (cleaved and uncleaved) for each sample. Data are presented in FIG. 8 and FIG. 9.

These data indicate that the anti-CFD antibodies potently and effectively blocked CFD mediated cleavage of C3bB in a dose-dependent manner.

Example 17.2—FB Cleavage Assay for 34I54I59D84S/54R101V

Figure 10:
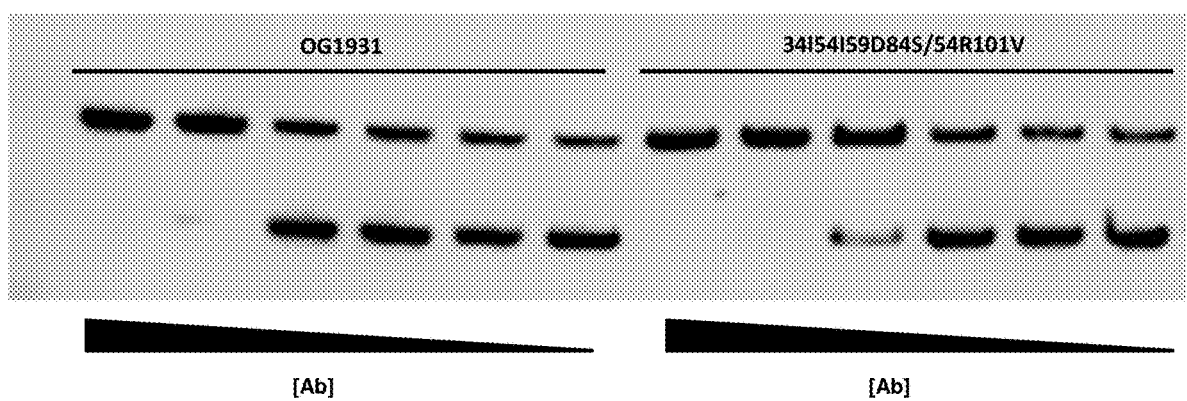
FIG. 10 shows an image of a Western blot of an FB cleavage assay for anti-CFD antibodies.
Figure 11:
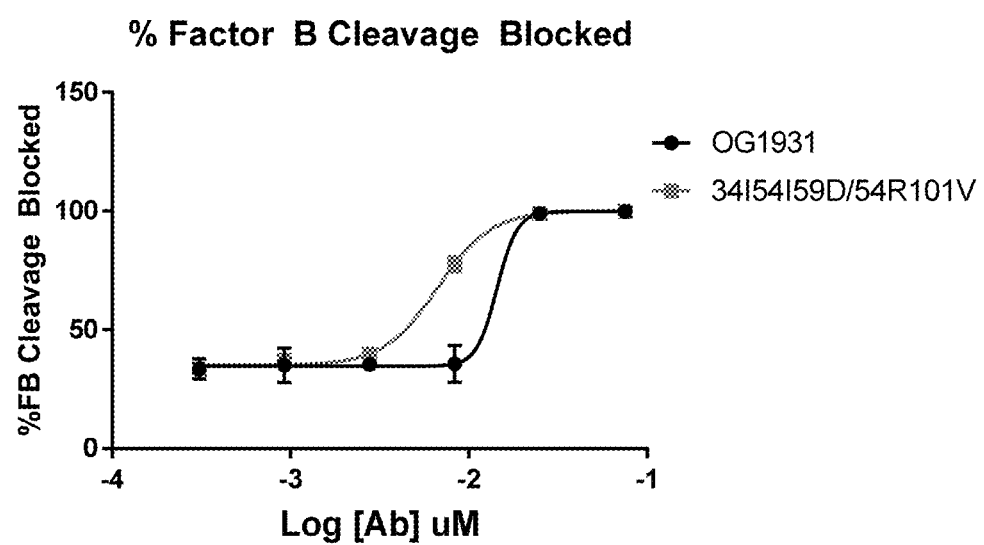
FIG. 11 shows a graph of the % of FB cleavage blocked in an FB cleavage assay for anti-CFD antibodies.

To determine whether anti-CFD antibodies (AFDs) block factor B (FB) cleavage, an FB cleavage assay was used. For the assay, 0.15 uM CFD (serum purified; CompTech cat. no. A136) was mixed with varying concentrations of AFDs (1:3 dilutions from 0.075 uM down to 0.00031 uM) in a final volume of 10 uls. The complexes were incubated at room temperature for 30 minutes. 0.5 uM of Factor B (FB; serum purified; A135 CompTech) and 0.5 uM C3b (serum purified; CompTech cat. no. A114) were combined and incubated for 45 minutes at room temperature in a final volume of 10 uls for each sample. 10 uls of FB/C3b complex was added to 10 uls of CFD/AFD so that the final concentrations of FB/C3b were 0.25 uM and CFD was 0.0375 uM in a final volume of 20 uls. The proteins were then incubated at 37° C. for 45 minutes. Following incubation, sample buffer with reducing agent was added to samples and run on a 4-12% Bis-Tris gel before being transferred to a nitrocellulose membrane for western blot analysis. Membranes were blocked for 1 hour in Odyssey® Blocking Buffer (LI-COR®) and then incubated with 1:1000 dilution of anti-Factor B antibody (Rabbit monoclonal antibody; EPR9288(B) Abcam) overnight. The blot was washed 3 times with PBS with 0.5% Tween®, and incubated with 1:10000 dilution of goat anti-Rabbit 800 secondary antibody (LI-COR®). The blot was then washed 3 times with PBS, once with water, and imaged on a LI-COR® Odyssey® Fc scanner. Factor B cleavage was quantified using Image Studio® Western Blot analysis software. The blocking ability of each antibody was calculated by taking the percentage of cleaved Factor B of the total Factor B (cleaved and uncleaved) for each sample. 34I54I59D84S (SEQ ID NO: 183 or 520)/54R101V (SEQ ID NO: 184 or 525) antibody was comparable or slightly better at blocking CFD mediated cleavage of CFB than OG1931. Data are presented in FIG. 10 and FIG. 11.

Under these conditions, Factor B cleavage was blocked completely by 34I54I59D84S/54R101V in a dose dependent manner with an EC50 of 7 nM.

Example 18—Binding Affinities of Humanized Anti-CFD Antibodies

Figure 18:
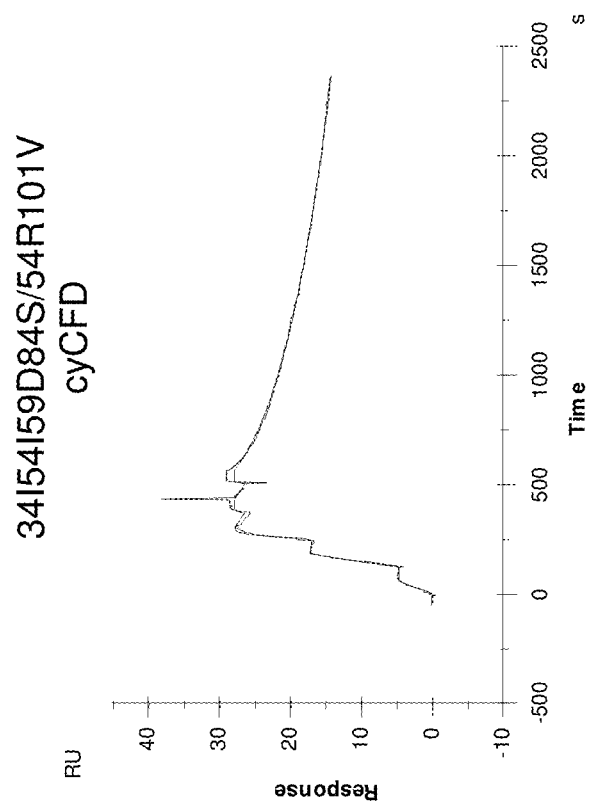
FIG. 18 shows binding affinity of 34I54I59D84S/54R101V to Cynomolgus CFD.

Antibodies were purified from Expi293 supernatants following a standard protocol. Antibodies were diluted to 0.5 ug/ml in HBS-EP+ buffer and captured on a protein A chip for 25 seconds to reach approximately 70 resonance units. 45 nM, 15 nM, 5 nM, 1.67 nM, and 0.56 nM serum purified Complement Factor D (diluted in HBS-EP+ buffer) or recombinant cynomolgus Complement Factor D (cyCFD) was flowed over the captured antibodies for 60 seconds in a single cycle kinetics method, and dissociated for 30 minutes. Binding kinetic information was obtained by the BIAevaluation software (GE). Representative data are presented in FIG. 18 and Table 18.1 and Table 18.2. In some embodiments, the construct 34I54I59D84S as the heavy chain and 54R101V as the light chain is especially advantageous.

Figure 19:
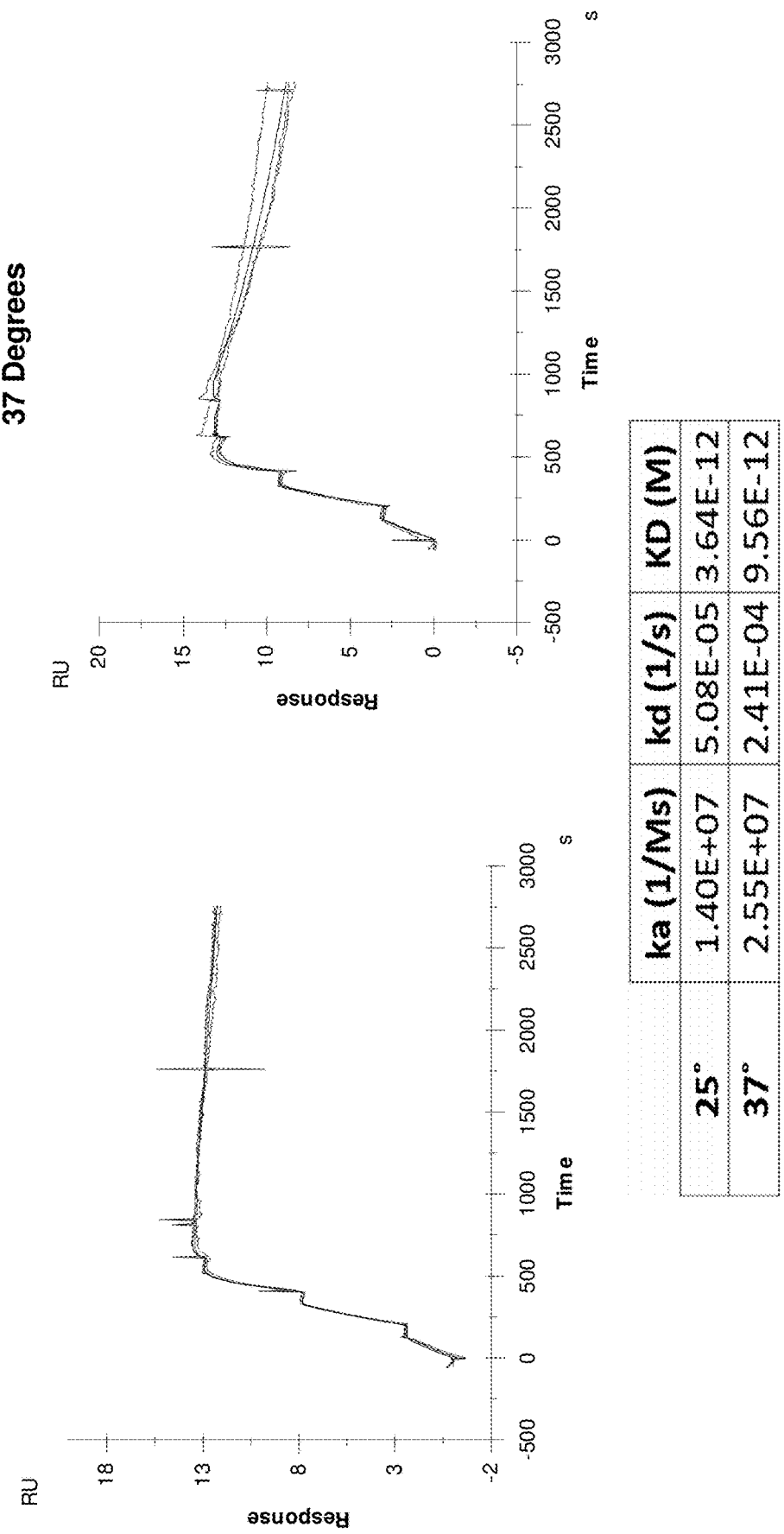
FIG. 19 shows binding affinities of 34I54I59D84S/54R101V to purified human CFD at 25 degree and 37 degree Celsius.
Figure 21:
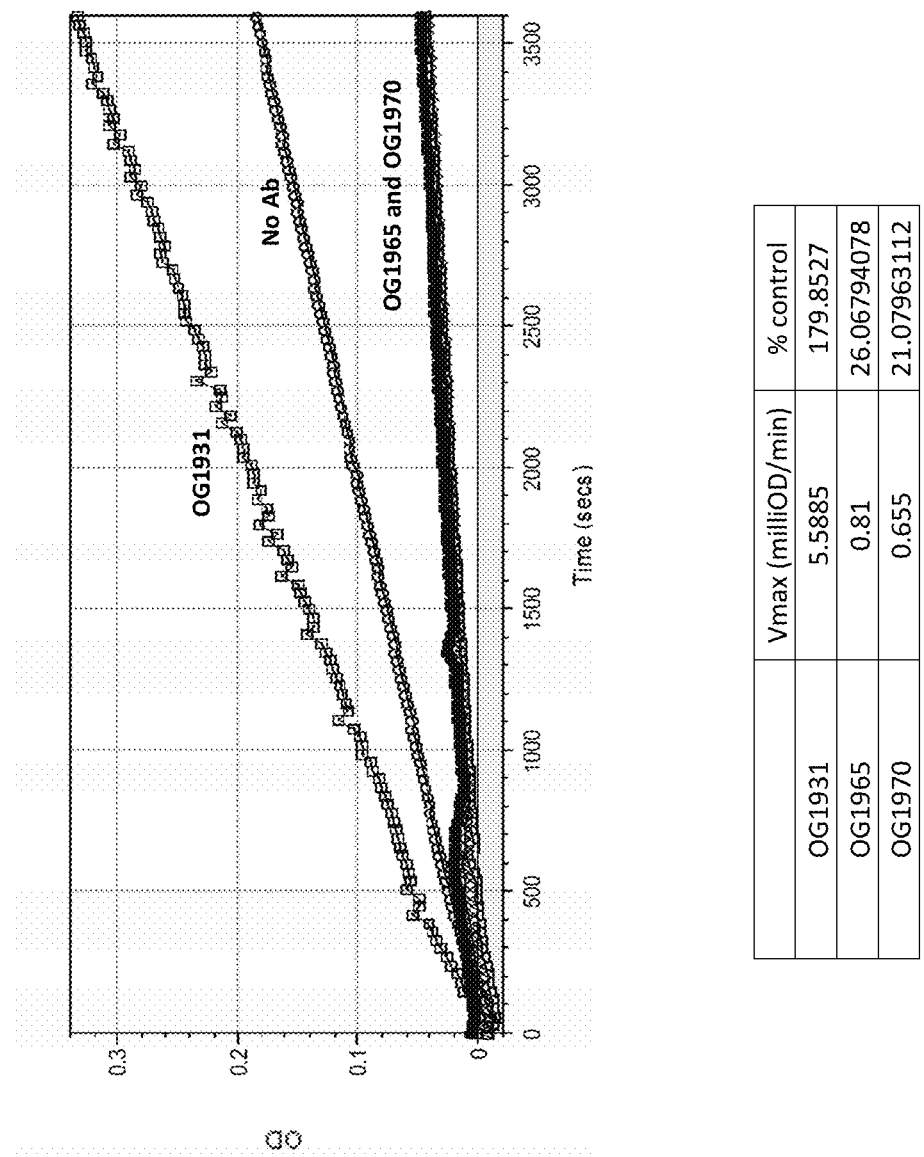

To better determine CFD binding kinetics by SPR of final candidate OG1965, a semi-covalent immobilization technique was employed. OG1965 was biotinylated using Thermo EZ-Link Maleimide-PEG2-Biotin kit at a 10:1 ratio. Approximately 1-2 biotin molecules were conjugated to each antibody molecule. 10,000 RUs of neutravidin (Thermo) was directly immobilized to a CM5 chip on a Biacore T200 following the standard amine coupling immobilization method. 50 RUs of OG1965 was captured on flow cell 2, and single cycle kinetics for binding to serum purified human CFD (15 nM, 5 nM, 1.67 nM, 0.56 nM, 0.19 nM) was performed at both 25 and 37 degrees. Data are shown in FIG. 19 and Table 18.3.

TABLE 18.1

Binding kinetics data for Final Candidates to serum purified human Complement Factor D

| Heavy | Light | 25 Degrees | | | 37 Degrees | | |
| --- | --- | --- | --- | --- | --- | --- | --- |
| | | ka (1/Ms) | kd (1/s) | KD (M) | ka (1/Ms) | kd (Vs) | KD (M) |
| OG1931 | OG1931 | 3.11E+07 | 1.36E−05 | 4.37E−13 | 2.94E+08 | 9.10E−04 | 3.10E−12 |
| 3I534I54I59D84S | 54R101V | 1.66E+07 | 1.69E−08 | 1.02E−15 | 3.50E+07 | 1.37E−04 | 3.92E−12 |
| 34I54I59D84S | 54R101V | 2.06E+07 | 9.02E−05 | 4.37E−12 | 4.00E+07 | 2.02E−04 | 5.04E−12 |
| 3I534I54I59D84S | 54G101V | 4.42E+06 | 1.81E−10 | 4.10E−17 | 1.21E+07 | 7.36E−05 | 6.11E−12 |
| 34I54I59D84S | 54G101V | 7.59E+06 | 5.18E−05 | 6.83E−12 | 1.45E+07 | 1.12E−04 | 7.74E−12 |
| D19 TAF | D19TAF | 1.38E+07 | 1.55E−03 | 1.13E−10 | 1.26E+07 | 6.28E−03 | 4.99E−10 |

TABLE 18.2

Binding kinetics data for OG1965 to cyno CFD (cyCFD) at 37 degrees

| Ligand | Sample | ka (1/Ms) | kd (1/s) | KD (M) |
|---|---|---|---|---|
| OG1965 | cyCFD | 3.49E+07 | 9.78E−04 | 2.80E−11 |

TABLE 18.3

Binding kinetics data for semi-covalently immobilized OG1965 at 25 and 37 degrees

| | Ka (1/Ms) | Kd (1/s) | KD (M) |
|---|---|---|---|
| 25° | 1.40E+07 | 5.08E−05 | 3.64E−12 |
| 37° | 2.55E+07 | 2.41E−04 | 9.56E−12 |

Example 19.1—Enzymatic Assay of Anti-CFD Antibodies

Proteolysis Assay—

Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog # D-8130, 100 mM stock in DMSO). 50 µLs of the diluted CFD is loaded into a 96 well clear plate, and 50 uls of AFD is added. The reaction is started by adding 100 µL of substrate/DTNB mixture to wells. A substrate blank containing 50 µL assay buffer and 50 µL substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/µg)=Adjusted Vmax*(OD/min)×well volume (L)×$10^{12}$ pmol/mol. ext. coeff($M^{-1}cm^{-1}$)×path corr.*(cm)×amount of enzyme (µg). *Adjusted for substrate blank, Using the extinction coefficient 13,260 $M^{-1}cm^{-1}$, *Using the path correction 0.320 cm. Data are presented in FIG. 12 and Table 19.1.1.

Figure 12:
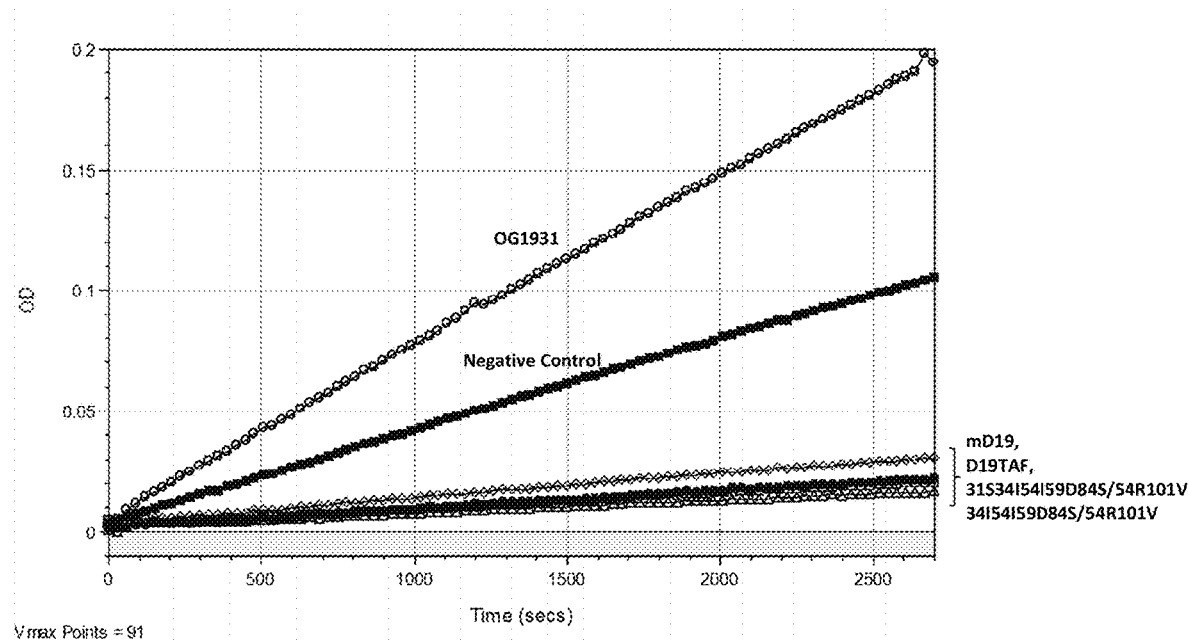
FIG. 12 shows effect of anti-CFD antibodies on the enzyme activity of human CFD for the synthetic substrate Z-L-Lys-SBzl hydrochloride.

FIG. 12 shows that KCD119 variants block enzymatic activity of human Complement Factor D (serum purified), while a control antibody (OG1931) enhances enzymatic activity relative to no antibody control or negative antibody (OG1321) control.

TABLE 19.1.1

Enzymatic Assay of anti-CFD antibodies

| | Vmax (OD/sec) | % no ab control |
|---|---|---|
| OG1931 | 4.231 | 203.06 |
| KCD119TAF | 0.408 | 19.58 |
| Mouse KCD119 | 0.318 | 15.26 |
| 31S34I54V59D84S/54R101V (SEQ ID NO: 184) | 0.596 | 28.60 |
| 34I54V59D84S/54R101V (SEQ ID NO: 184) | 0.486 | 23.32 |
| OG1321 | 2.335 | 112.06 |
| No Ab | 2.063 | 100.00 |

Example 19.2—Effect of Anti-CFD Antibodies on Alternative Compliment Dependent Hemolysis Assay To assess the ability of anti-CFD antibodies to inhibit alternative complement pathway, a hemolysis assay was used.

Hemolysis Assay—

For the hemolysis assay, rabbit red blood cells ("RBCs", CompTech #B301) are diluted or re-suspended and washed with $GVB^0$ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Normal human serum (NHS) were incubated with anti-CFD antibody (AFD) at room temperature for ten minutes in well of a round-bottom plate. Add the prepared RBCs to the wells with NHS/AFD on the incubation plate; incubate at room temperature for 35 minutes, mixing every 10 minutes. Stop the reaction with $GVB^0$/10 mM EDTA CompTech #B104).

Figure 13:
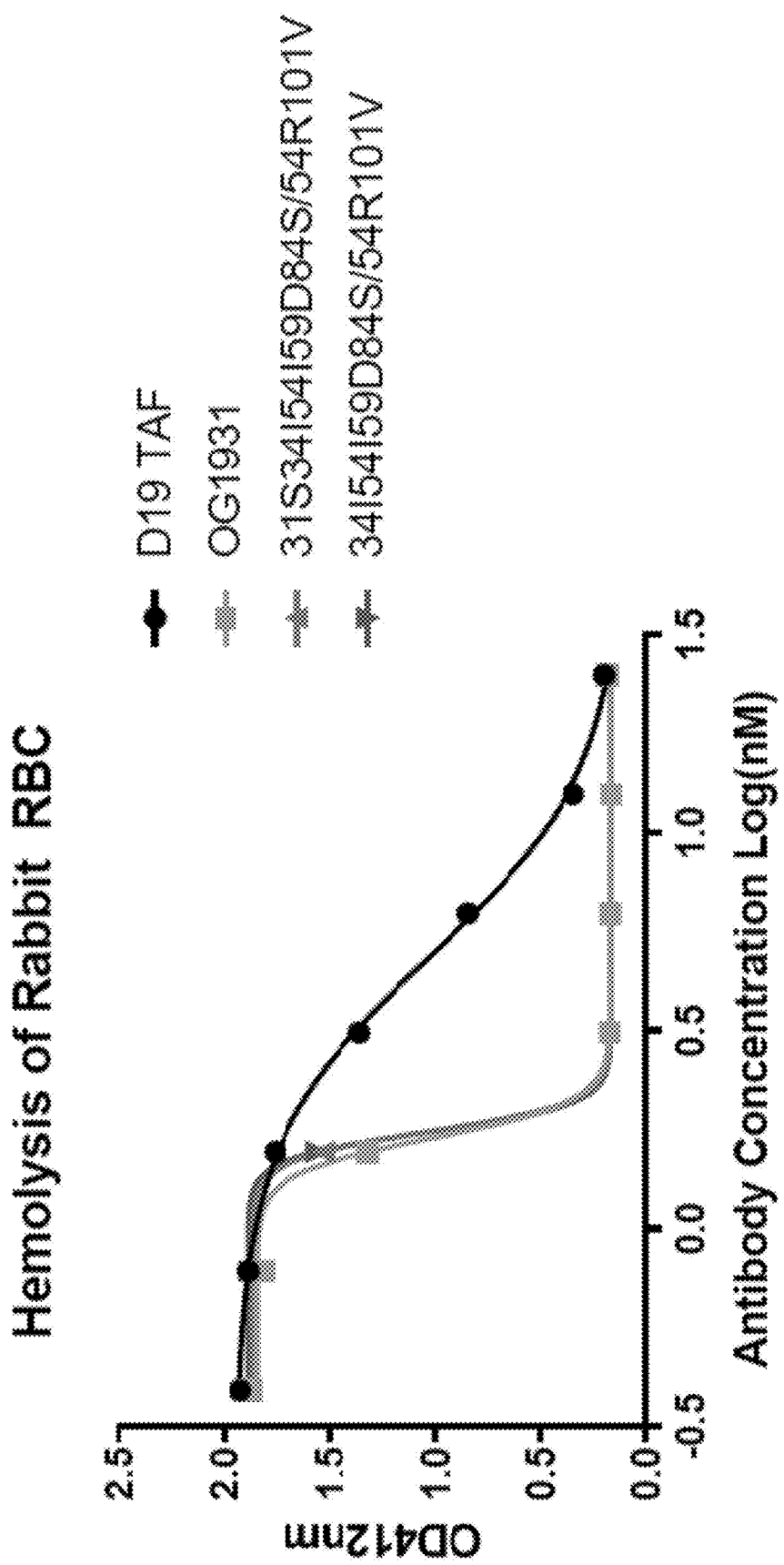
FIG. 13 shows the effect of anti-CFD antibodies on complement-mediated hemolysis of rabbit RBCs.

To measure lysis, supernatant is collected by centrifuging the plate at 1,500 rpm for 5 min, no break or low break. Supernatants are transferred to wells on a flat-bottom 96-well plate (200 uL per well). The plates are read using a SpectraMax Plus™, 25° C. at OD412 nm. In the analysis 100% of lysis: RBCs/NHS without ΔFD; Inhibition: RBCs/NHS/AFD. Percentage of inhibition is calculated as follows: 100× (OD RBCs/NHS)−(OD RBCs/NHS/AFD). Data are presented in FIG. 13

Figure 14:
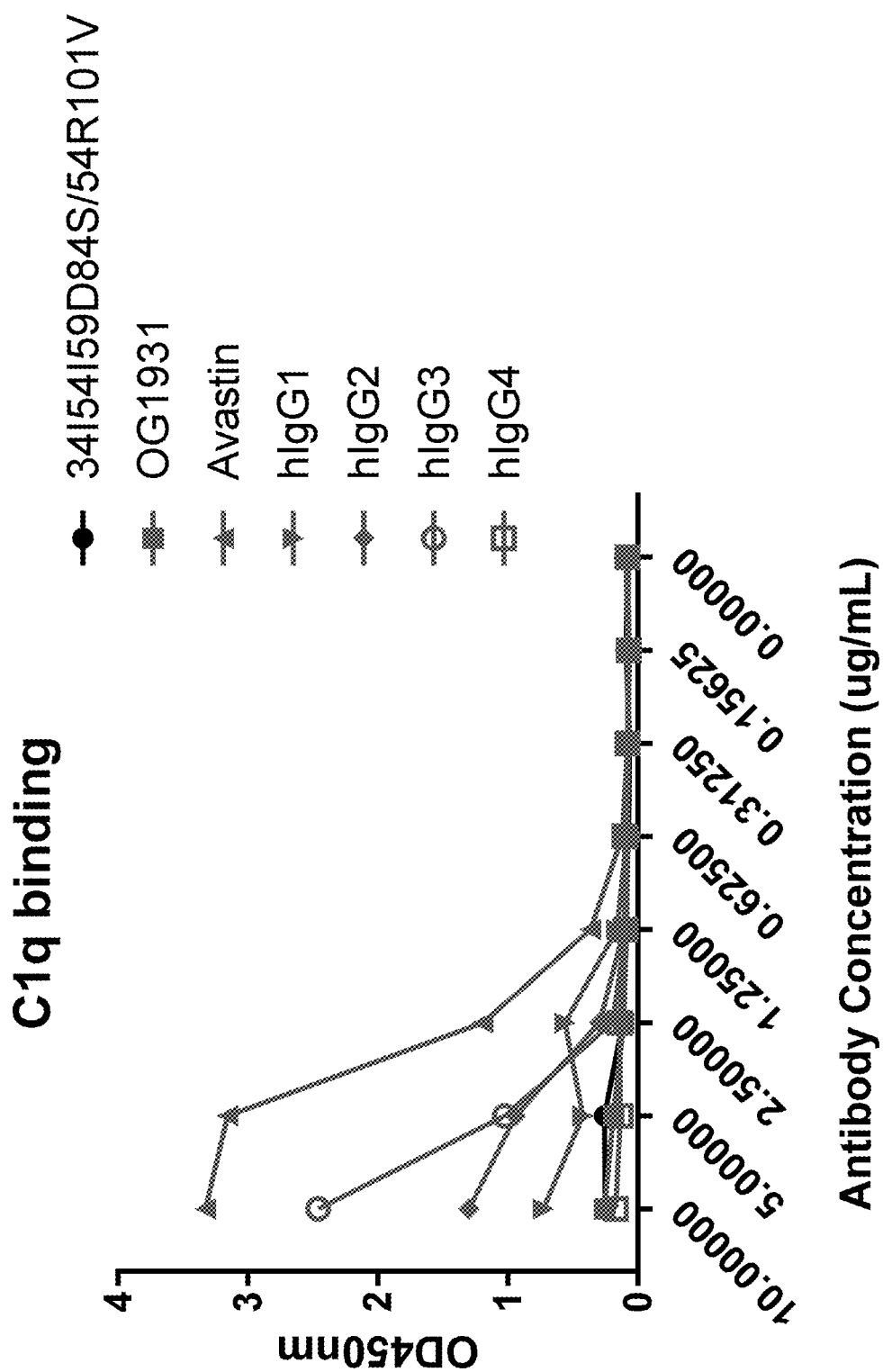
FIG. 14 shows results of binding of anti-CFD antibodies and controls to C1q.

Example 19.3—34I54I59D84S/54R101V has Diminished Effector Functions and does not Bind to Complement C1q Complement engagement liabilities was assessed by C1q ELISA binding. Briefly, antibody panel was titrated 1:2 from a top concentration of 10 ug/mL in 1×PBS for overnight coating at 4 C. Plates were then blocked After a 2 hour blocking step in 1% BSA, purified human C1q was then applied at 5 ug/mL in 1% BSA for 2 hours at room temperature followed by detection with HRP-conjugated anti-human C1q antibody and TMB development. Data are shown in FIG. 14.

Figure 15A:
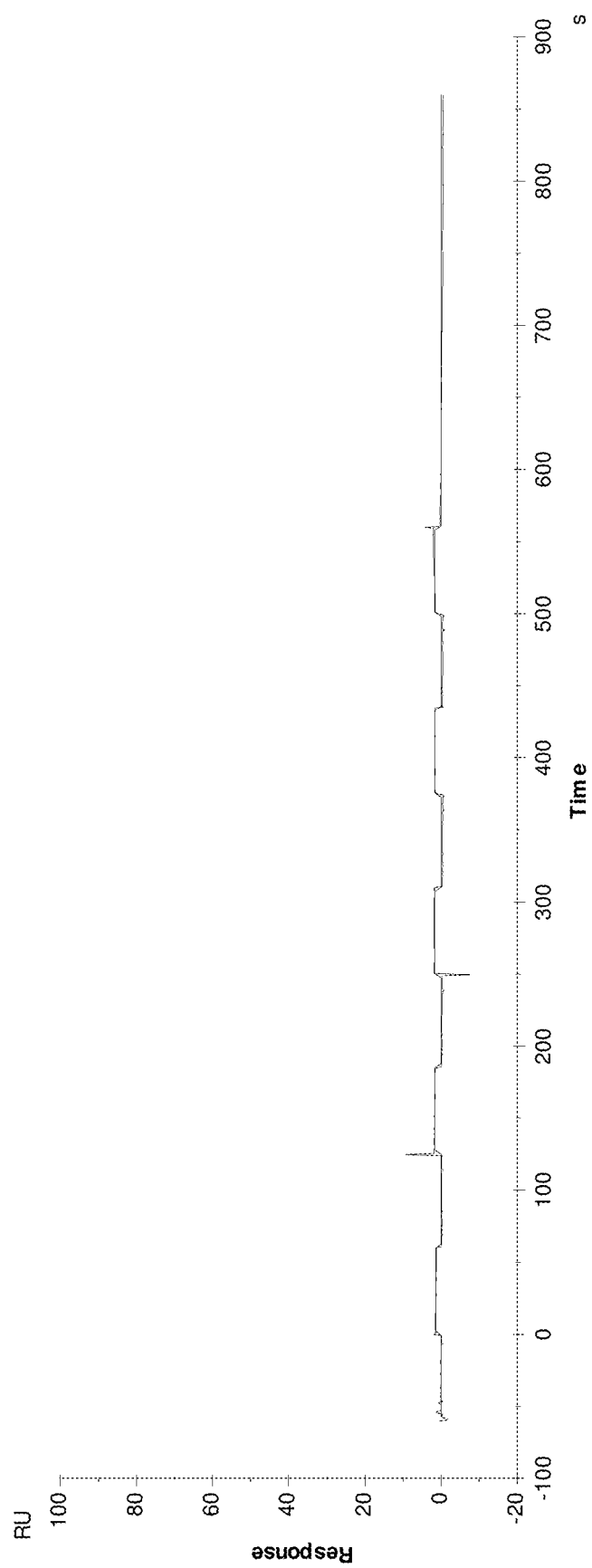
FIG. 15A shows binding kinetics of 34I54I59D84S/54R101V to FcγRI.
Figure 15B:
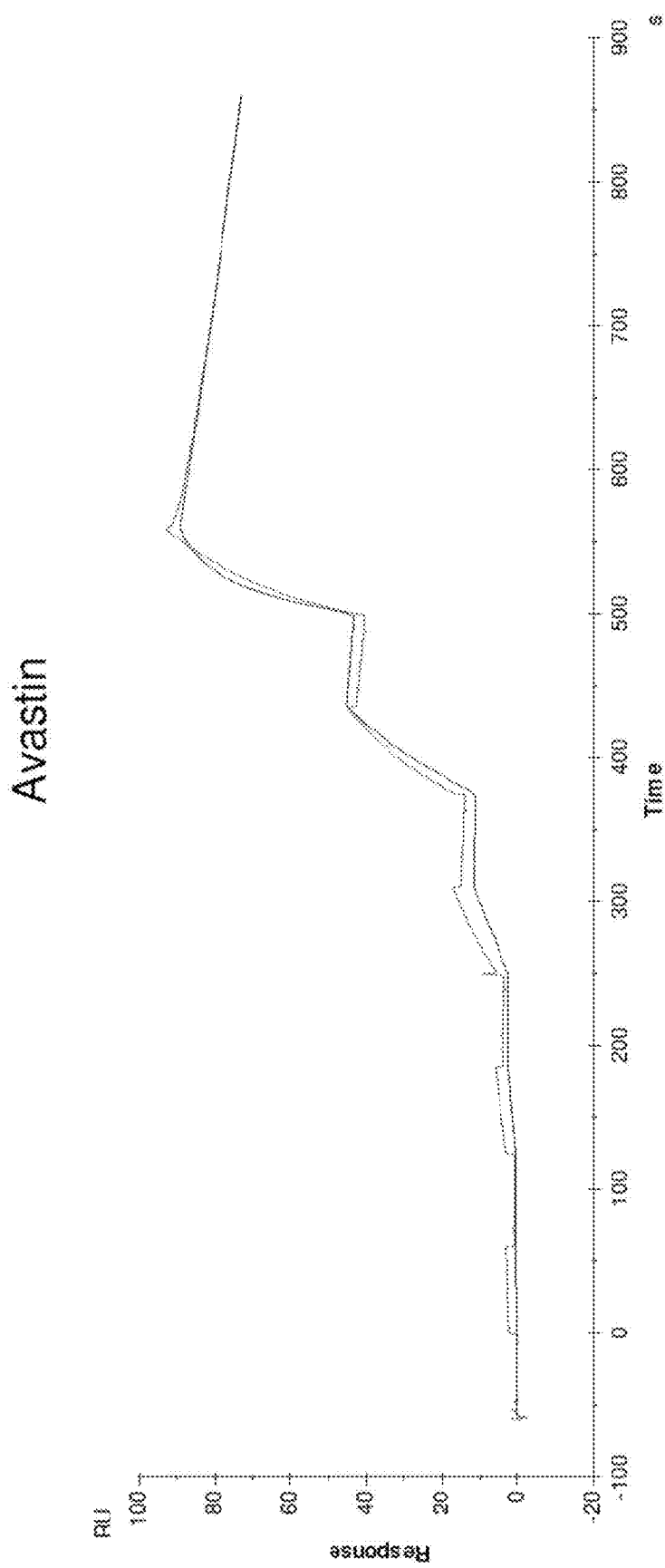
FIG. 15B shows binding kinetics of Avastin to FcγRI.
Figure 16A:
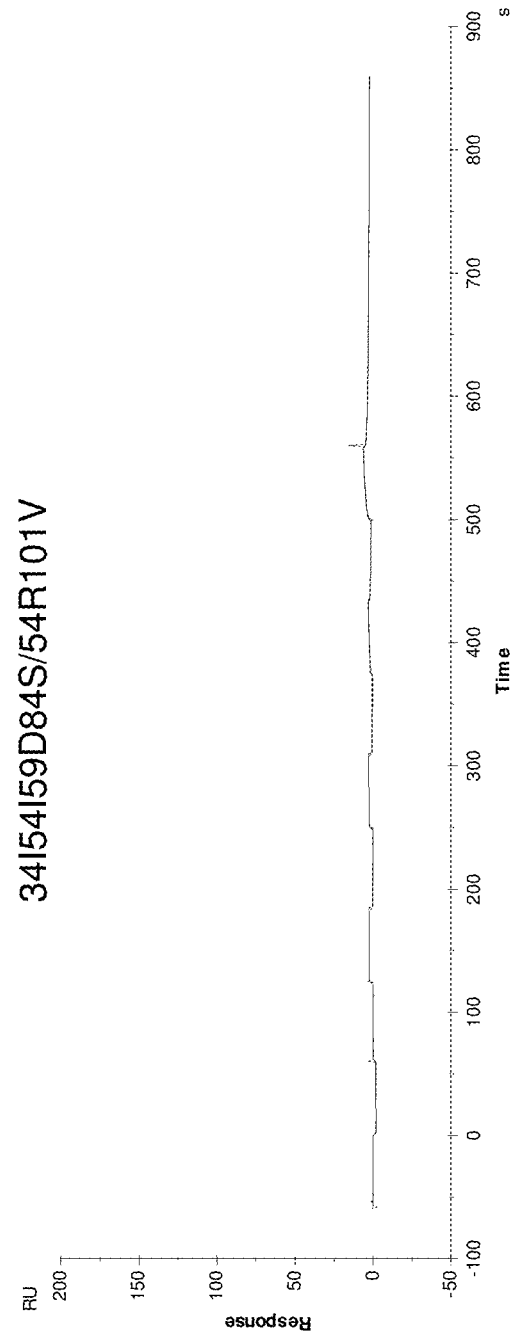
FIG. 16A shows binding kinetics of 34I54I59D84S/54R101V to FcγRIIIa.
Figure 16B:
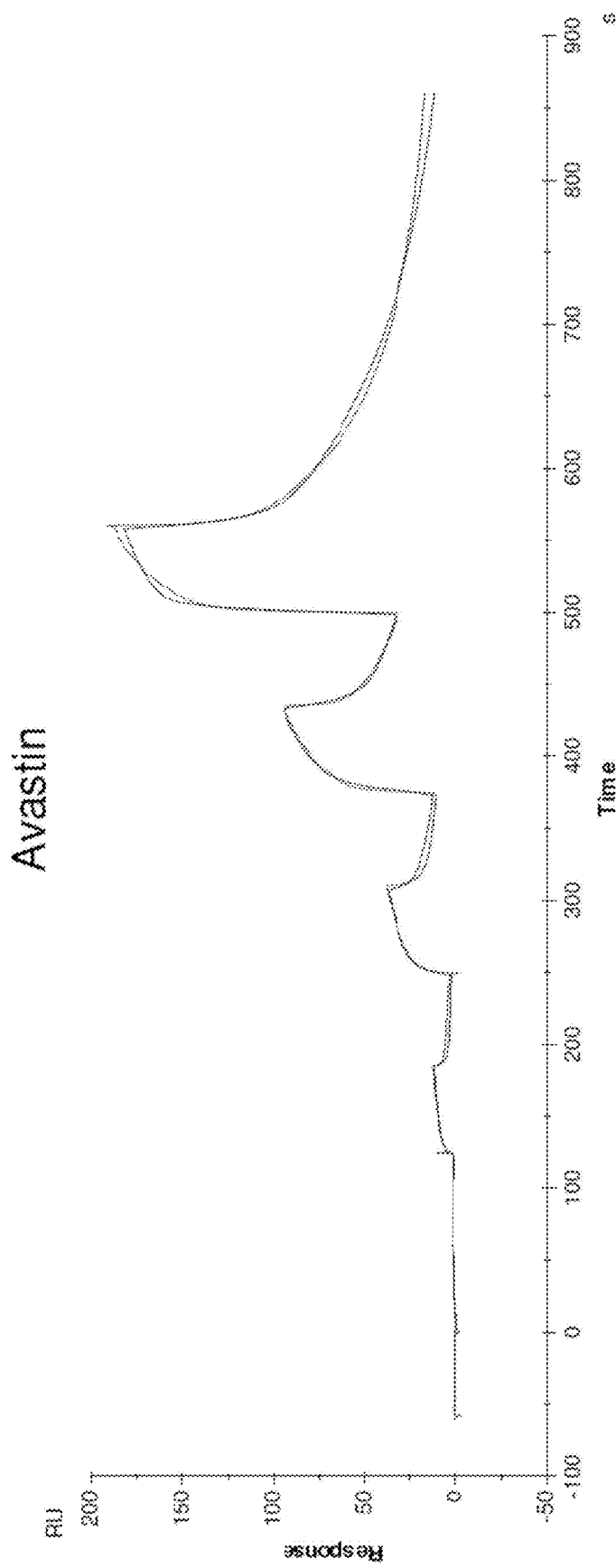
FIG. 16B shows binding kinetics of Avastin to FcγRIIIa.

Example 19.4—34I54I59D84S/54R101V has Diminished Effector Functions and does not Bind to FcγRI, FcγRIIIa, FcγRIIa, and FcγRIIIb For Fcγ receptor Binding Kinetics on Biacore, all binding kinetics were performed at 25° C. using a BIAcore T200. Briefly, an anti-his antibody was immobilized on a CM5 chip. Histidine-tagged FcγRI (FIG. 15A and FIG. 15B) and FcγRIIIa (FIG. 16A and FIG. 16B) at a concentration of 0.5 µg/mL prepared in HBS-EP buffer (0.01M HEPES pH7.4, 0.15M NaCl, 3 mM EDTA, 0.005% Tween-20) were injected independently for 60-s using a flow rate of 5 µL/min in the active flow cell only. Antibody candidate and Avastin, used as a positive control, were then injected over the reference and active flow cell using 60-s injections at 30 µL/mL, applying single-cycle kinetics method. Antibody concentration in the range of 0.48 to 300 nM were used for FcγRI and 7.8 nM to 2000 nM for FcγRIIIa. Following each run, flow cells were regenerated with a 60 s injection of 10 mM glycine pH 1.7 using a flow-rate of 50µ/mL. Data was double referenced, using subtraction of both reference flow cell and blank cycles. Analysis was performed using BIA evaluation software.

Figure 16C:
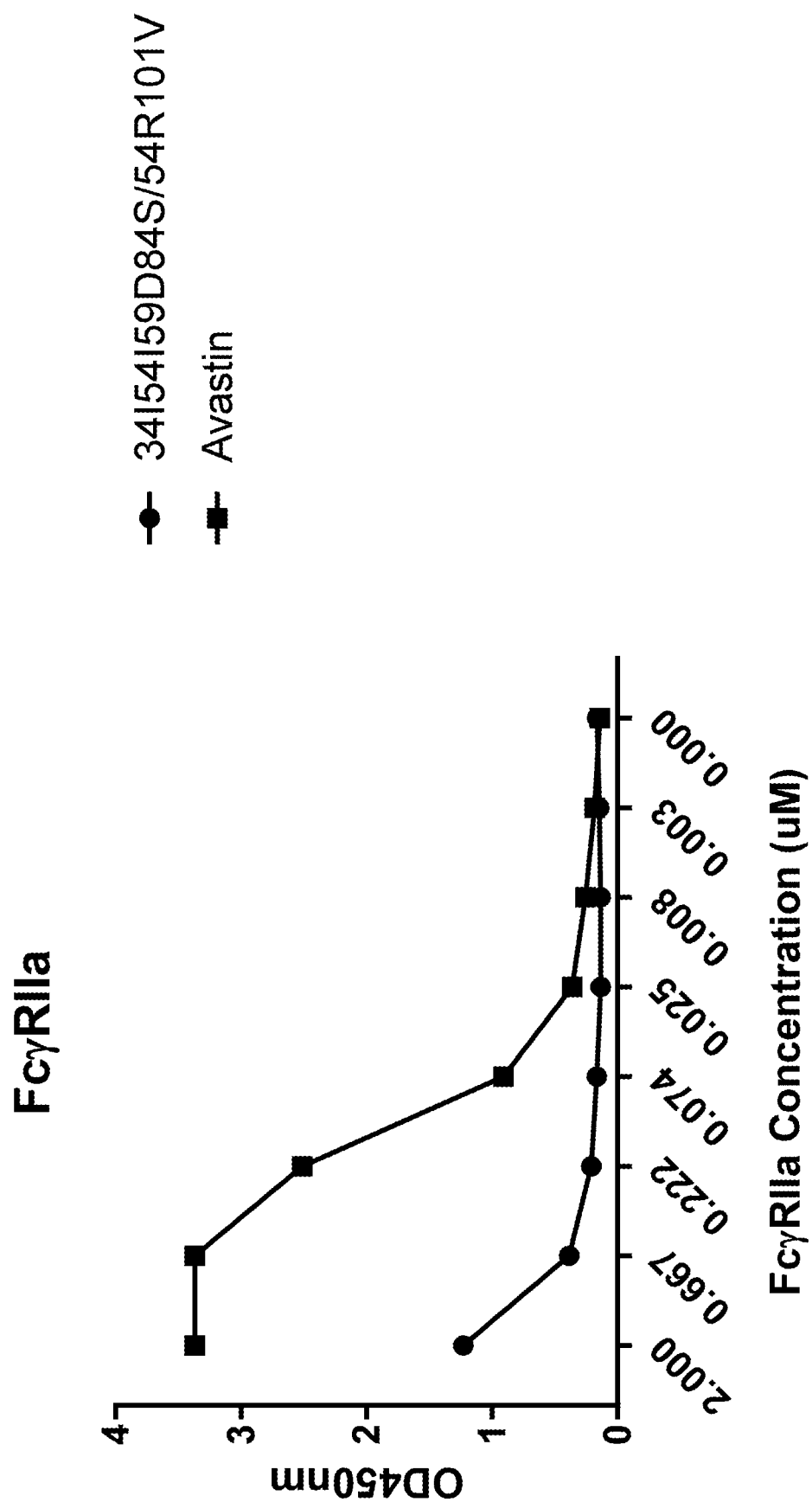
FIG. 16C shows binding of 34I54I59D84S/54R101V and Avastin to FcγRIIa.
Figure 16D:
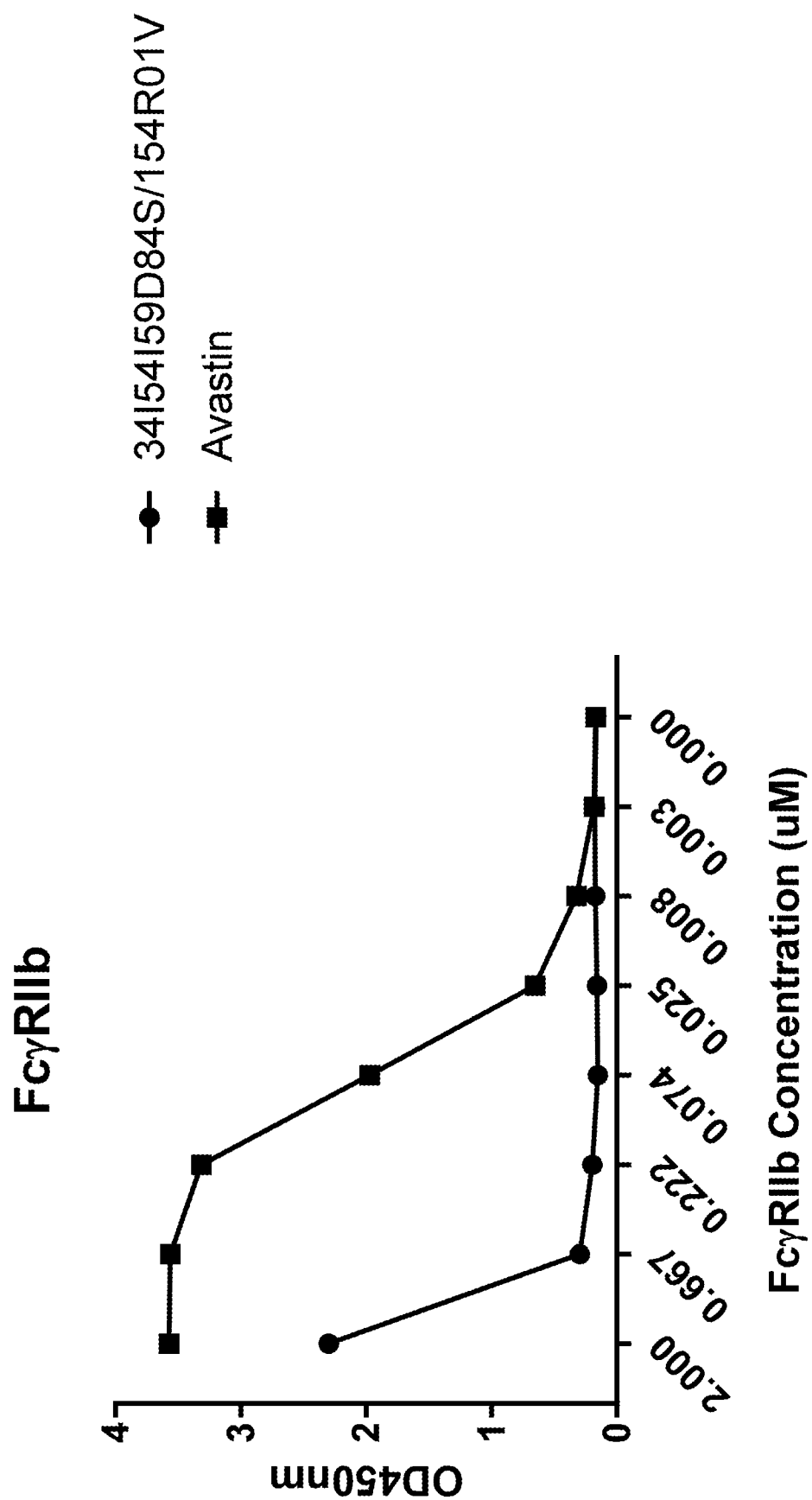
FIG. 16D shows binding of 34I54I59D84S/54R101V and Avastin to FcγRIIb.
Figure 16E:
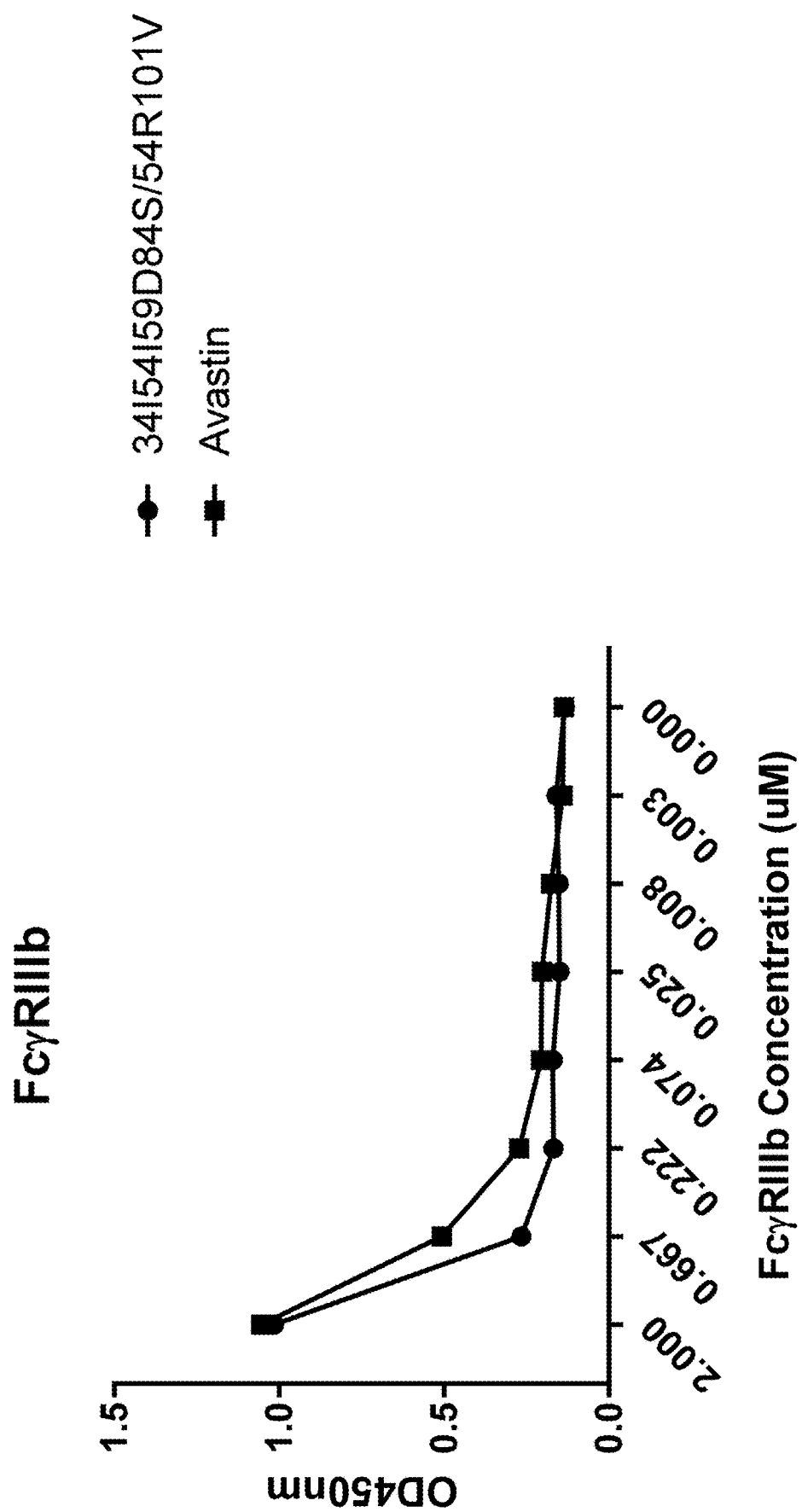
FIG. 16E shows binding of 34I54I59D84S/54R101V and Avastin to FcγRIIIb.

The binding to FcγRIIa (FIG. 16C), FcγIIb (FIG. 16D) and FcγIIIb (FIG. 16E) was assessed by ELISA. Briefly, the final candidate antibody along with Avastin, used as positive control, were coated at 2 uM in 1×PBS on Nunc MaxiSorp plates overnight at 4° C., followed by a 2 hour blocking step with 1% BSA in 1×PBS at room temperature. Recombinant His-tagged Fcγ receptors (R&D Systems) were titrated 1:3 from a top concentration of 2 uM in 1% BSA and incubated for 1 hour at 37° C. Following a series of washes, the plate was incubated with an HRP-conjugated anti-His antibody at 1:1000 for 1 hour at room temperature. Lastly, after a final wash, the plate was developed in TMB.

This antibody showed no significant binding to either FcγRIIa and FcγIIb compared to positive control avastin. Binding to FcγIIIb was minimal for both antibodies tested, in this assay format.

Example 20—Route 1 Synthesis of OG1802

A first route for the synthesis of OG1802 is as follows. First, TFA/amine salt initiator (Compound L) having the structure shown in FIG. 2A was synthesized as follows.

First, Compound K, having the structure shown in FIG. 2B was synthesized as follows. Into a 200 mL round bottom flask under nitrogen was placed Compound J (OG1563) (1.9 g, 2.67 mmol, 3.3 equiv)

COMPOUND J

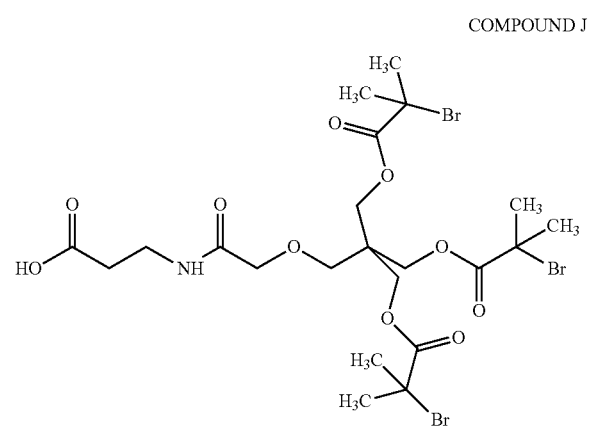 [SMILES: CC(C)(Br)C(=O)OCC(COCC(=O)NCCC(=O)O)(COC(=O)C(C)(C)Br)COC(=O)C(C)(C)Br]

and Compound E (0.525 g, 0.81 mmol, 1.0 equiv) (see FIG. 2L) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, O=CCH2O), 4.27 (s, 18H, CCH2OC=O), 6.74 (br t, 1H, CH2NHC=O), 7.69 (t, J=6.8 Hz, 3H, CH2NHC=O), 7.84 (t, J=6.0 Hz, 3H, CH2NHC=O).

LC-MS (ES, m/z): [(M+2H-boc)/2]+ Calcd for (C84H136Br9N7O33+2H-Boc)/2=1196.6; Found 1196.6.

Next Compound L (FIG. 2A) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): δ=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s, 2H, OCH2C), 3.3 (q, 6H, CH2CH2NHC=O), 3.4-3.59 (m, 20H, CH2), 3.87 (s, 6H, O=CCH2O), 4.27 (s, 18H, CCH2OC=O), 7.69-7.84 (m, 9H, both CH2NHC=O and NH3+).

LC-MS (ES, m/z): [(M+2H)/2]+ Calcd for (C84H136Br9N7O33+2H)/2=1196.6; Found 1197.4.

Next, Compound L (FIG. 2A) was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stirring). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a freeflowing white powder. Table 20.1 below sets forth polymer data for polymer employing compound L as an initiator.

TABLE 20.1

| Theor. MW (kDa) | Polymer ID No. | Initiator | Mn (kDa) | Mp (kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 2C) to the 750 kDa polymer referred to above to provide OG1802. Into a 20 mL vial was placed Polymer R3707 (750 kDa polymer made using L as initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH ~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 485 mgs as a white powder.

Example 21—Synthesis of Initiator OG1786

Figure 2E:
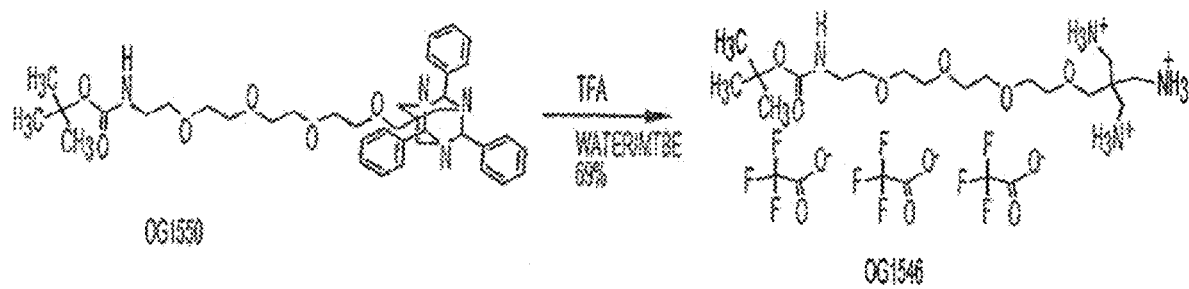
FIG. 2E shows the synthesis of OG1546 from OG1550.

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TFA) as shown in FIG. 2D. OG1786 is prepared as follows. First, OG1550 is reacted with TFA (trifluoro acetic acid) to produce OG1546 as depicted in FIG. 2E.

In a 1 L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH ~4, by pH paper).

The product was collected by lyophilization. 11.5 g white solid was obtained. This material is extremely hygroscopic, so best handled under nitrogen. The product was confirmed by LCMS.

Figure 2F:
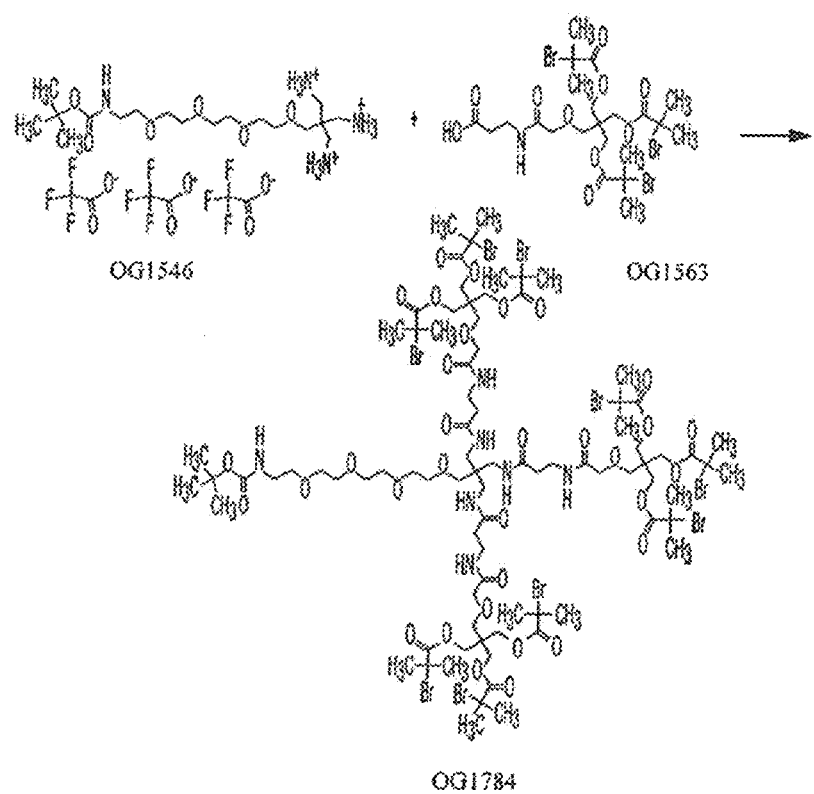
FIG. 2F shows the synthesis of OG1784 from OG1546 and OG1563.

The prepared OG1546 was then reacted with OG1563 to yield OG1784 (as depicted in FIG. 2F).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH~3). The organic phase was washed with water/saturated sodium chloride (100 ml/25 ml), and the aqueous phase was AQ3 (pH~3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 μm, product number 02915-20). The filtrate was split into three equal portions and purified in three runs.

The filtrate was loaded onto a RediSep Rf Gold C18 column (275 g, SN 69-2203-339, Lot#24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods. The isolated yield and the purity of the R5172 and R5228 lots are shown in Table 21.1.

TABLE 21.1

| | OG1784 lot | |
| --- | --- | --- |
| | R5172 | R5228 |
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Figure 2G:
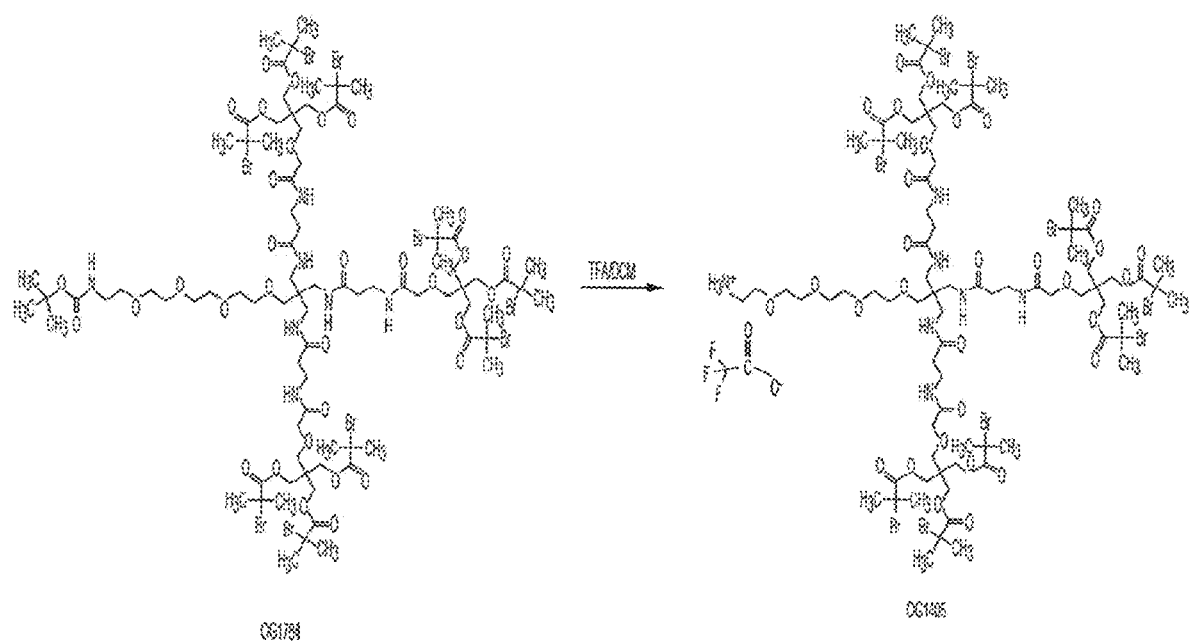
FIG. 2G shows the synthesis of OG1405 from OG1784.
Figure 2L:
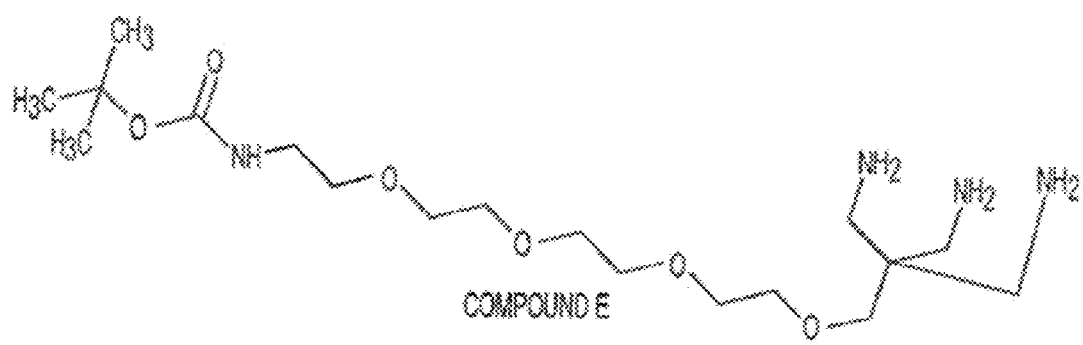
FIG. 2L shows Compound E.

Next OG1405 was prepared from OG1784 as depicted in FIG. 2G. In a 500 ml round bottom flask equipped with a magnetic stir bar was added OG1784 (20.9 g), followed by dichloromethane (50 ml) then trifluoroacetic acid (20 ml). The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed.

Next, OG1405 was reacted with OG1402 to prepare OG1785 as set forth in FIG. 2H. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml), and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 am, product number 02915-20) and split into three equal portions, each of which were individually purified as follows.

Portions were loaded onto Redi-Sep Gold C18 column (275 g, SN-69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS:

OG1785 was isolated as a foamy solid (R5329, 19.0 g, 83% yield, 95.1% purity (a/a 210 nm), stored under nitrogen at 4° C.

Next, the tert-butyloxycarbonyl protecting group on OG1785 was removed using trifluoroacetic acid (TFA) to produce OG1786 as depicted in FIG. 2I.

Example 22—Synthesis of Polymer OG1801

Polymer OG1801 is made first from the initiator OG1786. OG1801 has an amine functionality, which is more stable (than maleimide) during polymer synthesis. To synthesize polymer OG1801, a modified version of ATRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL of DMF under room temperature to make 100 mg/mL stock solution; sampled for initiator concentration and purity test; added the initiator solution to the flask under Argon. The reaction solution became dark brown and started thickening over time; sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, all the fractions were transferred to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 23—Synthesis of Polymer OG1802

Starting materials and reagents needed in the reaction are calculated based on batch input of OG1801. The linker is 3-maleimidopropionic acid, NHS ester. Added 30 ml of 0.5 M sodium phosphate (in WFI, pH 8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln. Added linker solution dropwise 815 uL per minute to the polymer sin with strong stirring. Took 5 min to added 4095 uL of linker solution. Reacted at room temperature for 30 min. Quenched reaction with 20 mL of 5% acetic acid to achieve a final pH of 5. Filtered the solution using 1 L vacuum filter (0.2 um).

OG1802 (shown in FIG. 2J) is then purified as follows: Milipore cross flow cassettes are used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 µM 1 L filter bottle. The polymer solution could be stored at 2-8° C. for up to 3 month before conjugation.

Example 24—Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

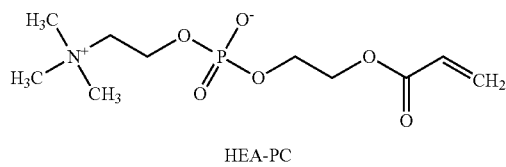 [SMILES: C=CC(=O)OCCOP(=O)([O-])OCC[N+](C)(C)C]

HEA-PC

HEA-PC was polymerized to the initiator shown in Example 20 as compound L.

TABLE 24.1

| Reactant | Name | Amount | MW |
|---|---|---|---|
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-(dimethylamino)ethyl]amine (Me6TREN) | 2.73 mg | 230.39 |
| Solvent A | N,N-Dimethylformamide (DMF) | 21.85 µl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 µl of dry DMF and a 200 mg/ml solution of ligand by dissolving 4.6 mg of Me6TREN in 23 µL of dry DMF. Dispense 8.25 µl of the stock solution of initiator and 13.6 µl of the ligand into a tube. Degas at −78° C. for 5 mn then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at −78° C. Rinse the vial with 200 µl of methanol and add it inside the reactor at −78° C. and then 0.5 mL of distilled water then another 200 µl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 uL) was added. Another 2-3 ml of methanol was added and the catalyst was allowed to oxidize overnight at 4° C. Conversion determined by 1H NMR was estimated to be 94%.

The next day the polymer was dialyzed and subjected to SEC/MALS analysis using Shodex SB806M_HQ column (7.8×300 mm) in 1×PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein.

Next, the maleimide Mal-PEG4-PFP (see Example 20 above) ester was snapped on to the HEA-PC polymer as shown in Example 20. The resulting maleimide functionalized HEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am-PC), having the following structure:

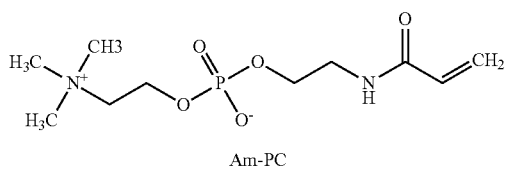 [SMILES: "Am-PC" ; C=CC(=O)NCCOP(=O)([O-])OCC[N+](C)(C)C]

Am-PC

The Am-PC was used for polymerization employing a 3 arm initiator (a TFA salt) having the structure:

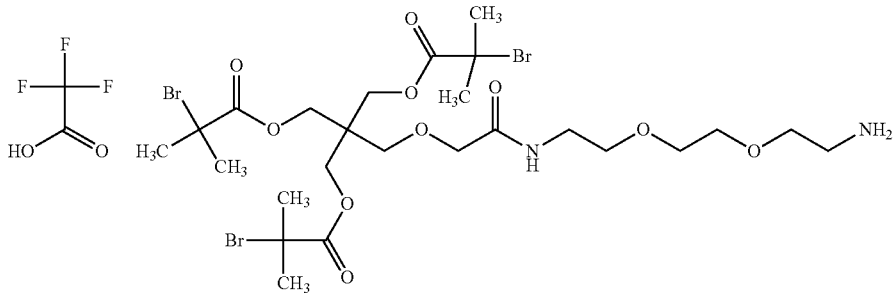 [SMILES: O=C(O)C(F)(F)F ; CC(C)(Br)C(=O)OCC(COCC(=O)NCCOCCOCCN)(COC(=O)C(C)(C)Br)COC(=O)C(C)(C)Br]

The synthesis of the Am-PC polymer was conducted as follows:

TABLE 24.2

| Reactant | Name/Identity | Amount | MW |
| --- | --- | --- | --- |
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 230.39 |
| Solvent A | N,N-Dimethylformamide (DMF) | 31.7 µl | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 uL of dry DMF. Add 19.7 uL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 mn. Add 1 mg of CuBr. Prepared a stock solution of CuBr$_2$ at 200 mg/mL by dissolving 4 mg CuBr$_2$ in 20 µL of DMF. Add 0.5 g of monomer (AmPC) to 1 mL of methanol (slow dissolution/viscous solution), followed by 1 uL of the stock solution of CuBr$_2$. Add the monomer solution dropwise to the reaction mixture above. Rinse with 1 mL of water. Degas the reaction mixture thoroughly (freeze-thaw). Let the reaction proceed for 24 hours.

Afterwards the Am-PC polymer may be dialyzed. The molecular weight of the above polymer was determined by SEC/MALS: Mn is 215 kDa, Mp: 250 kDa, PDI is 1.17. Conversion was estimated by 1H NMR to be 94%. A maleimide functionality can be added to the Am-PC polymer as discussed above for HEMA-PC and HEA-PC. Maleimide functionalized Am-PC polymer can be conjugated to a protein as described above.

Example 25—Reverse Ellman's Assay for Calculating Free Maleimide in a Compound

After addition of the maleimide functionality to polymer OG1801 to form OG1802 (see above), an Ellman's assay was used to determine the amount of functional maleimide expressed as percent function (i.e. conjugatable) in a sample. Thiol converted Ellman's reagent (DTNB) to TNB—then to TNB2—in water at neutral and alkaline pH, which gave off a yellow color (measured at 412 nm). A standard curve was established with cysteine. Since the maleimide reacts with thiol, this assay actually measured the thiol (cysteine) left. The inhibition was calculated as the molarity ratios of (original thiol—thiol left after maleimide polymer addition)/(original thiol) and is expressed as a percentage where the higher the percent the higher the maleimide functionalization.

Reagents Employed in Assay: A standard curve was prepared using the cysteine from 62.5 µM to 2 µM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 µM of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

Example 26—Purification and Decapping of OG1965

The OG1965 heavy and light chains may be cloned into expression plasmids and transfected into CHO cells. Cells can be grown up in appropriate media and harvested. OG1965 may be purified using Protein A affinity column capture and elution. The OG1965 cysteine at position 443 (L443C (EU numbering), or position 442C of seq ID 183) residue is typically "capped" or oxidized by chemicals in the cell culture media and is not available for conjugation. In this regard, purified OG1965 may be subjected to a decapping (i.e. reducing) procedure to remove the cap and enable the free (i.e. those not involved in Cys-Cys disulfide bonds) cysteine residue to be conjugated to the maleimide functionality of a polymer. Decapping may be done by mixing purified OG1965 protein with a 30× molar excess for 1 hour at ambient temperature of the reducing agent TCEP (3,3', 3"-Phosphanetriyltripropanoic acid). The reduction reaction with TCEP may be monitored by SDS-PAGE. Following reduction, the OG1965 protein may be buffer exchanged using a Pellicon XL Ultrafiltration Cassette with 20 mM Tris pH7.5, 100 mM NaCl, 0.5 mM TCEP buffer to remove the cap. The TCEP reagent may then be removed in the same buffer exchange setup with 20 mM Tris pH7.5, 100 mM NaCl. Reduced OG1965 may then be allowed to reoxidized using 15× molar excess of the oxidation agent DHAA (DeHydroxy Ascorbic Acid) for 1 hr at ambient temperature which again is monitored by SDS-PAGE assay. The DHAA reagent may then be removed in the same buffer exchange setup with 20 mM Tris pH7.5, 100 mM NaCl.

Example 27—Excipient Screening Experiment for Prevention of OG1802 Polymer Induced IgG1 Precipitation Conjugation reaction process setup was further developed with human IgG1 antibody (OG1898) to improve the conjugation efficiency which either SDS-PAGE or ion exchanger analysis was used for quantitative measurement.

Conditions tested included (1) varying polymer molar excess ratio from 3 to 20; (2) preadjusting the reaction solution pH to more acidic (e.g. pH 5.0) or basic (e.g. pH 8.5) from the standard neutral pH range (e.g. pH 6.5-7.5); (3) adding excipients, such as 0.1-1% polysorbate20 or tween20, 0.1-1% Sodium Dodecyl Sulfate (SDS), 6-10% trehalose or sucrose, 0.03-1 mM glutamic acid, 0.03-1 mM aspartic acid, 1-100 mM lysine or arginine, 1-100 mM urea, guanidine hydrochloride analog, 1-100 mM arginine, 0.03-1 mM PEG8000, or 20% ethanol.

Protein is known to carry net surface charge that helps protein solubility in aqueous solution. The amino acids are referred to as hydrophilic amino acids which include arginine, lysine, aspartic acid, and glutamic acid. At neutral pH 7 the side chains of these amino acids carry charges—positive for arginine and lysine, negative for aspartic acid, and glutamic acid. Altering the solution pH could modulate the intrinsic protein solubility which is therefore in some of the troubleshoot experiments mentioned above such as (2) this approach is applied. In theory, proteins solubility in aqueous solution differs depending on the level of hydrophobic or hydrophilic properties of the surface. Proteins with surfaces that have greater hydrophobic properties will readily precipitate. The addition of ions (e.g. NaCl or other salt) creates an electron shielding effect that nullifies some activity between water particles and the protein, reducing solubility as the proteins bind with each other and begin to aggregate. In the current situation, it is hypothesized that the biopolymer directly or indirectly modulates the protein surface charge and/or exposed surfaces in a manner that promotes the intermolecular hydrophobic interactions which results in protein precipitation.

Excipients that can modulate protein solubility include the following categories (i) detergents including neutral detergent (e.g. 0.1-1% polysorbate20 or tween20) or charged detergent (e.g. 0.1-1% Sodium Dodecyl Sulfate (SDS)) (ii) sugars (e.g. 6% Trehalose or 6% sucrose) (iii) negatively charged amino acids (e.g. 0.03-1 mM glutamic acid or 0.03-1 mM aspartic acid) or positively charged amino acids (e.g. 1-100 mM lysine or arginine) (iv) chaotropic agents or denaturants (e.g. 1-100 mM urea, guanidine hydrochloride analog or 1-100 mM arginine) (v) polyethylene glycol (e.g. 0.03-1 mM PEG8000); and (vi) organic solvent (e.g. 20% ethanol).

Other options that can be tested in regard to excipients include OG1898_R5782_5×R7473 (as a control), 5 mg/mL_R5782_5×R7473_pH4, 5 mg/mL_R5782_5×R7473_pH9, 5 mg/mL_R5782_5×R7473_1% Tween20, 5 mg/mL_R5782_5×R7473_0.1% Tween20, 5 mg/mL_R5782_5×R7473_1% SDS, 5 mg/mL_R5782_5×R7473_0.1% SDS, 5 mg/mL_R5782_5×R7473_6% Sucrose, 5 mg/mL_R5782_5×R7473_6% Trehalose, 5 mg/mL_R5782_5×R7473_0.03 mM Aspartic acid, 5 mg/mL_R5782_5×R7473_1 mM Aspartic acid, 5 mg/mL_R5782_5×R7473_0.03 mM Glutamic acid, 5 mg/mL_R5782_5×R7473_1 mM Glutamic acid, 5 mg/mL_R5782_5×R7473_1 mM Arginine, 5 mg/mL_R5782_5×R7473_100 mM Arginine, 5 mg/mL_R5782_5×R7473_1 mM Urea, 5 mg/mL_R5782_5×R7473_100 mM Urea, 5 mg/mL_R5782_5×R7473_0.03 mM PEG8000, 5 mg/mL_R5782_5×R7473_1 mM PEG8000, 5 mg/mL_R5782_5×R7473_20% EtOH, 5 mg/mL_R5782_5×R7473_1 mM Lysine, 5 mg/mL_R5782_5×R7473_100 mM Lysine. Reaction buffers include 20 mM Tris pH 7.4, 100 mM NaCl, sodium acetate. sodium carbonate.

In a further design of experiment (DOE) study, various excipients from each category mentioned above are selected based on their compatibility to the pharmaceutical manufacturing for human injectable use. In addition, extreme acidic pH at 4 and basic pH at 9 are also included in such evaluation. A standard IgG1 protein sample is selected for such evaluation which does not contain an engineered cysteine to minimize any potential interference of such unpaired cysteine residue.

Example 28—Conjugation of OG1965 to MPC Polymer

Decapped OG1965 may be conjugated to polymer OG1802 to yield OG1970 bioconjugate. An excess of OG1802 is used (3-20 fold molar excess). Conjugation can be monitored by cation-exchanger HPLC chromatography and driven to near completion. OG1970 conjugate may be purified via cation exchanger chromatography and buffer exchanged into the formulation buffer by ultrafiltration/diafiltration (UF/DF). OG1970 conjugate may be purified chromatographically as described above.

Example 29—Binding Kinetics of OG1965 and OG1970

To determine and directly compare binding kinetics of OG1965 and OG1970, they were subjected to biacore analysis as above by capturing the antibodies on a Protein A chip. 0.5 ug/ml of OG1965 was flowed at a rate of 10 uls/min over a protein A chip for 25 seconds. To accommodate the polymer, 5 ug/ml of OG1970 was flowed at a rate of 10 uls/ml for 3 minutes. Roughly equivalent levels of antibody were captured under these conditions. Serum purified human complement factor D was flowed over the captured antibodies at 15 nM, 5 nM, 1.67 nM, 0.56 nM, 18.7 nM. These analyses were performed in triplicate at 25 degrees. Both antibodies bound with single digit pM affinity.

Furthermore, the Kinetic Exclusion Assay (KinExA®) was used to measure the equilibrium binding affinity and kinetics between OG1965 or OG1970 and CFD in solution. The rate of association, $k_{on}$, was experimentally determined, while the rate of dissociation, $k_{off}$ was calculated based on the following equation: $k_{off}=K_d \times k_{on}$. Azlactone beads coated with OG1931 were used to capture a portion of free Complement Factor D from an equilibrated sample of OG1965 or OG1970. Captured Complement Factor D was detected with KCD004 (SEQ ID NOs: 341 & 342) conjugated with an AlexaFluor 647 fluorophore to makeKCD004-A647. The fluorescent signal was converted to a voltage signal that was directly proportional to the amount of free Complement Factor D in the equilibrated sample. The Azlactone-OG1931 column was used as the capture reagent for kinetic experiments and for equilibrium experiments. The amount of free Complement Factor D in the sample was measured pre-equilibrium, yielding data points that monitor the decrease in free Complement Factor D as the sample moved toward equilibrium. The KinExA Pro software performed a least squares analysis on the measured data to fit optimal solutions for the $K_d$ and the activity of the CBP to a curve representative of a 1:1 reversible bi-molecular interaction. The results from this assay showed that OG1965 and OG1970 bound with similar, single digit pM affinity at 37 degrees, and there is no significant difference in Kd, activity, or on-rates, indicating the biopolymer does not affect antibody interactions with CFD.

Both the KinExA Data and Biacore Data are Shown in FIG. 20 and Table 29.1.

TABLE 29.1

| Binding kinetics of OG1965 and OG1970 | | | | |
|---|---|---|---|---|
| Molecule | Platform (° C.) | $K_{on}$ (M) | $K_{off}$ (M) | $K_D$ (pM) |
| OG1965 | Biacore (25°) | $2.52 \times 10^7$ | $6.30 \times 10^{-5}$ | 2.50 |
|  | KinExA (37°) | $3.06 \times 10^7$ | $1.79 \times 10^{-4}$ | 5.86 |
| OG1970 | Biacore (25°) | $2.16 \times 10^7$ | $1.33 \times 10^{-4}$ | 6.14 |
|  | KinExA (37°) | $3.67 \times 10^7$ | $2.96 \times 10^{-4}$ | 8.07 |

Example 30—Enzymatic Assay of OG1965 and OG1970

To compare OG1970 functional behavior to OG1965, both molecules were subjected to the CFD enzymatic assay. OG1965 and OG1970 both effectively block enzymatic activity of CFD relative to no antibody control.

Proteolysis Assay—

Figure 21:
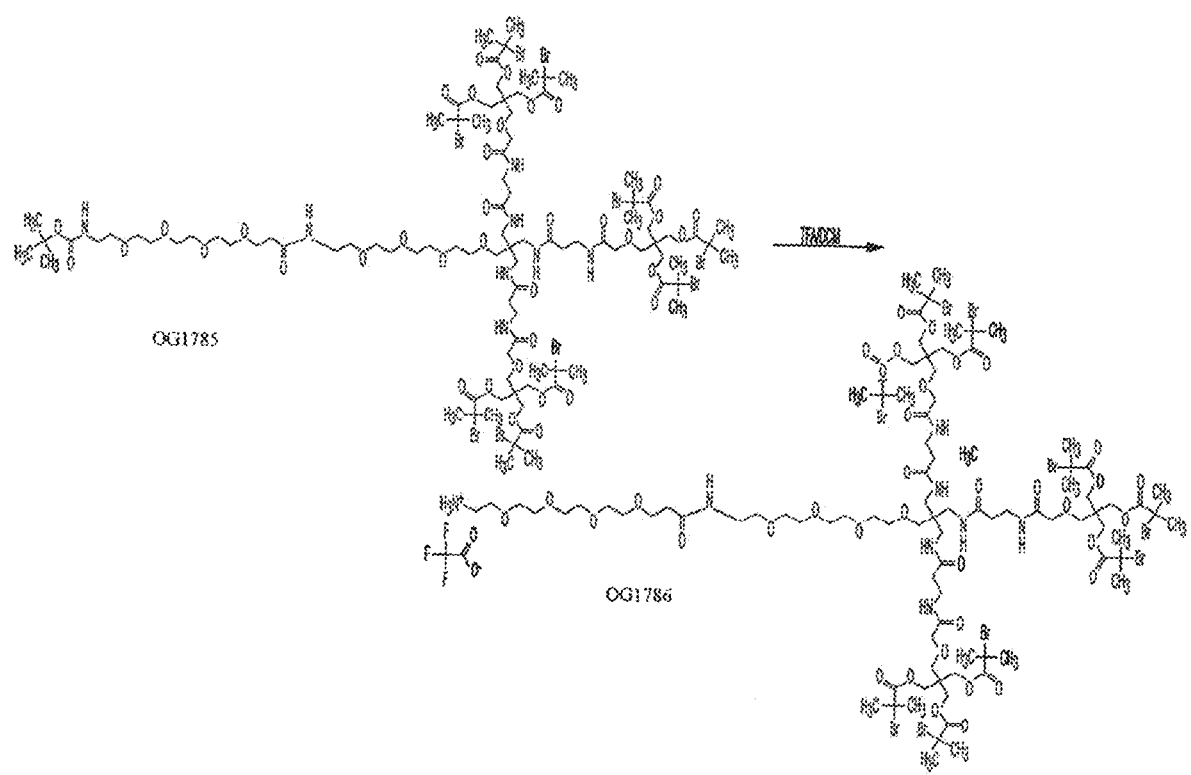
FIG. 21 shows effect of OG1965 and OG1970 on the enzymatic activity of human CFD to cleave a peptide substrate.

Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog # D-8130, 100 mM stock in DMSO). 50 μLs of the diluted CFD is loaded into a 96 well clear plate, and 50 uls of AFD is added. The reaction is started by adding 100 μLs of substrate/DTNB mixture to wells. A substrate blank containing 100 μLs assay buffer and 100 μLs substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/μg)=Adjusted Vmax*(OD/min)×well volume (L)×$10^{12}$ pmol/mol. ext. coeff($M^{-1}cm^{-1}$)×path corr.*(cm)×amount of enzyme (μg). *Adjusted for substrate blank, Using the extinction coefficient 13,260 $M^{-1}cm^{-1}$, *Using the path correction 0.320 cm. Data are shown in FIG. 21 and Table 30.1.

TABLE 30.1

Enzymatic assay comparing OG1970 vs. OG1965

| | Vmax (milliOD/min) | % control |
|---|---|---|
| OG1931 | 5.5885 | 179.8527 |
| OG1965 | 0.81 | 26.06794078 |
| OG1970 | 0.655 | 21.07963112 |

Example 31—FB Cleavage Assays for Assessing OG1965 and OG1970 Inhibition of CFD

Figure 22A:
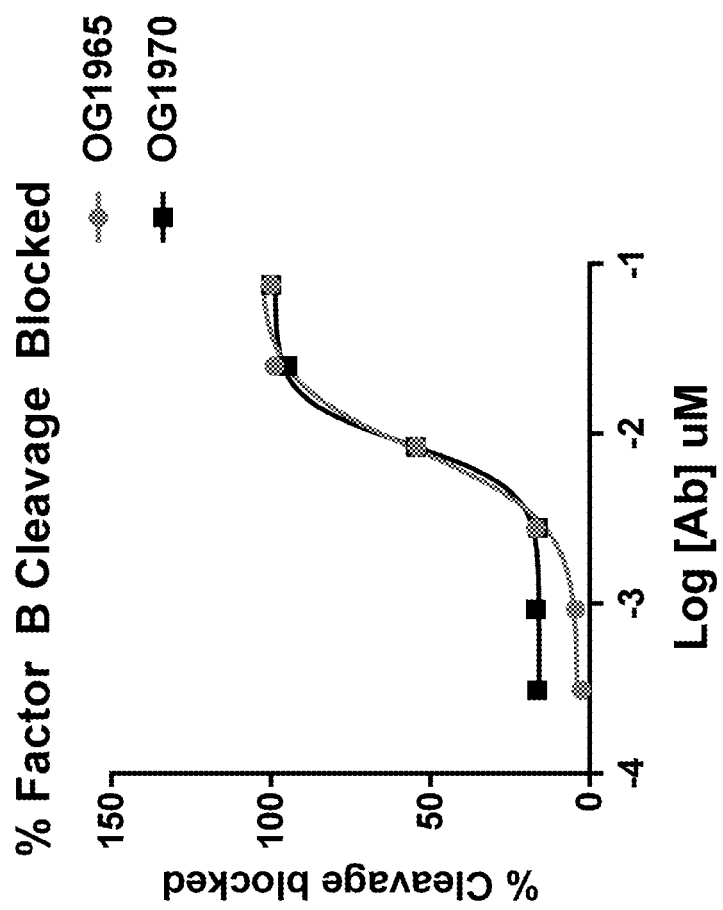
FIGS. 22A and 22B display the results (graph and gel) for the FB cleavage assay for OG1965 and OG1970.
Figure 22B:
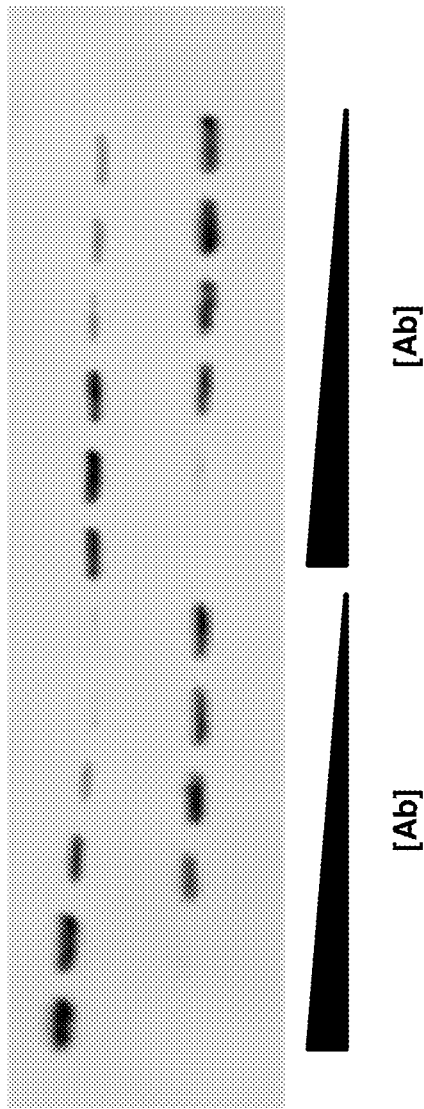

Factor D mediated cleavage of Factor B was performed exactly as in Example 17.2, only using AFD molecules OG1965 and OG1970. Under these conditions, the conjugated antibody and unconjugated antibodies perform roughly the same. Data are shown in FIGS. 22A and 22B.

Figure 22C:
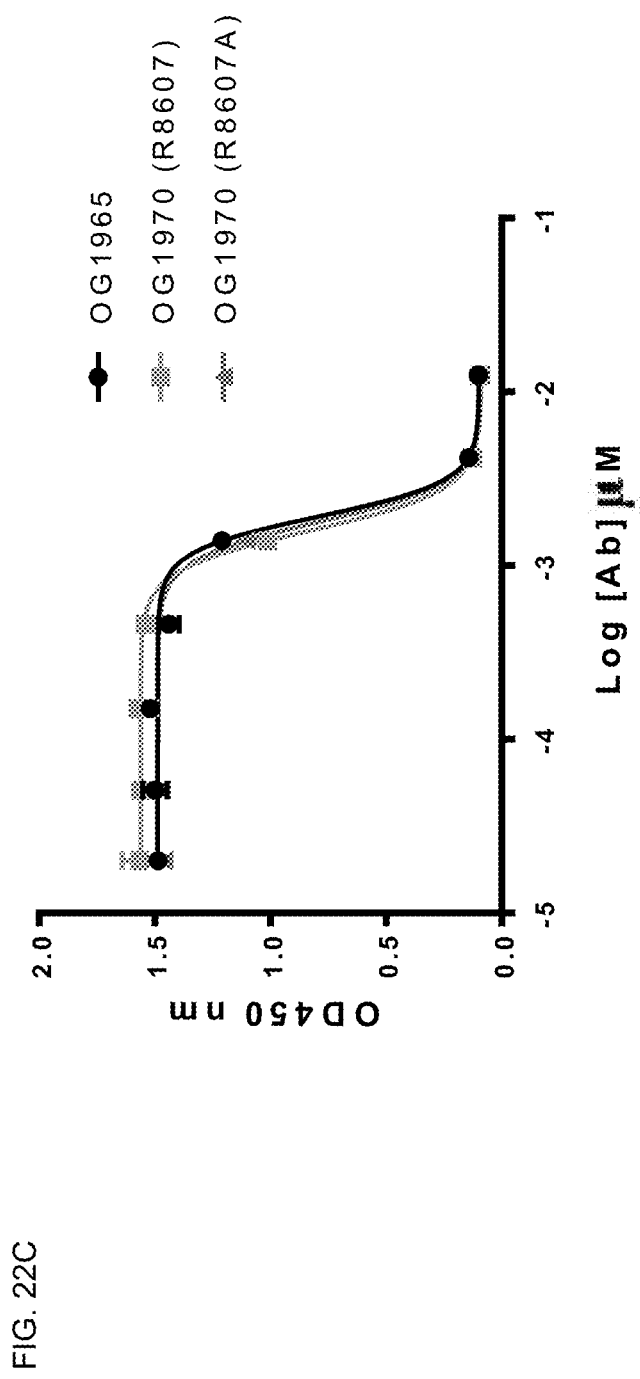
FIG. 22C displays FB cleavage assay using ELISA based method for OG 1965 and OG1970.

Furthermore, a FB cleavage assay using an ELISA based method was performed. All proteins and complexes were prepared using complex buffer (20 mM Hepes, 7.5, 2 mM MgCl2, 150 mM NaCl). In a 96 well plate, 25 nM Factor D (FD; serum purified; A136 Comptech) was mixed with increasing concentrations of anti-Factor D antibodies (aFD; 0.4 nM up to 0.1 uM in 1:3 dilution series) in a final volume of 55 uls. The complexes were incubated at room temperature for 45-60 minutes. 200 nM of Factor B (FB; serum purified; A135 CompTech) and 200 nM C3b (serum purified; A114 Comptech) were combined (final concentrations 100 nM each) and incubated for 45-60 minutes at room temperature in a final volume of 55 uls for each sample. 55 microliteres of FB/C3b complex was added to 55 microliteres of FD/aFD in the 96 well plate so that the final concentrations of FB/C3b were 50 nM and FD was 6.25 nM in a final volume of 110 microliteres. The complexes were then incubated at 37 degrees for 45 minutes. Following incubation, duplicates of 50 microliteres for each sample were added to a MicroVue Bb Plus ELISA kit strips (Quidel; A027). The ELISA was followed according to the manufacturer's protocol to detect Factor Bb that was released by CFD mediated cleavage of C3bB. As shown in FIG. 22C, OG1965 and OG1970 effectively block cleavage of C3bB (EC50 1.9 nM vs. 1.6 nM/1.8 nM respectively).

Example 32—Hemolysis Assay for OG1965 and OG1970

To assess the ability of anti-CFD antibodies to inhibit alternative complement pathway, a hemolysis assay was used.

Hemolysis Assay—

For the hemolysis assay, rabbit red blood cells ("RBCs", CompTech #B301) were diluted or re-suspended and washed with $GVB^0$ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Normal human serum (NHS) were incubated with anti-CFD antibody (AFD) at 37 degrees for 60 minutes in well of a round-bottom plate. The prepared RBCs were added to the wells with NHS/AFD on the incubation plate; incubated at room temperature for 35 minutes, and mixed every 10 minutes. The reaction was stopped with $GVB^0$/10 mM EDTA CompTech #B104).

Figure 23:
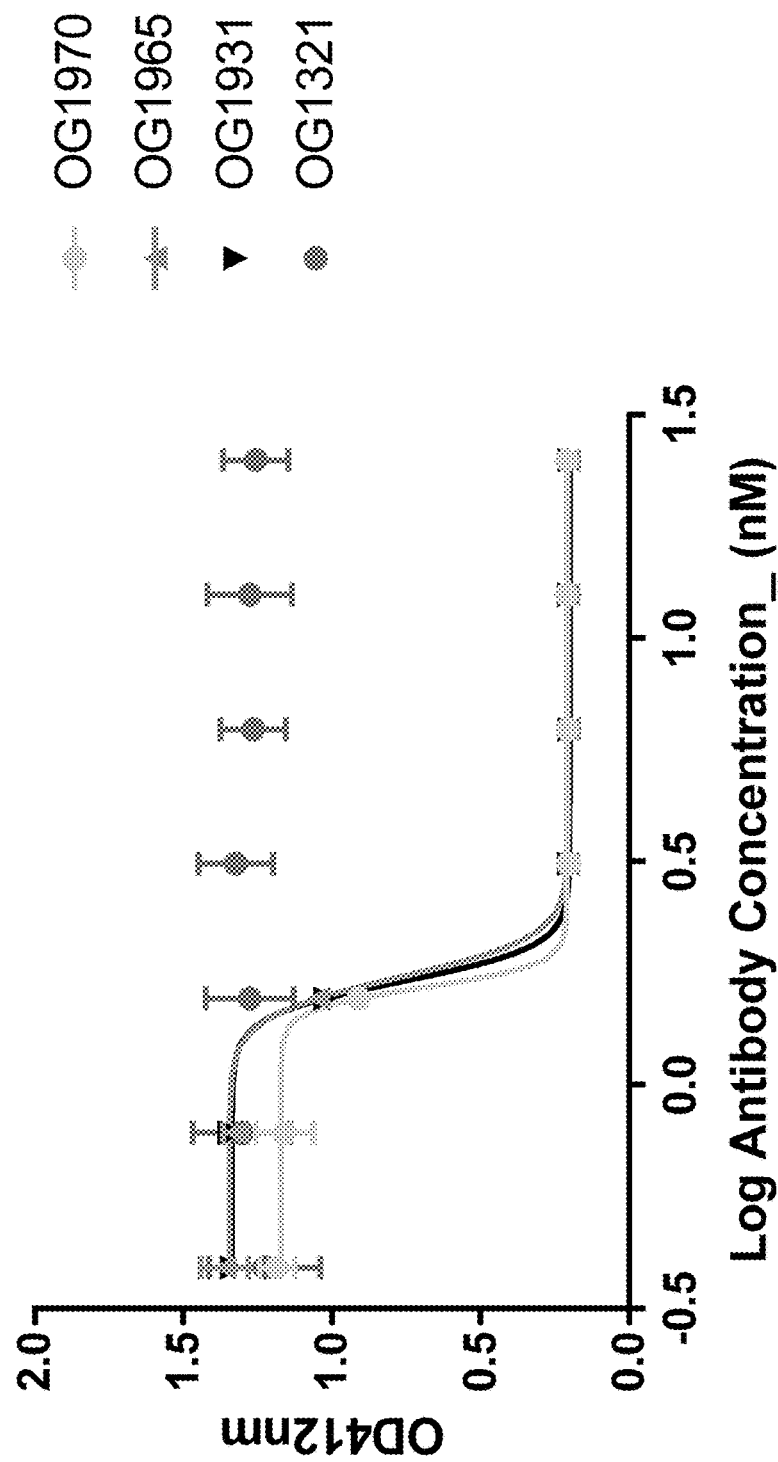
FIG. 23 displays the results of a hemolysis assay for OG1965 and OG1970 and controls.

To measure lysis, supernatant was collected by centrifuging the plate at 1,500 rpm for 5 min, no break or low break. Supernatants were transferred to wells on a flat-bottom 96-well plate (200 uL per well). The plates are read using a SpectraMax Plus™, 25° C. at OD412 nm. In the analysis 100% of lysis: RBCs/NHS without AFD; Inhibition: RBCs/NHS/AFD. Percentage of inhibition was calculated as follows: 100× (OD RBCs/NHS)−(OD RBCs/NHS/AFD). Data are presented in FIG. 23 and Table 32.1. OG1965 and OG1970 both potently inhibit alternative complement pathway-dependent hemolysis of rabbit RBC.

TABLE 32.1

EC50 of OG1931 and OG1965 in hemolysis assay

| | EC50 (nM) |
|---|---|
| OG1931 | 1.704 |
| OG1965 | 1.741 |
| OG1970 | 1.654 |

Example 33

Dry AMD

A patient presents with symptoms and signs of Dry AMD such as and not limited to difficulty reading in dim light confirmed by low luminance visual acuity testing or blurred regions in the visual field confirmed by microperimetry. Following one or more sessions of intraocular treatment with an antibody comprising SEQ ID NO:s 183 and 184, (which can be, in the alternative, conjugated so as to form OG1970), one will observe a decrease in the rate of progression and possible reversal of the symptoms and signs of the disorder. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 34

Wet AMD

A patient presents with Wet AMD in an eye and advanced Dry AMD in the other eye. They are considered a high risk patient to develop Wet AMD in the other eye. One or more sessions with intraocular treatment with an antibody comprising SEQ ID NO:s 183 and 184, (which can be, in the alternative, conjugated so as to form OG1970), will prevent (including delay) the conversion of Dry to Wet AMD. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 35

Diabetic Retinopathy

A patient present with symptoms Diabetic Retinopathy such as and not limited to difficulty in reading confirmed by near vision visual acuity. Ocular exam, OCT and Fluorescein Angiography reveals Diabetic Macular Edema and generalized Diabetic Retinopathy. Following one or more sessions of treatment with an antibody comprising SEQ ID NO:s 183 and 184, (which can be, in the alternative, conjugated so as to form OG1970) the symptoms will resolve, OCT reveals reduction in the macular edema or resolution and the diabetic retinopathy did not progress, regressed, or resolved. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 36

Paroxysmal Nocturnal Hemoglobinuria (PNH)

Hemolysis can cause one or more of the following symptoms in a patient with PNH: severe anemia, disabling fatigue, recurrent pain, shortness of breath, pulmonary hypertension, intermittent episodes of dark colored urine (hemoglobinuria), kidney disease, impaired quality of life and blood clots. Following one or more sessions of treatment with an antibody comprising SEQ ID NO:s 183 and 184, (which can be, in the alternative, conjugated so as to form OG1970) hemolysis is reduced and hemoglobin levels increase and stabilize. The antibody or bioconjugate can be administered alone or, in the alternative, in combination with another agent.

In some embodiments, the antibody or bioconjugate can be administered via intravenous or subcutaneous injections, at 0.1 to 30 mg/kg, once every 2 weeks, 1, 2, 3, or 4 months.

Example 37

RE: Expression, Purification, Crystallization and Structure Determination of OG1965-CFD
Methods
CFD and OG1965 Fab Expression and Purification:

Human mature CFD peptide with N-terminal His tag was expressed in Expi293 cells (Thermo Scientific) and purified from media using Ni-NTA resin (30 mM Tris pH 8.0, 200 mM Nacl and 250 mM imidazole) followed by size exclusion chromatography (30 mM HEPES pH 7.5 and 200 mM NaCl). OG1965 was expressed in CHO-S1 cells and purified using mAbSelect (GE Healthcare Life Sciences) by following manufacture's instruction.

Purified OG1965 was digested with crystalline papain (50:1 OG1965:crystalline papain ratio) in 10 mM DTT, 25 mM HEPES pH 7.5, 200 mM NaCl. The reaction was incubated for 4 hours at 37° C. Approximately 30 mg of mAb were digested and the resulting Fab fragments were alkylated with iodoacetamide and purified using a protein A resin. The presence of Fab chains at the flow through was confirmed by SDS-PAGE, while the absence of Fc chain was confirmed by ESI-MS.

CFD-Fab Complex Formation and Purification.

A mixture containing CFD and Fab proteins was prepared at an equimolar concentration, incubated at room temperature for one hour and later injected in a size exclusion (Superdex-200) column pre-equilibrated with 25 mM HEPES pH 7.5, 100 mM NaCl, and 3% (v/v) glycerol. Peak fractions containing Fab and CFD were identified by SDS-PAGE, pooled, concentrated to 10 mg/ml and carried out to crystallization experiments.

CFD-Fab Complex Crystallization.

Conditions for CFD-Fab complex crystallization were screened by the sitting drop vapor diffusion method with in-house and commercial crystallization screens at 4° C. and room temperature (RT). Protein crystals were obtained in three different conditions: A—0.1 M Bicine pH 9.0 and 20% PEG 6000 at RT; B—0.1 M Tris pH 8.0, 30% Peg 1000, and 0.1 M Sodium Malonate at RT; C—0.1 M Mes pH 6.0 and 20% PEG 6000 at 4° C. Crystals grown at room temperatures are thin plates and were seeded to get diffraction quality crystals. Meanwhile, crystal at 4° C. appeared after a week and present tetragonal morphology.

X-Ray Data Collection.

Crystals were flash-cooled by direct immersion in liquid nitrogen using mother liquor supplemented with 20% (v/v) ethylene glycol. X-ray intensity data were collected at the SER-CAT beam line of the Advanced Photon Source (APS) using Rayonix 300 high-speed detector. Crystals grown at room temperature (pH 9.0) diffracted to 2.7 Å, and belong to the triclinic space group $P_1$ with four complex molecules in the asymmetric unit. Whereas crystals grown at 4° C. (pH 6.0) diffracted to 2.4 Å, and belong to the tetragonal space group $P4_1 22$ with two complex molecules in the asymmetric unit. Data were indexed, integrated and scaled using the program HKL2000.

Structure Determination and Refinement.

The crystal structure of the complex was determined by molecular replacement with Phaser using the CFD (PDB: 1DSU) and Fab (PDB: 3HR5) monomers as the initial search models. The model was refined by rigid-body refinement followed by restrained refinement using REFMAC. All crystallographic calculations were performed with the CCP4 suite of programs. Model building of the complex in the electron density was done using the graphics program COOT. Most of the model was fitted well in the electron density especially at the antigen-antibody interface. After an iterative model building and refinement, relatively high R and freeR (R/freeR=0.27/0.32) were noticed due to the disorder of the constant domains (Cl and Ch1) in one of the four complex molecules. This disorder, as found in a number of Fab structures, is due to the flexible elbow angle between the variable and constant domains.

For the structure of the complex at pH 6.0, previously refined models of the CFD and Fab complex at pH 9 were used as search models to solve the structure. The structure at pH 6 presents better refinement statistics (R/freeR=0.22/0.28) and was selected for further validation using the Ramachandran plot and the program PROCHECK. The structural coordinates can be found in CTKDK001A.txt, filed herewith and incorporated by reference in its entirety.

Example 38

Structural Analysis of OG1965

CFD-Fab Interface Residue Analysis.

Figure 24A:
FIG. 24A shows OG1965 binding to CFD. Fab heavy and light chains are shown in surface representation, CFD is shown in ribbon. Figure was prepared using software PyMOL (Open-Source PyMOL 0.99rc6).
Figure 24B:
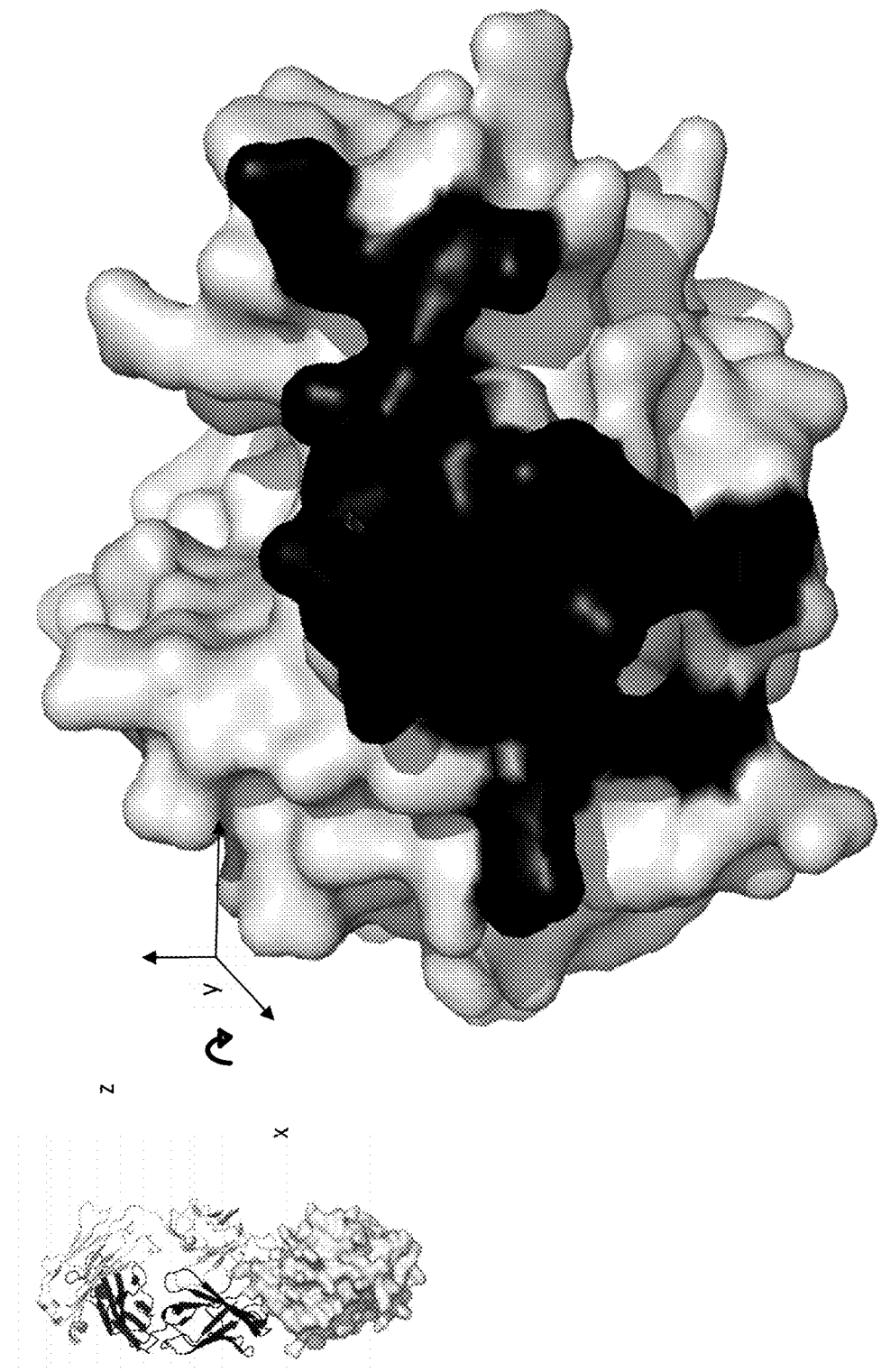
FIG. 24B shows the OG1965 binding region at the CFD domain. The figure displays CFD in surface representation, OG1965 heavy and light chains are presented in black and white ribbons, respectively. Buried surface residues between Fab and CFD are highlighted in black over CFD surface representation. Figure was prepared using software PyMOL (Open-Source PyMOL 0.99rc6).
Figure 25:
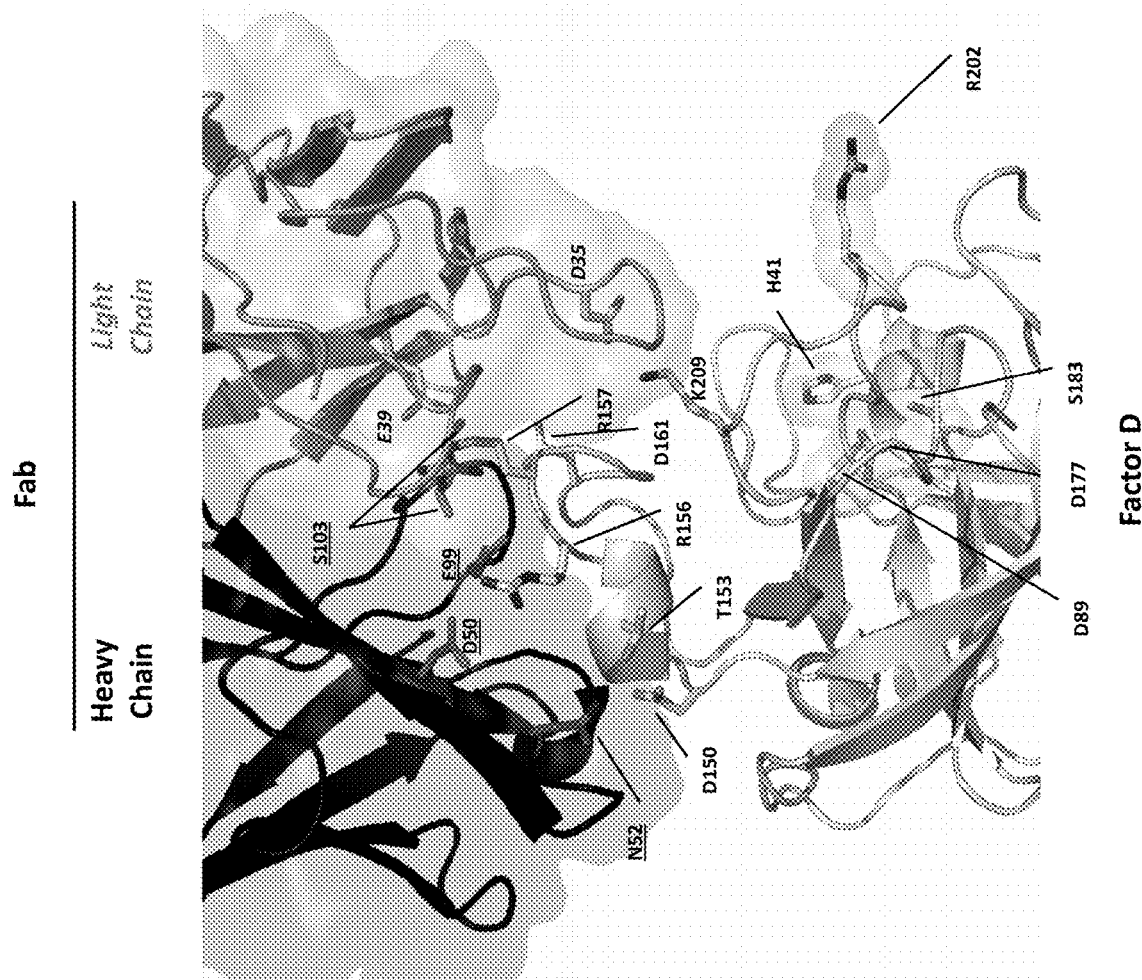
FIG. 25 shows residues (stick representation) at the CFD:Fab interface that are within a distance shorter than 3 Å. CFD is presented in ribbon, Fab heavy (underlined residues) and light chains (italicized residues) are presented in dark and light ribbons overlapped by transparent surface representations. Residues at the CFD active site (H41, D89, S183), self-inhibitory loop (R202) and S1 pocket (D177) are shown in sticks and highlighted by spheres. Figure was prepared using software PyMOL (Open-Source PyMOL 0.99rc6).
Figure 26A:
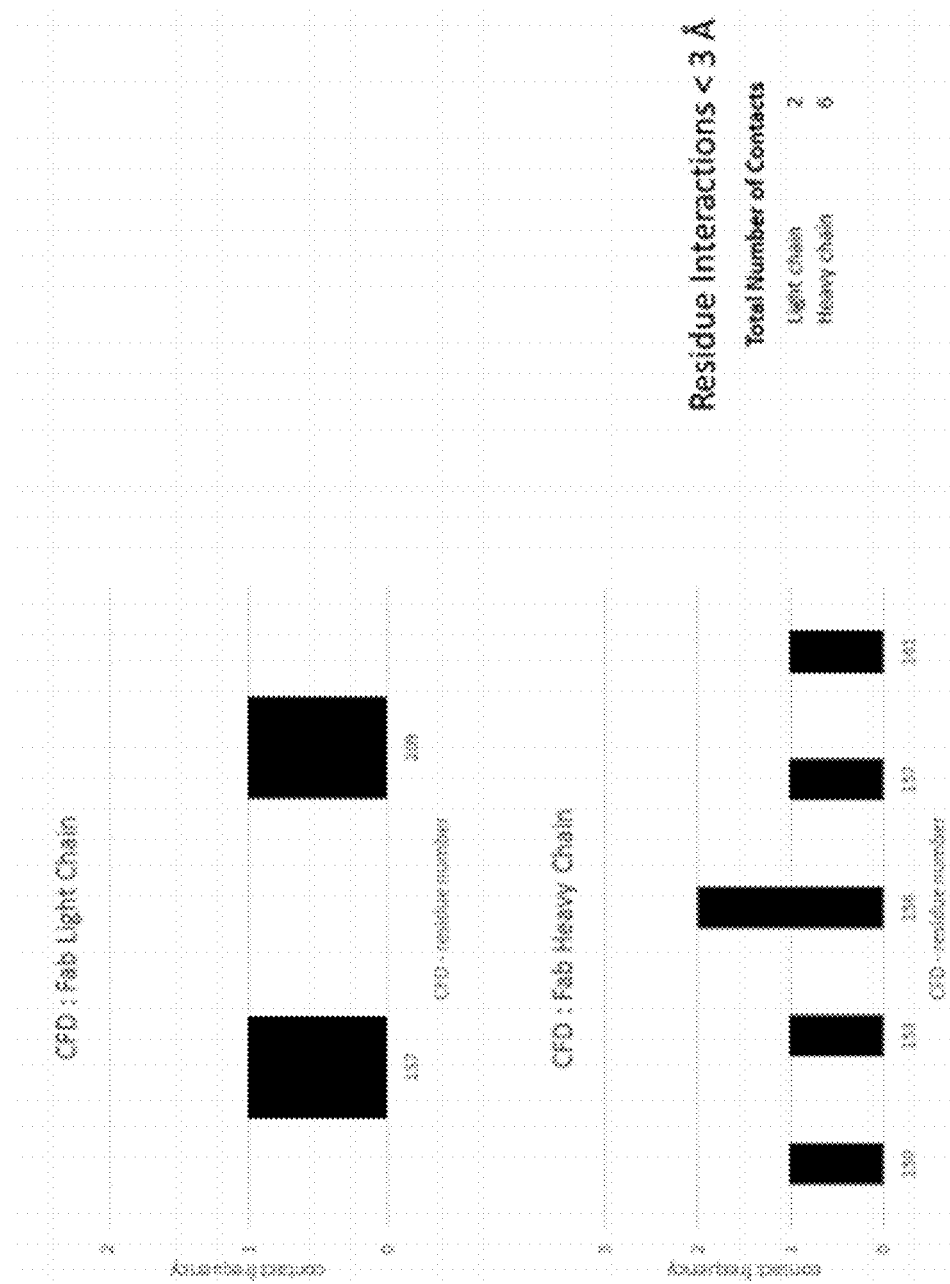
FIGS. 26A-26C show CFD and Fab residue contacts frequency. Top and bottom panels display the number of interactions between CFD and Fab light/heavy chains, respectively. Residue interactions were identified using an in-house Python-based algorithm developed to measure distances between inter-chain atoms. Contacts below 3 Å were selected and counted on a residue basis in FIG. 26A. Contacts below 5 Å were selected and counted on a residue basis in FIG. 26B. Contacts below 6 Å were selected and counted on a residue basis in FIG. 26C.
Figure 26B:
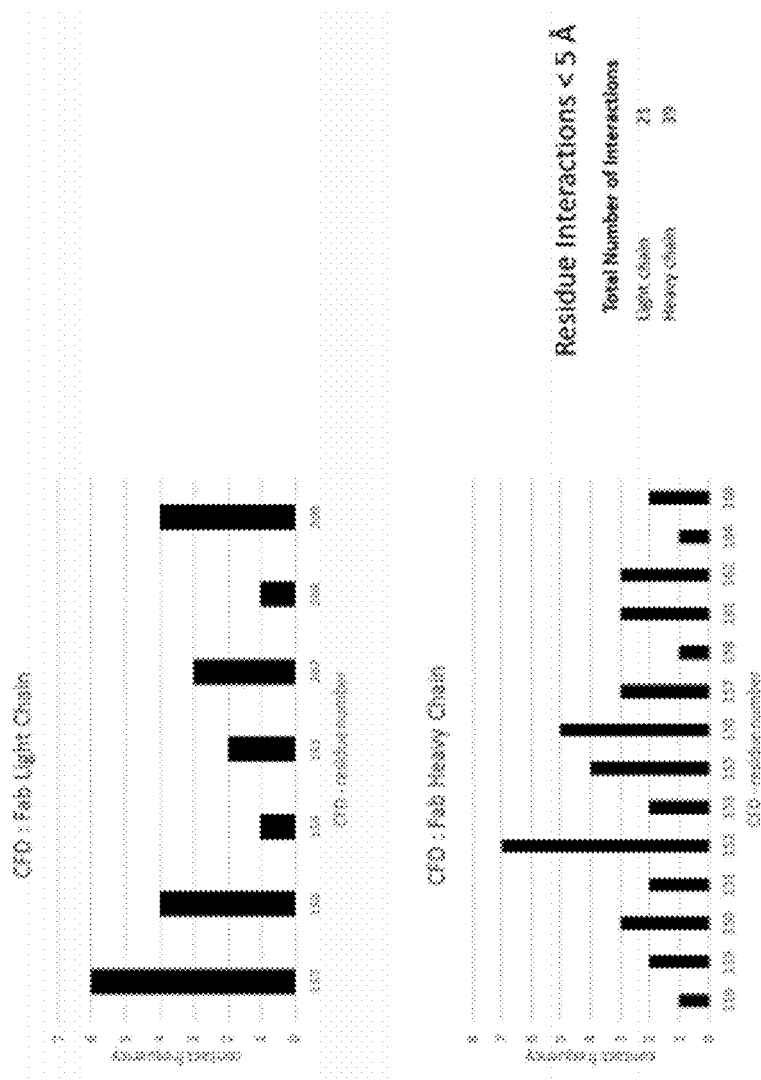
Figure 26C:
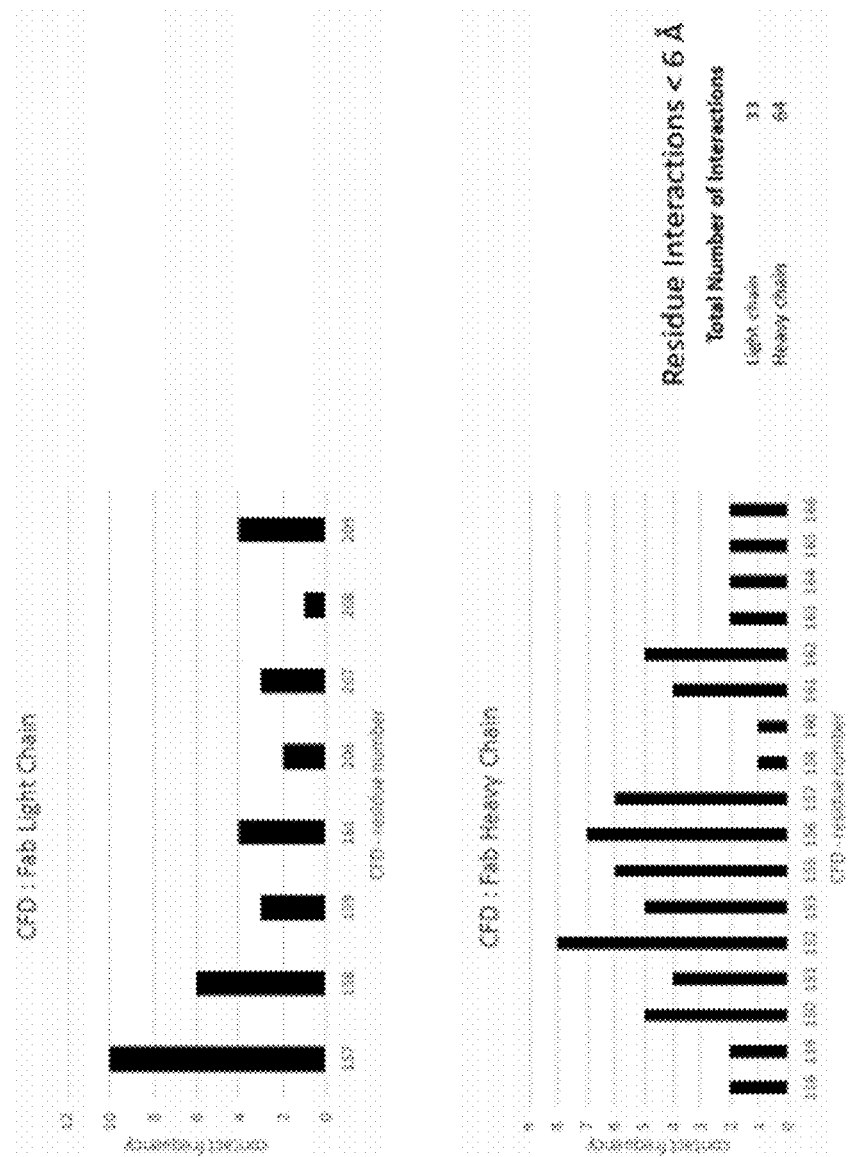

Residues at the interface between CFD and Fab (heavy and light chains) were identified using an in-house modified version of the PyMOL script InterfaceResidues available online at world wide web //pymolwiki "dot" org/index "dot" php/InterfaceResidues. This script calculates the accessible surface area (ASA) of residues in two situations: i) at the complex as a whole and ii) at the isolated chains. Then, it calculates the difference between ASA in both situations, residues with differences above a user-defined cutoff value (defined as 1 in this study) are identified as interface residues. This analysis was performed on chains A—CFD, H—Fab Heavy chain, L—Fab Light chain of OG1965. The antibody as bound to CFD is depicted in FIG. 24A. The atomic coordinates are in the accompanying text file, filed herewith (CTKDK001A.txt). Interface residues were mapped on the CFD surface representation as illustrated in FIG. 24B.

Interatomic Contact Distances at the CFD-Fab Complex.

Distances between inter-chain atoms were determined using an in-house Python-based algorithm following the equation described below:

distance=$\{(x_1-x_0)^2+(y_1-y_0)^2+(z_1-z_0)^2\}^{0.5}$, given two points in three dimensions are defined by $(x_0,y_0,z_0)$ and $(x_1,y_1,z_1)$.

Distance shorter than a user defined cutoff value (3, 5 and 6 angstroms in this study) were selected. To remove residue contact redundancy, only the shortest interatomic distance was chosen within a pair of residues. Those contacts were later grouped into clusters based on CFD residue numeration and counted. This analysis was performed on chains A—CFD, H—Fab Heavy chain, L—Fab Light chain of OG1965. Interface residues were mapped on the CFD surface representation as illustrated in FIGS. 25 and 26A-26C and Tables 38.1-38.3.

TABLE 38.1

List of residue contacts between CFD and Fab chains below 3 Å

| CFD | Heavy chain | Light chain |
| --- | --- | --- |
| D150 | N52 | |
| T153 | N52 | |
| R156 | D50, E99 | |
| R157 | E99 | E39 |
| D161 | S103 | |
| K209 | | D35 |

TABLE 38.2

List of residue contacts between CFD and Fab chains below 5 Å

| CFD | Heavy chain | Light chain |
| --- | --- | --- |
| D116 | D31 | |
| P119 | T55, I54 | |
| D150 | I54, N52, T55 | |
| R151 | I54, D31 | |
| A152 | T30, D31, Y32, I54, Y33, N52, P53 | |
| T153 | Y33, N52 | |
| N155 | D31, E99, G100, Y32 | |
| R156 | E99, Y33, D50, D59, N35 | |
| R157 | E99, S103, F104 | Y37, E39, G96, F94, Y41, V101 |
| T158 | E99 | Y37, N33, H31, G96 |
| H159 | | Y37 |
| D161 | G100, P101, S103 | R54, K55 |
| G162 | G100, P101, Y32 | |
| I164 | Y32 | |
| E166 | D31, T28 | |
| R207 | | N33, G34, S32 |
| K208 | | N33 |
| K209 | | N33, D35, Y37, K55 |

TABLE 38.3

List of residue contacts between CFD and Fab chains below 6 Å

| CFD | Heavy chain | Light chain |
| --- | --- | --- |
| D116 | D31, I54 | |
| P119 | I54, T55 | |
| D150 | I54, T55, N52, Y33, T30 | |
| R151 | T30, D31, I54, Y32 | |
| A152 | T30, D31, Y32, Y33, N52, I54, P53, E99 | |
| T153 | D31, Y33, N52, I54, T55 | |
| N155 | D31, Y32, E99, G100, P101, Y33 | |
| R156 | Y33, E99, G100, D50, N35, D59, W47 | |
| R157 | E99, G100, S103, F104, N35, P101 | Y37, E39, D35, K55, G96, F94, Q95, S97, V101, Y41 |
| T158 | E99 | N33, Y37, H31, G96, D35, S97 |
| H159 | | N33, Y37, D35 |
| H160 | G100 | |
| D161 | G100, P101, S103, E99 | R54, K55, E39, Y37 |
| G162 | Y32, E99, G100, P101, R98 | |
| A163 | Y32, G100 | |
| I164 | Y32, D31 | |
| T165 | Y32, D31 | |
| E166 | D31, T28 | |
| N206 | | S32, N33 |
| R207 | | N33, S32, G34 |
| K208 | | N33 |
| K209 | | N33, D35, Y37, K55 |

Example 39—CFB Binding Inhibition Assay

To determine whether anti-CFD antibodies inhibit CFD from binding to C3bB, a SPR approach was implemented to assess complex assembly. 200 RUs of C3b (Complement Technologie) in Acetate pH 5.0 buffer was amine coupled to a CM5 Series S sensor chip by following the immobilization wizard on Biacore instrument software. $CFD_{S183A}$ is a catalytically dead mutant of CFD that still binds to CFB without cleaving it. For complex assembly, 100 nM of recombinant human $CFD_{S183A}$ was complexed with 100 nM CFB by incubating the mixture in HBS+ with 2 mM MgCl2. The resulting complex was then incubated in the presence or absence of 100 nM OG1965, OG1970, or OG2063 (positive control; also named KCD004 (SEQ ID NOs: 341 and 342)).

Using HBS+ with 2 mM MgCl2 running buffer, 100 nM CFB (Complement Technologies) was injected for 60 seconds followed by CFB: $CFD_{S183A}$ complex or CFB: $CFD_{S183A}$:AFD mixtures for 60 seconds at 30 uls/min using the dual injection function. The complexes were allowed to dissociate for 5 minutes, and the surface was regenerated with 3M MgCl2 for 60 seconds at 50 uls/min. Sensorgrams were evaluated using Biacore T200 Evaluation Software (GE Life Sciences).

As shown in FIG. 27, CFB and CFB:$CFD_{S183A}$ bound to C3b with correlative increases in resonance units following injection. In the presence of OG2063, a non-blocking anti-CFD antibody, the response of KCD004:$CFD_{S183A}$ was significantly higher than what was observed for $CFD_{S183A}$ alone, which is indicative of C3bBD-mAb complex formation. OG1965/$CFD_{S183A}$ and OG1970/$CFD_{S183A}$ do not show any change in binding, supporting the position that $CFD_{S183A}$ does not effectively bind to C3bB when it is bound to OG1965 or OG1970. KCD004 is referenced elsewhere as SEQ ID NO: 341 and 342.

Example 40—Complement Activation on ARPE19 Cells

The retinal pigment epithelial cell line, ARPE19, (ATCC) was cultured on trans-well filters (Millipore) in DMEM with pyruvate until cells were pigmented (12-16 weeks). Anti-CFD molecules preincubated for 1 hour with 10% normal human serum (NHS) were added to ARPE19 cells at 37 degrees for 1 hour to induce complement activation. Supernatants were harvested and cells were fixed with 4% PFA.

Figure 28A:
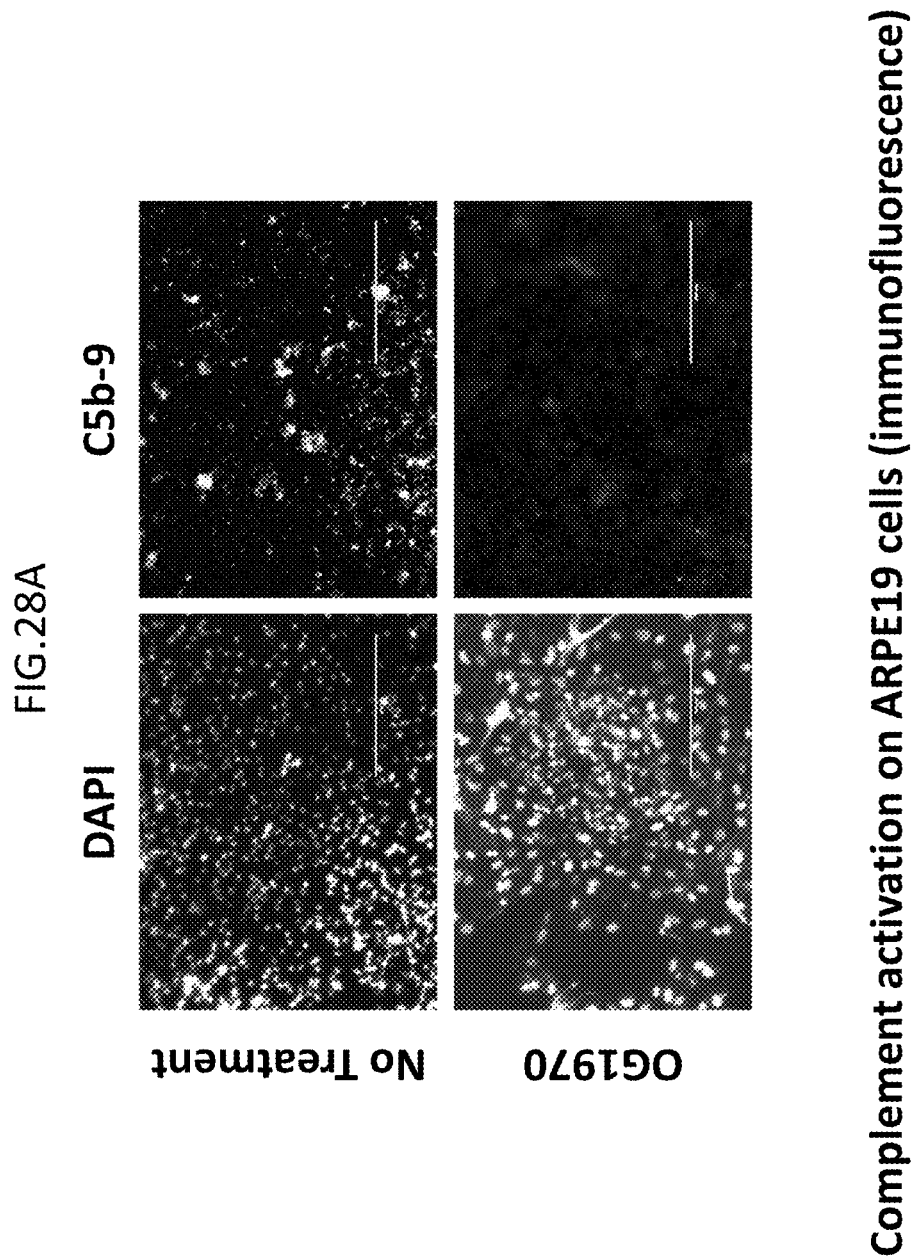
FIG. 28A and FIG. 28B utilize immunofluorescence and ELISA to observe CFB cleavage as well as formation of the terminal complement complex, C5b-9, on ARPE19 cells.

Immunofluorescence:

Fixed cells were incubated with αC5b-9 (Abcam), Donkey α-mouse-488 (Rockland Immunochemicals), and imaged on an EVOS fluorescence microscope (Life Technologies). Scale bar=400 μm. The results are shown in FIG. 28A and provide evidence that OG1970 effectively inhibited formation of the terminal complement complex C5b-9 on ARPE19 cells relative to cells subjected to serum alone.

Figure 28B:
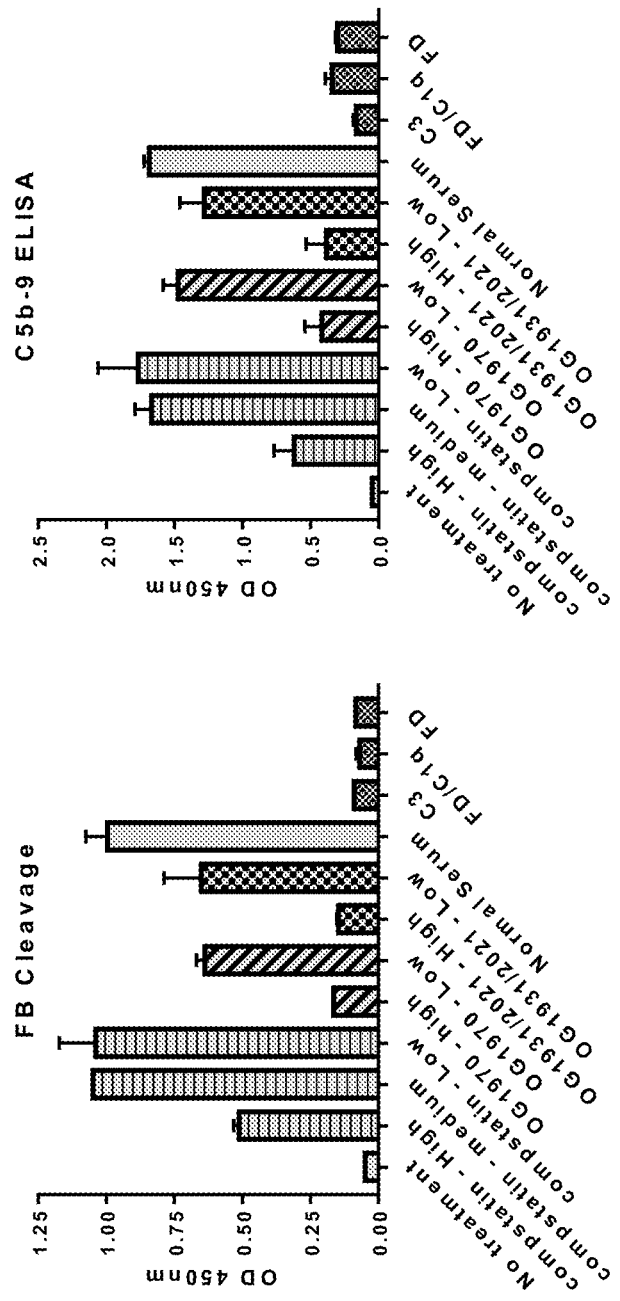

Bb and Cb5-9 Complex ELISAs:

Harvested supernatants were diluted 4-fold in Quidel diluent buffer before being added to MicroVue Bb Plus or MicroVue C5b-9 ELISA kit strips (Quidel). Manufacturer's instructions were followed and relative Bb or C5b-9 levels were measured at OD450 nm on a SpectraMax Plus. The results are shown in FIG. 28B as the average of replicates with standard deviation.

The results indicated that OG1970 inhibited C5b-9 complex formation as effectively as OG1931 and the classical pathway inhibitor Compstatin. OG1970 inhibition of CFB cleavage to Bb was superior to that of compstatin and comparable to OG1931 at both high and low doses tested. Additionally, OG1970 treated cells had similar levels of both Bb and C5b-9 as cells treated with C3 depleted sera (classical and alternative pathways), FD/C1q depleted sera (classical and alternative pathways), and FD depleted sera (alternative pathway), indicating that inhibition of CFD was sufficient for inhibiting the complement pathways under these conditions.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. An isolated antagonist antibody that specifically binds to complement factor D (CFD) and directly inhibits a proteolytic activity of CFD, wherein the antibody comprises:
a heavy chain variable region (VH) comprising:
a VH complementarity determining region 1 (CDR$_H$1) that is the CDR$_H$1 in SEQ ID NO: 520;
a CDR$_H$2 that is the CDR$_H$2 in SEQ ID NO: 520;
a CDR$_H$3 that is the CDR$_H$3 in SEQ ID NO: 520; and
a light chain variable region (VL) comprising:
a VL complementarity determining region 1 (CDR$_L$1) comprising H31, N33, G34 or E34 or F34 or S34, D35 or E35, T36 or S36 or V36, Y37, L38 or I38, and E39 (EU numbering);
a CDR$_L$2 comprising L51 or H51, I53 or V53, and K55 (EU numbering); and
a CDR$_L$3 comprising F94 or L94, Q95, G96, S97, V99 or N99 or Q99 or W99, P100, and P101 or V101 (EU numbering).

2. An isolated antagonist antibody that specifically binds to complement factor D (CFD), inhibits a proteolytic activity of CFD, and inhibits CFD binding to C3bB complex, wherein the antibody comprises:
a heavy chain variable region (VH) comprising:
a VH complementarity determining region 1 (CDR$_H$1) that is the CDR$_H$1 in SEQ ID NO: 520;
a CDR$_H$2 that is the CDR$_H$2 in SEQ ID NO: 520;
a CDR$_H$3 that is the CDR$_H$3 in SEQ ID NO: 520; and
a light chain variable region (VL) comprising:
a VL complementarity determining region 1 (CDR$_L$1) comprising H31, N33, G34 or E34 or F34 or S34, D35 or E35, T36 or S36 or V36, Y37, L38 or I38, and E39 (EU numbering);
a CDR$_L$2 comprising L51 or H51, I53 or V53, and K55 (EU numbering); and
a CDR$_L$3 comprising F94 or L94, Q95, G96, S97, V99 or N99 or Q99 or W99, P100, and P101 or V101 (EU numbering).

3. An isolated antagonist antibody that specifically binds to human complement factor D (CFD), wherein the antibody does not bind a human CFD mutant comprising mutations R157A and R207A, and wherein the antibody comprises:
a heavy chain variable region (VH) comprising an amino acid sequence at least 85% identical to SEQ ID NO: 520; and
a light chain variable region (VL) comprising an amino acid sequence at least 85% identical to SEQ ID NO: 525.

4. An isolated antagonist antibody comprising:
a heavy chain variable region (VH) comprising a VH complementarity determining region one (CDR1), VH CDR2, and VH CDR3, wherein:
the VH CDR1 comprises the amino acid sequence consisting of SEQ ID NO: 541;
the VH CDR2 comprises the amino acid sequence consisting of SEQ ID NO: 542; and
the VH CDR3 comprises the amino acid sequence consisting of SEQ ID NO: 543; and
a light chain variable region (VL) comprising a VL CDR1, VL CDR2, and VL CDR3, wherein:
the VL CDR1 comprises H31, N33, G34 or E34 or F34 or S34, D35 or E35, T36 or S36 or V36, Y37, L38 or I38, and E39 (EU numbering);
the VL CDR2 comprises L51 or H51, I53 or V53, and K55 (EU numbering); and
the VL CDR3 comprises F94 or L94, Q95, G96, S97, V99 or N99 or Q99 or W99, P100, and P101 or V101 (EU numbering).

5. An isolated antagonist antibody that binds to CFD, wherein the antibody comprises:
   a heavy chain comprising the amino acid sequence shown in SEQ ID NO: 183, with or without the C-terminal lysine; and
   a light chain comprising the amino acid sequence shown in SEQ ID NO: 184.

6. An isolated antagonist antibody that binds to CFD, wherein the antibody comprises:
   a VH comprising the amino acid sequence shown in SEQ ID NO: 520, or a sequence that is at least 90% identical thereto, having amino acid substitutions in residues that are not within a CDR of SEQ ID NO: 520; and
   a VL comprising:
      a VL complementarity determining region 1 (CDR$_L$1) comprising H31, N33, G34 or E34 or F34 or S34, D35 or E35, T36 or S36 or V36, Y37, L38 or I38, and E39 (EU numbering);
      a CDR$_L$2 comprising L51 or H51, I53 or V53, and K55 (EU numbering); and
      a CDR$_L$3 comprising F94 or L94, Q95, G96, S97, V99 or N99 or Q99 or W99, P100, and P101 or V101 (EU numbering).

7. An isolated antagonistic antibody that binds to CFD, the antibody comprising:
   a VH comprising:
      a CDR$_H$1 that is the CDR$_H$1 in SEQ ID NO: 520;
      a CDR$_H$2 that is the CDR$_H$2 in SEQ ID NO: 520; and
      a CDR$_H$3 that is the CDR$_H$3 in SEQ ID NO: 520;
   a VL comprising:
      a CDR$_L$1 that is the CDR$_L$1 in SEQ ID NO: 525;
      a CDR$_L$2 that is the CDR$_L$2 in SEQ ID NO: 525; and
      a CDR$_L$3 that is the CDR$_L$3 in SEQ ID NO: 525;
   at least one of the following mutations (EU numbering): L234A, L235A, and G237A; and
   at least one of the following mutations (EU numbering): Q347C or L443C.

8. The isolated antagonist antibody of claim 1, wherein the antibody does not bind a human CFD mutant comprising the mutations R157A and R207A.

9. The isolated antagonist antibody of claim 1, wherein the antibody blocks C3bB binding to CFD.

10. The isolated antagonist antibody of claim 1, wherein the antibody binds human CFD with an affinity of between about 0.1 pM to about 20 pM.

11. The isolated antagonist antibody of claim 1, wherein the heavy chain variable region (VH) of the antibody comprises three CDRs comprising the amino acid sequences shown in SEQ ID NO: 541, SEQ ID NO: 542, and SEQ ID NO: 543, and the light chain variable region (VL) of the antibody comprises three CDRs comprising the amino acid sequences shown in SEQ ID NO: 544, SEQ ID NO: 545, and SEQ ID NO: 546.

12. An isolated antagonist antibody that specifically binds to complement factor D (CFD), comprising:
   a heavy chain variable region (VH) comprising:
      a VH complementarity determining region 1 (CDR$_H$1) that is the CDR$_H$1 in SEQ ID NO: 520;
      a CDR$_H$2 that is the CDR$_H$2 in SEQ ID NO: 520;
      a CDR$_H$3 that is the CDR$_H$3 in SEQ ID NO: 520;
   a VL complementarity determining region 1 (CDR$_L$1) comprising H31, N33, G34 or E34 or F34 or S34, D35 or E35, T36 or S36 or V36, Y37, L38 or I38, and E39 (EU numbering);
   a CDR$_L$2 comprising L51 or H51, I53 or V53, and K55 (EU numbering); and
   a CDR$_L$3 comprising F94 or L94, Q95, G96, S97, V99 or N99 or Q99 or W99, P100, and P101 or V101 (EU numbering),
   wherein the antibody comprises an Fc region comprising one or more amino acid substitutions to reduce effector function, and wherein the antibody inhibits a proteolytic activity of CFD or inhibits CFD binding to C3bB complex.

13. A pharmaceutical composition comprising the isolated antagonistic antibody of claim 1, and a pharmaceutically acceptable carrier.

14. An isolated antagonist antibody, wherein the antibody binds an epitope on human CFD that is the same as the epitope recognized by an antibody comprising the amino acid sequences shown in SEQ ID NO: 520 and SEQ ID NO: 525, wherein the antibody directly inhibits a proteolytic activity of human CFD, wherein the antibody interacts with human CFD at one or more of the amino acids at position 157, 158, 159, 161, 206, 207, 208, 209, 116, 119, 150, 151, 152, 153, 155, 156, 162, 163, 164, 165, or 166 of SEQ ID NO: 1, when bound thereto.

15. An isolated antagonist antibody that specifically binds to complement factor D (CFD), wherein the antibody comprises:
   a heavy chain variable region (VH) comprising the amino acid sequence of any one of SEQ ID NOs: 515, 517-521; and
   a light chain variable region (VL) comprising the amino acid sequence of any one of SEQ ID NOs: 524-526.

16. A crystalized CFD-antibody complex, wherein the antibody comprises any one or more of the CDRs within SEQ ID NOs: 183 and 184.

17. An isolated antagonist antibody that binds an epitope on human CFD that is the same as the epitope recognized by an antibody comprising the amino acid sequences shown in SEQ ID NO: 45 and SEQ ID NO: 46,
   wherein the antibody comprises:
      a heavy chain variable region (VH) comprising 3 CDRs of the CDRs in SEQ ID NO: 19; and a light chain variable region (VH) comprising 3 CDRs of the CDRs in SEQ ID NO: 20; or
      a VH comprising 3 CDRs of the CDRs in SEQ ID NO: 17; and a VL comprising 3 CDRs of the CDRs in SEQ ID NO: 18; or
      a VH comprising 3 CDRs of the CDRs in SEQ ID NO: 49; and a VL comprising 3 CDRs of the CDRs in SEQ ID NO: 50; or
      a VH comprising 3 CDRs of the CDRs in SEQ ID NO: 45; and a VL comprising 3 CDRs of the CDRs in SEQ ID NO: 46; or
      a VH comprising 3 CDRs of the CDRs in SEQ ID NO: 5; and a VL comprising 3 CDRs of the CDRs in SEQ ID NO: 6; or
      a VH comprising 3 CDRs of the CDRs in SEQ ID NO: 47; and a VL comprising 3 CDRs of the CDRs in SEQ ID NO: 48; or
      a VH comprising 3 CDRs of the CDRs in SEQ ID NO: 51; and a VL comprising 3 CDRs of the CDRs in SEQ ID NO: 52; or
      a VH comprising 3 CDRs of the CDRs in SEQ ID NO: 43; and a VL comprising 3 CDRs of the CDRs in SEQ ID NO: 44; or
      a VH comprising 3 CDRs of the CDRs in SEQ ID NO: 53; and a VL comprising 3 CDRs of the CDRs in SEQ ID NO: 54; or a VH comprising 3 CDRs of the CDRs in SEQ ID NO: 7; and a VL comprising 3 CDRs of the CDRs in SEQ ID NO: 8; or a VH comprising 3 CDRs of the CDRs in SEQ ID NO: 15; and a VL comprising 3 CDRs of the CDRs in SEQ ID NO: 16.

18. The isolated antagonist antibody of claim 7, wherein the antibody is a humanized antibody.

19. The isolated antagonist antibody of claim 7, wherein the antibody is a human antibody.

20. The isolated antagonist antibody of claim 7, wherein the antibody comprises:

a heavy chain variable region (VH) comprising an amino acid sequence having at least 90% sequence identity to the sequence set forth in SEQ ID NO: 520.

21. The isolated antagonist antibody of claim 20, wherein the antibody comprises the mutations (EU numbering): L234A, L235A, and G237A.

22. An isolated antibody that binds to CFD, the antibody comprising:

a VH comprising:
a $CDR_H1$ that is the $CDR_H1$ in SEQ ID NO: 520;
a $CDR_H2$ that is the $CDR_H2$ in SEQ ID NO: 520;
a $CDR_H3$ that is the $CDR_H3$ in SEQ ID NO: 520; and a VL comprising:
a $CDR_L1$ that is the $CDR_L1$ in SEQ ID NO: 525;
a $CDR_L2$ that is the $CDR_L2$ in SEQ ID NO: 525; and
a $CDR_L3$ that is the $CDR_L3$ in SEQ ID NO: 525.

23. The isolated antagonist antibody of claim 22, wherein the antibody comprises a heavy chain comprising a human IgG Fc region.

24. The isolated antagonist antibody of claim 23, wherein the heavy chain comprises one or more of the following amino acid mutations (EU numbering):
L234A, L235A, G237A.

25. The isolated antagonist antibody of claim 24, wherein the heavy chain comprises the following amino acid mutations (EU numbering): L234A, L235A, and G237A.

26. The isolated antagonist antibody of claim 23, wherein the heavy chain comprises a Q347C or L443C (EU numbering) mutation.

27. The isolated antagonist antibody of claim 22, wherein the antibody is a humanized antibody.

28. The isolated antagonist antibody of claim 22, wherein the antibody is a human antibody.

29. The isolated antagonist antibody of claim 22, wherein the antibody comprises a heavy chain variable region (VH) comprising an amino acid sequence having at least 90% sequence identity to the sequence set forth in SEQ ID NO: 520.

30. The isolated antagonist antibody of claim 22, wherein the antibody comprises a light chain variable region (VL) comprising the amino acid sequence set forth in SEQ ID NO: 525.

31. An antibody comprising six complementarity determining regions (CDRs) comprising:

a VH comprising:
a complementarity determining region 1 ($CDR_H1$) that is the $CDR_H1$ in SEQ ID NO: 520;
a $CDR_H2$ that is the $CDR_H2$ in SEQ ID NO: 520;
a $CDR_H3$ that is the $CDR_H3$ in SEQ ID NO: 520;

a VL comprising:
a $CDR_L1$ that is the $CDR_L1$ in SEQ ID NO: 525;
a $CDR_L2$ that is the $CDR_L2$ in SEQ ID NO: 525; and
a $CDR_L3$ that is the $CDR_L3$ in SEQ ID NO: 525.

32. The antibody of claim 31, wherein the antibody comprises a heavy chain comprising a human IgG Fc region.

33. The antibody of claim 32, wherein the heavy chain comprises one or more of the following amino acid mutations (EU numbering): L234A, L235A, G237A.

34. The antibody of claim 33, wherein the heavy chain comprises the following amino acid mutations (EU numbering): L234A, L235A, and G237A.

35. The antibody of claim 32, wherein the heavy chain comprises a Q347C or L443C (EU numbering) mutation.

36. The antibody of claim 31, wherein the antibody is a humanized antibody.

37. The antibody of claim 31, wherein the antibody is a human antibody.

38. The antibody of claim 31, wherein the antibody comprise a heavy chain variable region (VH) comprising an amino acid sequence having at least 90% sequence identity to the sequence set forth in SEQ ID NO: 520.

39. The antibody of claim 31, wherein the antibody comprises a light chain variable region (VL) comprising the amino acid sequence set forth in SEQ ID NO: 525.

40. An antibody comprising:

a heavy chain comprising the amino acid sequence of SEQ ID NO: 183, with or without the C-terminal lysine; and a light chain comprising the amino acid sequence of SEQ ID NO: 184.

41. The isolated antagonist antibody of claim 1, wherein the VH comprises the amino acid sequence shown in SEQ ID NO: 520, or a sequence that is at least 90% identical thereto, having amino acid substitutions in residues that are not within a CDR of SEQ ID NO: 520.

42. The isolated antagonist antibody of claim 3, wherein the antibody comprises:

a heavy chain variable region (VH) comprising 3 CDRs of the CDRs in SEQ ID NO: 339; and a light chain variable region (VH) comprising 3 CDRs of the CDRs in SEQ ID NO: 340; or a VH comprising 3 CDRs of the CDRs in SEQ ID NO: 343; and a VL comprising 3 CDRs of the CDRs in SEQ ID NO: 344; or a VH comprising 3 CDRs of the CDRs in SEQ ID NO: 435; and a VL comprising 3 CDRs of the CDRs in SEQ ID NO: 436; or a VH comprising 3 CDRs of the CDRs in SEQ ID NO: 437; and a VL comprising 3 CDRs of the CDRs in SEQ ID NO: 438; or a VH comprising 3 CDRs of the CDRs in SEQ ID NO: 441; and a VL comprising 3 CDRs of the CDRs in SEQ ID NO: 442; or a VH comprising 3 CDRs of the CDRs in SEQ ID NO: 443; and a VL comprising 3 CDRs of the CDRs in SEQ ID NO: 444; or a VH comprising 3 CDRs of the CDRs in SEQ ID NO: 445; and a VL comprising 3 CDRs of the CDRs in SEQ ID NO: 446; or a VH comprising 3 CDRs of the CDRs in SEQ ID NO: 447; and a VL comprising 3 CDRs of the CDRs in SEQ ID NO: 448; or a VH comprising 3 CDRs of the CDRs in SEQ ID NO: 351; and a VL comprising 3 CDRs of the CDRs in SEQ ID NO: 352; or a VH comprising 3 CDRs of the CDRs in SEQ ID NO: 373; and a VL comprising 3 CDRs of the CDRs in SEQ ID NO: 374.

43. An The isolated antagonist antibody that binds to CFD, wherein the antibody comprises:
- a heavy chain variable region (VH) comprising 3 CDRs of the CDRs in SEQ ID NO: 339; and a light chain variable region (VH) comprising 3 CDRs of the CDRs in SEQ ID NO: 340; or
- a VH comprising 3 CDRs of the CDRs in SEQ ID NO: 343; and a VL comprising 3 CDRs of the CDRs in SEQ ID NO: 344; or
- a VH comprising 3 CDRs of the CDRs in SEQ ID NO: 435; and a VL comprising 3 CDRs of the CDRs in SEQ ID NO: 436; or
- a VH comprising 3 CDRs of the CDRs in SEQ ID NO: 437; and a VL comprising 3 CDRs of the CDRs in SEQ ID NO: 438; or
- a VH comprising 3 CDRs of the CDRs in SEQ ID NO: 441; and a VL comprising 3 CDRs of the CDRs in SEQ ID NO: 442; or
- a VH comprising 3 CDRs of the CDRs in SEQ ID NO: 443; and a VL comprising 3 CDRs of the CDRs in SEQ ID NO: 444; or
- a VH comprising 3 CDRs of the CDRs in SEQ ID NO: 445; and a VL comprising 3 CDRs of the CDRs in SEQ ID NO: 446; or
- a VH comprising 3 CDRs of the CDRs in SEQ ID NO: 447; and a VL comprising 3 CDRs of the CDRs in SEQ ID NO: 448; or
- a VH comprising 3 CDRs of the CDRs in SEQ ID NO: 351; and a VL comprising 3 CDRs of the CDRs in SEQ ID NO: 352; or
- a VH comprising 3 CDRs of the CDRs in SEQ ID NO: 373; and a VL comprising 3 CDRs of the CDRs in SEQ ID NO: 374; or
- a VH comprising 3 CDRs of the CDRs in SEQ ID NO: 387; and a VL comprising 3 CDRs of the CDRs in SEQ ID NO: 388; or
- a VH comprising 3 CDRs of the CDRs in SEQ ID NO: 385; and a VL comprising 3 CDRs of the CDRs in SEQ ID NO: 386; or
- a VH comprising 3 CDRs of the CDRs in SEQ ID NO: 389; and a VL comprising 3 CDRs of the CDRs in SEQ ID NO: 390; or
- a VH comprising 3 CDRs of the CDRs in SEQ ID NO: 391; and a VL comprising 3 CDRs of the CDRs in SEQ ID NO: 392; or
- a VH comprising 3 CDRs of the CDRs in SEQ ID NO: 509; and a VL comprising 3 CDRs of the CDRs in SEQ ID NO: 510; or
- a VH comprising 3 CDRs of the CDRs in SEQ ID NO: 485; and a VL comprising 3 CDRs of the CDRs in SEQ ID NO: 486; or
- a VH comprising 3 CDRs of the CDRs in SEQ ID NO: 495; and a VL comprising 3 CDRs of the CDRs in SEQ ID NO: 496; or
- a VH comprising 3 CDRs of the CDRs in SEQ ID NO: 471; and a VL comprising 3 CDRs of the CDRs in SEQ ID NO: 472; or
- a VH comprising 3 CDRs of the CDRs in SEQ ID NO: 337; and a VL comprising 3 CDRs of the CDRs in SEQ ID NO: 338; or
- a VH comprising 3 CDRs of the CDRs in SEQ ID NO: 423; and a VL comprising 3 CDRs of the CDRs in SEQ ID NO: 424; or
- a VH comprising 3 CDRs of the CDRs in SEQ ID NO: 439; and a VL comprising 3 CDRs of the CDRs in SEQ ID NO: 440; or
- a VH comprising 3 CDRs of the CDRs in SEQ ID NO: 459; and a VL comprising 3 CDRs of the CDRs in SEQ ID NO: 460; or
- a VH comprising 3 CDRs of the CDRs in SEQ ID NO: 477; and a VL comprising 3 CDRs of the CDRs in SEQ ID NO: 478; or
- a VH comprising 3 CDRs of the CDRs in SEQ ID NO: 461; and a VL comprising 3 CDRs of the CDRs in SEQ ID NO: 462; or
- a VH comprising 3 CDRs of the CDRs in SEQ ID NO: 493; and a VL comprising 3 CDRs of the CDRs in SEQ ID NO: 494.

44. An isolated antagonist antibody that binds to CFD, wherein the antibody comprises:
- a heavy chain variable region (VH) comprising 3 CDRs of the CDRs in SEQ ID NO: 339; and a light chain variable region (VH) comprising 3 CDRs of the CDRs in SEQ ID NO: 340; or
- a VH comprising 3 CDRs of the CDRs in SEQ ID NO: 343; and a VL comprising 3 CDRs of the CDRs in SEQ ID NO: 344; or
- a VH comprising 3 CDRs of the CDRs in SEQ ID NO: 435; and a VL comprising 3 CDRs of the CDRs in SEQ ID NO: 436; or
- a VH comprising 3 CDRs of the CDRs in SEQ ID NO: 437; and a VL comprising 3 CDRs of the CDRs in SEQ ID NO: 438; or
- a VH comprising 3 CDRs of the CDRs in SEQ ID NO: 441; and a VL comprising 3 CDRs of the CDRs in SEQ ID NO: 442; or
- a VH comprising 3 CDRs of the CDRs in SEQ ID NO: 443; and a VL comprising 3 CDRs of the CDRs in SEQ ID NO: 444; or
- a VH comprising 3 CDRs of the CDRs in SEQ ID NO: 445; and a VL comprising 3 CDRs of the CDRs in SEQ ID NO: 446; or
- a VH comprising 3 CDRs of the CDRs in SEQ ID NO: 447; and a VL comprising 3 CDRs of the CDRs in SEQ ID NO: 448; or
- a VH comprising 3 CDRs of the CDRs in SEQ ID NO: 393; and a VL comprising 3 CDRs of the CDRs in SEQ ID NO: 394; or
- a VH comprising 3 CDRs of the CDRs in SEQ ID NO: 417; and a VL comprising 3 CDRs of the CDRs in SEQ ID NO: 418; or
- a VH comprising 3 CDRs of the CDRs in SEQ ID NO: 387; and a VL comprising 3 CDRs of the CDRs in SEQ ID NO: 388; or
- a VH comprising 3 CDRs of the CDRs in SEQ ID NO: 385; and a VL comprising 3 CDRs of the CDRs in SEQ ID NO: 386; or
- a VH comprising 3 CDRs of the CDRs in SEQ ID NO: 389; and a VL comprising 3 CDRs of the CDRs in SEQ ID NO: 390; or
- a VH comprising 3 CDRs of the CDRs in SEQ ID NO: 391; and a VL comprising 3 CDRs of the CDRs in SEQ ID NO: 392; or
- a VH comprising 3 CDRs of the CDRs in SEQ ID NO: 509; and a VL comprising 3 CDRs of the CDRs in SEQ ID NO: 510; or
- a VH comprising 3 CDRs of the CDRs in SEQ ID NO: 485; and a VL comprising 3 CDRs of the CDRs in SEQ ID NO: 486; or
- a VH comprising 3 CDRs of the CDRs in SEQ ID NO: 495; and a VL comprising 3 CDRs of the CDRs in SEQ ID NO: 496; or a VH comprising 3 CDRs of the CDRs in SEQ ID NO: 471; and a VL comprising 3 CDRs of the CDRs in SEQ ID NO: 472.

45. An antibody or antigen binding fragment thereof, comprising:
  a heavy chain variable region (VH) comprising an amino acid sequence at least 90% identical to SEQ ID NO: 520; and
  a light chain variable region (VL) comprising an amino acid sequence at least 90% identical to SEQ ID NO: 525.

* * * * *